US 007332304B2

(12) United States Patent
Deng et al.

(10) Patent No.: US 7,332,304 B2
(45) Date of Patent: Feb. 19, 2008

(54) PROCESS AND MATERIALS FOR PRODUCTION OF GLUCOSAMINE AND N-ACETYLGLUCOSAMINE

(75) Inventors: Ming-De Deng, Manitowoc, WI (US); J. David Angerer, Hockessin, DE (US); Don Cyron, Lincoln University, PA (US); Alan D. Grund, Manitowoc, WI (US); Thomas A. Jerrell, Jr., Manitowoc, WI (US); Candice Leanna, Green Bay, WI (US); Owen Mathre, Wilmington, DE (US); Reinhardt Rosson, Manitowoc, WI (US); Jeff Running, Manitowoc, WI (US); Dave Severson, Two Rivers, WI (US); Linsheng Song, Manitowoc, WI (US); Sarah Wassink, Sheboygan, WI (US)

(73) Assignee: Arkion Life Sciences LLC, Wilmington, DE (US)

( * ) Notice: Subject to any disclaimer, the term of this patent is extended or adjusted under 35 U.S.C. 154(b) by 462 days.

(21) Appl. No.: 10/612,779

(22) Filed: Jul. 1, 2003

(65) Prior Publication Data

US 2004/0091976 A1    May 13, 2004

Related U.S. Application Data

(60) Provisional application No. 60/393,348, filed on Jul. 1, 2002.

(51) Int. Cl.
*C12P 19/26* (2006.01)
*C12Q 1/48* (2006.01)
*C12N 9/10* (2006.01)
*C12N 9/00* (2006.01)
*C12N 1/20* (2006.01)
*C12N 5/10* (2006.01)
*C12N 15/00* (2006.01)
*C12P 21/06* (2006.01)
*C07K 14/00* (2006.01)

(52) U.S. Cl. .................. 435/84; 435/15; 435/193; 435/183; 435/325; 435/252.3; 435/252.33; 435/69.1; 435/320.1; 530/350; 536/23.2

(58) Field of Classification Search ............. 435/15, 435/193, 183, 325, 252.3, 252.33, 69.1, 320.1, 435/84; 530/350; 536/23.2
See application file for complete search history.

(56) References Cited

U.S. PATENT DOCUMENTS

| 3,008,874 A | 11/1961 | Feeney et al. ............ 167/55 |
| 3,679,660 A | 7/1972 | Magnus .................. 260/211 |
| 3,683,076 A | 8/1972 | Rovati ................... 424/180 |
| 4,642,340 A | 2/1987 | Senin et al. ............ 536/55.2 |
| 5,246,840 A | 9/1993 | Nilsson ................. 435/101 |
| 5,731,184 A | 3/1998 | Fujishima et al. ......... 435/195 |
| 5,739,015 A | 4/1998 | Srinivasan ............... 435/101 |
| 5,744,325 A | 4/1998 | Fujishima et al. ......... 435/71.2 |
| 5,843,923 A | 12/1998 | Schleck et al. ............ 514/62 |
| 5,876,713 A | 3/1999 | Nishi et al. ............. 424/94.5 |
| 5,998,173 A | 12/1999 | Haynes et al. ............ 435/84 |
| 6,372,457 B1 | 4/2002 | Berry et al. |
| 6,486,307 B1 | 11/2002 | Gandhi et al. ............ 536/20 |
| 6,531,303 B1 | 3/2003 | Millis et al. ............. 435/155 |
| 2003/0181419 A1 | 9/2003 | Hwang et al. ............. 514/62 |

FOREIGN PATENT DOCUMENTS

| EP | 0614972 A2 | 9/1994 |
| EP | 0732400 A2 | 9/1996 |
| GB | 1056331 | 1/1967 |
| JP | 9234064 A2 | 9/1997 |
| RU | 2141965 | 11/1999 |
| WO | WO 97/31121 | 8/1997 |
| WO | WO 02/43653 | 6/2002 |
| WO | WO 02/066667 | 8/2002 |

OTHER PUBLICATIONS

Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247, 1991.*
Araki et al., 1975, *Eur. J. Biochem.*, 55, 71-78.
Bachmann, *Escherichia coli and Salmonella typhimurium cellular and molecular biology Mutant Derivatives of E. coli*, vol. 2:pp. 1190-1219, 1987.
Badet et al., 1987, *Biochemistry (Mosc)*. 26, 1940-1948.
Balbas et al., 1996, *Gene*, 172, 65-69.
Bearne, 1996, *J. Biol. Chem.*, 271, 3052-3057.
Bernheim et al., 1970, *J. Bacteriol.*, 101, 384-391.
Blattner et al., 1997, *Science*, 277, 1453-1474.
Bouffard et al., 1994, *J. Mol. Biol.*, 244, 269-278.
Brown et al., 1989, *Biochemical Society Transaction*, 18, 317-318.
Chen et al., 1998, *J. Agric. Food Chem.*, 46, 1971-1974.
Chen et al., 1998, *J. Agric. Food Chem.*, 46, 3207-3209.
Chen et al., 1987, *Molecular General Genetics*, 210, 331-337.
Cochet et al., 1995, *Archives of Biochemistry & Biophysics*, 324, 391-400.
Curtis et al., 1975, *J. Bacteriol.*, 122, 1189-1199.
Daniels et al., 1993, *Mol. Endocrinol.*, 7, 1041-1048.
Denisot et al., 1991, *Arch. Biochem. Biophys.*, 288, 225-230.
Domard et al., 1991, *Int. J. Biol. Macromol.*, 13, 105-109.

(Continued)

*Primary Examiner*—Delia M. Ramirez
(74) *Attorney, Agent, or Firm*—Sheridan Ross P.C.

(57) ABSTRACT

A biosynthetic method for producing glucosamine and N-acetylglucosamine is disclosed. Such a method includes the fermentation of a genetically modified microorganism to produce glucosamine and/or N-acetylglucosamine. Also disclosed are genetically modified microorganisms that are useful for producing glucosamine and N-acetylglucosamine. In addition, methods of recovering N-acetylglucosamine that has been produced by a fermentation process, including methods that result in N-acetylglucosamine of high purity, are described. Also disclosed is a method to produce glucosamine from N-acetylglucosamine.

67 Claims, 25 Drawing Sheets

OTHER PUBLICATIONS

Dutka-Malen et al., 1988, *Biochimie*, 70, 287-290.
Elliot et al., 1975, *Biochem. Biophys. Res. Commun.*, 64, 277-281.
Fawcett et al., 1995, *J. Bacteriol.*, 177, 1742-1750.
Fernandez-Herrero et al., 1995, *Mol. Microbiol.*, 17, 1-12.
Flores et al., 1996, *Nat. Biotechnol.*, 14, 620-623.
Freese et al., 1970, *J. Bacteriol.*, 101, 1046-1062.
Glaser et al., 1955, *J. Biol. Chem.*, 216, 67-79.
Golinelli-Pimpaneau et al., 1991, *Eur. J. Biochem.*, 201, 175-182.
Holmes et al., 1972, *J. Bacteriol.*, 111, 290-291.
Horlacher et al., 1997, *J. Biol. Chem.*, 272, 13026-13032.
Isaeva et al., 1987, *Izvestiya Akademii Nauk SSR*, 4, 937-939.
Jones-Mortimer et al., 1980, *J. Gen. Microbiol.*, 117, 369-376.
Joyce et al., 1984, *J. Bacteriol.*, 158, 636-643.
Kashige et al., 1994, *Carboyhdrate Research*, 257, 285-291.
Kauss et al., 1988, *Methods Enzymol.*, 161, 518-523.
Kimata et al., 1997, *Biochemistry (Mosc)*. 94, 12914-12919.
Knapp et al., 2002, *Tetrahedron Lett.*, 43, 6075-6078.
Konecny et al., 1982, in *Enzyme Engineering*, vol. 6:pp. 91-96, Plenum Press.
Lengeler, 1980, *Mol. Gen. Genet.*, 179, 49-54.
Leriche et al., 1996, *J. Am. Chem. Soc.*, 118, 1797-1798.
Leriche et al., 1997, *Eur. J. Biochem.*, 245, 418-422.
Marie et al., 1992, *Mol. Microbiol.*, 6, 843-851.
Martinou et al., 1995, *Carbohydr. Res.*, 273, 235-242.
McKnight et al., 1992, *J. Biol. Chem.*, 267, 25208-25212.
Mengin-Lecreulx et al., 1996, *The Journal of Biological Chemistry*, 271, 32-39.
Miclett et al., 2001, *The Journal of Biological Chemistry*, 37, 34840-34846.
Milewski, 1993, *Biochimistry et. Biophys Acta*, 1161, 279-284.
Mio et al., 1999, *J. Biol. Chem.*, 274, 424-429.
Miyazaki et al., 1979, *Chem. Pharm. Bull.*, 27, 532-535.
Mudri et al., 1992, *J. Biol. Chem.*, 267, 25208-25212.
Mukhija et al., 1996, *The Journal of Biological Chemistry*, 271, 14819-14824.
Novikov, 1999, *Russian J. Appl. Chem.*, 72, 156-161.
Novikov et al., 1997, *Russian J. Appl. Chem.*, 70, 1467-1470.
Obmolova et al., 1994, *J. Mol. Biol.*, 242, 703-705.
Oppon et al., 1998, *J. Bacteriol.*, 180, 3007-3012.
O'Shannessy et al., 1993, *Anal. Biochem.*, 212, 457-468.
O'Shea et al., 1993, *Anal. Chem.*, 65, 948-951.
Oyaizu, 1986, *Japanese J. Nutr.*, 44, 307-315.
Oyaizu, 1988, *Nippon Shikuhin Kogyo Gakkaishi*, 35, 771-775.
Oyaizu, 1988, *Nippon Shikuhin Kogyo Gakkaishi*, 35, 846-850.
Penneff et al., 2001, *The Journal of Biological Chemistry*, 276, 16328-16334.
Peri et al., 1990, *Biochemical and Cell Biology*, 68, 123-137.
Plumbridge, 1987, *Mol. Gen. Genet.*, 209, 618-620.
Plumbridge, 1998, *Mol. Microbiol.*, 27, 369-380.
Plumbridge, 2001, *Nucleic Acids Res.*, 29, 506-514.
Plumbridge et al., 1999, *J. Bacteriol.*, 181, 47-54.
Plumbridge, 1989, *Mol. Microbiol.*, 3, 505-515.
Plumbridge, 1990, *J. Bacteriol.*, 172, 2728-2735.
Plumbridge, 1991, *Mol. Microbiol.*, 5, 2053-2062.
Plumbridge, 1992, *J. Gen. Microbiol.*, 138, 1011-1017.
Plumbridge et al., 1993, *J. Bacteriol.*, 175, 4951-4956.
Pompeo et al., 2001, *J. Biol. Chem.*, 276, 3833-3839.
Pradel et al., 1988, *J. Bacteriol.*, 170, 4916-4923.
Roseman, 1957, *J. Biol. Chem.*, 226, 115-124.
Rowley et al., 1991, *J. Bacteriol.*, 173, 968-977.
Sarvas, 1971, *J. Bacteriol.*, 105, 467-471.
Sashiwa et al., 2001, *Chemistry Letters*, 308-309.
Sashiwa et al., 2001, *Japanese Soc. Chitin Chitosan*, 7, 257-260.
Schuster et al., 1993, *Nature*, 365, 343-347.
Shi and Xie 2002 *Huaxue Shiki* 24:93-94.
Shu 1998, *Journal Agricultural of Food Chemistry*, 46, 1129-1131.
Smith et al., 1996, *J. Bacteriol.*, 178, 2320-2327.
Souza et al., 1997, *Archives of Biochemistry & Biophysics*, 340, 338-346.
Sumoto et al., 1991, *Chem. Pharm. Bull.*, 39, 792-794.
Teplyakov et al., 1998, *Structure*, 6, 1047-1055.
Vogler et al., 1989, *J. Bacteriol.*, 171, 6586-6592.
Vogler et al., 1989, *Mol. Gen. Genet.*, 219, 97-105.
Walker et al., 1984, *Biochem. J.*, 224, 799-815.
Wanner, 1996, in *Escherichia coli and Salmonella: Cellular and Molecular Biology*, vol. 1:pp. 1357-1381, ASM Press.
Wanner, 1990, in *The Molecular Basis of Bacterial Metabolism*, vol. 41:pp. 152-163, Springer-Verlag.
Wanner, 1993, *J. Cell. Biochem.*, 51, 47-54.
Watanabe et al., 1990, *Argric. Biol. Chem.*, 54, 519-525.
Watzele et al., 1989, *J. Biol. Chem.*, 264, 8753-8758.
White, 1968, *Biochem. J.*, 106, 847-858.
White et al., 1967, *Biochem. J.*, 105, 121-125.
Wolfe et al., 1956, *Arch. Biochem. Biophys.*, 64, 489-497.
Wu et al., 1971, *J. Bacteriol.*, 105, 455-466.
Xin-Yi et al., 2001, *Journal of Changde Teachers University (Natural Science Edition)*, 13, 63-65.
Yamano et al., 1997, *Biosci. Biotechnol. Biochem.*, 61, 1349-1353.
Yamano et al., 1996, *Biosci. Biotechnol. Biochem.*, 60, 1320-1323.
Yamano et al., 1994, *Biosci. Biotechnol. Biochem.*, 58, 193-195.
Yamano et al., 2000, *Mar. Biotechnol.*, 2, 57-64.
Zalkin, 1985, *Methods of Enzymology*, 113, 278-281.
Zhang et al., 2003, *J. Cap. Elec.& Microchip Tech* pp. 33-37.
International Search Report dated May 23, 2007 for Application No. PCT/US03/20925.

\* cited by examiner

PROCESS AND MATERIALS FOR PRODUCTION OF GLUCOSAMINE AND N-ACETYLGLUCOSAMINE

CROSS REFERENCE TO RELATED APPLICATIONS

This application claims the benefit of priority under 35 U.S.C. § 119(e) from U.S. Provisional Application Ser. No. 60/393,348, filed Jul. 1, 2002, entitled, "Process and Materials for Production of Glucosamine and N-Acetylglucosamine." The entire disclosure of U.S. Provisional Application Ser. No. 60/393,348 is incorporated herein by reference.

FIELD OF THE INVENTION

The present invention relates to a method for producing glucosamine and N-acetylglucosamine by fermentation. The present invention also relates to genetically modified strains of microorganisms useful for producing glucosamine and N-acetylglucosamine. The present invention also relates to a method to recover N-acetylglucosamine or glucosamine from a fermentation process. The present invention also relates to a method to produce glucosamine from a source of N-acetylglucosamine.

BACKGROUND OF THE INVENTION

Amino sugars are usually found as monomer residues in complex oligosaccharides and polysaccharides. Glucosamine is an amino derivative of the simple sugar, glucose. N-acetylglucosamine is an acetylated derivative of glucosamine. Glucosamine, N-acetylglucosamine and other amino sugars are important constituents of many natural polysaccharides. For example, polysaccharides containing amino sugars can form structural materials for cells, analogous to structural proteins.

Glucosamine is manufactured as a nutraceutical product with applications in the treatment of osteoarthritic conditions in animals and humans, among other conditions. The market for glucosamine is experiencing tremendous growth. Furthermore, significant erosion of the world market price for glucosamine is not expected. N-acetylglucosamine is also a valuable pharmacological agent in the treatment of a wide variety of ailments. N-acetylglucosamine does not have any established negative side effects. Since N-acetylglucosamine is a valuable and important component of protein synthesis in the animal body it has a positive effect on tissue regeneration, N-acetylglucosamine has therapeutic potential in the prevention and/or treatment of a wide variety of diseases such as gastritis, food allergies, inflammatory bowel disease (IBD), diverticulitis, acute and chronic forms of rheumatoid arthritis and osteoarthritis, as well as the pathological conditions arising from metabolic disorders of the osteoarticular tissues.

Glucosamine is currently obtained by acid hydrolysis of chitin, a complex carbohydrate derived from N-acetyl-D-glucosamine. Alternatively, glucosamine can also be produced by acid hydrolysis of variously acetylated chitosans. Chitin, a copolymer of N-acetylglucosamine and glucosamine, is a common natural substance, found in arthropods and fungi. It can be obtained from inexpensive sources like arthropod refuse, e.g.: shellfish (lobster, shrimp, krill, crab, and prawn exoskeletons); insects used to biodegrade swine offal like the fly larvae; and more recently from waste fungal biomass used in citric acid production. The final product, salts of glucosamine, are relatively expensive because the relatively low chitin content in refuse sources requires large volumes of waste to be processed in order to obtain relatively small amounts of product, and because the processing itself is relatively low yield and energy and chemically intensive.

Common industrial practice is to purify the chitin by treating it with combinations of acids and bases to remove minerals, proteins and other impurities accompanying the offal starting material, and to then depolymerize and deacetylate the chitin in a single step to glucosamine through the use of concentrated hydrochloric acid at high temperature, long times and low yields. Glucosamine as a free base is very unstable and subject to degradation. Consequently stable salts such as the hydrochloride are produced. Other blends of salts are offered, usually using the hydrochloride as a base, in order to mimic forms that have been tested for efficacy in clinical settings like Viartril and DONA® 200-S. These compositions take the form of mixed salts with a molecular formula of (glucosamine)$_2$ sulfate-(NaCl)$_2$, and (glucosamine)$_2$ sulfate-(KCl)$_2$. More recently, salts of the structure (glucosamine)$_2$ sodium bisulfate-(HCl)$_2$, (glucosamine)$_2$potassium bisulfate-(HCl)$_2$ are being investigated as means to provide stable salts of glucosamine, at lower sodium and potassium dosages.

N-acetylglucosamine is not widely available in the marketplace. It is currently produced by the acetylation of glucosamine using an organic acetylating reagent such as acetic anhydride, an expensive and difficult step. These processes suffer from poor product yields (in the range of 50% conversion of substrate to glucosamine).

The common forms of glucosamine, being derived from shellfish, carry labels warning consumers of the potential for allergic reactions in persons sensitive to shellfish. Increasingly, consumers are seeking access to material that is free of all animal byproducts. Moreover, the availability of raw material (i.e., a source of chitin, such as crab shells) is becoming increasingly limited. Therefore, there is a need in the industry for a cost-effective method for producing high yields of glucosamine and N-acetylglucosamine for commercial sale and use.

PCT Publication No. WO 02/66667 disclosed glucosamine and method of making glucosamine from microbial biomass. This method of production overcomes problems associated with shellfish allergy, but it suffers from a major problem of low yield. More particularly, since the method relies on the biomass waste generated in a fermentation that is dedicated to the production of other products such as citric acid, it is not sufficient to produce quantities of glucosamine that meet the increasing market demand for the product. U.S. Pat. No. 6,372,457, incorporated herein by reference in its entirety, disclosed a process and materials for production of glucosamine by microbial fermentation. However, U.S. Pat. No. 6,372,457 does not disclose any method for the production of N-acetylglucosamine.

SUMMARY OF THE INVENTION

One embodiment of the present invention relates to a method to produce glucosamine or N-acetylglucosamine by fermentation. The method includes the steps of: (a) culturing in a fermentation medium a microorganism which comprises at least one genetic modification that increases the activity of glucosamine-6-phosphate acetyltransferase; and (b) collecting a product produced from the step of culturing which is selected from the group consisting of glucosamine-6-phosphate, glucosamine, glucosamine-1-phosphate, N-acetylglucosamine-1-phosphate, N-acetylglucosamine-6-phosphate, and N-acetylglucosamine. In one aspect, the genetic modification to increase the activity of glucosamine-6-phosphate acetyltransferase provides a result selected from the group consisting of: increased enzymatic activity of glucosamine-6-phosphate acetyltransferase; overexpression of glucosamine-6-phosphate acetyltransferase by the microorganism; reduced N-acetylglucosamine-6-phosphate product inhibition of the glucosamine-6-phosphate acetyltransferase; and increased affinity of glucosamine-6-phosphate acetyltransferase for glucosamine-6-phosphate. In another aspect, the microorganism is transformed with at least one recombinant nucleic acid molecule comprising a nucleic acid sequence encoding the glucosamine-6-phosphate acetyltransferase. In one aspect, the nucleic acid sequence encoding a glucosamine-6-phosphate acetyltransferase has at least one genetic modification which increases the enzymatic activity of the glucosamine-6-phosphate acetyltransferase. In another aspect, the glucosamine-6-phosphate acetyltransferase has an amino acid sequence that is at least about 35% identical, or at least about 50% identical, or at least about 70% identical, to an amino acid sequence selected from the group consisting of: SEQ ID NO:30, SEQ ID NO:32 and SEQ ID NO:34, wherein the glucosamine-6-phosphate acetyltransferase has enzymatic activity. In another aspect, the glucosamine-6-phosphate acetyltransferase has an amino acid sequence selected from the group consisting of SEQ ID NO:30, SEQ ID NO:32 and SEQ ID NO:34.

In another aspect of this embodiment of the invention, the microorganism further comprises at least one genetic modification that decreases the activity of glucosamine-6-phosphate deaminase. The genetic modification to decrease the activity of glucosamine-6-phosphate deaminase can include, but is not limited to, a partial or complete deletion or inactivation of an endogenous gene encoding the glucosamine-6-phosphate deaminase in the microorganism.

In one aspect of this embodiment of the invention, the microorganism further comprises at least one genetic modification that increases the activity of glucosamine-6-phosphate synthase. In one aspect, the microorganism is transformed with at least one recombinant nucleic acid molecule comprising a nucleic acid sequence encoding the glucosamine-6-phosphate synthase. Such a glucosamine-6-phosphate synthase can include a glucosamine-6-phosphate synthase comprising an amino acid sequence that is at least about 35% identical, or at least about 50% identical, or at least about 70% identical, to an amino acid sequence selected from: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20, wherein the glucosamine-6-phosphate synthase has enzymatic activity. In one aspect, the glucosamine-6-phosphate synthase comprises an amino acid sequence selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20. In one aspect, the glucosamine-6-phosphate synthase has a modification to reduce product inhibition of the glucosamine-6-phosphate synthase as compared to the wild-type glucosamine-6-phosphate synthase. Such a glucosamine-6-phosphate synthase can include, but is not limited to, a protein comprising an amino acid sequence selected from: SEQ ID NO:4, SEQ ID NO:6, SEQ ID NO:8, SEQ ID NO:10, SEQ ID NO:12, and SEQ ID NO:14. In a further aspect, this microorganism further comprises at least one genetic modification that decreases the activity of glucosamine-6-phosphate deaminase. The genetic modification to decrease the activity of glucosamine-6-phosphate deaminase can include, but is not limited to, a partial or complete deletion or inactivation of an endogenous gene encoding the glucosamine-6-phosphate deaminase in the microorganism.

Another embodiment of the present invention relates to a method to produce glucosamine or N-acetylglucosamine by fermentation, comprising: (a) culturing in a fermentation medium a microorganism which comprises at least one genetic modification that increases the activity of glucosamine-6-phosphate deaminase; and (b) collecting a product produced from the step of culturing which is selected from the group consisting of glucosamine-6-phosphate, glucosamine, glucosamine-1-phosphate, N-acetylglucosamine-1-phosphate, N-acetylglucosamine-6-phosphate, and N-acetylglucosamine. In this aspect, the genetic modification preferably provides a results selected from the group consisting of: overexpression of glucosamine-6-phosphate deaminase by the microorganism, increased enzymatic activity of glucosamine-6-phosphate deaminase, increased reverse reaction of glucosamine-6-phosphate deaminase to form increased glucosamine-6-phosphate, reduced forward reaction of glucosamine-6-phosphate deaminase to form reduced fructose-6-phosphate, increased affinity of glucosamine-6-phosphate deaminase for fructose-6-phosphate, reduced affinity of glucosamine-6-phosphate deaminase for glucosamine-6-phosphate, and reduced glucosamine-6-phosphate product inhibition of the glucosamine-6-phosphate deaminase. In one aspect, the microorganism is transformed with a recombinant nucleic acid molecule comprising a nucleic acid sequence encoding a glucosamine-6-phosphate deaminase. In one aspect the nucleic acid sequence encoding a glucosamine-6-phosphate deaminase has at least one genetic modification which increases the enzymatic activity of the glucosamine-6-phosphate deaminase. In one aspect, the glucosamine-6-phosphate deaminase has an amino acid sequence that is at least about 35% identical, or at least about 50% identical, or at least about 70% identical, to an amino acid sequence of SEQ ID NO:42, wherein the glucosamine-6-phosphate deaminase has enzymatic activity. In one aspect, the glucosamine-6-phosphate deaminase has an amino acid sequence of SEQ ID NO:42.

In one aspect of this embodiment, the microorganism further comprises a genetic modification to decrease the activity of glucosamine-6-phosphate synthase. For example, the genetic modification to decrease the activity of glucosamine-6-phosphate synthase can include, but is not limited to, a partial or complete deletion or inactivation of an endogenous gene encoding glucosamine-6-phosphate synthase in the microorganism.

In another aspect of this embodiment, the microorganism further comprises a genetic modification to increase the activity of glucosamine-6-phosphate N-acetyltransferase. The genetic modification can provide a result selected from: increased enzymatic activity of glucosamine-6-phosphate acetyltransferase; overexpression of glucosamine-6-phosphate acetyltransferase by the microorganism; reduced N-acetylglucosamine-6-phosphate product inhibition of the glucosamine-6-phosphate acetyltransferase; and increased affinity of glucosamine-6-phosphate acetyltransferase for glucosamine-6-phosphate. In one aspect, the microorganism is transformed with a recombinant nucleic acid molecule comprising a nucleic acid sequence encoding the glucosamine-6-phosphate N-acetyltransferase, as described for the previous embodiment herein. Various aspects of the glucosamine-6-phosphate N-acetyltransferase have been described above in the prior embodiment and are encompassed here. In one aspect, the microorganism further comprises a genetic modification to decrease the activity of glucosamine-6-phosphate synthase. Such a modification can include, but is not limited to, a partial or complete deletion or inactivation of an endogenous gene encoding glucosamine-6-phosphate synthase in the microorganism.

In yet another aspect of this embodiment, the microorganism further comprises a genetic modification to increase the activity of glucosamine-1-phosphate N-acetyltransferase. The genetic modification can provide a result selected from the group consisting of: increased enzymatic activity of glucosamine-1-phosphate N-acetyltransferase; reduced N-acetylglucosamine-1-phosphate uridyltransferase enzymatic activity; overexpression of an enzyme having glucosamine-1-phosphate N-acetyltransferase activity by the microorganism; increased affinity of glucosamine-1-phosphate N-acetyltransferase for glucosamine-1-phosphate; reduced affinity of an glucosamine-1-phosphate N-acetyltransferase/N-acetylglucosamine-1-phosphate uridyltransferase for N-acetylglucosamine-1-phosphate; and reduced N-acetylglucosamine-1-phosphate product inhibition of the glucosamine-1-phosphate N-acetyltransferase. In one aspect, the microorganism comprises a bifunctional glucosamine-1-phosphate N-acetyltransferase/N-acetylglucosamine-1-phosphate uridyltransferase, wherein the glucosamine-1-phosphate N-acetyltransferase activity is increased. In another aspect, the microorganism is transformed with a recombinant nucleic acid molecule comprising a nucleic acid sequence encoding a glucosamine-1-phosphate N-acetyltransferase/N-acetylglucosamine-1-phosphate uridyltransferase or a nucleic acid sequence encoding a glucosamine-1-phosphate N-acetyltransferase. In one aspect, the nucleic acid sequence encoding a glucosamine-1-phosphate N-acetyltransferase/N-acetylglucosamine-1-phosphate uridyltransferase or a glucosamine-1-phosphate N-acetyltransferase has at least one genetic modification which increases the activity of the glucosamine-1-phosphate N-acetyltransferase/N-acetylglucosamine-1-phosphate uridyltransferase or the glucosamine-1-phosphate N-acetyltransferase, respectively. In another aspect, the glucosamine-1-phosphate N-acetyltransferase/N-acetylglucosamine-1-phosphate uridyltransferase has an amino acid sequence that is at least about 35% identical to an amino acid sequence of SEQ ID NO:56, wherein the glucosamine-1-phosphate N-acetyltransferase/N-acetylglucosamine-1-phosphate uridyltransferase has glucosamine-1-phosphate N-acetyltransferase enzymatic activity. In another aspect, the glucosamine-1-phosphate N-acetyltransferase/N-acetylglucosamine-1-phosphate uridyltransferase has an amino acid sequence of SEQ ID NO:56. In another aspect, the truncated glucosamine-1-phosphate N-acetyltransferase/N-acetylglucosamine-1-phosphate uridyltransferase having glucosamine-1-phosphate N-acetyltransferase activity, and reduced or no N-acetylglucosamine-1-phosphate uridyltransferase activity, including but not limited to, a truncated glucosamine-1-phosphate N-acetyltransferase/N-acetylglucosamine-1-phosphate uridyltransferase having an amino acid sequence that is at least about 35% identical to an amino acid sequence of SEQ ID NO:58. In one aspect, the truncated glucosamine-1-phosphate N-acetyltransferase/N-acetylglucosamine-1-phosphate-uridyltransferase has an amino acid sequence of SEQ ID NO:58. In this aspect, the microorganism can further comprise a genetic modification to decrease the activity of glucosamine-6-phosphate synthase, such as is described above.

Yet another embodiment of the present invention relates to a method to produce glucosamine or N-acetylglucosamine by fermentation, comprising: (a) culturing in a fermentation medium a microorganism which comprises at least one genetic modification that decreases the activity of glucosamine-6-phosphate deaminase and at least one genetic modification that increases the activity of glucosamine-1-phosphate N-acetyltransferase; and (b) collecting a product produced from the step of culturing which is selected from the group consisting of glucosamine-6-phosphate, glucosamine, glucosamine-1-phosphate, N-acetylglucosamine-1-phosphate, N-acetylglucosamine-6-phosphate, and N-acetylglucosamine. In one aspect, the genetic modification to decrease the activity of glucosamine-6-phosphate deaminase comprises a partial or complete deletion or inactivation of an endogenous gene encoding the glucosamine-6-phosphate deaminase in the microorganism. In another aspect, the genetic modification to increase the activity of glucosamine-1-phosphate N-acetyltransferase provides a result selected from the group consisting of: increased enzymatic activity of glucosamine-1-phosphate N-acetyltransferase; reduced N-acetylglucosamine-1-phosphate uridyltransferase enzymatic activity; overexpression of an enzyme having glucosamine-1-phosphate N-acetyltransferase activity by the microorganism; increased affinity of glucosamine-1-phosphate N-acetyltransferase for glucosamine-1-phosphate; reduced affinity of an glucosamine-1-phosphate N-acetyltransferase/N-acetylglucosamine-1-phosphate uridyltransferase for N-acetylglucosamine-1-phosphate; and reduced N-acetylglucosamine-1-phosphate product inhibition of the glucosamine-1-phosphate N-acetyltransferase. Various aspects of such a bifunctional glucosamine-1-phosphate N-acetyltransferase/N-acetylglucosamine-1-phosphate uridyltransferase have been described in prior embodiments above, and are encompassed here as well.

In one aspect of this embodiment, the microorganism further comprises at least one genetic modification that increases the activity of glucosamine-6-phosphate synthase. Various aspects of such a modification have been described in prior embodiments above and are encompassed here.

Yet another embodiment of the invention relates to a method to produce glucosamine or N-acetylglucosamine by fermentation, comprising: (a) culturing in a fermentation medium a microorganism which comprises an endogenous glucosamine-6-phosphate acetyltransferase and at least one genetic modification to increase the activity of glucosamine-6-phosphate synthase; and (b) collecting a product produced from the step of culturing which is selected from the group consisting of glucosamine-6-phosphate, glucosamine, glucosamine-1-phosphate, N-acetylglucosamine-1-phosphate, N-acetylglucosamine-6-phosphate, and N-acetylglucosamine. In one aspect, the microorganism is transformed with at least one recombinant nucleic acid molecule comprising a nucleic acid sequence encoding the glucosamine-6-phosphate synthase. Various aspects of this modification have been described above and are encompassed herein. In one aspect, the microorganism further comprises at least one genetic modification that decreases the activity of glucosamine-6-phosphate deaminase, as has been described above. In one aspect, the method is a method to produce N-acetylglucosamine by fermentation, and wherein the step of collecting comprises collecting a product produced from the step of culturing which is selected from the group consisting of N-acetylglucosamine-1-phosphate, N-acetylglucosamine-6-phosphate, and N-acetylglucosamine.

In one aspect of any of the above-described embodiments, the expression of any of the above-referenced recombinant nucleic acid molecules is inducible, such as by, but not limited to, lactose. In one aspect, the microorganism further comprises a genetic modification to reduce inhibition of transcription induction by lactose. Such a genetic modification can include, but is not limited to, a partial or complete deletion or inactivation of a gene encoding a LacI repressor protein.

In any of the above-identified embodiments of the invention related to a method to produce glucosamine or N-acetylglucosamine by fermentation, the following discussion can apply. In one aspect, the step of culturing includes the step of maintaining the carbon source at a concentration of from about 0.5% to about 5% in the fermentation medium. In another aspect, the step of culturing is performed in a fermentation medium comprising yeast extract. In yet another aspect, the step of culturing is performed in a fermentation medium comprising a carbon source selected from the group consisting of glucose, fructose, a pentose sugar, lactose and gluconic acid. The pentose sugar can include, but is not limited to, ribose, xylose, and arabinose. In another aspect, the step of culturing is performed in a fermentation medium comprising glucose and ribose, and in another aspect, the step of culturing is performed in a fermentation medium comprising glucose and gluconic acid. In one aspect, the step of culturing is performed at a temperature of from about 25° C. to about 45° C., and in another aspect, at about 37° C. In one aspect, the step of culturing is performed at a pH of from about pH 4 to about pH 7.5 and in another aspect, at a pH of from about pH 6.7 to about pH 7.5, and in yet another aspect, at a pH of from about pH 4.5 to about pH 5.

In any of the above-described embodiments for a method to produce glucosamine or N-acetylglucosamine by a fermentation process, the microorganism can include any one or more of the following modifications. In one aspect, the microorganism further comprises a genetic modification to increase phosphoglucoisomerase activity in the microorganism. For example, the microorganism can be transformed with a recombinant nucleic acid molecule comprising a nucleic acid sequence encoding the phosphoglucoisomerase, which can include a phosphoglucoisomerase comprising an amino acid sequence of SEQ ID NO:105. In another aspect, the microorganism further comprises a partial or complete deletion or inactivation of phosphofructokinase in the microorganism. In another aspect, the microorganism further comprises a genetic modification to increase the activity of glutamine synthetase. For example, the microorganism can be transformed with a recombinant nucleic acid molecule comprising a nucleic acid sequence encoding the glutamine synthetase, which can include a glutamine synthetase comprising an amino acid sequence of SEQ ID NO:89. In another aspect, the microorganism further-comprises a genetic modification to increase the activity of glucose-6-phosphate dehydrogenase. For example, the microorganism can be transformed with a recombinant nucleic acid molecule comprising a nucleic acid sequence encoding the glucose-6-phosphate dehydrogenase, which can include a glucose-6-phosphate dehydrogenase comprising an amino acid sequence of SEQ ID NO:95. In another aspect, the microorganism further comprises a partial or complete deletion or inactivation of genes encoding enzymes responsible for glycogen synthesis in the microorganism, including but not limited to, ADP-glucose pyrophosphorylase, glycogen synthase and a branching enzyme. Preferably, none of the above-described modifications inhibit the ability of the microorganism to metabolize galactose.

In any of the above-described embodiments of a method to produce glucosamine and/or N-acetylglucosamine by fermentation, the step of collecting can include recovering an intracellular product from the microorganism selected from the group consisting of: intracellular glucosamine-6-phosphate, glucosamine-1-phosphate, N-acetylglucosamine-6-phosphate, N-acetylglucosamine-1-phosphate, N-acetylglucosamine and glucosamine or recovering an extracellular product from the fermentation medium selected from the group consisting of: glucosamine and N-acetylglucosamine. In one aspect, this step includes a step selected from: (a) purifying a product selected from the group consisting of glucosamine and N-acetylglucosamine from the fermentation medium; (b) recovering a product selected from the group consisting of glucosamine-6-phosphate, glucosamine-1-phosphate, N-acetylglucosamine-6-phosphate and N-acetylglucosamine-1-phosphate from the microorganism; (c) dephosphorylating a product selected from the group consisting of glucosamine-6-phosphate and glucosamine-1-phosphate to produce glucosamine; and (d) dephosphorylating a product selected from the group consisting of N-acetylglucosamine-6-phosphate and N-acetylglucosamine-1-phosphate to produce N-acetylglucosamine; (e) treating a product selected from the group consisting of N-acetylglucosamine, N-acetylglucosamine-6-phosphate and N-acetylglucosamine-1-phosphate to produce a glucosamine product selected from the group consisting of: glucosamine, glucosamine-6-phosphate and glucosamine-1-phosphate. In one aspect, step (e) comprises hydrolyzing the product selected from the group consisting of N-acetylglucosamine, N-acetylglucosamine-6-phosphate and N-acetylglucosamine-1-phosphate, under acid and heat conditions or by enzymatic deacetylation. In one aspect N-acetylglucosamine produced by the fermentation method is recovered by precipitating N-acetylglucosamine-containing solids from the fermentation broth. In another aspect, N-acetylglucosamine produced by the fermentation method is recovered by crystallizing N-acetylglucosamine-containing solids from the fermentation broth.

Another embodiment of the present invention relates to any of the above-described genetically modified microorganisms.

The genetically modified microorganism in any of the embodiments described above can include, but is not limited to, bacteria and fungi. In one aspect, the microorganism is selected from the group consisting of bacteria and yeast. Suitable bacteria include, but are not limited to, bacteria from a genus selected from the group consisting of: *Escherichia, Bacillus, Lactobacillus, Pseudomonas* and *Streptomyces*. Suitable bacteria further include, but are not limited to, bacteria from a species selected from the group consisting *Escherichia coli, Bacillus subtilis, Bacillus licheniformis, Lactobacillus brevis, Pseudomonas aeruginosa* and *Streptomyces lividans*. Suitable yeast include, but are not limited to, yeast from a genus selected from the group consisting of: *Saccharomyces, Candida, Hansenula, Pichia, Kluveromyces*, and *Phaffia*. Suitable yeast further include, but are not limited to, yeast from a species selected from the group consisting of: *Saccharomyces cerevisiae, Schizosaccharomyces pombe, Candida albicans, Hansenula polymorpha, Pichia pastoris, P. canadensis, Kluyveromyces marxianus* and *Phaffia rhodozyma*. Suitable fungi include, but are not limited to, fungi from a genus selected from the group consisting of: *Aspergillus, Absidia, Rhizopus, Chrysosporium, Neurospora* and *Trichoderma*. Suitable fungi further include, but are not limited to, fungi from a species selected from the group consisting of: *Aspergillus niger, A. nidulans, Absidia coerulea, Rhizopus oryzae, Chrysosporium lucknowense, Neurospora crassa, N. intermedia* and *Trichoderma reesei*.

Yet another embodiment of the present invention relates to a method to produce N-acetylglucosamine, comprising: (a) obtaining a fermentation broth containing solubilized N-acetylglucosamine that is a product of a fermentation process; and (b) recovering N-acetylglucosamine-containing solids from the fermentation broth. In one aspect, the method further includes removing cellular material from the fermentation broth. In one aspect, the method further includes decolorizing the fermentation broth. Such a step of decolorizing can include, but is not limited to, multiple N-acetylglucosamine crystallizations, activated carbon treatment, and chromatographic decolorization. In one aspect, the method further includes the step of contacting the fermentation broth with an ion exchange resin. For example, the step of contacting the fermentation broth with an ion exchange resin can include, but is not limited to, contacting the fermentation broth with an anion exchange resin and a cation exchange resin. The step of contacting the fermentation broth with an anion exchange resin and a cation exchange resin can include contacting the fermentation broth with a mixed bed of anion and cation exchange resins.

In one aspect of this embodiment, the step recovering comprises precipitating N-acetylglucosamine-containing solids from the fermentation broth.

In one aspect of this embodiment, the step recovering comprises crystallizing N-acetylglucosamine-containing solids from the fermentation broth.

In one aspect of this embodiment, the step of recovering comprises concentrating the fermentation broth containing solubilized N-acetylglucosamine. In one aspect, the step of concentrating is conducted at less than atmospheric pressure. In another aspect, the step of concentrating is conducted by membrane separation. In another aspect, the step of concentrating is conducted at a temperature of between about 40° C. and about 75° C. In another aspect, the step of concentrating is conducted at a temperature of between about 45° C. and about 55° C. in another aspect, the step of concentrating is conducted to achieve a solids content in the fermentation broth of at least about 30% solids. In another aspect, the step of concentrating is conducted to achieve a solids content in the fermentation broth of at least about 40% solids. In another aspect, the step of concentrating is conducted to achieve a solids content in the fermentation broth of at least about 45% solids. In another aspect, the method further includes cooling the fermentation broth after the step of concentrating. For example, the fermentation broth can be cooled to between about −5° C. and about 45° C., or in another aspect, to between about −5° C. and about room temperature, or in another aspect, to about room temperature.

Another aspect of the step of concentrating further includes, after the step of cooling, seeding the fermentation broth with crystals of N-acetylglucosamine. In one aspect, the seed crystals of N-acetylglucosamine are selected from the group consisting of N-acetylglucosamine crystals formed by nucleation in the fermentation broth and externally provided N-acetylglucosamine crystals.

In any of the various aspects of this embodiment, the step of recovering can include a step of contacting N-acetylglucosamine with a water miscible solvent. A water miscible solvent can include, but is not limited to, isopropyl alcohol (IPA), ethanol, methanol, acetone, tetrahydrofuran, dimethylsulfoxide, dimethylformamide, dioxane and acetonitrile.

In any of the various aspects of this embodiment, the method can further include a step of drying the recovered N-acetylglucosamine-containing solids. The step can include washing the dried N-acetylglucosamine-containing solids with a water miscible solvent.

In any of the various aspects of this embodiment, the method can include dissolving the recovered N-acetylglucosamine-containing solids to form an N-acetylglucosamine solution and recovering N-acetylglucosamine-containing solids from the solution.

In any of the various aspects of this embodiment, the method can further include filtration of the fermentation broth to remove bacterial endotoxins.

Yet another embodiment of the present-invention relates to a method to produce glucosamine from a source of N-acetylglucosamine, comprising: (a) obtaining a source of N-acetylglucosamine selected from the group consisting of: N-acetylglucosamine, N-acetylglucosamine-6-phosphate and N-acetylglucosamine-1-phosphate; and, (b) treating the source of N-acetylglucosamine of (a) to produce a glucosamine product selected from the group consisting of: glucosamine, glucosamine-6-phosphate and glucosamine-1-phosphate, from the source of N-acetylglucosamine. In one aspect, the source of N-acetylglucosamine is at least about 40% N-acetylglucosamine as a percentage of dry solids in the source. In another aspect, the source of N-acetylglucosamine is N-acetylglucosamine that has been produced by a fermentation process. In yet another aspect, the source of N-acetylglucosamine is a fermentation broth containing N-acetylglucosamine that was produced by a fermentation process, wherein the fermentation broth has been treated to substantially remove cellular material. In another aspect, the source of N-acetylglucosamine is provided as a solid or in a solution. In another aspect, the source of N-acetylglucosamine is suspended in an aqueous, low-boiling, primary or secondary alcohol.

In one aspect of this embodiment, step (b) of treating comprises hydrolyzing the source of N-acetylglucosamine under acid and heat conditions. In one aspect, the step of hydrolyzing is performed at a temperature of from about 60° C. to about 100° C. In another aspect, the step of hydrolyzing is performed at a temperature of from about 70° C. to about 90° C. In another aspect, the step of hydrolyzing is performed using a hydrochloric solution at a concentration of from about 10% by weight to about 40% weight by weight. In another aspect, the ratio of the weight of hydrochloric acid solution to the source of N-acetylglucosamine as a pure dry weight is from about 1:1 by weight to about 5:1 by weight. In another aspect, the step of hydrolyzing is performed for from about 10 minutes to about 24 hours.

In one aspect, the step of hydrolyzing comprises: (a) hydrolyzing the source of N-acetylglucosamine by combining the source of N-acetylglucosamine with a hydrochloric acid solution or a recycled hydrolysis mother liquor under heat conditions to produce a solution containing glucosamine hydrochloride; (b) cooling the solution of (a) to precipitate the glucosamine hydrochloride; and (c) recovering the precipitated glucosamine hydrochloride-containing solids from (b). In one aspect, the step (a) of hydrolyzing is performed by continuously blending the source of N-acetylglucosamine with a hydrochloric acid solution or a recycled hydrolysis mother liquor to maintain the source of N-acetylglucosamine as a dissolved solution, followed by addition of anhydrous hydrochloric acid under heat conditions to the solution of (a) to initiate hydrolysis and convert the N-acetylglucosamine to glucosamine hydrochloride. In another aspect, the hydrolysis mother liquor is hydrolysis solution that remains after recovering the precipitated glucosamine hydrochloride in step (c), wherein a primary or secondary alcohol is added to the hydrolysis solution prior to, during or after a hydrolysis step is performed. Such a primary or secondary alcohol can include, but is not limited to, methanol, isopropanol, ethanol, n-propanol, n-butanol and sec-butanol. In one aspect, the step of cooling is performed until the solution is from about −5° C. to about 40° C.

In another aspect, the step of recovering comprises: (i) collecting the precipitated glucosamine hydrochloride-containing solids; (ii) washing the glucosamine hydrochloride-containing solids with a water miscible solvent; and (iii) drying the glucosamine hydrochloride-containing solids.

In yet another aspect, the step of recovering comprises: (i) collecting the precipitated glucosamine hydrochloride-containing solids; (ii) dissolving the solids from (i) in water to form a solution; (iii) adjusting the pH of the solution of (ii) to between about 2.5 and 4; (iv) contacting the solution of (iii) with activated carbon to decolorize the glucosamine hydrochloride-containing solids; (v) removing the activated carbon from the solution of (iv); (vi) crystallizing glucosamine hydrochloride from the solution of (v). In this aspect, the step of crystallizing comprises concentrating the glucosamine hydrochloride at a temperature of less than about 70° C. In one aspect, the step of crystallizing comprises concentrating the glucosamine hydrochloride at a temperature of less than about 50° C. In another aspect, step of crystallizing comprises concentrating the glucosamine hydrochloride at less than atmospheric pressure. In another aspect, the method further includes recycling solution remaining after the crystallization step (vi) to step (i) of a subsequent recovery process. In another aspect, the method further includes recycling solution remaining after the crystallization step (vi) to a subsequent step of crystallization. In this aspect, the method can include washing the crystallized glucosamine hydrochloride from step (vi) with a water miscible solvent, including, but not limited to, methanol, isopropanol, ethanol, acetonitrile, acetone, tetrahydrofuran, dimethylsulfoxide, dimethylformamide and dioxane. In one aspect, the method further includes drying the crystallized glucosamine hydrochloride after washing at a temperature of less than about 70° C. for less than about 6 hours. The step of drying can be conducted at less than atmospheric pressure. In one aspect, the step of drying is conducted with an air sweep.

In another aspect of this embodiment, the source of N-acetylglucosamine is suspended in an aqueous, low-boiling, primary or secondary alcohol, and wherein the method comprises an additional step, between steps (a) and (b) of removing the acetic acid ester formed with the alcohol following hydrolysis or prior to recycling the hydrolysis solution for reuse. In one aspect, the acetic acid ester is removed by a process selected from the group consisting of: distillation, flashing, and concentration at less than atmospheric pressure. In another aspect, the step of hydrolyzing is performed at a temperature of between about 60° C. and about 100° C. In another aspect, the step of hydrolyzing is performed at the solution boiling point at one atmosphere. In another aspect, a step of hydrolyzing is performed at a ratio of hydrochloric acid solution to the source of N-acetylglucosamine as a dry weight of from about 3:1 by weight to about 5:1 by weight, and at a temperature of less than about 80° C. In one aspect, the method further includes the steps of washing the glucosamine hydrochloride recovered in step (c) with a water miscible solvent and/or drying the crystallized glucosamine hydrochloride as discussed above.

In yet another aspect of this embodiment of the invention, step (b) of treating comprises contacting the source of N-acetylglucosamine with a deacetylating enzyme to produce the glucosamine product. Such a deacetylating enzyme can include, but is not limited to, N-acetylglucosamine-6-P deacetylase, N-acetylglucosamine deacetylase, and/or a chitin deacetylase that has been modified to or selected for its ability to deacetylate an N-acetylglucosamine monomer to produce glucosamine. In one aspect, the glucosamine product by crystallization. In one aspect, the method includes recovering the glucosamine product by precipitation. In one aspect, the deacetylating enzyme is immobilized on a substrate. In one aspect, the step of contacting comprises contacting the source of N-acetylglucosamine with the deacetylating enzyme in the presence of an aqueous sodium or calcium chloride solution. In this aspect, the method can further include recovering the glucosamine product by crystallization or precipitation. In one aspect, the step of contacting comprises contacting the source of N-acetylglucosamine with the deacetylating enzyme in the presence of an alcohol to esterify the alcohol. In another aspect, the method further includes mixing a salt with the glucosamine product and contacting the mixture with an ion exchange medium, including, but not limited to, a chloride salt, a phosphate, a sulfate, an iodide and a bisulfate.

Yet another embodiment of the present invention relates to a method to produce glucosamine by fermentation, comprising: (a) culturing in a fermentation medium a microorganism which has been transformed with a recombinant nucleic acid molecule comprising a nucleic acid sequence encoding glucosamine-6-phosphate synthase, wherein expression of the recombinant nucleic acid molecule is controlled by a lactose induction, and wherein the step of culturing comprises: (i) growing the microorganism in the fermentation medium comprising glucose as a carbon source at a pH of from about pH 4.5 to about pH 7 and at a temperature of from about 25° C. to about 37° C.; (ii) inducing transcription of the nucleic acid sequence by addition of lactose to the fermentation medium in the absence of adding additional glucose to the medium; (iii) fermenting the microorganism after step (ii) in the presence of glucose at a pH of from about 4.5 to about 6.7 and at a temperature of from about 25° C. to about 37° C.; and (b) collecting a product produced from the step of culturing which is selected from the group consisting of glucosamine-6-phosphate and glucosamine. In one aspect, a source of trace elements is added to step (iii) of fermenting, including, but not limited to iron. In one aspect, step (ii) comprises growing the microorganism in the fermentation medium comprising glucose as a carbon source at a pH of about pH 6.9. In one aspect, step (iii) comprises fermenting the microorganism after step (ii) in the presence of glucose at a pH of from about 4.5 to about 5. In one aspect, step (iii) comprises fermenting the microorganism after step (ii) in the presence of glucose at a pH of about 6.7.

BRIEF DESCRIPTION OF THE FIGURES OF THE INVENTION

Figure 3:
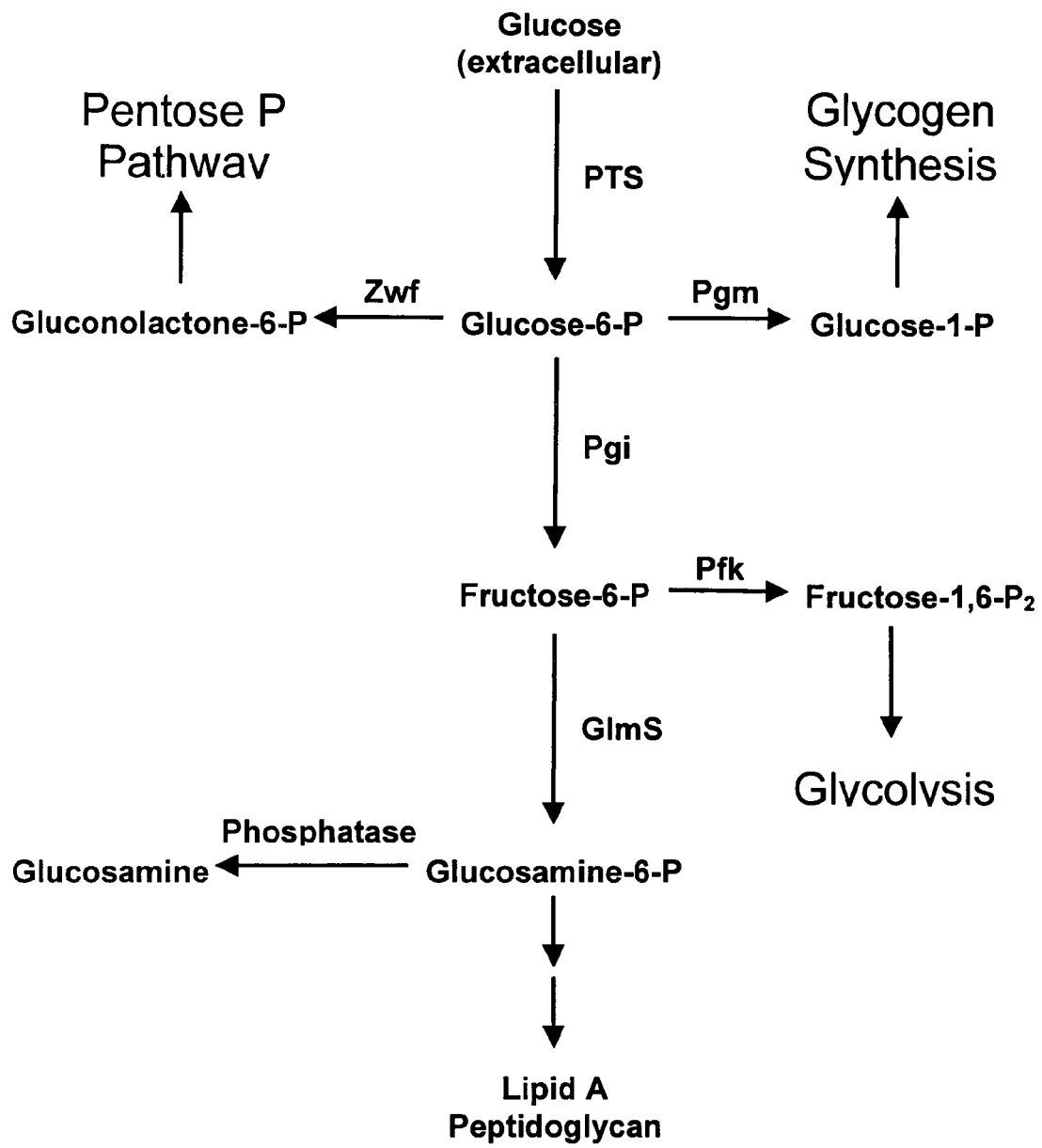

FIG. 3 is an outline of pathway from glucose to glucosamine and other competing pathways (PGI=phosphoglucoisomerase; PGM=phosphoglucomutase; PFK=phosphofructokinase; zwf=glucose-6-phosphate dehydrogenase; GlmS=glucosamine-6-P synthase; Phosphatase=phosphatase activities involved in hydrolysis of glucosamine-6-phosphate).

Figure 4:
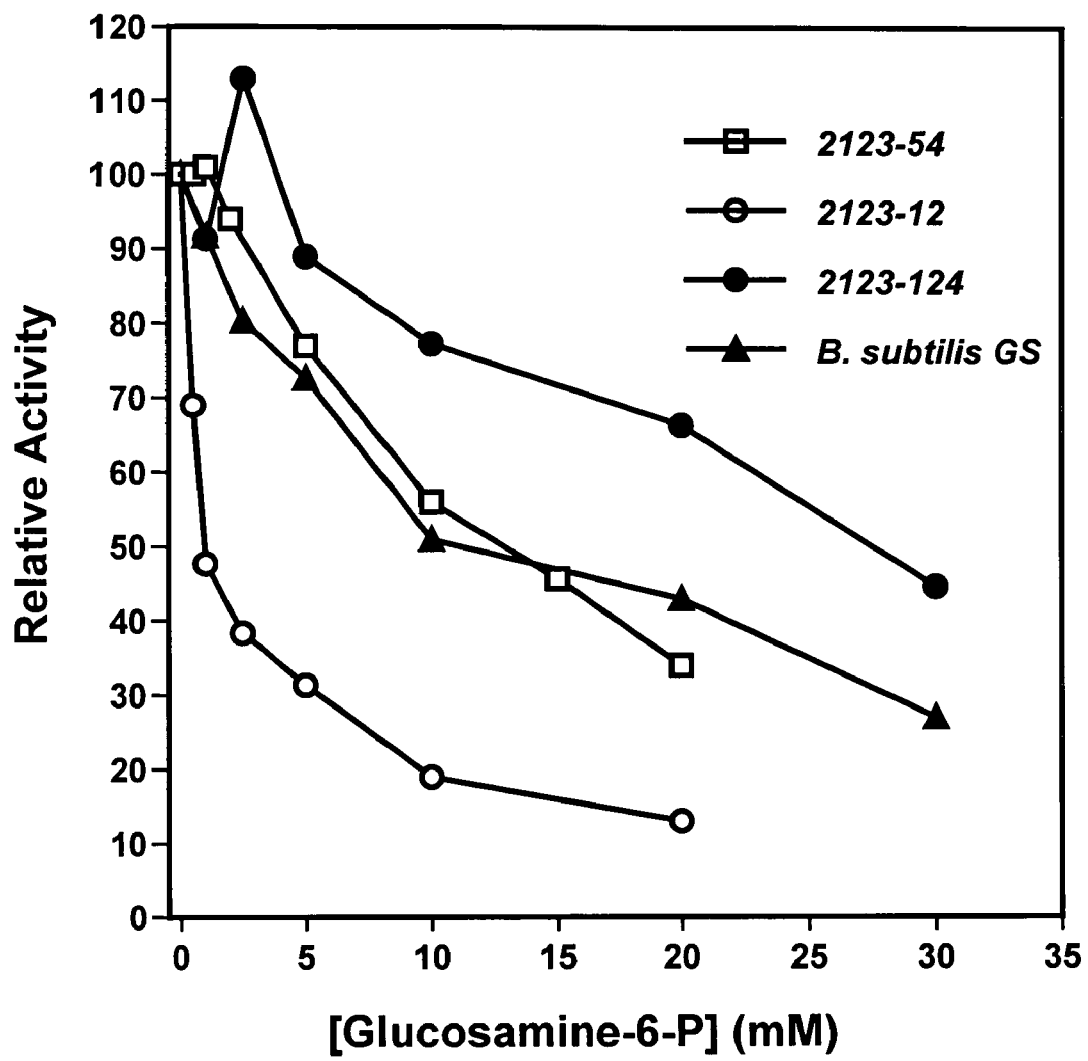

FIG. 4 is a line graph showing effects of glucosamine-6-phosphate on activity of the recombinant *Bacillus subtilis* GlmS enzyme.

Figure 5:
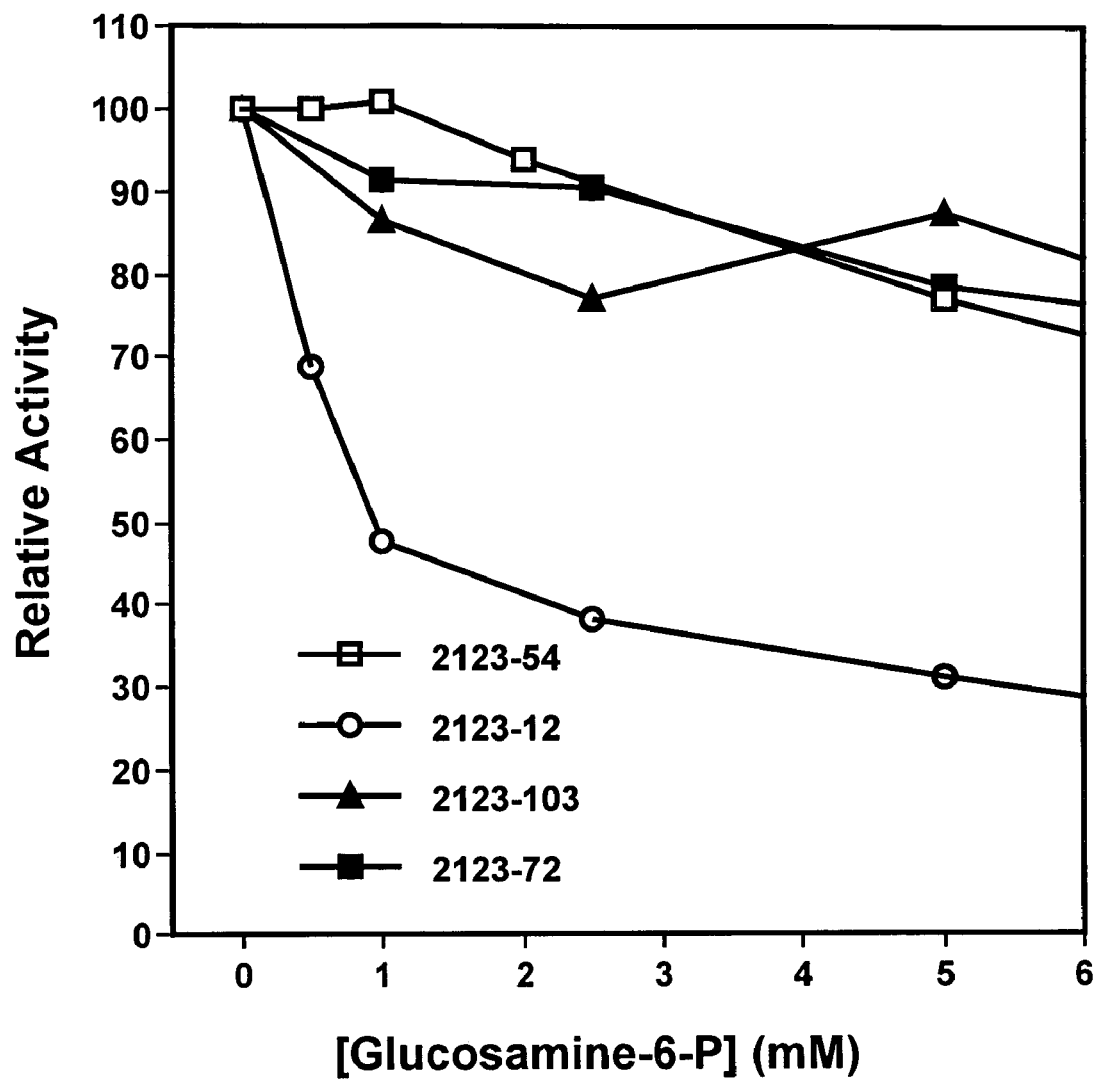

FIG. 5 is a graph showing glucosamine synthase activity of various GlmS proteins at low levels of glucosamine-6-phosphate.

Figure 6:
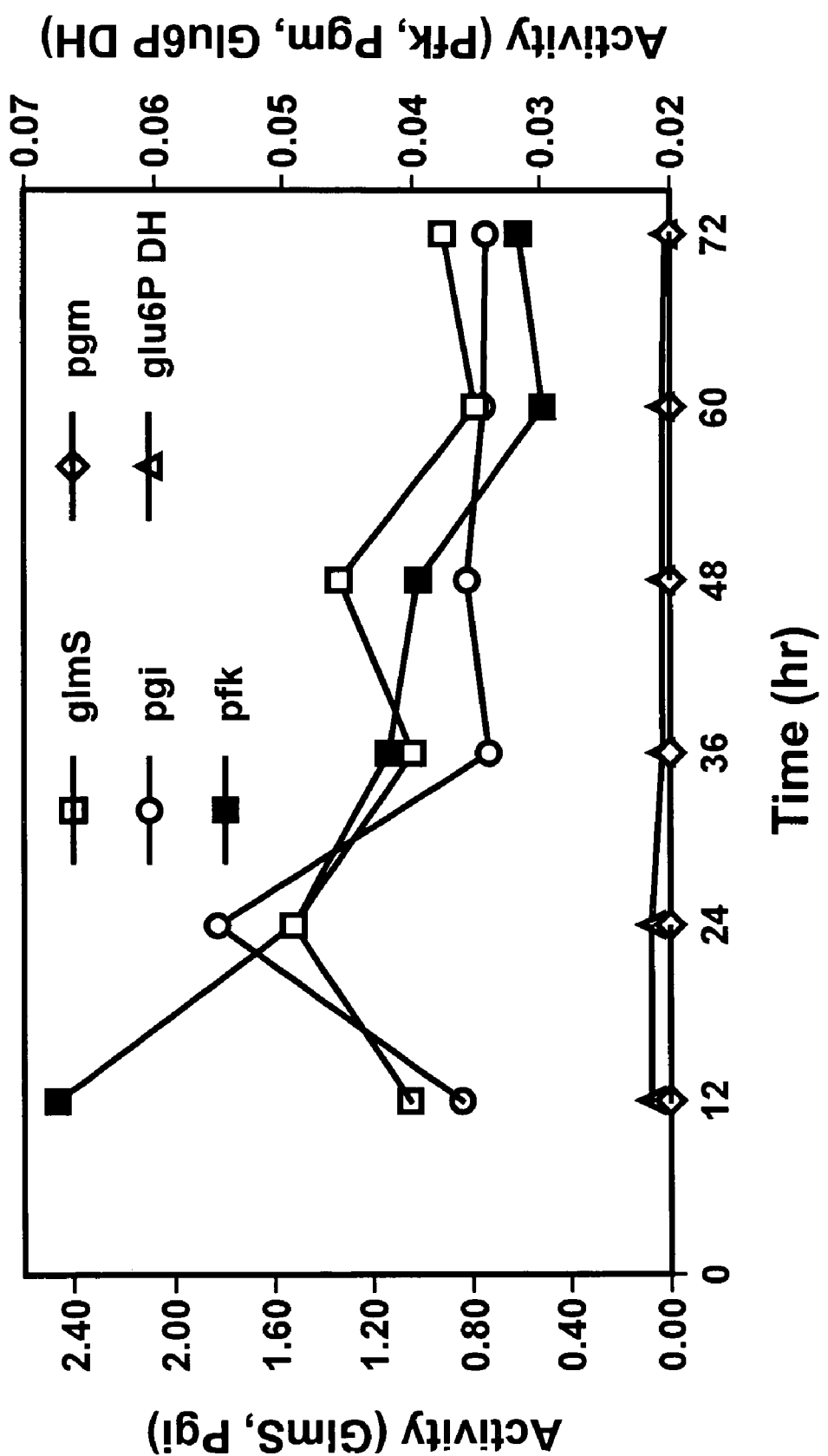

FIG. 6 is a graph showing changes of enzyme activities over time in a shake flask culture.

Figure 7:
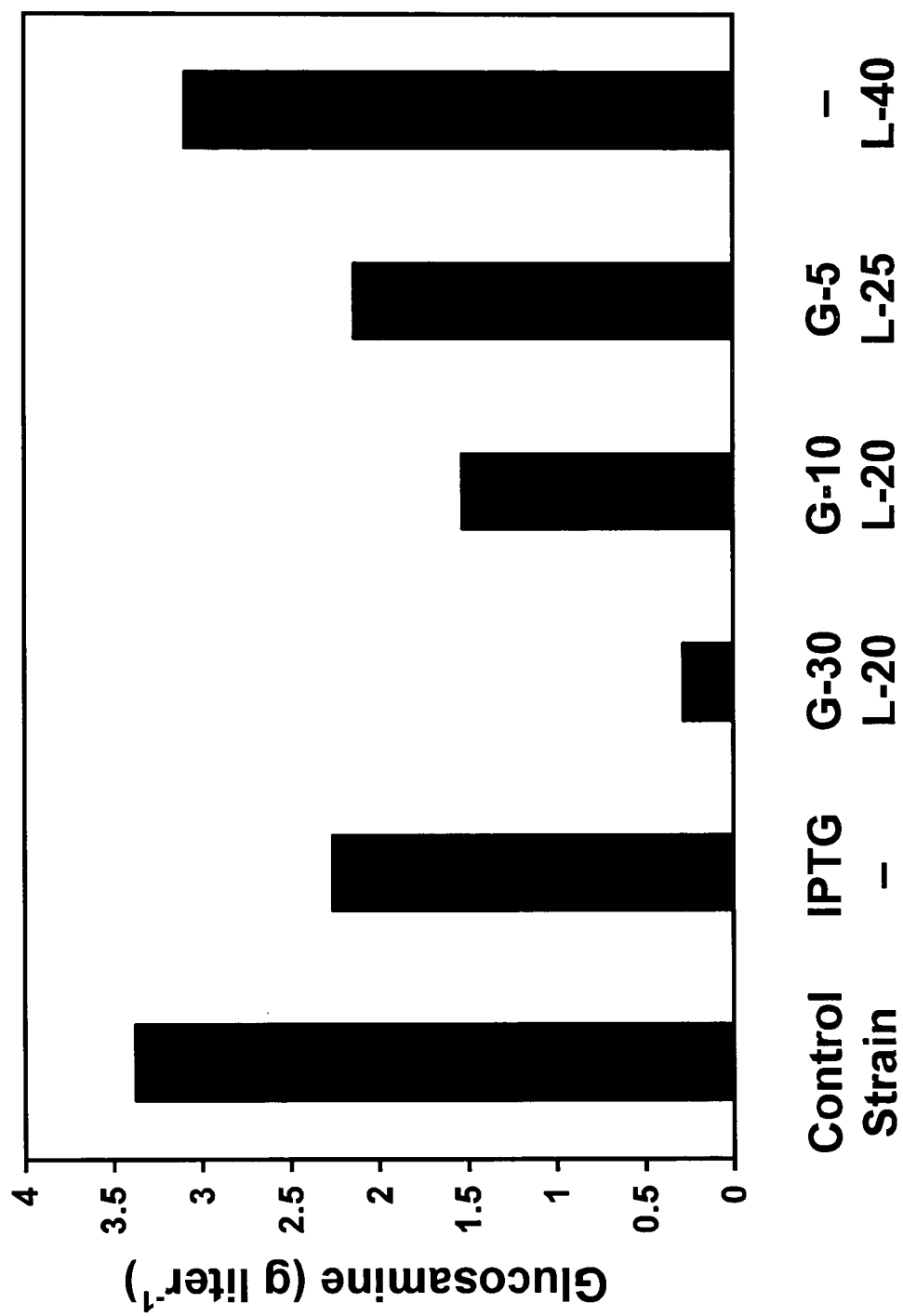

FIG. 7 is a bar graph showing the levels of glucosamine production induced by lactose under different conditions in shake flasks (the lactose inducible strain is 7107-16 and the control strain is 2123-54).

Figure 8:
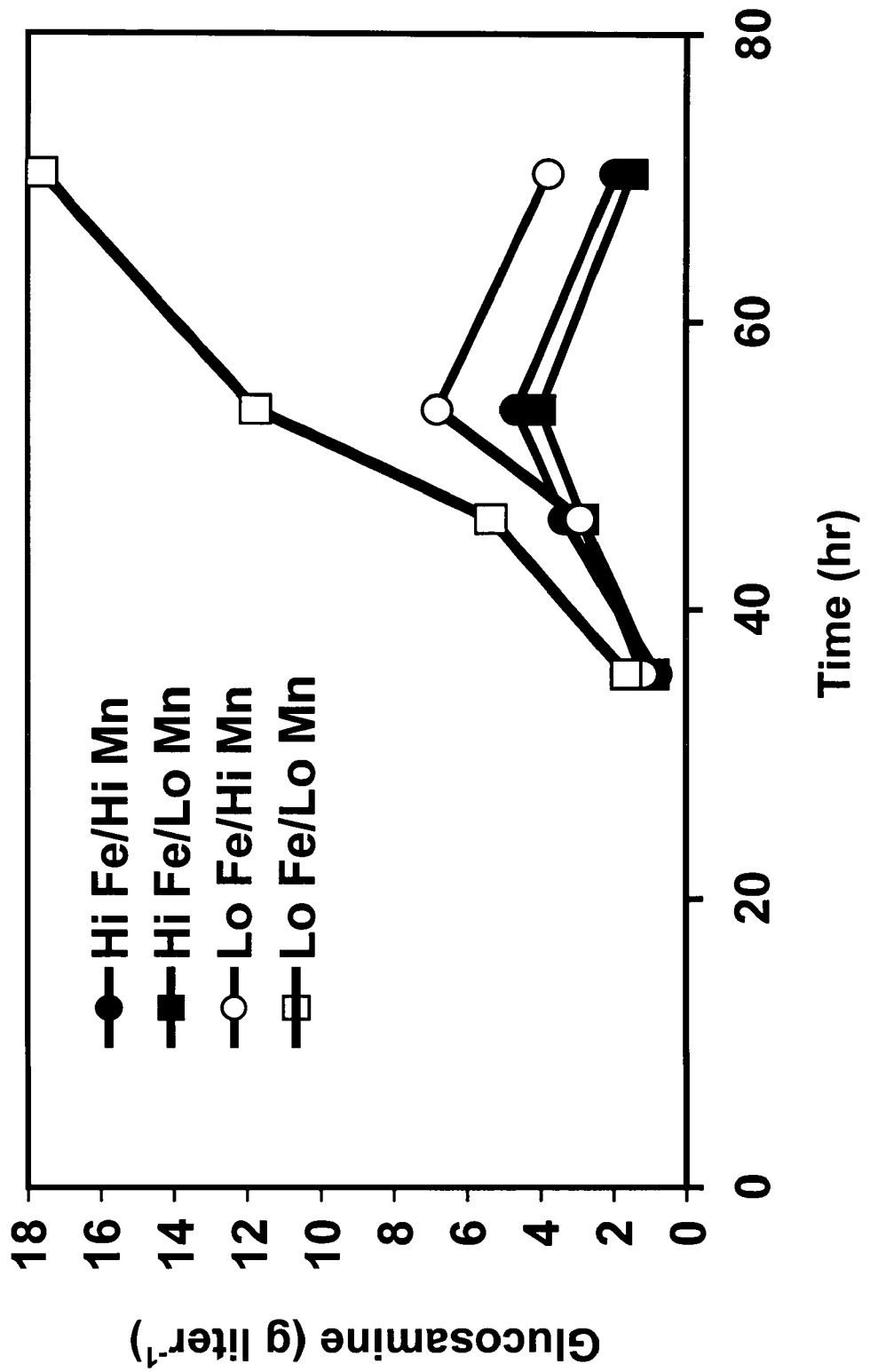

FIG. 8 is a line graph showing effects of trace elements on glucosamine production in cell cultures induced by lactose after an initial growth phase.

Figure 9:
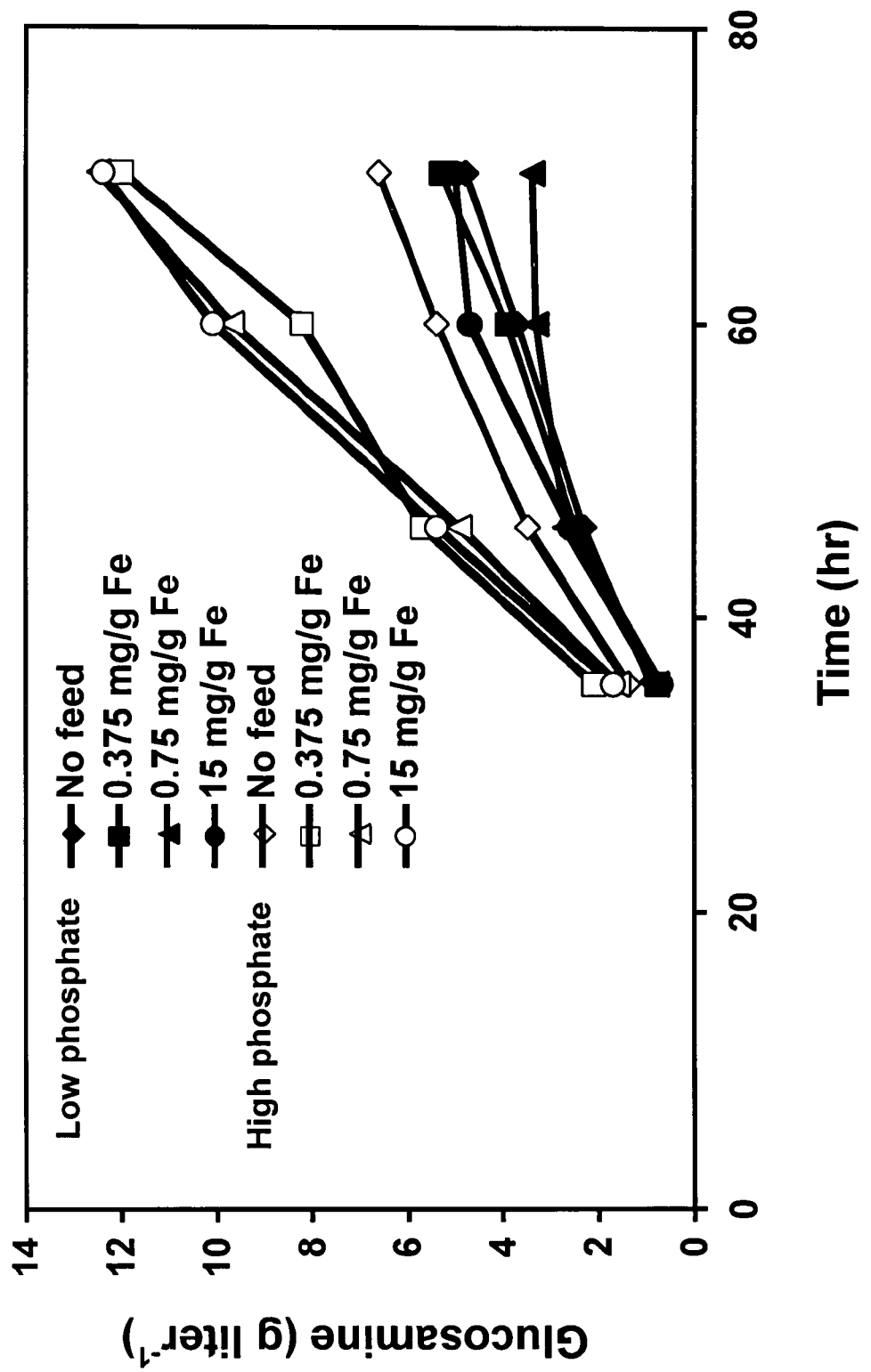

FIG. 9 is a line graph showing effects of phosphate levels and iron feed on glucosamine production in fermentors.

Figure 10:
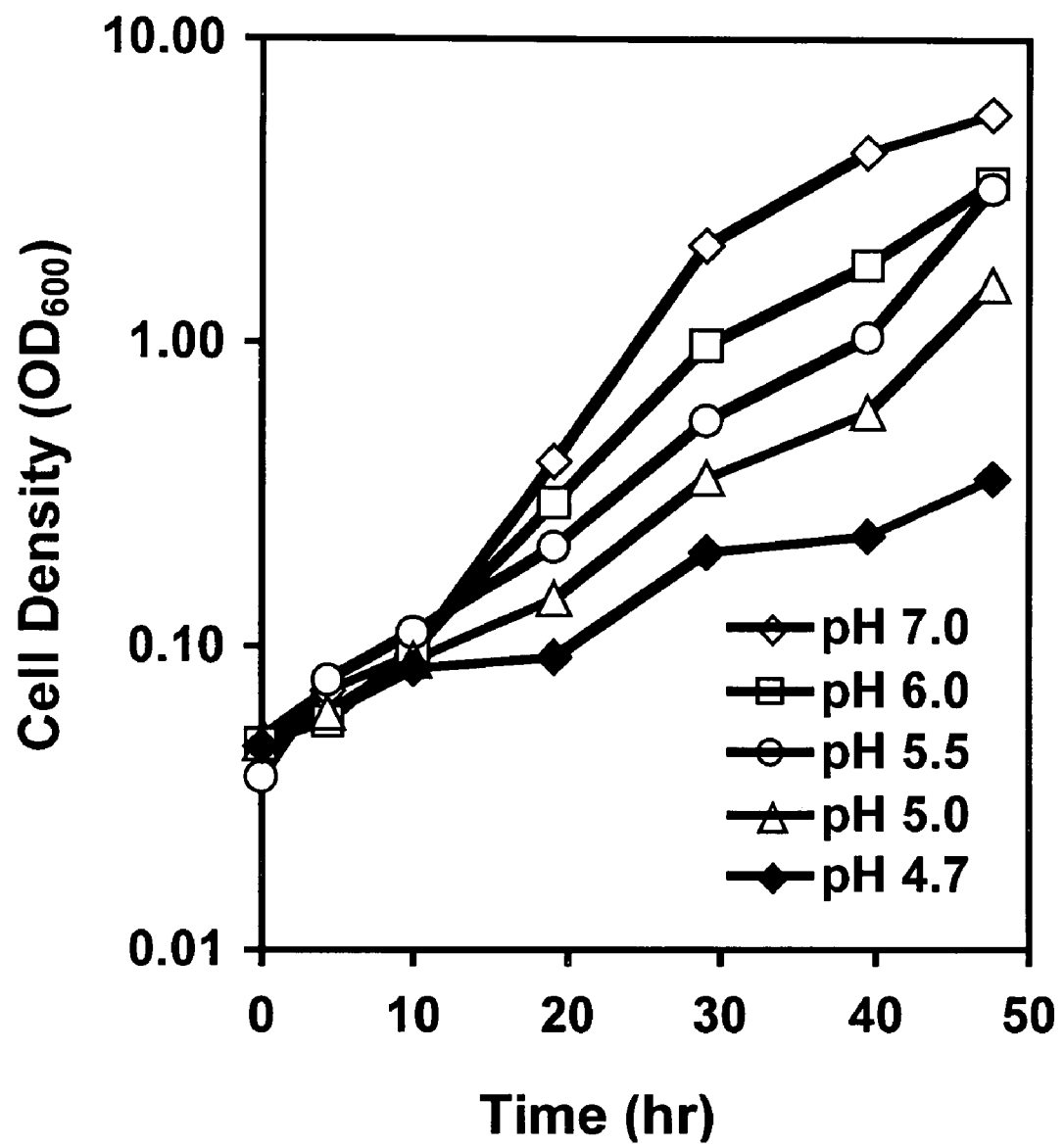

FIG. 10 is a line graph showing the growth curves of 7107-18 with 20 g $l^{-1}$ glucosamine at different pHs.

Figure 11:
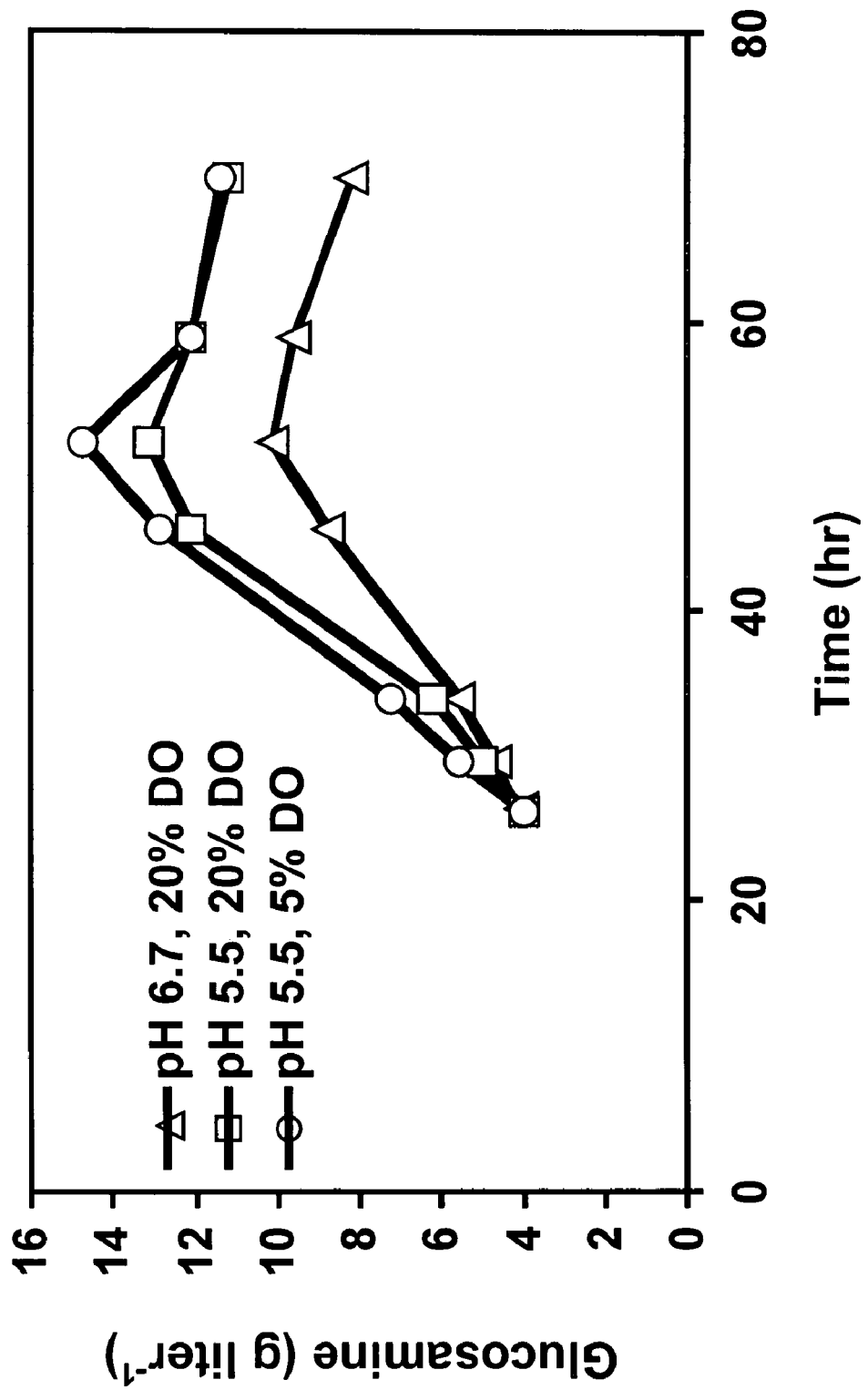

FIG. 11 is a line graph showing glucosamine production with strain 2123-54 in 1-liter fermentors under different environmental conditions.

Figure 12:
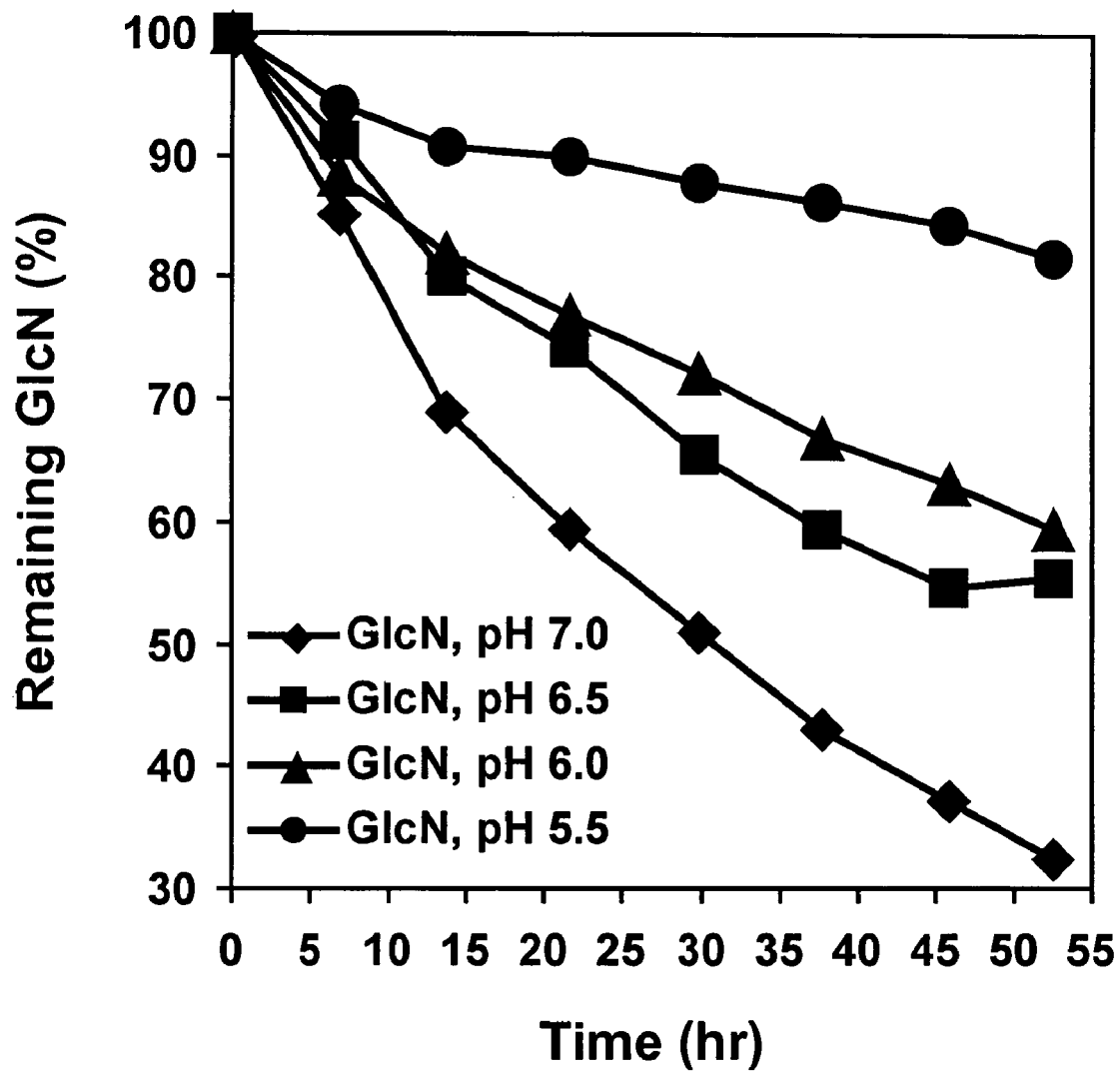

FIG. 12 is a line graph illustrating glucosamine degradation at different pHs (60 g $l^{-1}$ in M9A-glucose medium).

Figure 13:
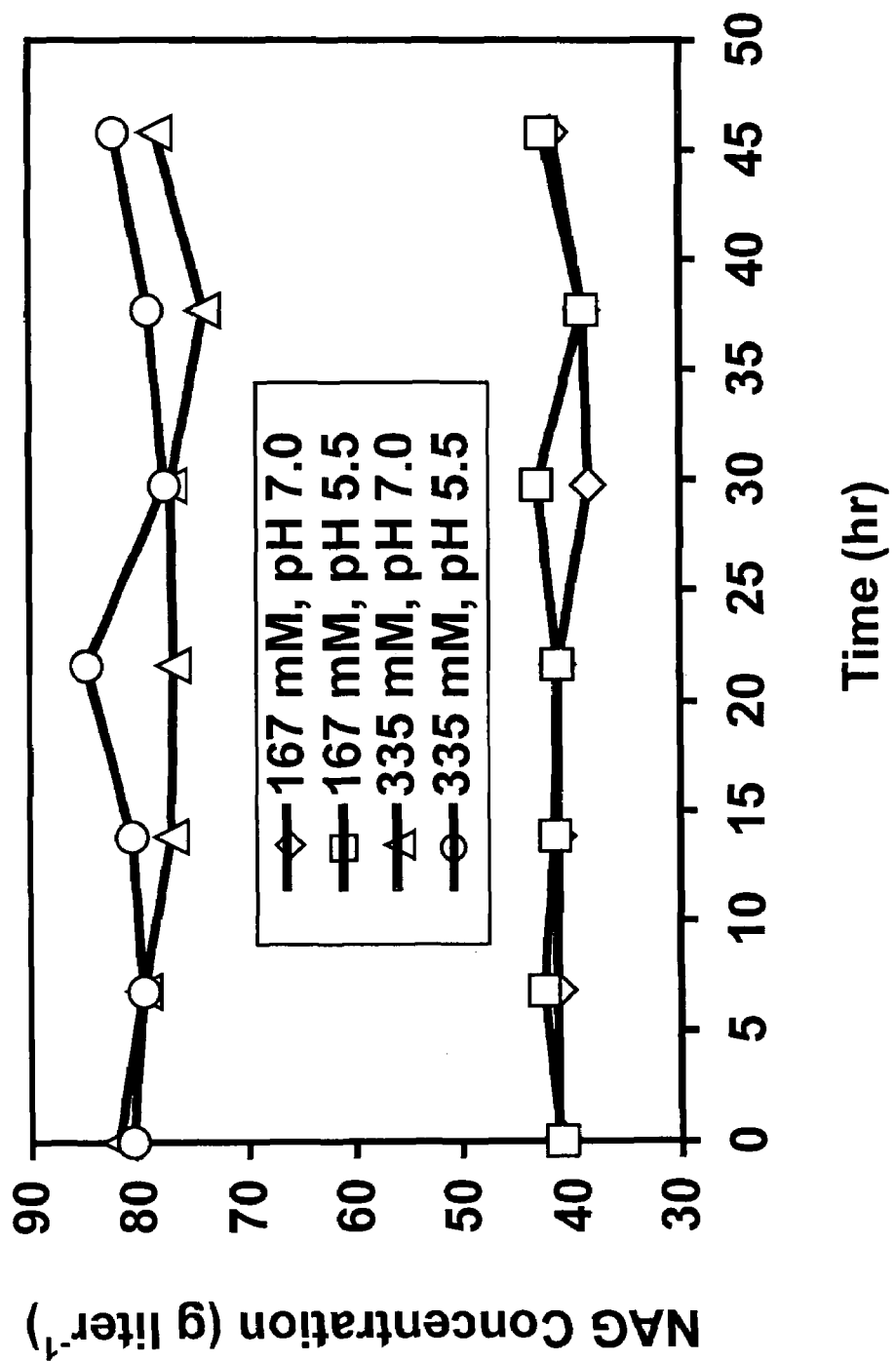

FIG. 13 is a line graph illustrating the stability of N-acetylglucosamine in M9A medium (without glucose)—stability was tested at two concentrations of N-acetylglucosamine (40 and 80 g $l^{-1}$) and two pHs (5.5 and 7.0).

Figure 14:
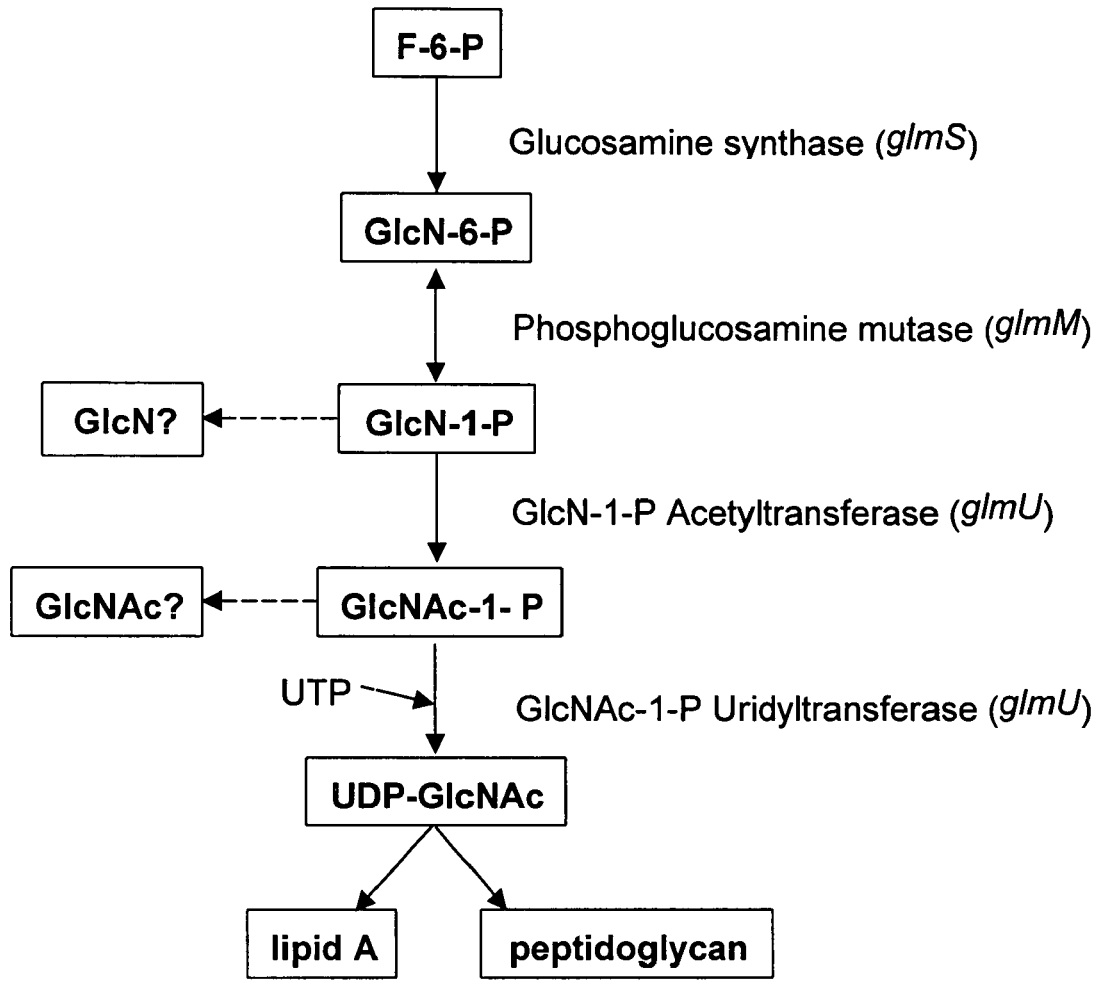

FIG. 14 is an outline of the alternative pathway for N-acetylglucosamine production.

Figure 15:
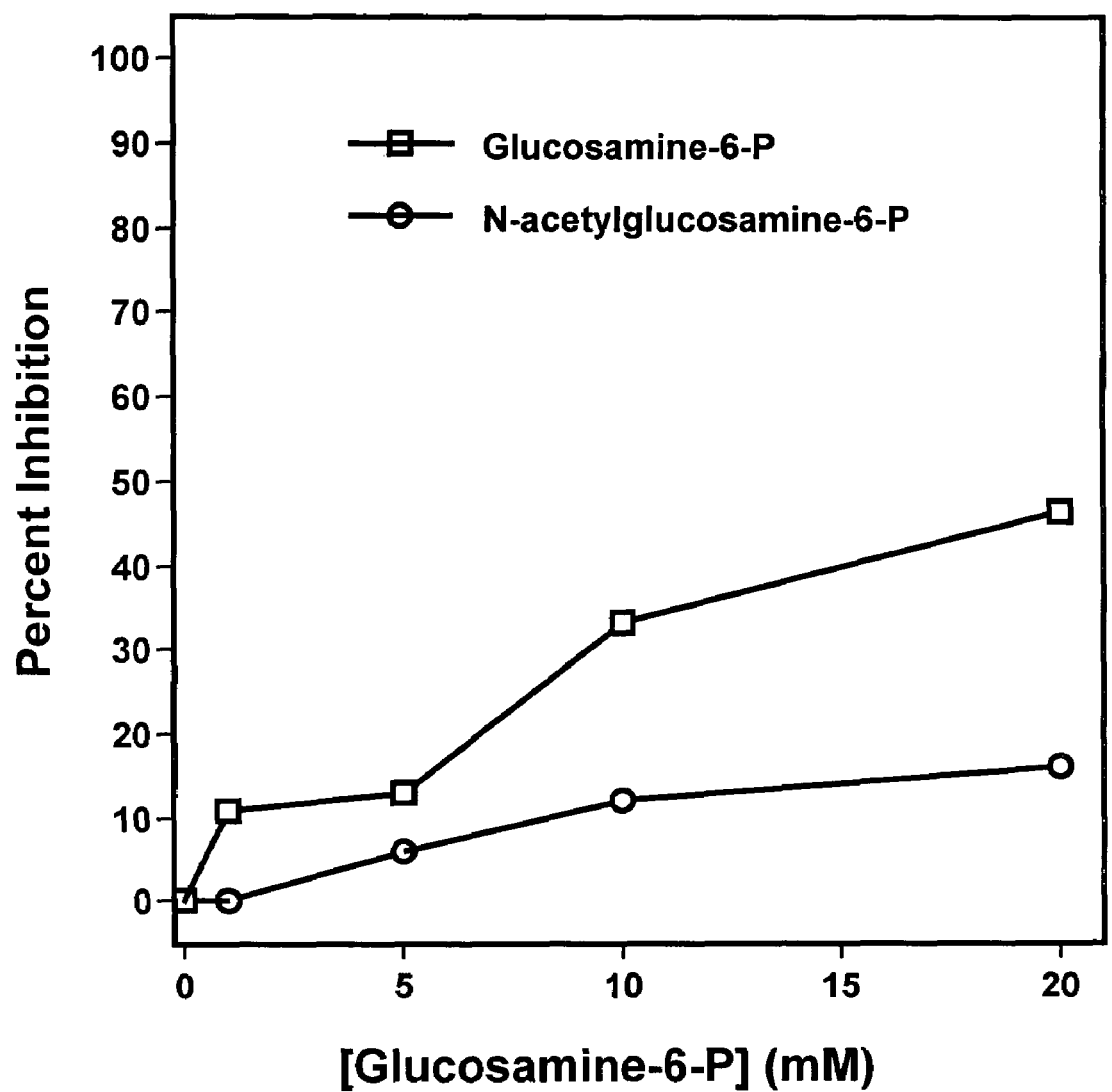

FIG. 15 is a line graph showing effect of phosphorylated amino sugars on phosphoglucoisomerase activity (Pgi).

Figure 16:
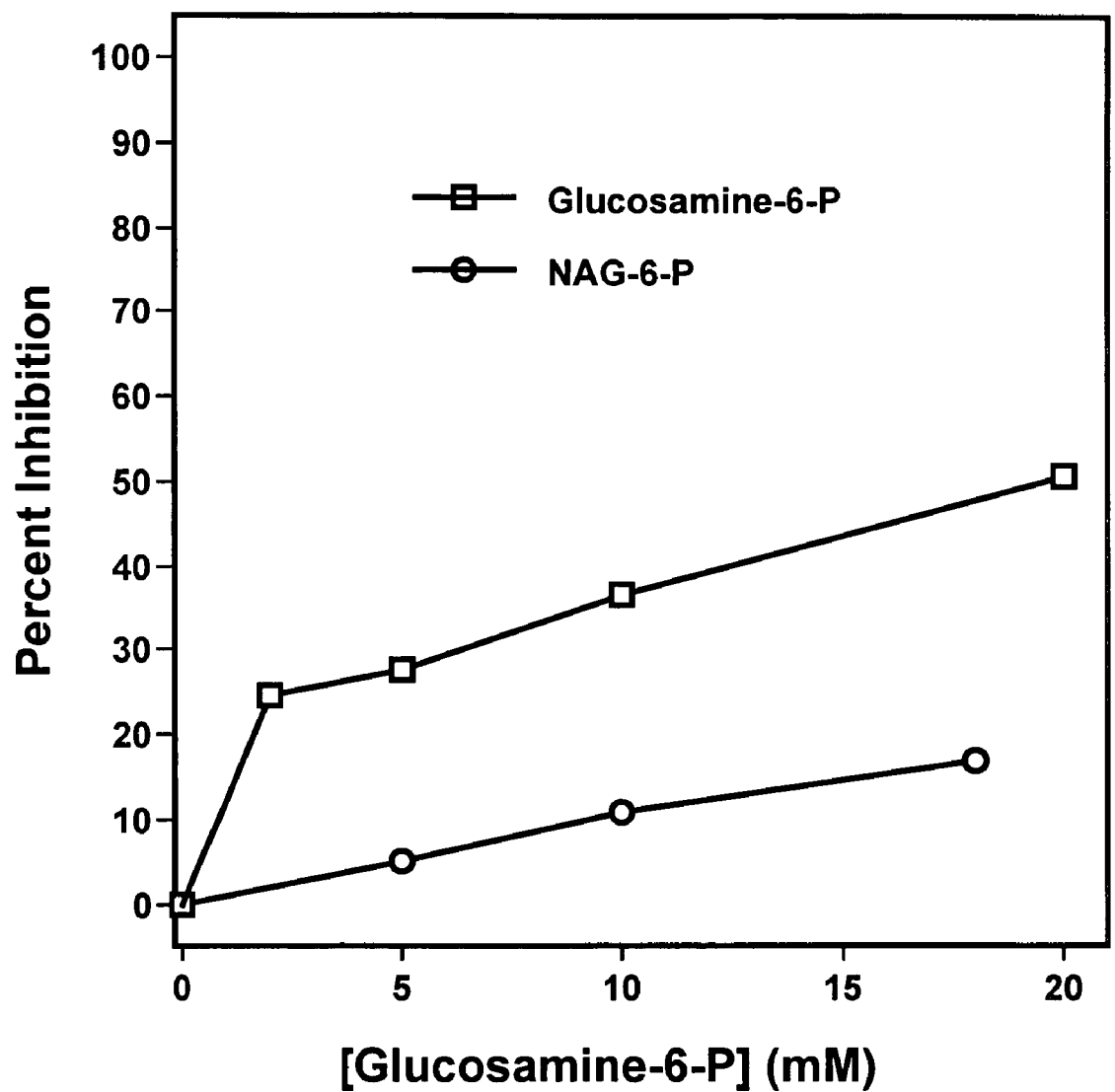

FIG. 16 is a line graph showing effect of phosphorylated amino sugars on glucose-6-phosphate-dehydrogenase.

Figure 17:
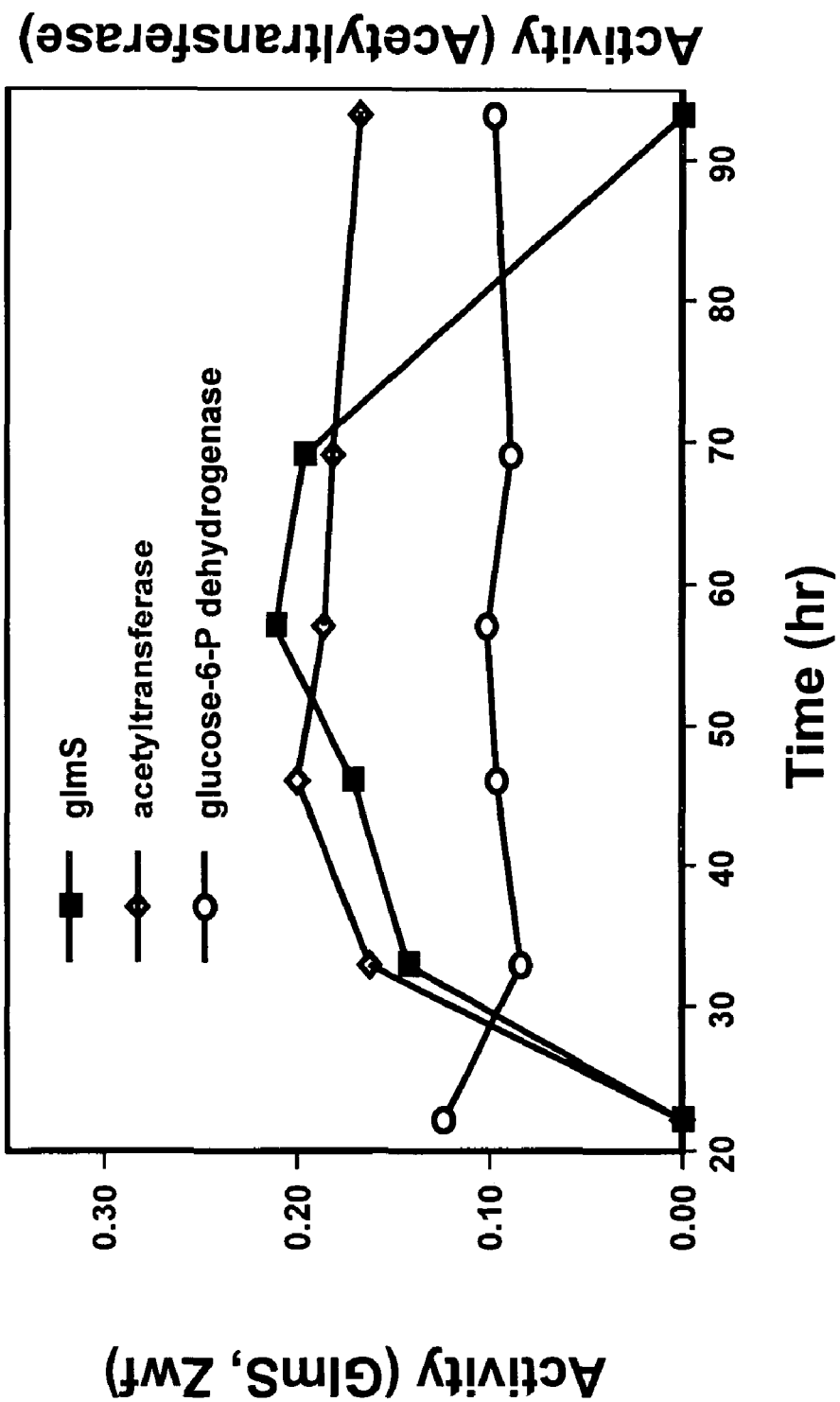

FIG. 17 is a line graph showing levels of enzyme activities during a N-acetylglucosamine fermentation.

Figure 18:
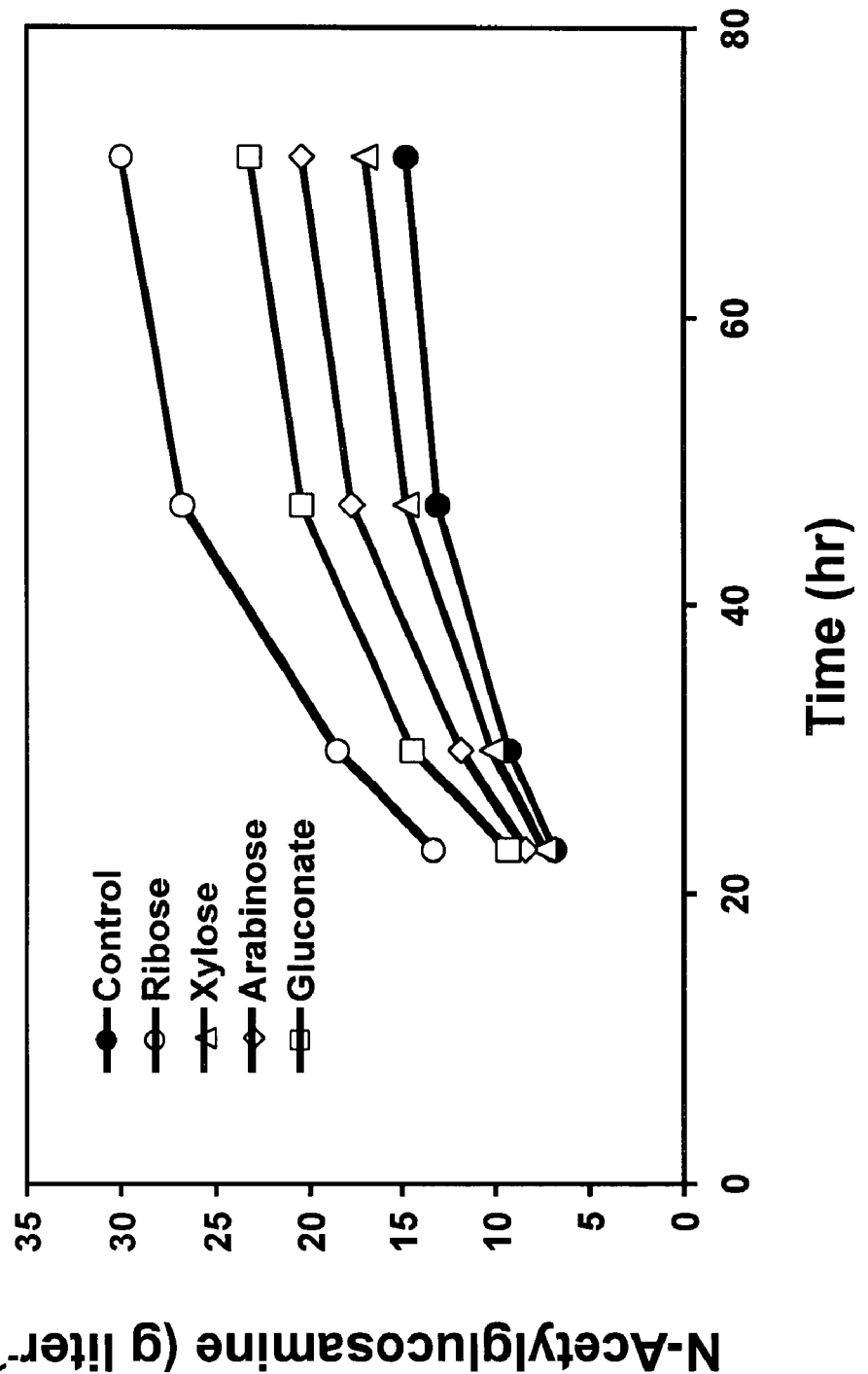

FIG. 18 is a line graph showing effects of pentose and gluconate on N-acetylglucosamine production in shake flask experiments (each sugar added to the medium at 10 g $l^{-1}$ in shake flasks).

Figure 19:
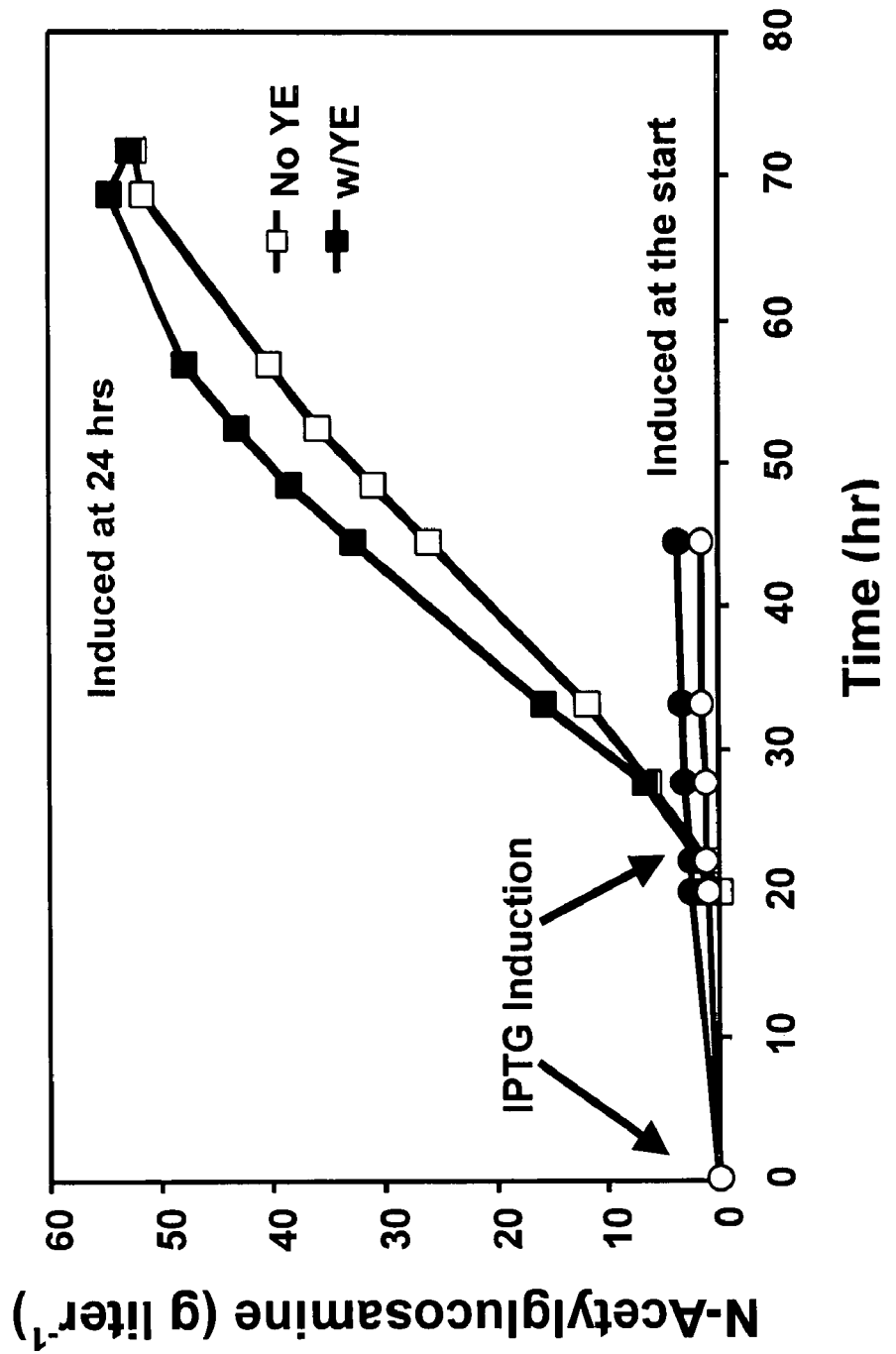

FIG. 19 is a line graph showing N-acetylglucosamine production by 7107-87#25 with early and later IPTG induction in fermentors.

Figure 20:
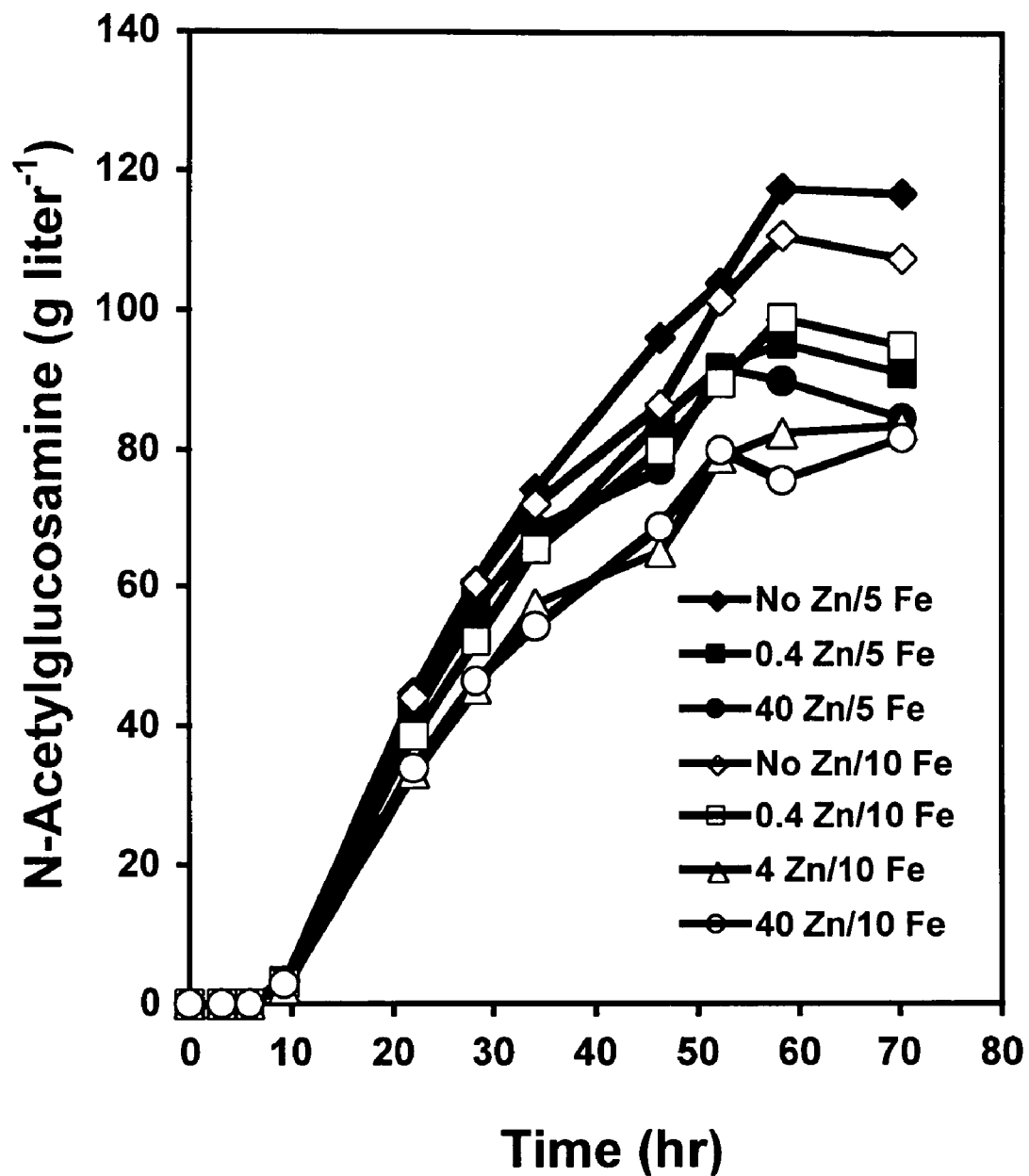

FIG. 20 is a line graph showing effects of zinc and iron concentrations on N-acetylglucosamine production, and particularly showing the beneficial effect of removing Zinc.

Figure 21:
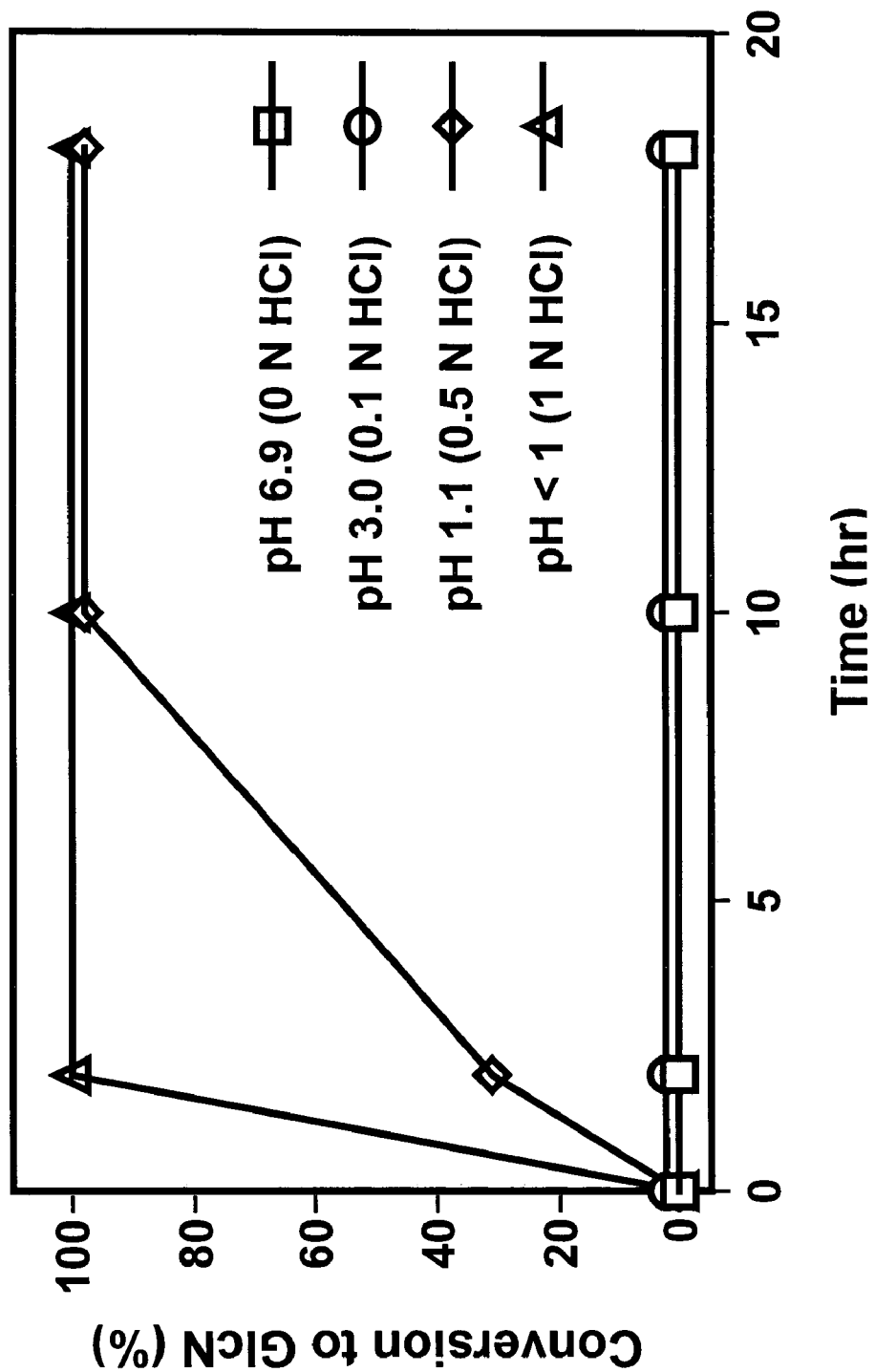

FIG. 21 is a line graph showing acid/heat hydrolysis of N-acetylglucosamine (10 g/l in M9A medium).

Figure 22:
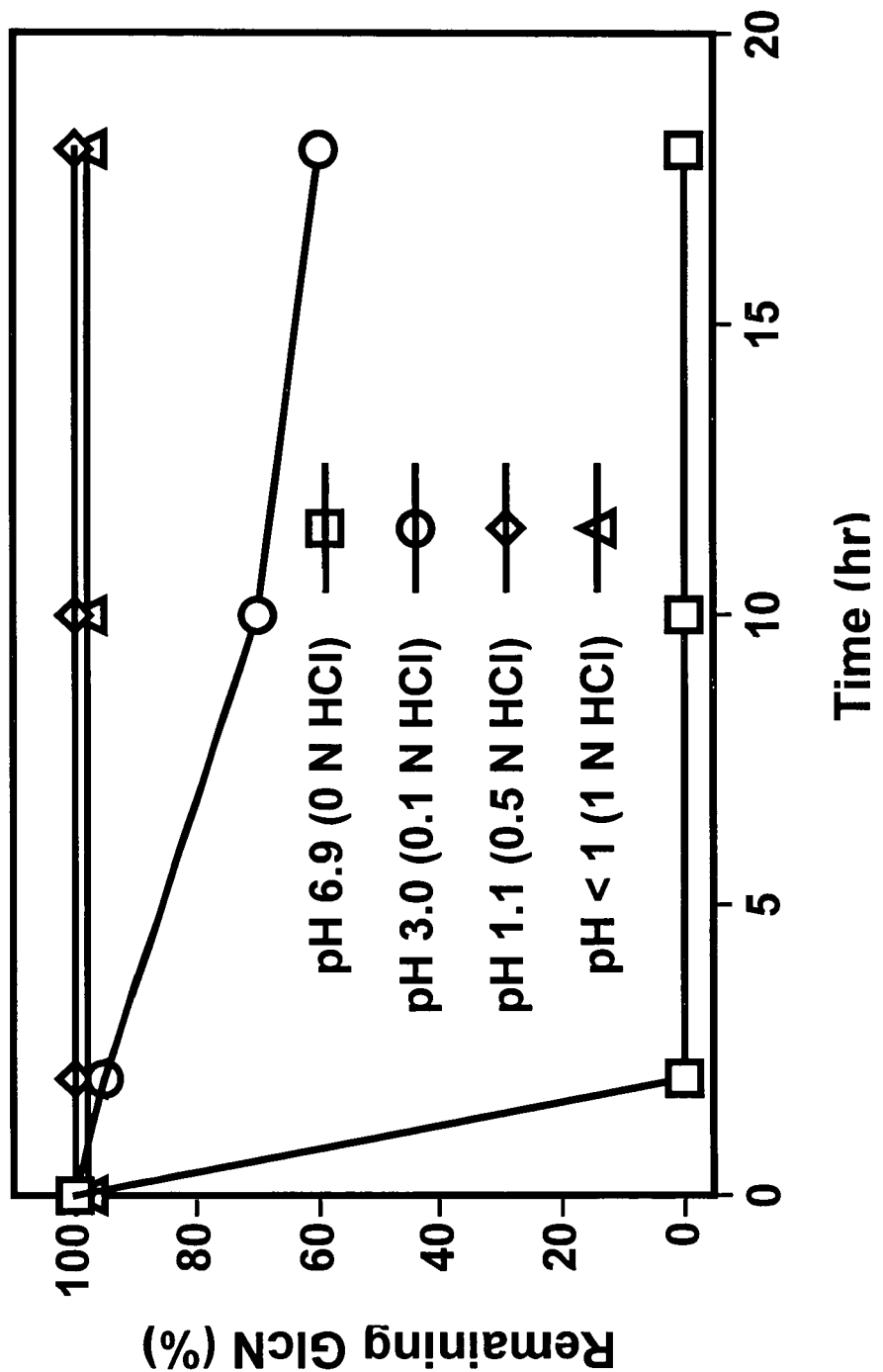

FIG. 22 is a line graph showing glucosamine stability under acid/heat hydrolysis conditions (10 g/l in M9A medium).

Figure 23:
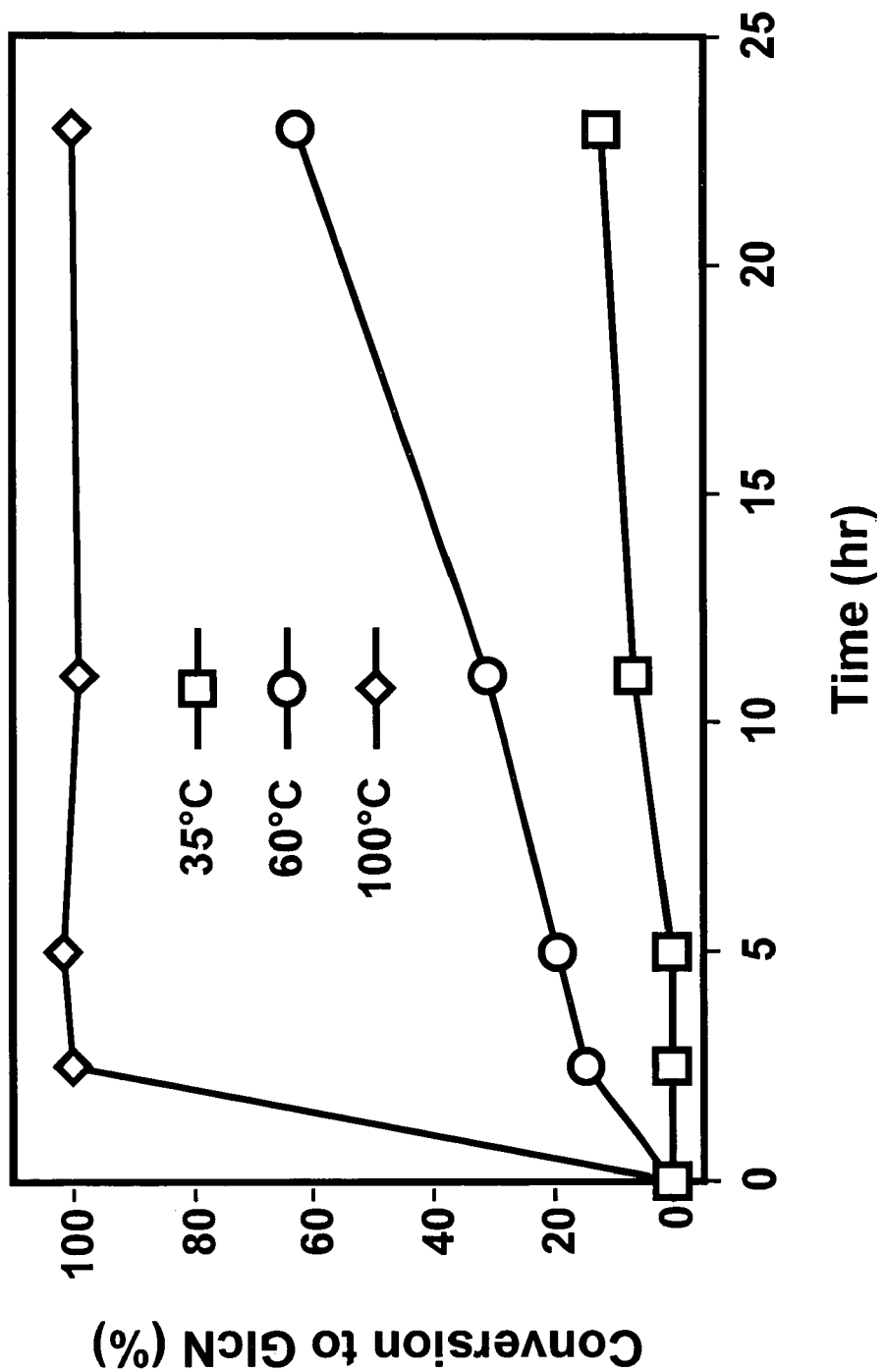

FIG. 23 is a line graph showing acid hydrolysis of N-acetylglucosamine (20 g/l in M9A medium) using 0.1N hydrochloric acid at different temperatures.

Figure 24:
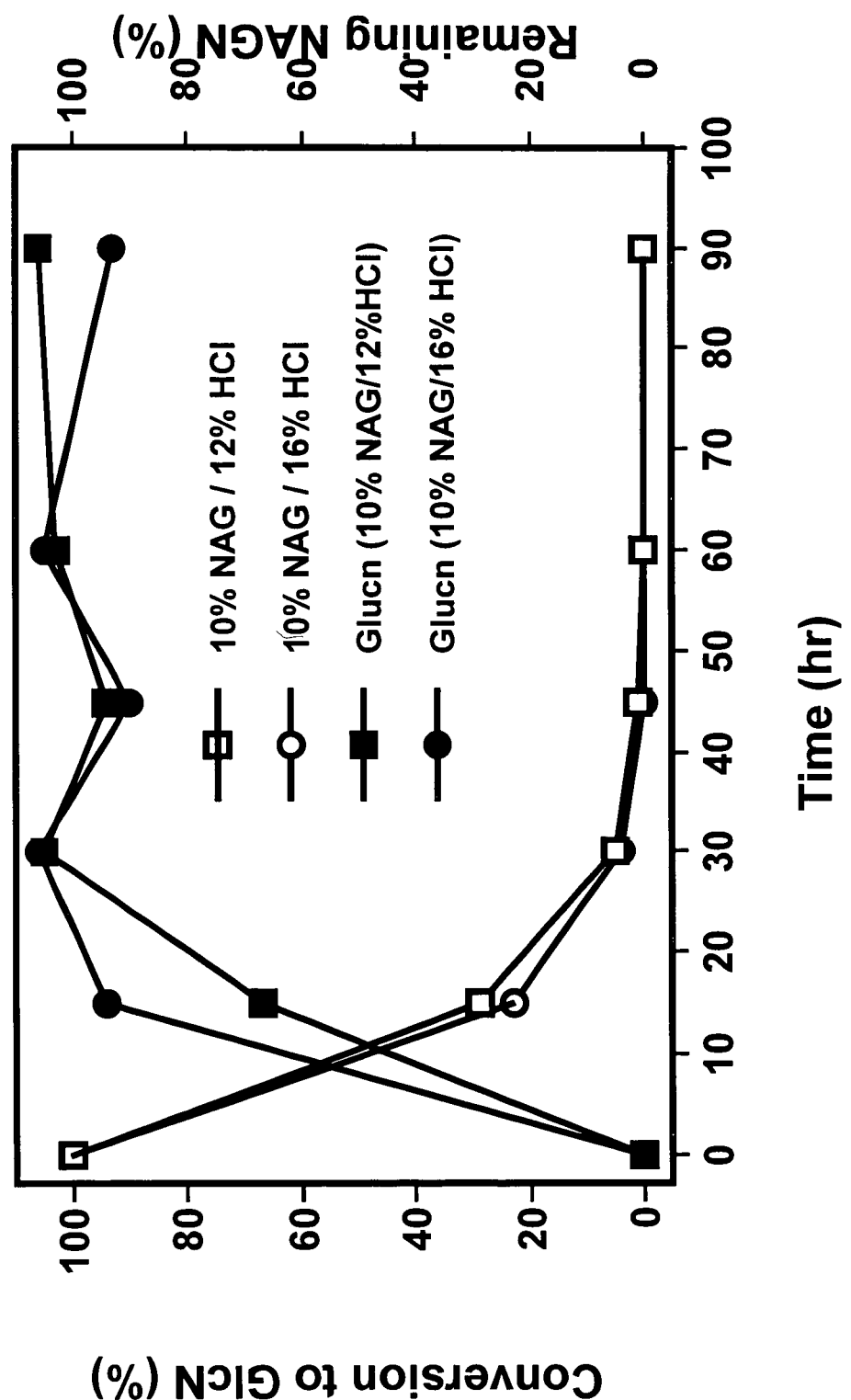

FIG. 24 is a line graph showing N-acetylglucosamine/glucosamine hydrolysis at 90° C.

Figure 25:
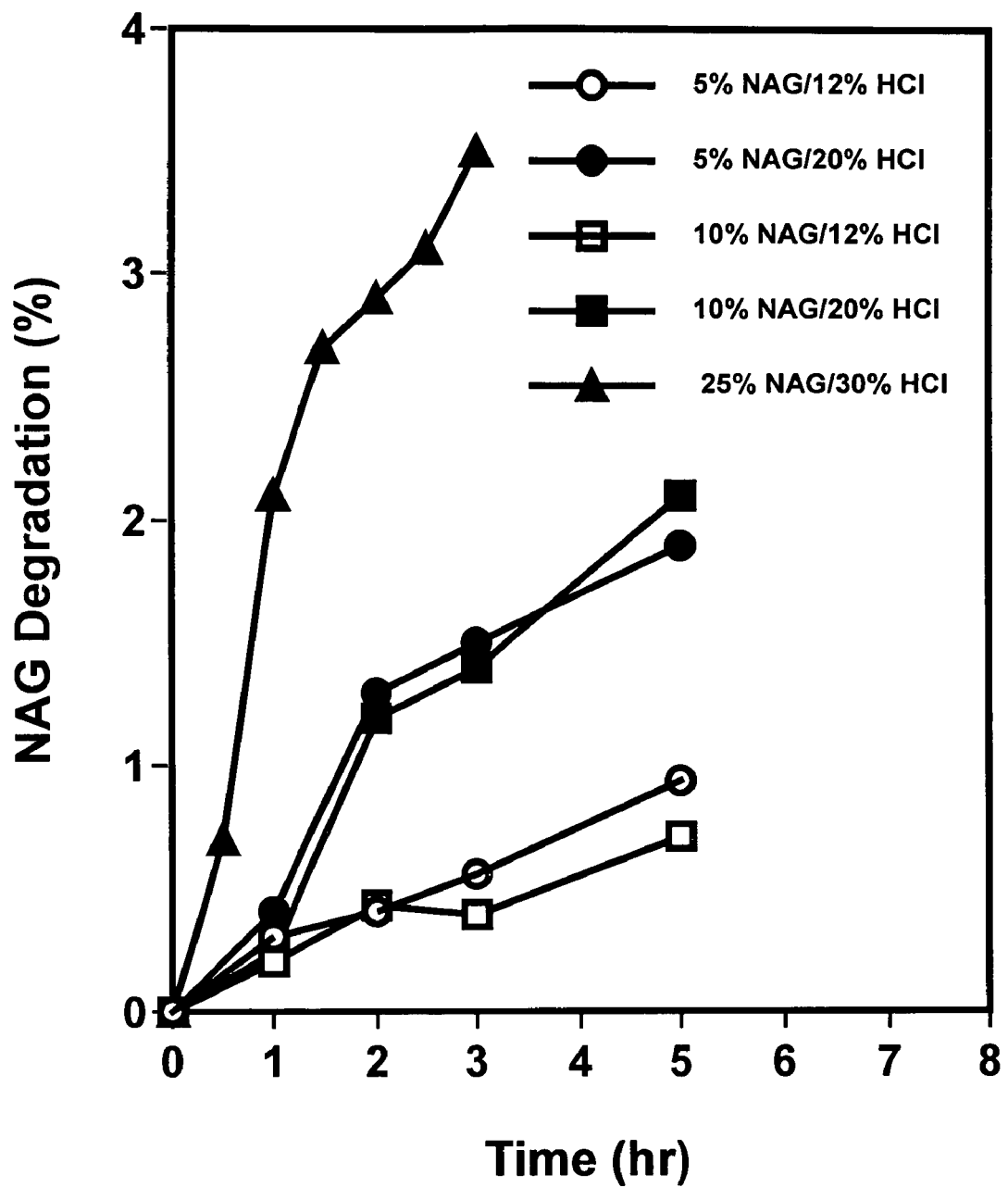

FIG. 25 is a line graph showing ammonia formation from N-acetylglucosamine/glucosamine hydrolysis at 90° C.

DETAILED DESCRIPTION OF THE INVENTION

The present invention relates to a biosynthetic method for producing glucosamine and N-acetylglucosamine. Such a method includes the fermentation of a genetically modified microorganism to produce glucosamine and/or N-acetylglucosamine. The present invention also relates to genetically modified microorganisms that are useful for producing glucosamine and N-acetylglucosamine. In addition, the present invention relates to methods of recovering N-acetylglucosamine that has been produced by a fermentation process, including methods that result in N-acetylglucosamine of high purity. The present invention also relates to a method to produce glucosamine from N-acetylglucosamine. Prior to the present invention, N-acetylglucosamine was produced by the acetylation of glucosamine, and therefore, it is not believed that a method to produce commercially useful glucosamine from N-acetylglucosamine has been described or was even commercially feasible. The present invention demonstrated for the first time direct production of N-acetylglucosamine through a totally natural biologic process.

More specifically, the present invention generally relates to methods to produce glucosamine and N-acetylglucosamine by fermentation of a microorganism. The methods include a first step of culturing in a fermentation medium a microorganism having a genetic modification in an amino sugar metabolic pathway which includes: a pathway for converting glucosamine-6-phosphate, glucosamine-1-phosphate, N-acetylglucosamine-6-phosphate or N-acetylglucosamine-1-phosphate into other compounds; a pathway for synthesizing glucosamine-6-phosphate, glucosamine-1-phosphate, N-acetylglucosamine-6-phosphate or N-acetylglucosamine-1-phosphate; a pathway for transport of glucosamine, glucosamine-6-phosphate, glucosamine-1-phosphate, N-acetylglucosamine, N-acetylglucosamine-6-phosphate or N-acetylglucosamine-1-phosphate out of the microorganism; a pathway for transport of glucosamine or N-acetylglucosamine into the microorganism, and a pathway which competes for substrates involved in the production of glucosamine-6-phosphate, to produce a product which can include intracellular glucosamine-6-phosphate, glucosamine-1-phosphate, N-acetylglucosamine-6-phosphate, N-acetylglucosamine-1-phosphate, N-acetylglucosamine and/or glucosamine, and/or extracellular glucosamine or N-acetylglucosamine from the microorganism. The methods also include a second step of collecting the product by recovering intracellular glucosamine-6-phosphate, glucosamine-1-phosphate, N-acetylglucosamine-6-phosphate, N-acetylglucosamine-1-phosphate, N-acetylglucosamine and/or glucosamine from the microorganism and/or collecting and/or recovering extracellular glucosamine or N-acetylglucosamine from the fermentation medium, which can include steps of recovery and purification (defined and discussed in detail below). N-acetylglucosamine, N-acetylglucosamine-6-phosphate and N-acetylglucosamine-1-phosphate recovered from the fermentation process of the invention can be deacetylated using the methods described herein to produce glucosamine, glucosamine-6-phosphate and glucosamine-1-phosphate.

The novel methods of the present invention for production of glucosamine and N-acetylglucosamine by fermentation are inexpensive and can produce a yield of glucosamine and N-acetylglucosamine that exceeds the yield of glucosamine and N-acetylglucosamine produced by current methods. In addition, by using a genetically modified microorganism as described herein, the method of the present invention can be easily modified to adapt to particular problems or changing needs relative to the production of glucosamine and N-acetylglucosamine. Furthermore, the process and materials disclosed in the present invention can be used and/or modified by those of skill in the art to produce other amino sugars such as poly-N-acetylglucosamine, poly-glucosamine, galactosamine, mannosamine, N-acetyl galactosamine, N-acetyl mannosamine and their derivatives.

The amino sugars, N-acetylglucosamine (GlcNAc) and glucosamine (GlcN), are fundamentally important molecules in microorganisms, because they are the precursors for the biosynthesis of major macromolecules, and in particular, glycoconjugates (i.e., macromolecules containing covalently bound oligosaccharide chains). For example, in *Escherichia coli*, N-acetylglucosamine and glucosamine are precursors for two macromolecules of the cell envelope, peptidoglycan and lipopolysaccharide. Mutations that block the biosynthesis of peptidoglycan or lipopolysaccharide are lethal, resulting in loss of integrity of the cell envelope and ultimately in cell lysis.

As used herein, the terms glucosamine, D-glucosamine and N-glucosamine can be used interchangeably. Similarly, the terms glucosamine-6-phosphate and N-glucosamine-6-phosphate can be used interchangeably, and the terms glucosamine-1-phosphate and N-glucosamine-1-phosphate can be used interchangeably. Glucosamine, glucosamine-6-phosphate and glucosamine-1-phosphate can be abbreviated as GlcN, GlcN-6-P and GlcN-1-P, respectively. N-acetylglucosamine can also be called 2-acetamido-2-deoxy-D-glucose. N-acetylglucosamine can also be written as N-acetyl glucosamine. Similarly to glucosamine and derivatives, the terms, N-acetylglucosamine, N-acetylglucosamine-6-phosphate and N-acetylglucosamine-1-phosphate can be abbreviated as GlcNAc (or D-GlcNAc), GlcNAc-6-P and GlcNAc-1-P, respectively. N-acetylglucosamine is also abbreviated as NAG.

Reference is made herein to the enzymes in an amino sugar metabolic pathway related to the production of the above-identified glucosamine and N-acetylglucosamine products. An amino sugar is an amino derivative of a saccharide (e.g., a saccharide having an amino group in place of a hydroxyl group). According to the present invention, an amino sugar metabolic pathway is any biochemical pathway involved in, or affecting, the biosynthesis, anabolism or catabolism of an amino sugar. As used herein, amino sugar metabolic pathways include pathways involved in the transport of amino sugars and their precursors into and out of a cell, and can also include biochemical pathways which compete for substrates involved in the biosynthesis or catabolism of an amino sugar. For example, the immediate precursor to one of the earliest formed amino sugars is fructose-6-phosphate (F-6-P), which, in a biochemical reaction (catalyzed by glucosamine synthase) or in a biochemical reaction with ammonium (catalyzed by glucosamine deaminase) forms glucosamine-6-phosphate. Fructose-6-phosphate is also an intermediate in the glycolysis pathway. Therefore, the glycolytic pathway competes with the glucosamine-6-phosphate biosynthetic pathway by competing for a substrate, fructose-6-phosphate. In addition, glucosamine-6-phosphate can be converted to other amino sugars and form constituents in various macromolecules by a series of biochemical reactions. As such, the fructose-6-phosphate/glucosamine-6-phosphate pathway, the glycolytic pathway, to the extent that it affects the biosynthesis of glucosamine-6-phosphate, and the glucosamine-6-phosphate/macromolecule biosynthesis pathway are all considered to be amino sugar metabolic pathways in the present invention.

Pathways for glutamine synthesis and metabolism determine the availability of glutamine (amino donor for glucosamine-6-phosphate synthesis) and thus affect the biosynthesis of glucosamine-6-phosphate. Therefore, all these pathways are all considered to be amino sugar metabolic pathways in the present invention. The synthesis of N-acetylglucosamine-6-phosphate from glucosamine-6-phosphate and the synthesis of N-acetylglucosamine-1-phosphate from glucosamine-1-phosphate require a supply of acetyl-CoA, which is also the substrate for the Krebs Cycle. Therefore, the Krebs Cycle competes with N-acetylglucosamine synthesis pathways for a substrate, acetyl-CoA. As such, the pathways for acetyl-CoA synthesis and metabolism affect N-acetylglucosamine biosynthesis and thus are all considered to be amino sugar metabolic pathways in the present invention.

For a variety of microorganisms, many of the amino sugar metabolic pathways have been elucidated. In particular, pathways for the biosynthesis and catabolism of glucosamine and N-acetylglucosamine and their phosphorylated derivatives have been elucidated in *Escherichia coli*. These pathways include the multiple transport systems for the utilization of these amino sugars as carbon sources. Genes encoding the enzymes and proteins directly related to the transport, catabolism and biosynthesis of amino sugars in *Escherichia coli* have been cloned and sequenced. In addition, mutant strains of *Escherichia coli* blocked in substantially every step of amino sugar metabolism have been isolated.

Figure 1:
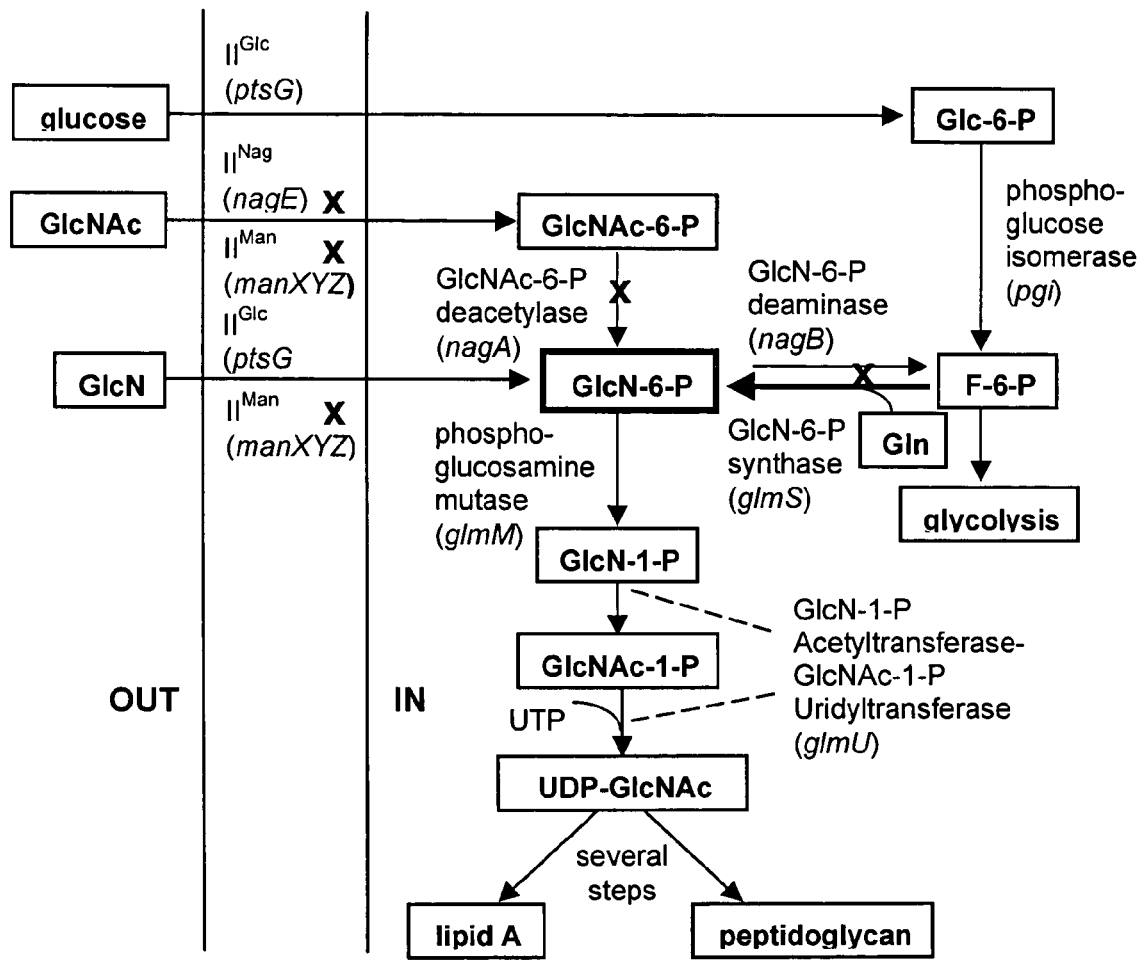
FIG. 1 is a schematic representation of the pathways for the biosynthesis and metabolism of glucosamine in recombinant *Escherichia coli*.

The known pathways for amino sugar metabolism for *Escherichia coli* are illustrated in FIG. 1. U.S. Pat. No. 6,372,457 described for the first time a glucosamine-producing microorganism that has glucosamine production capabilities that far exceed the glucosamine production capability of any known wild-type or mutant microorganism. As disclosed in U.S. Pat. No. 6,372,457, some steps of the catabolic pathway were blocked by gene inactivation (indicated by crosses), and the enzyme GlcN-6-P synthase, which catalyzes the synthesis of GlcN 6-P, was over-expressed (indicated by a heavy line) in a recombinant host cell. The present invention provides novel fermentation processes for the production of glucosamine that were not described in U.S. Pat. No. 6,372,457, including genetic modifications of production microorganisms as well as combinations of genetic modifications that were not described in U.S. Pat. No. 6,372,457 for the production of glucosamine. The present invention is also believed to be the first description of genetic modifications of microorganisms and fermentation processes for the production of N-acetylglucosamine.

As will be discussed in detail below, even though many of the pathways and genes involved in the amino sugar metabolic pathways have been elucidated, until the present invention, it was not known which of the many possible genetic modifications would be necessary to generate a microorganism that can produce commercially significant amounts of N-acetylglucosamine. Moreover, the novel genetic modifications and combinations thereof for the production of glucosamine as described herein had not previously been appreciated. Indeed, some of the genetic modifications for the production of glucosamine described herein are the opposite of what was described in the prior disclosure of a fermentation method for glucosamine production, U.S. Pat. No. 6,372,457, supra.

Figure 2:
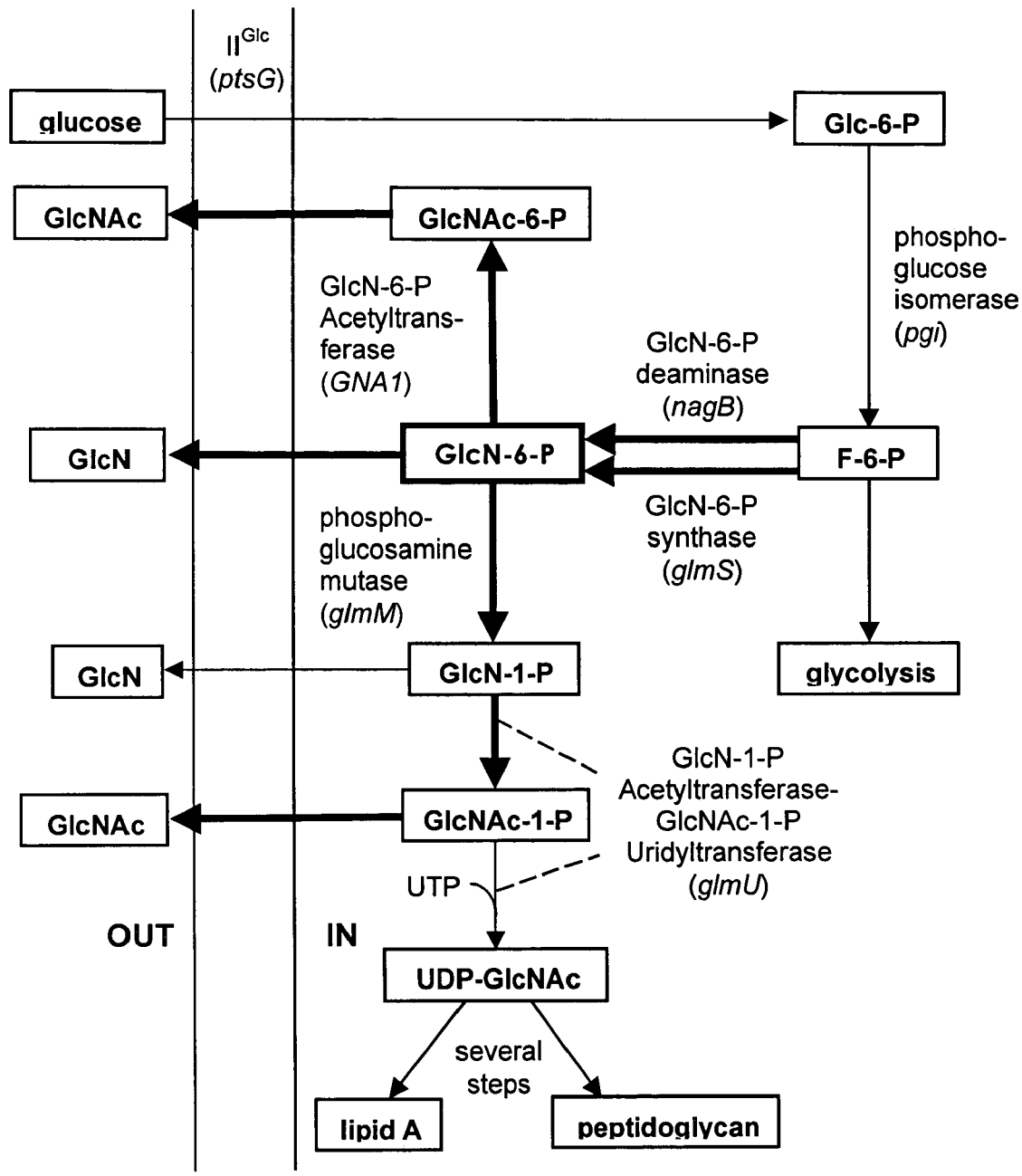
FIG. 2 is a schematic representation of the novel modifications to the pathways for the overproduction of glucosamine and/or N-acetylglucosamine in recombinant *E. coli*.

The amino sugar metabolic pathways of the microorganism, *Escherichia coli*, will be addressed as specific embodiments of the present invention. The major aspects of the genetic modifications in the amino sugar metabolic pathways disclosed in the present invention for the overproduction of glucosamine and/or N-acetylglucosamine are illustrated in FIG. 2. Referring to FIG. 2, the heavy arrows indicate creation of and/or increase in the metabolic flux by genetic engineering which are contemplated by the present invention. Several different approaches are disclosed for the synthesis of N-acetylglucosamine, including, but not limited to, modifications to GNA1 and/or NagB, and further including combinations of modifications to GlmS and GNA1, GlmS and GlmU, NagB and GNA1, and NagB and GlmU, alone or in further combination with other genetic modifications. By way of example, the present invention contemplates the over-expression or deletion of additional genes to optimize glucosamine/N-acetylglucosamine production. Referring to FIG. 3 and the table below, this figure illustrates the involvement of various other enzymes in the metabolism of glucose and the formation of N-glucosamine, and the table shows various modifications that could be additionally made to the microorganism hosts of the invention in order to optimize glucosamine and/or N-acetylglucosamine production. All of these embodiments are described in detail below. It will be appreciated that other microorganisms have similar amino sugar metabolic pathways, as well as genes and proteins having similar structure and function within such pathways. As such, the principles discussed below with regard to *Escherichia coli* are applicable to other microorganisms and are expressly encompassed by the present invention.

| Target | Modification | Objective |
|---|---|---|
| Glutamine synthase (glnA) | Over-expression | Increase the pool of glutamine |
| Phosphoglucoisomerase (pgi) | Over-expression | Increase the pool of fructose-6-P |
| Lactose transporter (lacY) | Over-expression | Increase efficacy in lactose uptake and reduce glucose repression on lactose induction |
| Glucose-6-P dehydrogenase (zwf) | Over-expression | Relieve inhibitory effects of phosphorylated amino sugars on pentose phosphate pathway |
| lac operon repressor (lacI) | Deletion | Delete one of two lacI genes to reduce glucose repression on lactose induction |
| lac promoter | Replacement | Replace the lac promoter with the lacUV5 promoter to alleviate glucose represssion on lactose induction |
| Glycogen synthesis enzyme (glg operon) | Deletion/insertion | Block glycogen synthesis |
| Galactose operon (gal) | Deletion/insertion | Galactose inducible production |
| Phosphofructokinase A (pfkA) | Deletion | Uncouple glucosamine/N-acetylglucosamine synthesis from cell energy metabolism and acetate formation |

It is known in the art that the enzymes having the same biological activity may have different names depending on from what organism the enzyme is derived. The following is a general list of alternate names for many of the enzymes referenced herein and specific names of genes encoding such enzymes from some organisms. The enzyme names can be used interchangeably, or as appropriate for a given sequence or organism, although the invention intends to encompass enzymes of a given function from any organism.

For example, the enzyme generally referred to herein as "glucosamine-6-phosphate synthase" catalyzes the formation of glucosamine-6-phosphate and glutamate from fructose-6-phosphate and glutamine. The enzyme is also known as glucosamine-fructose-6-phosphate aminotransferase (isomerizing); hexosephosphate aminotransferase; D-fructose-6-phosphate amidotransferase; glucosamine-6-phosphate isomerase (glutamine-forming); L-glutamine-fructose-6-phosphate amidotransferase; and GlcN6P synthase. The glucosamine-6-phosphate synthase from *E. coli* and other bacteria is generally referred to as GlmS. The glucosamine-6-phosphate synthase from yeast and other sources is generally referred to as GFA or GFAT.

Glucosamine-6-phosphate synthases from a variety of organisms are known in the art and are contemplated for use in the genetic engineering strategies of the present invention. For example, the glucosamine-6-phosphate synthase from *Escherichia coli* is described herein. The glucosamine-6-phosphate synthase from *E. coli* has an amino acid sequence represented herein by SEQ ID NO:2, which is encoded by a nucleic acid sequence represented herein by SEQ ID NO:1. Also described herein is the glucosamine-6-phosphate synthase from *Bacillus subtilis*, which has an amino acid sequence represented herein by SEQ ID NO:16, encoded by a nucleic acid sequence represented herein by SEQ ID NO:15. Also described herein is the glucosamine-6-phosphate synthase from *Saccharomyces cerevisiae*, which is known in that organism as glucosamine-fructose-6-phosphate aminotransferase (GFA 1), and which has an amino acid sequence represented herein by SEQ ID NO:18, encoded by a nucleic acid sequence represented herein by SEQ ID NO:17. Also described herein is the glucosamine-6-phosphate synthase from *Candida albicans*, which is also known in that organism as glucosamine-fructose-6-phosphate aminotransferase (GFA 1), and which has an amino acid sequence represented herein by SEQ ID NO:20, encoded by a nucleic acid sequence represented herein by SEQ ID NO:19. Also included in the invention are glucosamine-6-phosphate synthases which have one or more genetic modifications that produce a result chosen from: increased enzymatic activity of glucosamine-6-phosphate synthase; reduced product inhibition of the glucosamine-6-phosphate synthase; and increased affinity of glucosamine-6-phosphate synthase for its substrates. In general, according to the present invention, an increase or a decrease in a given characteristic of a mutant or modified enzyme is made with reference to the same characteristic of a wild-type (i.e., normal, not modified) enzyme from the same organism which is measured or established under the same or equivalent conditions (discussed in more detail below).

Also described herein are several glucosamine-6-phosphate synthases with genetic modifications that result in a reduced product inhibition of the enzyme activity. Such modifications to a glucosamine-6-phosphate synthase were also described in detail in U.S. Pat. No. 6,372,457, although at least one additional, distinct GlmS mutant having reduced product inhibition is described herein (SEQ ID NO:14). Glucosamine-6-phosphate synthase enzymes from *E. coli* that have reduced product inhibition have amino acid sequences including, but not limited to, those represented by SEQ ID NO:4, SEQ ID NO:6, SEQ ID NO:8, SEQ ID NO:10, SEQ ID NO:12, and SEQ ID NO:14 (encoded by SEQ ID NO:3, SEQ ID NO:5, SEQ ID NO:7, SEQ ID NO:9, SEQ ID NO:11, and SEQ ID NO:13, respectively). Moreover, a table describing amino acid positions in SEQ ID NO:14 relative to the wild-type sequence (SEQ ID NO:2) that result in an enzyme with reduced product inhibition is provided as Table 7. SEQ ID NO:4 has the following mutations with respect to SEQ ID NO:2: Ile to Thr at position 4, Ile to Thr at position 272, and Ser to Pro at position 450. SEQ ID NO:6 has the following mutations with respect to SEQ ID NO:2: Ala to Thr at position 39, Arg to Cys at position 250, and Gly to Ser at position 472. SEQ ID NO:8 has the following mutations with respect to SEQ ID NO:2: Leu to Pro at position 469. SEQ ID NOs:10 and 12 each have at least the following mutation with respect to SEQ ID NO:2: Gly to Ser at position 472. A glucosamine-6-phosphate synthase having a mutation at any one or more of the positions listed in Table 7, including any combination of the mutations shown therein, or a glucosamine-6-phosphate synthase having any of the additional mutations represented in any of SEQ ID NOs:4, 6, 8, 10, 12 or 14, including any combination thereof, is contemplated by the present invention. Moreover, homologous modifications can be made in glucosamine-6-phosphate synthases from other microorganisms. Finally, some naturally occurring glucosamine-6-phosphate synthases have less product inhibition than glucosamine-6-phosphate synthases from other microorganisms. For example, the present inventors have demonstrated that the wild-type glucosamine-6-phosphate synthase from *Bacillus subtilis* exhibits a product resistance very comparable to the *E. coli* mutant GlmS enzymes (see Examples section).

The enzyme generally referred to herein as glucosamine-6-phosphate acetyltransferase converts glucosamine-6-phosphate and acetyl-CoA to N-acetylglucosamine-6-phosphate, releasing CoA. The enzyme is also known as glucosamine-phosphate N-acetyltransferase, phosphoglucosamine transacetylase and phosphoglucosamine acetylase. The yeast enzyme is generally referred to as GNA1. Glucosamine-6-phosphate acetyltransferases from a variety of organisms are known in the art and are contemplated for use in the genetic engineering strategies of the present invention. For example, the glucosamine-6-phosphate acetyltransferase from *Saccharomyces cerevisiae* is described herein. The glucosamine-6-phosphate acetyltransferase from *Saccharomyces cerevisiae* has an amino acid sequence represented herein by SEQ ID NO:30, which is encoded by a nucleic acid sequence represented herein by SEQ ID NO:29. Also described herein is the glucosamine-6-phosphate acetyltransferase from *Candida albicans*, which has an amino acid sequence represented herein by SEQ ID NO:32, encoded by a nucleic acid sequence represented herein by SEQ ID NO:31. Also described herein is the glucosamine-6-phosphate acetyltransferase from *Arabidopsis thaliana*, which has an amino acid sequence represented herein by SEQ ID NO:34, encoded by a nucleic acid sequence represented herein by SEQ ID NO:33. Also included in the invention are glucosamine-6-phosphate acetyltransferases that have a genetic modification that produces a result selected from: increased enzymatic activity of glucosamine-6-phosphate acetyltransferase; overexpression of glucosamine-6-phosphate acetyltransferase by the microorganism; reduced N-acetylglucosamine-6-phosphate product inhibition of the glucosamine-6-phosphate acetyltransferase; and increased affinity of glucosamine-6-phosphate acetyltransferase for glucosamine-6-phosphate.

The enzyme generally referred to herein as glucosamine-6-phosphate deaminase catalyzes a reversible reaction of glucosamine-6-phosphate and water to form fructose-6-phosphate and ammonium. The enzyme is also known as glucosamine-6-phosphate isomerase; GlcN6P deaminase; phosphoglucosaminisomerase; phosphoglucosamine isomerase; glucosamine phosphate deaminase; 2-amino-2-deoxy-D-glucose-6-phosphate ketol isomerase (deaminating). In *E. coli* and other bacteria, the enzyme is generally known as NagB. Glucosamine-6-phosphate deaminases from a variety of organisms are known in the art and are contemplated for use in the genetic engineering strategies of the present invention. For example, the glucosamine-6-phosphate deaminase from *Escherichia coli* is described herein. The glucosamine-6-phosphate deaminase from *E. coli* has an amino acid sequence represented herein by SEQ ID NO:42, which is encoded by a nucleic acid sequence represented herein by SEQ ID NO:41. Also included in the invention are glucosamine-6-phosphate deaminases that have a genetic modification that produces a result selected from: increased enzymatic activity of glucosamine-6-phosphate deaminase, increased reverse reaction of glucosamine-6-phosphate deaminase to form increased (more) glucosamine-6-phosphate, reduced forward reaction of glucosamine-6-phosphate deaminase to form reduced (less) fructose-6-phosphate, increased affinity of glucosamine-6-phosphate deaminase for fructose-6-phosphate, reduced affinity of glucosamine-6-phosphate deaminase for glucosamine-6-phosphate, and reduced glucosamine-6-phosphate product inhibition of the glucosamine-6-phosphate deaminase.

The enzyme generally referred to herein as glucosamine-1-phosphate N-acetyltransferase converts glucosamine-1-phosphate and acetyl-CoA to N-acetylglucosamine-1-phosphate, releasing CoA. The enzyme is known in *E. coli* and other bacteria as GlmU. The bacterial GlmU enzyme is a bifunctional enzyme, (i.e., it has two enzyme functions it has also the function of N-acetylglucosamine-1-phosphate uridyltransferase, which is also known as UDP-N-acetylglucosamine pyrophosphorylase, UDP-N-acetylglucosamine diphosphorylase). Glucosamine-1-phosphate N-acetyltransferases from a variety of organisms are known in the art and are contemplated for use in the genetic engineering strategies of the present invention. For example, the glucosamine-1-phosphate N-acetyltransferase from *Escherichia coli*, which is actually the bifunctional glucosamine-1-phosphate N-acetyltransferase/N-acetylglucosamine-1-phosphate uridyltransferase, is described herein. The glucosamine-1-phosphate N-acetyltransferase/N-acetylglucosamine-1-phosphate uridyltransferase from *E. coli* has an amino acid sequence represented herein by SEQ ID NO:56, which is encoded by a nucleic acid sequence represented herein by SEQ ID NO:55. Also described herein is a truncated mutant of the *E. coli* glucosamine-1-phosphate N-acetyltransferase/N-acetylglucosamine-1-phosphate uridyltransferase, wherein the portion encoding the N-acetylglucosamine-1-phosphate uridyltransferase has been deleted, effectively leaving an enzyme with only the glucosamine-1-phosphate N-acetyltransferase activity. This truncated glucosamine-1-phosphate N-acetyltransferase/N-acetylglucosamine-1-phosphate uridyltransferase has an amino acid sequence represented herein by SEQ ID NO:58, encoded by a nucleic acid sequence represented herein by SEQ ID NO:57. Also included in the invention are glucosamine-1-phosphate N-acetyltransferases that have a genetic modification that produces a result selected from: increased enzymatic activity of glucosamine-1-phosphate N-acetyltransferase; reduced N-acetylglucosamine-1-phosphate uridyltransferase enzymatic activity (if the enzyme is a bifunctional enzyme); increased affinity of glucosamine-1-phosphate N-acetyltransferase for glucosamine-1-phosphate; reduced affinity of an glucosamine-1-phosphate N-acetyltransferase/N-acetylglucosamine-1-phosphate uridyltransferase for N-acetylglucosamine-1-phosphate (if the enzyme is a bifunctional enzyme); and reduced N-acetylglucosamine-1-phosphate product inhibition of the glucosamine-1-phosphate N-acetyltransferase.

The enzyme generally referred to herein as N-acetylglucosamine-6-phosphate deacetylase hydrolyzes N-acetylglucosamine-6-phosphate to glucosamine-6-phosphate and acetate. The enzyme is known in E. coli and other bacteria as NagA. N-acetylglucosamine-6-phosphate deacetylases from a variety of organisms are known in the art and are contemplated for use in the genetic engineering strategies of the present invention. For example, the N-acetylglucosamine-6-phosphate deacetylase from Escherichia coli is described herein. The N-acetylglucosamine-6-phosphate deacetylase from E. coli has an amino acid sequence represented herein by SEQ ID NO:84; which is encoded by a nucleic acid sequence represented herein by SEQ ID NO:85. Also included in the invention are N-acetylglucosamine-6-phosphate deacetylases that have a genetic modification that produces a result selected from: increased activity of glucosamine-6-phosphate deacetylase; increased reverse reaction of glucosamine-6-phosphate deacetylase to form increased N-acetyl glucosamine-6-phosphate; reduced forward reaction of glucosamine-6-phosphate deacetylase to form reduced glucosamine-6-phosphate; increased affinity of glucosamine-6-phosphate deacetylase for glucosamine-6-phosphate; reduced affinity of glucosamine-6-phosphate deacetylase for N-acetyl glucosamine-6-phosphate; reduced N-acetyl glucosamine-6-phosphate product inhibition of the glucosamine-6-phosphate deacetylase.

The enzyme generally referred to herein as phosphoglucosamine mutase catalyzes the conversion between glucosamine-6-phosphate and glucosamine-1-phosphate. The enzyme is generally known in E. coli and other bacteria as GlmM. Phosphoglucosamine mutases from a variety of organisms are known in the art and are contemplated for use in the genetic engineering strategies of the present invention. For example, the phosphoglucosamine mutase from Escherichia coli is described herein. The phosphoglucosamine mutase from E. coli has an amino acid sequence represented herein by SEQ ID NO:54, which is encoded by a nucleic acid sequence represented herein by SEQ ID NO:53. Also included in the invention are phosphoglucosamine mutases that have a genetic modification that produces a result selected from: increased activity of phosphoglucosamine mutase; increased forward reaction of phosphoglucosamine mutase to form increased glucosamine-1-phosphate; reduced reverse reaction of phosphoglucosamine mutase to form reduced glucosamine-6-phosphate; increased affinity of phosphoglucosamine mutase for glucosamine-6-phosphate; reduced affinity of phosphoglucosamine mutase for glucosamine-1-phosphate; and reduced glucosamine-1-phosphate product inhibition of the phosphoglucosamine mutase.

The enzyme generally referred to herein as phosphoglucoisomerase catalyzes the interconversion of glucose-6-phosphate to fructose-6-phosphate. The enzyme is generally known in E. coli and other bacteria as phosphoglucoisomerase or Pgi. Phosphoglucoisomerases from a variety of organisms are known in the art and are contemplated for use in the genetic engineering strategies of the present invention. For example, the phosphoglucoisomerase from Escherichia coli is described herein. The phosphoglucoisomerase from E. coli has an amino acid sequence represented herein by SEQ ID NO:105, which is encoded by a nucleic acid sequence represented herein by SEQ ID NO:104.

The enzyme generally referred to herein as phosphofructokinase catalyzes the formation of fructose-1,6,-biphosphate from fructose 6-phosphate (F-6-P). The major phosphofructokinase in E. coli, encoded by pfkA, provides 90% of the phosphofructokinase activity. The remaining 10% of activity is supplied by the minor phosphofructokinase, encoded by pfkB. The phosphofructokinase enzyme is generally known in E. coli and other bacteria as phosphofructokinase or Pfk. Phosphofructokinases from a variety of organisms are known in the art and are contemplated for use in the genetic engineering strategies of the present invention. For example, the PfkA from Escherichia coli is described herein.

The enzyme generally referred to herein as glutamine synthetase catalyzes the conversion of L-glutamate to L-glutamine in a reaction requiring $NH_3$ and ATP. The enzyme is generally known in E. coli and other bacteria as glutamine synthetase, or GlnA. Glutamine synthetases from a variety of organisms are known in the art and are contemplated for use in the genetic engineering strategies of the present invention. For example, the glutamine synthetase from Escherichia coli is described herein. The glutamine synthetase from E. coli has an amino acid sequence represented herein by SEQ ID NO:89, which is encoded by a nucleic acid sequence represented herein by SEQ ID NO:88.

The enzyme generally referred to herein as glucose-6-phosphate dehydrogenase catalyzes the first step in the pentose phosphate pathway, converting glucose-6-phosphate into glucono-1,5-lactone. The enzyme is generally known in E. coli and other bacteria as glucose-6-phosphate dehydrogenase, encoded by zwf. Glucose-6-phosphate dehydrogenases from a variety of organisms are known in the art and are contemplated for use in the genetic engineering strategies of the present invention. For example, the glucose-6-phosphate dehydrogenase from Escherichia coli is described herein. The glucose-6-phosphate dehydrogenase from E. coli has an amino acid sequence represented herein by SEQ ID NO:95, which is encoded by a nucleic acid sequence represented herein by SEQ ID NO:94.

A number of enzymes are responsible for glycogen synthesis in a microorganism. Such enzymes include, but are not limited to, ADP-glucose pyrophosphorylase, glycogen synthase and a branching enzyme.

Other genes referenced herein include, but are not limited to: N-acetylglucosamine transporter ($II^{Nag}$), mannose transporter ($EIIM,P/II^{man}$), glucose transporter ($II^{Glc}$), and/or a phosphatase. The genes in E. coli correspond to: nagC, nagD, nagE (N-acetylglucosamine transporter ($II^{Nag}$)); manXYZ (mannose transporter ($EIIM,P/III^{man}$)); ptsG (glucose transporter ($II^{Glc}$)) or a phosphatase gene, respectively. The nagC gene encodes a regulatory protein that acts as a repressor of the nag regulon as well as both an activator and repressor of the glmU operon. The function of the nagD gene is not known, but is believed to be related to amino sugar metabolism as it resides within the nag regulon. The nag genes (nagA, nagB, nagC, nagD, nagE) involved in the degradation of glucosamine and N-acetyl-glucosamine exist as a regulon (i.e., the nag regulon) located at 15 min on the Escherichia coli chromosome. The mannose transporter ($EIIM,P/II^{man}$) (manXYZ) is responsible for the transport of glucosamine into the cell. The glucose transporter ($II^{Glc}$) (ptsG) transports glucose into the cell but can serve as a secondary transporter for glucosamine. Phosphatases are well known in the art as catalyzing the dephosphorylation of sugar phosphates and proteins.

One embodiment of the present invention relates to a method to produce glucosamine and/or N-acetylglucosamine by fermentation. Such a method generally includes the steps of (a) culturing in a fermentation medium a microorganism which comprises at least one specific genetic modification that is disclosed herein as being useful for increasing the production of glucosamine and/or N-acetylglucosamine in the microorganism; and (b) collecting a product produced from the step of culturing which is selected from the group consisting of glucosamine-6-phosphate, glucosamine, glucosamine-1-phosphate, N-acetylglucosamine-1-phosphate, N-acetylglucosamine-6-phosphate, and N-acetylglucosamine. More particularly, the products can include intracellular glucosamine-6-phosphate, glucosamine-1-phosphate, N-acetylglucosamine-6-phosphate, N-acetylglucosamine-1-phosphate, N-acetylglucosamine and/or glucosamine which are collected from the microorganism and/or extracellular glucosamine or N-acetylglucosamine which are collected from the fermentation medium. In one aspect, N-acetylglucosamine, N-acetylglucosamine-6-phosphate and N-acetylglucosamine-1-phosphate are hydrolyzed under acid/heat conditions where the hydrolysis products (glucosamine, glucosamine-6-phosphate and glucosamine-1-phosphate) are stable. In another aspect, N-acetylglucosamine, N-acetylglucosamine-6-phosphate and N-acetylglucosamine-1-phosphate are deacetylated by using a deacetylating enzyme. Recovery and purification methods are discussed in detail below.

In general, a genetically modified microorganism useful in a method of the present invention typically has at least one modified gene involved in at least one amino sugar metabolic pathway which results in (a) reduced ability to convert glucosamine-6-phosphate, glucosamine-1-phosphate, N-acetylglucosamine-6-phosphate and/or N-acetylglucosamine-1-phosphate into other compounds (i.e., inhibition of glucosamine-6-phosphate, glucosamine-1-phosphate, N-acetylglucosamine-6-phosphate and/or N-acetylglucosamine-1-phosphate catabolic or anabolic pathways), (b) an enhanced ability to produce (i.e., synthesize) glucosamine-6-phosphate, glucosamine-1-phosphate, N-acetylglucosamine-6-phosphate and/or N-acetylglucosamine-1-phosphate, (c) a reduced ability to transport glucosamine and/or N-acetylglucosamine into the cell, (d) an enhanced ability to transport glucosamine-6-phosphate, glucosamine-1-phosphate, N-acetylglucosamine-6-phosphate, N-acetylglucosamine-1-phosphate, glucosamine and/or N-acetylglucosamine out of the cell, and/or (e) a reduced ability to use substrates involved in the production of glucosamine-6-P for competing biochemical reactions, and/or (f) a reduced ability to use acetyl-CoA (involved in the production of N-acetylglucosamine-6-phosphate and N-acetylglucosamine-1-phosphate) for competing biochemical reactions.

In general, a microorganism having a genetically modified amino sugar metabolic pathway has at least one genetic modification, as discussed in detail below, which results in a change in one or more amino sugar metabolic pathways as described above as compared to a wild-type microorganism cultured under the same conditions. Such a modification in an amino sugar metabolic pathway changes the ability of the microorganism to produce an amino sugar. As discussed in detail below, according to the present invention, a genetically modified microorganism preferably has an enhanced ability to produce glucosamine and/or N-acetylglucosamine as compared to a wild-type microorganism of the same species (and preferably the same strain), which is cultured under the same or equivalent conditions. Equivalent conditions are culture conditions which are similar, but not necessarily identical (e.g., some changes in medium composition, temperature, pH and other conditions can be tolerated), and which do not substantially change the effect on microbe growth or production of glucosamine or N-acetylglucosamine by the microbe.

An amino sugar metabolic pathway which affects the production of glucosamine and/or N-acetylglucosamine can generally be categorized into at least one of the following kinds of pathways: (a) pathways for converting glucosamine-6-phosphate, glucosamine-1-phosphate, N-acetylglucosamine-6-phosphate and N-acetylglucosamine-1-phosphate into other compounds, (b) pathways for synthesizing glucosamine-6-phosphate, (c) pathways for transporting glucosamine and/or N-acetylglucosamine into a cell, (d) pathways for transporting glucosamine, glucosamine-6-phosphate, glucosamine-1-phosphate, N-acetylglucosamine-6-phosphate, N-acetylglucosamine-1-phosphate and/or N-acetylglucosamine out of a cell, and (e) pathways which compete for substrates involved in the production of glucosamine-6-phosphate.

Development of a microorganism with enhanced ability to produce glucosamine and/or N-acetylglucosamine by genetic modification can be accomplished using both classical strain development and molecular genetic techniques. In general, the strategy for creating a microorganism with enhanced glucosamine and/or N-acetylglucosamine production is to (1) inactivate or delete at least one, and preferably more than one of the amino sugar metabolic pathways in which production of glucosamine-6-phosphate is negatively affected (e.g., inhibited), and (2) amplify at least one, and preferably more than one of the amino sugar metabolic pathways in which glucosamine-6-phosphate production is enhanced.

In one embodiment of the present invention, enhancement of the ability of a microorganism to synthesize glucosamine-6-phosphate, glucosamine-1-phosphate, N-acetylglucosamine-6-phosphate and/or N-acetylglucosamine-1-phosphate can be accomplished by amplification of the expression (e.g., overexpression) of the glucosamine-6-phosphate synthase gene (glmS), and/or by amplification of the expression of the glucosamine-6-phosphate deaminase gene, which in *Escherichia coli* is the nagB gene, the product of which is glucosamine-6-phosphate deaminase. Glucosamine-6-phosphate deaminase catalyzes the forward reaction in which glucosamine-6-phosphate is deaminated to form fructose-6-phosphate and ammonium. Glucosamine-6-phosphate deaminase also catalyzes the reverse reaction in which fructose-6-phosphate and ammonium form glucosamine-6-phosphate. The reverse reaction of the glucosamine-6-phosphate deaminase is different from the action of glucosamine-6-phosphate synthase because in the synthase reaction fructose-6-phosphate and glutamine form glucosamine-6-phosphate and glutamic acid. An adequate intracellular supply of glutamine is critical for the glucosamine-6-phosphate synthase reaction. Inspection of the synthetic and degradative pathways for glucosamine-6-phosphate reveals the presence of a potential futile cycle whereby continuous interconversion of fructose-6-phosphate and glucosamine-6-phosphate results in wasteful depletion of glutamine. Therefore, use of the reverse action of the glucosamine-6-phosphate deaminase has an advantage over the glucosamine-6-phosphate synthase since the deaminase uses ammonium as the amino donor rather than an amino acid (glutamine). The glucosamine-6-phosphate deaminase catalyzes the reversible reaction with a kinetic equilibrium in favor of the degradation of glucosamine-6- phosphate into fructose-6-phosphate and ammonium. Therefore, as another embodiment of the present invention, a mutagenized form of glucosamine-6-phosphate deaminase or an over-expressed glucosamine-6-phosphate deaminase, with an increased activity of the reverse action and a decreased activity of the forward reaction is used for production of glucosamine and/or N-acetylglucosamine. Another embodiment of the present invention is to provide a microorganism having a glucosamine-6-phosphate deaminase with increased Vmax, increased specific activity, increased stability, increased affinities to substrates fructose-6-phosphate and ammonium, and reduced product inhibition by glucosamine-6-phoshat. A glucosamine-6-phosphate deaminase with such improvements can be isolated from nature or produced by any suitable method of genetic modification or protein engineering. For example, computer-based protein engineering can be used for this purpose. See for example, Maulik et al., 1997, *Molecular Biotechnology: Therapeutic Applications and Strategies*, Wiley-Liss, Inc., which is incorporated herein by reference in its entirety. Amplification of the expression of glucosamine-6-phosphate deaminase can be accomplished in *Escherichia coli*, for example, by introduction of a recombinant nucleic acid molecule encoding the nagB gene. Since the glucosamine-6-phosphate synthase in the host strain can catalyze the synthesis of glucosamine-6-phosphate, the amplification of the expression of glucosamine-6-phosphate deaminase should be analyzed in a mutant *Escherichia coli* strain which has a inactivated glmS gene. While elimination of glucosamine-6-phosphate synthase activity in this organism is not required, it is one embodiment of the invention.

By way of example for other enzymes and other proteins described herein, a modified glucosamine-6-phosphate deaminase can be a mutated (i.e., genetically modified) glucosamine-6-phosphate deaminase gene, for example, and can be produced by any suitable method of genetic modification. For example, a recombinant nucleic acid molecule encoding glucosamine-6-phosphate deaminase can be modified by any method for inserting, deleting, and/or substituting nucleotides, such as by error-prone PCR. In this method, the gene is amplified under conditions that lead to a high frequency of misincorporation errors by the DNA polymerase used for the amplification. As a result, a high frequency of mutations are obtained in the PCR products. The resulting glucosamine-6-phosphate deaminase gene mutants can then be screened for by testing the mutant genes for the ability to confer increased glucosamine production onto a test microorganism, as compared to a microorganism carrying the non-mutated recombinant glucosamine-6-phosphate deaminase nucleic acid molecule. Therefore, it is an embodiment of the present invention to provide a microorganism which is transformed with a genetically modified recombinant nucleic acid molecule comprising a nucleic acid sequence encoding a mutant, or homologue, glucosamine-6-phosphate deaminase protein. Such glucosamine-6-phosphate deaminase proteins can be referred to herein as glucosamine-6-phosphate deaminase homologues (described in detail below).

In one aspect of the invention, overexpression of either glmS or nagB is crucial for the intracellular accumulation of glucosamine-6-phosphate and ultimately for production of glucosamine and/or N-acetylglucosamine, since the level of glucosamine-6-phosphate synthase/or glucosamine-6-phosphate deaminase in the cell will control the redirection of carbon flow away from glycolysis and into glucosamine-6-phosphate synthesis.

For production of N-acetylglucosamine, glucosamine-6-phosphate must be converted to N-acetylglucosamine-6-phosphate or N-acetylglucosamine-1-phosphate, which is then dephosphorylated and/or secreted into the culture broth. In one embodiment of the present invention, enhancement of the ability of a microorganism to synthesize N-acetylglucosamine-6-phosphate and N-acetylglucosamine is accomplished by amplification of the expression of the glucose-6-phosphate acetyltransferase gene, which, by way of example only, in *Saccharomyces cerevisiae* is the GNA1 gene, the product of which is glucosamine-6-phosphate acetyltransferase. In another embodiment of the present invention, enhancement of the ability of a microorganism to synthesize N-acetylglucosamine-6-phosphate and N-acetylglucosamine is accomplished by amplification of the expression of the N-acetyl glucose-6-phosphate deacetylase gene, which in *Escherichia coli* is the nagA gene, the product of which is N-acetylglucosamine-6-phosphate deacetylase. The deacetylase catalyzes the conversion of N-acetylglucosamine-6-phosphate to glucosamine-6-phosphate in the forward reaction. It also catalyzes the reverse reaction to convert glucosamine-6-phosphate to N-acetylglucosamine. N-acetylglucosamine-6-phosphate deacetylase catalyzes the reversible reaction with a kinetic equilibrium in favor of the deacetylation of N-acetylglucosamine-6-phosphate to glucosamine-6-phosphate. Therefore, as another embodiment of the present invention, a mutagenized form of N-acetylglucosamine-6-phosphate deacetylase with an increased activity of the reverse activity of the reverse action and a decreased activity of the forward reaction is used for production of glucosamine and/or N-acetylglucosamine.

Since the glucosamine-6-phosphate synthase (GlmS) is strongly inhibited by the product glucosamine-6-phosphate, amplification of the expression of the glucosamine-6-phosphate acetyltransferase gene (GNA1) and/or N-acetylglucosamine-6-phosphate deacetylase gene (nagA) can reduce the intracellular level of glucosamine-6-phosphate, reduce the product inhibition of GlmS enzyme, and thus increase production of glucosamine and/or N-acetylglucosamine.

In another embodiment of the present invention, enhancement of the ability of a microorganism to synthesize glucosamine and N-acetylglucosamine is accomplished by amplification of the expression of the phosphoglucosamine mutase gene, which in *Escherichia coli* is the glmM gene, the product of which is phosphoglucosamine mutase. The phosphoglucosamine mutase catalyzes the conversion of glucosamine-6-phosphate to glucosamine-1-phosphate. Since the glucosamine-6-phosphate synthase (GlmS) is strongly inhibited by the product glucosamine-6-phosphate, amplification of the expression of the phosphoglucosamine mutase gene can reduce the intracellular level of glucosamine-6-phosphate, reduce the product inhibition of GlmS enzyme, and thus increase production of glucosamine and/or N-acetylglucosamine.

In another embodiment of the present invention, enhancement of the ability of a microorganism to synthesize glucosamine and/or N-acetylglucosamine is accomplished by amplification of the expression of the bifunctional glucosamine-1-phosphate N-acetyltransferase/N-acetylglucosamine-1-phosphate uridyltransferase gene, which in *Escherichia coli* is the glmU gene, the product of which is glucosamine-1-phosphate N-acetyltransferase/N-acetylglucosamine-1-phosphate uridyltransferase. The invention also includes the amplification of expression or increased activity of a protein having glucosamine-1-phosphate N-acetyltransferase activity. The bi-functional enzyme catalyzes the conversion of glucosamine-1-phosphate to N-acetylglucosamine-1-phosphate (as glucosamine-1-phosphate N-acetyltransferase) and converts the product further to UDP-N-acetylglucosamine (as N-acetylglucosamine-1-phosphate uridyltransferase). Therefore, as another embodiment of the present invention, a mutagenized form of glucosamine-1-phosphate N-acetyltransferase/N-acetylglucosamine-1-phosphate uridyltransferase with an increased activity of the acetyltransferase action and a decreased activity of the uridyltransferase action is used for production of glucosamine and/or N-acetylglucosamine. The glmU gene is an essential gene for *Escherichia coli* growth since glucosamine-1-phosphate N-acetyltransferase/N-acetylglucosamine-1-phosphate uridyltransferase functions -phosphate within the amino sugar metabolic pathway in which glucosamine-6-phosphate is incorporated, through a series of biochemical reactions, into macromolecules. A mutagenized form of GlmU enzyme with an increased activity of the acetyltransferase action and a decreased activity of the uridyltransferase action needs to be used in a host strain with a wild-type glmU gene so that macro molecules derived from glucosamine can be synthesized to support cell growth.

Glucosamine and/or N-acetylglucosamine synthesis is closely connected to many different pathways of glucose metabolism as outlined in FIG. 3. Glucose is taken up by the cell and is simultaneously converted to glucose-6-P. Glucose is metabolized by number of pathways, including those shown in the figure. In the glucosamine synthesis pathway, glucose-6-P is isomerized to fructose-6-phosphate, followed by the GlmS mediated conversion of fructose-6-phosphate to glucosamine-6-phosphate. Finally, glucosamine-6-phosphate is dephosphorylated and secreted. A major competing alternative route for glucose-6-phosphate is its entry into glycolysis via phosphofructokinase. Another important alternate routes for glucose-6-phosphate is its oxidation to gluconolactone-6-phosphate (the entry into the pentose phosphate pathway). Additionally, glucose-6-phosphate could be converted to glucose-1-phosphate, from which glycogen is made and stored in the cell. It is in the scope of the present invention to modulate other competing pathways to maximize the production of glucosamine and/or N-acetylglucosamine as described in detail below.

Bacterial cells accumulate glycogen as the major form of stored carbon reserve. Glycogen synthesis involves three enzymes: ADP-glucose pyrophosphorylase, also known as glucose-1-phosphate adenyltransferase), glycogen synthase, and a branching enzyme. These enzymes catalyze, respectively, the synthesis of the monosaccharide donor (ADP-glucose) from glucose-1-phosphate, the polymerization of these monosaccharide units to form a (1,4) polymer of glucose, and the rearrangement of this polymer to generate (1-6) branches in the chain. ADP-glucose pyrophosphorylase is a pivotal enzyme in glycogen synthesis and is strongly modulated by allosteric effectors. For example, 3-phosphoglycerate stimulates enzyme activity, while orthophosphate inhibits the activity. These effectors may play key roles in vivo in the control of glycogen synthesis. The amount of glycogen in the cells accounts for 10 to 60% of their dry weight according to growth conditions. Generally, glycogen accumulates under conditions where the supply of carbon and energy was plentiful and nitrogen was the limiting nutrient. A depletion of phosphate in the growth medium also results in a higher amount of glycogen in the cell. The sole function of ADP-glucose in bacteria is to serve as a precursor for glycogen synthesis. In *E. coli* mutants with glycogen synthesis blocked cell growth was not detrimentally affected. Blocking glycogen synthesis may make more carbon source available to glucosamine/N-acetylglucosamine production.

To maximize glucosamine/N-acetylglucosamine production the phosphoglucoisomerase (encoded by the pgi gene) could be manipulated. Overexpression of the pgi gene could increase the conversion of glucose-6-P to fructose-6-P the direct substrate for the synthesis of glucosamine-6-P.

Glucose is needed to support cell growth and glucosamine synthesis. Phosphofructokinases (PfkA and PfkB, with the former being the major isoenzyme) catalyze the conversion of fructose-6-P to fructose-1,6-biphosphate. The reaction operates in competition to glucosamine-6-P synthesis. In controlling carbon flux, it would be desirable to modulate expression of PfkA and/or PfkB to make more glucose-6-P directed to the glucosamine pathway. To maximize glucosamine synthesis, the supply of glucose should not be limited, but excess glucose usually leads to acetate formation. Since acetate accumulation inhibits cell growth and signals a down turn of the general cellular metabolism, it should be avoided. One approach to managing the carbon supply is to uncouple the carbon flux to glucosamine synthesis from that of cell growth and acetate formation. This could be accomplished by deleting the pfkA gene and supplying cells with fructose for growth. In pfkA knockout mutants the flux of fructose-6-phosphate to glycolysis will be greatly restricted. Therefore, virtually all of the glucose can be used for glucosamine synthesis while cell growth and energy production will be supplied by feeding fructose, which is transported into the cell and phosphorylated to fructose-1-phosphate. The later will be further phosphorylated to fructose-1,6-diphosphate.

Literature suggests that phosphorylated amino sugars were inhibitory to enzymes of the pentose phosphate pathway. Indeed, N-acetylglucosamine production caused cell growth inhibition that could be relieved by feeding intermediates of the pathway such as gluconate and ribose. Supplementation with gluconate and pentose compounds was also found to increase N-acetylglucosamine production. To overcome inhibition by amino sugars, enzymes of the pentose phosphate pathway, such as glucose-6-P dehydrogenase (encode by the zwf) gene) can be overexpressed.

Glucosamine/N-acetylglucosamine synthesis consumes glutamine, the amino donor. The synthesis of glutamine involves glutamine synthase encoded by the glnA gene. Overexpression of the glnA gene could increase the pool of glutamine and thus increase glucosamine/N-acetylglucosamine.

Therefore, having generally described some of the preferred modifications according to the invention, in one embodiment, the microorganism comprises at least one genetic modification that increases the activity of glucosamine-6-phosphate acetyltransferase in the microorganism. Preferably, the genetic modification to increase the activity of glucosamine-6-phosphate acetyltransferase provides a result selected from: increased enzymatic activity of glucosamine-6-phosphate acetyltransferase; overexpression of glucosamine-6-phosphate acetyltransferase by the microorganism; reduced N-acetyl glucosamine-6-phosphate product inhibition of the glucosamine-6-phosphate acetyltransferase; and/or increased affinity of glucosamine-6-phosphate acetyltransferase for glucosamine-6-phosphate. In one aspect, the microorganism is transformed with at least one recombinant nucleic acid molecule comprising a nucleic acid sequence encoding the glucosamine-6-phosphate acetyltransferase. Such a nucleic acid molecule can include a nucleic acid sequence encoding a glucosamine-6-phosphate acetyltransferase that has at least one genetic modification which increases the enzymatic activity of the glucosamine-6-phosphate acetyltransferase, or produces any of the above-described results. The function and representative sequences for glucosamine-6-phosphate acetyltransferases have been described above.

In another embodiment, the microorganism comprises at least one genetic modification that increases the activity of glucosamine-6-phosphate synthase. Preferably, the genetic modification to increase the activity of the glucosamine-6-phosphate synthase produces a result selected from: increased enzymatic activity of glucosamine-6-phosphate synthase; overexpression of the glucosamine-6-phosphate synthase; reduced product inhibition of the glucosamine-6-phosphate synthase; and increased affinity of glucosamine-6-phosphate synthase for its substrates. In one aspect, the microorganism is transformed with at least one recombinant nucleic acid molecule comprising a nucleic acid sequence encoding the glucosamine-6-phosphate synthase. Such a nucleic acid molecule can include a nucleic acid sequence encoding a glucosamine-6-phosphate synthase that has at least one genetic modification which increases the enzymatic activity of the glucosamine-6-phosphate synthase, that reduces the product inhibition of the glucosamine-6-phosphate synthase, or produces any of the above-described results. The function and representative sequences for glucosamine-6-phosphate synthases have been described above.

In another embodiment, the microorganism comprises at least one genetic modification that decreases the activity of glucosamine-6-phosphate synthase. In one aspect, the genetic modification to decrease the activity of glucosamine-6-phosphate synthase is a partial or complete deletion or inactivation of an endogenous gene encoding glucosamine-6-phosphate synthase in the microorganism.

In yet another embodiment, the microorganism comprises at least one genetic modification that increases the activity of glucosamine-6-phosphate deaminase. Preferably, the genetic modification to increase the activity of the glucosamine-6-phosphate deaminase produces a result selected from: overexpression of glucosamine-6-phosphate deaminase by the microorganism, increased enzymatic activity of glucosamine-6-phosphate deaminase, increased reverse reaction of glucosamine-6-phosphate deaminase to form increased (more) glucosamine-6-phosphate, reduced forward reaction of glucosamine-6-phosphate deaminase to form reduced (less) fructose-6-phosphate, increased affinity of glucosamine-6-phosphate deaminase for fructose-6-phosphate, reduced affinity of glucosamine-6-phosphate deaminase for glucosamine-6-phosphate, and reduced glucosamine-6-phosphate product inhibition of the glucosamine-6-phosphate deaminase. In one aspect, the microorganism is transformed with at least one recombinant nucleic acid molecule comprising a nucleic acid sequence encoding the glucosamine-6-phosphate deaminase. Such a nucleic acid molecule can include a nucleic acid sequence encoding a glucosamine-6-phosphate deaminase that has at least one genetic modification which increases the enzymatic activity of the glucosamine-6-phosphate deaminase, or produces any of the above-described results. The function and representative sequences for glucosamine-6-phosphate deaminases have been described above.

In another embodiment, the microorganism comprises at least one genetic modification that decreases the activity of glucosamine-6-phosphate deaminase. In one aspect, the genetic modification to decrease the activity of glucosamine-6-phosphate deaminase is a partial or complete deletion or inactivation of an endogenous gene encoding glucosamine-6-phosphate deaminase in the microorganism.

In yet another embodiment, the microorganism comprises at least one genetic modification that increases the activity of glucosamine-1-phosphate N-acetyltransferase. Preferably, the genetic modification provides a result selected from: increased enzymatic activity of glucosamine-1-phosphate N-acetyltransferase; reduced N-acetyl glucosamine-1-phosphate uridyltransferase enzymatic activity; overexpression of an enzyme having glucosamine-1-phosphate N-acetyltransferase activity by the microorganism; increased affinity of glucosamine-1-phosphate N-acetyltransferase for glucosamine-1-phosphate; reduced affinity of an glucosamine-1-phosphate N-acetyltransferase/N-acetyl glucosamine-1-phosphate uridyltransferase for N-acetyl glucosamine-1-phosphate; and/or reduced N-acetyl glucosamine-1-phosphate product inhibition of the glucosamine-1-phosphate N-acetyltransferase. In one aspect, the microorganism is transformed with at least one recombinant nucleic acid molecule comprising a nucleic acid sequence encoding the glucosamine-1-phosphate N-acetyltransferase or an enzyme comprising the activity of a glucosamine-1-phosphate N-acetyltransferase. Such a nucleic acid molecule can include a nucleic acid sequence encoding a glucosamine-1-phosphate N-acetyltransferase that has at least one genetic modification which increases the enzymatic activity of the glucosamine-1-phosphate N-acetyltransferase, or produces any of the above-described results. The function and representative sequences for glucosamine-1-phosphate N-acetyltransferases have been described above.

In another embodiment, the genetically modified microorganism comprises at least one genetic modification that increases the activity of N-acetylglucosamine-6-phosphate deacetylase. Preferably, the genetic modification that increases the activity of N-acetylglucosamine-6-phosphate deacetylase produces a result selected from: increased activity of the N-acetylglucosamine-6-phosphate deacetylase; overexpression of the N-acetylglucosamine-6-phosphate deacetylase; increased reverse action of the N-acetylglucosamine-6-phosphate deacetylase to form N-acetylglucosamine-6-phosphate; reduced or more preferably eliminated forward action of the N-acetylglucosamine-6-phosphate deacetylase to form glucosamine-6-phosphate. In one aspect, the microorganism is transformed with at least one recombinant nucleic acid molecule comprising a nucleic acid sequence encoding the N-acetylglucosamine-6-phosphate deacetylase. Such a nucleic acid molecule can include a nucleic acid sequence encoding a N-acetylglucosamine-6-phosphate deacetylase that has at least one genetic modification which increases the enzymatic activity of the N-acetylglucosamine-6-phosphate deacetylase, or produces any of the above-described results. The function and representative sequences for N-acetylglucosamine-6-phosphate deacetylases have been described above.

In another embodiment, the genetically modified microorganism comprises at least one genetic modification that increases the activity of phosphoglucosamine mutase. Preferably, the genetic modification that increases the activity of phosphoglucosamine mutase produces a result selected from: increased activity of phosphoglucosamine mutase; overexpression of phosphoglucosamine mutase; increased action of the phosphoglucosamine mutase to form glucosamine-1-phosphate, and/or reduced or more preferably eliminated action of the phosphoglucosamine mutase to form glucosamine-6-phosphate. In one aspect, the microorganism is transformed with at least one recombinant nucleic acid molecule comprising a nucleic acid sequence encoding the phosphoglucosamine mutase. Such a nucleic acid molecule can include a nucleic acid sequence encoding a phosphoglucosamine mutase that has at least one genetic modification which increases the enzymatic activity of the phosphoglucosamine mutase, or produces any of the above-described results. The function and representative sequences for phosphoglucosamine mutases have been described above.

In any of the embodiments described herein, the genetically modified microorganism can have at least one additional genetic modification to increase phosphoglucoisomerase activity in the microorganism. Preferably, the genetically modified microorganism can have at least one additional genetic modification to increase phosphoglucoisomerase produces a results selected from: increased activity of phosphoglucoisomerase, overexpression of phosphoglucoisomerase, increased affinity of the phosphoglucoisomerase for its substrate. In one aspect, the microorganism is transformed with at least one recombinant nucleic acid molecule comprising a nucleic acid sequence encoding the phosphoglucoisomerase. Such a nucleic acid molecule can include a nucleic acid sequence encoding a phosphoglucoisomerase that has at least one genetic modification which increases the enzymatic activity of the phosphoglucoisomerase, or produces any of the above-described results. The function and representative sequences for phosphoglucoisomerase have been described above.

In any of the embodiments described herein, the genetically modified microorganism can have at least one additional genetic modification to decrease phosphofructokinase activity in the microorganism. In one aspect, the genetic modification to decrease the activity of phosphofructokinase is a partial or complete deletion or inactivation of an endogenous gene encoding phosphofructokinase in the microorganism. The function and representative sequences for phosphofructokinases have been described above.

In any of the embodiments described herein, the genetically modified microorganism can have at least one additional genetic modification to increase glutamine synthetase activity in the microorganism. Preferably, the genetically modified microorganism can have at least one additional genetic modification to increase glutamine synthetase produces a results selected from: increased activity of glutamine synthetase, overexpression of glutamine synthetase, increased affinity of the glutamine synthetase for its substrate. In one aspect, the microorganism is transformed with at least one recombinant nucleic acid molecule comprising a nucleic acid sequence encoding the glutamine synthetase. Such a nucleic acid molecule can include a nucleic acid sequence encoding a glutamine synthetase that has at least one genetic modification which increases the enzymatic activity of the glutamine synthetase, or produces any of the above-described results. The function and representative sequences for glutamine synthetase have been described above.

In any of the embodiments described herein, the genetically modified microorganism can have at least one additional genetic modification to increase glucose-6-phosphate dehydrogenase activity in the microorganism. Preferably, the genetically modified microorganism can have at least one additional genetic modification to increase glucose-6-phosphate dehydrogenase produces a results selected from: increased activity of glucose-6-phosphate dehydrogenase, overexpression of glucose-6-phosphate dehydrogenase, increased affinity of the glucose-6-phosphate dehydrogenase for its substrate. In one aspect, the microorganism is transformed with at least one recombinant nucleic acid molecule comprising a nucleic acid sequence encoding the glucose-6-phosphate dehydrogenase. Such a nucleic acid molecule can include a nucleic acid sequence encoding a glucose-6-phosphate dehydrogenase that has at least one genetic modification which increases the enzymatic activity of the glucose-6-phosphate dehydrogenase, or produces any of the above-described results. The function and representative sequences for glucose-6-phosphate dehydrogenase have been described above.

In any of the embodiments described herein, the genetically modified microorganism can have at least one additional genetic modification to decrease the activity of one or more enzymes responsible for glycogen synthesis in the microorganism. Such enzymes include, but are not limited to, glycogen synthesis comprise ADP-glucose pyrophosphorylase, glycogen synthase and a branching enzyme. In one aspect, the genetic modification to decrease the activity of enzymes responsible for glycogen synthesis is a partial or complete deletion or inactivation of one or more of the endogenous gene encoding enzymes responsible for glycogen synthesis in the microorganism.

In any of the embodiments described herein, the genetically modified microorganism can have at least one additional genetic modification to increase the activity of a phosphatase. The initial intracellular products in the genetically modified microorganism described herein are glucosamine-6-phosphate, glucosamine-1-phosphate, N-acetylglucosamine-6-phosphate, N-acetylglucosamine-1-phosphate, N-acetylglucosamine and/or glucosamine. In many microorganisms, including *Escherichia coli*, an adequate intracellular supply of ammonium is critical for the glucosamine-6-phosphate deaminase reaction. Glucosamine-6-phosphate, glucosamine-1-phosphate, N-acetylglucosamine-6-phosphate and N-acetylglucosamine-1-phosphate are typically dephosphorylated to glucosamine and/or N-acetylglucosamine prior to transport out of the cell. Nonetheless, it is yet another embodiment of the present invention to provide a microorganism which is genetically modified to have a suitable phosphatase activity for the dephosphorylation of glucosamine-6-phosphate, glucosamine-1-phosphate, N-acetylglucosamine-6-phosphate and/or N-acetylglucosamine-1-phosphate. Such a phosphatase can include, but is not limited to, for example, alkaline phosphatase, acid phosphatase, phospho-sugar phosphatase and phosphoamino sugar phosphatase. In a preferred embodiment, such an *Escherichia coli* has an enhanced (i.e., increased) level of phosphatase activity (i.e., phosphatase action).

In any of the embodiments described above, the microorganism can have at least one an additional genetic modification to increase or decrease the activity of an enzyme selected from the group of: N-acetylglucosamine deacetylase, glucosamine-6-phosphate deaminase, N-acetylglucosamine transporter ($II^{Nag}$), glucosamine synthase, phosphoglucosamine mutase, glucosamine-1-phosphate N-acetyltransferase/N-acetylglucosamine-1-phosphate uridyltransferase, mannose transporter ($EIIM,P/III^{man}$), phosphofructokinase, glucose transporter ($II^{Glc}$), glucosamine-6-phosphate acetyltransferase and/or a phosphatase. The genes in *E. coli* correspond to: NagA, nagB, nagC, nagD, nagE, glmS, glmM, glmU, manXYZ, pfkA, pfkB, ptsG, GNA1 or a phosphatase gene, respectively.

Various of the above-identified genetic modifications can be combined to produce microorganisms having more than one modification, as desired to enhance the production of glucosamine and/or N-acetylglucosamine by the microorganism. For example, in one embodiment, the microorganism has the following genetic modifications: (1) a genetic modification to increase the activity of glucosamine-phosphate N-acetyltransferase; and (2) a genetic modification to increase the activity of the glucosamine-6-phosphate synthase. In a more preferred embodiment, the microorganism also has a genetic modification to decrease the activity of the glucosamine-6-phosphate deaminase.

In another embodiment, the microorganism has the following genetic modifications: (1) a genetic modification to increase the activity of the glucosamine-phosphate N-acetyltransferase; and (2) a genetic modification to increase the activity of the glucosamine-6-phosphate deaminase. In a more preferred embodiment, the microorganism also has a genetic modification to decrease the activity of glucosamine-6-phosphate synthase.

In another embodiment, the microorganism has the following genetic modifications: (1) a genetic modification to increase the activity of the glucosamine-6-phosphate deaminase; and (2) a genetic modification to increase the activity of glucosamine-1-phosphate N-acetyltransferase/N-acetylglucosamine-1-phosphate uridyltransferase, and preferably to increase glucosamine-1-phosphate N-acetyltransferase activity and/or reduce N-acetylglucosamine-1-phosphate uridyltransferase activity. In a more preferred embodiment, the microorganism also has a genetic modification to decrease the activity of glucosamine-6-phosphate synthase.

In another embodiment, the microorganism has the following genetic modifications: (1) a genetic modification to increase the activity of the glucosamine-6-phosphate synthase; and (2) a genetic modification to increase the activity of glucosamine-1-phosphate N-acetyltransferase/N-acetylglucosamine-1-phosphate uridyltransferase, and preferably to increase glucosamine-1-phosphate N-acetyltransferase activity and/or reduce N-acetylglucosamine-1-phosphate uridyltransferase activity. In a more preferred embodiment, the microorganism also has a genetic modification to decrease the activity of glucosamine-6-phosphate deaminase.

In another embodiment, a genetically modified microorganism useful in a fermentation method of the invention has an endogenous glucosamine-6-phosphate acetyltransferase (e.g., yeast have an endogenouse glucosamine-6-phosphate acetyltransferase) and also at least one genetic modification to increase the activity of glucosamine-6-phosphate synthase. In a more preferred embodiment, the microorganism also has a genetic modification to decrease the activity of glucosamine-6-phosphate deaminase.

In another embodiment, a genetically modified microorganism useful in a fermentation method of the invention is transformed with a recombinant nucleic acid molecule encoding glucosamine-6-phosphate synthase, glucosamine-6-phosphate deaminase, glucosamine-6-phosphate acetyltransferase, N-acetylglucosamine-6-phosphate deacetylase, phosphoglucosamine mutase or glucosamine-1-phosphate N-acetyltransferase/N-acetylglucosamine-1-phosphate uridyltransferase operatively linked to a transcription control sequence. The recombinant nucleic acid molecule can have a genetic modification which affects the action of the enzyme. Expression of the recombinant nucleic acid molecule increases expression and/or biological activity of the glucosamine-6-phosphate synthase, glucosamine-6-phosphate deaminase, glucosamine-6-phosphate acetyltransferase, N-acetylglucosamine-6-phosphate deacetylase, phosphoglucosamine mutase or glucosamine-1-phosphate N-acetyltransferase/N-acetylglucosamine-1-phosphate uridyltransferase by the microorganism as compared to the level of expression or biological activity of the protein in the absence of the recombinant nucleic acid molecule. In a preferred embodiment, the recombinant nucleic acid molecule is integrated into the genome of the microorganism. In a further embodiment, the microorganism has at least one additional genetic modification in a gene encoding a protein selected from the group of glucosamine-6-phosphate synthase, glucosamine-6-phosphate deaminase, N-acetylglucosamine-6-phosphate deacetylase, N-acetyl-glucosamine-specific enzyme II$^{Nag}$, phosphoglucosamine mutase, glucosamine-1-phosphate N-acetyltransferase/N-acetylglucosamine-1-phosphate uridyltransferase, phosphofructokinase, Enzyme II$^{Glc}$ of the PEP:glucose PTS, EIIM,P/III$^{Man}$ of the PEP:mannose PTS, glucosamine-6-phosphate acetyl transferase and/or a phosphatase. The genetic modification increase or decreases the action of the protein, except in the case of the phosphatase, in which the action of the phosphatase is preferably increased. In another preferred embodiment, the microorganism has a modification in genes encoding N-acetylglucosamine-6-phosphate deacetylase, glucosamine-6-phosphate deaminase and N-acetyl-glucosamine-specific enzyme II$^{Nag}$ wherein the genetic modification decreases or increase action of the protein. In one embodiment, the genetic modification is a deletion of at least a portion of the genes.

In another embodiment, a genetically modified microorganism of the present invention has a recombinant nucleic acid molecule encoding glucosamine-6-phosphate synthase glucosamine-6-phosphate deaminase, glucosamine-6-phosphate acetyltransferase, N-acetylglucosamine-6-phosphate deacetylase, phosphoglucosamine mutase or glucosamine-1-phosphate N-acetyltransferase/N-acetylglucosamine-1-phosphate uridyltransferase operatively linked to a transcription control sequence; and at least one genetic modification in a gene encoding a protein selected from the group of N-acetylglucosamine-6-phosphate deacetylase, glucosamine-6-phosphate deaminase, N-acetyl-glucosamine-specific enzyme II$^{Nag}$, phosphoglucosamine mutase, glucosamine-1-phosphate N-acetyltransferase-N-acetylglucosamine-1-phosphate uridyltransferase, phosphofructokinase, glucosamine-6-phosphate acetyltransferase, Enzyme II$^{Glc}$ of the PEP:glucose PTS, and/or EIIM,P/III$^{Man}$ the PEP:mannose PTS. The genetic modification increase or decreases action of the protein and expression of the recombinant nucleic acid molecule increases expression of the enzymes by the microorganism. In another embodiment, the microorganism has at least one genetic modification in a phosphatase gene, such that the phosphatase encoded by such gene has increased action. In a preferred embodiment, the recombinant nucleic acid molecule is integrated into the genome of the microorganism.

Various other combinations of the mutations described herein are encompassed by the invention and many are described in the Examples section.

Furthermore, the process and materials disclosed in the present invention can be used and/or modified by those skilled in the art to produce other amino sugars such as poly-N-acetylglucosamine, poly-glucosamine, galactosamine, mannosamine, N-acetyl galactosamine, N-acetyl mannosamine and their derivatives.

As described above, to produce significantly high yields of glucosamine and/or N-acetylglucosamine by the fermentation method of the present invention, a microorganism is genetically modified to enhance production of glucosamine and/or N-acetylglucosamine. As used herein, a genetically modified microorganism has a genome which is modified (i.e., mutated or changed) from its normal (i.e., wild-type or naturally occurring) form. In one aspect, such an organism can endogenously contain and express a gene encoding the protein of interest, and the genetic modification can be a genetic modification of the gene, whereby the modification has some effect (e.g., increase, decrease, delete) on the expression and/or activity of the gene. In another aspect, such an organism can endogenously contain and express a gene encoding the protein of interest, and the genetic modification can be an introduction of at least one exogenous nucleic acid sequence (e.g., a recombinant nucleic acid molecule), wherein the exogenous nucleic acid sequence encodes the protein of interest and/or a protein that affects the activity of the protein or gene encoding the protein. The exogenous nucleic acid molecule to be introduced into the microorganism can encode a wild-type protein or it can have one or more modifications that affect the expression and/or activity of the encoded protein as compared to the wild-type or normal protein. In yet another aspect, the organism does not necessarily endogenously (naturally) contain the gene encoding the protein of interest, but is genetically modified to introduce at least one recombinant nucleic acid molecule encoding a protein having the biological activity of the protein of interest. Again, the recombinant nucleic acid molecule can encode a wild-type protein or the recombinant nucleic acid sequence can be modified to affect the expression and/or activity of the encoded protein as compared to a wild-type protein. In other embodiments, various expression control sequences (e.g., promoters) can be introduced into the microorganism to effect the expression of an endogenous gene in the microorganism. Various embodiments associated with each of these aspects will be discussed in greater detail below.

As used herein, a genetically modified microorganism can include any genetically modified microorganism, including a bacterium, a protist, a microalgae, a fungus, or other microbe. Such a genetically modified microorganism has a genome which is modified (i.e., mutated or changed) from its normal (i.e., wild-type or naturally occurring) form and/or is modified to express extrachromosomal genetic material (e.g., a recombinant nucleic acid molecule), such that the desired result is achieved (e.g., increased, decreased, or otherwise modified enzyme expression and/or activity and/or modified production of glucosamine or N-acetylglucosamine as a result of the modification(s)). More particularly, the modification to the microorganism can be achieved by modification of the genome of the microorganism (e.g., endogenous genes) and/or by introducing genetic material (e.g., a recombinant nucleic acid molecule) into the microorganism, which can remain extrachromosomal or can be integrated into the host microbial genome. As such, the genetic modification can include the introduction or modification of regulatory sequences which regulate the expression of endogenous or recombinantly introduced nucleic acid sequences in the microorganism, the introduction of wild-type or modified recombinant nucleic acid molecules (e.g., encoding wild-type or modified proteins), the modification of endogenous genes in the microorganism, or any other modification which results in the microorganism having the specified characteristics with regard to enzyme expression and/or biological activity. Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted and/or modified (i.e., mutated; e.g., by insertion, deletion, substitution, and/or inversion of nucleotides), in such a manner that such modifications provide the desired effect within the microorganism. According to the present invention, a genetically modified microorganism includes a microorganism that has been modified using recombinant technology.

In one embodiment of the present invention, a genetic modification of a microorganism increases or decreases the activity of a protein involved in an amino sugar metabolic pathway according to the present invention. Such a genetic modification includes any type of modification and specifically includes modifications made by recombinant technology and/or by classical mutagenesis. As used herein, genetic modifications which result in a decrease in gene expression, in the function of the gene, or in the function of the gene product (i.e., the protein encoded by the gene) can be referred to as inactivation (complete or partial), deletion, interruption, blockage, silencing or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action or activity of enzymes discussed herein generally refers to any genetic modification in the microorganism in question which results in decreased expression and/or functionality (biological activity) of the enzymes and includes decreased activity of the enzymes (e.g., specific activity), increased inhibition or degradation of the enzymes as well as a reduction or elimination of expression of the enzymes. For example, the action or activity of an enzyme of the present invention can be decreased by blocking or reducing the production of the enzyme, reducing enzyme activity, or inhibiting the activity of the enzyme. Combinations of some of these modifications are also possible. Blocking or reducing the production of an enzyme can include placing the gene encoding the enzyme under the control of a promoter that requires the presence of an inducing compound in the growth medium. By establishing conditions such that the inducer becomes depleted from the medium, the expression of the gene encoding the enzyme (and therefore, of enzyme synthesis) could be turned off. Blocking or reducing the activity of an enzyme could also include using an excision technology approach similar to that described in U.S. Pat. No. 4,743,546, incorporated herein by reference. To use this approach, the gene encoding the enzyme of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

Genetic modifications that result in an increase in gene expression or function can be referred to as amplification, overproduction, overexpression, activation, enhancement, addition, or up-regulation of a gene. More specifically, reference to increasing the action (or activity) of enzymes or other proteins discussed herein generally refers to any genetic modification in the microorganism in question which results in increased expression and/or functionality (biological activity) of the enzymes or proteins and includes higher activity of the enzymes (e.g., specific activity or in vivo enzymatic activity), reduced inhibition or degradation of the enzymes and overexpression of the enzymes. For example, gene copy number can be increased, expression levels can be increased by use of a promoter that gives higher levels of expression than that of the native promoter, or a gene can be altered by genetic engineering or classical mutagenesis to increase the biological activity of an enzyme. Combinations of some of these modifications are also possible.

In general, according to the present invention, an increase or a decrease in a given characteristic of a mutant or modified enzyme (e.g., enzyme activity) is made with reference to the same characteristic of a wild-type (i.e., normal, not modified) enzyme that is derived from the same organism (from the same source or parent sequence), which is measured or established under the same or equivalent conditions. Similarly, an increase or decrease in a characteristic of a genetically modified microorganism (e.g., expression and/or biological activity of a protein, or production of a product) is made with reference to the same characteristic of a wild-type microorganism of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the microorganism is measured, as well as the type of assay used, the host microorganism that is evaluated, etc. As discussed above, equivalent conditions are conditions (e.g., culture conditions) which are similar, but not necessarily identical (e.g., some conservative changes in conditions can be tolerated), and which do not substantially change the effect on microbe growth or enzyme expression or biological activity as compared to a comparison made under the same conditions.

Preferably, a genetically modified microorganism that has a genetic modification that increases or decreases the activity of a given protein (e.g., an enzyme) has an increase or decrease, respectively, in the activity (e.g., expression, production and/or biological activity) of the protein, as compared to the activity of the wild-type protein in a wild-type microorganism, of at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, or any percentage, in whole integers between 5% and 100% (e.g., 6%, 7%, 8%, etc.). The same differences are preferred when comparing an isolated modified nucleic acid molecule or protein directly to the isolated wild-type nucleic acid molecule or protein (e.g., if the comparison is done in vitro as compared to in vivo).

In another aspect of the invention, a genetically modified microorganism that has a genetic modification that increases or decreases the activity of a given protein (e.g., an enzyme) has an increase or decrease, respectively, in the activity (e.g., expression, production and/or biological activity) of the protein, as compared to the activity of the wild-type protein in a wild-type microorganism, of at least about 2-fold, and more preferably at least about 5-fold, and more preferably at least about 10-fold, and more preferably about 20-fold, and more preferably at least about 30-fold, and more preferably at least about 40-fold, and more preferably at least about 50-fold, and more preferably at least about 75-fold, and more preferably at least about 100-fold, and more preferably at least about 125-fold, and more preferably at least about 150-fold, or any whole integer increment starting from at least about 2-fold (e.g., 3-fold, 4-fold, 5-fold, 6-fold, etc.).

The genetic modification of a microorganism to provide increased or decreased activity (including expression, specific activity, in vivo activity, etc.) preferably affects the activity of a glucosamine and/or N-acetylglucosamine biosynthetic pathway or amino sugar metabolic pathway in the microorganism, whether the pathway is endogenous and genetically modified, endogenous with the introduction of one or more recombinant nucleic acid molecules into the organism, or provided completely by recombinant technology. According to the present invention, to "affect the activity of a glucosamine and/or N-acetylglucosamine biosynthetic pathway" includes any genetic modification that causes any detectable or measurable change or modification in the glucosamine and/or N-acetylglucosamine biosynthetic pathway expressed by the organism as compared to in the absence of the genetic modification. A detectable change or modification in the glucosamine and/or N-acetylglucosamine biosynthetic pathway can include, but is not limited to, a detectable change in the production of at least one product in the glucosamine and/or N-acetylglucosamine biosynthetic pathway, or a detectable change in the production of intracellular and/or extracellular glucosamine or N-acetylglucosamine by the microorganism.

In one embodiment of the present invention, a genetic modification includes a modification of a nucleic acid sequence encoding a particular enzyme or other protein as described herein. Such a modification can be to the endogenous enzyme or protein, whereby a microorganism that naturally contains such a protein is genetically modified by, for example, classical mutagenesis and selection techniques and/or molecular genetic techniques, include genetic engineering techniques. Genetic engineering techniques can include, for example, using a targeting recombinant vector to delete a portion of an endogenous gene or to replace a portion of an endogenous gene with a heterologous sequence, such as a sequence encoding an improved enzyme or other protein or a different promoter that increases the expression of the endogenous enzyme or other protein. Genetic engineering techniques can also include overexpression of a gene using recombinant technology.

For example, a non-native promoter can be introduced upstream of at least one gene encoding an enzyme or other protein of interest in the amino sugar metabolic pathway described herein. Preferably the 5' upstream sequence of a endogenous gene is replaced by a constitutive promoter, an inducible promoter, or a promoter with optimal expression under the growth conditions used. This method is especially useful when the endogenous gene is not active or is not sufficiently active under the growth conditions used.

In another aspect of this embodiment of the invention, the genetic modification can include the introduction of a recombinant nucleic acid molecule encoding a enzyme or protein of interest into a host. The host can include: (1) a host cell that does not express the particular enzyme or protein, or (2) a host cell that does express the particular enzyme or protein, wherein the introduced recombinant nucleic acid molecule changes or enhances the activity of the enzyme or other protein in the microorganism. The present invention intends to encompass any genetically modified microorganism, wherein the microorganism comprises at least one modification suitable for a fermentation process to produce glucosamine or N-acetylglucosamine according to the present invention.

A genetically modified microorganism can be modified by recombinant technology, such as by introduction of an isolated nucleic acid molecule into a microorganism. For example, a genetically modified microorganism can be transfected with a recombinant nucleic acid molecule encoding a protein of interest, such as a protein for which increased expression is desired. The transfected nucleic acid molecule can remain extrachromosomal or can integrate into one or more sites within a chromosome of the transfected (i.e., recombinant) host cell in such a manner that its ability to be expressed is retained. Preferably, once a host cell of the present invention is transfected with a nucleic acid molecule, the nucleic acid molecule is integrated into the host cell genome. A significant advantage of integration is that the nucleic acid molecule is stably maintained in the cell. In a preferred embodiment, the integrated nucleic acid molecule is operatively linked to a transcription control sequence (described below) which can be induced to control expression of the nucleic acid molecule.

A nucleic acid molecule can be integrated into the genome of the host cell either by random or targeted integration. Such methods of integration are known in the art. For example, E. coli strain ATCC 47002 contains mutations that confer upon it an inability to maintain plasmids which contain a ColE1 origin of replication. When such plasmids are transferred to this strain, selection for genetic markers contained on the plasmid results in integration of the plasmid into the chromosome. This strain can be transformed, for example, with plasmids containing the gene of interest and a selectable marker flanked by the 5'- and 3'-termini of the E. coli lacZ gene. The lacZ sequences target the incoming DNA to the lacZ gene contained in the chromosome. Integration at the lacZ locus replaces the intact lacZ gene, which encodes the enzyme P-galactosidase, with a partial lacZ gene interrupted by the gene of interest. Successful integrants can be selected for P-galactosidase negativity. A genetically modified microorganism can also be produced by introducing nucleic acid molecules into a recipient cell genome by a method such as by using a transducing bacteriophage. The use of recombinant technology and transducing bacteriophage technology to produce several different genetically modified microorganism of the present invention is known in the art and is described in detail in the Examples section.

Vectors and methods were described by Hamilton et al. (1989, J. Bacteriol. 171:4617-4622) to make targeted gene deletion and gene integration in E. coli chromosome by temperature shift. The method was adapted to develop different glucosamine production E. coli strains. The protocols for gene integration include the following major steps. The first step is to clone the sequence of the target site and make an internal deletion and/or insert the foreign gene to be integrated at the deletion site. The second step is to subclone the fragment containing these sequences into a temperature sensitive integrative vector containing a temperature sensitive replication origin and an antibiotic selection marker. The third step is to transform the integrative vector into the E. coli host strain and select for clones with the entire plasmid integrated into the chromosome through single crossover recombination event under non-permissive temperature (42° C.). The fourth step is to grow the cells of selected clones in liquid culture at permissive temperature (30° C.). Cells with the integrated plasmid have a tendency to lose the plasmid. Cells that have lost the portion of the replication origin and antibiotic resistance gene or the entire plasmid will outgrow in the culture. Typically, this step was accomplished by inoculating a 50-ml LB medium with cells from a pool of two to ten clones and growing the culture for 24 hrs. The culture was passed to a fresh medium at a 1,000-fold dilution and grown for another period of 24 hrs. Fifth, cells were plated and clones that had lost the antibiotic resistance were selected. Gene specific selection procedures could be used, depending on the nature of integrated gene or deleted gene. Typically for screening clones, PCR was carried out using a primer set that could distinguish the clones with the intended change in the chromosome from its native form by the size of PCR products. Clones were confirmed by Southern Blot analysis using probes specific to the integrated or deleted DNA sequence.

It is to be understood that the present invention discloses a method comprising the use of a microorganism with an ability to produce commercially useful amounts of glucosamine and/or N-acetylglucosamine in a fermentation process (i.e., preferably an enhanced ability to produce glucosamine and/or N-acetylglucosamine compared to a wild-type microorganism cultured under the same conditions). As used herein, a fermentation process is a process of culturing cells, such as microorganisms, in a container, bioreactor, fermenter, or other suitable culture chamber, in order to produce a product from the cells (i.e., the cells produce a product during the culture process). The product is typically a product useful for experimental or commercial purposes. The fermentation method of the present invention is achieved by the genetic modification of one or more genes encoding a protein involved in an amino sugar metabolic pathway which results in the production (expression) of a protein having an altered (e.g., increased or decreased) function as compared to the corresponding wild-type protein. Such an altered function enhances the ability of the genetically engineered microorganism to produce glucosamine and/or N-acetylglucosamine. It will be appreciated by those of skill in the art that production of genetically modified microorganisms having a particular altered function as described elsewhere herein (e.g., an enhanced ability to produce glucosamine-6-phosphate, glucosamine-1-phosphate, N-acetylglucosamine-6-phosphate and/or N-acetylglucosamine-1-phosphate) such as by the specific selection techniques described in the Examples, can produce many organisms meeting the given functional requirement, albeit by virtue of a variety of different genetic modifications. For example, different random nucleotide deletions and/or substitutions in a given nucleic acid sequence may all give rise to the same phenotypic result (e.g., decreased action of the protein encoded by the sequence). The present invention contemplates any such genetic modification which results in the production of a microorganism having the characteristics set forth herein.

According to one embodiment of the present invention, a genetically modified microorganism includes a microorganism which has an enhanced ability to synthesize glucosamine-6-phosphate, glucosamine-1-phosphate, N-acetylglucosamine-6-phosphate and/or N-acetylglucosamine-1-phosphate. According to the present invention, "an enhanced ability to synthesize" a product refers to any enhancement, or up-regulation, in an amino sugar metabolic pathway related to the synthesis of the product such that the microorganism produces an increased amount of the product compared to the wild-type microorganism cultured under the same conditions.

In one aspect of the invention, a genetically modified microorganism useful in a fermentation method produces at least about 1 g/L, and preferably at least about 5 g/L, and more preferably, at least about −10 g/L, and even more preferably, at least about 20 g/L, and even more preferably, at least about 30 g/L, and even more preferably, at least about 40 g/L, and even more preferably, at least about 50 g/L, and even more preferably, at least about 60 g/L, and even more preferably, at least about 70 g/L, and even more preferably, at least about 80 g/L, and even more preferably, at least about 90 g/L, and even more preferably, at least about 100 g/L, and even more preferably, at least about 110 g/L, and even more preferably, at least about 120 g/L, and even more preferably at least about 150 g/L, and even more preferably at least about 180 g/L, or any higher amount, or any amount between at least about 1 g/L and at least about 500 g/L, in whole integers (e.g., 2 g/L, 3 g/L, etc.) of: glucosamine, glucosamine-6-phosphate, glucosamine-1-phosphate, N-acetylglucosamine, N-acetylglucosamine-6-phosphate and/or N-acetylglucosamine-1-phosphate, when cultured under any suitable culture conditions, and particularly under any of the culture conditions as described herein. In another aspect, a genetically modified microorganism useful in a fermentation method of the present invention produces at least about 2-fold more glucosamine, glucosamine-6-phosphate, glucosamine-1-phosphate, N-acetylglucosamine, N-acetylglucosamine-6-phosphate and/or N-acetylglucosamine-1-phosphate, and preferably at least about 5-fold, and more preferably at least about 10-fold, and more preferably at least about 25-fold, and more preferably at least about 50-fold, and even more preferably at least about 100-fold, and even more preferably, at least about 200-fold, including any fold increase between at least 2-fold and at least 200-fold, in whole integer increments (i.e., at least 3-fold, at least 4-fold, etc.), more glucosamine, glucosamine-6-phosphate, glucosamine-1-phosphate, N-acetylglucosamine, N-acetylglucosamine-6-phosphate and/or N-acetylglucosamine-1-phosphate than a wild-type (i.e., non-modified, naturally occurring) microorganism of the same species (and preferably strain) cultured under the same conditions or equivalent conditions as the genetically modified microorganism. A number of specific microorganisms having such characteristics are identified in the Examples section.

In another aspect, a genetically modified microorganism useful in a fermentation method of the present invention produces at least about 1 g/L of glucosamine when cultured for about 24 hours at 37° C. to a cell density of at least about 8 g/L by dry cell weight, in a pH 7.0 fermentation medium comprising: 14 g/L K$_2$HPO$_4$, 16 g/L KH$_2$PO$_4$, 1 g/L Na$_3$Citrate.2H$_2$O, 5 g/L (NH$_4$)$_2$SO$_4$, 20 g/L glucose, 10 mM MgSO$_4$, 1 mM CaCl$_2$, and 1 mM IPTG. In another aspect, a genetically modified microorganism useful in a fermentation method of the present invention produces at least about 1 g/L of glucosamine when cultured for about 10 to about 60 hours at from about 28° C. to about 37° C. to a cell density of at least about 8 g/L by dry cell weight, in a pH 7.0 fermentation medium comprising: 14 g/L K$_2$HPO$_4$, 16 g/L KH$_2$PO$_4$, 1 g/L Na$_3$Citrate.2H$_2$O, 5 g/L (NH$_4$)$_2$SO$_4$, 20 g/L glucose, 10 mM MgSO$_4$, 1 mM CaCl$_2$, and from about 0.2 mM to about 1 mM IPTG. In a preferred embodiment, the amount of IPTG is about 0.2 mM.

A microorganism to be used in the fermentation method of the present invention (e.g., a host cell or production organism) is any microorganism (e.g., a bacterium, a protist, an alga, a fungus, or other microbe), and is most preferably a bacterium, a yeast or a fungus. Suitable bacterial genera include, but are not limited to, *Escherichia, Bacillus, Lactobacillus, Pseudomonas* and *Streptomyces*. Suitable bacterial species include, but are not limited to, *Escherichia coli, Bacillus subtilis, Bacillus licheniformis, Lactobacillus brevis, Pseudomonas aeruginosa* and *Streptomyces lividans*. Suitable genera of yeast include, but are not limited to, *Saccharomyces, Schizosaccharomyces, Candida, Hansenula, Pichia, Kluyveromyces,* and *Phaffia*. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus* and *Phaffia rhodozyma*. Suitable fungal genera include, but are not limited to, *Aspergillus, Absidia, Rhizopus, Chrysosporium, Neurospora* and *Trichoderma*. Suitable fungal species include, but are not limited to, *Aspergillus niger, A. nidulans, Absidia coerulea, Rhizopus oryzae, Chrysosporium lucknowense, Neurospora crassa, N. intermedia* and *Trichoderm reesei*. Particularly preferred strains of *Escherichia coli* include K-12, B and W, and most preferably, K-12. Although *Escherichia coli* is one preferred bacteria and is used to exemplify various embodiments of the invention, it is to be understood that any microorganism that produces glucosamine and/or N-acetylglucosamine, and can be genetically modified to enhance production of glucosamine and/or N-acetylglucosamine can be used in the method of the present invention. A microorganism for use in the fermentation method of the present invention can also be referred to as a production organism.

In a preferred embodiment, the genetically modified microorganism is a bacterium or a yeast, and more preferably, a bacterium of the genus Escherichia, and even more preferably, *Escherichia coli*. A genetically modified *Escherichia coli* preferably has a modification in a gene which includes, but is not limited to, nagA, nagB, nagC, nagD, nagE, manXYZ, glmM, pfkB, pfkA, glmU, glmS, GNA1, ptsG or a phosphatase gene. In another embodiment, such a genetically modified *Escherichia coli* has a deletion of nag regulon genes, and in yet another embodiment, a deletion of nag regulon genes and a genetic modification in manXYZ genes such that the proteins encoded by the manXYZ genes have decreased action.

According to the present invention, reference to a particular enzyme or other protein herein refers to any protein that has at least one biological activity of the wild-type reference protein, including full-length proteins, fusion proteins, or any homologue of a naturally occurring protein (including natural allelic variants, fragments, related proteins from different organisms and synthetically or artificially derived variants (homologues)). A homologue (mutant, variant, modified form) of a reference protein includes proteins which differ from the naturally occurring reference protein in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). One preferred homologue is a biologically active fragment of a naturally occurring protein. Other preferred homologues of naturally occurring proteins useful in the present invention are described in detail below. Therefore, an isolated nucleic acid molecule of the present invention can encode the translation product of any specified protein open reading frame, domain, biologically active fragment thereof, or any homologue of a naturally occurring protein or domain which has biological activity.

An isolated protein, according to the present invention, is a protein that has been removed from its natural milieu (i.e., that has been subject to human manipulation) and can include purified proteins, partially purified proteins, recombinantly produced proteins, and synthetically produced proteins, for example. Several recombinantly produced proteins are described in the Examples section. As such, "isolated" does not reflect the extent to which the protein has been purified. In addition, and by way of example by referencing a hypothetical protein called "protein X" (i.e., any enzyme or protein of used in the invention can be substituted for the term), an "E. coli protein X" refers to a protein X (including a homologue of a naturally occurring protein X) from E. coli or to a protein X that has been otherwise produced from the knowledge of the structure (e.g., sequence) and perhaps the function of a naturally occurring protein X from E. coli. In other words, an E. coli protein X includes any protein X that has substantially similar structure and function of a naturally occurring protein X from E. coli or that is a biologically active (i.e., has biological activity) homologue of a naturally occurring protein X from E. coli as described in detail herein. As such, an E. coli protein X can include purified, partially purified, recombinant, mutated/modified and synthetic proteins. This discussion applies similarly to protein X from other microorganisms as disclosed herein.

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications in homologues, as compared to the wild-type protein, either agonize, antagonize, or do not substantially change, the basic biological activity of the homologue as compared to the naturally occurring protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). The biological activity of the enzymes and proteins used herein have been described in detail above. For example, the enzyme generally referred to herein as "glucosamine-6-phosphate synthase" catalyzes the formation of glucosamine-6-phosphate and glutamate from fructose-6-phosphate and glutamine. Modifications of a protein, such as in a homologue, may result in proteins having the same level of biological activity as the naturally occurring protein, or in proteins having decreased or increased biological activity as compared to the naturally occurring protein. Modifications which result in a decrease in expression or a decrease in the activity of the protein, can be referred to as inactivation (complete or partial), down-regulation, or decreased action of a protein. Similarly, modifications which result in an increase in expression or an increase in the activity of the protein, can be referred to as amplification, overproduction, activation, enhancement, up-regulation or increased action of a protein. A functional subunit, homologue, or fragment of a given protein is preferably capable of performing substantially the same (e.g., at least qualitatively the same) biological function of the native protein (i.e., has biological activity). It is noted that a functional subunit, fragment or other homologue of a protein is not necessarily required to have the same level of biological activity as the reference or wild-type protein in order to be considered to have the biological activity of the reference or wild-type protein (i.e., a qualitative similarity is sufficient). In one embodiment, it is preferred that modifications in homologues as compared to the wild-type protein do not substantially decrease the basic biological activity of the protein as compared to the naturally occurring protein. Increased biological activity (e.g., increased enzyme activity) may be desirable in a homologue. Homologues may also have differences in characteristics other than the functional, or enzymatic, activity of the protein as compared to the naturally occurring form, such as a decreased sensitivity to inhibition by certain compounds as compared to the naturally occurring protein.

According to the present invention, an isolated protein, including a biologically active homologue or fragment thereof, has at least one characteristic of biological activity of the wild-type, or naturally occurring protein. Methods of detecting and measuring protein expression and biological activity include, but are not limited to, measurement of transcription of the protein, measurement of translation of the protein, measurement of cellular localization of the protein, measurement of binding or association of the protein with another protein, measurement of binding or association of the gene encoding the protein regulatory sequences to a protein or other nucleic acid, measurement of an increase, decrease or induction of biological activity of the protein in a cell that expresses the protein.

Methods to measure protein expression levels of a protein according to the invention include, but are not limited to: western blotting, immunocytochemistry, flow cytometry or other immunologic-based assays; assays based on a property of the protein including but not limited to, ligand binding, enzyme activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365: 343-347 (1993)). Other suitable assays for measuring the binding of one protein to another include, for example, immunoassays such as enzyme linked immunoabsorbent assays (ELISA) and radioimmunoassays (RIA), or determination of binding by monitoring the change in the spectroscopic or optical properties of the proteins through fluorescence, UV absorption, circular dichrosim, or nuclear magnetic resonance (NMR). Assays for measuring the enzymatic activity of a protein used in the invention are well known in the art and many are described in the Examples section.

Many of the enzymes and proteins involved in the amino sugar metabolic pathway and which represent desirable targets for modification and use in the fermentation processes described herein have been described above in terms of function and amino acid sequence (and nucleic acid sequence encoding the same) of representative wild-type or mutant proteins. In one embodiment of the invention, homologues of a given protein (which can include related proteins from other organisms or modified forms of the given protein) are encompassed for use in a genetically modified organism of the invention. Homologues of a proteins encompassed by the present invention can comprise an amino acid sequence that is at least about 35% identical, and more preferably at least about 40% identical, and more preferably at least about 45% identical, and more preferably at least about 50% identical, and more preferably at least about 55% identical, and more preferably at least about 60% identical, and more preferably at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical, or any percent identity between 35% and 99%, in whole integers (i.e., 36%, 37%, etc.) to an amino acid sequence disclosed herein that represents the amino acid sequence of an enzyme or protein that can be modified or overexpressed according to the invention. Preferably, the amino acid sequence of the homologue has a biological activity of the wild-type or reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer; A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett*. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
  Reward for match=1
  Penalty for mismatch=−2
  Open gap (5) and extension gap (2) penalties
  gap x_dropoff (50) expect (10) word size (11) filter (on)

For blastp, using 0 BLOSUM62 matrix:
  Open gap (11) and extension gap (1) penalties
  gap x_dropoff (50) expect (10) word size (3) filter (on).

A protein referenced and/or used in the present invention can also include proteins having an amino acid sequence comprising at least 30 contiguous amino acid residues of the amino acid sequence of the reference protein (i.e., 30 contiguous amino acid residues having 100% identity with 30 contiguous amino acids of either of the above-identified sequences). In a preferred embodiment, a protein referenced and/or used in the present invention includes proteins having amino acid sequences comprising at least 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350 contiguous amino acid residues of the amino acid sequence of the reference protein. In one embodiment, such a protein has a biological activity of the reference protein.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, a protein referenced or used in the present invention, including a homologue, includes a protein having an amino acid sequence that is sufficiently similar to the naturally occurring protein amino acid sequence that a nucleic acid sequence encoding the homologue is capable of hybridizing under moderate, high, or very high stringency conditions (described below) to (i.e., with) a nucleic acid molecule encoding the naturally occurring protein (i.e., to the complement of the nucleic acid strand encoding the naturally occurring protein). Preferably, a given homologue is encoded by a nucleic acid sequence that hybridizes under moderate, high or very high stringency conditions to the complement of a nucleic acid sequence that encodes the wild-type or reference protein.

A nucleic acid sequence complement of reference nucleic acid sequence refers to the nucleic acid sequence of the nucleic acid strand that is complementary to the strand which encodes a protein. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes an amino acid sequence of a protein, and/or with the complement of the nucleic acid sequence that encodes such protein. Methods to deduce a complementary sequence are known to those skilled in the art. It should be noted that since amino acid sequencing and nucleic acid sequencing technologies are not entirely error-free, the sequences presented herein, at best, represent apparent sequences of the referenced proteins of the present invention.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem*. 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, T$_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated T$_m$ of a particular hybrid, and wash conditions typically include a combination of salt and temperature conditions that are approximately 12-20° C. below the calculated T$_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Homologues can, in one embodiment, be the result of natural allelic variation or natural mutation. Homologues of a given protein can also be naturally occurring proteins having substantially the same function from different organisms with at least some structural similarity (e.g., at least about 35% identity) to one another at the nucleic acid or amino acid level as described herein. Homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding a given protein is a gene that occurs at essentially the same locus (or loci) in the genome as the gene which encodes the given protein, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

The minimum size of a protein and/or homologue of the present invention is, in one aspect, a size sufficient to have the desired biological activity of the protein. In another embodiment, a protein of the present invention is at least 30 amino acids long, and more preferably, at least about 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350 amino acids long. There is no limit, other than a practical limit, on the maximum size of such a protein in that the protein can include a portion of a given protein or a full-length protein, plus additional sequence (e.g., a fusion protein sequence), if desired. Suitable fusion segments for use with the present invention include, but are not limited to, segments that can: enhance a protein's stability; provide other desirable biological activity (e.g., a second enzyme function); and/or assist with the purification of a protein (e.g., by affinity chromatography).

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

Embodiments of the present invention include the use and/or manipulation of nucleic acid molecules that encode enzymes or other proteins in the amino sugar metabolic pathways described herein. A nucleic acid molecule of the present invention includes a nucleic acid molecule comprising, consisting essentially of, or consisting of, a nucleic acid sequence encoding any of the enzymes or other proteins described herein.

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid-molecule has been purified, but indicates that the molecule does not include an entire genome or an entire chromosome in which the nucleic acid molecule is found in nature. An isolated nucleic acid molecule can include a gene, such as a glucosamine-6-phosphate synthase gene described herein. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., are heterologous sequences). Isolated nucleic acid molecules can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on protein biological activity. Allelic variants and protein homologues (e.g., proteins encoded by nucleic acid homologues) have been discussed in detail above.

A nucleic acid molecule homologue can be produced using a number of methods known to those skilled in the art (see, for example, Sambrook et al., ibid.). For example, nucleic acid molecules can be modified using a variety of techniques including, but not limited to, classical mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to encode a protein having the desired biological activity, or sufficient to form a probe or oligonucleotide primer that is capable of forming a stable hybrid with the complementary sequence of a nucleic acid molecule encoding the natural protein (e.g., under moderate, high or very high stringency conditions, and preferably under very high stringency conditions). As such, the size of a nucleic acid molecule of the present invention can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein encoding sequence, a nucleic acid sequence encoding a full-length protein (including a complete gene).

Knowing the nucleic acid sequences of certain nucleic acid molecules of the present invention, and particularly any of the nucleic acid molecules described in detail herein, allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes of to screen appropriate libraries or DNA and PCR amplification of appropriate libraries or DNA using oligonucleotide primers. Preferred libraries to screen or from which to amplify nucleic acid molecule include bacterial and yeast genomic DNA libraries, and in particular, *Escherichia coli* genomic DNA libraries. Techniques to clone and amplify genes are disclosed, for example, in Sambrook et al., ibid.

Another embodiment of the present invention includes a recombinant nucleic acid molecule comprising a recombinant vector and a nucleic acid molecule comprising a nucleic acid sequence encoding an amino acid sequence having a biological activity of any of the enzymes or other proteins in an amino sugar metabolic pathway as described herein. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to bind to the target gene such that the target gene and the insert undergo homologous recombination, whereby the endogenous target gene is deleted, inactivated or attenuated (i.e., by at least a portion of the endogenous target gene being mutated or deleted).

Typically, a recombinant nucleic acid molecule includes at least one nucleic acid molecule of the present invention operatively linked to one or more expression control sequences, including transcription control sequences and translation control sequences. As used herein, the phrase "recombinant molecule" or "recombinant nucleic acid molecule" primarily refers to a nucleic acid molecule or nucleic acid sequence operatively linked to an expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence (e.g., a transcription control sequence and/or a translation-control sequence) in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast, or into plant cells. In microbial systems and plant systems, the term "transformation" is used to describe an inherited change due to the acquisition of exogenous nucleic acids by the microorganism or plant and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

A recombinant cell is preferably produced by transforming a bacterial or yeast cell (i.e., a host cell) with one or more recombinant molecules, each comprising one or more nucleic acid molecules operatively linked to an expression vector containing one or more transcription control sequences. The phrase, operatively linked, refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. In the present invention, expression vectors are typically plasmids. Expression vectors of the present invention include any vectors that function (i.e., direct gene expression) in a yeast host cell or a bacterial host cell, preferably an *Escherichia coli* host cell. Preferred recombinant cells of the present invention are set forth in the Examples section.

Nucleic acid molecules of the present invention can be operatively linked to expression vectors containing regulatory sequences such as transcription control sequences translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in yeast or bacterial cells and preferably, *Escherichia coli*. A variety of such transcription control sequences are known to those skilled in the art.

It is preferred that the recombinant nucleic acid molecules comprising nucleic acid sequences encoding various enzymes and proteins described herein (including homologues thereof) be cloned under control of an artificial promoter. The promoter can be any suitable promoter that will provide a level of gene expression required to maintain a sufficient level of the encoded protein in the production organism. Suitable promoters can be promoters inducible by different chemicals (such as lactose, galactose, maltose and salt) or changes of growth conditions (such as temperature). Use of inducible promoter can lead to an optimal performance of gene expression and fermentation process. Preferred promoters can also be constitutive promoters, since the need for addition of expensive inducers is therefore obviated. Such promoters include normally inducible promoter systems that have been made functionally constitutive or "leaky" by genetic modification, such as by using a weaker, mutant repressor gene. Particularly preferred promoters to be used are lac, $P_L$ and T7. The gene dosage (copy number) can be varied according to the requirements for maximum product formation. In one embodiment, the recombinant genes are integrated into the host genome.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present, invention include, but are not limited to, operatively linking nucleic acid molecules to high-copy number plasmids, integration of the nucleic acid molecules into the host cell chromosome, addition of vector stability sequences to plasmids, substitutions or modifications of transcription control signals (e.g., promoters, operators, enhancers), substitutions or modifications of translational control signals, modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein. Such modifications are described in detail in the Examples section.

One or more recombinant molecules of the present invention can be used to produce an encoded product of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable cells are any microorganisms (e.g., a host cell or production organism) is any microorganism (e.g., a bacterium, a protist, an alga, a fungus, or other microbe), and is most preferably a bacterium, a yeast or a fungus. Suitable bacterial genera include, but are not limited to, *Escherichia, Bacillus, Lactobacillus, Pseudomonas* and *Streptomyces*. Suitable bacterial species include, but are not limited to, *Escherichia coli, Bacillus subtilis, Bacillus licheniformis, Lactobacillus brevis, Pseudomonas aeruginosa* and *Streptomyces lividans*. Suitable genera of yeast include, but are not limited to, *Saccharomyces, Schizosaccharomyces, Candida, Hansenula, Pichia, Kluyveromyces*, and *Phaffia*. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus* and *Phaffia rhodozyma*. Suitable fungal genera include, but are not limited to, *Aspergillus, Absidia, Rhizopus, Chrysosporium, Neurospora* and *Trichoderma*. Suitable fungal species include, but are not limited to, *Aspergillus niger, A. nidulans, Absidia coerulea, Rhizopus oryzae, Chrysosporium lucknowense, Neurospora crassa, N. intermedia* and *Trichoderm reesei*. Host cells can be either untransfected cells or cells that are already transfected with at least one other recombinant nucleic acid molecule.

Additional embodiments of the present invention include any of the genetically modified microorganisms described herein and microorganisms having the identifying characteristics of the microorganisms specifically identified in the Examples. Such identifying characteristics can include any or all genotypic and/or phenotypic characteristics of the microorganisms in the Examples, including their abilities to produce glucosamine and/or N-acetylglucosamine.

As noted above, in the method for production of glucosamine and/or N-acetylglucosamine of the present invention, a microorganism having a genetically modified amino sugar metabolic pathway is cultured in a fermentation medium for production of glucosamine and/or N-acetylglucosamine. An appropriate, or effective, fermentation medium refers to any medium in which a genetically modified microorganism of the present invention, when cultured, is capable of producing glucosamine and/or N-acetylglucosamine. Such a medium is typically an aqueous medium comprising assimilable carbon, nitrogen and phosphate sources. Such a medium can also include appropriate salts, minerals, metals and other nutrients. One advantage of the genetic modifications to a microorganism described herein is that although such genetic modifications significantly alter the metabolism of amino sugars, they do not create any nutritional requirements for the production organism. Thus, a minimal-salts medium containing glucose, fructose, lactose, glycerol or a mixture of two or more different compounds as the sole carbon source is preferably used as the fermentation medium. The use of a minimal-salts-glucose medium is the most preferred medium for the glucosamine and/or N-acetylglucosamine fermentation and it will also facilitate recovery and purification of the products. In one aspect, yeast extract is a component of the medium.

Microorganisms of the present invention can be cultured in conventional fermentation bioreactors. The microorganisms can be cultured by any fermentation process which includes, but is not limited to, batch, fed-batch, cell recycle, and continuous fermentation. Preferably, microorganisms of the present invention are grown by batch or fed-batch fermentation processes.

In one embodiment of the present invention, before inoculation, the fermentation medium is brought up to the desired temperature, typically from about 20° C. to about 45° C., preferably from about 25° C. to about 45° C., or 25° C. to about 40° C., with temperatures of from about 25° C. to about 37° C., and in some embodiments, about 30° C. or about 37° C. being more preferred. Fermentation conditions can include culturing the microorganisms of the invention at any temperature between about 20° C. and about 40° C., in whole increments (i.e., 21° C., 22° C., etc.). It is noted that the optimum temperature for growth and glucosamine and/or N-acetylglucosamine production by a microorganism of the present invention can vary according to a variety of factors. For example, the selection of a particular promoter for expression of a recombinant nucleic acid molecule in the microorganism can affect the optimum culture temperature. One of ordinary skill in the art can readily determine the optimum growth and glucosamine and/or N-acetylglucosamine production temperature for any microorganism of the present invention using standard techniques, such as those described in the Examples section for one microorganism of the present invention.

The medium is inoculated with an actively growing culture of the genetically modified microorganism in an amount sufficient to produce, after a reasonable growth period, a high cell density. The cells are grown to a cell density of at least about 10 g/l, preferably between about 10 g/l and about 40 g/l, and more preferably at least about 40 g/l. This process typically requires about 10-60 hours.

Sufficient oxygen must be added to the medium during the course of the fermentation to maintain cell growth during the initial cell growth and to maintain metabolism, and glucosamine and/or N-acetylglucosamine production. Oxygen is conveniently provided by agitation and aeration of the medium. Conventional methods, such as stirring or shaking, may be used to agitate and aerate the medium. Preferably the oxygen concentration in the medium is greater than about 15% of the saturation value (i.e., the solubility of oxygen in the medium at atmospheric pressure and about 30-40° C.) and more preferably greater than about 20% of the saturation value, although excursions to lower concentrations may occur if fermentation is not adversely affected. It is further understood that the oxygen level can be allowed to reach very low levels for any appropriate amount of time during the fermentation if it enhances stability and formation of glucosamine and/or N-acetylglucosamine during the production process. The oxygen concentration of the medium can be monitored by conventional methods, such as with an oxygen electrode. Other sources of oxygen, such as undiluted oxygen gas and oxygen gas diluted with inert gas other than nitrogen, can be used.

Since the production of glucosamine and/or N-acetylglucosamine by fermentation is preferably based on using glucose as the sole carbon source, in a preferred embodiment, in *Escherichia coli*, the PEP:glucose PTS will be induced. Accordingly, even in the absence of a functional EIIM,P/III$^{Man}$ of the PEP:mannose PTS (e.g., in an *Escherichia coli* having a manXYZ mutation), the product, glucosamine, will still be taken up by the cells via the induced glucose transport system. In the presence of excess glucose, however, uptake of glucosamine is severely repressed. Thus, it is one embodiment of the present invention to prevent uptake of the glucosamine product by maintaining an excess of glucose in the fermentation bioreactor. As used herein, "an excess" of glucose refers to an amount of glucose above that which is required to maintain the growth of the microorganism under normal conditions, such as the culturing conditions described above.

Preferably, the glucose concentration is maintained at a concentration of from about 0.05% to about 15% weight/volume of the fermentation medium. In another embodiment, the glucose concentration is maintained at a concentration of from about 0.5 g/L to about 150 g/L of the fermentation medium, and even more preferably, from about 5 g/L to about 100 g/L of the fermentation medium, and even more preferably from about 5 g/L to about 20 g/L. In one embodiment, the glucose concentration of the fermentation medium is monitored by any suitable method (e.g., by using glucose test strips), and when the glucose concentration is at or near depletion, additional glucose can be added to the medium. In another embodiment, the glucose concentration is maintained by semi-continuous or continuous feeding of the fermentation medium. The parameters disclosed herein for glucose can be applied to any carbon source used in the fermentation medium of the present invention. It is further understood that the carbon source can be allowed to reach undetectable levels for any appropriate amount of time during the fermentation if it enhances the glucosamine and/or N-acetylglucosamine production process. Other carbon sources that can be used in the fermentation method of the present invention, include, but are not limited to, fructose, a pentose sugar, lactose and gluconic acid. Pentose sugars include, but are not limited to, ribose, xylose, and arabinose. In one aspect, the step of culturing is performed in a fermentation medium comprising glucose and ribose.

It is a further embodiment of the present invention to supplement and/or control other components and parameters of the fermentation medium, as necessary to maintain and/or enhance the production and stability of glucosamine and/or N-acetylglucosamine. For example, in one embodiment, the fermentation medium includes ammonium sulfate, and the ammonium sulfate concentration in the culture medium is supplemented by the addition of excess ammonium sulfate. Preferably, the amount of ammonium sulfate is maintained at a level of from about 0.1% to about 1% (weight/volume) in the fermentation medium, and preferably, at about 0.5%. In yet another embodiment, the pH of the fermentation medium is monitored for fluctuations in pH. In the fermentation method of the present invention, the pH is preferably maintained at a pH of from about pH 4.0 to about pH 8.0, an in one aspect, at a pH of from about pH 4 to about pH 7.5, and in another aspect, at a pH of from about pH 6.7 to about pH 7.5, and in another embodiment, at a pH of from about pH 4.5 to about pH 5. While preferred embodiments are described above, the fermentation process can be conducted at any pH between pH 4 and pH 8, in increments of 0.1 (i.e., pH 4.1, pH 4.2, pH 4.3, etc.). In the method of the present invention, if the starting pH of the fermentation medium is pH 7.0, by way of example, the pH of the fermentation medium is monitored for significant variations from pH 7.0, and is adjusted accordingly, for example, by the addition of sodium hydroxide. Since the optimal pH for stability and formation rates of glucosamine and/or N-acetylglucosamine can be different from the optimal pH for cell growth, a protocol of two phases (or more than two phases) can be used. With such protocols, cells are initially grown at a pH optimal for fast production of biomass, then a different pH is used to maximize synthesis of glucosamine and/or N-acetylglucosamine while minimizing degradation of glucosamine and/or N-acetylglucosamine.

A further embodiment of the present invention is to redirect carbon flux from acetate production to the production of less toxic byproducts. By such methods, problems of toxicity associated with an excess of glucose in the fermentation medium can be avoided. Methods to redirect carbon flux from acetate production are known in the art.

In a batch, fed-batch and/or continuous fermentation-process of the present invention, fermentation is continued until the formation of glucosamine and/or N-acetylglucosamine, as evidenced by the accumulation of extracellular glucosamine and/or N-acetylglucosamine, essentially ceases. The total fermentation time is typically from about 40 to about 60 hours, and more preferably, about 48 hours. In a continuous fermentation process, glucosamine and/or N-acetylglucosamine can be removed from the bioreactor as it accumulates in the medium. The method of the present invention results in production of a product which can include intracellular glucosamine-6-phosphate, glucosamine-1-phosphate, N-acetylglucosamine-6-phosphate, N-acetylglucosamine-1-phosphate, N-acetylglucosamine and/or glucosamine; or extracellular glucosamine or N-acetylglucosamine.

For glucosamine and N-acetylglucosamine synthesis, different genes were overexpressed using the E. coli pET expression system. Gene expression is inducible by IPTG and lactose. The cost of IPTG would make glucosamine manufacture prohibitively expensive. Therefore, the use of IPTG would ideally be eliminated from the fermentation process. Lactose is relatively inexpensive and can be used in large scale production process. For lactose induction, lactose needs first to be converted to allolactose, the true inducer, by β-galactosidase in the cell. With glucosamine production strains such as 2123-54, lactose could not be used as inducer since the strain is negative for β-galactosidase. This was due to the deletion and disruption of the lacZ gene by the insertion of T7-glmS*54 expression cassette at the locus.

In principle, several different methods could be used to eliminate the dependence on IPTG. One approach illustrated in the present invention is to restore the lacZ gene. This was accomplished by integrating the T7-glmS*54 expression cassette at a different site other than lacZ in the chromosome;

Integration at the galK site would leave the lacZ gene intact. Lac⁺ strains are potentially inducible by lactose, which is much less expensive than IPTG. The galK site was chosen for integration of the T7-glmS*54 expression cassette because the integrant stains would also be Gal⁻. It was reported that in such strains galactose could be used as an inducer for lac promoters. Therefore, in addition to induction by allolactose, galactose generated through lactose hydrolysis could further enhance the induction. This maybe beneficial when a sub-optimal amount of lactose was used in the glucosamine production process. Integration could also be at any other site where an insertion would not cause any negative impact on cell growth and N-acetylglucosamine or/glucosamine production.

Lactose induction is subject to glucose repression. Glucosamine production did not occur when a high level of glucose was present in the culture. However, once glucose was consumed, lactose was utilized and glucosamine production was induced. The ratio of glucose versus lactose was shown to affect enzyme expression and glucosamine/N-acetylglucosamine production. Glucose repression takes place by repressing the native lac operon. In the presence of glucose, the synthesis of lactose transporter (LacY) and β-galactosidase (LacZ) were repressed, thus few inducer molecules (allolactose and galactose) were produced for the induction of T7 RNA polymerase. The detailed mechanism of glucose repression is still a subject of investigation. It appears that glucose repression acts on two levels. One level of repression is through the cAMP mediated action on the lac promoter sequence. The other is through the inhibition of lactose uptake, which is caused by glucose transporter proteins, i.e. enzyme IIA$^{Glc}$ (encoded by the crr gene) and IICB$^{Glc}$ (encoded by the ptsG gene). The lacUV5 promoter is not sensitive to glucose repression, but exclusion of lactose (the inducer) from entering the cells prevents induction.

Glucose repression could be minimized by using optimized growth and induction protocols. Different genetic modifications could also be introduced to minimize glucose repression. One approach was to replace the native lac promoter in the lac operon by the lacUV5 promoter, which is believed to not be repressed by glucose. Glucose repression could also be minimized by genetic modifications of the crr gene. Another approach was to delete one of the lacI repressor genes. In some glucosamine and N-acetylglucosamine production E. coli strains, there are two copies of lacI repressor gene, one in the native lac operon, the other in the DE3 element. Deletion of either lacI gene increased the resistance to glucose repression and glucosamine/N-acetylglucosamine production. Since lactose is transported into the cells through the lactose permease encoded by lacy, lactose induction could be affected by lacY over-expression.

Glucosamine and or N-acetylglucosamine levels are not only determined by the rate of synthesis but also by the rate of cellular metabolism and degradation if the product is not stable under the fermentation conditions. As disclosed in the present invention, glucosamine was found to be very unstable at the typical pH range used for E. coli growth. Glucosamine and or its degradation products also caused toxic effects on strain 7107-18. Toxicity was observed even when glucosamine at concentration as low as 20 g l⁻¹ was pre-incubated in the medium (pH 7.0) for 3.5 hrs prior to cell inoculation. The toxicity was attributed to at least partially to GlcN degradation products in media with a starting pH of 7.0. GlcN is more stable at lower pH, glucosamine is not degraded at pH 4.7 or below.

For developing an economic process, glucosamine synthesis must be maximized while product degradation minimized. In addition, a GlcN production protocol operated in fermentors at relatively low pH would not only preserve the synthesized GlcN, this process would also protect the cells by reducing the concentration of toxic breakdown products. These benefits must be balanced against the reduced growth rate and metabolic activity of cells grown this way. Continued GlcN synthesis requires the constant generation of energy in the cells, and cells growing slowly at these lower pHs may not be able to generate enough of the energy required.

Generally, *E. coli* grows very slowly at pH lower than 6-7. It would be useful to isolate *E. coli* mutants that exhibit improved growth characteristics at low pH. Alternatively, an enhanced glucosamine synthesis pathway could be engineered in other bacteria and yeast species that normally grow under low pH conditions. For example, *Saccharomyces cerevisiae* grow optimally at between pH 4 and pH 5.

A novel strategy was developed to overcome the problem of product degradation. The glucosamine synthesis pathway in *E. coli* was extended by over-expressing glucosamine-6-P N-acetyltransferase (GNA1) which leads to the synthesis of N-acetylglucosamine-6-P. With this strain, it could be demonstrated that N-acetylglucosamine-6-P was produced and secreted efficiently to the medium as N-acetylglucosamine. N-acetylglucosamine is very stable over wide ranges of pH and temperature. The product can be easily converted back to glucosamine using mild acid conditions. By using this strategy, the titer of N-acetylglucosamine was elevated several-fold higher than in glucosamine production strain. N-acetylglucosamine was also recovered as a final product.

Several factors may contribute to the high titer of N-acetylglucosamine production in the simple mineral medium. The first factor is the stability of N-acetylglucosamine. This does not only preserve the product but also avoids the toxic effects of glucosamine degradation products. Secondly, the N-acetylation step serves as a strong force to pull the pathway flux to this destination. It is interesting to note that when NagB enzyme was overexpressed in the absence of GlmS and GNA1 enzymes, it only functions to the degree sufficient to provide amino sugar for cell survival and growth. When GNA1 enzyme was co-expressed with NagB, it resulted in multi-gram level production of N-acetylglucosamine, demonstrating the driving power of the acetylation reaction in the pathway. Thirdly, the synthesis of N-acetylglucosamine utilizes acetyl-CoA as the donor of the acetyl group. Although this may be regarded as a kind of metabolic burden to the cells, it actually serves to avoid acetate formation, and thus prevent negative effects caused by acetate accumulation on the cell culture. Acetate formation could also be minimized by genetic modification of the enzymes involved in acetate synthesis.

The combination of NagB and GNA1 offers an interesting pathway from fructose-6-P to N-acetylglucosamine-6-P. Unlike GlmS which uses glutamine and fructose-6-P as substrates, the NagB enzyme catalyzes the direct assimilation of ammonium into N-acetylglucosamine-6-P. Moreover, NagB protein is about 30 kDa, much smaller than GlmS protein (about 70 kDa). It was found that as compared to the GlmS protein, a larger portion of NagB protein was in the soluble protein fraction when over-expressed in *E. coli*.

GlmS enzyme is generally subject to strong product inhibition. The use of a product resistant GlmS enzyme played an important role in elevating the titer of glucosamine and probably also in elevating the titer of N-acetylglucosamine. Product resistant GlmS mutants were created by in vitro mutagenesis. Such mutants could also be isolated from nature. This was illustrated by demonstrating product resistance of a native *B. subtilis* GlmS.

The following are exemplary protocols for optimized production of glucosamine and N-acetylglucosamine. These are merely examples of some operable and preferred embodiments of the invention and are not to be construed as the only embodiments of the invention. Several preferred fermentation protocols and parameters of the fermentation process, both for flask cultures and fermentor cultures, are described in detail in the Examples section.

The following is a description of a typical protocol for lactose-induced glucosamine fermentation process according to the present invention:

| | |
|---|---|
| Strain: | Recombinant *E. coli* |
| Induction: | 30 g/l lactose added (as a 35% feed ramped slowly over a 10 hour period) after a cell density of 10 g/l is reached. Glucose feed is suspended during this procedure to prevent glucose repression. After the lactose has all been added, glucose feed is re-instated. |
| Feed: | 50% glucose with 5 ug $FeSO_4$-$7H_2O$/g glucose and 0.33 ug $MnSO_4$-$H_2O$/g glucose, glucose fed at limiting concentrations. |
| Fermentation Time: | 72 hours |
| Fermentation Mode: | Fed Batch, with 50% glucose added as required, maintain limiting concentrations of glucose |
| Inoculum: | 5% by volume |
| pH: | 6.9 during growth, then 6.7 after induction, controlled by 10 N $NH_4OH$ |
| Temperature: | 30° C., switched to 25° C. after induction |
| Oxygen: | Dissolved $O_2$ at 20% or greater, controlled by agitation |
| Aeration: | 0.5 to 1 vvm |
| Medium: | Component      Concentration |

| Component | Concentration |
|---|---|
| $KH_2PO_4$ | 14 g $l^{-1}$ |
| $K_2HPO_4$ | 16 g $l^{-1}$ |
| $Na_3$-citrate | 1 g $l^{-1}$ |
| $(NH_4)_2SO_4$ | 5 g $l^{-1}$ |
| $CaCl_2$-$H_2O$ | 0.05 g $l^{-1}$ |
| $MgSO_4$-$7H_2O$ | 0.6 g $l^{-1}$ |
| $FeSO_4$-$7H_2O$ | 3 mg $l^{-1}$ |
| $ZnSO_4$-$7H_2O$ | 3.8 mg $l^{-1}$ |
| $MnSO_4$-$H_2O$ | 0.33 mg $l^{-1}$ |
| $CuSO_4$-$5H_2O$ | 0.1 mg $l^{-1}$ |
| $NaMoO_4$-$2H_2O$ | 0.1 mg $l^{-1}$ |
| $H_3BO_3$ | 0.1 mg $l^{-1}$ |
| $CoCl_2$-$6H_2O$ | 0.1 mg $l^{-1}$ |
| Glucose | >200 g $l^{-1}$, as needed |
| Mazu 204 defoamer | 0.25 g $l^{-1}$ |

In the above-described medium, all components are added before sterilization except glucose (added incrementally) and Fe, Zn, Mn, Cu, B, Mo, Co trace elements (added after sterilization).

The following is a description of a typical protocol for a N-acetylglucosamine fermentation process according to the present invention:

| | |
|---|---|
| Strain: | Recombinant *E. coli* |
| Induction: | 5 to 10 g $l^{-1}$ lactose added in a single point addition after a cell density of 15 to 20 g $l^{-1}$ is reached. Glucose feed is not suspended during this procedure, but remains steady at 6.5 g $l^{-1}$ $hr^{-1}$ (based on initial volume). |
| Feed: | 65% glucose without any amendments, glucose fed at limiting concentrations |
| Fermentation Time: | 60 to 72 hours |
| Fermentation Mode: | Fed Batch, with 65% glucose added as required, maintain limiting concentrations of glucose |
| Inoculum: | 2.5% to 5% by volume |

-continued

| | |
|---|---|
| pH: | 6.9 throughout, controlled with 12 N NH$_4$OH |
| Temperature: | 37° C. throughout |
| Oxygen: | Dissolved O$_2$ at 20% or greater, controlled by agitation |
| Aeration: | 0.5 to 1 vvm |
| Medium: | |

| Component | Concentration (amount per liter) |
|---|---|
| KH$_2$PO$_4$ | 6.67 g |
| Citric acid | 3.25 g |
| CaCl$_2$-H$_2$O | 0.05 g |
| MgSO$_4$-7H$_2$O | 2.5 g |
| FeSO$_4$-7H$_2$O | 5 mg |
| ZnSO$_4$-7H$_2$O | 3.8 mg |
| MnSO$_4$-H$_2$O | 0.33 mg |
| CuSO$_4$-5H$_2$O | 0.1 mg |
| CoCl$_2$-6H$_2$O | 0.1 mg |
| Glucose | >200 g, as needed |
| Mazu 204 defoamer | 0.25 g |

In the above-described medium, all components are added before sterilization except glucose (added incrementally). Initial pH is near 3.0 after sterilization and adjusted to 6.9 with NH$_4$OH before inoculation.

The method of the present invention further includes a step of collecting the product, which can be intracellular glucosamine-6-phosphate, glucosamine-1-phosphate, N-acetylglucosamine-6-phosphate, N-acetylglucosamine-1-phosphate, N-acetylglucosamine and/or glucosamine, and/or extracellular glucosamine and/or extracellular N-acetylglucosamine. The general step of collecting can include steps of recovering the product (defined below) and also purifying the product, as desired. The detailed discussion of the methods for recovery and purification are provided below. To "collect" a product such as glucosamine or N-acetylglucosamine can simply refer to collecting the product from the fermentation bioreactor and need not imply additional steps of separation, recovery, or purification. For example, the step of collecting can refer to removing the entire culture (i.e., the microorganism and the fermentation medium) from the bioreactor, removing the fermentation medium containing extracellular glucosamine and/or N-acetylglucosamine from the bioreactor, and/or removing the microorganism containing intracellular glucosamine-6-phosphate, glucosamine-1-phosphate, N-acetylglucosamine-6-phosphate, N-acetylglucosamine-1-phosphate, N-acetylglucosamine and/or glucosamine from the bioreactor. The term "recovering" or "recover", as used herein, refers to reducing solubility conditions of the glucosamine or N-acetylglucosamine solution to the point where glucosamine or N-acetylglucosamine, respectively, becomes insoluble and either precipitates out of solution or crystallizes. These steps can be followed by further purification steps. Glucosamine and N-acetylglucosamine are preferably recovered in substantially pure forms. As used herein, "substantially pure" refers to a purity that allows for the effective use of the glucosamine and/or N-acetylglucosamine as a nutraceutical compound for commercial sale. In one embodiment, the glucosamine and/or N-acetylglucosamine products are preferably separated from the production organism and other fermentation medium constituents. Methods to accomplish such separation are described below.

Preferably, by the method of the present invention, at least about 1 g/L of product (i.e., glucosamine, N-acetylglucosamine, glucosamine-6-phosphate, glucosamine-1-phosphate, N-acetylglucosamine-6-phosphate and/or N-acetylglocosamine-1-phosphate) are collected or recovered from the microorganism and/or fermentation medium. More preferably, by the method of the present invention, at least about 5 g/L, and even more preferably, at least about 10 g/L, and even more preferably, at least about 20 g/L and even more preferably, at least about 50 g/L, and even more preferably at least about 75 g/L, and even more preferably at least about 100 g/L, and even more preferably at least about 120 g/L of product are recovered, and any whole increment between at least about 1 g/L and at least about 120 g/L (i.e., 2 g/L, 3 g/L, etc.). In one embodiment, the product is recovered in an amount from about 1 g/L to at least about 120 g/L.

Typically, most of the glucosamine and/or N-acetylglucosamine produced in the present process are extracellular. The microorganism can be removed from the fermentation medium by conventional methods, such as by filtration or centrifugation. In one embodiment, the step of collecting or of recovering the product includes the purification of glucosamine and/or N-acetylglucosamine from the fermentation medium. Glucosamine and/or N-acetylglucosamine can be recovered from the cell-free fermentation medium by conventional methods, such as chromatography, extraction, crystallization (e.g., evaporative crystallization), membrane separation, reverse osmosis and distillation. In a preferred embodiment, glucosamine and/or N-acetylglucosamine are recovered from the cell-free fermentation medium by crystallization. In another embodiment, the step of recovering the product includes the step of concentrating the extracellular glucosamine and/or N-acetylglucosamine.

In one embodiment, glucosamine-6-phosphate, glucosamine-1-phosphate, N-acetylglucosamine-6-phosphate, N-acetylglucosamine-1-phosphate, N-acetylglucosamine and/or glucosamine accumulate intracellularly, the step of recovering the products includes isolating glucosamine-6-phosphate, glucosamine-1-phosphate, N-acetylglucosamine-6-phosphate, N-acetylglucosamine-1-phosphate, N-acetylglucosamine-1-phosphate, N-acetylglucosamine and/or glucosamine from the microorganism. For example, the products can be collected by lysing the microorganism cells by a method which does not degrade the products (glucosamine, N-acetylglucosamine, glucosamine-6-phosphate, glucosamine-1-phosphate, N-acetylglucosamine-6-phosphate and/or N-acetylglucosamine-1-phosphate), centrifuging the lysate to remove insoluble cellular debris, and then recovering the products glucosamine, N-acetylglucosamine, glucosamine-6-phosphate, glucosamine-1-phosphate, N-acetylglucosamine-6-phosphate and/or N-acetylglucosamine-1-phosphate by a conventional method as described above.

The initial intracellular products in the genetically modified microorganism described herein are glucosamine-6-phosphate, glucosamine-1-phosphate, N-acetylglucosamine-6-phosphate, N-acetylglucosamine-1-phosphate, N-acetylglucosamine and/or glucosamine, It is generally accepted that phosphorylated intermediates are dephosphorylated during export from the microorganism, most likely due to the presence of alkaline phosphatase, acid phosphatase, sugar phosphatase or amino sugar phosphatase in the periplasmic space of the microorganism. In one embodiment of the present invention, glucosamine-6-phosphate, glucosamine-1-phosphate, N-acetylglucosamine-6-phosphate and/or N-acetylglucosamine-1-phosphate are dephosphorylated before or during exp phosphatases in order to facilitate the production of the desired products, glucosamine and/or N-acetylglucosamine. In this embodiment, the need for amplification of a recombinantly provided phosphatase activity in the cell or treatment of the fermentation medium with a phosphatase is obviated. In another embodiment, the level of phosphatase in the production organism is increased by a method including, but not limited to, genetic modification of an endogenous phosphatase gene or by recombinant modification of the microorganism to express a phosphatase gene. In yet another embodiment, the collected fermentation medium is treated with a phosphatase after glucosamine-6-phosphate, glucosamine-1-phosphate, N-acetylglucosamine-6-phosphate and/or N-acetylglucosamine-1-phosphate are released into the medium, such as when cells are lysed as described above.

As noted above, the process of the present invention produces significant amounts of extracellular glucosamine and/or N-acetylglucosamine. In particular, the process produces extracellular glucosamine and/or N-acetylglucosamine such that greater than about 50% of total glucosamine and/or N-acetylglucosamine are extracellular, more preferably greater than about 75% of total glucosamine and/or N-acetylglucosamine are extracellular, and most preferably greater than about 90% of total glucosamine and/or N-acetylglucosamine are extracellular. By the method of the present invention, production of an extracellular glucosamine and/or N-acetylglucosamine concentration can be achieved which is greater than about 1 g/l, more preferably greater than about 5 g/l, even more preferably greater than about 10 g/l, and even more preferably greater than about 20 g/L, and even more preferably greater than about 50 g/l, and even more preferably greater than about 75 g/l, and even more preferably greater than about 100 g/l, and even more preferably greater than about 120 g/l.

Another embodiment of the present invention relates to a novel means to produce N-acetylglucosamine. The method includes obtaining a fermentation broth containing solubilized N-acetylglucosamine produced by a fermentation process, such as is discussed above, and recovering N-acetylglucosamine-containing solids from the fermentation broth. According to the present invention, N-acetylglucosamine that is produced by a fermentation process is N-acetylglucosamine that is a product of the fermentation process. In other words, the fermentation process of culturing cells results in production of N-acetylglucosamine by the cells. The term recovering or recover refers to reducing solubility conditions of the N-acetylglucosamine solution to the point where N-acetylglucosamine becomes insoluble and either precipitates out of solution or crystallizes. Fermentor broth containing N-acetylglucosamine, residual media and cellular matter can be treated first by removing the cellular material and bacterial endotoxins. Prior to removal of cellular material, cells in the fermentation broth can be lysed by using different methods, including but not limited to: sonication, osmotic disruption, grinding/beading, French press, homogenization, explosive decompression, solvent treatments, critical point extraction and freeze/thaw. Removal of cellular material and endotoxins can be achieved by micro- or ultrafiltration or a combination thereof. Other techniques known in the art include centrifugation and diafiltration. Following removal of cellular material, the solution can be tested to verify adequate removal of endotoxins.

Prior to the step of recovering N-acetylglucosamine-containing solids from the fermentation broth, the fermentation broth can be decolored and/or deashed. If both of these processes are conducted, either one can be performed first. However, by performing the deashing step first, the decolorization requirements are reduced because of color removal by the deashing process, such as by the use of ion exchange resins. The step of decolorizing can be conducted by multiple N-acetylglucosamine crystallizations, activated carbon treatment, and chromatographic decolorization. The use of chromatographic decolorization can include the use of ion exchange resins (not for ion exchange, but just for color absorption), Dow Optipore SD-2 resin and classical silica based-chromatographic media.

The step of deashing can be conducted by contacting the fermentation broth with an ion exchange resin, which can include contacting the fermentation broth with an anion exchange resin and/or a cation exchange resin. In one embodiment, a mixed bed of both an anion and a cation exchange resin is used. Cation removal can be performed on either strong acid or weak acid ion exchange resins, while weak base resins are preferred due to their enhanced ability to remove organic acids produced in the fermentation. Cation removal is typically chosen to precede anion removal because the effluent from the cation exchanger has a reduced pH, while that from the anion exchanger has an elevated pH. N-acetylglucosamine has a demonstrated tendency to epimerize at high pH, producing measurable levels of N-acetylmannosamine. Anion removal can be conducted with either strong or weak base resins. The resultant purified solution carries very little ionic material and consists mostly of water, N-acetylglucosamine, and carbohydrates from the fermentor feed unconsumed during fermentation. The N-acetylglucosamine purity of this intermediate product is typically greater than about 90% of the stream's total dry solids content. If further polishing is desired to complete deashing, then a mixed bed ion exchange step can be applied. In this case, both cationic and anionic resins occupy the same ion exchanger, and the largely deashed fermentor broth is passed through this bed. Although a mixed bed ion exchange can also take the place of the separate cation and anion exchangers, and although this offers the added benefit of minimizing the magnitude of the changes in broth pH, it is more convenient to operate separate beds because of the need to separate the ion exchange resins prior to regeneration, with the concomitant higher risk of resin loss.

The step of recovering N-acetylglucosamine-containing solids from the fermentation broth can include precipitating and/or crystallizing N-acetylglucosamine-containing solids from the fermentation broth. Typically, prior to the recovering step, the fermentation broth is concentrated to provide a higher concentration of solubilized N-acetylglucosamine to enable precipitation or crystallization. The step of concentrating can be conducted under vacuum (i.e., at less than atmospheric pressure) or by membrane separation. In preferred embodiments, the step of concentrating is conducted at a temperature of between about 40° C. and about 75° C., and more preferably at a temperature of between about 45° C. and about 55° C. The step of concentrating is typically conducted to achieve a solids content in the fermentation broth of at least about 30% solids, more preferably at least about 40% solids, and more preferably at least about 45% solids.

After concentration, the fermentation broth is typically cooled. Such cooling can be passive, i.e., simply allowing the broth to come to room temperature, or it can be active, such as by the use of freeze dryers, spray chillers, prillers, flakers, and blenders or extruders equipped with cooling jackets. The step of cooling a concentrated broth, alone, can be sufficient for recovery of N-acetylglucosamine-containing solids. For example, the fermentation broth can be cooled to between about −5° C. and about 45° C., between about −5° C. and about room temperature, or to about room temperature.

Recovering N-acetylglucosamine-containing solids from the fermentation broth can also include the step of seeding the fermentation broth with N-acetylglucosamine crystals to promote recovery by growth of existing crystals. Crystals can be provided by nucleation in the fermentation broth or as externally provided N-acetylglucosamine crystals. In the first instance, the fermentation broth is concentrated and/or cooled until some nucleation occurs by forcing the super-saturated solution into the labile regime but then cooling more slowly to avoid additional nucleation and promote growth of existing crystals. Alternatively, N-acetylglucosamine crystals, produced by any method, can be introduced into the fermentation broth as seed crystals.

Recovering N-acetylglucosamine-containing solids from the fermentation broth can be enhanced by contacting N-acetylglucosamine in the broth with a water miscible solvent. It has been found that N-acetylglucosamine is very insoluble in water miscible solvents, such as isopropyl alcohol (IPA), ethanol, methanol, acetone, tetrahydrofuran, dimethylsulfoxide, dimethylformamide, dioxane and acetonitrile. Therefore, by introduction of such a water miscible solvent into the broth, the N-acetylglucosamine will become less soluble and will further recovery.

Recovery processes of the invention can be conducted as either batch or continuous crystallizations of the fermentor broth. Crystals formed during the concentration process can be continuously harvested by filter or centrifuge while the mother liquor is recycled for further concentration, or they can remain with the mother liquor until the solids level mandates removing them.

After recovery of N-acetylglucosamine-containing solids, the solids can be separated from the fermentation broth, such as by centrifuging or filtering. The resulting solid cake can be dried by any of a variety of techniques known to those skilled in the art, such as vacuum drying, but such step is preferably accomplished at reduced temperature to prevent degradation and color formation. The final dried product will typically be at least about 50% dried solids, more preferably at least about 70% dried solids and more preferably at least about 85% dried solids. Prior to drying, the recovered solids can be washed with a water miscible solvent, such as those discussed above. Such a washing step results in stabilization of the product, for example, to prevent color formation.

In another embodiment, recovered N-acetylglucosamine-containing solids are further purified by dissolving the solids and recovering the solids in a second recovery step. The second recovery step can include any of the recovery process steps described above. The need for a second cycle of recovery is determined by the desired end product purity and the starting purity.

Employing the various recovery processes described above, N-acetylglucosamine of high purity can be prepared. In particular, processes of the present invention can produce N-acetylglucosamine that is at least about 70% pure, more preferably at least about 90% pure, and more preferably at least about 99% pure.

Various recovery process embodiments are preferred. For example, cell-free broth can be used to produce solid N-acetylglucosamine without further ion removal, by decolorizing with activated carbon; concentrating to approximately 45% dry solids or higher in a vacuum evaporator, which can be multi-stage for energy efficiency (e.g., preferred conditions are liquor temperatures between 45° C. and 55° C. at a vacuum of approximately 600 mm Hg.); seeding the warm concentrate with pure N-acetylglucosamine, and allowing it to cool while agitating. The cooled broth is filtered or centrifuged and a solid cake is recovered. The recovered solid can be vacuum-dried and used as an intermediate in the production of pure N-acetylglucosamine or glucosamine salts; and if the N-acetylglucosamine purity is 87% or higher, pure N-acetylglucosamine can be produced from a single crystallization. Alternatively to seeding, cooling, and solids recovery from mother liquor, the supersaturated stream can be forced to solidify by cooling. Suitable cooling devices include freeze dryers, spray chillers, prillers, flakers, and blenders or extruders equipped with cooling jackets. The resultant solid can be further dried.

In another preferred recovery embodiment, recovered N-acetylglucosamine can be redissolved in water without prior drying, and subjected to a second cycle: concentration, seeding, cooling and solids collection. The collected solids are washed with a water miscible solvent and dried under vacuum. The need for double crystallization is determined by the beginning purity of the N-acetylglucosamine. When purity, as a percentage of the dry solids, is 87% or higher, a single crystallization is required. When the purity is 70%, a double crystallization is required.

Another preferred recovery embodiment is a single crystallization to generate pure N-acetylglucosamine by using material that has been decolorized and concentrated at temperatures reaching 70° C., or by redissolving a partially purified material at 70° C. and allowing it to cool to room temperature. The recovered solid is washed with a water-miscible solvent and dried.

In another preferred recovery embodiment, cell-free fermentor broth that has been deashed is further purified by separation on a simulated moving bed chromatographic system, using chromatographic media, including cation exchange resins. Once an about 98% pure stream is obtained, vacuum concentration prepares the material for stabilization treatment described below.

In another preferred recovery embodiment, in order to achieve high recoveries of N-acetylglucosamine that have high purity and are color-stable, exhibiting less than 1% weight loss due to decomposition on drying at 105° C., a water-miscible solvent is employed. By starting with relatively high purity N-acetylglucosamine, for example 93% achieved by decolorizing and deashing, it is possible to remove water by vacuum concentration, and then by adding a water soluble solvent, to precipitate additional pure product. The process of treating the precipitated product with water-bearing miscible solvents facilitates the subsequent drying step, wherein the residual water is prevented from potentiating a degradation reaction.

Another embodiment of the invention relates to a method to produce glucosamine from N-acetylglucosamine. For production of glucosamine as a final product, N-acetylglucosamine can be hydrolyzed to produce glucosamine as a final product. The hydrolysis can be done directly with N-acetylglucosamine produced in the fermentation without being first isolated from fermentation or, alternatively, the hydrolysis can be carried on N-acetylglucosamine after being isolated from the fermentation, such as the N-acetylglucosamine recovered using any of the methods described above. Additionally, one can use any other available source of N-acetylglucosamine in this method of the invention. Prior to the present invention, N-acetylglucosamine was produced by the acetylation of glucosamine using an organic acetylating reagent, or by the enzymatic hydrolyzation of N-acetyglucosamine directly from chitin, which parallels the acid hydrolysis process traditionally used to produce glucosamine from chitin. Therefore, there was no need for the reverse reaction to produce glucosamine as an end product from N-acetylglucosamine.

Accordingly, a source of N-acetylglucosamine as described herein need not refer to a pure source of N-acetylglucosamine, but rather any source (solid or solution) that contains an amount of N-acetylglucosamine for conversion to glucosamine. Glucosamine hydrochloride can be produced both from the N-acetylglucosamine that has been produced is by a fermentation process as described above and then recovered from the fermentation broth as described in detail above, or the process can use N-acetylglucosamine produced by fermentation directly as a fermenter concentrate that has had the cellular material removed, but without removing either the residual color or ionic constituents. Alternatively, any other suitable source of N-acetylglucosamine can be used in the present method, including N-acetylglucosamine produced by other methods, such as the enzymatic hydrolysis of chitin. In a preferred embodiment, glucosamine hydrochloride is produced from a source of N-acetylglucosamine comprising at least about 30% N-acetylglucosamine as a percentage of the total solids in the source, and more preferably, the source comprises at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, as a percentage of the total solids in the source. In general, glucosamine hydrochloride is produced from a source of N-acetylglucosamine comprising any percentage of N-acetylglucosamine from at least about 1% to 100%, in whole integers (i.e., 1%, 2%, 3%, . . . 98%, 99%, 100%), The N-acetylglucosamine can be used in the reaction as a solid or as a solution in water, or as a solution in an aqueous low boiling primary or secondary alcohol, including, but not limited to, ethanol, methanol, n-propanol, isopropanol, n-butanol, or sec-butanol. In a preferred embodiment, the source of N-acetylglucosamine comprises at least about 40% N-acetylglucosamine as a percentage of the total dry solids in the source.

In one embodiment, the glucosamine hydrochloride can be produced from a source of N-acetylglucosamine using hydrolysis under acid and heat conditions. Acid hydrolysis techniques are known in the art. The present invention provides a specific adaptation of this chemical reaction to the conversion of N-acetylglucosamine to glucosamine hydrochloride. The hydrolysis reaction releases one mole of acetic acid, and consumes one mole each of hydrochloric acid and water for every mole of N-acetylglucosamine converted to glucosamine hydrochloride. Many combinations of water, hydrochloric acid and N-acetylglucosamine successfully perform the reaction, thus it is possible to use anhydrous hydrochloric acid, dry N-acetylglucosamine and water as reactants, or to bring water in with either or both of the N-acetylglucosamine and hydrochloric acid. The reaction is carried out with excess water and hydrochloric acid. The important parameters are reaction time and temperature, as well as residual hydrochloric acid concentration. The reaction is cooled after conversion is complete, and the residual concentration of excess hydrochloric acid as well as the ending temperature establishes the solubility of the glucosamine hydrochloride product. Excess levels of solubility cause reduced per-pass recovery of glucosamine hydrochloride and reduce yield. Glucosamine can degrade and the reactions accomplishing this occur in solution. The reaction rate is related to temperature, the concentration of N-acetylglucosamine and/or glucosamine in solution, and the concentration of hydrochloric acid in solution. Successful conditions include temperatures from 60° C. to 100° C., with temperatures from 70° C. to 90° C. being more preferred. Acceptable ratios of hydrochloric acid solution to N-acetylglucosamine solid range from 1:1 by weight to 5:1 by weight, with 3:1 being preferred and 2.5:1 being more preferred. Acceptable concentrations of hydrochloric acid solution range from 10-40% w/w, and more preferably from about 10% w/w to 37% w/w. Anhydrous hydrochloric acid can be substituted for aqueous, providing that the heat of dilution is managed and there is adequate solution to fully dissolve the N-acetylglucosamine. The sequence of addition and temperature at addition are of lesser importance, as all combinations are successful. The time to conduct the reaction varies with the temperature of reaction and acid concentration, and ranges from 10 minutes for concentrated acid at high temperatures to 3 hours or more (e.g., up to 24 hours) for dilute acids at low temperatures. The solution is cooled to 4° C. in order to precipitate the glucosamine hydrochloride. Higher and lower temperatures are acceptable (e.g., any temperature between about −5° C. and about 40° C.), but 4° C. was chosen as a convenient temperature to minimize residual glucosamine hydrochloride in the hydrolysis solution at commercially convenient conditions. For more impure hydrolysis solutions, that is solutions where the relative dry solids composition of glucosamine hydrochloride is lower, a slower cooling rate and additional holding time at the ending temperature are required to return the hydrolysis solution to saturation. Solution agitation mitigates, but does not overcome the hindrance posed by impurities to the crystallization process.

Since the hydrolysis reaction is conducted with excess hydrochloric acid, the hydrolysis solution after cooling and removing glucosamine hydrochloride process has the capability to be used again for hydrolysis. As the acetic acid coproduct increases in concentration and the reactant hydrogen chloride is consumed in each hydrolysis cycle, the hydrolysis solution becomes less active and the reactions take longer to complete. It is possible to replenish the hydrogen chloride by supplying it in its gaseous form to reconstitute this reactant, but the increase of acetic acid coproduct from each reaction cycle poses an increasing obstacle to simple hydrolysate solution recycle. This can be overcome by esterifying the acetic acid through the addition of a primary or secondary alcohol, either prior to, during or following the hydrolysis step. The acetic acid forms an ester with the alcohol which then can be removed by distillation, flashing or vacuum evaporation prior to, during or following N-acetylglucosamine hydrolysis.

N-acetylglucosamine can be continuously blended with recycled hydrolysis mother liquor in order to ensure it becomes or remains dissolved. Subsequently, replacement anhydrous hydrochloric acid is added, which raises the solution temperature to initiate the hydrolysis reaction and maintain adequate residual acid concentration to minimize glucosamine hydrochloride solubility. Pressure can be controlled above atmospheric, and elevated temperature is selected to permit using minimum reactor residence time. After the complete conversion of N-acetylglucosamine to glucosamine hydrochloride, the reaction is cooled and glucosamine hydrochloride recovered by filtration or centrifugation. The filtrate or centrate are recycled through the cooler until the goal temperature of about 4° C. is reached and the majority of the glucosamine hydrochloride is recovered. The centrate or filtrate is then recycled for reuse. Adequate water to make up reaction losses comes in with the N-acetylglucosamine. The accumulation of reaction coproducts like acetic acid are removed by conducting a continuous purge of the mother liquor, by separating the residual hydrochloric acid from the purge stream and returning it for subsequent reuse, or by esterifying it with a primary or secondary alcohol and drying it as esters.

Details regarding recovery of glucosamine from the hydrolysis process described herein are similar to those described above for the recovery of N-acetylglucosamine and are incorporated herein for the recovery of glucosamine. Some preferred aspects of glucosamine recovery are discussed below and in the Examples section.

Filtration or centrifugation can then recover the solid glucosamine salt. Recovered molar yields range from 50% to 90% based on N-acetylglucosamine. Glucosamine purity after alcohol washing and drying typically range from 96% to 100%. The wet cake recovered from the centrifuge or filter is washed with alcohol to minimize the tendency of the product to form lumps during drying. The product is then dried under vacuum in a vacuum dryer or Wyssmont type dryer until loss on drying meets product specifications.

It is possible to start with recovered N-acetylglucosamine hydrolysis filter- or centrifuge-cake, which can be either washed or not. The cake is dissolved in water to a concentration of approximately 25% (w) at room temperature under agitation. A base, such as sodium hydroxide or potassium hydroxide is added to bring the pH up to between 2.5-4. Once the pH is adjusted, the fully dissolved solution is treated with activated carbon. For example, in the batch mode, 0.02 grams of Darco G-60 or equivalent activated carbon is added per gram glucosamine hydrochloride and mixed for a minimum of 30 minutes. The mixture is filtered to remove the carbon. The carbon is then rinsed with an amount of water approximately equal to the amount of glucosamine hydrochloride being recrystallized to elute any glucosamine hydrochloride entrained in the carbon and filter equipment. Alternatively, the solution can be passed through a granular packed bed of activated carbon, with a subsequent elution step to recover entrained glucosamine hydrochloride prior to regeneration or disposal of the expended activated carbon.

The clear solution is then heated to 50° C. under vacuum and agitation. A 50-60 cm Hg vacuum has been used. Approximately half of the volume is removed by evaporation and the solids are recovered from the remaining solution by filtration, centrifugation or other appropriate means to recover recrystallized glucosamine hydrochloride. The remaining solution is returned for further recovery. The solids are collected, rinsed with a water-miscible solvent, including, but not limited to: methanol, ethanol, n-propanol, isopropanol, n-butanol, sec-butanol, acetone, tetrahydrofuran, dimethysulfoxide, dimethylformamide, or dioxane, and dried.

When recrystallizing from single-use hydrolysate, the liquid is further evaporated to a point where solids are visible and the volume is estimated to be around 20-30% of the starting volume. An equal volume of water-miscible solvent is added as a liquid precipitant, the solids are recovered from the resultant solution by filtration, centrifugation or other appropriate means to recover recrystallized glucosamine hydrochloride. The remaining solution is then cooled, for example to 4° C., and filtered to recover the remaining glucosamine hydrochloride.

When recrystallizing from multiple-use hydrolysate, the activated carbon treated hydrolysate of the subsequent cycle is added to the recovered solution of the current cycle to make up for the volume removed by evaporation and solids recovery. Approximately half volume is then removed by evaporation and the cycle is repeated.

The purity of the recrystallized glucosamine hydrochloride is dependent on the amount of salts due to the neutralization of the excess acid and other impurities carried forward from the first, hydrolysate, crystallization step. This is controlled by substituting a single-use hydrolysis recrystallization step for the multiple-use hydrolysis crystallization step when the recovered glucosamine hydrochloride ceases to meet purity specifications. The resultant precipitated glucosamine hydrochloride recovered during the miscible-solvent precipitation is redissolved and incorporated as a part of a subsequent series of recrystallizations.

The recovered glucosamine hydrochloride wet cake should contain alcohol to minimize the tendency of the product to form lumps and darken during drying. It is then dried under vacuum in a vacuum dryer or Wyssmont type dryer until loss on drying meets product specifications.

In one embodiment, the step of hydrolyzing comprises the steps of: (a) hydrolyzing the source of N-acetylglucosamine by combining the source of N-acetylglucosamine with a hydrochloric acid solution or a recycled hydrolysis mother liquor under heat conditions to produce a solution containing glucosamine hydrochloride; (b) cooling the solution of (a) to precipitate the glucosamine hydrochloride; and (c) recovering the precipitated glucosamine hydrochloride-containing solids from (b). In one aspect, the step of hydrolyzing can be performed by continuously blending the source of N-acetylglucosamine with a hydrochloric acid solution or a recycled hydrolysis mother liquor to maintain the source of N-acetylglucosamine as a dissolved solution, followed by addition of anhydrous hydrochloric acid under heat conditions to the solution of (a) to initiate hydrolysis and convert the N-acetylglucosamine to glucosamine hydrochloride. In another aspect, the recycled hydrolysis mother liquor is hydrolysis solution that remains after recovering the precipitated glucosamine hydrochloride in step (c), wherein a primary or secondary alcohol is added to the hydrolysis solution prior to, during or after a hydrolysis step is performed. In this aspect, the step of cooling can be performed until the solution is from about −5° C. to about 40° C.

The step of recovering can comprise: (i) collecting the precipitated glucosamine hydrochloride-containing solids; (ii) washing the glucosamine hydrochloride-containing solids with a water miscible solvent (including, but not limited to, methanol, isopropanol, ethanol, acetonitrile, acetone, tetrahydrofuran, dimethylsulfoxide, dimethylformamide and dioxane); and (iii) drying the glucosamine hydrochloride-containing solids.

In another aspect, the step of recovering can include: (i) collecting the precipitated glucosamine hydrochloride-containing solids; (ii) dissolving the solids from (i) in water to form a solution; (iii) adjusting the pH of the solution of (ii) to between about 2.5 and 4 (e.g., by adding a base, by washing to remove the acid, passing over ion exchange media, or any other suitable method); (iv) contacting the solution of (iii) with activated carbon to decolorize the glucosamine hydrochloride-containing solids; (v) removing the activated carbon from the solution of (iv); and (vi) crystallizing glucosamine hydrochloride from the solution of (v). In this aspect, the step of crystallizing comprises concentrating the glucosamine hydrochloride at a temperature of less than about 70° C., and more preferably at a temperature of less than about 50° C. In one aspect, the step of crystallizing comprises concentrating the glucosamine hydrochloride at less than atmospheric pressure. In another aspect, the process further includes comprising recycling solution remaining after the crystallization step (vi) to step (i) of a subsequent recovery process or to a subsequent step of crystallization (e.g., a recrystallization).

In another aspect, when the source of N-acetylglucosamine is suspended in an aqueous, low-boiling, primary or secondary alcohol, the hydrolysis method can include an additional step, prior to cooling the solution, of removing the acetic acid ester formed with the alcohol following hydrolysis or prior to recycling the hydrolysis solution for reuse. The acetic acid ester is removed by a process including, but not limited to: distillation, flashing, and concentration at less than atmospheric pressure. In this embodiment, the step of hydrolyzing is performed at a temperature of between about 60° C. and about 100° C., and preferably at the solution boiling point at one atmosphere.

In another aspect, when the hydrolysis is conducted under relatively high acid to N-acetylglucosamine ratios (e.g., from about 3:1 to about 5:1) and at a relatively low temperature (e.g., less than about 80° C.), the crystal quality of the glucosamine produced can be high enough to avoid the need to recrystallize the glucosamine. In this embodiment, the single crystallization step is followed by a wash in a water miscible solvent as described previously herein and then a step of drying as described above.

Indeed, any of the methods of hydrolysis and recovery described herein can further include a step of washing the crystallized glucosamine hydrochloride from step (vi) with a water miscible solvent, as described previously herein, followed by a step of drying. In one aspect, the crystallized glucosamine hydrochloride is dried at a temperature of less than about 70° C. for less than about 6 hours, and in another embodiment, at a temperature of less than about 50° C. for less than about 3 hours. The step of drying can be conducted in the presence or absence of a vacuum and in the presence or absence of an air or inert gas sweep.

Another method for converting N-acetylglucosamine to glucosamine is to use an enzyme hydrolysis procedure. Enzyme processes to hydrolyze N-acetylglucosamine in the fermentation broth or after its recovery are described in the Examples section. Three types of enzymes are candidates: N-acetylglucosamine-6-P deacetylase (EC 3.5.1.25, NagA), N-acetylglucosamine deacetylase (EC 3.5.1.33), and chitin deacetylase.

The deacetylases described by Fujishima et al. were identified as N-acetylglucosamine-6-P deacetylases (EC 3.5.1.25, NagA). Their affinity and efficacy with N-acetylglucosamine 6-P were much higher than with N-acetylglucosamine. However, N-acetylglucosamine-6-P deacetylase purified from E. coli does not act on N-acetylglucosamine.

The enzyme N-acetylglucosamine-6-P deacetylase (EC 3.5.1.25, NagA) is well known for its role of converting N-acetylglucosamine-6-P to glucosamine-6-P, a necessary step in the cellular metabolism of N-acetylglucosamine, N-acetylmannosamine and neuraminic acid. Normally, this enzyme such the recombinant E. coli NagA protein is not active on non-phosphorylated N-acetylglucosamine. DNA sequences coding for the N-acetylglucosamine 6-P deacetylase (nagA gene) were determined in many different organisms. It is not know if there exists a deacetylase that is only active on N-acetylglucosamine (thus distinctive from NagA).

Chitin deacetylase (EC 3.5.1.41) catalyzes deacetylation of the N-acetylglucosamine units in chitin, resulting in chitosan. Chitin deacetylase activity is usually determined by using as substrate glycol chitin (partially O-hydroxyethylated chitin) radiolabeled in N-acetyl groups. The enzyme also acts on mycrocrystalline chitin and carboxymethyl-chitin (soluble derivative). However, it was reported that chitin deacetylase from Mucor rouxii does not deacetylate N-acetylglucosamine monomer or 2-3 oligomers (Araki and Ito, 1975. Eur. J. Biochem. 55:71-78, which is incorporated herein by reference in its entirety). Although there were no indications that normal chitin deacetylase deacetylate glucosamine monomer, chitin deacetylase variants with such activity could be isolated from nature or created in vitro.

A number of acyl transferases can remove the acetyl group from a substrate and transfer it to another substrate (Konecny, et al.). Although there were no indications that such enzymes can deacetylate N-acetylglucosamine, acyl transferase variants with such activity could be isolated from nature or generated in vitro.

Deacetylation of N-acetylglucosamine could be carried out by an acyl transferase contained in or isolated from organisms with a native acyl transferase or organisms with a recombinant acyl transferase. Recombinant acyl transferase could be improved by random or directed mutagenesis and/or by protein engineering.

In applications of acyl transferase or deacetylase technology to convert N-acetylglucosamine to glucosamine, there is the potential for product degradation through a variety of mechanisms due the well-known instability of glucosamine in solution, especially when outside a low pH environment that would otherwise protonate the nitrogen atom.

Simple pH reduction, while appropriate to acid hydrolysis, becomes problematic for enzymatic catalysis. Enzymes are more likely to be denatured when they are exposed to an unbuffered or non-neutral pH environment. Moreover, high salt loads are often associated with enzyme denaturation.

Consequently, it is proposed to employ known enzyme immobilization technology (discussed below) to fix the enzyme conformation and reduce the impact of exposure to high ionic concentrations and reduce expensive enzyme consumption. Further, it is proposed to take advantage of the relatively low solubility of glucosamine hydrochloride in comparison with other salts, such as sodium acetate, calcium acetate, sodium chloride and calcium chloride.

By presenting an appropriate enzyme with an aqueous sodium or calcium chloride solution and N-acetylglucosamine, the equilibrium reaction will proceed to form highly soluble sodium or calcium acetate, which serves as a pH buffer for the enzyme. The reaction also produces relatively insoluble, but stable, glucosamine hydrochloride, which can be crystallized or precipitated from solution by evaporative concentration or use of liquid precipitants. As the glucosamine separates from solution, it draws the equilibrium reaction forward, consuming additional N-acetylglucosamine. The remaining mother liquor will contain residual dissolved glucosamine hydrochloride, sodium or calcium acetate, sodium or calcium chloride and a minor amount of unreacted N-acetylglucosamine. Treating this mother liquor with alcohol as a liquid precipitant separates the soluble sodium or calcium acetate from the less soluble glucosamine hydrochloride, sodium or calcium chloride and N-acetylglucosamine, which can be recycled to the beginning of the enzymatic conversion process.

Still another approach for converting N-acetylglucosamine enzymatically to glucosamine hydrochloride is to use the catalytic enzyme to esterify an alcohol by transferring the acetyl group from N-acetylglucosamine and to an added alcohol. Removing the ester formed during hydrolysis drives the reaction forward to consume N-acetylglucosamine, generating glucosamine free base.

Glucosamine free base formed from enzymatic hydrolysis can be stabilized by passing it as a mixture with a chloride salt solution, e.g. sodium chloride, over a cation exchange resin in the hydrogen form, wherein the salt cation is exchanged for hydrogen ion, and stable glucosamine hydrochloride is formed, while the ion exchange resin retains the salt cations. In this same manner, a selection of any of a variety of salts, including but not limited to phosphates, sulfates, iodides, and bisulfates can be blended with the glucosamine free base, which upon passing over a cation exchange column will be converted to known stable acid salts, including (glucosamine)$_2$ sulfate—(NaCl)$_2$, (glucosamine)$_2$ sulfate—(KCl)$_2$, (glucosamine)$_2$ sulfate, glucosamine hydrochloride, glucosamine hydroiodide, glucosamine phosphate, (glucosamine)$_2$potassium bisulfate—(HCl)$_2$, and (glucosamine)$_2$ sodium bisulfate—(HCl)$_2$.

Therefore, in one aspect, the recombinant deacetylating enzyme discussed above is bound to a solid support, i.e., an immobilized enzyme. As used herein, an enzyme (e.g., a deacetylase) bound to a solid support includes immobilized isolated enzyme, immobilized cells which contain the enzyme, such as a recombinant enzyme (including immobilized bacterial, fungal (e.g., yeast), microalgal, insect, plant or mammalian cells), stabilized intact cells and stabilized cell/membrane homogenates. Stabilized intact cells and stabilized cell/membrane homogenates include cells and homogenates from naturally occurring microorganisms expressing the enzyme or from genetically modified microorganisms, insect cells or mammalian cells as disclosed elsewhere herein which have been genetically modified to express the enzyme (e.g., by recombinant technology). Thus, although methods for immobilizing enzymes are discussed below, it will be appreciated that such methods are equally applicable to immobilizing bacterial and other cells and in such an embodiment, the cells can be lysed.

A variety of methods for immobilizing an enzyme are disclosed in Industrial Enzymology 2nd Ed., Godfrey, T. and West, S. Eds., Stockton Press, New York, N.Y., 1996, pp. 267-272; Immobilized Enzymes, Chibata, I. Ed., Halsted Press, New York, N.Y., 1978; Enzymes and Immobilized Cells in Biotechnology, Laskin, A. Ed., Benjamin/Cummings Publishing Co., Inc., Menlo Park, Calif., 1985; and Applied Biochemistry and Bioengineering, Vol. 4, Chibata, I. and Wingard, Jr., L. Eds, Academic Press, New York, N.Y., 1983, which are incorporated herein in their entirety.

Briefly, a solid support refers to any solid organic supports, artificial membranes, biopolymer supports, or inorganic supports that can form a bond with the enzyme without significantly effecting the activity of the isolated enzyme. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand. Preferably, the solid support is selected from the group consisting of stabilized intact cells and/or crude cell homogenates. Preparation of such supports requires a minimum of handling and cost. Additionally, such supports provide excellent stability of the enzyme.

Enzymes can be bound to a solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports in a bead form are particularly well-suited; The particle size of an adsorption solid support can be selected such that the immobilized enzyme is retained in the reactor by a mesh filter while the substrate (e.g., the oil) is allowed to flow through the reactor at a desired rate. With porous particulate supports it is possible to control the adsorption process to allow enzymes or bacterial cells to be embedded within the cavity of the particle, thus providing protection without an unacceptable loss of activity.

Each publication and reference cited or described herein is incorporated by reference in its entirety.

The following experimental results are provided for the purposes of illustration and are not intended to limit the scope of the invention.

EXAMPLES

The following is a list of various genetically modified microorganisms referenced and/or described herein. Some of the strains were described in U.S. Pat. No. 6,372,457, supra, and were used as parent strains for the genetic modifications described specifically herein.

E. coli Strains

| Strain No | Description | Reference |
| --- | --- | --- |
| W3110 | F$^-$ mcrA mcrB IN(rrnD-rrnE) 1 λ$^-$ ATCC25947, a derivative of E. coli K-12 | ATCC |
| 7101-17 (DE3) | Tet$^R$::Δnag manXYZ DE3 | U.S. Pat. No. 6,372,457 |
| 2123-4 | Tet$^R$::Δnag manXYZ DE3 T7lac-glmS*4::ΔlacZ Cam$^R$ | ib. |
| 2123-12 | Tet$^R$::Δnag manXYZ DE3 T7lac-glmS::ΔlacZ Cam$^R$ | ib. |
| 2123-54 | Tet$^R$::Δnag manXYZ DE3 T7lac-glmS*54::ΔlacZ Cam$^R$ | ib. |
| 2123-59 | Tet$^R$::Δnag manXYZ DE3 T7lac-glmS*59::ΔlacZ Cam$^R$ | ib. |
| 2123-64 | Tet$^R$::Δnag manXYZ DE3 T7lac-glmS*64::ΔlacZ Cam$^R$ | ib. |
| 2123-72 | Tet$^R$::Δnag manXYZ DE3 T7lac-glmS*72::ΔlacZ Cam$^R$ | ib. |
| 2123-103 | Tet$^R$::Δnag manXYZ DE3 T7lac-glmS*103::ΔlacZ Cam$^R$ | ib. |
| 2123-124 | Tet$^R$::Δnag manXYZ DE3 T7lac-glmS*124::ΔlacZ Cam$^R$ | ib. |
| 7107-16 | Tet$^R$::Δnag manXYZ DE3 T7-glmS*54::galK | Example 6 |
| 7107-18 | Tet$^R$::Δnag manXYZ DE3 T7-glmS*54::galK | ib. |
| 7107-22 | Tet$^R$::Δnag manXYZ DE3 pET24d(+) Kan$^R$ | Example 2 |
| 7107-23 | Tet$^R$::Δnag manXYZ DE3 pET24d(+)/T7-CaGFA1 Kan$^R$ | ib. |
| 7107-24 | Tet$^R$::Δnag manXYZ DE3 pET24(d+)/T7-BsglmS Kan$^R$ | ib. |
| 7107-58 | Tet$^R$::Δnag manXYZ DE3 pET23b(+)/T7-CaGFA1 Kan$^R$ | Example 2 |
| 7107-60 | Tet$^R$::Δnag manXYZ DE3 pET23b(+)/T7-CaGFA1-M Kan$^R$ | ib. |

-continued

E. coli Strains

| Strain No | Description | Reference |
|---|---|---|
| 7107-84 | 7107-18, ΔlacI(DE3) | Example 28 |
| 7107-88 | 7107-18, pET24d(+) Kan$^R$ | Example 13 |
| 7107-87 | 7107-18, pET24d(+)/T7-ScGNA1 Kan$^R$ | ib. |
| 7107-90 | 7107-18, ΔpfkA | Example 22 |
| 7107-92 | 7107-18, T7-ScGNA1::ΔmanXYZ | Example 16 |
| 7107-93 | 7107-18, pET24d(+)/T7-AtGNA1 Kan$^R$ | Example 13 |
| 7107-95 | 7107-18, T7-ScGNA1::ΔmanXYZ pET24d(+) Kan$^R$ | Example 24 |
| 7107-96 | 7107-18, T7-ScGNA1::ΔmanXYZ pET24d(+)/T7-zwf Kan$^R$ | ib. |
| 7107-101 | Tet$^R$::Δnag manXYZ DE3 pET24(+)/T7-ScGFA1 Kan$^R$ | Example 2 |
| 7107-117 | 7107-18, pET24d(+)/T7-CaGNA1 Kan$^R$ | Example 13 |
| 7107-118 | 7107-18, T7-glnA::ΔpfkB | Example 23 |
| 7107-119 | ib. | ib. |
| 7107-120 | ib. | ib. |
| 7107-124 | 7107-18, T7-ScGNA1::ΔmanXYZ pET24d(+)/T7-pgi Kan$^R$ | Example 26 |
| 7107-125 | 7107-18, T7-glnA::ΔpfkB T7-ScGNA1::ΔmanXYZ | Example 23 |
| 7107-126 | 7107-18, T7-glnA::ΔpfkB T7-ScGNA1::ΔmanXYZ | ib. |
| 7107-133 | 7107-18, T7-glnA::ΔpfkB, T7-ScGNA1::ΔmanXYZ | ib. |
| 7107-136 | 7107-18, T7-ScGNA1::ΔmanXYZ T7-pgi::ΔaraBAD | Example 26 |
| 7107-141 | ib. | ib. |
| 7107-163 | 7107-18, pET24d(+)/T7-glnA Kan$^R$ | Example 23 |
| 7107-214 | Tet$^R$::Δnag manXYZ DE3 pET24d(+)/T7-glmS Kan$^R$ | Example 2 |
| 7107-308 | 7107-18, ΔglgXCA | Example 27 |
| 7107-309 | ib. | ib. |
| 7107-310 | 7107-18, lacUV5 promoter replacing the lac promoter | Example 28 |
| 7107-313 | 7107-18, lacUV5 replacement ΔlacI (lac) | ib. |
| 7107-314 | 7107-18, lacUV5 replacement ΔlacI (lac) | ib. |
| 7107-315 | 7107-18, lacUV5 replacement ΔlacI (lac) | ib. |
| 7107-321 | Tet$^R$::Δnag manXYZ DE3 T7-glmS*54::Δnag | Example 29 |
| 7107-325 | Tet$^R$::Δnag manXYZ DE3 T7-glmS*54::Δnag T7-ScGNA1::ΔmanXYZ | ib. |
| 7107-326 | ib. | ib. |
| 7107-327 | ib. | ib. |
| 7107-328 | ib. | ib. |
| 7107-512 | UV mutagenized 7107-92 (i.e. 7107-18, T7-ScGNA1::ΔmanXYZ | Example 21 |
| 7107-513 | UV mutagenized 7107-92 (i.e. 7107-18, T7-ScGNA1::ΔmanXYZ) | ib. |
| 7107-602 | 7107-18, ΔpfkA T7-ScGNA1::ΔmanXYZ | Example 22 |
| 7107-603 | ib. | ib. |
| 7107-606 | 7107-18, T7-ScGNA1::ΔmanXYZ T7-zwf::ΔrhaBAD | Example 24 |
| 7107-607 | 7107-18, T7-ScGNA1::ΔmanXYZ T7-ScGNA1::ΔfuclK (two copies of ScGNA1) | Example 16 |
| 7107-608 | 7107-18, T7-ScGNA1::ΔmanXYZ T7-ScGNA1::ΔfuclK T7-ScGNA1::ΔtreB (three copies of ScGNA1) | ib. |
| 7107-609 | 7107-18, T7-ScGNA1::ΔmanXYZ T7-ScGNA1::ΔfuclK T7-ScGNA1::ΔmelAB (three copies of ScGNA1) | ib. |
| 7107-610 | ib. | ib. |
| 7107-611 | ib. | ib. |
| 7107-612 | 7107-18, T7-ScGNA1::ΔmanXYZ T7-ScGNA1::ΔfuclK T7-ScGNA1::ΔtreB T7-ScGNA1::ΔmelAB (four copies of ScGNA1) | ib. |
| 7107-613 | ib. | ib. |
| 7107-633 | 7107-18, T7-ScGNA1::ΔmanXYZ T7-ScGNA1::ΔfuclK zwf::ΔrhaBAD | Example 25 |
| 7107-634 | 7107-18, T7-ScGNA1::ΔmanXYZ zwf::ΔrhaBAD | ib. |
| 7107-636 | 7107-18, pET24d(+)/T7-nagB Kan$^R$ | Example 14 |
| 7107-637 | ib. | ib. |
| 7107-638 | ib. | ib. |
| 7107-645 | Tet$^R$::Δnag manXYZ DE3 T7-nagB::ΔpfkB | ib. |
| 7107-646 | Tet$^R$::Δnag manXYZ DE3 T7-nagB::ΔpfkB ΔglmS | ib. |
| 7107-660 | Tet$^R$::Δnag manXYZ DE3 T7-nagB::ΔpfkB ΔglmS T7-ScGNA1::ΔmanXYZ | ib. |
| 7107-661 | ib. | ib. |
| 7107-667 | Tet$^R$::Δnag manXYZ DE3 pET24d(+)/T7-glmU Kan$^R$ | Example 15 |
| 7107-668 | ib. | ib. |
| 7107-669 | Tet$^R$::Δnag manXYZ DE3 pET24d(+)/T7-glmM Kan$^R$ | ib. |
| 7107-670 | ib. | ib. |
| 7107-671 | Tet$^R$::Δnag manXYZ DE3 pET24d(+)/T7-glmU-t Kan$^R$ | ib. |
| 7107-672 | ib. | ib. |
| 7107-678 | 7107-18, T7-glmU::Δnag | ib. |
| 7107-679 | ib. | ib. |
| 7107-680 | 7107-18, T7-glmUt::Δnag | ib. |
| 7107-681 | ib. | ib. |
| 7107-682 | 7107-18, T7-glmM::Δglg | ib. |
| 7107-683 | 7107-18, T7-glmM::Δglg (glmM oriented opposite to glg) | ib. |

-continued

E. coli Strains

| Strain No | Description | Reference |
|---|---|---|
| 7107-685 | 7107-18, T7-glmU::Δnag T7-glmM::Δglg (glmM oriented opposite to glg) | ib. |
| 7107-687 | 7107-18, T7-glmUt::Δnag T7-glmM::Δglg (glmM oriented opposite to glg) | ib. |
| 7107-689 | 7107-18, T7-glmU::Δnag T7-glmM::Δglg | ib. |
| 7107-692 | 7107-18, T7-glmUt::Δnag T7-glmM::Δglg | ib. |

Note:
1) All strains listed in the table were derived from the same parent strain W3110.
2) The majority of strains listed in the table were developed from strain 7107-18 (Tet$^R$:: nag manXYZ DE3 T7-glmS*54::galK). To simplify, the genotype of these strains are listed as 7107-18 plus new changes.
3) Genes from other sources than E. coli are identified with two letters. Sc: Saccharomyces cerevisiae, Ca: Candita albicans, At: Arabidopsis thaliana, Bs: Bacillus subtilis.
4) For gene integration, the inserted expression cassttte is oriented the same as the gene or operon of the target site except when it is indicated otherwise.

Example 1

The following example describes mutant screening for better glucosamine producers.

U.S. Pat. No. 6,372,457, incorporated herein by reference in its entirety, described recombinant E. coli strains that produce glucosamine at high levels. These strains were constructed using a metabolic engineering approach. This approach is consisted of three steps. This first step was to introduce mutations that restrict metabolism and import of glucosamine and its 6-phosphate derivative. The second step was to over-express the E. coli glmS gene coding for glucosamine synthase (GlmS), the key biosynthetic enzyme. The third step was to minimize product inhibition of the GlmS by in vitro mutagenesis of the enzyme. The recombinant strain 2123-54 contained a product-resistant recombinant E. coli glmS mutant gene under T7 promoter control and showed the highest product titer in shake flask culture in a simple mineral salt medium supplemented with glucose. This strain was used as a reference to evaluate new strains for further improvements. It was also used in experiments designed to improve cell growth and IPTG induced glucosamine production.

Genotype of IPTG-Inducible Glucosamine Production Strain 2123-54:

2123-54 was derived from a laboratory E. coli K-12 strain designated W3110. The relevant genotype was described in Table 1.

The nag and manXYZ mutations were shown to have a positive influence on glucosamine production and continued to be carried into new production strains. By using the T7 expression system the E. coli wild type glmS gene was over-expressed and a few-fold higher level of glucosamine production was produced using IPTG induction. Since the E. coli wild type GlmS is strongly inhibited by its product, glucosamine-6-P, pools of E. coli glmS mutants were created by error-prone PCR and screened by plate feeding assay for increased glucosamine production. The expression constructs expressing glmS* mutants in the improved glucosamine producers were integrated in the chromosome at the lacZ site to generate stable production strains. Many mutant strains synthesized a glucosamine synthase that was product resistant. In shake flask experiments, these mutant strains produced drastically increased levels of glucosamine as compared to the strain with the E. coli wild type glmS expression construct. The strain 2123-54 (with the T7-glmS*54 expression construct) produced over 11 g glucosamine per liter.

Developing a Simplified Shake Flask Screening Method:

As described in U.S. Pat. No. 6,372,457, different glucosamine production strains: were grown in a mineral salt medium supplemented with glucose for glucosamine production in shake flask culture. In previous experiments, as they became depleted, glucose and ammonium sulfate were fed to the culture, leading to a continuous glucosamine production. However, this requires frequent monitoring and

TABLE 1

Genotype of Glucosamine Production Strain 2123-54

| Genetic Change | Description |
|---|---|
| Tet$^R$ at Δnag | Replacement of the nag regulon sequence with a tetracycline resistance marker for eliminating genes for glucosamine-6-phosphate metabolism and glucosamine uptake |
| manXYZ mutation | Mutation eliminating mannose-specific sugar transport system, which also transports glucosamine |
| lacZ::T7-glmS*54 | An integrated construct for overexpressing the glmS gene encoding for GlcN6P synthase. The glmS gene is placed under control by the T7 promoter. The construct is integrated into the E. coli chromosome in the lacZ gene. The *54 designation indicates mutations in glmS which result in an enzyme resistant to feedback inhibition by its product |
| DE3 | Genetic element which encodes the gene for T7 RNA polymerase driven by the lacUV promoter which is inducible by IPTG | feeding (every 6-8 hrs) for a period of 3 days. Therefore, it was desirable to develop a shake flask culture protocol that was simpler, yet reliable for evaluating different glucosamine production strains.

The simple mineral salt medium used in glucosaminee production was M9A (Table 2). A three-step protocol was developed for strain evaluation. First, cells freshly grown on LB plates were used to start a culture in 3-ml LB, which was grown at 37° C. for about 8 hrs. Second, 1.5-ml of the culture was used to inoculate 50 ml of M9A medium in a 250-ml shake flask and the culture was incubated at 37° C. and shaken at 225 rpm for about 16 hrs (overnight). Cell density of the culture was measured at 600 nm. This step was included for cells to adapt to the minimal medium and for reproducible results of glucosamine production. Third, aliquots of cells were added to 50 ml of M9A medium containing IPTG (0.2 mM) in a 250-ml shake flask. The initial cell OD was 0.3. Cells were incubated at 37° C. and shaken at 225 rpm for 72 hrs. Samples (1 ml) were taken at 24, 48 and 72 hrs to determine levels of glucosamine in the culture broth. At the 24 and 48 hr time points, pH was adjusted to 7.0 by addition of small amount of NaOH and glucose was added at 20 g $l^{-1}$. Under these experimental conditions, the control strain 2123-54 produced about 6 g $l^{-1}$ glucosamine at 72 hrs.

TABLE 2

M9A and M9B medium used for glucosamine production*

| Macroelements (g $l^{-1}$) | M9A | M9B |
|---|---|---|
| KH$_2$PO$_4$ | 14 | 6 |
| K$_2$HPO$_4$ | 16 | 24 |
| Na$_3$Citrate-2H$_2$O | 1 | 1 |
| (NH$_4$)$_2$SO$_4$ | 7.5 | 7.5 |
| MgSO$_4$-7H$_2$O | 0.25 | 0.25 |
| CaCl$_2$-2H$_2$O | 0.015 | 0.015 |
| Glucose | 20 | 20 |
| pH | 7.0 | 7.0 |

*For fermentation the medium is supplemented with antifoam (Mazu 204 and 0.25 ml $l^{-1}$)

Mutant Screening in Shake Flask Experiments:

About 150 recombinant *E. coli* strains with integrated glmS mutant constructs were re-evaluated using the optimized protocol. Glucosamine was assayed following the colorimetric method using Ehrlich's reagent. The strain 2123-72 and 2123-103 produced glucosamine at levels slightly higher than 2123-54 (Table 3).

TABLE 3

IPTG induced glucosamine production in shake flask culture

| | Glucosamine (g $l^{-1}$) | | |
|---|---|---|---|
| Strains | 24 hr | 48 hr | 72 hr |
| 2123-54 | 2.085 (100%)* | 5.599 (100%)* | 6.462 (100%)* |
| 2123-72 | 2.141 (103%) | 6.699 (120%) | 7.791 (120%) |
| 2123-103 | 2.390 (115%) | 7.230 (129%) | 8.712 (135%) |

*The percentage of numbers shown in the parentheses are relative to the values from 2123-54 at different time points.

Evaluation of High Glucosamine Producing Strains 2123-72 and 2123-103 in 1-Liter Fermentors:

The potentially better glucosamine production strains, 2123-72 and 2123-103 were compared to 2123-54 in 1-liter fermentors. Fermenters were set up with an initial volume of 475 ml of M9A medium supplemented with antifoam (Mazu 204 at 0.25 ml $l^{-1}$) and trace elements (Table 4). Fermentations were run using 75% NH$_4$OH for pH control to 6.9. Temperature was maintained at 30° C. throughout the fermentation. Aeration and agitation were adjusted to maintain a dissolved oxygen concentration of 20% of air saturation. 65% glucose was fed to the cultures with feed rate controlled by computer program to achieve a growth rate of 0.40 hr$^{-1}$ at inoculation and a maximum rate of 5 ml/hr by 6 hours. Fermentation allowed for precise control of pH, oxygen, and glucose concentration. Higher glucosamine concentration was achieved in the fermentors than in flasks.

Two sets of each strain were run under two different conditions. One set of fermentors started with a low glucose concentration (10 g $l^{-1}$, glucose limiting) and the other is set started with a higher concentration of glucose (40 g $l^{-1}$, excess glucose). The excess glucose conditions more closely resemble the shake flask growth conditions. The glucose limiting conditions were normally used in fermentation experiments and generally led to higher glucosamine production with 2123-54. The cultures were all induced with IPTG from the start of the fermentation. Under either glucose limiting or excess conditions, both strains 2123-72 and 2123-103 performed better than 2123-54, producing up to 14 g $l^{-1}$ glucosamine by 50 hrs, as compared to production of up to 10 g$l^{-1}$ glucosamine by 50 hours for 2123-54 (data not shown).

TABLE 4

Trace elements supplemented to growth medium used in some experiments

| Microelements | mg $l^{-1}$ |
|---|---|
| CoCl$_2$-6H$_2$O | 0.87 |
| H$_3$BO$_3$ | 1.72 |
| CuCl$_2$-2H$_2$O | 0.60 |
| FeCl$_3$-6H$_2$O | 10.50 |
| MnCl$_2$-4H$_2$O | 12.00 |
| ZnCl$_2$ | 1.50 |
| Na$_2$MoO$_4$-2H$_2$O | 1.50 |

Example 2

The following example describes over-expressing different glmS genes for glucosamine production.

Bacterial glucosamine synthase genes (glmS) and the yeast homologues (GFA genes) were cloned and expressed in *E. coli* to demonstrate their utility in glucosamine metabolic pathway engineering. Different genes were amplified from *Bacillus subtilis*, *Saccharomyces cerevisiae* and *Candida albicans* by PCR and placed under T7 promoter control in the expression vector pET24d(+). The constructs were transformed into the *E. coli* strain 7101-17(DE3) and maintained as free replicating plasmids. Additionally, the *C. albicans* GFA1 gene driven by the T7 promoter was integrated in the chromosome at the lacZ site in 7101-17 (DE3). Strains hosting different glmS and GFA genes were evaluated for gene expression and glucosamine production using IPTG induction.

*B. subtilis* glmS Gene Cloning:

The *B. subtilis* glmS gene contains an open reading frame of 1803 bp and encodes a protein of about 65 kDa (599 residues, excluding the initiator methionine which is usually removed in the cells). The nucleotide sequence of the *B. subtilis* glmS open reading frame is listed in SEQ ID NO:15.

The deduced amino acid sequence for the *B. subtilis* GlmS protein is listed in SEQ ID NO:16. The glmS gene was amplified by PCR from the strains ATCC 23856 and ATCC 23857. The forward primer contained the ATG start codon and a Bsa I site (SEQ ID NO:21): 5'-GAT CGG TCT CGC ATG TGT GGA ATC GTA GGT TAT ATC GGT C-3'. The reverse primer contained the stop codon and a Xho I site (SEQ ID NO:22): 5'-GAT CCT CGA GTT ACT CCA CAG TAA CAC TCT TCGCAA GGT TAC G-3.

PCR products of expected size were ligated into pET24d (+) (Novagen Inc, Wisconsin). The vector was predigested with the enzymes Nco I and Xho I. The recombinant plasmids pSW 07-15#83 were confirmed by restriction analysis and transformed into 7101-17(DE3), generating *E. coli* strains 7107-24 (glmS gene from *B. subtilis* ATCC23856) and 7107-25 (glmS gene from *B. subtilis* ATCC23857). As a control, the empty vector pET24d(+) was also transformed into 7101-17(DE3), generating the strain 7107-22.

*S. cerevisiae* GFA1 Gene Cloning:

The *S. cerevisiae* GFA1 open reading frame has 2154 bp and codes for a peptide of 716 residues (excluding the initiator methionine). The nucleotide sequence of the *S. cerevisiae* GFA1 open reading frame is listed in SEQ ID NO:17. The deduced amino acid sequence for the *S. cerevisiae* GFA1 protein is listed in SEQ ID NO:18. The protein size predicted from the sequence is about 80 kDa. No introns are present in the GFA1 gene sequence, therefore, the gene was amplified from genomic DNA prepared from the strain *S. cerevisiae* S288C (ATCC204508).

The forward primer, including the ATG start codon and a Bsa I site, had the following sequence (SEQ ID NO:23): 5'-GAT CGG TCT CGC ATG TGT GGT ATC TTT GGT TAC-3'. The reverse primer, including the stop codon and an EcoR I site, had the following sequence (SEQ ID NO:24): 5'-GAT CGA ATT CTT ATT CGA CGG TAA CAG ATT TAG-3'.

The PCR product of about 2.2 kb was cloned into pPCR-Script Amp SK(+). Recombinant plasmids were confirmed by restriction enzyme digestions. The *S. cerevisiae* GFA1 fragment was isolated by digestion with EcoR I and Bsa I and ligated into the EcoR I and Nco I sites of pET24d(+). The recombinant plasmid was confirmed by restriction analysis and transformed into 7101-17(DE3), generating the *E. coli* strain 7107-101.

*Candida albicans* GFA1 Cloning:

The *C. albicans* GFA1 gene is free of introns and its 2142-bp open reading frame encodes a peptide of about 80 kDa (712 residues, excluding the initiator methionine). The nucleotide sequence of the *C. albicans* GFA1 open reading frame is listed in SEQ ID NO:19. The deduced amino acid sequence for the *C. albicans* GFA1 protein is listed in SEQ ID NO:20. The GFA1 coding sequence was amplified from the strain ATCC10261 by PCR using a forward primer and a reverse primer. The forward primer contained the ATG start codon and a Bsa I site: 5'-GAT CGG TCT CGC ATG TGT GGT ATT TTT GGT TAC GTC-3' (SEQ ID NO:25). The reverse primer contained the stop codon and a Xho I site: 5'-GAT CCT CGA GTT ACT CAA CAG TAA CTG ATT TAG CC-3' (SEQ ID NO:26).

The PCR product was cloned into the vector pMOSBlue (Amersham Pharmacia Biotech, New Jersey) and recombinant plasmids were confirmed by restriction enzyme digestion. The Bsa I-Xho I fragment was isolated and ligated into pET24d(+) prepared by digestion with Nco I and Xho I. The resultant plasmid was transformed into the host 7101-17 (DE3), generating the *E. coli* strain 7107-23.

The *C. albicans* GFA1 gene was also cloned into the expression vector pET23b(+) (Novagen Inc). Unlike pET24d(+), this vector does not contain a lac operator sequence downstream from the T7 promoter. The absence of the lac operator could result in a higher recombinant protein expression level. The *C. albicans* GFA1 coding sequence was amplified by PCR from the yeast genomic DNA. The forward primer contained the ATG start codon and a Nde I site: 5'-GCG GGT ACC CAT ATG TGT GGT ATT TTT GGT TAC GT-3' (SEQ ID NO:27). The reverse primer contained a BamHI site: 5'-GCG GGA TCC TTA CTC AAC AGT AAC TGA TTT AGC CA-3' (SEQ ID NO:28). The PCR products of correct size were ligated into pET23b at the Nde I and BamHI sites. The recombinant plasmid was confirmed by restriction analysis and transformed into the expression host 7101-17(DE3), generating *E. coli* strains 7107-58 and 7107-59. As a control, the empty vector pET23b was also transformed into 7101-17(DE3), generating the strain 7107-57.

Overexpression of the *Candida albicans* GFA1 protein using the *E. coli* pET expression system was previously described in a publication (P. Sachadyn et al., Protein Expression and Purification 19, 343-349 2000). However, glucosamine production was not demonstrated or discussed at all. In addition, the reported GFA1 gene was cloned from a different *C. albicans* strain (ATCC13153). Although two GFA1 proteins have the same amino acid sequences, the GFA1 gene from ATCC13153 has the residues Leu 29 and Ala 655 coded by CTA and GCC, respectively, instead of TTA and GCT as in ATCC10261. An attempt was made to test if the use of different codons at the residues Leu 29 and Ala 655 has an impact on GFA1 gene expression in *E. coli*. Site directed mutagenesis using a strategy based on the Stratagene QuikChange® Site-Directed Mutagenesis Kit (Stratagene, CA) was performed to convert the Leu 29 codon to CTA and the Ala 655 codon to GCC in the plasmid pET23b(+)/*C. albicans* GFA1, creating the plasmid pET23b (+)/*C. albicans* GFA1-M. The presence of both mutations in the new plasmid was confirmed by sequencing and the plasmid was transformed into 7101-17(DE3), generating *E. coli* strains 7107-60 and 7107-61.

GlmS and GFA Protein Over-Expression:

Strains transformed with pET vectors containing different glmS and GFA1 genes were grown in LB medium to demonstrate GlmS and GFA1 protein expression. First, cells were grown in LB medium in test tubes at 37° C. overnight. The medium was supplemented with kanamycin (25 mg l$^{-1}$) to maintain plasmids. Then an inoculum of 50-μl overnight culture was used to start a 50-ml culture in a 250-ml baffled flask. Cultures were incubated at 37° C. and shaken at 225 rpm for 3 hrs. At that point, IPTG was added to a final concentration of 1 mM. After an induction period of 3 hrs, cultures were harvested for SDS-PAGE analysis. As a negative control, cells with the empty pET24d(+) vector were also grown and analyzed. For comparison, *E. coli* cells with the wild-type *E. coli* glmS gene and mutant glmS*54 gene driven by the T7 promoter and integrated in the chromosome at the lacZ site were also grown as above without antibiotic selection.

SDS-PAGE was carried out by following the standard methods. When the T7-*E. coli* glmS expression cassette was carried in pET plasmids or integrated in the chromosome, the GlmS protein was expressed at very high levels (data not shown). Cells hosting the plasmids pET24d(+)/T7-*B. subti-* lis glmS over-expressed a protein of about 65 kDa, the expected size of the GlmS protein (data not shown). The expression level from the integrated cassette was comparable to the cells expressing the *E. coli* glmS gene contained in pET plasmids.

Cells hosting the *S. cerevisiae* GFA1 gene showed a clearly over-expressed protein band of the expected size for the yeast protein (80 kDa, data not shown). In the strain 7107-23, containing the T7-*C. albicans* GFA1 expression cassette (data not shown), the synthesis of the 80-kDa protein band was not apparent when compared to the strain with the empty vector (data not shown). However, the GFA1 band was over-expressed in the strains 7107-58 and 7107-59 containing the *C. albicans* GFA1 gene carried by the vector pET23b(+)-based vector (data not shown). The expression level was clearly higher than in the strain 7107-23 with the pET24d(+)-based vector. The use of alternative codons for Leu 29 and Ala 655 did not affect *C. albicans* GFA 1 protein expression in *E. coli*.

All together, the expression levels of the yeast GFA1 genes in *E. coli* were low as compared to bacterial glmS genes. This is commonly observed when attempting to express eukaryotic genes in *E. coli* hosts.

Glucosamine-6-Phosphate Synthase Activity Assay:

For measurement of enzyme activity and glucosamine production, different strains were grown in M9A medium. A three-step protocol was used for preparing the cultures. First, cells freshly grown on LB plates were used to start a culture in 3-ml LB, which was grown at 37° C. for about 6 hrs. Second, 1.5-ml of the culture was used to inoculate 50 ml of M9A in a 250-ml baffled flask and the culture was incubated at 37° C. and shaken at 225 rpm for about 16 hrs (overnight). This step was included for cells to adapt to the minimal medium and for reproducible results of glucosamine production. Third, aliquots of cells were added to 50 ml of M9A medium containing IPTG (1 mM) in a 250-ml baffled flask. The initial cell density was adjusted to 0.3 $OD_{600}$. Cells were incubated at 37° C. and shaken at 225 rpm for 24 hrs. Following centrifugation, the culture broth was used in glucosamine assays and the cell pellet was used to determine glucosamine synthase activity. Data from representative experiments are shown in Table 5.

The enzyme activity was readily detectable in *E. coli* cells expressing the *B. subtilis* glmS genes (encoding SEQ ID NO:16). The activity level was comparable to the cells with a construct containing the *E. coli* glmS (encoding SEQ ID NO:2) and *E. coli* glmS*54 mutant (encoding SEQ ID NO:6) genes. However, only a trace amount of enzyme activity could be detected in cells hosting the yeast GFA1 genes (encoding SEQ ID NO:18 and SEQ ID NO:20). The activity data from cultures in M9A medium were generally consistent with the results of SDS-gel analysis of cells grown in LB medium. Low protein expression levels appeared to be one of the main reasons accounting for poor enzyme activity in cells hosting the yeast GFA1 genes.

Glucosamine Production by Expressing Different glmS and GFA1 Genes:

Only a very low level of glucosamine was produced and secreted into the culture medium of 7101-17(DE3) cells transformed with an empty vector pET24d(+) (Table 5). Expression of a bacterial glmS gene (*E. coli* glmS or *B. subtilis* glmS) resulted in a greater than 50-fold increase in glucosamine production. A several-fold increase in glucosamine level was also observed in the cultures expressing yeast GFA1 genes. As compared to pET24d(+), the use of pET23b(+) led to a higher level of *C. albicans* GFA1 protein and a higher level of glucosamine production. Change of the Leu 29 and Ala 655 codons in the *C. albicans* GFA1 gene did not affect glucosamine production levels. These observations were generally consistent with the results of SDS-PAGE analysis. As observed in enzyme activity assays, integration of the T7-*E. coli* glmS expression cassette in the chromosome appeared to be beneficial, as a higher glucosamine level was produced in the strain 2123-12 than in 7107-214. Clearly, the *E. coli* strain with *E. coli* glmS*54 integrated in the chromosome was superior for glucosamine production when compared to other tested strains.

TABLE 5

Glucosamine synthase activity and glucosamine production in *E. coli* strains expressing different glmS and GFA1 homologues

| Strain Number | Strain description | Enzyme activity (nmol $min^{-1}$ $mg^{-1}$) | Glucosamine (mg $l^{-1}$) |
|---|---|---|---|
| 7107-22 | pET24d(+) | trace | 5 |
| 7107-24 | pET24d(+)/T7-*B. subtilis* glmS 23856 | 637 | 128 |
| 7107-101 | pET24d(+)/T7-*S. cerevisea* GFA1 | trace | 47 |
| 7107-23 | pET24d(+)/T7-*C. albicans* GFA1 | trace | 23 |
| 7107-58 | pET23b(+)/T7-*C. albicans* GFA1 | trace | 54 |
| 7107-60 | pET23b(+)/T7-*C. albicans* GFA1-M | trace | 58 |
| 7107-214 | pET24d(+)/T7-*E. coli* glmS | 297 | 37 |
| 2123-12 | lacZ::T7-*E. coli* glmS | 613 | 75 |
| 2123-54 | lacZ::T7-*E. coli* glmS*54 | 803 | 2,029 |

Notes:
1) Host cell: *E. coli* 7101-17 (DE3). Genotype: nagΔ, manXYZ DE3.
2) Cell culture: 30° C. for 26 hrs in shake flasks containing M9A medium supplemented with 7.5 g $(NH_4)_2SO_4$ per liter and 40 g glucose per liter.
3) *C. albicans* GFA1 (M): Leu 29 and Ala 655 codons changed from TTA and GCT to CTA and GCC, respectively.

Example 3

The following example shows the characterization of different product-resistant GlmS enzymes: *E. coli* GlmS mutants and wild type *B. subtillus* GlmS.

Different glucosamine synthetase enzymes, including native *B. subtillus* GlmS, native *E. coli* GlmS and mutant *E. coli* GlmS, were studied in vitro. Cells of various *E. coli* strains were grown in the M9A medium, harvested, and frozen. Cells extracts were prepared and the glucosamine synthetases were characterized and compared. The DNA sequences were determined for two additional *E. coli* glmS mutants that showed strong product resistance and led to high glucosamine production in recombinant *E. coli*.

Sensitivity to Inhibition by Glucosamine-6-P:

Enzyme sensitivities to the reaction product glucosamine-6-P were examined. Initial velocity was examined at saturating glutamine and fructose-6-phosphate levels over a range of 0-30 mM glucosamine-6-P. Exemplary results are shown in FIGS. 4 and 5. The *E. coli* native GlmS enzyme from the strain 2123-12 loses about 50% activity at 1 mM level of glucosamine-6-P. Activity continues to decrease with increasing levels of glucosamine-6-P. In strain 2123-54, 1 mM glucosamine-6-P essentially has no effect on enzyme activity. Above this level inhibition is fairly linear, with roughly 50% activity remaining at 10 mM glucosamine-6-P. Mutant GlmS enzymes from other strains such as 2123-4, 2123-59, 2123-64, 2123-72, 2123-103 and 2123-124 also showed reduced sensitivity to GlcN-6-P inhibition. FIG. 5 shows activity at relatively "low" [glucosamine-6-P]. This figure highlights the dramatic difference between the wild type GlmS and these mutant GlmS strains. Even fairly low levels of glucosamine-6-P significantly inhibit the native GlmS enzyme.

When the wild type *Bacillus* glmS gene was over-expressed in *E. coli*, it led to a higher level glucosamine production than over-expression of the wild type *E. coli* glmS gene. Interestingly, the native *Bacillus* enzyme showed a product resistance very comparable to the *E. coli* mutant GlmS enzymes (FIG. 4). Activity of the *B. subtillus* enzyme was measured at 0, 2 and 4 mM glucosamine-6-P. The enzyme has a Km (fructose-6-phosphate) of 0.62 mM, and a Ki (glucosamine-6-P) of 1.25 mM (data not shown).

A secondary plot of nonlinear regression values for Vmax versus [inhibitor] yielded a inhibition constant (Ki) of 0.56 mM for strain 2123-12. The Mutants 2123-54 and the *B. subtilis* enzyme have higher Ki values (Table 6). Measured Ki constants for several of these mutants are 4 to 8 times the value for the native enzyme in strain 2123-12. From shake flask studies it is apparent that decreased sensitivity to glucosamine-6-P allows higher glucosamine levels to accumulate. This strongly suggests that the intracellular [glucosamine-6-P] is fairly high (multi millimolar) in the recombinant *E. coli* strains, resulting in decreased glucosamine synthetase activity. Drastically reduced sensitivity to glucosamine-6-P inhibition offers the simplest explanation for the increased glucosamine synthesis in strains over-expressing the mutant *E. coli* GlmS and wild type *Bacillus* GlmS enzymes.

Affinity to Substrates Fructose-6-P and Glutamine:

Michaelis-Menten constants for glutamine and fructose-6-phosphate were determined using crude extracts (Table 6). With the wild-type *E. coli* GlmS enzyme (strain 2123-12), nonlinear regression yielded values of 0.20 mM (fructose-6-phosphate) and 0.17 mM (glutamine). Analogous experiments with a mutant GlmS*54 (strain 2123-54) yielded the values of 0.64 mM (fructose-6-phosphate) and 0.73 mM (glutamine). These values are slightly higher than those obtained with the native enzyme. The *Bacillus subtilis* GlmS enzyme expressed in *E. coli* (strains 7107-24) showed a Km (fructose-6-P) value very similar to the mutant *E. coli* enzyme GlmS*54.

TABLE 6

Characteristics of different GlmS enzymes

| Enzyme sources | Ki (GlcN-6-P) (mM) | Km (fructose-6-P) (mM) | Km (glutamine) (mM) |
| --- | --- | --- | --- |
| WT *E. coli* GlmS | 0.56 | 0.20 | 0.17 |
| Mutant *E. coli* GlmS*54 | 4.00 | 0.64 | 0.73 |
| Mutant *E. coli* GlmS*110 | 1.60 | 0.41 | ND* |
| Mutant *E. coli* GlmS*124 | 3.50 | 1.10 | ND |
| Mutant *E. coli* GlmS*69 | 1.50 | 0.35 | ND |
| Mutant *E. coli* GlmS*72 | 1.40 | 0.95 | ND |
| Wild type Bacillus GlmS | 1.25 | 0.62 | ND |

*ND: Not determined

Thermal Stability:

Denaturation at 50° C. was used to measure possible differences in thermal stability of different GlmS enzymes. Crude extracts were incubated at 50° C. and sampled over a 90-minute period. The samples were assayed for glucosamine synthetase activity at 25° C. with saturating levels of all substrates.

There does not appear to be any significant correlation between thermal stability at 50° C. and production of glucosamine (data not shown). Strain 2123-124 has the lowest stability but has been shown to be one of the best glucosamine production strains. There is little significant difference in thermal stability between strains 12, 54 and 59, yet from other experiments, the inventors know that strain 54 is a much better strain for glucosamine production.

Example 4

The following example describes a GlmS sequence analysis.

Strains 2123-72 and 2123-103 were derived from the host strain 7101-17(DE3) by transformation and integration experiments with plasmids pK1N23-72 and pKLN23-103, respectively. The glmS regions (glmS*72 and glmS*103) in these plasmids were sequenced. The nucleotide sequence of the *E. coli* glmS*72 mutant coding sequence is listed as SEQ ID NO:13. The deduced amino acid sequence of the *E. coli* GlmS*72 protein is listed as SEQ ID NO:14.

Interestingly, it turned out that both mutants have the same mutations that resulted in amino acid substitutions at positions 15, 387, 450 and 525 (Table 7). The residues at the relevant positions in the *E. coli* wild type GlmS (SEQ ID NO:2), mutant GlmS*49 (SEQ ID NO:4), GlmS*54 (SEQ ID NO:6) and GlmS* 124 (SEQ ID NO:8) are listed for comparison. The GlmS*72 has no common mutations, with respect to other product resistant GlmS mutants, except for the change of a serine to proline at position 450 which was also found in both GlmS*49 and GlmS*72. Interestingly, three GlmS mutant enzymes (GlmS*49, 72 and 124) have a mutation resulting in a change of one residue to proline in the region 450 to 469. GlmS*54 also has a residue change at position 472: a glycine replaced with a serine. These data suggest that changes in this region of the protein may play an important role in product resistance of the enzyme.

TABLE 7

Base changes in the *E. coli* mutant glmS gene coding for a product resistant glucosamine synthase

| Position* | 15 | 387 | 450 | 525 |
| --- | --- | --- | --- | --- |
| WT glmS | Glu (GAA) | Asp (GAT) | Ser (TCT) | Glu (GAA) |
| Mutant glmS*72 | Lys (AAA) | Val (GTT) | Pro (CCT) | Gly (GGA) |

*For simplicity, positions are given according to the numbering of the deduced amino acid sequence.

The nucleotide sequences of different bacterial glmS coding sequences were analyzed using the Megalign Program, J. Hein Method, Lasergene software (DNA Star, Inc, Madison, Wis.) with the standard settings. The amino acid sequences deduced from the nucleotide sequences were also compared using the Megalign Program, Lipman-Pearson Protein Alignment, Lasergene software (DNA Star) with the standard settings. Results are shown in Table 8.

TABLE 8

Peptide size and homology of glucosamine synthase enzyme from different microorganisms

| GlmS | Number of Amin Acids* | Peptide Size (kDa) | Peptide Sequence Homology (% identity)** | | | |
|---|---|---|---|---|---|---|
| | | | E. coli | B. subtilis | S. cerevisiae | C. albicans |
| E. coli | 608 | 67 | | 41 (50) | 42 (47) | 42 (46) |
| B. subtilis | 599 | 65 | | | 36 (45) | 36 (45) |
| S. cerevisiae | 716 | 80 | | | | 72 (72) |
| C. albicans | 712 | 79 | | | | |

*The numbers of amino acid residues does not include the initiator methionine, which is removed enzymatically after translation.
**Homology at the nucleotide level is shown in parentheses.

The *Bacillus subtilis* glmS gene encodes for a glucosamine synthase of 599 amino acid residues (SEQ ID NO:16) (excluding the initiator methionine, which is normally removed enzymatically after translation), 9 residues short than the *E. coli* homologue. The amino acid residues of the Bacillus GlmS protein that correspond to the positions where mutations were found in different product resistant *E. coli* GlmS mutants are listed in Table 9 for comparison. Interestingly, at six out of ten positions, the Bacillus enzyme has a different residue with respect to the *E. coli* wild type GlmS although none of the changes is the same as in the *E. coli* mutant enzymes.

TABLE 9

Amino acid residue changes in produce resistant mutant *E. coli* GlmS and wild type *B. subtilis* GlmS*

| | | E. coli mutant GlmS | | | | B. subtilis |
|---|---|---|---|---|---|---|
| Position | E. coli wt GlmS | GlmS*49 | GlmS*54 | GlmS*124 | GlmS*72 | wt GlmS** |
| 4 | Ile | Thr | | | | |
| 15 | Glu | | | | Lys | |
| 39 | Ala | | Thr | | | Gln |
| 250 | Arg | | Cys | | | Pro |
| 272 | Ile | Thr | | | | Tyr |
| 387 | Asp | | | | Val | |
| 450 | Ser | Pro | | | Pro | Asp |
| 469 | Leu | | | Pro | | Phe |
| 472 | Gly | | Ser | | | |
| 525 | Glu | | | | Gly | His |

*Only the residues that are different from the ones in the *E. coli* wild type GlmS protein are shown.
**The positions for the Bacillus GlmS sequence are based on the alignment with the *E. coli* wild type GlmS sequence due to small gaps in the alignment.

Example 5

The following example demonstrates enzyme activities during glucosamine production in shake flask culture.

Various enzyme activities relevant to glucosamine production were examined both in shake flasks and in fermentators. The involvement of these enzymes in the metabolism of glucose and the formation of N-glucosamine is outlined in FIG. 3. Glucose is taken up by the cell and is simultaneously converted to glucose-6-P. Glucose is metabolized by number of pathways, including those shown in the figure. In the glucosamine synthesis pathway, glucose-6-P is isomerized to fructose-6-phosphate, followed by the GlmS mediated conversion of fructose-6-phosphate to glucosamine-6-phosphate. Finally, glucosamine-6-phosphate is dephosphorylated and secreted. A major competing alternative route for glucose-6-phosphate is its entry into glycolysis via phosphofructokinase. Another important alternate routes for glucose-6-phosphate is its oxidation to gluconolactone-6-phosphate (the entry into the pentose phosphate pathway). Additionally, glucose-6-phosphate could be converted to glucose-1-phosphate, from which glycogen is made and stored in the cell.

Results of enzyme analysis in a shake flask experiment using strain 2123-54 are shown in FIG. 6. Cells were grown in M9A medium and were induced with 0.2 mM IPTG from the start of the culture. Glucosamine synthase (GlmS) activity was high throughout the entire experiment. There was a high level of GlmS activity at 12 hours and that increased further by 24 hours. Afterwards, the GlmS activity appeared to decline. However, this decrease was not dramatic. Activity at 72 hours was still high, and was basically the same as what was observed at 12 hours. Thus, GlmS activity did not appear to decrease significantly during the course of the experiment.

Phosphoglucoisomerase (Pgi) activity was high at 12 hours, and increased significantly by 24 hours. After this it returned to the level seen at 12 hours and remained at that level for the rest of the experiment. Clearly, formation of fructose-6-phosphate from glucose should not have been limited by low Pgi activity in these cells under this set of experimental conditions.

The other major route for fructose-6-phosphate is glycolysis. The first committed step here is mediated by phosphofructokinase (Pfk). The highest Pfk activity was observed at 12 hours, and although it decreased over the next 48 hours, the activity remained detectable. This activity pattern is typical for Pfk. Activity is highest during exponential growth, and then decreases as cells enter stationary phase.

Glucose-6-phosphate dehydrogenase (Glu6P DH) was detected in extracts. This enzyme feeds carbon from glucose into the pentose phosphate pathway for regeneration of NADPH. Activity of this enzyme was quite low relative to others measured, fairly stable, and decreased slightly after the first 24 hours of the experiment. Activity of phosphoglucomutase (Pgm) was found to be very low under the experimental conditions.

Example 6

The following Example describes the development of recombinant E. coli strains for lactose inducible glucosamine production.

In order to develop a commercially viable process for glucosamine production, two factors were necessary. First was to increase glucosamine titer. The second was to eliminate the use of IPTG in the fermentation process, because the cost of IPTG causes glucosamine manufacture to be prohibitively expensive. Strains for glucosamine production that were developed during the early stage of the research program required IPTG in the culture medium to induce the expression of glucosamine synthase.

A Strategy for Eliminating IPTG from the Fermentation Process

The requirement for IPTG in the fermentation process stems from the mode of overexpression of the glmS gene, encoding GlcN6P-synthase, in the production strains such as 2123-54. The glmS gene was isolated from E. coli chromosomal DNA and cloned into an expression vector behind a promoter from bacteriophage T7. This promoter is very powerful and very specific. It is not recognized by E. coli RNA polymerase, but rather, by the T7 RNA polymerase. T7 RNA polymerase is provided in a genetic element designated DE3, which contains the gene for T7 RNA polymerase driven by the E. coli lac promoter and lac operator. It is the use of these promoter and operator that necessitates induction with IPTG. The lac promoter is subject to negative control by the lac repressor, encoded by the lacI gene. In the absence of inducer, the lac repressor binds to the lac operator and prevents expression of genes downstream from the operator, in this case the T7 RNA polymerase gene. In the absence of T7 RNA polymerase, the recombinant glmS gene is not expressed. In the presence of IPTG, the lac repressor will not bind to the operator with the result that the T7 RNA polymerase gene is expressed allowing overexpression of glmS.

Another inducer of the lac promoter is allolactose. This is a byproduct of the action of b-galactosidase on lactose. Glucosamine production strains such as 2123-54 are negative for b-galactosidase due to the deletion and disruption of the lacZ gene. In the presence of a functional lacZ gene, however, lactose could be converted to allolactose, initiating the cascade of reactions described above that would lead to expression of glmS.

In light of the above, there are several methods for eliminating dependence on IPTG. One approach illustrated in the present example is to restore the lacZ gene. This can be done by integrating the T7-glmS*54 expression cassette at a different site in the chromosome. Integration at the galK site would leave the lacZ gene intact. Lac$^+$ strains are potentially inducible by lactose, which is much less expensive than IPTG. The galK site was chosen because the integrant stains would also be Gal$^-$. It was reported that in such strains galactose could be used as an inducer for lac promoters. Moreover, galactose generated through lactose hydrolysis could enhance lactose induction. This may enhance the induction when a sub-optimal amount of lactose was used in the glucosamine production process. In theory, when the T7-glmS*54 expression cassette is inserted at the galK site in strain 7101-17(DE3) the resulting strain would be analogous to strain 2123-54, but glucosamine production would be inducible with either lactose, galactose or IPTG.

A General Protocol for Gene Integration or Deletion in Targeted Site on the Chromosome by Temperature Selection Vectors and methods were described by Hamilton et al. (1989, J. Bacteriol. 171:4617-4622) to make targeted gene deletion and gene integration in E. coli chromosome by temperature shift. The method was adapted to develop different glucosamine production E. coli strains. The protocols for gene integration include the following major steps. The first step is to clone the sequence of the target site and make an internal deletion and/or insert the foreign gene to be integrated at the deletion site. The second step is to subclone the fragment containing these sequences into a temperature sensitive integrative vector containing a temperature sensitive replication origin and an antibiotic selection marker. The third step is to transform the integrative vector into the E. coli host strain and select for clones with the entire plasmid integrated into the chromosome through single crossover recombination event under non-permissive temperature (42° C.). The fourth step is to grow the cells of selected clones in liquid culture at permissive temperature (30° C.). Cells with the integrated plasmid have a tendency to lose the plasmid. Cells that have lost the portion of the replication origin and antibiotic resistance gene or the entire plasmid will outgrow in the culture. Typically, this step was accomplished by inoculating a 50-ml LB medium with cells from a pool of two to ten clones and growing the culture for 24 hrs. The culture was passed to a fresh medium at a 1,000-fold dilution and grown for another period of 24 hrs. Fifth, cells were plated and clones that had lost the antibiotic resistance were selected. Gene specific selection procedures could be used, depending on the nature of integrated gene or deleted gene. Typically for screening clones, PCR was carried out using a primer set that could distinguish the clones with the intended change in the chromosome from its native form by the size of PCR products. Clones were confirmed by Southern Blot analysis using probes specific to the integrated or deleted DNA sequence.

Development of Vectors for T7glmS*54 Integration at the galK Site by Temperature Selection A vector containing a portion of the E. coli gal operon sequence, the kanamycin resistance selection marker from plasmid pUC4K (Amersham Pharmacia Biotech, Piscataway, N.J.) and the temperature sensitive pSC101 replication origin from pMAK705 (Hamilton, et al., 1989, J. Bacteriol. 171:4617-4622) was developed for gene integration at the galK site using a temperature selection protocol. A portion of the E. coli gal operon sequence (3.3 kb) was amplified by PCR from E. coli strain W3110. The PCR product contained the sequence galTKM (starting at 14 bp upstream to the ATG start codon of the galT coding sequence, and ending at 68 bp following the stop codon of the galM coding sequence) and was cloned into vector pCRScript Amp SK(+), generating the recombinant plasmid pKLN23-157. A 0.7-kb deletion was made in the galK sequence (between the restriction sites Sfo I and Mlu I) and unique restriction sites were added (Sal I, Bgl II, and Mcs I at the site of the deletion, creating plasmid pKLN07-1. A kanamycin resistance cassette was isolated as a Pst I fragment from pUC4K (Amersham Pharmacia Biotech, Piscataway, N.J.) by Pst I digestion and a treatment with T4 DNA Polymerase to produce blunt ends. The fragment was ligated into the Not I site (blunted with T4 DNA Polymerase) of the plasmid pKLN07-1 (orientation undetermined). The kan:: galTKM fragment was removed from the plasmid as a BamH I/Sac II (ends blunted with T4 DNA Polymerase) fragment and ligated with a Pvu II/Sma I fragment containing the temperature sensitive replicon of pMAK705 (Hamilton, et al., 1989, *J. Bacteriol.* 171:4617-4622), creating plasmid pSW07-4. The expression cassette T7-glmS*54 was digested from the plasmid pKLN23-54 (disclosed in U.S. Pat. No. 6,372,457) as a Not I fragment and ends made blunt with T4 DNA Polymerase. The fragment was cloned into pSW07-4 at the Msc I site, generating plasmid pSW07-9.

Selection for Lactose Inducible Strains

Following transformation of the *E. coli* strain 7101-17 (DE3) with pSW07-9, a protocol adapted from Hamilton et al. (1989) was used for temperature sensitive selection of integration mutants. For plasmids with the temperature sensitive replicon from pMAK705, plasmid replication can take place at 30° C., but plasmid integration is forced at non-permissive temperature (42° C.) under antibiotic selection. Incubating transformed cells at 42° C. thus selected for strains that had integrated the plasmid. This was done by plating cells on plates containing kanamycin, incubating plates at 42° C. and selecting colonies. Usually, the entire plasmid was integrated into the chromosome by homologous recombination. The single crossover event could take place in the galT or galM regions.

Due to the replication origin, cells with the integrated plasmid have a tendency to loop out the plasmid from the chromosome. While cells with the entire plasmid integrated grow very poorly at 30° C., cells that have lost the plasmid or the portion of the replication origin display normal growth. Therefore, when cells selected at 42° C. were grown at 30° C., cells that have lost the plasmid outgrow the cells retaining the plasmid. In principal, there were two different ways for the cell to lose the plasmid through homologous recombination. They either lose the entire plasmid, resulting in a revertent strain with the native gal operon, or lose only the plasmid part containing the replication origin and selection marker, resulting in a strain with the T7-glmS*54 sequence integrated at the galK site. Cells from colonies isolated from 42° C. selection were incubated in liquid culture at 30° C., plated on plates containing no antibiotic. Since the integration resulted in the inactivation of the galK gene, integrant strains were unable to utilize galactose as the sole carbon sources. Galactose plates were used to screen for such integrant strains, which were then confirmed by Southern Blot hybridization using galK sequence as probe. These lactose-inducible glucosamine production strains were designated 7107-16 and 7107-18.

Example 7

This example describes lactose inducible glucosamine production.

Strains with the T7-glmS*54 expression cassette integrated at the galK site (7107-16 and 7107-18) produce high levels of glucosamine after induction by either IPTG or lactose. The control strain (2123-54) under IPTG induction yielded 4.2 g/l. Glucosamine yields in lactose inducible strains were comparable to IPTG-induced 2123-54. Glucosamine levels in 2123-54 and a lactose inducible strain are shown in FIG. 7.

Glucosamine synthase activity was assayed in samples of lactose induced cultures. Cells were grown in the M9A medium containing different amounts of glucose and/or lactose (numbers indicating grams per liter). Enzyme activity and glucosamine were assayed after 24-hr growth. As shown in Table 10, lactose induces GlmS activity and glucosamine synthesis. Lactose induction was affected by the amount of glucose in the medium. High levels of glucose showed a strong repression on lactose induction. Strain 7107-18 was selected for further development of the lactose induction protocol. The strain was evaluated under various lactose induction schemes in shake flasks and 1-liter fermentors.

TABLE 10

Glucosamine synthase activity and glucosamine production levels in lactose inducible strain 7107-16

| Growth Conditions[1] | GlmS activity[2] ($\mu$ mol min$^{-1}$ mg$^{-1}$) | GlcN (gl$^{-1}$) |
|---|---|---|
| 30 glucose/0.2 mM IPTG | 0.107 | 2.386 |
| 30 glucose/20 lactose | 0.046 | 0.202 |
| 5 glucose/25 lactose | 1.140 | 2.042 |
| /40 lactose | 0.840 | 2.810 |

Note:
[1]Cells were grown in the M9A medium containing different amounts of glucose and/or lactose (numbers indicating grams per liter).
[2]Enzyme activity and glucosamine were assayed after 24-hr growth.

Lactose Induction and Glucose Repression:

In a fermentation experiment, different lactose levels were tried, along with a feed of either lactose or glucose after lactose induction. Glucosamine level was monitored over a 72 hour period. The first protocol for lactose induction was similar to IPTG induction, in that lactose was added before inoculation (with no glucose, since glucose represses the lac operon), followed by glucose feeding to supply carbon for growth, GlcN formation and biomass maintenance. When cells were grown on 40 g l$^{-1}$ lactose and fed continuously with a lactose feed, cells continued to consume lactose. This caused significant levels of galactose to accumulate, up to 40 g l$^{-1}$. Glucosamine production level was similar to that of 2123-54 under IPTG induction (about 10 g l$^{-1}$).

Cells were grown on 40 g l$^{-1}$ lactose for 24 hrs, and were then switched to a glucose feed. Under these conditions, cells stopped lactose utilization and galactose remained constant at 10 g l$^{-1}$ throughout the remainder of the trial. Glucosamine production continued at a good rate, reaching a level comparable to that of strain 2123-54. This result indicates that glucosamine production can be supported strictly by glucose after lactose utilization is stopped. This also implies that induction requires only small amounts of lactose resulting in accumulation of only low levels of galactose. Reduced need for lactose and reduced accumulation of galactose are both desirable for cost reduction and product recovery.

Induction schemes using increased lactose of 50 and 60 g/l, followed by glucose feeding showed continued lactose utilization for some time after the glucose addition. This indicates that repression by glucose was incomplete at higher levels of lactose, or that the induced enzyme continued to function at an adequate level to sustain glucosamine production following glucose addition.

Since it was desirable to use lower levels of lactose, and the experiments showed that the glucose repression could be minimized at the lowest lactose level tested, even lower levels of lactose were tested. Further development work was focused on establishing the minimum level of lactose required for induction, the optimal timing and duration of induction, and the merit of an initial growth phase with glucose prior lactose induction. The latter might be especially important when higher cell densities are desired in controlled fermentation.

An attempt was made to grow cells on glucose until cells were glucose depleted, followed by induction with lactose. Growth on glucose was allowed to reach a cell density of approximately 17 g $l^{-1}$, and then a slow lactose feed was started. Under these conditions GLcN production reached 10 g $l^{-1}$. This strategy was used in later experiments for GlcN production.

Effect of Acetate:

Acetate is a common by-product in *E. coli* fermentation. It is formed even under aerobic conditions when glucose is in excess, when growth rates exceed a critical level, or when the rates of glycolysis and oxidation of the metabolites formed are unbalanced due to the saturation of the respiration capacity. Addition of acetate to cultures showed a significant negative effect on both growth and glucosamine accumulation. Acetate was also shown to accumulate during glucosamine production. The level of trace elements affected the level of acetate formation (see below).

Strategies to reduce acetate accumulation through process development included limited growth by slow glucose feeding, such that glucose did not become saturating. This strategy was employed throughout the program. Certain conditions could result in significant levels of acetate, such as high trace elements or potassium limitation. Low pH increased the inhibitory effect of acetate.

Effect of Temperature:

As disclosed in U.S. Pat. No. 6,372,457, the preferred temperature for growth and glucosamine production was 30° C. Higher growth temperature (37° C.) lead to higher growth rates, increased glucose uptake, and ultimately inhibitory acetate levels. Higher temperature can also lead to the formation of inclusion bodies that contain insoluble/inactive recombinant GlmS protein. Studies in flasks showed a significant decrease in acetate levels and a comparable GLcN level when the temperature was shifted from 30° C. to 25° C. after induction. Therefore, low temperature (25° C.) to reduce acetate accumulation was evaluated in fermentors. Results showed that at lower temperature, acetate accumulation was reduced, even under conditions of glucose accumulation.

Effect of Trace Elements:

In order to grow biomass to higher density, certain trace elements are required, especially iron, zinc, and manganese. An initial titration of the whole trace element package showed that biomass production was limited when the levels of trace elements were too low. It was then determined that iron was the main limiting growth factor, but if in excess it would lead to lower GLcN titers and higher acetate levels. Manganese had similar but weak effects on cell density and GLcN levels in flask culture. Manganese effects appeared to be additive to iron effects. The negative effect of manganese was confirmed in fermentors (FIG. 8). It was found that an adequate supply of iron was necessary in order for the cells to become adequately induced by lactose. Therefore, a critical concentration range had to be established to balance growth requirements, induction requirements, and the effects on acetate and GLcN production. The limitation of iron, manganese, and zinc to restrict carbon flow from glycolysis has precedence in the process improvement for citric acid fermentation.

After several experiments, a final scheme was established: 3 mg $l^{-1}$ iron sulfate in the medium and iron sulfate added to glucose feed at a ratio of 5 μg $g^{-1}$ glucose. At an initial level of 3 mg iron sulfate in the medium, iron addition to the glucose feed solution was required to maintain a low level of biomass growth and extend GLcN production.

Effect of Phosphate Concentration:

Phosphorus is a necessary macronutrient for cells, mainly being used for nucleic acid synthesis, phospholipids, and coenzymes. Phosphorylated metabolic intermediates are also necessary for cellular metabolism. High phosphate concentration in the M9A medium serves also as a way to buffer the pH in the culture that is not readily controllable under flask conditions. However, scaling up of this medium to fermentation scale means that phosphate would be in great excess beyond normal biomass requirements. The high salt levels presented a problem for product recovery. Therefore, it was desired to reduce the phosphate level. Several trials with decreasing phosphate levels showed better growth, but much poorer GLcN production. For example, when lowering the potassium phosphate level from 30 g $l^{-1}$ to 6 g $l^{-1}$, growth was improved while GLcN production was greatly reduced (FIG. 9).

Example 8

This example describes the effects of pH on growth of the lactose-inducible glucosamine production strain 7107-18.

As shown in Example 11, glucosamine is unstable at the regular pH range used for *E. coli* growth. Glucosamine also caused toxic effects on strain 7107-18. Toxicity was observed even when glucosamine at concentration as low as 20 g $l^{-1}$ was pre-incubated in the medium (pH 7) for 3.5 hrs prior to cell inoculation. The toxicity was attributed to at least partially to GlcN degradation products in media with a starting pH of 7.0. GlcN is more stable at lower pH, glucosamine is not degraded at or below pH 4.7. However, low pH levels are known to limit cell growth. Therefore, experiments were conducted in which 7107-18 was grown at pH 7.0, 6.0, 5.5, 5.0 and 4.7. The main objectives were to study cell growth at these lower pHs (with GlcN), and to see if the previously observed cell death caused by GlcN degradation could be reduced at lower pHs.

Batches of M9A medium with 40 g $l^{-1}$ glucose and 20 g $l^{-1}$ GlcN were adjusted to five different pHs. One set of flasks was immediately inoculated with 7107-18 cells. Replicate flasks of the same media were incubated without cells for 10 hours, before inoculation. Seven times over 48 hours, flasks were sampled to measure pH, $OD_{600}$, and GlcN concentration. At each sample point, the pH of the culture was readjusted back to the initial settings.

Without glucosamine pre-incubation, cell culture at pH 7.0 showed good growth even with 20 g l$^{-1}$ glucosamine in the medium (FIG. 10). Between pH 7.0 and 4.7, the growth rate decreased as pH decreased. However, cells continued to show significant growth at pH 4.7.

Similar to previous observations, cells did not grow well after the medium was pre-incubated with glucosamine at pH 7.0. Cell growth after inoculation into pre-incubated medium was observed. The growth was very poor across all pH levels tested. This appeared to result from a combination of the effects of lower pH and of glucosamine degradation on cell culture.

Based on these experiments, it looked feasible to grow 7107-18 cells at pH levels lower than 7.0 in order to minimize product loss and toxic effects caused by glucosamine breakdown. However, the optimal pH and culture conditions must be adjusted carefully: lower pH levels could stabilize glucosamine but they also negatively affect cellular metabolism and cell growth. A GlcN production protocol in fermentors run at relatively low pH levels would certainly help preserve any GlcN which is made, protecting the cells in the process by reducing the concentration of breakdown products. These benefits must be balanced against the reduced metabolic activity of cells grown this way. Continued GlcN synthesis requires the constant generation of energy in the cells, and cells growing slowly at these lower pH levels did not appear capable of generating enough of the energy required.

Example 9

This example describes fermentation at lower pH to stabilize glucosamine.

The normal optimal growth pH for *E. coli* is near neutral (pH 7.0), and a pH of 6.7 to 6.9 was used initially for GLcN fermentations. However, it was found that GLcN is subject to degradation in solution, especially neutral to alkaline pH. The organism is sensitive to pH, and does not grow well as pH decreases. Therefore, tests were conducted to determine the effects of low pH on glucosamine synthesis and accumulation following a growth phase. Effect of dissolved oxygen level was also tested, since glucosamine degradation was believed to be oxidative. Cells were grown at pH 6.7 to reach a high cell density. After the culture was induced, the pH was dropped from 6.7 to 5.5, and the level of dissolved oxygen was also dropped from 20% to 5% saturation. In this example, the best glucosamine accumulation was at low pH, and lower oxygen level also appeared to be beneficial (FIG. 11). At least some of the improvement was due to lower degradation, as continued imposition of the pH and oxygen variables showed much lower degradation at low pH in the culture after cessation of glucosamine accumulation at a low but sustaining glucose feed.

Example 10

This Example describes a summary of conditions used for the lactose-induced glucosamine fermentation process.

Fermentation process was developed using recombinant *E. coli* strain 7107-18 for lactose induced production of glucosamine. The product titer was about 20 g l$^{-1}$ glucosamine at 72 hrs. To those skilled in the art, the process can further be optimized based on the observations disclosed in the present invention. Methods developed for other fermentation processes may also be applied to the glucosamine fermentation process to enhance the performance. The major factors and elements of the process disclosed in the present invention are summarized below.

| | |
|---|---|
| Strain: | Recombinant *E. coli* |
| Induction: | 30 g/l lactose was added (as a 35% feed ramped slowly over a 10 hour period) after a cell density of 10 g/l is reached. Glucose feed was suspended during this procedure to prevent glucose repression. After the lactose had all been added, glucose feed was re-instated. |
| Feed: | 50% glucose with 5 μg FeSO$_4$-7H$_2$O/g glucose and 0.33 μg MnSO$_4$-H$_2$O/g glucose, glucose fed at limiting concentrations. |
| Fermentation Time: | 72 hours |
| Fermentation Mode: | Fed Batch, with 50% glucose was added as required, maintained limiting concentrations of glucose. |
| Inoculum: | 5% by volume |
| pH: | 6.9 during growth, then 6.7 after induction, controlled by 10 N NH$_4$OH |
| Temperature: | 30 C, switched to 25 C after induction |
| Oxygen: | Dissolved O$_2$ at 20% or greater, controlled by agitation |
| Aeration: | 0.5 to 1 vvm |

| Medium: | Component | Concentration |
|---|---|---|
| | KH$_2$PO$_4$ | 14 g l$^{-1}$ |
| | K$_2$HPO$_4$ | 16 g l$^{-1}$ |
| | Na$_3$-citrate | 1 g l$^{-1}$ |
| | (NH$_4$)$_2$SO$_4$ | 5 g l$^{-1}$ |
| | CaCl$_2$-H$_2$O | 0.05 g l$^{-1}$ |
| | MgSO$_4$-7H$_2$O | 0.6 g l$^{-1}$ |
| | FeSO$_4$-7H$_2$O | 3 mg l$^{-1}$ |
| | ZnSO$_4$-7H$_2$O | 3.8 mg l$^{-1}$ |
| | MnSO$_4$-H$_2$O | 0.33 mg l$^{-1}$ |
| | CuSO$_4$-5H$_2$O | 0.1 mg l$^{-1}$ |
| | NaMoO$_4$-2H$_2$O | 0.1 mg l$^{-1}$ |
| | H$_3$BO$_3$ | 0.1 mg l$^{-1}$ |
| | CoCl$_2$-6H$_2$O | 0.1 mg l$^{-1}$ |
| | Glucose | >200 g l$^{-1}$, as needed |
| | Mazu 204 defoamer | 0.25 g l$^{-1}$ |

All components were added before sterilization except glucose (added incrementally) and Fe, Zn, Mn, Cu, B, Mo, Co trace elements (added after sterilization).

Example 11

This Example describes glucosamine and N-acetylglucosamine stability, and their effects on *E. coli*.

Stability of Glucosamine:

Glucosamine stability was tested in cell-free M9A medium (14 g l$^{-1}$ K$_2$HPO$_4$, 16 g l$^{-1}$ KH$_2$PO$_4$, 1 g l$^{-1}$ Na$_3$citrate.2H$_2$O, 5 g l$^{-1}$ (NH$_4$)$_2$SO$_4$, 10 mM MgSO$_4$, 1 mM CaCl$_2$, pH 7.0) supplemented with 40 g l$^{-1}$ glucose. Glucosamine was prepared as a 30% glucosamine-HCl concentrated solution and was added to final concentrations of 0, 4, 13, 26 and 42 g l$^{-1}$ (50 ml total in 250-ml flask). The pH of the medium was adjusted to pH 6.9. Flasks were placed on a shaker and agitated at about 225 rpm. Glucosamine levels and pH were monitored at 30° C. for about 24 hours. Glucosamine was found to be unstable and its degradation was concentration-dependent, with the degradation rates being higher at higher glucosamine concentrations. More than half of the glucosamine degraded in less than a day in medium with 42 g l$^{-1}$ glucosamine. The degradation was only about 25% when the starting glucosamine concentration was 4 g l$^{-1}$. Glucosamine degradation was accompanied by a decline of pH in the medium. In the 42 g l$^{-1}$ glucosamine sample the pH in the medium was lowered by 0.7 units (from 6.9 to 6.2) after a 24-hr period, as compared to a pH change of only about 0.15 units in medium without glucosamine.

The breakdown of glucosamine (60 g $l^{-1}$) at four starting pH levels was monitored at 30° C. in cell-free M9A-glucose (40 g $l^{-1}$) for 52 hours. At each sampling time, the solutions were readjusted to their original pH. Each condition was run in triplicate. As shown in FIG. 12, degradation was strongly pH-dependent, occurring faster at higher pH. The loss of glucosamine was 68% at pH 7.0 as compared to 18% at pH 5.5. Extrapolation of degradation rates versus pH suggests that no breakdown would occur below a pH of about 4.7.

As glucosamine degrades, the solution developed a yellow-amber color. The extent of color formation can be estimated by absorption at 360-400 nm. Except for an early sampling period during which degradation rates were faster, there was a strong correlation between the amount of degraded glucosamine and the density of amber color in the medium. At the two lowest pH levels, there was a noticeable lag between the disappearance of glucosamine and the appearance of the color, indicating that the colored compound is not the direct degradation product of glucosamine. After the degradation rates slowed at all pH levels tested, the ratio of degraded glucosamine to yellow color was constant.

Little is known about the molecular events involved in glucosamine degradation and color formation. There are reports about thermal degradation of glucosamine in water and under dry conditions (Shu, 1998, Journal of Agricultural and Food Chemistry, vol. 46, pp. 1129-1131; Chen and Ho, 1998, Journal of Agricultural and Food Chemistry, vol. 46, pp. 1971-1974, both incorporated herein by reference in their entirety). However, it is not known if the same types of chemical events take place under mild conditions used in the present studies. Although workers have observed formation of brown products from glucosamine and studied antioxidative activities of the brown products (Oyaizu and Mankoto, 1988, Nippon Shokuhin Kogyo Gakkaishi, vol. 35, pp. 771-775, incorporated herein by reference in its entirety), the brown products were not chemically identified in their studies. Considering the molecular structure of glucosamine, both the aldehyde and amino groups could be involved in degradation and/or polymerization. Color development indicates formation of conjugated double bands and complex structures.

To test the involvement of the aldehyde group, degradation was monitored in M9A medium containing 30 g $l^{-1}$ glucosamine with and without 40 g $l^{-1}$ glucose. If the aldehyde group is involved, the presence of glucose would affect the rate of glucosamine degradation/polymerization. No significant difference in glucosamine breakdown was observed. This observation suggests to a role of the amino group in glucosamine degradation.

Effects of Glucosamine on *E. coli* 7107-18:

Glucosamine is vital for *E. coli* growth since it is a precursor for the synthesis of important cell wall components. *E. coli* is also capable of using Glucosamine and N-acetylglucosamine as the sole carbon source. The catabolism of the amino sugars requires a functional glucosamine deaminase encoded by the nagB gene, which was deleted in strain 7107-18. As expected, 7107-18 could not grow on plates containing glucosamine as the sole carbon source. Experiments were carried out to investigate if glucosamine affects *E. coli* 7107-18 cell growth and survival in medium containing 40 g $l^{-1}$ glucose. Growth of freshly inoculated cultures was slightly inhibited by 10 and 20 g of glucosamine per liter. Glucosamine at 40 g per liter prevented cell growth and began to kill the cells after about 16 hours of incubation, as shown by cell plating. After 52 hrs, the viable count leveled off at about one-fifth the original number.

More experiments were carried out to investigate the toxic effect of glucosamine on *E. coli* 7107-18. Cells inoculated immediately into M9A-glucose (40 g $l^{-1}$) containing 35 g $l^{-1}$. glucosamine grew reasonably well, while cells died rapidly when inoculated into the identical medium which was pre-incubated for a period as short as 3.5 hours. This shows that the killing is largely due to glucosamine degradation product(s) formed in the medium before inoculation. It is not known why cells can survive and grow if inoculated immediately after the medium is made. One explanation could be that glucosamine is sequentially degraded to products A, B, C and D. Cells could have the ability to tolerate or assimilate earlier products at relatively low levels while the later products and/or higher levels of earlier products could be more toxic. This hypothesis is consistent with the observation that higher glucosamine concentrations and longer pre-incubation times resulted in lower levels of viable counts. With 35 g $l^{-1}$ glucosamine, viable counts leveled off at $10^5$-fold less than inoculation levels. Cells died in the medium with 50 g $l^{-1}$ glucosamine even without medium pre-incubation.

Stability of N-Acetylylucosamine:

It appears that the amino group plays an important role in degradation, as suggested by the effects of pH. If this is true, N-acetylglucosamine should be much more stable. In addition, the pH effects may not be as dramatic as they are with glucosamine. The stability of N-acetylglucosamine was tested in an experiment similar to the glucosamine degradation studies. The stability of 80 and 40 g $l^{-1}$ N-acetyl glucosamine at pH 5.5 and 7.0 was monitored in medium M9A-without glucose over a period of two days. No significant degradation occurred (FIG. 13). This is in sharp contrast to the degradation seen with glucosamine. When glucosamine breaks down, an amber color develops in the medium. No such color formation was seen in M9A medium containing N-acetyl glucosamine over a period of 48 hours. Additionally, there was no significant drop in pH during incubation. The results confirm that the free amino group is the key functional group involved in glucosamine breakdown and/or polymerization.

Effects of N-Acetyl Glucosamine on *E. coli* 7107-18:

Cells were inoculated into M9A-glucose (40 g/L) containing 62 g/L N-acetyl glucosamine. No significant growth inhibition was observed, even when the medium was pre-incubated for more than eight hours.

In summary, N-acetylglucosamine does not have negative effects on *E. coli* strain 7107-18 and it is much more stable than glucosamine. Therefore, there is a potential advantage of producing N-acetylglucosamine instead of glucosamine. It is known that glucosamine is transported into the cells and phosphorylated through the mannose transporter whose subunits are encoded by the manXYZ genes and through the glucose transporter encoded by the ptsG gene. Although the manXYZ genes were deleted in the strain 7107-18, glucosamine uptake can still take place by the glucose transporter. With high concentrations in the medium, significant amounts of glucosamine could get into the cells. Due to the deletion of the genes encoding for the mannose transporter (manXYZ) and the N-acetyl glucosamine transporter (nagE) in 7107-18, N-acetyl glucosamine could accumulate to high levels within the medium without being transported back into the cell. This represents another possible advantage of producing N-acetyl glucosamine over glucosamine.

Example 12

This Example describes an HPLC method for glucosamine determination.

It is desirable to develop a simple HPLC method to chromatographically quantitate glucosamine. Characteristics of the desired method should include minimal sample preparation and reasonably accurate determination of glucosamine. The method presented here is based on that described by Way et al. (J. Liq. Chromatography & Related Technol. 23:2861. 2000). Modification of the mobile phase in Way et al.'s procedure allowed for the resolution of the glucosamine peak from other peaks observed in shake flask cell culture samples.

| Method description: | |
|---|---|
| Column: | Phenomenex Prodigy ODS(3) $C_{18}$ – 5μ, 150 × 4.6 mm (Phenomenex, Torrance, CA) |
| Mobile phase: | MeOH: aqueous buffer (1:4 v/v). The aqueous buffer consisted of 10 mM sodium acetate and 10 mM sodium octanesulfonate, pH 5.1. The complete mobile phase was prepared as follows. To 1 liter of deionized water, 0.8 g sodium acetate and 2.16 g sodium octanesulfonate (Sigma-ultrapure) was added. After dissolving the salts, pH was adjusted to 5.1 +/– 0.1 using glacial acetic acid. To this 1-liter solution 250 ml methanol was added and the solution degassed. Reservoir and column were kept at room temperature. |
| Flow rate: | 0.7 ml/minute |
| Detector: | refractive index detector at 30° C. |
| Sample: | 10 μl in M9A medium |

Injection of the sterile M9A growth medium resulted in two major peaks on a chromatogram. Additionally, the chromatogram is essentially unchanged if M9A lacking glucose, calcium and magnesium salts was analyzed. Injection of glucosamine in M9A resulted in a single additional distinct peak. Under these conditions glucosamine eluted at about 13 minutes with a very large negative peak immediately following it. Additionally, it was unsuccessful to increase resolution by varying pH, ionic strength, methanol (MeOH) concentration, or octanesulfonate concentration. This negative deflection always follows the glucosamine peak. The usual way to remove such a negative deflection is to dilute the sample in mobile phase. However, even diluting samples twenty fold did not completely remove the negative deflection, and such high dilution is not practical for samples from shake flasks or fermentors.

It was found that integrating using peak height instead of peak area allowed for fairly accurate quantitation of glucosamine in the approximate range of 500-10,000 parts per million (ppm). To determine the range it was necessary to prepare the standards in M9A rather than in water or mobile phase. Thus, all samples were prepared in the M9A growth medium and any dilutions were made using M9A as well. For each sample the running time was 20 min.

Method Validation:

First, several standards of glucosamine in M9A were prepared. Repeated injections gave fairly accurate (+/−5%) results.

Second, shake flask samples were analyzed by both calorimetric assay and HPLC. Values obtained were generally within 10% of the colorimetric assay. Close agreement between HPLC and the colorimetric method should not necessarily be expected due to the standard deviation inherent to the calorimetric assay. For example, two samples (both 10,000 ppm) assayed by the calorimetric method gave values of 8.9 and 9.3 g $l^{-1}$.

Third, shake flask samples were spiked with known amounts of glucosamine and assayed. The undiluted shake flask sample produced a value of 1479 ppm. After dilution with an equal volume of a 5000-ppm glucosamine standard, the diluted flask sample produced a value of 3440 (expected 3240). Part of the discrepancy from the expected value is most likely contributed by M9A. In fact M9A alone will give a false glucosamine "value" of around 100 PPM.

Shake flask culture samples were assayed by both the HPLC method and the calorimetric methods. Results are shown in Table 11. The culture supernatants were obtained by centrifugation and filtration to remove particles, and stored at −20° C. until analysis. HPLC was calibrated using a single point 2500 ppm standard solution prepared in M9A medium. After thawing, samples were immediately analyzed by HPLC. After remaining in the autosampler overnight, the samples were analyzed again. Agreement was very good between the two methods. Samples stored at −20° C. for several weeks showed no decrease in glucosamine concentration. Keeping filtered samples at room temperature overnight did not result in any decrease in glucosamine concentration.

TABLE 11

Comparison of the HPLC method and colorimetric method for glucosamine quantification*

| Sample ID | Colorimetric Method | HPLC (0 hours) | HPLC (24 hours) |
|---|---|---|---|
| D1 | 4505 | 4900 | 4963 |
| D2 | 4138 | 4641 | 4618 |
| E2 | 451 | 533 | 589 |
| F1 | 1643 | 1856 | 1815 |
| F2 | 1938 | 1875 | 1968 |
| H1 | 1380 | 1365 | 1439 |
| H2 | 1341 | 1379 | 1548 |

*Culture samples were centrifuged and filtered to remove particles, and stored at −20° C. until the assays. HPLC analysis was run with the thawed samples (0 hour) and repeated after the samples were left overnight in the autosampler at room temperature (24 hours). Glucosamine concentrations were shown in PPM.

Example 13

This Example describes over-expression of glucosamine-6-phosphate N-Acetyltransferase 1 genes (GNA1) for N-acetylglucosamine production.

The following Example describes the cloning and over-expression of different glucosamine-6-phosphate N-Acetyltransferase 1 genes (GNA1) in recombinant *E. coli* for increased synthesis of N-acetylglucosamine. The feasibility of the strategy was demonstrated with pET-based expression vectors containing the GNA1 genes from yeast *Saccharomyces cerevisiae* (ScGNA1), yeast *Candida albicans* (CaGNA1) and higher plant *Arabidopsis thaliana* (AtGNA1).

GNA1 cloning and expression were carried out by cloning the coding sequence of the GNA1 gene behind a T7lac promoter in a pET vector and transforming the recombinant pET plasmids into lactose inducible glucosamine production strain *E. coli* 7107-18. Functional expression of the gene was determined by SDS-PAGE and enzyme activity assay. Synthesis of N-acetylglucosamine was monitored in shake flask experiments.

Cloning the *S. cerevisiae* GNA1 Gene for Over-Expression in *E. coli*:

For cloning and expression of the *S. cerevisiae* GNA1 gene (ScGNA1), primers were synthesized based on the published sequence of the GNA1 gene (Murakami et al., 1995, Nat. Genet. 10, pp. 261-268, herein by reference in its entirety). Primers were used to amplify the GNA1 coding sequence from genomic DNA isolated from *S. cerevisiae* strain S288C using polymerase chain reaction (PCR). The primers used for amplification were forward primer 07-83 and reverse primer 07-84 and had the following sequences: 07-83: 5'-GATCGGTCTCGCATGAGCTTACCCGATG-GATTTTATATAAGGC-3' (SEQ ID NO:35); 07-84: 5'-GATCCTCGAGCTATTTTCTAATTTG-CATTTCCACGCCTGC-3' (SEQ ID NO:36). Primer 07-83 contains a Bsa I restriction endonuclease site (GGTCTC, represented in nucleotides 5-10 of SEQ ID NO:35) followed by 31 nucleotides of the GNA1 coding sequence starting from its ATG start codon (represented in nucleotides 13-43 of SEQ ID NO:36). Primer 07-84 contains a Xho I restriction endonuclease site (CTCGAG, represented in nucleotides 5-10 of SEQ ID NO:36) followed by 30 nucleotides of the GNA1 coding sequence starting at its translation stop codon (represented in nucleotides 11-40 of SEQ ID NO:36). PCR amplification was conducted using a standard protocol to generate a fragment of DNA containing the entire ScGNA1 coding sequence flanked by the Bsa I and Xho I sites.

The PCR product containing the GNA1 sequence was cloned into vector pCR-Script Amp SK(+) (Stratagene, LaJolla, Calif.), generating plasmid pSW07-60. The ScGNA1 fragment was isolated from the plasmid PSW07-60 by Bsa I and Xho I digestion and cloned at the Nco I and Xho I sites of the expression vector pET24d(+) (Novagen, Inc., Madison, Wis., creating plasmid SW07-60. Cloning in this manner places the ScGNA1 sequence behind the T7-lac promoter of pET24d(+), generating an expression cassette of T7-lac-ScGNA1.

Cloning the *C. albicans* GNA1 Gene for Over-Expression in *E. coli*:

For cloning and expression of *C. albicans* GNA1 (CaGNA1), primers were synthesized based on published sequence of the GNA1 (Mio et al., 1999, J. Biol. Chem. 274, pp.424-429, herein by reference in its entirety). Primers 07-92 and 07-93 were used to amplify the GNA1 coding sequence from *Candida albicans* ATCC10261 genomic DNA using PCR. Forward primer 07-92 and reverse primer 07-93 had the following sequences: 07-92: 5'-GATCG-GTCTCGCATGATGTTACCACAAGGTTATAC-3' (SEQ ID NO:37) and 07-93: 5'-GATCCTCGAGCTAGAATCTA-CATACCATTTCAAC-3' (SEQ ID NO:38). Primer 07-92 contains a Bsa I restriction endonuclease site (GGTCTC, represented in nucleotides 5-10 of SEQ ID NO:37) followed by 23 nucleotides of the GNA1 coding sequence starting from its ATG start codon (represented in nucleotides 13-35 of SEQ ID NO:37). Primer 07-93 contains a Xho I restriction endonuclease site (CTCGAG, represented in nucleotides 5-10 of SEQ ID NO:38) followed by 24 nucleotides of the GNA1 coding sequence starting at its translation stop codon (represented in nucleotides 11-34 of SEQ ID NO:38). PCR amplification was conducted under standard conditions to generate a fragment of DNA containing the entire CaGNA1 coding sequence flanked by the Bsa I and Xho I sites.

The PCR product containing the CaGNA1 sequence was ligated into the SrfI site of vector pCR-Script Amp SK(+) (Stratagene, LaJolla, Calif.), generating plasmid pKLN07-33. The CaGNA1 fragment was isolated from plasmid pKLN07-33 with restriction enzymes Bsa I and Xho I and cloned at the Nco I and Xho I sites of the expression vector pET24d(+) (Novagen, Inc., Madison, Wis.), creating plasmids pKLN07-34 and pKLN07-35. Cloning in this manner places the CaGNA1 sequence behind the T7lac promoter of pET24d(+), generating an expression cassette of T7lac-CaGNA1.

Cloning the Arabidopsis GNA1 Gene for Over-Expression in *E. coli*:

For cloning and expression of *Arabidopsis thaliana* GNA1 (AtGNA1), primers 07-94 and 07-95 were synthesized based on published sequence of the GNA1 (Genebank AL391144). The primers were used to amplify the GNA1 coding sequence from BAC clone F14F8 (Arabidopsis Biological Resource Center DNA Stock Center, Columbus, Ohio) using PCR. Forward primer 07-94 and reverse primer 07-95 had the following sequences: 07-94: 5'-GATG-GTCTCGCATGGCTGAGACATTCAAGATC-3' (SEQ ID NO:39), and 07-95: 5'-GATCCTCGAGTTAATCGAAG-TACTTAGACATTTGAATC-3' (SEQ ID NO:40). Primer 07-94 contains a Bsa I restriction endonuclease site (GGTCTC, represented in nucleotides 4-9 of SEQ ID NO:39) followed by 21 nucleotides of the GNA1 coding sequence starting from its ATG start codon (represented in nucleotides 12-32 of SEQ ID NO:39). Primer 07-95 contains a Xho I site (CTCGAG, represented in nucleotides 5-10 of SEQ ID NO:40) followed by 24 nucleotides of the GNA1 coding sequence starting at its translation stop codon (represented in nucleotides 11-38 of SEQ ID NO:40). PCR amplification was conducted using a standard protocol to generate a fragment of DNA containing the entire GNA1 coding sequence flanked by the Bsa I and Xho I sites. The PCR fragment was digested with restriction endonucleases Bsa I and Xho I and cloned at the Nco I and Xho I sites of the expression vector pET24d(+) (Novagen, Inc., Madison, Wis.) creating plasmid pSW07-70. Cloning in this manner places the AtGNA1 sequence behind the T7lac promoter of pET24d(+), generating an expression cassette of T7lac-AtGNA1.

Functional Expression of Different Recombinant GNA1 Genes and N-Acetylglucosamine Production in *E. coli*

The recombinant plasmids pSW07-62 (containing the *S. cerevisiae* GNA1 gene), pKLN07-34 (containing the *C. albicans* GNA1 gene), and pSW07-70 (containing the *A. thaliana* GNA1 gene) were transformed into *E. coli* strain 7107-18, generating strains 7107-87, 7107-117 and 7107-93, respectively. Control strain 7107-88 was prepared by transforming the empty vector into the same host. Following a standard protocol, cell cultures of transformants were grown in LB medium and induced with 1 mM IPTG. Samples were taken from induced cultures for SDS-PAGE analysis to confirm GNA1 protein overexpression. The predicted protein sizes of the AtGNA1, CaGNA1 and ScGNA1 are 17 kDa, 16.9 kDa, and 18.1 kDa, respectively. Overexpressed proteins of the predicted sizes were seen in samples from the induced cultures expressing the various GNA1 genes. In all cases, the overexpressed protein appeared to be very soluble. As expected, no overexpressed protein near the predicted size of the GNA1 gene was seen in control strain 7107-88.

Screening of the different *E. coli* strains was conducted to confirm functional expression of the recombinant GNA1 genes. Strains hosting the *S. cerevisiae*, *C. albicans* and *A. thaliana* GNA1 expression vectors were grown in M9B production medium [6 g $l^{-1}$ $KH_2PO_4$, 24 g $l^{-1}$ $K_2HPO_4$, 1 g $l^{-1}$ $Na_3Citrate-2H_2O$, 10 g $l^{-1}$ $(NH_4)_2SO_4$ (phosphate adjusted to pH 7.4) plus trace metals (0.2 mg $l^{-1}$ $FeSO_4\cdot7H_2O$, 0.015 mg $l^{-1}$ $ZnSO_4\cdot7H_2O$, 0.015 mg $l^{-1}$ $MnSO_4$—$H_2O$, 0.001 mg $l^{-1}$ $CuSO4$-$5H_2O$, 0.001 mg $l^{-1}$ $NaMoO_4$-$2H_2O$, 0.001 mg $l^{-1}$ $H_3BO_3$, and 0.001 mg $l^{-1}$ $COCl_2\cdot6H_2O$) supplemented with 40 g $l^{-1}$ glucose, 10 g $l^{-1}$ ribose, 5 g $l^{-1}$ yeast extract, 0.6 g $l^{-1}$ $MgSO_4\cdot7H_2O$, 0.05 g $l^{-1}$ $CaCl_2\cdot2H_2O$, 25 mg $l^{-1}$ kanamycin, and 0.2 mM IPTG. At 24 hours, glucose was added to 30 g $l^{-1}$ per day total based on HPLC results, and 5 g $l^{-1}$ $(NH_4)_2SO_4$ was added to flasks where levels had fallen below 1 g $l^{-1}$. Duplicate flasks were made of each strain so that one flask could be harvested at 24 hours and the other at 48 hours for enzyme analysis and determination of N-acetylglucosamine and acetate levels.

Glucosamine synthase (GlmS) activity was assayed, and all strains exhibited good activity levels. Samples were also assayed for glucosamine-6-P N-acetyltransferase (GNA1) enzyme activity following the method described by Mio et al. (Journal of Biological Chemistry, 1999, 274, pp. 424-429 (Table 12). As expected, the control strain did not show a significant level of GNA1 activity. Expression of the yeast and higher plant GNA1 genes led to high acetyltransferase activity. These GNA1 transformants also synthesized N-acetylglucosamine at very high levels (Tables 12 and 13). Acetyltransferase activities in strains expressing the GNA1 genes from *S. cerevisiae* (7107-87) and *C. albicans* (7107-117) were comparable. However, N-acetylglucosamine production was four times higher in strains expressing the *S. cerevisiae* gene. Although GNA1 enzyme activity in strains with the *A. thaliana* gene was lower than the strains with the *C. albicans* gene, N-acetylglucosamine production was higher in the former than in the latter. Clearly, there is no simple correlation between GNA1 activity levels and N-acetylglucosamine production; the GNA1 enzymes from various sources may have differences in enzyme characteristics. The data demonstrate the utility of different GNA1 genes in metabolic engineering to produce N-acetylglucosamine. Among the three GNA1 genes tested, the *S. cerevisiae* GNA1 outperformed the others in terms of N-acetylglucosamine production. Therefore, the *S. cerevisiae* GNA1 gene was selected for later research work disclosed in the present invention.

TABLE 12

Glucosamine synthase and acetyltransferase activities in stains expressing three different GNA1 genes.

| Construct | Strain | Enzyme activity | | GlcNAc |
|---|---|---|---|---|
| | | GlmS | GNA1 | (g $l^{-1}$) |
| Vector | 7107-88 | 0.53 | 0.06 | 0 |
| *S. cerevisiae* GNA1 | 7107-87(25) | 0.48 | 19.0 | 24.6 |
| *C. albicans* GNA1 | 7107-117(1) | 0.37 | 21.7 | 6.3 |
| | 7107-117(2) | 0.42 | 19.9 | 6.0 |
| | 7107-117(3) | 0.29 | 25.2 | 6.0 |
| *A. thaliana* GNA1 | 7107-93(1) | 0.50 | 6.3 | 13.3 |
| | 7107-93(2) | 0.14 | 5.6 | 10.7 |

(1) Enzyme activity is expressed in μmol $min^{-1}$ $mg^{-1}$ protein.
(2) N-acetylglucosamine levels were determined in samples taken at 23-hr time point.
(3) Numbers in the parentheses indicate different siblings.

Strain 7107-18 produces high levels of glucosamine that can be detected by HPLC. However, little or no free glucosamine (below 0.5 g $l^{-1}$) could be detected in strains that were over-expressing the acetyltransferase gene. This clearly indicated no significant buildup of the intermediate glucosamine-6-P in the GNA1 transformants, confirming that enzyme GNA1 was the main driving force for high level production of N-acetylglucosamine.

Accumulation of acetate is a recognized obstacle to achieving high levels of recombinant protein and other fermentation products in *E. coli*. With excess glucose in the medium, *E. coli* cells tend to synthesize high levels of acetate and other organic acids, usually resulting in growth inhibition. Acetate production has been a problem in glucosamine production *E. coli* strains. However, N-acetylglucosamine production strains accumulated little or no acetate at the 23-hour timepoint under conditions where the control strain accumulated multi-gram levels of acetate. The synthesis of N-acetylglucosamine consumes acetyl-CoA, the precursor for acetate formation. Although the use of acetyl-CoA will be a metabolic burden imposed on the cell, the re-direction of acetyl-Co A to N-acetylglucosamine production apparently represents a significant benefit by avoiding acetate accumulation. It is important to note that the N-acetylglucosamine producing strains showed higher cell densities than the control strains (Table 13).

TABLE 13

Cell growth and N-acetylglucosamine production in *E. coli* strains transformed with different GNA1 expression constructs.

| Strain | Construct | Growth (OD$_{600}$) | | Acetate (g $l^{-1}$) | | GlcNAc (g $l^{-1}$) | |
|---|---|---|---|---|---|---|---|
| | | 23 hrs | 48 hrs | 23 hrs | 48 hrs | 23 hrs | 48 hrs |
| 7107-88 | Vector | 3.75 | 4.2 | 4.4 | 5.2 | ND* | ND |
| 7107-87 | *S. cerevisiae* GNA1 | 7.80 | 12.0 | ND | ND | 11.7 | 24.6 |
| 7107-117 | *C. albicans* GNA1 | 10.00 | 13.8 | 0.5 | 5.1 | 5.1 | 6.1 |
| 7107-93 | *A. thaliana* GNA1 | 8.70 | 13.2 | ND | 4.0 | 8.0 | 12.0 |

Sequence Analysis of Different GNA1 Enzymes:

Significant differences were observed in terms of specific activity and NAG production in *E. coli* strains overexpressing the various GNA1 genes. However, since all enzymes catalyze the same reaction, homology would be expected between the various GNA1 at nucleotide and protein levels. SEQ ID NO:29 contains the coding sequence of the *S. cerevisiae* GNA1 gene. SEQ ID NO:29 encodes the *S. cerevisiae* GNA1 amino acid sequence represented here by SEQ ID NO:30. SEQ ID NO:33 contains the coding sequence of the *A. thaliana* GNA1 gene. SEQ ID NO:33 encodes the *A. thaliana* GNA1 amino acid sequence represented here by SEQ ID NO:34. SEQ ID NO:31 contains the coding sequence of the *C. albicans* GNA1 gene. SEQ ID NO:31 encodes the *C. albicans* GNA1 amino acid sequence represented here by SEQ ID NO:32. When aligned by the J. Hein DNA Alignment method (DNAStar reference), nucleotide sequences exhibited significant homology. The ScGNA1 and At-GNA1 coding sequences share 49.7% identity, while the ScGNA1 and CaGNA1 coding sequences share 53.1% identity. The CaGNA1 and AtGNA1 coding sequences share 47.2% identity.

Translation of the coding sequences into amino acid sequences revealed significant homology among the various GNA1 proteins when aligned by the Lipman-Pearson Protein Alignment method (DNAStar, Inc., Madison, Wis.). As seen on Table 14, the ScGNA1 sequence (SEQ ID NO:30) shares 44% identity with the CaGNA1 sequence (SEQ ID NO:32) and 38.9% identity with the AtGNA1 (SEQ ID NO:34) sequence. Some regions appeared to be more highly conserved; for example, amino acids GHIED were conserved in all sequences (aligning with amino acids 96-100 of the ScGNA1 sequence (SEQ ID NO:30)). Also, a 20 residue region corresponding to ScGNA1 residues 129-148 of SEQ ID NO:30 was highly conserved. This region had 75% identity to the corresponding region in CaGNA1 sequence and 70% identity to the corresponding region in AtGNA1 sequence.

TABLE 14

Peptide size and homology of the ScGNA1, AtGNA1, and CaGNA1.

| GNA1 | Number of Amino Acids | Peptide Size (kDa) | Peptide Sequence Homology (% identity)* | | |
|---|---|---|---|---|---|
| | | | ScGNA1 | AtGNA1 | CaGNA1 |
| ScGNA1 | 158 | 18 | | 38.9 (49.7) | 44.0 (53.1) |
| AtGNA1 | 148 | 17 | | | 37.6 (47.2) |
| CaGNA1 | 148 | 17 | | | |

*Homology at the nucleotide level is shown in parentheses.

Example 14

This Example describes the construction of strains producing N-acetyl glucosamine through the overexpression of the *E. coli* nagB and the *S. cerevisiae* GNA1.

The nagB gene, part of the nag regulon, encodes the glucosamine-6-phosphate deaminase (NagB), is involved in the pathway for catabolism of N-acetyl glucosamine (GlcNAc) as part of the nag regulon. The nag regulon consists of the operon nagBA CD and the divergently transcribed nagE (Plumbridge, JA., 1991, Mol. Microbiol. 8:2053-2062). Exogenous GlcNAc is phosphorylated as it is transported into the cell, forming GlcNAc-6-P. The nagA gene product, encoding the N-acetyl glucosamine-6-phosphate deacetylase, converts the GlcNAc-6-P to GlcN-6-P. NagB then catalyzes the conversion of GlcN-6-P to fructose-6-phosphate (F-6-P).

The glmS gene product in *E. coli* catalyzes the synthesis of GlcN-6-P, an essential intermediate in the pathway for the formation of lipopolysaccharide and peptidoglycan. Therefore, mutants with a defective glmS are dependent on exogenous GlcN or GlcNAc. However, NagB has been shown to catalyze the reaction normally performed by GlmS, converting F-6-P to GlcN-6-P. In fact, transformation of glmS mutants with a high-copy plasmid expressing the glucosamine-6-phosphate deaminase (nagB) has been shown to suppress the glmS mutation (J Bac 1989 December; 171(12):6589-6592). Since NagB can catalyze the conversion of F-6-P to GlcN-6-P, it is possible that overexpression of the nagB in place of glmS*54 in our production strains could result in an accumulation of glucosamine. If the T7lac-ScGNA1 cassette was also present in the strain, the GlcN-6-P could be converted to GlcNAc-6-P and accumulate as NAG in the medium.

To test the efficiency of glucosamine or N-acetyl glucosamine production by overexpression of the nagB gene, the methods and protocols described for GNA1 cloning and integration was adapted to clone and integrate a T7lac-nagB expression cassette at the pfkB site in the chromosome of *E. coli* 7101-17(DE3). The endogenous glmS gene will also need to be inactivated in this strain. The glmS sequence is located downstream from the glmU sequence with no obvious promoter sequence upstream of glmS. It appears that glmU and glmS form an operon glmUS. The glmS sequence and some flanking sequences was amplified by PCR from *E. coli* genomic DNA, cloned into a plasmid vector. Appropriate restriction digestion was used to remove an internal fragment from the glmS sequence. The glmS sequence with internal deletion was ligated to the temperature sensitive replication origin and the kanamycin selection marker to create an integration vector. The temperature selection protocol was used to select for mutants with the glmS deletion. Since glucosamine is vital for cell wall synthesis, glucosamine needs to be supplied in the culture medium for the growth of the mutants.

Cloning the nagB Gene for Over-Expression in *E. coli*

Using information based on the published sequence of the *E. coli* nagB gene (Peri et al., 1990, Biochem. Cell Biol. 68, pp.123-137, herein by reference in its entirety), primers were designed to amplify the nagB coding sequence. The nagB coding sequence was amplified by PCR from *E. coli* W3110 genomic DNA using forward primer 07-141 and reverse primer 07-142, which had the following sequences: 07-141 5'-GATGGTCTCGCATGAGACTGATCCCCCTGAC-3' (SEQ ID NO:43) and 07-142 5'-GATCCTCGAGTTACA-GACCTTTGATATTTTCTGCTTCTAATTC-3' (SEQ ID NO:44)

Primer 07-141 contains a Bsa I restriction endonuclease site (GGTCTC, represented in nucleotides 4-9 of SEQ ID NO:43) followed by 20 nucleotides of the nagB coding sequence starting from its ATG start codon (represented in nucleotides 12-31 of SEQ ID NO:43). Primer 07-142 contains a Xho I restriction endonuclease site (CTCGAG, represented in nucleotides 5-10 of SEQ ID NO:44) followed by 33 nucleotides of the nagB coding sequence from its translational stop codon (represented in nucleotides 11-43 of SEQ ID NO:44). The *E. coli* nagB coding sequence and NagB amino acid sequence are represented by SEQ ID NO:41 and SEQ ID NO:42, respectively.

The PCR fragment containing the nagB coding sequence was digested with restriction endonucleases Bsa I and Xho I and ligated at the Nco I and Xho I sites of plasmid pET24d(+) (Novagen, Inc., Madison, Wis.), generating plasmid pSW07-93. Cloning in this manner places the nagB sequence behind the T7-lac promoter of pET24d(+), generating an expression cassette of T7-lac-nagB.

Overexpression of the nagB Gene

Plasmids pSW07-93#3, #8 and #16 were transformed into strain 7101-17(DE3), generating strains 7107-636, 7107-637, and 7107-638, respectively. The pET24d(+) plasmid was also transformed into strain 7101-17(DE3) to generate negative control strain 7107-639. A standard induction experiment was performed in which cell cultures of the transformants were grown in LB medium and induced with 1 mM IPTG. Samples were taken from induced cultures at various timepoints for SDS-PAGE to confirm NagB protein overexpression. The predicted size for the overproduced NagB protein is 29.8 kDa. A protein corresponding to the expected size of NagB was overproduced in strain 7107-636 and 7107-637. No overproduced protein of this size was apparent in control strain 7107-639. Protein samples from 2 hours after induction indicated that most of the overproduced NagB protein was in the soluble fraction. However, at 4 hours after induction, only about 25% of the protein appeared in the soluble fraction.

Integration of the T7lac-nagB Cassette at the pfkB Locus in the Chromosome

Having confirmed successful overproduction of NagB, the next step was to integrate the T7lac-nagB expression cassette into the chromosome of E. coli 7101-17(DE3). It was decided to target integration to the pfkB gene of the E. coli chromosome. The pfkB gene encodes for a minor phosphofructokinase that supplies 10% of the total phosphofructokinase activity present in E. coli. Therefore, targeting integration to this site should not impair growth or N-acetyl glucosamine production.

Several cloning steps were required to develop a vector to direct integration of the T7lac-nagB cassette at pfkB of the chromosome in strain 7101-17(DE3). The first step was to clone a region from the E. coli genome containing the pfkB coding sequencing plus flanking regions. Primers were designed based on published sequences (Blattner et al., 1997, Science 227(5331):1453-1474) to amplify the pfkB plus flanking genomic regions from E. coli W3110 genomic DNA. Primers 07-16 and 07-17, used to amplify the pfkB region by PCR, had the following sequences: 07-16 5'-GATCGCCGGCTTACATGCTGTAGC CCAGC-3' (SEQ ID NO:45) and 07-17 5'-GATCCTGCAGTCATGCT-GCTAATAATCT ATCC-3' (SEQ ID NO:46).

Primer 07-16 contains a Nae I site (GCCGGC, represented in nucleotides 5-10 of SEQ ID NO:45) and amplifies from 1045 nucleotides upstream of the pfkB coding sequence start codon (represented in nucleotides 11-29 of SEQ ID NO:45). Primer 07-17 adds a Pst I site (CTGCAG, represented in nucleotides 5-10 of SEQ ID NO:46) and amplifies from 1357 basepairs downstream of the pfkB stop codon (represented in nucleotides 11-32 of SEQ ID NO:46). Ligation of the 3332 basepair PCR product containing the pfkB plus flanking regions into the SrfI site of pPCR-Script Amp SK(+) (Stratagene, LaJolla, Calif.) generated plasmid pKLN07-14.

The T7-lac-nagB cassette was amplified from plasmid pSW07-93#3 (see above) under standard PCR conditions with forward primer 07-145 and reverse primer 07-146. The primers have the following sequences: 07-145 5'-GATC-TACGTAAGCAACCGCACCTGT GGC-3' (SEQ ID NO:47) and 07-146 5'-GATCCAATTGATCCGGATAT-AGTTCCTCCTT TCAGC-3' (SEQ ID NO:48).

Primer 07-145 contains a SnaB I site (TACGTA, represented in nucleotides 5-10 of SEQ ID NO:47) and amplifies from 76 nucleotides upstream of the T7 promoter (represented in nucleotides 11-28 of SEQ ID NO:47). Primer 07-146 contains an Mfe I site (CAATTG, represented in nucleotides 5-10 of SEQ ID NO:48) and amplifies from 25 basepairs downstream of the T7 terminator (represented in nucleotides 11-36 of SEQ ID NO:48).

The next cloning step was ligation of the T7lac-nagB cassette into plasmid pKLN07-14. Plasmid pKLN07-14 was digested with restriction endonucleases SnaB I and Mfe I, removing a 523-bp portion of the pfkB coding sequence. The PCR fragment containing the T7lac-nagB cassette was digested with restriction endonucleases SnaB I and Mfe I and ligated at the SnaB I and Mfe I sites of pKLN07-14, generating plasmid pSW07-97. Plasmid pSW07-97 therefore contains the pfkB plus flanking genomic regions with a 523 nucleotide region of the pfkB coding sequence replaced with the T7lac-nagB cassette.

The fragment containing ORFb1722-DpfkB::T7-lac-nagB-ORFb1725 plus part of the pPCR-Script MCS was digested from plasmid pSW07-97 with restriction endonucleases Not I and Sal I. A fragment containing the temperature sensitive replicon plus kanamycin resistance cassette was excised from plasmid pKLN07-21 (previously described) with restriction endonucleases Not I and Sal I. The two fragments were ligated together, generating plasmid pSW07-98.

Plasmid pSW07-98 was used to generate E. coli strains with the T7lac-nagB at DpfkB of the chromosome. Following transformation of E. coli 7101-17(DE3) with pSW07-98, the temperature selection protocol was used to select for strains with the T7-lac-nagB integrated at the pfkB site. The resulting strains were designated 7107-645, and strains were confirmed by standard high stringency Southern hybridization using the nagB coding sequence as probe.

Deletion of the glmS Gene in the E. coli Strains with an Integrated T7lac-nagB Cassette To delete the glmS gene E. coli strain 7107-645, a glmS sequence replacement vector was developed. Several steps were required to construct the vector. The first step was to amplify the region of the genome containing the glmS gene plus flanking sequence. This fragment would next be ligated with the fragment from pKLN07-21 (previously described) containing the temperature sensitive replicon and kanamycin resistance cassette. Finally, a portion of the glmS coding sequence would be excised from the resulting plasmid, generating the integrative vector to target the glmS deletion to the E. coli genome.

For the first step, primers were synthesized based on the published sequence of the glmS gene plus flanking regions (reference). The primers were used to amplify a fragment containing the glmU, glmS, and pstS genes from E. coli W3110 genomic DNA. The primers used for amplification were designated 07-139 and 07-140 and had the following sequences: 07-139, 5'-GATGCGGCCGCATGT-TGAATAATGCTATGAGCGTAGTGATC-3' (SEQ ID NO:49) and 07-140, 5'-GATCGTCGACTTAGTACAGCG-GCTTACCGCTACTGTC-3' (SEQ ID NO. 50).

Forward primer 07-139 contains the first 30 nucleotides of the glmU coding sequence from its ATG start codon (represented in nucleotides 12-41 of SEQ ID NO:49) preceded by a Not I restriction endonuclease site (GCGGCCGC, represented in nucleotides 4-11 of SEQ ID NO:49). Reverse primer 07-140 contains the last 27 nucleotides of the pstS coding sequence starting from its translational stop codon (represented in nucleotides 11-37 of SEQ ID NO:50) preceded by a Sal I restriction endonuclease site (GTCGAC, represented in nucleotides 5-10 of SEQ ID NO:50). PCR was conducted under standard conditions to generate a fragment containing the glmU-glmS-pstS coding sequences flanked by Not I and Sal I restriction endonuclease sites.

The PCR fragment was digested with restriction endonucleases Not I and Sal I. The temperature sensitive replicon plus kanamycin resistance cassette fragment was excised from plasmid pKLN07-21 (previously described) with restriction endonucleases Not I and Sal I. The two fragments were ligated together, generating plasmid pSW07-94#43.

Plasmid pSW07-94#43 was digested with restriction endonuclease Sac II, removing 980 nucleotides of the glmS coding sequence. The remainder of the plasmid was ligated to itself, generating an integration vector, pSW07-95.

In an attempt to improve frequency of recombination for generating the glmS mutation on the *E. coli* chromosome, plasmid pSW07-99 was also constructed by adding 772 nucleotides of the region upstream of glmU to plasmid pSW07-95. Primers were synthesized based on the published sequence of the glmU gene plus flanking regions (reference). The primers were used to amplify a fragment containing 772 nucleotides upstream of the glmU start codon and the first 246 nucleotides of the glmU coding sequence from *E. coli* W3110 genomic DNA. The primers used for amplification were designated 07-147 and 07-148 and had the following sequences: 07-147,5'-GATGCGGC-CGCATGGCAATGACTTACCACC TGGAC-3' (SEQ ID NO:51) and 07-148, 5'-CGTACCCAGCTGCTCTGCCT-GAAGCA CCC-3' (SEQ ID NO:52).

Forward primer 07-147 contains the first 24 nucleotides of the atpC coding sequence (represented in nucleotides 12-35 of SEQ ID NO:51) preceded by a Not I restriction endonuclease site (GCGGCCGC, represented in nucleotides 4-11 of SEQ ID NO:51). Reverse primer 07-148 contains 29 nucleotides of the glmU coding sequence (represented in nucleotides 1-29 of SEQ ID NO:52) starting from 246 basepairs downstream of its ATG start codon. PCR was conducted under standard conditions to generate a fragment containing the region of genomic DNA from the atpC start codon to nucleotide 246 of the glmU coding sequence. The PCR product was digested with restriction endonucleases Not I and SexA I and ligated into the Not I and SexA I sites of plasmid pSW07-95#6, generating plasmid pSW07-99.

Plasmids pSW07-95 and pSW07-99 were used to generate *E. coli* strains with the glmS deletion on the chromosome. Following transformation of *E. coli* strains 7107-645 (20), 7107-645(30), and 7107-645(43) with plasmid pSW07-95 or pSW07-99, the temperature selection protocol was used to select for strains with the glmS deletion. Glucosamine (2 g l$^{-1}$) was added to all flasks for passaging and all plates following passaging. Kanamycin-sensitive strains were selected and screened using a standard PCR protocol for the presence of the glmS deletion. Potential glmS deletion strains identified by PCR were plated to LB plates without added glucosamine to look for reduced growth. Some of the strains had limited growth on LB plates, while others exhibited no growth. These strains were confirmed as having the glmS deletion by Southern hybridization under high stringency conditions using a 2.0-kb fragment containing the glmS coding sequence. The resulting strains were designated 7107-646.

Functional Expression of nagB and the Effect on Glucosamine Production

Shake Flask Screen 61 was conducted to test strains 7107-646 for glucosamine production and enzyme activity. Strains were tested in flasks containing M9B medium [6 g l$^{-1}$ KH$_2$PO$_4$, 24 g l$^{-1}$ K$_2$HPO$_4$, 1 g l$^{-1}$ Na$_3$Citrate-2H$_2$O, 10 g l$^{-1}$ (NH$_4$)$_2$SO$_4$ (phosphate adjusted to pH 7.4) plus trace metals (0.2 mg l$^{-1}$ FeSO$_4$-7H$_2$O, 0.015 mg l$^{-1}$ ZnSO$_4$-7H$_2$O, 0.015 mg l$^{-1}$ MnSO$_4$—H$_2$O, 0.001 m g l$^{-1}$ CuSO4-5H$_2$O, 0.001 mg l$^{-1}$ NaMoO$_4$-2H$_2$O, 0.001 mg l$^{-1}$ H$_3$BO$_3$, and 0.001 mg l$^{-1}$ CoCl$_2$-6H$_2$O)] supplemented with 10 g l$^{-1}$ glucose, 0.6 g l$^{-1}$ MgSO$_4$-7H$_2$O, 0.05 g l$^{-1}$ CaCl$_2$-2H$_2$O and 0.2 mM IPTG. Cultures were grown at 30° C. for 24 hours and then placed at 25° C. The pH of each culture was adjusted to 7.2 at 24 and 48 hours. At 24 and 48 hours, glucose was added to flasks to approximately 30 g l$^{-1}$ per day total, and 5 g l$^{-1}$ (NH$_4$)$_2$SO$_4$ was added to flasks in which levels had fallen below 1 g l$^{-1}$. Samples were taken at 24 and 48 hours and the glucosamine concentration in the culture supernatant was measured using the modified Elson-Morgan assay as described in U.S. Pat. No. 6,372,457. No glucosamine was detected in any of the samples. 48 hour samples from strain 7107-646#7 and 7107-646#20 were tested for NagB activity. These strains had enzyme activities of 58 and 53 mmol min$^{-1}$ mg$^{-1}$, compared with no detectable activity in the control strain 7101-17(DE3), indicating successful overexpression of nagB. The fact that the 7107-646 strains grew as well or better than control strain 7101-17(DE3) in this experiment indicated that the overexpressed nagB is capable of suppressing the glmS mutation. However, overexpression of nagB did not result in increased glucosamine accumulation.

Integration of T7lac-ScGNA1 Cassette

Overexpression of nagB in glmS deletion strains resulted in no accumulation of glucosamine, potentially due to the fact that NagB normally catalyzes the deamination of GlcN-6-P. The small amount of GlcN-6-P produced by the NagB enzyme might be quickly converted back to fructose-6-P, preventing any accumulation of GlcN-6-P. However, if a GNA1 enzyme was introduced, GNA1 would convert GlcN-6-P to GlcNAc-6-P and continuously drive the formation of glucosamine-6-phosphate from fructose-6-phosphate. To test this possibility, the T7lac-ScGNA1 cassette was integrated at manXYZ of strains 7107-646(3) and 7107-646(7). GNA1 integration was carried out with plasmid pSW07-68#25 as detailed in Example 16. Kanamycin-sensitive strains were screened by a standard PCR protocol for the presence of the T7lac-ScGNA1 at the site of the manXYZ deletion. Strains positive by PCR were confirmed by standard high stringency Southern hybridization using a fragment containing the ScGNA1 coding sequence as probe. Resulting strains 7107-660 and 7107-661, derived from strains 7107-646(3) and 7107-646(7), respectively, were tested for NAG accumulation.

Functional Expression of nagB and N-Acetyl Glucosamine Production in *E. coli*

Shake Flask Screen 67 was conducted to test strains with the glmS deletion, T7lac-nagB cassette at pfkB, and T7lac-ScGNA1 cassette at manXYZ for N-acetyl glucosamine production. Strains 7107-660(1), 7107-660(4), 7107-661(1), 7107-661(2), and 7107-661(3), as well as control strains 7101-17 and 7107-607(2), were grown in shake flasks containing M9B medium (previously described) supplemented with g l$^{-1}$ glucose, 10 g l$^{-1}$ lactose, 0.6 g l$^{-1}$ MgSO$_4$-7H$_2$O, and 0.05 g l$^{-1}$ CaCl$_2$-2H$_2$O. Cultures were grown at 37° C. for 8 hours and then placed at 30° C. 8 hours after inoculation, glucose was added to 25 g l$^{-1}$ and pH was adjusted to 7.2. At 24, 31, 48, and 56 hours, glucose was added based on HPLC results to 30-40 g l$^{-1}$ per day total, (NH$_4$)$_2$SO$_4$ was added to 5 g l$^{-1}$ in flasks with levels below 1 g l$^{-1}$, and pH was adjusted to 7.2. At 27 hours, lactose was added to 5 g l$^{-1}$. Samples were removed at 8, 24, 48 and 72 hours for HPLC analysis of NAG levels. Cell cultures were harvested at 72 hours to assay glucosamine-6-phosphate acetyltransferase (GNA1), glucosamine synthase (GlmS), and glucosamine-6-phosphate deaminase (NagB) activities.

Enzyme assays confirmed that the 7107-660 and 7107-661 strains lacked functional GlmS protein. As expected, NagB activity was elevated in these strains. Glucosamine-6-phosphate acetyltransferase activity was similar to that seen in control strain 7107-607(2), indicating functional expression of the GNA1 protein in these strains.

The glmS deletion strains overexpressing the nagB and GNA1 were capable of producing N-acetyl glucosamine (Table 15). Strain 7107-661 performed the best, producing 75% of the level of NAG achieved with production strain 7107-607#2. Interestingly, strain 7107-660(1) showed NagB activity 20 fold lower than other siblings and as a consequence produced a much lower level of GlcNAc. It appears that the glucosamine-6-P acetyltransferase helps drive the reaction catalyzed by NagB in the direction of glucosamine-6-phosphate formation. The data demonstrate the functionality of a novel biological pathway for N-acetylglucosamine synthesis. Furthermore, overexpression of nagB in conjunction with GNA1 is an efficient method for producing N-acetyl glucosamine in E. coli.

TABLE 15

Enzyme activities and GlcNAc production in glmS mutant strains over xpressing nagB.

| Construct | Strain | Enzyme Activity | | | GlcNAc (g l$^{-1}$) |
| --- | --- | --- | --- | --- | --- |
|  |  | NagB | GlmS | GNA1 |  |
| control | 7101-17 | 0.0 | 0.08 | 0.0 | 0.0 |
| glmS*54, 2 copies of GNA1 | 7107-607(2) | 0.0 | 0.22 | 3.8 | 30.0 |
| glmS deletion, nagB and GNA1 | 7107-660(1) | 2.0 | 0.0 | 3.5 | 5.5 |
|  | 7107-660(4) | 42 | 0.0 | 2.9 | 18.7 |
| glmS deletion, nagB and GNA1 | 7107-661(1) | 52 | 0.0 | 3.5 | 22.0 |
|  | 7107-661(2) | 62 | 0.0 | 4.1 | 22.1 |
|  | 7107-661(3) | 58 | 0.0 | 3.9 | 24.2 |

1)Enzyme activities and N-acetyl glucosamine levels were determined in samples taken at the 72 hour timepoint.
2)Enzyme activity is expressed in µmol min$^{-1}$ mg$^{-1}$ protein.
3)Numbers in parentheses indicate different siblings.

Example 15

This Example describes cloning and overexpression of the glmM and glmU genes for N-acetylglucosamine production in strain 7107-18.

In E. coli, the glmM and glmU genes encode the enzymes that catalyze the first three steps by which GlcN-6-P is converted to UDP-GlcNAc. UDP-GlcNAc is required for the synthesis of essential cell-envelope components. GlmM catalyzes the interconversion of GlcN-6-P and GlcN-1-P by a two-step ping-pong reaction mechanism in which GlcN-1,6-diphosphate serves as both the first product and the sec active only in a phosphorylated form, although in vivo enzyme activation is unknown. In strains overproducing GlmM at high levels, the total amount of phosphorylated enzyme was not increased, indicating that the level of GlmM phosphorylation may be tightly regulated (Mengin-Lecreulx and van Heifenoort, J. Biol. Chem. 1996 271:32-39). GlmU is a bifunctional enzyme with separate uridyltransferase (N-terminal) and acetyltransferase (C-terminal) domains. The acetyltransferase domain is responsible for catalyzing the conversion of GlcN-1-P to GlcNAc-1-P; the uridyltransferase domain then converts GlcNAc-1-P to UDP-GlcNAc. In a recent publication, truncated versions of GlmU were expressed with N-terminal His$_6$tags and assayed for acetyltransferase and uridyltransferase activities (Pompeo et al., J. Biol. Chem. 2001 276:3833-3839). A truncated form of GlmU with uridyltransferase activity decreased by a factor of 1320 relative to full-length GlmU was obtained by deleting the first 78 N-terminal amino acids residues from the protein. This truncated GlmU protein retained 66% of the acetyltransferase activity seen in the full-length GlmU.

FIG. 14 shows the bacterial pathway by which GlcN-6-P is converted to UDP-GlcNAc through the action of the GlmM and GlmU enzymes. Overexpression of glmM, glmU, truncated glmU, or a combination of glmM and glmU may result in an accumulation of N-acetyl glucosamine in the medium. Therefore, strains were constructed for overexpression of these genes.

Cloning the glmM Gene for Over-Expression in E. coli:

For cloning and expression of the E. coli glmM gene, primers were synthesized based on the published sequence of the glmM gene (Mengin-Lecreulx, and van Heijenoort, J. Biol. Chem., 1996, 271:32-39). The glmM coding sequence was amplified by PCR under standard conditions from E. coli W3110 genomic DNA using forward primer 07-163 and reverse primer 07-164. The primers have the following sequences: 07-163: 5' GATCGGTCTC GCATGAG-TAATCGTAAATATTTC 3' (SEQ ID NO:59) and 07-164:5' GATCCTCGAG TTAAACGGCTTTTACTGCATC3' (SEQ ID NO:60).

Primer 07-163 contains a Bsa I restriction endonuclease site (GGTCTC, represented in nucleotides 5-10 of SEQ ID NO:59) followed by 21 nucleotides of the glmM coding sequences starting from its ATG start codon (represented in nucleotides 13-33 of SEQ ID NO:59). Primer 07-164 contains a Xho I restriction endonuclease site (CTCGAG, represented in nucleotides 5-10 of SEQ ID NO:60) followed by 21 nucleotides of the glmM coding sequence starting at its translational stop codon (represented in nucleotides 11-31 of SEQ ID NO:60). E. coli glmM coding sequence and GlmM amino acid sequence are represented as SEQ ID NO:53 and SEQ ID NO:54, respectively. PCR amplification was conducted under standard conditions to generate a fragment of DNA containing the entire glmM coding sequence flanked by Bsa I and Xho I restriction endonuclease sites. The PCR product was digested with restriction enzymes Bsa I and Xho I and ligated at the Nco I and Xho I sites of plasmid pET24d(+) (Novagen, Inc., Madison, Wis.), generating plasmid pSW07-109. Cloning in this manner places the glmM sequence behind the T7lac promoter of pET24d(+), generating the T7lac-glmM expression cassette.

Cloning the glmU Gene for Over-Expression in E. coli:

For cloning and expression of the E. coli glmU gene, primers were synthesized based on the published sequence of the glmU gene (Mengin-Lecreulx, and van Heijenoort, J. Bac., 1993, 175:6150-6157). The glmU coding sequence was amplified by PCR under standard conditions from E. coli W3110 genomic DNA using forward primer 07-161 and reverse primer 07-162. The primers have the following sequences: 07-161: 5'GATCGGTCTC GCATGT- TGAATAATGCTATGAGC3' (SEQ ID NO:61) and 07-162: 5'GATCCTCGA GTCACTTTTTCTTTACCGGACGAC3' (SEQ ID NO:62).

Primer 07-161 contains a Bsa I restriction endonuclease site (GGTCTC, represented in nucleotides 5-10 of SEQ ID NO:61) followed by 21 nucleotides of the glmU coding sequence starting at its ATG start codon (represented in nucleotides 13-33 of SEQ ID NO:61). Primer 07-162 contains a Xho I site (CTCGAG, represented in nucleotides 5-10 of SEQ ID NO:62) followed by 23 nucleotides of the glmU coding sequence starting at its translational stop codon (represented in nucleotides 11-33 of SEQ ID NO:62). *E. coli* glmU coding sequence and GlmU amino acid sequence are represented by SEQ ID NO:55 and SEQ ID NO:56, respectively. PCR amplification was conducted under standard conditions to generate a fragment of DNA containing the entire glmU coding sequence flanked by Bsa I and Xho I restriction endonuclease sites. The PCR product was digested with restriction enzymes Bsa I and Xho I and ligated at the Nco I and Xho I sites of plasmid pET24d(+) (Novagen, Inc., Madison, Wis.), generating plasmid pSW07-108. Cloning in this manner places the glmM sequence behind the T7lac promoter of pET24d(+), generating an expression cassette of T7lac-glmU.

Cloning and Expression of a N-Terminal Truncated GlmU Enzyme (GlmUt)

The truncated glmU coding sequence was amplified by PCR under standard conditions from *E. coli* W3110 genomic DNA using forward primer 07-165 and reverse primer 07-162. Primer 07-165 had the following sequence: 07-165: 5' GATGGTCTCGCAT GGAGCAGCTGGGTACGGGTC 3' (SEQ ID NO:63).

Primer 07-165 contains a Bsa I restriction endonuclease site (GGTCTC, represented in nucleotides 4-9 of SEQ ID NO:63) and the glmU CDS sequence starting at 232 bp downstream of the ATG start codon (represented in nucleotides 15-33 of SEQ ID NO:63). This results in a deletion of the first 77 amino acids of the GlmU protein. A start codon was also incorporated into primer 07-165. The PCR product generated with primers 07-165 and 07-162 contains the glmU coding sequence with the first 77 amino acid residues deleted. *E. coli* N-terminal truncated glmU coding sequence and N-terminal truncated GlmU amino acid sequence are represented by SEQ ID NO:57 and SEQ ID NO:58, respectively. The PCR product was digested with Bsa I and Xho I ligated at the Nco I and Xho I sites of plasmid pET24d(+) (Novagen, Inc., Madison, Wis.), generating plasmid pSW07-110. Cloning in this manner places the truncated glmU (glmUt) sequence behind the T7lac promoter of pET24d(+), generating an expression cassette of T7lac-glmUt.

Overexpression of GlmM, GlmU and GlmUt Proteins in *E. coli*

Plasmids pSW07-108, pSW07-109, and pSW07-110, containing the glmU, glmM or glmUt, were transformed into strain 7101-17(DE3), generating strains listed in Table 16. The empty vector pET24d(+) was transformed into strain 7101-17(DE3), generating control strain 7107-22. A standard induction experiment was performed in which cell cultures of the transformants were grown in LB medium and induced with 1 mM IPTG. Samples were taken from induced cultures at various timepoints for SDS-PAGE to confirm protein overexpression. The predicted size for the GlmU, GlmM and GlmUt proteins were 51 kDa, 50 kDa and 42 kDa, respectively. Protein bands of predicted sizes on SDS-PAGE were seen in samples from strains overexpressing the glmU, glmM and glmUt. No overexpressed proteins near the predicted sizes of GlmU, GlmM, or GlmUt were seen in the control strain. Total and soluble fractions of samples from induced cultures were determined by SDS-PAGE. As judging by visual estimation, about 20% of the GlmU protein was in the soluble fraction. However, little soluble protein was seen with the truncated version of the GlmU protein. Similarly, little GlmM protein was in soluble form.

TABLE 16

Strains containing different plasmids for GlmU, N-terminal truncated GlmU and GlmM proteins.

| Strain | Description | Overexpressed Protein |
|---|---|---|
| 7107-667 | 7101-17(DE3)/pSW07-108#1 | GlmU |
| 7107-668 | 7101-17(DE3)/pSW07-108#3 | GlmU |
| 7107-669 | 7101-17(DE3)/pSW07-109#29 | GlmM |
| 7107-670 | 7101-17(DE3)/pSW07-109#30 | GlmM |
| 7107-671 | 7101-17(DE3)/pSW07-110#53 | Truncated GlmU |
| 7107-672 | 7101-17(DE3)/pSW07-110#54 | Truncated GlmU |
| 7107-22 | 7101-17(DE3)/pET24d(+) | Empty Vector Control |

Integration of T7lac-glmU and T7lac-glmUt at the Site of the nag Deletion

SDS-PAGE gels indicated successful overexpression of the GlmU and GlmUt proteins in *E. coli*. Therefore, a strategy was developed to integrate the expression cassettes into the chromosome of production strain 7107-18. The target chosen for integration was the site of the nag deletion on the chromosome of strain 7107-18. In the early stages of construction of glucosamine production strains, the nag operon was deleted and a tetracycline resistance cassette inserted at the site of the deletion on the chromosome following P1 transduction with phage prepared from strain IBPC590 (Plumbridge, 1989, *Mol. Microbiol.* 3:506-515; Plumbridge, 1991, *Mol. Microbiol.* 5:2053-2062, Plumbridge, 1992, *J. Gen. Microbiol.* 138:1011-1017). Therefore, targeting integration to this region of the chromosome should not affect growth or glucosamine production in the strain.

As part of the strategy to develop a vector to target integration of the T7lac-glmU cassette at the site of the nag deletion of the chromosome, the T7lac-glmU fragment was amplified by PCR from plasmid pSW07-108#1. PCR was performed under standard conditions with primers GNT7nagA1-5 and 07-120. The primers have the following sequences: GNT7nagA 1-5: 5'GCGACGCTCTCCCGGGT-GCGACTCCTGCATTA3' (SEQ ID NO:64) and 07-120: 5' GATCTGTACAATCCGGATATAGTTCCTC-CTTTCAGCAAA AAACCCC3' (SEQ ID NO:65).

The forward primer GNT7nagA1-5 incorporates a Xma I restriction endonuclease site (CCCGGG, represented in nucleotides 11-16 of SEQ ID NO:64) and amplifies from 296 basepairs upstream of the T7 promoter. Primer 07-120 contains a BsrG I restriction endonuclease site (TGTACA, represented in nucleotides 5-10 of SEQ ID NO:65) and amplifies from 25 basepairs downstream of the T7 terminator.

Plasmid pCALG43 (described in Example 29) contains sequence flanking the nag deletion of the production strains, the temperature sensitive replicon from pMAK705 (Hamilton et al., 1989, *J. Bac.* 171(9):4617-4622, herein by reference of its entirety) and the kanamycin resistance cassette of plasmid pUC4K (Amersham Pharmacia Biotech, Piscataway, N.J.). The PCR product containing the T7lac-glmU cassette was digested with restriction enzymes Xma I and BsrG I and ligated at the Age I and BsrG I sites of pCALG43. The resulting plasmid, pSW07-112, can be used to direct integration of the T7lac-glmU cassette to the site of the nag deletion on the chromosome of our production strains.

To generate a plasmid for integration of the T7lac-glmU (truncated) cassette at Dnag, the same strategy and PCR primers were used, except that plasmid pSW07-110#53 served as template for PCR. The resulting plasmid was designated pSW07-113.

Plasmids pSW07-112 and pSW07-113 were used to generate E. coli strains with the T7lac-glmU cassette or the T7lac-glmUt cassette integrated at the site of the nag deletion on the chromosome. Following transformation of E. coli 7107-18 with the plasmids, the temperature selection protocol described in Example 13 was used to select for strains containing the insertions. Kanamycin-sensitive colonies were screened by PCR for the presence of the glmU expression cassettes at the site of the nag deletion. Strains positive by PCR were confirmed by Southern hybridizations conducted under high stringency conditions using the truncated glmU PCR product as probe. Strains 7107-678 and 7107-679 were confirmed as having the T7lac-glmU integrated at the site of the nag deletion. Strains 7107-680 and 7107-681 were confirmed as having the T7lac-glmUt integrated at the site of the nag deletion.

Integration of the T7lac-glmM at the Site of the glg Deletion

SDS-PAGE gels indicated successful overexpression of the GlmM protein in E. coli. Therefore, a strategy was developed to integrate the T7lac-glmM cassette into the chromosome of production strain 7107-18. The target chosen for integration was the glg operon. The glg region had previously been targeted for deletion in an effort to increase carbon flow through the glucosamine and N-acetylglucosamine production pathways by blocking the glycogen synthesis pathway. This mutation had no detrimental effect on growth or NAG production. Therefore, integration of the T7lac-glmM cassette at this chromosomal site should not negatively affect production strains.

As part of the strategy to develop a vector to target integration of the T7lac-glmM cassette at the glg site, the T7lac-glmM fragment was amplified by PCR from plasmid pSW07-109#29. PCR was performed under standard conditions with primers GNT7nagA1-5 and GNT7nagA2-3. The primers have the following sequences: GNT7nagA1-5: 5'GCGACGCTCTCCCGGGTGCGACTCCTGCATTA3' (SEQ ID NO:66) and GNT7nagA2-3: 5'GCGCTAAT-CAAGTTTTCCCGGGTCGAGGTGCCGTAA3' (SEQ ID NO:67).

Primer GNT7nagA1-5 incorporates an Xma I site (CCCGGG, represented in nucleotides 11-16 of SEQ ID NO:66) and amplifies from 296 basepairs upstream of the T7 promoter. Primer GNT7nagA2-3 also incorporates a Xma I site (CCCGGG, represented in nucleotides 17-22 of SEQ ID NO:67) and amplifies from 254 basepairs downstream of the T7 terminator. The resulting PCR fragment was digested with restriction endonuclease Xma I and ligated into the Age I site of plasmid pCALG28-2 (described in Example 29). This generated plasmids pSW07-111 #3, with the T7lac-glmM cassette ligated in the same orientation with the gig operon, and pSW07-111 #4, with the T7lac-glmM cassette ligated in the opposite orientation of the glg operon. These plasmids can be used to direct integration of the T7lac-glmM to the glg region of the production strain.

Following transformation of E. coli 7107-18 with plasmid pSW07-111#3 or pSW07-111#4, the temperature selection protocol was used to select for strains containing the T7-lac-glmM at the glg site. Southern hybridizations were conducted under high stringency conditions using the glmM coding sequence as probe. Strain 7107-682 was confirmed as having the T7-lac-glmM integrated at the glg site in the chromosome (glmM CDS in the same orientation as the interrupted glg genes). Strain 7107-683 was confirmed as having the T7-lac-glmM integrated at the glg site in the chromosome (glmM CDS in the opposite orientation as the interrupted glg genes).

GlmM/GlmU Assays

Various strains containing over-expressed GlmM (mutase), GlmU (acetyltransferase/uridyltransferase), and N-terminal truncated GlmU were examined. Activities of these enzymes were assayed in selected strains from this screen. Phosphoglucosamine mutase (GlmM) was assayed using a coupled reaction in the glucosamine-1-phosphate to glucosamine-6-P direction. The glucosamine-6-P formed was quantitatively converted to 6-phosphogluconate using glucosamine-6-P deaminase (NagB), phosphoglucoisomerease and glucose-6-P dehydrogenase. Formation of NADH allowed monitoring the reaction at 340 nm. Glucosamine-1-phosphate acetyltransferase (GlmU) was assayed using glucosamine-1-phosphate and acetyl-CoA. Formation of free CoA was measured in endpoint assay using the reagent dithiobis (2-nitrobenzoic acid) (DTNB). Formation of free CoA was monitored at 410 nm.

Levels of enzyme activities and levels of glucosamine and N-acetylglucosamine are summarized in Table 17. Significant amounts of N-acetylglucosamine were produced in strains having overexpressed GlmU, either the native form or the N-terminal truncated version. Activities of this enzyme were generally 30-50 fold higher than the control strain 7017-18 which showed only a very low level of activity. Significant free glucosamine also was formed in these strains. Overexpression of GlmM protein did not lead to higher activity. Under the experimental conditions, overexpression of GlmM alone did not allow formation of significant amount of N-acetylglucosamine. Moreover, overexpression of GlmM plus GlmU did not result in increased levels of N-acetylglucosamine relative to GlmU strains. As literature reported, the GlmM enzyme is subject to regulation of phosphorylation, which was not addressed here. It is anticipated that the creation and use of GlmM mutant enzymes which bypass phosphorylation regulation and or have other improved kinetic features could increase the efficiency of N-acetylglucosamine synthesis by the pathway of GlmS-GlmM-GlmU, or NagB-GlmM-GlmU.

TABLE 17

Analysis of strains over-expressing GlmM, GlmU and GlmUt (N-terminal truncated GlmU).

| Strain | Genotyp* | Enzyme Activities ($\mu$mol min$^{-1}$ mg$^{-1}$ protein) | | Metab lites (g l$^{-1}$) | |
|---|---|---|---|---|---|
| | | GlmM | GlmU | NAG | Glucosamine |
| 7017-18 | glmS | 0.019 | 0.008 | 0.2 | 4.5 |
| 7017-607(2) | glmS GNA1 | | 0.083 | 5.2 | ND |
| 7017-678(1) | glmS glmU | 0.030 | 0.480 | 1.3 | 2.5 |
| 7017-678(2) | glmS glmU | | 0.360 | 1.2 | 2.7 |
| 7017-680(1) | glmS glmUt | 0.032 | 0.500 | 1.1 | 2.1 |

TABLE 17-continued

Analysis of strains over-expressing GlmM, GlmU
and GlmUt (N-terminal truncated GlmU).

| Strain | Genotyp* | Enzyme Activities (μmol min$^{-1}$ mg$^{-1}$ protein) | | Metab lites (g l$^{-1}$) | |
|---|---|---|---|---|---|
| | | GlmM | GlmU | NAG | Glucosamine |
| 7017-683(1) | glmS glmM | 0.045 | 0.027 | 0.3 | 2.9 |
| 7017-689(1) | glmS glmM glmU | 0.046 | 0.310 | 0.9 | 1.4 |
| 7017-687(1) | glmS glmM glmUt | 0.055 | 0.170 | 0.3 | 2.6 |

*All the listed recombinant genes were over-expressed under the T7 promoter control.
glmS = glucosamine synthetase
glmM = phosphoglucosamine mutase
glmU = glucosamine-1-phosphate acetyltransferase
glmUt = N-terminal truncated version of GlmU.

Example 16

This Example describes integration of one or more copies of the T7lac-ScGNA1 cassette into the chromosome of glucosamine or N-acetylglucosamine production strains.

Overexpression of the ScGNA1 using vector pET24d(+) resulted in N-acetyl glucosamine production of 24 g l$^{-1}$ after 72 hour culture (Table 1). To avoid the use of 0.25 antibiotics in cultures and to maximize N-acetyl glucosamine production, it was decided to integrate the T7lac-ScGNA1 expression cassette into the chromosome. Since it was not known how many copies of the T7lac-ScGNA1 expression cassette will be optimal for NAG production, it was decided to integrate multiple copies of the cassette into the chromosome. The insertion sites for integration were selected based on the assumption that the targeted genes are not essential to cell growth or N-acetylglucosamine production. Four target sites were selected: manXYZ, fucIK, treB and melAB.

The general strategy and protocols of temperature selection described in 13 were adapted to GNA1 integration in the chromosome. Different temperature sensitive integrative vectors were developed, each containing a temperature sensitive replication origin, an antibiotic selection marker and the T7lac-ScGNA1 expression cassette. For each vector, the T7lac-ScGNA1 expression cassette was isolated from the recombinant plasmid pSW07-62#25 and inserted in a fragment of E. coli DNA sequence cloned from the intended integration site. Integrative vectors were transformed into E. coli host strains and clones with integrated ScGNA1 were selected using the temperature shift procedures.

The same methods and protocols can be used to integrate other GNA1 homologues from different origins. To those skilled in the art, it is anticipated that modifications and changes may be needed to adapt these methods and protocols to each specific gene. Such modification and changes include, but are not limited to, the use of different restriction sites for cloning and different locations for integration in the chromosome.

GNA1 Integration at the manXYD Site (One Copy of GNA1):

The T7lac-ScGNA1 expression cassette was subcloned for integration at the manXYZ site in the chromosome in 7107-18. E. coli manXYD is an operon encoding a complex of three proteins involved in the uptake and phosphorylation of mannose. The operon can be deleted without affecting E. coli growth in medium containing glucose as carbon source. For GNA1 gene integration at the manXYZ site, a plasmid containing the E. coli manXYZ sequence was developed. Primers was synthesized based on the published sequence of E. coli manXYZ (Blattner et al, 1997, Science 277(5331), pp. 1453-1474, herein by reference of its entirety) to amplify the manXYZ operon plus flanking regions from E. coli W3110 genomic DNA using the standard PCR method. The primers used for amplification were forward primer 07-87 and the reverse primer 07-88, which had the following sequences: 07-87: 5'GATGCGGCCGCACTGCAGTAAT-TACCGCATCCAAC3' (SEQ ID NO:68) and 07-88: 5'GAT-GTCGACACCGATTGATGCAGCAAATGCATCC3' (SEQ ID NO:69).

Primer 07-87 contains a Not I restriction endonuclease site (GCGGCCGC, represented in nucleotides 4-11 of SEQ ID NO:68) and starts at 905 base pairs upstream of the manX ATG start codon. Primer 07-88 contains a Sal I site (GTC-GAC, represented in nucleotides 4-9 of SEQ ID NO:69) and starts from 1010 base pairs downstream from the manZ translational stop codon. PCR was performed using a standard protocol to generate the fragment containing the manXYZ plus flanking regions flanked by Not I and Sal I restriction sites. This fragment was cloned into vector pCR˚2.1-TOPO˚ (Invitrogen, Carlsbad, Calif.), generating plasmid pSW07-65#7.

To generate a deletion in manXYZ, plasmid pSW07-65#7 was digested with restriction enzyme Hpa I. This released a 2647 bp portion of the plasmid containing most of the coding sequence of manXYZ. Additionally, the T7lac-ScGNA1 fragment was excised from plasmid pSW07-62#25 (previously described in Example 13) using restriction endonuclease Nae I. Plasmid pSW07-62#25 contains Nae I sites at 46 base pairs upstream of the T7 promoter and 164 base pairs downstream of the T7 terminator. The Nae I fragment containing T7lac-ScGNA1 sequence was ligated into the Hpa I sites of pSW07-65#7. As this ligation was a blunt-end ligation, the T7lac-ScGNA1 fragment might ligate into the plasmid in either orientation. Therefore restriction enzyme digestion was used to screen for plasmids with the T7lac-ScGNA1 cassette inserted in the same orientation as manXYZ. The resulting plasmid was designated pSW07-66#25.

To create a temperature sensitive integrative vector, a fragment containing the temperature sensitive replicon of pMAK705 (Hamilton et al., 1989, J. Bac. 171(9):4617-4622, herein by reference of its entirety) and the kanamycin resistance cassette of plasmid pUC4K (Amersham Pharmacia Biotech, Piscataway, N.J.) was excised from plasmid pKLN07-21 using restriction enzymes Not I and Sal I. Plasmid pKLN07-21 was constructed by PCR amplification of the temperature sensitive replicon from plasmid pSW07-4 (described in Example 6), ligation of the PCR product into the vector pPCR-Script$^{AMP}$SK(+) (Stratagene Cloning Systems, La Jolla, Calif.), and addition of the kanamycin resistance cassette from plasmid pUC4K (Amersham Pharmacia Biotech, Piscataway, N.J.).

Restriction enzymes Not I and Sal I were used to excise the fragment containing the T7lac-ScGNA1 plus manXYZ flanking region from plasmid pSW07-66#25. This fragment was then ligated with the Not I/Sal I fragment containing the temperature sensitive replication origin and the kanamycin resistance marker from pKLN07-21, generating plasmid pSW07-68#5. This plasmid had a temperature sensitive replication origin, a kanamycin selection marker and a T7lac-ScGNA1 expression cassette that is flanked by 5' upstream and 3' downstream sequences from the manXYZ locus.

Plasmid pSW07-68#5 was used to generate E. coli strains with T7lac-ScGNA1 integrated at the manXYZ site. As described in U.S. Pat. No. 6,372,457, the manXYZ operon in the strain 7107-18 was mutated by P1 phage transduction. Following transformation of the E. coli strain 7107-18 with pSW07-68#5, the temperature selection protocol described in Example 6 was used to select strains with the T7-lac-ScGNA1 sequence integrated at the manXYZ site. Kanamycin-sensitive strains were screened by PCR for the presence of the T7lac-ScGNA1 cassette at the fuc regulon. Strains were confirmed by Southern hybridization using standard high stringency conditions and the ScGNA1 coding sequence as probe. The resultant strain with one copy of T7lac-ScGNA1 was designated 7107-92.

Integration of a Second Copy of GNA1 at the ƒucIK Site:

Integration of a second copy of the T7lac-ScGNA1 cassette was directed to the region of the chromosome encoding for enzymes involved in utilization of L-fucose as an alternative carbon source. The ƒucP (encoding L-fucose permease), ƒucI (encoding L-fucose isomerase), ƒucK (encoding L-fuculose kinase) and ƒucU (unknown protein) genes form an operon involved in L-fucose dissimilation. The ƒucR gene encodes a regulatory protein that activates the L-fucose dissimilation regulon. Integration of the T7lac-ScGNA1 cassette at the fucose operon should not affect the ability of E. coli to grow in medium with glucose as carbon source, nor should it affect its ability to synthesize N-acetyl glucosamine.

As part of the strategy to develop an integrative vector to target the ƒuc region, primers were synthesized based on published sequence of the fucose regulon (Chen et al., Mol. Gen. Genet. 1987 210:331-337). The ƒucIKU and ƒucR genes were amplified from E. coli W3110 genomic DNA under standard PCR conditions using primers 07-113 and 07-114, which have the following sequences: 07-113: 5'GATGCGGCCGCGCAAGGCAACAGC AAACTGGC-3' (SEQ ID NO:70) and 07-114: 5'-GATCGGATCCTCAG-GCTGTTACCA AAGAAGTTGCAACCTGGC-3' (SEQ ID NO:71).

Primer 07-113 contains a Not I restriction endonuclease site (GCGGCCGC, represented in nucleotides 4-11 of SEQ ID NO:70) and amplifies from 824 bp downstream of the ƒucI ATG start codon (represented in nucleotides 12-32 of SEQ ID NO:70). Primer 07-114 contains a BamH I site (GGATCC, represented in nucleotides 5-10 of SEQ ID NO:71) followed by 32 nucleotides of the ƒucR coding sequence starting at its translational stop codon (represented in nucleotides 11-42 of SEQ ID NO:71). PCR was conducted under standard conditions to generate a fragment containing the ƒucIKU and ƒucR sequence flanked by BamH I and Not I restriction endonuclease sites. This fragment was ligated into pPCR-Script Amp SK(+) (Stratagene Cloning Systems, La Jolla, Calif.), generating plasmid pSW07-75. Plasmid pSW07-75 was digested with restriction endonucleases Hpa I and BsrG I, removing a 1239 basepair fragment containing a portion of the ƒucI and ƒucK genes.

The T7lac-ScGNA1 cassette was amplified by PCR from plasmid pSW07-62#25 using standard conditions. PCR amplification was performed with forward primer 07-115 and reverse primer 07-112, which have the following sequences: 07-115: 5'GATCTGTAC AAGCAACCGCAC-CTGTGGC3' (SEQ ID NO:72) and 07-112: 5'GAT-CAGCGCTA TCCGGATATAGTTCCTCCTTTCAG-CAAAAAACCCC3'). (SEQ ID NO:73).

Primer 07-115 contains a BsrG I site (TGTACA, represented in nucleotides 5-10 of SEQ ID NO:72) and amplifies from 76 basepairs upstream of the T7 promoter sequence of pSW07-62#25. Primer 07-112 contains an Afe I site (AGCGCT, represented in nucleotides 5-10 of SEQ ID NO:73) and amplifies from 25 basepairs downstream of the T7 terminator sequence of pSW07-62#25. The PCR fragment was digested with BsrG I and Afe I and ligated into the BsrG I and Hpa I sites of plasmid pSW07-75, generating plasmid pSW07-76. The recombinant plasmid contained T7lac-ScGNA1 cassette ligated into the site of the ƒucIK deletion.

To create a temperature sensitive integrative vector, a fragment containing the temperature sensitive replicon of pMAK705 (Hamilton et al., 1989, J. Bac. 171(9):4617-4622, herein by reference of its entirety) and the kanamycin resistance cassette of plasmid pUC4K (Amersham Pharmacia Biotech, Piscataway, N.J.) was excised from plasmid pKLN07-21 using restriction enzymes Not I and Kpn I. Plasmid pKLN07-21 was constructed by PCR amplification of the temperature sensitive replicon from plasmid pSW07-4 (described in Example 6), ligation of the PCR product into the vector pPCR-Script™SK(+) (Stratagene Cloning Systems, La Jolla, Calif.), and addition of the kanamycin resistance cassette from plasmid pUC4K (Amersham Pharmacia Biotech, Piscataway, N.J.).

Restriction enzymes Not I and Kpn I were used to excise the fragment containing the T7lacScGNA1 plus ƒuc flanking region from plasmid pSW07-76. This fragment was then ligated with the Not I/Kpn I fragment containing the temperature sensitive replication origin and the kanamycin resistance marker from pKLN07-21, generating plasmid pSW07-77. This plasmid had a temperature sensitive replication origin, a kanamycin selection marker and a T7lac-ScGNA1 expression cassette that is flanked by 5' upstream and 3' downstream sequences from the fuc regulon. Plasmid pSW07-77 can be used to direct integration of T7lac-ScGNA1 cassette at the fuc regulon of E. coli.

Plasmid pSW07-77 was transformed into strain 7107-92#1. The temperature selection protocol was used to select strains with the T7-lac GNA1 sequence integrated at the A ƒucIK site. The resulting strains were designated 7107-607 (2), 7107-607(3), and 7107-607(4).

Integration of a Third Copy of GNA1 at the treB Site:

Integration of a third copy of the T7-lac-ScGNA1 cassette was directed to the region of the chromosome encoding for enzymes involved in utilization of trehalose as an alternative carbon source. The treB and treC genes, encoding the trehalose transporter and trehalose 6-P hydrolase, respectively form an operon. The treR gene encodes the repressor protein that controls the operon, which is inducible by trehalose-6-phosphate (Horlacher, R., and Boos, W., 1997, J. Biol. Chem., 272(20):13026-13032). As with previous targets, integration of the T7lac-ScGNA1 at the trehalose regulon should not affect the ability of E. coli to grow in medium with glucose as carbon source, nor should it affect its ability to synthesize N-acetyl glucosamine.

As part of the strategy to develop an integrative vector to target the treB region, primers were synthesized based on published sequence to amplify the treR, treB, and treC genes from E. coli W3110 genomic DNA (Blattner et al., 1997, Science 227(5331):1453-1474). PCR amplification was performed using primers 07-117 and 07-118, which have the following sequences: 07-117: 5' GAGCGGCCGCATG- CAAAATCGGCTGACCATC3' (SEQ ID NO:74) and 07-118: 5' GATCGGGCCCTTACTTCTGTAACCACCA-GACAG CCTC3' (SEQ ID NO:75).

Primer 07-117 contains a Not I restriction endonuclease site (GCGGCCGC, represented in nucleotides 3-10 of SEQ ID NO:74) followed by 21 nucleotides of the treR coding sequence from its ATG start codon (represented in nucleotides 11-31 of SEQ ID NO:74). Primer 07-118 contains an Apa I restriction endonuclease site (GGGCCC, represented in nucleotides 5-10 of SEQ ID NO:75) followed by 27 nucleotides of the treC coding sequence starting at its translational stop codon (represented in nucleotides 11-37 of SEQ ID NO:75). PCR amplification was conducted using a standard protocol to generate a fragment of DNA containing the treR, treB and treC genes flanked by Not I and Apa I restriction sites. The 4.2 kb PCR product was ligated into plasmid pPCR-Script™SK(+) (Stratagene Cloning Systems, La Jolla, Calif.), creating plasmid pSW07-78#20.

Plasmid pSW07-78#20 was digested with restriction endonuclease Bgl II and treated with T4 DNA polymerase under standard conditions to blunt the ends of the fragment. The blunted fragment was next digested with restriction endonuclease BsrG I. This double digestion with Bgl I and BsrG I removed a 130 basepair region of the treB coding sequence from plasmid pSW07-78#20, leaving the plasmid fragment with one sticky end (BsrG I) and one blunt end.

The next step was to ligate the T7lac-ScGNA1 cassette into the BsrG I and Bgl II (filled) site of plasmid pSW07-78#20. To accomplish this, the T7lac-ScGNA1 cassette was amplified by PCR from plasmid pSW07-62#25 under standard conditions using forward primer 07-115 (SEQ ID NO:72) and reverse primer 07-112 (SEQ ID NO:73). Primer 07-115 contains a BsrG I site (TGTACA, represented in nucleotides 5-10 of SEQ ID NO:72) and amplifies from 76 basepairs upstream of the T7 promoter sequence of pSW07-62#25. Primer 07-112 contains an Afe I site (AGCGCT, represented in nucleotides 5-10 of SEQ ID NO:73) and amplifies from 25 basepairs downstream of the T7 terminator sequence of pSW07-62#25. The PCR fragment was digested with BsrG I and Afe I and ligated into the BsrG I and Bgl II (filled) site of plasmid pSW07-78#20, generating plasmid pSW07-83.

To create a temperature sensitive integrative vector, a fragment containing the temperature sensitive replicon of pMAK705 (Hamilton et al., 1989, J. Bac. 171(9):4617-4622, herein by reference of its entirety) and the kanamycin resistance cassette of plasmid pUC4K (Amersham Pharmacia Biotech, Piscataway, N.J.) was excised from plasmid pKLN07-21 using restriction enzymes Not I and Apa I.

Restriction enzymes Not I and Apa I were used to excise the fragment containing the T7lac-ScGNA1 plus tre flanking region from plasmid pSW07-83. This fragment was ligated with the Not I-Apa I fragment from plasmid pKLN07-21 containing the temperature sensitive replication origin and the kanamycin resistance marker, resulting in plasmid pSW07-84. Plasmid pSW07-84 can be used to direct integration of T7-lac-ScGNA1 cassette at the treB of E. coli.

Plasmid pSW07-84#1 was transformed into strains 7107-607(2), 7107-607(3), and 7107-607(4). The temperature selection protocol was used to select strains with the T7-lac GNA1 sequence integrated at the treB site. Kanamycin-sensitive colonies were screened by PCR for the presence of the T7lac-ScGNA1 cassette at treB of the chromosome. Strains were confirmed by Southern hybridization using standard high stringency conditions and the ScGNA1 coding sequence as probe as having three copies of the T7lac-ScGNA1 cassette integrated in the chromosome. These strains were designated 7107-608(1) and 7107-608(2).

Integration of a Fourth Copy of GNA1 at the melRAB Site:

Integration of a fourth copy of the T7lac-ScGNA1 cassette into NAG production strains was targeted to the melR and melAB region of the chromosome. In E. coli, this region encodes proteins involved in the melibiose uptake and hydrolysis. The melA and melB genes, encoding alpha galactosidase and melibiose permease II, respectively, form an operon. The divergently transcribed melR gene encodes the regulator of the melibiose operon. As with previous targets for integration, integration of the T7lac-ScGNA1 cassette at me/AB of the genome should not affect the ability of E. coli to grow in medium with glucose as carbon source, nor should it affect its ability to synthesize N-acetyl glucosamine.

As part of the strategy to develop an integrative vector to target the melAB region, primers 07-122 and 07-123 were synthesized based on published sequence of the melR, melA and melB genes of E. coli (Blattner et al, 1997, Science 277(5331), pp.1453-1474). PCR was conducted under standard conditions to amplify a fragment containing the melR, melA and melB genes from E. coli W3110 genomic DNA. Forward primer 07-122 and reverse primer 07-123 have the following sequences: 07-122: 5'GATGCGGCCGCT-TAGCC GGGAAACGTCTGGCGGC3' (SEQ ID NO:76) and 07-123: 5'GATCGTCGACTCAGG CTTTCACAT-CACTCACTGCACC3' (SEQ ID NO:77).

Primer 07-122 contains a Not I restriction endonuclease site (GCGGCCGC, represented in nucleotides 4-11 of SEQ ID NO:76) followed by 23 nucleotides of the melR coding sequence starting from the translational stop codon (represented in nucleotides 12-34 of SEQ ID NO:76). Primer 07-123 contains a Sal I restriction endonuclease site (GTC-GAC, represented in nucleotides 5-10 of SEQ ID NO:77) followed by 27 nucleotides of the melB coding sequence starting from the translational stop codon (represented in nucleotides 11-37 of SEQ ID NO:77). The PCR fragment containing the melR and melAB coding sequences flanked by Not I and Sal I restriction endonuclease sites was ligated into vector pPCR-Script Amp SK (+) (Stratagene), generating plasmid pSW07-81#5.

The next step in vector construction was to ligate the T7lac-ScGNA1 cassette into the melAB region of plasmid pSW07-81#5. Plasmid pSW07-81#5 was digested with restriction endonucleases Bgl II and AsiS I, removing a 1676 basepair fragment containing the entire melA coding sequence and the first 199 nucleotides of the melB coding sequence.

The T7lac-ScGNA1 cassette was amplified by PCR from plasmid pSW07-62#25 under standard conditions with forward primer 07-124 and reverse primer 07-125, which have the following sequences: 07-124: 5'GATGGATCCAG-CAACCGCACCTGTGGC3' (SEQ ID NO:78) and 07-125: 5'GATGCGATCGCTATAGTTCCTCCTTTCAGCAAAA AACCC3' (SEQ ID NO:79)

Primer 07-124 contains a BamH I site (GGATCC, represented in nucleotides 4-9 of SEQ ID NO:78) and amplifies from 76 nucleotides upstream of the T7 promoter of plasmid pSW07-62#25. Primer 07-125 contains an AsiS I site (GC-GATCGC, represented in nucleotides 4-11 of SEQ ID NO:79) and amplifies from 18 nucleotides downstream of the T7 terminator of plasmid pSW07-62#25. The PCR product containing the T7lac-ScGNA1 was digested with restriction endonucleases BamH I and AsiS I and ligated with the Bgl II and AsiS I fragment from pSW07-81#5, generating plasmid pSW07-82. Plasmid pSW07-82 therefore contained the mel genes in vector pPCR-Script (AmpSK(+), with the 1676 basepair melAB region replaced with the T7lac-ScGNA1 cassette.

To create a temperature sensitive integrative vector, a fragment containing the temperature sensitive replicon of pMAK705 (Hamilton et al., 1989, J. Bac. 171(9):4617-4622, herein by reference of its entirety) and the kanamycin resistance cassette of plasmid pUC4K (Amersham Pharmacia Biotech, Piscataway, N.J.) was excised from plasmid pKLN07-21 using restriction enzymes Not I and Sal I.

Plasmid pSW07-82 was digested with restriction endonucleases Not I and Sal I isolate the fragment containing the mel genes interrupted with the T7lac-ScGNA1 cassette. This fragment was then ligated with the Not I and Sal I fragment from plasmid pKLN07-21 containing the temperature sensitive replication origin and the kanamycin resistance marker. The resulting plasmid pSW07-84 can be used to direct integration of T7-lac-ScGNA1 cassette at the melAB of E. coli.

Plasmid pSW07-84 was transformed into strains 7107-608(1) and 7107-608(2). The temperature selection protocol described in Example 6 was used to select strains with the T720 lac GNA1 sequence integrated at the melAB site. Kanamycin-sensitive colonies were screened by PCR for the presence of the T7lac-ScGNA1 cassette at melAB of the chromosome. Strains were confirmed by Southern hybridization using standard high stringency conditions with the ScGNA1 coding sequence as probe as having four copies of the T7lac-ScGNA1 cassette integrated in the chromosome. These resulting strains, derived from 7107-608(1) and 7107-608(2), were designated 7107-612 and 7107-613, respectively.

Plasmid pSW07-84 was also transformed into strains 7107-607(2), 7107-607(3), and 7107-607(4) to add a third copy of the T7lac-ScGNA1 to the chromosome. Strains were screened as above and confirmed by Southern hybridization using standard high stringency conditions with the ScGNA1 coding sequence as probe as having three copies of the T7lac-ScGNA1 cassette integrated in the chromosome. These strains, derived from strains 7107-607(2), 7107-607(3), and 7107-607(4), were designated as 7107-609, 7107-610 and 611, respectively Effects of GNA1 Gene Copy Number on GNA1 Expression Levels and N-Acetylglucosamine Production To evaluate the effect of gene copy number on GNA1 expression levels and N-acetylglucosamine production, strains with varying copy numbers of the integrated T7lac-ScGNA1 cassette were tested in shake flask. Samples were taken to analyze GNA1 protein expression by enzyme activity assay and determination of NAG titers.

Shake flask Screen 53 was conducted to evaluate the effect of copy number of the integrated T7-lac-ScGNA1 cassette on glucosamine synthase (GlmS) activity, glucosamine-6-phosphate acetyltransferase (GNA1) activit were grown in M9B medium (previously described) supplemented with supplemented with 0.6 g l$^{-1}$ MgSO$_4$-7H$_2$O, 0.05 g l$^{-1}$ CaCl$_2$-2H$_2$O, 10 g l$^{-1}$ glucose, 40 g l$^{-1}$ lactose, 5 g l$^{-1}$ ribose and 5 g l$^{-1}$ yeast extract. Cultures were grown at 30° C. for the first 24 hours and then placed at 25° C. At 24 and 48-hour timepoints, the pH of the cultures was adjusted to 7.2, glucose was added to each flask to 30 g l$^{-1}$ per day total based on HPLC results, and ammonium sulfate additions of 5 g l$^{-1}$ were made to flasks with ammonium levels below 1 g l$^{-1}$. Samples were removed at 24, 48 and 72 hours to evaluate NAG production and enzyme assays. All strains tested grew to comparable OD$_{600}$ and had comparable glucosamine synthase activity (Table 18). There was a notable correlation between glucosamine-6-phosphate acetyltransferase activity and T7-lac-ScGNA1 copy number, with the strains containing three copies having the highest specific activity. However, this increased specific activity did not result in increased NAG production in the shake flask experiment.

TABLE 18

Comparison of growth, enzyme activity, and GlcNAc production in strains with multiple copies of the T7-lac-ScGNA1 cassette integrated in the chromosome.

| Strain | GNA1 copy number | A$_{600}$ | Enzyme Activity | | GlcNAc (g l$^{-1}$) |
|---|---|---|---|---|---|
| | | | GlmS | GNA1 | |
| 7107-92(1) | 1 | 12.0 | 0.59 | 3.0 | 30.0 |
| 7107-607(2) | 2 | 12.0 | 0.59 | 5.8 | 28.8 |
| 7107-608(1) | 3 | 12.8 | 0.55 | 9.1 | 29.3 |
| 7107-608(2) | 3 | 13.5 | 0.43 | 7.9 | 29.7 |
| 7107-609(1) | 3 | 11.3 | 0.37 | 8.2 | 24.7 |
| 7107-610(1) | 3 | 12.0 | 0.40 | 8.4 | 26.3 |
| 7107-611(1) | 3 | 12.0 | 0.44 | 7.4 | 26.4 |

1) Enzyme activities and N-acetyl glucosamine levels were determined from the 72 hour timepoint.
2) Enzyme activity is expressed in μmol min$^{-1}$ mg$^{-1}$ protein.
3) Numbers in parentheses indicate different sibling.

Evaluation of Strains with Varying Copy Numbers of the Integrated T7lac-ScGNA1 Cassette in 1 Liter Fermentors Strains 7107-92(1), 7107-607(2), 7107-608(2), and 7107-612(1), containing the integrated T7lac-ScGNA1 cassette at copy numbers ranging from 1 to 4, respectively, were evaluated in 1-L fermenters. Fermenters 237-240 were set up with an initial volume of 475 ml. Components of the fermentation medium are listed in Table 19. Fermentations were run using 75% NH$_4$OH to control pH at 6.9. Temperature was maintained at 37° C. throughout the fermentation. Aeration and agitation were adjusted to maintain a dissolved oxygen concentration of 20% of air saturation. 65% glucose was fed to the cultures with feed rate controlled by computer program to achieve a growth rate of 0.40 hr$^{-1}$ at inoculation and a maximum rate of 5 ml hr$^{-1}$ by 6 hours. Cultures were induced with food grade lactose added at 5 g l$^{-1}$ at 10 hours, with continued glucose feed.

TABLE 19

Fermentation medium used to test effects of GNA1 copy number on N-acetylglucosamine production.

| Component | Amount (g l$^{-1}$) |
|---|---|
| H$_3$PO$_4$ | 4.79 |
| KOH | 3.15 |
| Citric acid-H$_2$O | 3.56 |
| (NH$_4$)$_2$SO$_4$ | 5 |
| MgSO$_4$-7 H$_2$O | 2.5 |
| CaCl$_2$-2 H$_2$O | 0.05 |
| Trace Metals | * |
| Mazu 204 Antifoam | 0.25 |

*Trace metal composition is 5 m l$^{-1}$ FeSO$_4$-7H$_2$O, 3.75 mg l$^{-1}$, ZnSO$_4$-7H$_2$O, 0.6 mg l$^{-1}$ MnSO$_4$-H$_2$O, 0.1002 mg l$^{-1}$ CuSO4-5H$_2$O and 0.1002 mg l$^{-1}$ CoCl$_2$-6H$_2$O.

Results of the fermentation are summarized as follows. The copy number of the GNA1 cassette has a slight affect on NAG levels. By the end of the fermentation, strain 7107-608(2), containing three copies of the T7lac-ScGNA1 cassette, produced 16% more NAG than the strain with one copy and 5% more NAG than the strain with two copies of the cassette. In this experiment, addition of the fourth copy of the T7lac-ScGNA1 did not achieve an improvement over strain 7107-608(2). Nonetheless, the utility of increasing the T7-lac-ScGNA1 copy number in production strains has been validated.

Example 17

The following Example describes the effects of phosphorylated sugars on glucosamine synthase.

Glucosamine synthetase activity was examined in the presence of various phosphorylated sugars. Crude enzyme extracts was prepared from cells of 7017-18 grown in shake flasks for 24 hours with lactose induction. Results are summarized in Table 20 below. The data indicates that previously observed glucosamine-6-P showed strong inhibition on glucosamine synthetase at relatively high concentration. Glucosamine-1-P also inhibited the enzyme at 10 mM. No inhibition was observed with the N-acetylglucosamine phosphates.

TABLE 20

Effects of different phosphorylated sugars on the E. coli glucosamine synthase GlmS*54

| Addition | Activity (%) |
|---|---|
| control | 100 |
| glucosamine-6-P (10 mM) | 70 |
| glucosamine-6-P (20 mM) | 46 |
| glucosamine-1-P (10 mM) | 79 |
| N-acetylglucosamine-6-P (10 mM) | 100 |
| N-acetylglucosamine-6-P (20 mM) | 100 |
| N-acetylglucosamine-1-P (10 mM) | 100 |

Example 18

This Example describes the biochemical effects of phosphorylated sugars on other enzymes relevant to N-acetylglucosamine synthesis.

Previous discussions on potential toxic effects of phosphorylated sugars (compounds such as glucosamine-6-P) have been limited to enzymes directly involved in metabolism of amino sugars. However, the general phenomenon of sugar toxicity has long been observed in various mutants impaired in sugar metabolism. This has generally been attributed to build up of abnormally high levels of phosphorylated sugar intermediates which inhibit one or more enzyme targets and metabolically poison the cell. Product inhibition of GlmS is one example of this.

FIG. 3 suggests a number of possibilities for other possible targets. A paper (J. Bacteriol. 101:384. 1970) dealing with mutants impaired in amino sugar metabolism describes this phenomenon and shows that pentose sugars can reverse the inhibition. Therefore, effects of glucosamine-6-P and N-acetylglucosamine-6-P on several of the enzymes were examined.

Glucosamine-6-P is reported as an inhibitor of Pgi in publication (Arch. Biochem. Biophys. 64: 489. 1956). FIG. 15 shows Pgi (phosphoglucoisomerase inhibition by two amino sugars). Inhibition is observed with both compounds, but significantly less so with N-acetylglucosamine-6-P.

Glucosamine-6-P is reported as an inhibitor of phosphoglucoisomerase (J. Biol. Chem. 216:67. 1955). FIG. 16 shows effects of phosphorylated amino sugars on glucose-6-P dehydrogenase (zwf), the entry point for glucose-6-P into the pentose phosphate pathway. Here again glucosamine-6-P appears to be a more potent inhibitor of the enzyme than N-acetylglucosamine-6-P. Similar trends were seen with phosphoglucomutase (Pgm).

The inhibitory effect of glucosamine-6-P on the above mentioned and possibly other enzymes involved in carbohydrate metabolism may certainly be an explanation for the apparent ceiling on glucosamine productivity observed in 7017-18. Presumably, high concentrations of glucosamine-6-P interfere with activity of several enzymes. Addition of the acetyltransferase (GNA1) to the pathway presumably leads to much lower intracellular levels of glucosamine-6-P. This certainly could be the primary reason for increased productivity along with the enhanced stability of N-acetylglucosamine.

N-acetylglucosamine-6-P really does not significantly inhibit Zwf or Pgi in the in vitro assays performed. Positive effects of ribose and gluconate on cell growth and N-acetylglucosamine synthesis suggest that one or more steps in the pentose phosphate pathway are affected by phosphorylated amino sugars. On the other hand, glucosamine N-acetyltransferase did not show any significant product inhibition by N-acetylglucosamine-6-P.

Example 19

This Example describes enzyme activities during N-acetylglucosamine production in fermentors.

Various enzyme activities relevant to N-acetylglucosamine production were examined in fermentors. Enzymes assayed were glucosamine synthase (GlmS), glucosamine N-acetyltransferase (GNA1) and glucose-6-phosphate dehydrogenase, which is a key enzyme in pentose phosphate pathway (see FIG. 3).

Strains with GNA1 Plasmids (Fermentor #102):

Relevant enzyme activity was examined in samples of 7017-87(25) from fermentations 102. This strain contains the acetyltransferase gene construct on plasmids. This run produced 80 g/l N-acetylglucosamine. Results of enzyme activities and N-acetylglucosamine concentrations are shown in FIG. 17. High acetyltransferase activity was observed soon after induction and it remained high throughout the run. Interestingly, acetyltransferase activity was present even at 90+hours, while by this time glucosamine synthetase activity had disappeared. N-acetylglucosamine production essentially ceased at around 70 hours. Glucose-6-P dehydrogenase activity was constant throughout the run.

Strains with Integrated GNA1 Constructs (Fermentors #121-128).

These runs used E. Coli strain 7017-92(1) containing the integrated acetyltransferase construct. Fermentation variables examined were amounts of iron added in the medium, extra iron feeding, and levels of phosphate buffer (1×=40 g $l^{-1}$). Enzyme activities are summarized in Table 21. Except for the lowest iron level used in fermentation 121, glucosamine synthetase and acetyltransferase activities were very high throughout the experiment in the other seven fermentors. As previously observed, acetyltransferase activity tends to remain at a high level. Glucosamine synthetase activity was clearly adequate at the other iron levels (5-20 PPM) examined with or without additional iron feed. Lower iron gave higher N-acetylglucosamine activity but lower glucosamine synthetase activity. This decreased activity was still adequate for high N-acetylglucosamine production

TABLE 21

Enzyme activities in N-acetylglucosamine fermentation
(fermentors #121 through 128)

| Sample | Hours | GlmS ($\mu$mol min$^{-1}$, mg$^{-1}$ protein) | GNA1 | [NAG] (g l$^{-1}$) | Iron (mg l$^{-1}$) | Fe Feed | Phosphate |
|---|---|---|---|---|---|---|---|
| 121-2 | 24 | 0.0 | 0.0 | 7.1 | 2.5 | + | 1X |
| 121-5 | 46 | 0.0 | 0.5 | 23 | | | |
| 121-7 | 70 | 0.0 | 0.6 | 29 | | | |
| 122-2 | 24 | 0.0 | 0.0 | 6.0 | 5 | + | 1X |
| 122-5 | 46 | 0.43 | 5.7 | 56 | | | |
| 122-7 | 70 | 0.40 | 6.3 | 88 | | | |
| 122-8 | 95 | 0.18 | 5.5 | 88 | | | |
| 123-2 | 24 | 0.0 | 0.0 | 5.7 | 10 | + | 1X |
| 123-5 | 46 | 0.81 | 7.5 | 49 | | | |
| 123-7 | 70 | 0.99 | 10 | 77 | | | |
| 124-2 | 24 | 0.0 | 0.0 | 6.0 | 20 | + | 1X |
| 124-5 | 46 | 0.81 | 5.4 | 50 | | | |
| 124-7 | 70 | 0.96 | 6.5 | 76 | | | |
| 125-2 | 24 | 0.0 | 0.0 | 5.8 | 5 | − | 1X |
| 125-5 | 46 | 0.43 | 5.2 | 57 | | | |
| 125-7 | 70 | 0.30 | 5.7 | 92 | | | |
| 126-2 | 24 | 0.0 | 0.0 | 7.0 | 10 | − | 1X |
| 126-5 | 46 | 0.57 | 3.7 | 68 | | | |
| 126-7 | 70 | 1.0 | 5.5 | 83 | | | |
| 127-2 | 24 | 0.0 | 0.0 | 4.3 | 20 | − | 1X |
| 127-5 | 46 | 0.61 | 5.1 | 49 | | | |
| 127-7 | 70 | 0.80 | 5.7 | 78 | | | |
| 128-2 | 24 | 0.0 | 0.0 | 7.0 | 10 | + | 0.2X |
| 128-5 | 46 | 0.49 | 7.7 | 44 | | | |
| 128-7 | 70 | 0.63 | 10 | 69 | | | |

Note:
1)Levels of iron in the medium are amounts of feSO$^4$-7H$_2$O (mg l$^{-1}$).
2)Iron feed was provided in glucose at 5 $\mu$g FeSO$_4$-7 H$_2$O per g glucose.
3)Phosphate levels: 1X =40 g l$^{-1}$ potassium phosphate.

Example 20

This example describes metabolic engineering of *Saccharomyces cerevisiae* for the production of glucosamine and N-acetylglucosamine. Particularly, genes encoding for product-resistant glucosamine synthase, *E. coli* glmS*54 and *Bacillus subtilis* glmS, and *S. cerevisiae* GNA1 gene encoding for glucosamine-6-phosphate N-acetyltransferase were cloned into yeast expression vectors and introduced into the yeast for over-expression.

The major elements described in previous examples for glucosamine and N-acetylglucosamine production is the over-expression of a product-resistant GlmS enzyme and a GNA1 enzyme. In hosts having a native GNA1 gene such as *S. cerevisiae* and *Candida albicans*, over-expressing a product resistant GlmS could lead to an increased level of N-acetylglucosamine production. However, the main products of amino sugars could be glucosamine or N-acetylglucosamine. To produce N-acetylglucosamine as the main product, GNA1 gene needs to be over-expressed.

Glucosamine degradation is a bottleneck in attempts to produce glucosamine at neutral fermentation pH. Since some yeast and bacteria such *S. cerevisiae* are adapted to relatively low pH and grow normally in the pH range of 4-5 where glucosamine is stable, over-expressing a product-resistant GlmS enzyme in this type of host could lead to the development of a commercially viable process for direct production of glucosamine. Moreover, since *S. cerevisiae* is a GRAS organism and it does not produce endotoxins, it maybe a preferred fermentation host to produce glucosamine/N-acetylglucosamine for some applications of the products.

Cloning of the *E. coli* Mutant glmS*54 Gene for Expressing in Yeast

The *E. coli* mutant glmS*54 gene was cloned into expression vector yEp352-ADH1. This vector is derived from yEp352 (Hill et al., 1986 Yeast 2:163-167) using standard techniques. It replicates to multiple copies per yeast cell and it contains the alcohol dehydrogenase (ADH) promoter and terminator. The vector has an ampicillin resistance marker for selection in *E. coli* and an URA3 marker for selection in yeast.

Forward primers nMD7107-021 and reverse primer nMD7107-022 were designed for PCR amplification of the coding sequence of the *E. coli* mutant glmS*54 gene. Restriction sites were incorporated at the ends to facilitate cloning. The glmS*54 coding sequence was amplified by PCR under standard conditions using forward primer nMD7107-021 (Sac I) and reverse primer nMD7107-022 (Hind II) that have the following sequences: nMD7107-021 (Sac I): 5'-AGCTGAGCTCATGTGTGGAATTGTTG-GCGCGA-3' (SEQ ID NO: 80) and nMD7107-022(Hind I): 5'-TACGAAGCTTACTCAACCGTAACCGATTTTGC-3' (SEQ ID NO:81). Primer nMD7107-021 contains 22 nucleotides of the glmS*54 coding sequence represented in nucleotides 11-32 of SEQ ID NO:80, and primer nMD7107-022 contains 24 nucleotides of the glmS*54 coding sequence represented in nucleotides 9-32 of SEQ ID NO:81.

Plasmids pKLN23-54 containing the *E. coli* glmS*54 gene (described in U.S. Pat. No. 6,372,457) were used as the DNA templates in PCR reactions. A single band of PCR products of the expected size was generated under standard PCR conditions using the Taq polymerase. The PCR products were digested with restriction enzymes Sac I and Hind III, purified through agarose-gel and cloned into the yEP352-ADH-1 vector that was predigested with the same enzymes. DNA ligation products were transformed into *E. coli* Top 10 cells (obtained from Invitrogen Life Technologies, Carlsbad, Calif.) on ampicillin selection. First, pools of colonies (10 per pool) were screened by PCR using the forward and reverse primers. Then, individual clones in positive pools were identified by PCR and confirmed by restriction digestions. Recombinant plasmids MD7107-238 and MD7107-239 contained the *E. coli* glmS*54 gene in the yeast expression cassette with the ADH promoter and terminator.

The recombinant plasmids were transformed into cells of *S. cerevisiae* SWY5 following the LiOAc method described by Geitz et al. (1995). The yeast strain has the ura and his auxotrophic selection markers. Yeast transformants were selected on plates of SCE-minus medium supplemented with L-histidine at 20 mg l$^{-1}$ (Table 22). Transformed yeast cell lines will be analyzed to determine GlmS and GNA1 activities, and levels of glucosamine and N-acetylglucosamine.

TABLE 22

SC-minus medium for yeast growth

| Component | Amount (g l$^{-1}$) |
|---|---|
| Yeast Nitrogen base without amino acid (YNB) | 6.7 |
| glucose | 20 |
| L-arginine | 0.02 |
| L-methionine | 0.02 |
| L-tyrosine | 0.03 |
| L-isoleucine | 0.03 |
| L-lysine | 0.03 |
| L-phenylalanine | 0.05 |
| L-glutamate | 0.1 |
| L-asparate | 0.1 |
| L-valine | 0.15 |
| L-threonine | 0.2 |
| L-serine | 0.4 |

Cloning of the *B. subtilis* glmS Gene for Expressing in Yeast

The *B. subtilis* wild-type glmS was cloned into expression vector yEp352-ADH1. Forward primer nMD7107-023 and reverse primer nMD7107-024 were synthesized to amplify the coding sequence of the *B. subtilis* wild-type glmS gene. Restriction sites were incorporated at the ends to facilitate cloning. The glmS coding sequence was amplified by PCR under standard conditions using forward primer nMD7107-023 and reverse primer nMD7107-024 that have the following sequences: nMD7107-023(Kpn I): 5'AGCTGGTAC-CATGTGTGGAATCGTAGGTTATATC-3' (SEQ ID NO:82) and nMD7107-024 (Sph I): 5'-TACGCATGCT-TACTCCACAGTAACACTCTTCGC A-3' (SEQ ID NO:83). Primer nMD7107-023 contains 24 nucleotides of the glmS coding sequence represented in nucleotides 11-34 of SEQ ID NO:82, and primer nMD7107-024 contains 25 nucleotides of the glmS coding sequence represented in nucleotides 10-34 of SEQ ID NO:83.

Plasmid pSW07-15#83 containing the Bacillus glmS gene (plasmid described in Example 2) was used as the DNA templates in PCR reactions. A single band of PCR products of the expected size was generated under standard PCR conditions using the Taq polymerase. The PCR products were digested with appropriate restriction enzymes, purified through agarose-gel and cloned into the yEP352-ADH-1 vector predigested with the same enzymes. DNA ligation products were transformed into *E. coli* Top10 cells (Invitrogen Life Technologies, Carlsbad, Calif.) on ampicillin selection. First, 10 pools of colonies (10 per pool) were screened by PCR using the forward and reverse primers. Then, individual clones in positive pools were identified by PCR and confirmed by restriction digestions. Plasmids MD7107-240 and MD7107-241 contained the Bacillus glmS gene in the yeast expression cassette with the ADH promoter and terminator.

The recombinant plasmids were transformed into cells of *S. cerevisiae* SWY5. Yeast transformants were selected on plates of SCE-minus medium supplemented with L-histidine at 20 mg l$^{-1}$. Transformed yeast cell lines are analyzed to determine GlmS and GNA1 activities, and levels of glucosamine and N-acetylglucosamine.

Cloning of the *S. cerevisiae* GNA1 for Over-Expression in Yeast

The fragment containing the ScGNA1 coding sequence was digested from plasmid pSW07-60#3 (previously described in Example 13) using restriction endonucleases EcoR I and Sac I. The resulting fragment was ligated into the EcoR I and Sac I sites of shuttle vector pADH313-956. Cloning in this manner places the ScGNA1 coding sequence between the ADH1 promoter and terminator. This vector contains a histidine selection marker. The resulting plasmids, pSW07-114 (#1 and #18) were transformed into cells of *S. cerevisiae* SWY5. Yeast transformants were selected on plates of SCE-minus medium supplemented with uracil at 20 mg l$^{-1}$. Transformed yeast cell lines will be analyzed to determine GlmS and GNA1 activities, and levels of glucosamine and N-acetylglucosamine.

The plasmids with the ScGNA1 expression cassette are also be transformed into yeast cell lines that have already been transformed with the *E. coli* glmS*54 construct or the *Bacillus* glmS construct.

Example 21

This Example describes random mutagenesis of the *E. coli* strain 7107-92 for improving N-acetylglucosamine production.

Strain 7107-92 (with T7-glmS*54 and T7-ScGNA1 integrated into the chromosome, described in Example 16) was mutagenized with UV light and 882 isolated colonies were assayed with the GlcN auxotroph bioassay as described in the U.S. Pat. No. 6,372,457 B 1. Glucosamine auxotroph strain *E. coli* 2123-15 was used as the indicator strain. Based on halo size, 19 mutants were selected and streaked for isolation and five colonies of each were reevaluated. Two mutant strains, 7107-512 and 7107-513, showed the largest halo diameters. They were saved for evaluation in flask culture. Mutant *E. coli* strains 7107-512 (ATCC No. _____) and 7107-513 (ATCC No. _____) were deposited on Jul. 1, 2003, with the American Type Culture Collection (ATCC), P.O. Box 1549, Manassas, Va. 20108, USA, under the terms of the Budapest Treaty on the International Recognition of the Deposit of Microorganisms for the Purpose of Patent Procedure.

The mutants were compared to the parent strain. All strains were grown in M9B medium with 5 g l$^{-1}$ ribose and 5 g l$^{-1}$ yeast extract under two different conditions. One set of cultures was grown in a medium with 30 g l$^{-1}$ glucose and 0.2 mM IPTG (IPTG induction). The other set of cultures was grown in the medium with 10 g l$^{-1}$ glucose and 40 g l$^{-1}$ lactose. The culture became lactose-induced once glucose was depleted (lactose induction). Under IPTG induction, N-acetylglucosamine production by mutant 7107-512 was comparable to the parent strain. Mutant 7107-513 produced more glucosamine than the parent strain, 36% more at 71-hr time point. As observed previously, the parent strain produced higher levels of N-acetylglucosamine under lactose induction than under IPTG induction. Two mutants produced the same level of glucosamine, which was about 28% higher than the parent strain at the 71-hr time point. The loci of the mutations were not determined and the mechanisms for the improved N-acetylglucosamine production in the muatnts are not known. Since only about 900 mutant clones were screened, the data clearly demonstrated the potential to further improve the production host by random mutagenesis.

TABLE 23

N-acetylglucosamine production in UV light mutants

| Experiment | Strains | N-acetyglucosamine (g l$^{-1}$) | | |
|---|---|---|---|---|
| | | 23 hrs | 47 hrs | 71 hrs |
| IPTG induction | 7107-92 | 7.2 | 11.8 | 13.8 |
| | 7107-512 | 7.0 | 12.0 | 13.0 |
| | 7107-513 | 7.2 | 14.6 | 18.7 |
| Lactose induction | 7107-92 | 4.7 | 13.3 | 23.3 |
| | 7107-512 | 8.0 | 19.0 | 29.9 |
| | 7107-513 | 7.1 | 17.4 | 29.8 |

Example 22

The following Example describes the generation of a mutant NAG production strain with a ƒƒkA deletion such that NAG production can be uncoupled from growth.

Phosphofructokinase is a main regulatory enzyme in glycolysis that catalyzes the formation of fructose-1,6-biphosphate from fructose 6-phosphate (F-6-P). The major phosphofructokinase in *E. coli*, encoded by pƒkA, provides 90% of the phosphofructokinase activity. The remaining 10% of activity is supplied by the minor phosphofructokinase, encoded by pƒkB. In NAG production strains, the overexpressed GlmS*54 catalyzes the conversion of F-6-P to glucosamine-6-phosphate (GlcN-6-P), which can then be converted to GlcNAc-6-P through the action of the overexpressed glucosamine-6-phosphate acetyltransferase (GNA1) from *Saccharomyces cerevisiae*.

The rationale for the experiments described in Example 22 is as follows. Growth of a pƒkA mutant strain on a combination of carbon sources (i.e. glucose and fructose) may allow growth to be uncoupled from NAG production. Since pƒkA mutants do not grow well with glucose as carbon source, fructose would be used for cell growth. Imported fructose would be converted to fructose-1,6-biphosphate through the actions of the ƒruA and ƒruK gene products, allowing its entry into the glycolytic pathway. Glucose would be phosphorylated upon its uptake, and the resultant glucose-6-phosphate converted to F-6-P by the pgi gene product, phosphoglucose isomerase. With pƒkA gene deletion, only the minor PƒkB isozyme would be responsible for the conversion of F-6-P to F-1,6-biphosphate. The conversion could become restricted. As a consequence, there might be increased amounts of the F-6-P available for conversion to glucosamine-6-phosphate by the overexpressed GlmS*54. Therefore, deletion of pƒkA may reduce the flow of F-6-P into the glycolytic pathway, potentially allowing more carbon to divert toward glucosamine production. In production strains overexpressing the ScGNA1, this may ultimately result in higher NAG titers.

Generation of pƒkA Deletion Strains

The pƒkA deletion was added to the genome of the production strain using the temperature sensitive selection method. This required construction of an integrative vector to target the pƒkA region for deletion. The first step in vector construction was to amplify the sequence containing the pƒkA coding sequence plus flanking regions from *E. coli* W3110 genomic DNA. Primers were synthesized based on the published sequence of the pƒkA plus flanking regions from the *E. coli* genome (Blattner et al, 1997, Science 277(5331):14531474). The primers used for PCR amplification were forward primer 07-89 and reverse primer 07-90 and had the following sequences: 07-89: 5'GAGCGGCCG-CATGAATCAA TCTTATGGACGGC3' (SEQ ID NO:86) and 07-90: 5'GAGTCGACTCAGCGTTTGC TGATCT-GATCGAACGTAC3' (SEQ ID NO:87).

Primer 07-89 contains a Not I site (GCGGCCGC, represented in nucleotides 3-10 of SEQ ID NO:86) and amplifies the ATG start codon of the yiiP coding sequence, located 1083 basepairs upstream of the pƒkA ATG start codon (represented in nucleotides 11-32 of SEQ ID NO:86). Primer 07-90 contains a Sal I site (GTCGAC, represented in nucleotides 3-8 of SEQ ID NO:87) and amplifies from the translational stop codon of the sbp coding sequence, located 1310 basepairs downstream of the pƒkA stop codon (represented in nucleotides 9-37 of SEQ ID NO:87). PCR was performed using a standard protocol to generate the fragment containing the yiiP, pƒkA, and sbp coding sequences flanked by Not I and Sal I restriction endonuclease sites. This fragment was cloned into vector pPCR-Script$^{AMP}$SK (+) (Stratagene Cloning Systems, La Jolla, Calif.) using materials and instructions supplied by the manufacturer. The resulting plasmid was designated pSW07-61.

To generate a temperature sensitive integrative vector, a fragment containing the temperature sensitive replicon of pMAK705 (Hamilton et al., 1989, J. Bac. 171 (9):4617-462) and the kanamycin resistance cassette of plasmid pUC4K (Amersham Pharmacia Biotech, Piscataway, N.J.) were excised from plasmid pKLN07-21 with restriction endonucleases Not I and Sal I. The pƒkA plus flanking regions was digested from plasmid pSW07-61 with restriction enzymes Not I and Sal I. The two fragments were ligated together, generating plasmid pSW07-63.

To create a deletion in the coding sequence of pƒkA plasmid pSW07-63 was digested to completion with Pvu II, followed by a partial digestion with Ahd I. This removed a 781 basepair fragment of the pƒkA coding sequence. The fragment containing the pƒkA deletion was treated with T4 DNA polymerase to fill in the ends and the resulting blunt-ended fragment ligated to itself, resulting in plasmid pSW07-64.

To generate a strain containing the pfkA deletion, plasmid pSW07-64 was transformed into *E. coli* 7107-18. Following the temperature sensitive selection and passaging protocol, kanamycin-sensitive colonies were screened for slowed growth on defined medium plates containing glucose as carbon source. Strains were confirmed by standard high stringency Southern hybridization using a 1153 basepair fragment containing a portion of the yiiP and the pƒkA sequence. These strains were designated as 7107-90(1) and 7107-90(2).

Pfk specific activities of 0.054 and 0.035 mmol min$^{-1}$ mg$^{-1}$ protein were observed in strains 7107-90(1) and 7107-90(2), respectively. A specific activity of 0.78 mmol min$^{-1}$ mg$^{-1}$ was detected in the control strain 7107-87(25), which had the wild type pfkA gene. Therefore, the pƒkA mutants have roughly 5-6% Pfk activity observed in the control strain. This residual Pfk activity is undoubtedly contributed by the PfkB isozyme.

Integration of the T7-lac-ScGNA1 Cassette into the Chromosome of Strains 7107-90(1) and 7107-90(2).

The 7107-90 strains were derived from glucosamine production strain 0.7107-18; therefore, they do not produce measurable NAG. In order to generate a NAG production strain with the pfkA deletion, the T7-lac-ScGNA1 expression cassette needs to be introduced into the strain. Following the strategy described earlier, an expression cassette of T7-lac-ScGNA1 was integrated at the manXYZ site of the chromosome in strains 7107-90(1) and 7107-90(2), generating strains 7107-602 and 7107-603, respectively. These strains were confirmed by standard high stringency Southern hybridization using a fragment containing the ScGNA1 coding sequence as probe as having an integrated T7lac-ScGNA1 at the site of the manXYZ deletion.

Shake Flask Analysis of Strain 7107-602 and 7107-603

Strains 7107-602(1) and 7107-603(1) were tested in Shake Flask Screen 48 using varied mixes of glucose/fructose. Cultures were induced with 0.2 mM IPTG after 24 hours. Interestingly, these strains produced almost no acetate under any of the conditions tested, although they did not produce more NAG than the control strain 7107-92(1) (data not shown). Shake Flask Screen 53 again tested strains 7107-602(1) and 7107-603(1) under conditions for lactose induction. Again, no acetate was produced in these strains and NAG levels were similar to that seen in control strain 7107-92(1).

To further evaluate acetate formation in strain 7107-602 (1), Shake Flask Screen 56 was conducted under conditions which normally increase acetate formation, including addition of yeast extract (YE), ribose, or high trace elements (TE). Cultures were grown in modified M9B medium [6 g/l $KH_2PO_4$, 24 g/l $K_2HPO_4$, 1 g/l $Na_3Citrate.2H_2O$, 10 g/l $(NH_4)_2SO_4$ (phosphate adjusted to pH 7.4)]. Low levels of trace metals (0.3 mg/l $FeSO_4-7H_2O$, 0.375 mg/l $ZnSO_4-7H_2O$, 0.02 mg/l $MnSO_4$—$H_2O$, 0.001 mg/l $CuSO_4-5H_2O$, 0.001 mg/l $NaMoO_4-2H_2O$, 0.001 mg/l $H_3BO_3$, and 0.001 mg/l $COCl_2-6H_2O$) or high levels of trace metals (12 mg/l $FeSO_4-7H_2O$, 0.375 mg/l $ZnSO_4-7H_2O$, 0.8 mg/l $MnSO_4$—$H_2CuSO4-5H_2O$, 0.001 mg/l $NaMoO_4-2H_2O$, 0.001 mg/l $H_3BO_3$, and 0.001 mg/l $CoCl_2-6H_2O$) were added as indicated in Table 24. Cultures were supplemented with 0.6 g/l $MgSO_4-7H_2O$, 0.05 g/l $CaCl_2-2H_2O$, 10 g/l glucose, and 20 g/l lactose. Additionally, 5 g/l ribose and/or 5 g/l yeast extract was added to cultures as indicated in Table 24. Culture were grown at 37° C. for 24 hours and then switched to 25° C. At 12 hours, 20 g/l glucose was added to cultures in which it was depleted and pH was adjusted to 7.2. At 24, 30, 48, and 54 hours, pH of cultures was adjusted to 7.2 and glucose was added to 30 g/l per day total based on HPLC results 5 g/l $(NH_4)_2SO_4$ was added at 24, 30, 48, and 52 hours to flasks in which levels had fallen below 1 g/l.

TABLE 24

Effect of varied levels of trace elements, ribose, and yeast extract on acetate formulation in strains 7107-602(1) and 7107-92(1).

| Strain | Conditions | | | Time | | Acetate | GlcNAc |
|---|---|---|---|---|---|---|---|
| | TE | Ribose | YE | (hr) | $OD_{600}$ | g/l | g/l |
| 7107-602(1) | Low | 5 g/l | 5 g/l | 24 | 4.5 | 0 | 8.6 |
| | | | | 48 | 9.6 | 0 | 18.2 |
| | | | | 72 | 13.2 | 0 | 14.2 |
| | High | 5 g/l | 5 g/l | 24 | 4.75 | 0 | 8.7 |
| | | | | 48 | 9.0 | 0 | 22.8 |
| | | | | 72 | 12.9 | 7.2 | 22.3 |
| | Low | None | 5 g/l | 24 | 4.5 | 0 | 6.8 |
| | | | | 48 | 4.8 | 0 | 15.6 |
| | | | | 72 | 10.8 | 0 | 28.2 |
| | High | None | 5 g/l | 24 | 4.5 | 0 | 6.8 |
| | | | | 48 | 9.0 | 0 | 16.4 |
| | | | | 72 | 12.0 | 9.8 | 16.3 |
| | Low | 5 g/l | None | 24 | 1.75 | 0 | 4.15 |
| | | | | 48 | 2.4 | 0 | 13.0 |
| | | | | 72 | 5.4 | 0 | 23.0 |
| | High | 5 g/l | None | 24 | 1.0 | 0 | 4.35 |
| | | | | 48 | 4.8 | 2.2 | 13.2 |
| | | | | 72 | 10.5 | 0 | 27.8 |
| 7107-92(1) (Control) | Low | 5 g/l | 5 g/l | 24 | 8.5 | 0 | 7.0 |
| | | | | 48 | 12.6 | 6.1 | 18.6 |
| | | | | 72 | 13.8 | 13.6 | 15.8 |
| | High | 5 g/l | 5 g/l | 24 | 7.5 | 0 | 5.2 |
| | | | | 48 | 12.6 | 8.4 | 13.6 |
| | | | | 72 | 12.9 | 14.4 | 11.7 |
| | Low | None | 5 g/l | 24 | 9.0 | 0 | 4.9 |
| | | | | 48 | 15.0 | 7.8 | 9.7 |
| | | | | 72 | 15.0 | 15.0 | 9.2 |
| | High | None | 5 g/l | 24 | 9.5 | 0 | 5.4 |
| | | | | 48 | 12.6 | 10.9 | 7.6 |
| | | | | 72 | 13.2 | 17.1 | 7.4 |
| | Low | 5 g/l | None | 24 | 7.0 | 0 | 4.2 |
| | | | | 48 | 7.2 | 1.8 | 16.6 |
| | | | | 72 | 7.8 | 3.7 | 19.2 |
| | High | 5 g/l | None | 24 | 10.0 | 0 | 7.17 |
| | | | | 48 | 13.2 | 7.4 | 13.10 |
| | | | | 72 | 13.2 | 13.0 | 11.7 |

Even under conditions designed to induce the control strain 7107-92(1) to produce high levels of acetate, acetate production in strain 7107-602(1) is either null or comparatively low (Table 23). Furthermore, although OD measurements tended to be lower for strain 7107-607(2), generally a higher NAG titer was seen in these cultures. Therefore, the pfkA mutant strain appeared suitable for use as a NAG production host.

Example 23

This Example describes cloning and overexpression of the glutamine synthetase (glnA) gene, the integration of a T7lac-glnA cassette into the *E. coli* chromosome, and the effects of glnA gene over-expression on GlcN/GlcNAc production.

Glutamine is a primary product of ammonia assimilation that provides nitrogen for amino sugars, as well as for other compounds. The glutamine synthetase, encoded by glnA, catalyzes the conversion of L-glutamate to L-glutamine in a reaction requiring $NH_3$ and ATP. L-glutamine is required for the biosynthesis of glucosamine-6-phosphate; GlmS catalyzes the reaction by which L-glutamine and F-6-P are converted to D-glucosamine-6-P and L-glutamine. For maximal levels of GlcN/GlcNAC production, it is essential that adequate levels of glutamine are present in the cell. Overexpression of the glnA gene may increase levels of glutamine, and ultimately increase GlcN and or NAG titer.

Cloning and Overexpression of the *E. coli* glnA Gene

For cloning and overexpression of the *E. coli* glnA, primers were synthesized based on the published sequence of the glnA gene (Blattner et al, 1997, Science 277(5331): 14531474). The nucleotide sequence of the *E. coli* glnA gene coding sequence is listed in the sequence file identified as SEQ ID NO:88. The deduced amino acid sequence of the E. coli GlnA protein is listed in the sequence file identified as SEQ ID NO:89. The primers were used to amplify the glnA coding sequence from E. coli 7101-17(DE3) genomic DNA using PCR. The primers used for amplification were forward primer 07-gln and reverse primer 07-15 and had the following sequences: 07-gln: 5'GATCGGTCTCGCATGTCCGCT-GAACAC GTACTGAC3' (SEQ ID NO:90) and 07-15: 5'GATCCTCGAGTTAGACGCTGTA GTACAGCTC3' (SEQ ID NO:91).

Primer 07-gln contains a Bsa I site (GGTCTC, represented in nucleotides 5-10 of SEQ ID NO:90) and 23 nucleotides of the glnA coding sequence from its ATG start codon (represented in nucleotides 13-35 of SEQ ID NO:90). Primer 07-15 contains a Xho I site (CTCGAG, represented in nucleotides 5-10 of SEQ ID NO:91) and 21 nucleotides of the glnA coding sequence from its translational stop codon (represented in nucleotides 11-31 of SEQ ID NO:91). PCR was conducted under standard conditions to generate a fragment containing the glnA coding sequence flanked by Bsa I and Xho I restriction endonuclease sites.

The PCR fragment containing glnA was digested with restriction endonucleases Bsa I and Xho I and ligated at the Nco I and Xho I sites of vector pET24d(+) (Novagen, Inc., Madison, Wis.), generating plasmid pKLN07-28. Cloning in this manner places the glnA sequence behind the T7lac promoter of pET24d(+), generating an expression cassette of T7lac-glnA.

Functional Expression of the Recombinant glnA in E. coli

To test functional expression of the glnA, recombinant plasmid pKLN07-28 was transformed into strain 7107-18, generating strains 7107-163. Control strain 7107-88 was prepared by transforming 7107-18 with the pET24d(+) empty vector. A standard induction protocol was followed in which cell cultures were grown in LB and induced with 1 mM IPTG. Samples were taken from induced cultures for SDS-PAGE to confirm GlnA protein overexpression. The predicted protein size of the GlnA protein is about 52 kDa. An overexpressed protein of about 52 kDa was seen. Most of the overproduced protein appears to be insoluble, with little seen in the soluble fractions. No such overexpressed protein was seen in the control strain, indicating that the overexpressed protein is GlnA enzyme.

Construction of a Vector to Direct Integration of the T7lac-glnA into the E. coli Chromosome Having confirmed successful overexpression of the glnA gene, the next step was to integrate the T7lac-glnA cassette into the genome of production strains. An integrative vector was constructed for this purpose. The E. coli pfkB gene was chosen as a target site for integration. The pfkB encodes for the minor isozyme of phosphofructokinase in E. coli, which accounts for only 10% of the total phosphofructokinase activity. Therefore, integration of the cassette at this locus should not significantly affect the performance of the strain.

As part of the strategy for generating the integrative vector, the pfkB plus flanking regions was amplified from E. coli W3110 genomic DNA by PCR. Primers were synthesized based on the published sequence of the pfkB plus its flanking regions (Blattner et al, 1997, Science 277(5331): 1453-1474). The primers used to amplify the pfkB region were forward primer 07-16 and reverse primer 07-17 and had the following sequences: 07-16: 5'GATCGCCGGCT-TACATGCTGTAGCCCAGC3' (SEQ ID NO:92) and 07-17: 5'GATCCTGCAGTCATGCTGCTAATAATC-TATCC3' (SEQ ID NO:93).

Primer 07-16 contains a Nae I restriction endonuclease site (GCCGGC, represented in nucleotides 5-10 of SEQ ID NO:92) and 19 basepairs of ORFb1722 starting at its putative translational stop codon, located 1042 basepairs upstream of the pfkB start codon (represented in nucleotides 11-29 of SEQ ID NO:92). Primer 07-17 contains a Pst I restriction endonuclease site (CTGCAG, represented in nucleotides 5-10 of SEQ ID NO:93) and 22 basepairs of ORFb1725 starting at its putative translational stop codon, located 1357 basepairs downstream of the translational stop codon of the pfkB coding sequence (represented in nucleotides 11-32 of SEQ ID NO:93). PCR was conducted under standard conditions to generate a fragment containing the ORFb1722, pfkB, ORFb1724, and ORFb1725 sequences flanked by Nae I and Pst I restriction endonuclease sites. The resulting fragment was ligated into vector pPCR-Script SK(+) (Stratagene Cloning Systems, La Jolla, Calif.), generating plasmid pKLN07-14.

The next step was to add the kanamycin resistance cassette of plasmid pUC4K (Amersham Pharmacia Biotech, Piscataway, N.J.) to plasmid pKLN07-14. The kanamycin resistance cassette was excised from pUC4K with restriction endonuclease Pst I. Plasmid pKLN07-14 was likewise digested with restriction endonuclease Pst I, which removed a 412 basepair fragment of the plasmid including 386 basepairs of the ORFb1725 putative coding sequence. The kanamycin resistance cassette was ligated into the Pst I sites of the backbone of plasmid pKLN07-14, generating plasmids pKLN07-17. Plasmid pKLN07-17 was next digested with restriction endonucleases SnaB I and Btr I, removing 870 basepairs of the pfkB coding sequence from the plasmid.

The fragment containing the T7lac-glnA cassette was excised from plasmid pKLN07-28 with restriction endonuclease Nae I, generating a fragment containing the T7lac-glnA cassette flanked by 50 basepairs upstream of the T7 promoter and 164 basepairs downstream of the T7 terminator from vector pET24d(+). The Nae I fragment was ligated into the SnaB I and Btr I sites of plasmid pKLN07-17, generating plasmid pKLN07-29.

The final step was to add the temperature sensitive replicon from pMAK705 to the fragment from plasmid pKLN07-29 containing the T7lac-glnA cassette in the site of the pfkB deletion and the kanamycin resistance cassette. Plasmid pKLN07-29 was digested with restriction endonucleases Not I and Kpn I to release the fragment containing the T7lac-glnA and kanamycin resistance cassette from the pPCR-Script backbone. Plasmid pKLN07-20 (previously described) was digested with Not I and Kpn I, excising the fragment containing the temperature sensitive replicon. The two fragments were ligated together, generating plasmid pKLN07-30, containing the temperature sensitive replicon, kanamycin resistance cassette, and E. coli genomic sequence with the T7lac-glnA cassette ligated into the site of the pfkB deletion. Plasmid pKLN07-30 can be used to direct integration of the T7lac-glnA cassette at the pfkB of the chromosome following the temperature sensitive selection and passaging protocol.

Plasmid pKLN07-30 was transformed into glucosamine production strain 7107-18. Following temperature sensitive selection and passaging, kanamycin sensitive colonies were screened for the presence of the T7lac-glnA cassette at the site of the pfkB deletion using a standard PCR protocol. Several strains identified by PCR were confirmed by high stringency Southern hybridization using a fragment containing the glnA coding sequence as probe. These strains were designated 7107-118 through 7107-123.

Integration of the T7lac-ScGNA1 Cassette into the Chromosome of Strains 7107-118, 7107-119, and 7107-120

Strains 7107-118, 7107-119, and 7107-120 were derived from glucosamine production strain 7107-18; therefore, they do not produce measurable NAG. In order to generate a NAG production strain with the glnA expression cassette, the T7lac-ScGNA1 expression cassette needs to be introduced into the strain. As described previously, an expression cassette of T7-lac-ScGNA1 was integrated at the manXYZ of the chromosome in strains 7107-118,7107-119, and 7107-120, generating strains 7107-125 (derived from 7107-119), 7107-126 (derived from 7107-120), 7107-132 (derived from 7107-118), 7107-133 (derived from 7107-118), and 7107-134 (derived from 7107-119). These strains were confirmed by standard high stringency Southern hybridization using a fragment containing the ScGNA1 coding sequence as probe as having an integrated T7lac-ScGNA1 at the site of the manXY deletion.

Shake Flask Screen 51: Testing Overexpression of the Integrated T7lac-glnA in NAG Production Background Shake Flask Screen 51 was conducted to evaluate strains 7107-125, 7107-126, and 7107-133 containing the integrated T7lac-glnA cassette. Cultures were grown in M9B medium supplemented with trace metals and the following substances: 0.6 g/l MgSO$_4$-7H$_2$O, 0.05 g/l CaCl$_2$-2H$_2$O, 10 g/l glucose, 40 g/l lactose, 5 g/l ribose, and 5 g/l yeast extract. Cultures were grown at 30° C. for 24 hours and then switched to 25° C. At 24 and 48 hours, the pH of cultures was adjusted to 7.2 and glucose added to 30 g/l, 5 g/l (NH$_4$)$_2$SO$_4$ was added at 24 and 48 hours to flasks in which levels had fallen below 1 g/l. Samples were taken at 24, 48, and 72 hours for OD and determination of NAG levels. Cultures were harvested at 72 hours for analysis of enzyme activities.

As seen in Table 25, the strains overexpressing the glnA performed somewhat better than control strain 7107-92(1), producing about 8% more NAG. None were ever exhausted of ammonia so nitrogen was not limiting. Enzyme activities of GlmS and GNA1 in the glnA overexpression strains are comparable to control strain 7107-92(1). In summary, it appears that glnA overexpression offers a slight improvement in NAG titers which may be accentuated under optimized conditions.

TABLE 25

Cell growth, enzyme activity, and GlcNAc production in strains overexpressing glnA.

| Strain | Construct | OD$_{600}$ | Enzyme Activity | | GlcNAc g/l |
|---|---|---|---|---|---|
| | | | GlmS | GNA1 | |
| 7107-92(1) | control | 9.75 | 0.34 | 3.2 | 24.3 |
| 7107-125 | T7lac-glnA | 10.10 | 0.36 | 3.3 | 26.5 |
| 7107-126 | T7lac-glnA | 9.75 | 0.25 | 3.0 | 26.0 |
| 7107-133 | T7lac-glnA | 9.75 | 0.31 | 2.8 | 26.7 |

1) OD, enzyme activities, and GlcNAc levels were measured in the 72-hour timepoint samples.
2) Enzyme activities are reported in µmol min$^{-1}$ mg$^{-1}$ protein.

Fermentation Experiment to Test NAG Production Strains with Integrated T7lac-glnA Strain 7107-133, containing the integrated T7lac-glnA cassette, was next evaluated in a 1-liter fermentor. The fermentor was set up with an initial volume of 475 ml. Components of the fermentation medium are listed in Table 26. Fermentations were run using 75% NH$_4$OH for pH control to 6.9. Temperature was maintained at 37° C. throughout the fermentation. Aeration and agitation were adjusted to maintain a dissolved oxygen concentration of 20% of air saturation. 65% glucose was fed to the cultures with feed rate controlled by computer program to achieve a growth rate of 0.40 hr$^{-1}$ at inoculation and a maximum rate of 5 ml/hr by 6 hours. Cultures were induced with food grade lactose added at 5 g/l at 10 hours, with continued glucose feed.

Fermentation results from strain 7107-133 were compared with those from strain 7107-92(1), previously run in Fermentation 237 under identical conditions. Both of these strains contain one copy of an integrated T7lac-ScGNA1 cassette. Results indicate that the presence of the T7lac-glnA cassette in strain 7107-133 may offer a slight advantage over strain 7107-92(1). Strain 7107-133 achieved 107.1 g/l NAG at 59.6 hrs compared with 96.6 g/l NAG at 59.8 hours in strain 7107-92(1).

TABLE 26

Components of fermentation medium.

| Component | Amount (g l$^{-1}$) |
|---|---|
| H$_3$PO$_4$ | 4.79 |
| KOH | 3.15 |
| Citric acid —H$_2$O | 3.56 |
| (NH$_4$)$_2$SO$_4$ | 5 |
| Mg SO$_4$—7H$_2$0 | 2.5 |
| CaCl$_2$—2H$_2$O | 0.05 |
| Trace Metals | * |
| Mazu 204 Antifoam | 0.25 |

*Trace metal composition is 5 mg/l FeSO$_4$—7H$_2$O, 3.75 mg/l ZnSO$_4$—7H$_2$O, 0.6 mg/l MnSO$_4$—H$_2$O, 0.1002 mg/l CuSO4—5H2O, 0.1002 mg/l CoCl$_2$—6H$_2$O.

Example 24

This Example describes cloning, overexpression of the glucose-6-phosphate dehydrogenase (zwf) gene, integration of a T7lac-zwf cassette into the E. coli chromosome and effect of overexpressing zwf under T7 promoter control on NAG production.

The pentose phosphate pathway provides intermediates for amino acid, nucleotides, and cell wall biosynthesis. Furthermore, the oxidative portion of the pentose phosphate pathway is an important source of NADPH in the cell. The zwf gene of E. coli encodes the glucose-6-phosphate dehydrogenase (G6PDH), which catalyzes the first step in the pentose phosphate pathway, converting glucose-6-phosphate into glucono-1,5-lactone. Expression of the zwf gene is coordinated with the cellular growth rate (Rowley, D. and Wolf, R., J. Bac., 1991, 173(3):968-977).

Literature describes E. coli isolates incapable of growth on NAG or GlcN (J. Bac., 1970, 101:384-391). The authors speculated that the accumulation of amino sugar phosphates may inhibit the reactions catalyzed by phosphohexose isomerase and glucose-6-phosphate dehydrogenase, resulting in pentose starvation. Add reversed the growth inhibition of those strains.

Recombinant E. coli strains producing GlcN/GlcNAc may accumulate amino sugar phosphates to certain levels. If this is the case, addition of gluconate or pentoses such as ribose should result in increased growth and NAG production. Shake flask experiments conducted with NAG production strain 7107-87#25 demonstrated that addition of ribose or gluconate resulted in both growth and NAG titer increases. Thus it appears that the NAG production strain was experiencing pentose starvation which could be alleviated by addition of pentoses or gluconate.

As a strategy to alleviate pentose starvation without adding exogenous pentoses, it was decided to overexpress the zwf gene in the NAG production strains. It was speculated that overexpression of the zwf might reduce the inhibition of phosphorylated amino sugars on the pentose phosphate pathway. If so, this could eliminate the need to supply additional pentoses or gluconate to enhance NAG titer in our strains.

Cloning and Expression of the E. coli zwf

For cloning and expression of the E. coli zwf primers were synthesized based on the published sequence of the zwf gene (Blattner et al, 1997, Science 277(5331): 1453-1474). The nucleotide sequence of the E. coli zwf gene coding sequence is listed in the sequence file identified as SEQ ID NO:94. The deduced amino acid sequence of the E. coli ZWF protein is listed in the sequence file identified as SEQ ID NO:95. The primers were used to amplify the zwf coding sequence from E. coli W3110 genomic DNA using PCR. The primers used for amplification were forward primer 07-101 and reverse primer 07-102 and had the following sequences: 07-101: 5' GATCGGTCTCGCATG-GCGGTAACGCAAACAGC 3' (SEQ ID NO:96) and 07-102: 5' GATCCTCGAGTTACTCAAACTCATTC-CAGGAACG ACC 3' (SEQ ID NO:97).

Primer 07-101 contains a Bsa I restriction endonuclease site (GGTCTC, represented in nucleotides 5-10 of SEQ ID NO:96) and 20 nucleotides of the zwf coding sequence from its ATG start codon (represented in nucleotides 13-32 of SEQ ID NO:96). Primer 07-102 contains a Xho I restriction endonuclease site (CTCGAG, represented in nucleotides 5-10 of SEQ ID NO:97) and 27 nucleotides of the zwf coding sequence starting from its translational stop codon (represented in nucleotides 11-37 of SEQ ID NO:97). PCR was conducted under standard conditions to generate a fragment containing the zwf coding sequence flanked by Bsa I and Xho I restriction endonuclease sites.

The PCR fragment was digested with restriction endonucleases Bsa I and Xho I and ligated at the Nco I and Xho I sites of vector pET24d(+) (Novagen, Inc., Madison, Wis.), generating plasmid pSW07-71. Cloning in this manner places the zwf sequence behind the T7lac promoter of pET24d(+), generating an expression cassette of T7lac-zwf.

Functional Expression of the Recombinant ZWF Protein in E. coli

Plasmids pSW07-71 #17, #20, and #33, each containing the T7lac-zwf expression cassette in pET24d(+), were transformed into the NAG production strain 7107-92(1), generating strains 7107-96(1) (transformed with pSW07-71 # 17), 7107-96(2) and 7107(transformed with pSW07-71#20), and 7107-96(4) (transformed with pSW07-71#33). Control strain 7107-95 was prepared by transformation of strain 7107-92(1) with pET24d(+). A standard induction protocol was followed in which cell cultures were grown in LB and induced with 1 mM IPTG. Samples were taken from the induced cultures for SDS-PAGE. Results confirmed overproduction of a protein of about 56 kDa, corresponding to the predicted size of the G6PDH protein. However, most of the overproduced protein appeared to be in the insoluble form.

After 4 hours of IPTG induction, cell cultures were harvested to assay glucose-6-phosphate dehydrogenase activity. Strains 7107-96 (2), 7107-96(3), and 7107-96(4) had G6PDH activity of 69.7, 78.1, and 90.1 mmol min$^{-1}$ mg$^{-1}$ protein, compared with 0.04 mmol min$^{-1}$ mg$^{-1}$ protein for control strain 7107-95. This confirmed that the zwf was successfully overexpressed in the NAG production strain.

Integration of the T7lac-zwf Cassette into the Chromosome of E. coli

Having confirmed functional expression of the recombinant ZWF protein in E. coli 7107-92# 1, the next step was to stably integrate the T7lac-zwf cassette into the chromosome of NAG production strains. An integrative vector was designed to target integration of the cassette to the rha region of the genome. The rhaBAD genes of E. coli form an operon encoding rhamnulokinase, L-rhamnose isomerase, and rhamnulose-1-phosphate aldolase, respectively. These genes are involved in utilization of rhamnose as an alternative carbon source and are considered nonessential genes. Therefore, interruption of this region should not affect growth or NAG production.

The first step in generating the integrative vector was to clone the rhaBAD region from E. coli W3110 genomic DNA. Primers were synthesized based on the published sequence of the rhaBAD operon plus its flanking regions (Blattner et al, 1997, Science 277(5331):1453-1474). The primers used to amplify the rha region were forward primer 07-107 and reverse primer 07-108 and had the following sequences: 07-107: 5' CGAATATCACGCGGTGACCAGT-TAAAC 3' (SEQ ID NO:98) and 07-108: 5' CACAGTGT-GCCGATGATTTTGACC 3' (SEQ ID NO:99).

Primer 07-107 amplifies from 1096 bases upstream of the rhaB start codon. Primer 07-108 amplifies from 977 bases downstream of the rhaD stop codon. PCR was conducted under standard conditions to generate a fragment containing the rhaBAD operon plus flanking sequences. The PCR fragment was cloned into vector pPCR-Script™SK(+) (Stratagene Cloning Systems, La Jolla, Calif.), generating plasmid pSW07-72.

The next step in generation of the integrative vector was to add the T7lac-zwf cassette into plasmid pSW07-72. The T7-lac-zwf cassette was amplified by PCR from plasmid pSw07-71 using standard conditions. PCR amplification was performed with forward primer 07-111 and reverse primer 07-112, which have the following sequences: 07-111: 5' GACCAATGGCCTAATGGAGCAACCGCACCTGTGGC 3' (SEQ ID NO:100) and 07-112: 5' GATCAGCGCTATC-CGGATATAGTTCCTCCTTTCAGCAAAAAACCCC 3' (SEQ ID NO:101).

Primer 07-111 contains an Xcm I restriction endonuclease site (CCANNNNNNNN TGG, represented in nucleotides 3-17 of SEQ ID NO:100) and amplifies from 80 bp upstream of the T7 promoter sequence of pET24d(+) (represented in nucleotides 18-35 of SEQ ID NO:100). Primer 07-112 contains an Afe I restriction endonuclease site (AGCGCT, represented in nucleotides 5-10 of SEQ ID NO:101) and amplifies from 25 bp downstream of the T7 terminator (represented in nucleotides 11-46 of SEQ ID NO:101). The resulting 1.8-kb PCR product was digested with restriction endonucleases Xcm I and Afe I.

Plasmid pSW07-72 was digested with restriction enzymes Xcm I and Afe I, excising a 3.6 kb fragment from the pSW07-72 backbone. The PCR fragment containing the T7lac-zwf with Xcm I and Afe I ends was ligated into the site of the excision in plasmid pSW07-72, generating plasmid pSW07-73. Plasmid pSW07-73 therefore has a 3.6 kb deletion of almost the entire rhaBAD operon, with the T7-lac-zwf inserted at the site of the deletion.

The final step in construction of the integrative plasmid was to add the temperature sensitive replicon and kanamycin resistance cassette from plasmid pKLN07-21. Plasmid pKLN07-21 was digested with Not I and Kpn I, excising the fragment containing the temperature sensitive replicon and kanamycin resistance cassette. Plasmid pSW07-73 was digested with restriction enzymes Not I and Kpn I, releasing the fragment containing the T7lac-zwf with rhaBAD flanks from the pPCR-Script backbone. The two fragments were ligated together, generating plasmid pSW07-74. Plasmid pSW07-74 can be used to direct integration of the T7lac-zwf at the rha region of the E. coli chromosome.

Plasmid pSW07-74 was transformed into NAG production strain 7107-92(1). Following temperature sensitive selection and passaging, kanamycin sensitive colonies were screened for the presence of the T7lac-zwf cassette at the site of the rhaBAD deletion using a standard PCR protocol. Several strains identified by PCR were confirmed by high stringency Southern hybridization using a 1.0-kb fragment of the zwf coding sequence as probe. These strains were designated 7107-606(1), 7107-606(2), 7107-606(3), and 7107-606(4).

NAG Production in Strains with an Integrated T7lac-zwf Cassette

Shake Flask Screen 46 was conducted to evaluate the effect of overexpressing zwf under T7 promoter control on NAG production in strains 7107-606(1) and 7107-606(3). As discussed above, it was speculated that overexpression of zwf could relieve pentose starvation and abolish growth inhibition caused by phosphorylated amino sugars. Cultures were grown in M9B medium (previously described) supplemented with 0.6 g/l MgSO$_4$-7H$_2$O, 0.05 g/l CaCl$_2$.2H$_2$O, 40 g/l glucose, and 0.2 mM IPTG (for flasks with late induction, IPTG was added at 24 hours). 10 g/l ribose and 5 g/l yeast extract was added to cultures as indicated in Table 27. Cultures were incubated at 30° C. for 24 hours and then switched to 25° C. At 24 and 48 hours, the pH of cultures was adjusted to 7.2 and glucose added to 30 g/l per day total. 5 g/l (NH$_4$)$_2$SO$_4$ was added at 24 and 48 hours to flasks in which levels had fallen below 1 g/l. Samples were removed at 24, 48, and 72 hours for determination of OD and NAG levels. Cultures were harvested at 72 hours for enzyme analysis.

strain. However, GlmS activity tended to be diminished in strains overexpressing the zwf, and NAG production levels did not reach the levels seen in control strain 7107-92(1). This indicates that too much carbon may be funneling through the pentose phosphate pathway, away from the glucosamine pathway.

Example 25

This Example describes cloning of the glucose-6-phosphate dehydrogenase (zwf) gene, the integration of the zwf gene with its native promoter into the E. coli chromosome and effects of zwf-overexpression under its native promoter control on cell growth and NAG production.

Cloning of E. coli zwf with its Native Promoter and Regulatory Regions

As described in Example 24, strains were constructed with an integrated T7lac-zwf cassette as part of the strategy to improve growth and NAG production. It was speculated that overexpression of the zwf might reduce the inhibition of phosphorylated amino sugars on the pentose phosphate pathway. If so, this could eliminate the need to supply additional pentoses or gluconate to enhance NAG titer in our strains.

The 7107-606 strains containing an integrated T7lac-zwf cassette did grow somewhat better than the control strain, indicating partial alleviation of pentose starvation. However, they did not perform as well as the control strain with regard to NAG production. This may be due to the use of the strong T7 promoter, which might lead to an expression level of ZWF protein that is much too high. Excessive activity of glucose-6-Phosphate dehydrogenase could funnel undesirably high amounts of carbon through the pentose phosphate pathway.

Therefore, it was decided to overexpress the zwf with its native promoter so that expression of zwf would be regulated by the cell. In E. coli, zwf is subject to growth-rate dependent regulation. Additionally, the zwf is a member of the soxRS regulon and the multiple antibiotic resistance (mar) regulon. Therefore, cloning of the native zwf should

TABLE 27

The effect of varying induction time, ribose addition, and yeast extract addition on growth, enzyme activity, and GlcNAc production in strains overexpressing zwf.

| Strain | Conditions | | | | Enzyme Activities[2] | | | GlcNAc |
| --- | --- | --- | --- | --- | --- | --- | --- | --- |
| | Ribose | YE | IPTG | OD$_{600}$ | GlmS | GNA1 | G6PDH | g/l |
| 7107-92(1) | 10 g/l | 5 g/l | 0.2 mM | 13.0 | 0.21 | 6.7 | 0.36 | 12.9 |
| | None | 5 g/l | 0.2 mM | 10.5 | 0.15 | 2.8 | ND[3] | 7.7 |
| | None | None | 0.2 mM[1] | 6.5 | 0.11 | 0.0 | ND | 4.4 |
| 7107-606(1) | 10 g/l | 5 g/l | 0.2 mM | 12.5 | 0.12 | 3.0 | 21.8 | 6.4 |
| | None | 5 g/l | 0.2 mM | 13.0 | 0.06 | 0.4 | 13.8 | 5.5 |
| | None | None | 0.2 mM[1] | 6.75 | 0.0 | 0.0 | 29.2 | 2.4 |
| 7107-606(3) | 10 g/l | 5 g/l | 0.2 mM | 11.5 | 0.04 | 1.73 | 18.8 | 6.3 |
| | None | 5 g/l | 0.2 mM | 12.5 | 0.13 | 1.93 | 17.2 | 5.4 |
| | None | None | 0.2 mM[1] | 6.75 | 0.0 | 0.0 | 41.8 | 2.6 |

[1]IPTG added at 24 hours for late induction
[2]Enzyme activities reported in μmol/min/mg protein
[3]ND: not determined The results indicate that strains overexpressing the zwf driven by the T7 promoter had G6PDH activities 50 to 100 times greater than in the control strains. The zwf overexpression did improve growth slightly in the cultures with no added ribose when compared with growth of the control include not only the native promoter, but regulatory regions such as the "Soxbox" as well (Fawcett, W. and Wolf, R., 1995, J. Bac. 177(7):1742-1750). The presence of two copies of the zwf on the chromosome could result in increased flow through the pentose phosphate pathway without greatly affecting carbon flow through other pathways, such as that for NAG production.

For cloning and expression of the E. coli zwf, primers were synthesized based on the published sequence of the zwf gene (Blattner et al, 1997, Science 277(5331): 1453-1474). The primers were used to amplify the zwf coding sequence plus regulatory regions from E. coli W3110 genomic DNA using PCR. The primers used for amplification were reverse primer 07-129 and forward primer 07-130 and had the following sequences: 07-129: 5'GAT-GCTAGCTAACCGGAGCTCATAGGGC3' (SEQ ID NO:102) and 07-130: 5'GATTTCGAATGATCAGTGTCA-GATTTTTACCC3' (SEQ ID NO: 103).

Forward primer 07-130 contains a BstB I site (TTCGAA, represented in nucleotides 4-9 of SEQ ID NO:102) and amplifies from 203 basepairs upstream of the zwf start codon. Reverse primer 07-129 contains a Nhe I site (GCTAGC, represented in nucleotides 4-9 of SEQ ID NO:103) and amplifies from 154 basepairs downstream of the zwf stop codon. PCR was conducted under standard conditions to generate a 1.8-kb fragment flanked by Nhe I and BstB I restriction endonuclease sites.

Integration of the Recombinant zwf into the Chromosome of E. coli

An integrative vector was designed to target integration of the zwf cassette to the rha region of the genome. The rhaBAD genes of E. coli form an operon encoding rhamnulokinase, L-rhamnose isomerase, and rhamnulose-1-phosphate aldolase, respectively. These genes are involved in utilization of rhamnose as an alternative carbon source and are considered nonessential genes. Therefore, interruption of this region should not affect the growth or NAG production in our strains.

Plasmid pSW07-72#45 (described in Example 24) was utilized in the first step for generation of the integrative vector. This plasmid, containing the rhaBAD operon plus flanking sequence, was digested with restriction endonucleases BstB I and Nhe I. This removed a 702 basepair fragment containing a portion of the rhaB and rhaA coding sequences from the plasmid. The PCR fragment containing the zwf coding sequence plus regulatory regions was digested with restriction endonucleases BstB I and Nhe I and ligated into the BstB I and Nhe I sites of pSW07-72#45, generating plasmid pSW07-86.

Plasmid pSW07-86 was digested with restriction enzymes Kpn I and Not I to release the 6.9-kb fragment containing the zwf flanked by the rha genes. This fragment was ligated with the 4.2 kb Kpn I/Not I fragment from pKLN07-21, containing the temperature sensitive replicon from pMAK705 (Hamilton et al., 1989, J. Bac. 171(9):4617-4622) and the kanamycin resistance cassette from pUC4K (Amersham Pharmacia Biotech, Piscataway, N.J.). The resulting plasmid, pSW07-87, can be used for directing integration of the zwf to the rhaBA region of the E. coli chromosome Plasmid pSW07-87 was transformed into strains 7107-92 (1) and 7107-607(2), which contained one or two copies of the ScGNA1 cassette, respectively. Following temperature sensitive selection and passaging, kanamycin sensitive colonies were screened for the presence of the T7lac-zwf cassette at the site of the rhaBA deletion using a standard PCR protocol. Several strains identified by PCR were confirmed by high stringency Southern hybridization using a fragment containing the zwf coding sequence as probe. Strains derived from 7107-607(2) were designated 7107-633 and strains derived from 7107-92(1) were designated 7107-634.

Overexpression of the zwf under Native Promoter Control in NAG Production Strains Screening included strains 7107-633 and 7107-634 to evaluate the effect of overexpressing the zwf under native promoter control on NAG production. Cultures were grown in M9B medium (previously described) supplemented with 0.6 g/l MgSO$_4$-7H$_2$O, 0.05 g/l CaCl$_2$-2H$_2$O, 5 g/l yeast extract, 10 g/l glucose, and 40 g/l lactose. Strains were grown for 24 hours at 30° C. and then switched to 25° C. for the remainder of the experiment. At 24 and 48 hours, the pH of each culture was adjusted to 7.2 and glucose added to 30 g/l per day based on HPLC results. 5 g/l (NH$_4$)$_2$SO$_4$ was added at 24 and 48 hours to flasks in which levels had fallen below 1 g/l. Samples were removed at 24, 48 and 72 hours for determination of OD and NAG levels. Results are shown in Table 28.

TABLE 28

Growth and GlcNAc production in strains overexpressing zwf with its native promoter.

| | | OD$_{600}$ | | GlcNAc (g/l) | |
|---|---|---|---|---|---|
| Strain | Description | 48 hr | 72 hr | 48 hr | 72 hr |
| 7107-92(1) | 1 GNA1 | 8.5 | 12.0 | 9.6 | 16.0 |
| 7107-607(2) | 2 GNA1 | 10.0 | 13.8 | 10.4 | 16.3 |
| 7107-606(4) | 1 GNA1; T7lac-zwf | 11.5 | 14.4 | 11.9 | 19.7 |
| 7107-634(1) | 1 GNA1; zwf | 12.0 | 13.8 | 11.6 | 16.9 |
| 7107-634(2) | 1 GNA1; zwf | 10.0 | 12.6 | 12.7 | 21.4 |
| 7107-633(1) | 2 GNA1; zwf | 10.0 | 13.2 | 10.4 | 17.8 |
| 7107-633(5) | 2 GNA1; zwf | 9.5 | 12.6 | 9.8 | 17.3 |

Results indicate that with the zwf overexpressed either with the native or T7 promoter increased cell growth, indicating at least partial alleviation of pentose starvation. Production of NAG was also increased in several of the strains. For example, strain 7107-634(2) produced about 25% more NAG than control strain 7107-92(1). In this experiment, strains with two copies of the T7lac-ScGNA1 cassette with the overexpressed zwf were not improved over those with one copy of the cassette and the overexpressed zwf.

Evaluation of Strain Overexpressing the zwf Gene in 1-Liter Fermentors

Strains overexpressing the zwf were next evaluated in 1-L fermentors. These results were also compared with those from strain 7107-92(1), previously run in a separate fermentation under identical conditions. Fermentors were set up with an initial volume of 475 ml. Components of the fermentation medium are listed in Table 26. Fermentations were run using 75% NH$_4$OH for pH control to 6.9. Temperature was maintained at 37° C. throughout the fermentation. Aeration and agitation were adjusted to maintain a dissolved oxygen concentration of 20% of air saturation. 65% glucose was fed to the cultures with feed rate controlled by computer program to achieve a growth rate of 0.40 hr$^{-1}$ at inoculation and a maximum rate of 5 ml/hr by 6 hours. Cultures were induced with food grade lactose added at 5 g/l at 10 hours, with continued glucose feed.

Fermentation results indicated that strain 7107-606(1) achieved a higher OD$_{600}$ than control strains, particularly at earlier timepoints. This may be due to the increased pentose supply in this strain. On the other hand, strains overexpressing the zwf with its native promoter grew to about the same OD$_{600}$ as the control strain. In this experiment, none of the strains overexpressing zwf surpassed control strain 7107-607(2) or 7107-92(1) in GlcNAc production. However, conditions for the fermentation were optimized for the production strains 7107-92(1) and 7107-607(2). It is possible that zwf over-expressing strains may require slightly different fermentation conditions to show their full potentials in improving growth and NAG production.

Example 26

This Example describes cloning of the phosphoglucose isomerase (pgi) gene, the integration of a T7lac-pgi cassette into the E. coli chromosome and effects of pgi gene overexpression on NAG production.

The E. coli pgi gene encodes phosphoglucose isomerase, an enzyme that catalyzes the interconversion of glucose-6-phosphate to fructose-6-phosphate. Overexpression of the pgi may increase the pool of F-6-P in cells, and thus lead to higher GlcN/GlcNAc production. To test this possibility, the pgi gene was cloned and overexpressed in the E. coli NAG production background.

Cloning and Overexpression of the E. coli pgi

For cloning and overexpression of the E. coli pgi, primers were synthesized based on the published sequence of the pgi gene (Blattner et al, 1997, Science 277(5331): 1453-1474). The nucleotide sequence of the E. coli pgi gene coding sequence is listed in the sequence identified as SEQ ID NO:104. The deduced amino acid sequence of the E. coli PGI enzyme is listed in the sequence identified as SEQ ID NO:105. The primers were used to amplify the pgi coding sequence from E. coli W3110 genomic DNA by PCR. Forward primer 07-103 and reverse primer 07-104 were used for the amplification and had the following sequences. 07-103: 5' GATCGGTCTCGCATGAAAAACATCAATC-CAACGCAGAC 3' (SEQ ID NO:106) and 07-104: 5'GATCCTCGAGTTAACCGCGCCACGCTTTATAGC 3' (SEQ ID NO:107).

Primer 07-103 contains a Bsa I site (GGTCTC, represented in nucleotides 5-10 of SEQ ID NO:106) and 26 nucleotides of the pgi coding sequence from its ATG start codon (represented in nucleotides 13-38 of SEQ ID NO:106). Primer 07-104 contains a Xho I site (CTCGAG, represented in nucleotides 5-10 of SEQ ID NO:107) and 23 nucleotides of the pgi coding sequence from its translational stop codon (represented in nucleotides 11-33 of SEQ ID NO:107). PCR amplification was conducted under standard conditions to generate a fragment containing the pgi coding sequence flanked by Bsa I and Xho I restriction endonuclease sites.

The PCR fragment was digested with restriction endonucleases Bsa I and Xho I and ligated at the Nco I and Xho I sites of vector pET24d(+) (Novagen, Inc., Madison, Wis.), generating plasmids PKLNO736 and PKLNO7-37. Cloning in this manner places the pgi sequence behind the T7lac promoter of pET24d(+), generating an expression cassette of T7lac-pgi.

Functional Expression of the Recombinant gi in E. coli

Plasmid pKLN07-36 was transformed into NAG production strain 7107-92(1), generating strain 7107-124. Control strain 7107-95 was generated by transforming 7107-92(1) with the pET24d(+) empty vector. A standard induction protocol was followed in which cell cultures were grown in LB and induced with 1 mM IPTG. Samples were taken from the induced and noninduced cultures for SDS-PAGE. Results confirmed overproduction of a protein of about 62 kDa, corresponding to the predicted size of the PGI protein. Total and soluble protein amounts were determined by SDS-PAGE 4 hours after IPTG induction. Samples from strains 7107-124(1) and 7107-124(2) showed overproduction of the 62 kDa protein, indicating successful overexpression of the recombinant PGI protein. The presence of the overproduced protein in both induced and noninduced cultures indicates leaky expression of the pgi gene in the absence of inducer. No such protein band is seen in samples from control stain 7107-95. At least half of the total PGI protein appears to be in the soluble form.

After four hours of induction, cultures were harvested to determine phosphoglucose isomerase activity. Strains 7107-124(1), 7107-124(2), and 7107-124(3) were found to have Pgi specific activities of 242, 158, and 215 mmol min$^{-1}$ mg$^{-1}$ protein, respectively, compared with 0.94 mmol min$^{-1}$ mg$^{-1}$ protein in control stain 7107-95. This confirms successful overexpression of the Pgi protein, reaching levels of 100 to 200 folds higher compared to the control.

Construction of a Vector to Direct Integration of the T7lac-pgiA into the E. coli Chromosome Having confirmed functional expression of the pgi, the next step was to construct a vector to target integration of the T7lac-pgi cassette into the chromosome of E. coli. The target chosen for integration was the araBAD region of the E. coli genome. The araBAD operon, encoding for the L-ribulokinase, L-arabinose isomerase and L-ribulose-5-P 4-epimerase proteins, is involved in the utilization of L-ara proteins catalyze the conversion of L-arabinose to D-xylulose-5-phosphate, an intermediate in the pentose phosphate shunt. Since L-arabinose is not used as a carbon source in NAG fermentation process, gene integration at this site should not affect cell growth or NAG production.

The first step in generating the integrative vector was to clone the region of the genome containing the araBAD operon. Primers were synthesized based on the published sequence of the araBAD operon (Blattner et al, 1997, Science 277(5331):1453-1474). The primers used to amplify the araBAD region were forward primer 07-105 and reverse primer 07-106 and had the following sequences: 07-105: 5' GGATCCTACCTGACGCTTTTTA TCGCAACTC 3' (SEQ ID NO:108) and 07-106: 5'CGGACGCACATCGGCCTCG-TAG AC 3' (SEQ ID NO:109).

Primer 07-105 amplifies from 74 basepairs downstream of the ATG start codon of araB and primer 07-106 amplifies from 404 basepairs downstream of the araD translational stop codon. The resulting 4.7-kb PCR fragment containing the araBAD operon was ligated into vector pPCR-Script™SK(+) (Stratagene Cloning Systems, La Jolla, Calif.), generating plasmid pKLN07-38.

The next step was to add the T7lac-pgi cassette from plasmid pKLN07-37 to plasmid pKLN07-38. The T7lac-pgi cassette was amplified by PCR from plasmid pKLN07-37 with forward primer 07-109 and reverse primer 07-110 that had the following sequences: 07-109: 5' GATTCCGGAAG-CAACCGCACCTGTGGC 3' (SEQ ID NO:110) and 07-110: 5' GATCACCTGGTTATAGTTCCTC-CTTTCAGCAAAAAACCC 3' (SEQ ID NO:111)

Primer 07-109 contains a BspE I restriction endonuclease site (TCCGGA, represented in nucleotides 4-9 of SEQ ID NO:1110) and amplifies from 80 basepairs upstream of the T7 promoter of pET24d(+). Primer 07-110 contains a SexA I restriction endonuclease site (ACCTGGT, represented in nucleotides 5-11 of SEQ ID NO:111) and amplifies from 18 basepairs downstream of the T7 promoter of pET24d(+). PCR was conducted under standard conditions to generate a fragment containing the T7lac-pgi cassette flanked by BspE I and SexA I restriction endonuclease sites. The PCR fragment was subsequently digested with restriction endonuclease BspE I and SexA I.

Plasmid pKLN07-38 was digested with restriction endonucleases BspE I and SexA I, excising a 2477 basepair fragment containing the last 621 basepairs of the araB coding sequence, the entire araA coding sequence, and the first 59 basepairs of the araD coding sequence. The digested T7lac-pgi PCR fragment (described above) was ligated into the BspE I and SexA I, sites of pKLN07-38, generating plasmid pKLN07-41. Plasmid pKLN07-41, therefore, has a 2.4 kb deletion of a portion of the araBAD operon, with the T7-lac-pgi inserted at the site of the deletion.

For the final cloning step, the fragment containing the araBAD sequence with the T7lac-pgi insertion was digested from plasmid pKLN07-41 with restriction endonucleases Not I and Sal I. This fragment was ligated with the 4.2 kb Sal 1/Not I fragment from pKLN07-21, containing the temperature sensitive replicon from pMAK705 (Hamilton et al., 1989, J. Bac. 171(9):4617-4622) and the kanamycin resistance cassette from pUC4K (Amersham Pharmacia Biotech, Piscataway, N.J.). The resulting plasmid, pKLN07-47, can be used for directing integration of the pgi to the araBAD region of the E. coli chromosome.

Strain 7107-92(1) was transformed with plasmid pKLN07-47. The temperature selection protocol was performed. Kanamycin sensitive colonies were screened by PCR under standard conditions for the presence of the T7lac-pgi at the site of the araBAD deletion on the chromosome. Several strains identified by PCR were confirmed by high stringency Southern hybridization using a fragment containing the pgi coding sequence as probe. These strains were designated 7107-136 through 7107-141.

Shake Flask Evaluation of Strain 7107-136 and 7107-141

Screening of strains included strains 7107-136 and 7107-141 to evaluate the effects of overexpression of the pgi on NAG production. Cultures were grown in M9B medium (previously described) supplemented with 0.6 g/l MgSO$_4$-7H$_2$O, 0.05 g/l CaCl$_2$-2H$_2$O, 5 g/l yeast extract, 5 g/l ribose, 10 g/l glucose, and 40 g/l lactose. Strains were grown for 24 hours at 30° C. and then switched to 25° C. for the remainder of the experiment. At 24 and 48 hours, the pH of each culture was adjusted to 7.2 and glucose added to 30 g/l per day based on HPLC results. 5 g/l (NH$_4$)$_2$SO$_4$ was added at 24 and 48 hours to flasks in which levels had fallen below 1 g/l. Samples were removed at 24, 48, and 72 hours for determination of OD and NAG levels. Cultures were harvested at 72 hours for enzyme analysis. Results are shown in Table 29.

TABLE 29

Growth and GlcNAc production in strains overexpressing the pgi.

| Strain | Description | OD$_{600}$ 48 hr | OD$_{600}$ 72 hr | GlcNAc (g/l) 48 hr | GlcNAc (g/l) 72 hr |
|---|---|---|---|---|---|
| 7107-92(1) | 1 GNA1 | 12.0 | 12.0 | 19.3 | 30.0 |
| 7107-136 | 1 GNA1; T7lac-pgi | 12.75 | 13.5 | 16.0 | 27.4 |
| 7107-141 | 1 GNA1; T7lac-pgi | 13.1 | 12.4 | 18.5 | 29.5 |

In this experiment, no significant improvement was seen in strains with the overexpressed pgi. However, under optimized shake flask or fermentation conditions, the overexpressed pgi may positively influence growth and/or NAG production.

Evaluation of Strain 7107-141 in 1 Liter Fermentation

Strain 7107-141, overexpressing the pgi, was next evaluated in a 1-L fermenter. Results were compared with those from strain 7107-92(1), previously run in a separate fermentation under identical conditions. Fermenters were set up with an initial volume of 475 ml. Components of the fermentation medium are listed in Table 3. Fermentations were run using 75% NH$_4$OH for pH control to 6.9. Temperature was maintained at 37° C. throughout the fermentation. Aeration and agitation were adjusted to maintain a dissolved oxygen concentration of 20% of air saturation. 65% glucose was fed to the cultures with feed rate controlled by computer program to achieve a growth rate of 0.40 hr$^{-1}$ at inoculation and a maximum rate of 5 ml/hr by 6 hours. Cultures were induced with food grade lactose added at 5 g/l at 10 hours, with continued glucose feed.

Similar to the shake flask experiments, no significant improvement in glucosamine production was seen in strains overexpressing the pgi gene. However, as discussed previously, under conditions optimized for these strains, pgi overexpression may positively influence growth and/or NAG production.

Example 27

The following Example describes development of glucosamine/N-acetylglucosamine production strains in which the glycogen synthesis is blocked by deletion of glgXCA genes. It also demonstrates the effects of blocking glycogen synthesis on glucosamine/N-acetylglucosamine production.

Bacteria cells accumulate glycogen as the major form of stored carbon reserve. Glycogen synthesis involves three enzymes: ADP-glucose pyrophosphorylase, glycogen synthase and a branching enzyme. These enzymes catalyze, respectively, the synthesis of the monosaccharide donor (ADP-glucose) from glucose-1-phosphate, the polymerization of these monosaccharide units to form an a (1-4) polymer of glucose, and the rearrangement of this polymer to generate a (1-6) branches in the chain. The ADP-glucose pyrophosphorylase is a pivotal enzyme in glycogen synthesis and is strongly modulated by allosteric effectors. Genes involved in glycogen synthesis and degradation are organized as a glg operon (glgBXCAP), including glgB (1,4-alpha-glucan branching enzyme), glgX (glycosyl hydrolase, debranching enzyme), glgC (ADP-glucose pyrophosphorylase), glgA (glycogen synthase), and glgP (glycogen-maltotetraose phosphorylase). In an effort to increase carbon flow to the glucosamine and N-acetylglucosamine production pathways the glycogen synthesis pathway was blocked by gene deletion in the strains producing glucosamine and N-acetylglucosamine.

PCR primers of the following sequences were synthesized to clone sequences from the glg operon. GNglgBXCAP1-5: 5'-GAGTCATCCGGATACAGTACGCGA-3' (SEQ ID NO:112) and GNglgBXCAP2-3: 5'-ATAAACCAGC-CGGGCAAATGG-3' (SEQ ID NO:113).

PCR amplification with the primers using standard conditions resulted in the generation of a 5737-bp fragment of the glg operon from E. coli strain W3110. The amplified sequence spans from glgB through glgP. The PCR product was ligated into pCR®2.1-TOPO® (Invitrogen TOPO TA Cloning Kit, Catalog # K4500-01), generating the recombinant plasmid pCALG18-1.

pCALG18-1 was digested with Age I to delete the 3' portion of glgX, the entire glgC, and the 5' portion of glgP from the plasmid. The remaining portion of the plasmid was re-circulated to generate pCALG21-1. This recombinant plasmid contains the truncated glg operon (glgXCAD).

To generate the plasmid needed to integrate glgXCAD into the genomes of glucosamine and/or N-acetylglucosamine producing strains two further procedures were required. First, the Kan$^r$ gene from pUC4K (Amersham Pharmacia Biotech, Catalog # 27-4958-01, GenBank Accession # X06404) was added to pCALG21-1 to generate pCALG23-1. Second, the temperature sensitive replication origin from pMAK705 (Hamilton, C., et al, 1989, Journal of Bacteriology, 171:9, pp 4617-4622) was added to pCALG23-1 to generate pCALG28-1. To accomplish the first procedure, pCALG21-1 and pUC4K were both digested with BamH I. BamH I digestion linearizes pCALG21-1 upstream of the glgXCA deletion site and releases the Kan$^r$ fragment from pUC4K. The linearized pCALG21-1 and Kan$^r$ fragments were ligated to generate pCALG23-1. To generate pCALG28-1, the Kan$^r$-glgXCAD fragment from pCALG23-1 was PCR amplified using oligonucleotides GNTOPO2-5 (SEQ ID NO:114) and GNTOPO3-4 (SEQ ID NO:115). Sequence of GNTOPO2-5: 5'-CGCCAAGCTTG-GTACCG-3' (SEQ ID NO:114). The primer sequence is identical to nucleotides 230 to 246 of pCR®2.1-TOP®. Sequence of GNTOPO3-4: 5'-CCCTCTAGATGCAT-GCTCGAG-3' (SEQ ID NO:115). The sequence is reverse complimentary to nucleotides 334 to 354 of pCR®2.1-TOPO®.

The PCR products were ligated to the Sma I fragment containing the temperature sensitive replication origin isolated from pMAK705. The resultant recombinant plasmid pCALG28-1 contains Kan$^r$, the glgXCAD sequences and the temperature sensitive replication origin.

Generation of strains deficient in glycogen synthesis was accomplished by replacement of endogenous glgBXCAP sequences with the recombinant glgXCAD sequence. pCALG28-1 was transformed into E. coli strain 7107-18 and clones in which the endogenous glgBXCAP was replaced with the recombinant glgXCAD sequence from pCALG28-1 were generated using the temperature selection procedure. The desired clones were further identified by PCR screening and confirmed by an iodine vapor test. The PCR screening was conducted using oligonucleotides GNglgBXCAP3-5 (SEQ ID NO:136) and GNglgBXCAP43 (SEQ ID NO:137). The sequence of GNglgBXCAP3-5 is as follows: 5'-GGCG-GCTTAAAATGTCCTGAATG-3' (SEQ ID NO:136). The primer is located further upstream to the 5' end of the glgBXCAP PCR fragment generated from the oligonucleotides GNglgBXCAP1-5 (SEQ ID NO:112) and GNglgBX-CAP2-3 (SEQ ID NO:113). The sequence of GNglgBX-CAP4-3 is: 5'-CGAAATCATCGTTGCCAGTAACTTTACG-3' (SEQ ID NO:137). The primer is located further downstream to the 3' end of the glgBXCAP PCR fragment generated from the oligonucleotides GNglgBXCAP1-5 (SEQ ID NO:112) and GNglgBXCAP2-3 (SEQ ID NO:113).

In the PCR screening two strains produced PCR products of the expected size (2295 bp) for the glgXCAD sequences. These two strains were named 7107-308 and 7107-309. The strains were then subjected to an iodine vapor test to demonstrate that that neither of these strains was able to accumulate glycogen. To perform the test, plates with 7107-18, 7107-308, and 7107-309 cells were exposed to the vapors from iodine crystals. Only strain 7107-18 turned a dark brown color, indicating the presence of glycogen.

Shake Flask Experiments to Test NAG Production in Glycogen Deficient Strains

A shake flask screen evaluated strains with glycogen synthesis blocked by glg deletion. Strains were grown in M9B medium supplemented with 40 g l$^{-1}$ glucose, 10 g l$^{-1}$ ribose and 5 g l$^{-1}$ yeast extract. There appears to be some interesting differences among strains with glg deletion. Some glg deletion strains (e.g. 7107-604) grew better than the control but produced a lower level of NAG. Strain 7107-605-1 showed a growth comparable to the control but with a 12% improvement in NAG titer.

TABLE 30

Growth and NAG production in glg deletion strains in shake flask experiments.

| Strain | | OD | | | NAG (g l$^{-1}$) | |
|---|---|---|---|---|---|---|
| | | 23 hrs | 47 hrs | 71 hrs | 23 hrs | 47 hrs | 71 hrs |
| Control | 7107-92(1) | 4.2 | 10 | 10.5 | 6.7 | 10 | 10 |
| glg deletion | 7107-604(1) | 8.4 | 12 | 12 | 6.3 | 7.1 | 7.6 |
| | 7107-604-(2) | 8.1 | 12 | 12.5 | 6.5 | 7.7 | 7.6 |
| | 7107-605(1) | 4.2 | 10 | 11.5 | 6.9 | 10.4 | 11.2 |
| | 7107-605(2) | 4.7 | 10.5 | 11 | 6.2 | 10.3 | 10.9 |

Example 28

The following Example demonstrates the effects of deletion of one of two lacI genes and replacement of the lac promoter with the lacUV5 promoter on the alleviation of glucose repression and glucosamine/N-acetylglucosamine production.

It has been known that the presence of glucose in the media represses expression from the lac promoter in E. coli. The lac operon encodes three proteins: LacZ, LacY, and LacA. The lacZ gene encodes the enzyme, b-galactosidase, which cleaves lactose into glucose and galactose and also converts lactose into allolactose, a true inducer of the operon. Allolactose induces the lac operon by interacting with the repressor (encoded by the lacI gene) and to prevent it from binding at the lac operator. The lacY gene encodes the lactose permease that controls the influx of lactose into the cell. The lacA gene encodes thiogalactoside transacetylase (galactoside acetyltransferase), an enzyme that may assist in cellular detoxification of nonmetabolizable pyranosides.

Transcription of the lac operon requires the binding of the lac promoter sequence by the complex CRP:cAMP, a complex formed between cAMP and its receptor protein (CRP). It has been believed that glucose represses the lac operon by reducing cAMP levels in the cells. The lacUV5 promoter is a mutant version of the lac promoter containing specific nucleotide changes. Due to these changes the lac promoter no longer requires the binding by the CRP:cAMP complex to activate transcription. This suggest that lac operon under lacUV5 control would not be susceptible to glucose repression. Therefore, the lac promoter was replaced by the lacUV5 promoter (represented herein by SEQ ID NO:135) in N-acetylglucosamine and/or glucosamine producing E. coli strains to minimize glucose repression.

Some N-acetylglucosamine and/or glucosamine producing strains contain two copies of lacI repressor gene. One is a component of the native lac operon and the other is found in the DE3 element. The amount of cellular lacI repressor protein could affect the strength of repression. Therefore, deletion of one of the lacI genes could affect lactose induction of glucosamine/N-acetylglucosamine production.

Replacement of the lac Promoter with the lacUV5 Promoter

Several precursor plasmids were generated prior to the construction of the plasmid used to integrate the lacUV5 promoter into N-acetylglucosamine and/or glucosamine producing strains.

Generation of the first precursor plasmid included the PCR amplification of the mphRlacIlacZ fragment from *E. coli* strain W3110 was performed using oligonucleotide primers GNmphRlacIlacZ1-5 (SEQ ID NO:116) and GNmphRlacIlacZ2-3 (SEQ ID NO:117). The sequence of GNmphRlacIlacZ1-5 was as follows: 5'-ATTGTGCGCT-CAGTATAGGAAGG-3' (SEQ ID NO:116), and that of GNmphRlacIlacZ2-3: 5'-CGATACTGACGGGCTCCAG-3' (SEQ ID NO:117). The correct-sized PCR product containing the mphRlacIlacZ sequence was cloned into pCR®2.1-TOPO® to generate pCALG3-1.

The next precursor plasmid resulted from a site-directed mutagenesis (Stratagene® QuikChange® XL Site-Directed Mutagenesis Kit, Catalog # 200517) of pCALG3-1 using oligonucleotides GNlacdel2-5 (SEQ ID NO:118) and GNlacdel3-5 (SEQ ID NO:119). The sequence of GNlacdel2-5 was: 5'-(phosphorylated) GCAAAAC-CTTTCGCGGTCACCCATGATAGCGCCCG-3' (SEQ ID NO:118). The primer sequence is identical to the W3110 lacI sequence except for the ATGG to CACC changes made to add the BstE II site (represented from nucleotide 15-21 of SEQ ID NO:118) 5' of the lacI start codon. The sequence of GNlacdel3-5: 5'-(phosphorylated) CGGGCGCTAT-CATGGGTGACCGCGAAA-GGTTTTGC-3' (SEQ ID NO:119). The oligonucleotide sequence is reverse complementary to the W3110 lacI sequence except for the CCAT to GGTG changes made to add the BstE II site (represented from nucleotide 15-21 of SEQ ID NO:119) 5' of the lacI start codon.

Site-directed mutagenesis of pCALG3-1 using oligonucleotides GNlacdel2-5 (SEQ ID NO:118) and GNlacdel3-5 (SEQ ID NO:119) added a BstE II site 5' of the lac start codon to generate pCALG5-1. This recombinant plasmid consists of the mphRlacIlacZ sequence with a BstE II site 5' of the lacI start codon in the backbone of pCR®2.1-TOPO®.

Next, pCALG5-1 was digested with BstE II and the fragment containing 3' sequences of lacI, a portion of the lacZ gene with the lac promoter, pCR®2.1-TOPO®, and sequences from mphR was isolated. The isolated fragment from pCALG5-1 was ligated to itself to generate pCALG10-1. The recombinant pCALG10-1 plasmid contains mphR sequences, lacID, the lac promoter, lacZ sequences in the backbone of pCR®2.1-TOPO®.

Next, pCALG10-1 was digested with BstE II and Nde I and the fragment containing pCR®2.1-TOPO® and the mphR sequences was isolated. The isolated pCALG10-1 fragment was then ligated to two PCR products. The first PCR product, generated from pCAL610-1, contained the lacZ sequence with an Nde I site added immediately 5' of the lacZ start codon. Using PCR under standard conditions and oligonucleotide primers GNLacZ1-5 (SEQ ID NO:120) and GNLacZ2-3 (SEQ ID NO:121), the portion of pCALG10-1 containing the lacZ sequence was amplified. The sequence of GNLacZ1-5 is as follows: 5'-CACAGGAAACACATAT-GACCATGATTACGG-3' (SEQ ID NO:120). The primer sequence is identical to nucleotides 1921 to 1950 of pCALG10-1 (the lac promoter/lacZ junction) except for G1932C and C1933A nucleotide changes to add an Nde I site (represented by nucleotides 12-17 of SEQ ID NO:120). The sequence of GNLacZ2-3 is: 5'-CCACCATGATATTCG-GCAAGCAG-3' (SEQ ID NO:121). The sequence is reverse complimentary to nucleotides 6523 to 6545 of pCALG10-1.

Using PCR under standard conditions and oligonucleotide primers GNLacuv53-5 (SEQ ID NO:122) and GNLacuv54-3 (SEQ ID NO:123), the second PCR product, the lacUV5 promoter from strain 7101-17(DE3), was amplified. The sequence of GNLacuv53-5 is: 5'-CCTTTCGCG-GTCACCAGCAAA-3' (SEQ ID NO:122). The sequence is identical to nucleotides 1253 to 1273 of pCALG10-1 and encompasses the endogenous BstE II site (represented by nucleotide sequences 9 to 15 of SEQ ID NO:122) within lacI. The sequence of GNLacuv54-3 is: 5'-CCGTAAT-CATGGTCATATGTGTTTCCTGTG-3' (SEQ ID NO:123). The sequence is reverse complimentary to nucleotides 1921 to 1950 of pCALG10-1 (the lac promoter/lacZ junction) except for C1932G and G1933T nucleotide changes to add an Nde I site (represented by nucleotides 14 through 19 of SEQ ID NO:123).

The PCR-generated lacUV5 promoter fragment was digested with BstE II plus Nde I, and purified. Similarly, the PCR product containing the lacZ sequence was digested with Nde I and purified. To generate the next precursor plasmid the mphR fragment (Nde I-BstE II) from pCALG10-1, the lacUV5 promoter fragment (BstE II-Nde I), and the lacZ fragment (Nde I-Nde I) were ligated together. The resultant recombinant plasmid, pCALG16-3, contains mphR sequences, lacID, lacUV5 promoter, lacZ sequences (in the opposite order as in the native form of the sequences) in the vector pCR®2.1-TOPO®. The correct lacUV5 promoter sequences of pCALG16-3 were confirmed by sequencing.

Next, the lacZ fragment in pCALG10-1 was PCR amplified using standard conditions and oligonucleotide primers GNLacZ1-5 (SEQ ID NO:120) and GNlacZ3-3 (SEQ ID NO:124).

The nucleotide sequence of GNlacZ3-3 is: 5'-GAC-GAAGCGGCCGCGTAAACG-3' (SEQ ID NO:124). The sequence is reverse complimentary to nucleotides 3618 to 3638 of pCALG10-1 except for the T3625C, C3626G, and C3630G nucleotides changes to add a Not I site (represented by nucleotides 7 to 14 of SEQ ID NO:124).

The lacZ PCR fragment was digested with Nde I and Not I and isolated. Additionally, pCALG16-3 was digested with Nde I to Not I and the fragment containing pCR®2.1-TOPO®, sequences from mphR, lacID, and the lacUV5 promoter was isolated. The lacZ PCR fragment and the pCALG16-3 fragment containing pCR®2.1-TOPO®, sequences from mphR, lacID, and the lacUV5 promoter were ligated together to produce pCALG20-1. The recombinant pCALG20-1 plasmid contains pCR®2.1-TOPO®, sequences from mphR, lacID, the lacUV5 promoter (with a Nde I site immediately 5' of the lacZ start codon), and the lacZ coding region in the 5' to 3' orientation.

The previously constructed pCALG3-1 was used along with pCALG20-1 to generate the next precursor plasmid. Both pCALG3-1 and pCALG20-1 were digested with Apa I. The pCALG20-1 fragment containing the lacUV5 promoter and lacZ sequences and the pCALG3-1 fragment containing pCR®2.1-TOPO®, mphR sequences, and full-length lacI were isolated and ligated together to produce pCALG22-1. The recombinant pCALG22-1 contains mphR sequences, full-length lacI, the lacUV5 promoter (with a Nde I site immediately 5' of the lacZ start codon), lacZ sequences, and pCR®2.1-TOPO®.

pCALG22-1 and pUC4K (Amersham Pharmacia Biotech, Catalog # 27-4958-01, GenBank Accession # X06404) were used to generate the next precursor plasmid. pCALG22-1 and pUC4K were both digested with BamH I. The pCALG22-1 fragment containing mphR sequences, full-length lacI, the lacUV5 promoter, lacZ sequences, and pCR®2.1-TOPO® and the pUC4K fragment containing Kan$^r$ were isolated and ligated together to generate pCALG25-1. The recombinant pCALG25-1 consists of Kan$^r$, mphR sequences, full-length lacI, the lacUV5 promoter (with a Nde I site immediately 5' of the lacZ start codon), lacZ sequences, and pCR®2.1-TOPO®.

To generate the next precursor plasmid, pCALG25-1 and pKLN07-20 (described elsewhere) were digested with Kpn I and Not I. The pCALG25-1 fragment containing Kan$^r$, mphR sequences, full-length lacI, the lacUV5 promoter, and lacZ sequences and the pKLN07-20 fragment containing the temperature sensitive replication origin from pMAK705 (described previously) were isolated and ligated together to generate pCALG29-1. The recombinant pCALG29-1 plasmid contains Kan$^r$, mphR sequences, full-length lacI, the lacUV5 promoter (with a Nde I site immediately 5' of the lacZ start codon), lacZ sequences, and the temperature sensitive region from pMAK705.

After constructing pCALG29-1 it was thought that this would be the final integrative vector. However, it was subsequently determined out that addition of the Nde I site immediately 5' of the lacZ start codon inhibited proper expression of lacZ. Therefore, pCALG29-1 was subjected to site-directed mutagenesis (Stratagene® QuikChange® XL Site-Directed Mutagenesis Kit, Catalog # 200517) to destroy the Nde I site and replace the Nde I nucleotide changes with the endogenous lacUV5 nucleotides. To make the necessary changes to pCALG29-1, pCALG29-1 was subjected to site-directed mutagenesis using oligonucleotides GNlacZ-Nde1 (SEQ ID NO:125) and GNlacZ-Nde2 (SEQ ID NO:126) to produce pCALG3'-1.

The nucleotide sequence of GNlacZ-Nde1 is as follows: 5'-CACACAGGAAA CAGCTATGACCATGATTACG-GATTC-ACTGG-3' (SEQ ID NO:125). The sequence is identical to nucleotides 1919 to 1959 of pCALG10-1. The nucleotide sequence of GNlacZ-Nde2 is as follows: 5'-CCAGTGAATCCGTAATCATGGTCAT-AGCTGTTTCCTG-TGTG-3' (SEQ ID NO:126). The sequence is reverse complimentary to nucleotides 1919 to 1959 of pCALG10-1.

The resultant recombinant pCALG31-1 plasmid contains Kan$^r$, mphR sequences, full-length lacI, the lacUV5 promoter (with endogenous nucleotides immediately 5' of the lacZ start codon), lacZ sequences, and the temperature sensitive replication origin from pMAK705.

The recombinant pCALG31-1 was transformed into 7107-18 and clones with the lacUV5 promoter replacement were generated using the temperature selection procedure. To identify the correct clones, genomic DNA was prepared and the lacUV5 promoter region was PCR amplified. The PCR products were then sequenced to confirm the presence of the lacUV5 promoter. One strain generated a PCR product of the expected size and had the correct DNA sequence. This strain was named 7107-310.

LacI Deletion and Replacement of the lac Promoter with the lacUV5 Promoter

To generate the plasmid needed to delete lacI from the lac operon and replace the lac promoter with the lacUV5 promoter in N-acetylglucosamine and/or glucosamine producing strains two precursor plasmids were developed. To generate the first precursor plasmid, pCALG20-1 (see above) and pUC4K (Amersham Pharmacia Biotech, Catalog #27-4958-01, GenBank Accession # X06404) were digested with BamH I. The pCALG20-1 fragment containing mphR sequences, lacID, the lacUV5 promoter (with a Nde I site immediately 5' of the lacZ start codon), lacZ sequences, and pCR®2.1-TOPO® and the pUC4K fragment containing Kan$^r$ were isolated and ligated together to generate pCALG26-1. The recombinant pCALG26-1 consists of Kan$^r$, mphR sequences, lacID, the lacUV5 promoter (with a Nde I site immediately 5' of the lacZ start codon), lacZ sequences, and pCR®2.1-TOPO®.

To generate the next precursor plasmid, pCALG26-1 and pKLN07-20 (described elsewhere) were digested with Kpn I and Not I. The pCALG26-1 fragment containing Kan$^r$, mphR sequences, lacID, the lacUV5 promoter (with a Nde I site immediately 5' of the lacZ start codon), and lacZ sequences and the pKLN07-20 fragment containing the temperature sensitive replication origin from pMAK705 (described previously) were isolated and ligated together to generate pCALG30-1. The recombinant pCALG30-1 plasmid contains Kan$^r$, mphR sequences, lacID, the lacUV5 promoter (with a Nde I site immediately 5' of the lacZ start codon), lacZ sequences, and the temperature sensitive replication origin from pMAK705.

After constructing pCALG30-1 it was thought that this would be the final integrative vector. However, it was subsequently determined out that addition of the Nde I site immediately 5' of the lacZ start codon inhibited proper expression of lacZ. Therefore, pCALG30-1 was subjected to site-directed mutagenesis (Stratagene® QuikChange® XL Site-Directed Mutagenesis Kit, Catalog # 200517) to destroy the Nde I site and replace the Nde I nucleotide changes with the endogenous lacUV5 nucleotides. To make the necessary changes to pCALG30-1, pCALG30-1 was subjected to site-directed mutagenesis using oligonucleotides GNlacZ-Nde1 (SEQ ID NO:125) and GNlacZ-Nde2 (SEQ ID NO:126) to produce pCALG32-2. The resultant recombinant pCALG32-2 plasmid contains Kan$^r$, mphR sequences, lacID, the lacUV5 promoter (with endogenous nucleotides immediately 5' of the lacZ start codon), lacZ sequences, and the temperature sensitive region from pMAK705.

The recombinant pCALG32-2 was transformed into 7107-18 and clones with the lacUV5 promoter replacement were generated using the temperature selection procedure. To identify the correct clones, genomic DNA was prepared and the lacUV5 promoter region was PCR amplified. The PCR products were then sequenced to confirm the presence of the lacUV5 promoter. Three strains generated the PCR product of the expected size and had the correct DNA sequence. These strains were named 7107-313, 7107-314, and 7107-315.

LacI Deletion from the DE3 Element

To delete the lacI gene from the DE3 element in the genome of production strains, the temperature sensitive selection method described in Example 13 was used. This strategy involved construction of an integrative vector to target the DE3 element for the lacI deletion. For the first step of construction, the region containing the lacI of the DE3 element was amplified by PCR from *E. coli* 7107-73 genomic DNA. Primers were synthesized based on the published sequence of the T7 RNAP and the attB region of the *E. coli* genome (Blattner et al, 1997, Science 277(5331): 1453-1474). Forward primer 07-74 and reverse primer 07-48 were used for the amplification and had the following sequences: 07-74: 5' GATCCCGGGAACGGACGATTA- GAGATCACC 3' (SEQ ID NO:127) and 07-48: 5' GTCA-GAGAAGTCGTTCTTAGCGATG 3' (SEQ ID NO:128).

Forward primer 07-74 added a Sma I site (CCCGGG, represented in nucleotides 4-9 of SEQ ID NO:127) and amplified from 1194 basepairs upstream of the attB site of the *E. coli* genome. Reverse primer 07-48 amplified from 36 basepairs upstream of the T7 gene 1 ATG start codon. The resulting ~3.2 kb PCR fragment was ligated into vector pPCR-Script™SK(+) (Stratagene Cloning Systems, La Jolla, Calif.), generating plasmids pSW07-53 #7 and #17. DNA sequencing revealed that the PCR product contained the region of the genome upstream of the attB site plus the lacI lacZ' fragment from the DE3 element.

To generate the deletion of the lacI, plasmid pSW07-53#17 was digested with restriction endonucleases Mlu I and Sfo I to remove 640 basepair fragments of the lacI coding sequence. The remainder of the pSW07-53 plasmid was treated with T4 DNAP to produce blunt ends and then ligated onto itself, generating plasmid pSW07-55#13.

The fragment containing the DE3 sequence with the lacI deletion was digested from plasmid pSW07-55#13 with restriction endonucleases Not I and Sal I. This fragment was ligated with the 4.2 kb Sal I and Not I fragment from pKLN07-21, containing the temperature sensitive replicon from pMAK705 (Hamilton et al., 1989, J. Bac. 171(9):4617-4622) and the kanamycin resistance cassette from pUC4K (Amersham Pharmacia Biotech, Piscataway, N.J.). The resulting plasmid, pKLN07-56#13, was used to generate a deletion of the lacI of the DE3 element on the *E. coli* chromosome.

To generate a strain with the lacI deletion of the DE3 element, *E. coli* 7107-18 was transformed with plasmid pSW07-56#13. Following temperature sensitive selection and passaging protocol, strains were screened using a standard PCR protocol for the presence of the deletion. Several strains identified by PCR were confirmed by high stringency Southern hybridization using a fragment containing a portion of the lac and lacZ fragment of the DE3 element as probe. These strains were designated 7107-84(1) through 7107-84(4).

Glucosamine Production in Strains with lacID and/or the lacUV5 Promoter Replacement in Shake Flasks Strain 7107-84(1) contains only one functional lacI gene, as opposed to strain 7107-18 with two functional lacI genes. Shake Flask Screen 42 was conducted to determine the effect of the lacI deletion of strain 7107-84(1) on lactose induction. In the presence of excess glucose and lactose, induction by lactose should be inhibited in strain 7107-18 due to the LacI repressor protein binding to the lac operator, preventing transcription. This inhibition by glucose should be reduced in strain 7107-84(1), as less LacI repressor protein should be present to bind the lac operator, allowing increased transcription from the lac promoters. This should increase pools of the T7 RNAP in the cells, resulting in increased transcription from the T7lac-glmS*54 cassette. Ultimately, higher levels of glucosamine should result in strain 7107-84(1). Likewise, strains containing the lacI deletion is the lac operon (e.g. 7107-313, 7107-314 and 7107-315) should have higher levels of GlcN production upon lactose inductions.

*E. coli* strains with the lacI gene deleted from the lac operon (7107-310), with the lacI gene deleted from the DE3 element (7107-84#1), and with the lacI deletion from the lac operon in which the lac promoter was replaced with the lacUV5 promoter (7107-313, 7107-314, and 7107-315) were compared to strain 7107-18 in shake flask experiments.

All strains were grown in flasks containing M9B medium: 6 g/l $KH_2PO_4$, 24 g/l $K_2HPO_4$, 1 g/l $Na_3Citrate-2H_2O$, 10 g/l $(NH_4)_2SO_4$ (pH adjusted to 7.4 by phosphate), and trace metals (0.2 mg/l $FeSO_4-7H_2O$, 0.015 mg/l $ZnSO_4-7H_2O$, 0.015 mg/l $MnSO_4—H_2O$, 0.001 mg/l $CuSO_4-5H_2O$, 0.001 mg/l $NaMoO_4-2H_2O$, 0.001 mg/l $H_3BO_3$, and 0.001 mg/l $CoCl_2-6H_2O$), supplemented with 0.6 g/l $MgSO_4-7H_2O$ and 0.05 g/l $CaCl_2-2H_2O$. To test glucose repression the flasks contained various amounts of glucose and lactose. The amounts of glucose and lactose used in the flasks are shown in Table 4 and Table 5. The cultures were grown at 30° C., with shaking at 225 rpm, for 24 hours and were then placed at 25° C., with shaking at 225 rpm, for the remainder of the experiment. At 24 and 48 hours, each culture was adjusted to pH 7.0, glucose was added to the flasks to approximately 30 g/l, and 5 g/l $(NH_4)_2SO_4$ was added to the cultures in which the level of ammonia had fallen below 1 g/l. Samples were collected at 24 and 48 hours. At each time point the glucosamine concentration in the culture supernatant was measured using the modified Elson-Morgan assay as described in U.S. Pat. No. 6,372,457 B 1. Glucosamine levels are shown in Table 31.

As expected, strains 7107-18, 7107-84(1), 7107-310 and 7107-313 performed similarly in the presence of glucose alone or lactose alone. Little GlcN production is seen in either strain when grown in glucose, as no inducer is present. When the strains were grown with lactose as inducer, significant accumulations of glucosamine occurred with both strains. However, when strains were grown in the presence of both glucose and lactose, removal of one copy of the lacI gene from the chromosome significantly impacted lactose induction and, therefore, glucosamine titers. Strain 7107-313 and 7107-84(1) achieved about 6-8 times the level of glucosamine seen in strain 7107-18 at the 48-hour timepoint. This confirms the concept that decreased LacI repressor protein allows increased transcription from lac promoters, resulting in increased levels of glucosamine production.

TABLE 31

Glucosamine concentration in different samples from Shake Flask Screen 42

| Strain Name | Genotype | Glucose (g l$^{-1}$) | Lactose (g l$^{-1}$) | Glucosamine Concentration (g l$^{-1}$) 24 hours | 48 hours |
|---|---|---|---|---|---|
| 7107-18 | galKΔ::T7-lac-glmS*54 | 0 | 40 | 1.5 | 4.3 |
| | | 30 | 0 | 0 | 0.2 |
| | | 30 | 20 | 0.1 | 0.4 |
| 7107-84#1 | galKΔ::T7-lac-glmS*54, lacIΔ at DE3 element | 0 | 40 | 1.7 | 4.9 |
| | | 30 | 0 | 0 | 0.2 |
| | | 30 | 20 | 0.8 | 3.2 |
| 7107-310 | galKΔ::T7-lac-glmS*54, lacUV5 promoter | 0 | 40 | 1.8 | 4.4 |
| | | 30 | 0 | 0.3 | 0.2 |
| | | 30 | 20 | 0.3 | 0.4 |
| 7107-313 | galKΔ::T7-lac-glmS*54, lacUV5 promoter, lacIΔ at lac operon | 0 | 40 | 1.6 | 4.2 |
| | | 30 | 0 | 0 | 0.2 |
| | | 30 | 20 | 0.7 | 2.3 |

Integration of the T7lac-ScGNA1 Cassette in Strains with lacID and/or the lacUV5 Promoter Replacement To evaluate the effect of the lacI deletion on glucose de-repression in NAG production strains, it was necessary to add the T7lac-ScGNA1 cassette to the chromosome of strain 7107-84(1) and 7107-84(2). The methods and protocols described for GNA1 cloning and integration by temperature sensitive selection with plasmid pSW07-68#5 were employed as detailed elsewhere. Resulting strains 7107-97 and 7107-98 were confirmed by standard high stringency Southern hybridization using the ScGNA1 coding sequence as probe as having the T7lac-ScGNA1 integrated at the site of the manXYZ deletion of the chromosome.

Similarly, other versions of potentially glucose de-repressed strains were constructed. Strain 7107-310 was constructed by altering the promoter of the lac operon to the lacUV5 version of the promoter. Strains 7107-313, 7107-314, and 7107-315 were constructed by deleting the chromosomal copy of the lacI gene in addition to altering the promoter of the lac operon to the lacUV5 version of the promoter. To evaluate the effect of these mutations on glucose de-repression in a NAG production background, T7lac-ScGNA1 cassette was added to the chromosome of the strains. The methods and protocols described for GNA1 cloning and integration by temperature sensitive selection with plasmid pSW07-68#25 were employed for strains 7107-310 and 7107-313. Resulting strains 7107-129 and 7107-130 (from strain 710-310) and 7107-131 (from strain 7107-313) were confirmed as having the T7lac-ScGNA1 integrated by the site of the manXYZ deletion of the chromosome using high stringency Southern hybridization with the ScGNA1 coding sequence as the probe.

N-Acetylglucosamine Production in Strains with lacID and/or the lacUV5 Promoter Replacement in Shake Flasks Screening was conducted to evaluate the effect of the lacI deletion of the DE3 element on glucose de-repression in a NAG production strain. Strains 7107-97 and 7107-98(2) were tested with varying levels of glucose and lactose, with or without ribose addition. NAG production strain 7107-92 (1), with two copies of lacI, was included as a control. Cultures were grown in M9B medium (previously described) supplemented with 0.6 g/l MgSO$_4$-7H$_2$O, 0.05 g/l CaCl$_2$-2H$_2$O, varied concentrations of glucose and lactose, and 5 g/l yeast extract. Strains were initially grown on 10 g/l glucose with a switch to lactose utilization once the glucose was depleted. Excess glucose conditions (in the presence of lactose) were also used to determine sensitivity to glucose repression. Each variable was performed with or without ribose addition. Cultures were grown at 30° C. for 24 hours and then switched to 25° C. for the remainder of the experiment. At 24- and 48-hour timpoints, the pH was adjusted to 7.2 and glucose added to a total of 30 g/l. 5 g/l (NH$_4$)$_2$SO$_4$ was added at 24 hours and 48 hours to flasks in which levels had fallen below 1 g/l. Samples were analyzed for NAG production at 24, 48, and 72 hours.

The control strain performed well in non-repressing conditions, yielding over 20 g/l NAG, but produced only about 5 g/l with excess glucose (Table 32). One mutant strain (7107-98) performed similarly to the control, but the other one, (7107-97), showed glucose resistance, producing over 20 g/l NAG even when excess glucose was present. In fact, this strain also appeared to outperform the control under non-repressing conditions in terms of NAG production and acetate accumulation. The addition of ribose to cultures did not significantly increase growth or NAG titers in this experiment. Overall results indicate that deletion of the lacI of the DE3 element does at least partially alleviate glucose repression, resulting in improved NAG titers in the production strain.

TABLE 32

Effect of the lacI deletion of the DE3 element on glucose de-repression in the presence of varying amounts of glucose and lactose.

| Strain | Initial Sugars (g l$^{-1}$) | | | OD$_{600}$ | Acetate (g l$^{-1}$) | NAG (g l$^{-1}$) |
| --- | --- | --- | --- | --- | --- | --- |
|  | Glucose | Lactose | Ribose |  |  |  |
| 7107-92(1) | 10 | 40 | 5 | 9.8 | 0 | 20.9 |
| (control) | 30 | 20 | 5 | 14.0 | 6.2 | 5.0 |
|  | 40 | 20 | 5 | 12.0 | 6.2 | 4.5 |
| 7107-97 | 10 | 40 | 5 | 15.0 | 0 | 26.2 |
|  | 30 | 20 | 5 | 15.5 | 0 | 25.4 |
|  | 40 | 20 | 5 | 14.0 | 2.6 | 21.7 |
| 7107-98(2) | 10 | 40 | 5 | 16.0 | 4 | 14.2 |
|  | 30 | 20 | 5 | 15.0 | 9.4 | 7.7 |
|  | 40 | 20 | 5 | 14.5 | 10.1 | 8.0 |
| 7107-92(1) | 10 | 40 | None | 10.5 | 0 | 17.6 |
|  | 30 | 20 | None | 14.5 | 6.4 | 5.7 |
|  | 40 | 20 | None | 14.5 | 6.9 | 5.7 |
| 7107-97 | 10 | 40 | None | 12.5 | 3.4 | 16.2 |
|  | 30 | 20 | None | 14.5 | 0 | 24.5 |
|  | 40 | 20 | None | 15.5 | 0 | 21.9 |
| 7107-98(2) | 10 | 40 | None | 14.5 | 7.3 | 12.0 |
|  | 30 | 20 | None | 14.0 | 7.8 | 7.7 |
|  | 40 | 20 | None | 14.5 | 9.0 | 7.3 |

(1)Strains: Control 7107-92(1): two lacI genes. 7107-97 and 7107-98(2): only one lacI gene (the one in DE3 was deleted).
(2)OD$_{600}$, acetate levels, and NAG levels are from the 72-hour timepoint.

Another screening was conducted to evaluate strains 7107-129, 7107-130 and 7107-131 for glucose de-repression. NAG production strain 7107-92(1), with two copies of lac, was included as a control. Cultures were grown in M9B medium (previously described) supplemented with 0.6 g/l MgSO$_4$-7H$_2$O, 0.05 g/l CaCl$_2$-2H$_2$O, varied concentration of glucose and lactose, 5 g/l ribose, and 5 g/l yeast extract. Strains were initially grown on 10 g/l glucose with a switch to lactose once the glucose was depleted for confirmation of induction by lactose. Excess glucose conditions (in the presence of lactose) in which glucose was always present were also used to test strain 7107-131 to determine sensitivity to glucose with respect to induction. Cultures were grown at 30° C. for 24 hours and then switched to 25° C. for the remainder of the experiment. The pH was adjusted to 7.2 and glucose added to a total of 30 g/l per day at 24 and 48-hour timepoints. 5 g/l (NH$_4$)$_2$SO$_4$ was added at 24 hours and 48 hours to flasks in which levels had fallen below 1 g/l. Samples were analyzed for NAG production at 24, 48, and 72 hours.

As seen in Table 33, one of the lacUV5 mutant strains (7107-130) and the lacUV5 mutant strain with the lacI deletion (7107-131) performed better than control strain 7107-92(1) when initially grown on glucose with a switch to lactose after glucose depletion. In conditions of excess glucose, strain 7107-131 outperformed control strain 7107-92(1), producing about 30% more NAG. This confirms that deletion of either copy of the lac will help alleviate glucose repression, allowing induction to occur in the presence of excess glucose and improving NAG titers.

TABLE 33

The effect of lacI deletion and/or the lacUV5 promoter on NAG production under conditions of glucose limiting or excess

| Strain | Initial Sugars (g l$^{-1}$) | | OD$_{600}$ | Acetate (g l$^{-1}$) | NAG (g l$^{-1}$) |
|---|---|---|---|---|---|
| | Glucose | Lactose | | | |
| Glucose limiting conditions: | | | | | |
| 7107-92(1) | 10 | 40 | 9.75 | 2.4 | 24.3 |
| 7107-129 | 10 | 40 | 9.75 | 2.0 | 23.3 |
| 7107-130 | 10 | 40 | 11.25 | 3.0 | 30.4 |
| 7107-131 | 10 | 40 | 11.25 | 2.2 | 31.6 |
| Glucose excess conditions: | | | | | |
| 7107-92(1) | 40 | 10 | 12.75 | 6.4 | 5.3 |
| | 40 | 20 | 13.5 | 6.5 | 5.8 |
| 7107-131 | 40 | 10 | 15.0 | 5.7 | 15.4 |
| | 40 | 10 | 13.87 | 6.0 | 14.2 |
| | 40 | 20 | 15.75 | 4.0 | 21.0 |
| | 40 | 20 | 14.25 | 5.0 | 18.6 |

(1)Strains: Control strain 7107-92(1): lacI(lac), lacI(DE3) 7107-129, 7107-130: lacUV5, lacI(lac), lacI(DE3) 7107-131: lacUV5, lacIΔ(lac), lacI(DE3)
(2)OD$_{600}$, acetate levels, and NAG levels are from the 72-hour timepoint.

Example 29

The following Example demonstrates the effects of restoration of galactose utilization on N-acetylglucosamine and/or glucosamine accumulation.

Lactose-induced N-acetylglucosamine and/or glucosamine producing strains containing the galKΔ::T7-lac-glmS*54 construct are unable to use galactose as a carbon source due to the galKΔ. These strains accumulate galactose due to the cleavage of lactose into glucose and galactose by b-galactosidase. In an effort to decrease galactose accumulation in these strains the T7-lac-glmS*54 expression cassette needs to be integrated into a different chromosomal location. The previously constructed N-acetylglucosamine and/or glucosamine producing strains contain nagΔ::Tet$^r$. The nagΔ::Tet$^r$ portion of the genome was transferred from the parent strain IBPC590 (Plumbridge (1991) Mol. Microbiol. 5, 2053-2062) by P1 phage transduction as described in U.S. Pat. No. 6,372,457 B1. The presence of Tet$^r$ in the production strains is not desirable. Therefore, replacement of Tet$^r$ with T7-lac-glmS*54 would not only serve as an integration site for T7-lac-glmS*54, it would also remove Tet$^r$ in the same process.

Integration of the ΔgalkT7-lac-glmS*54 construct into 7101-17(DE3), to produce strain 7107-18 (described previously in Example 7), has led to a significant increase in glucosamine production. Additionally, integration of the manXYZΔ::T7-lac-Sc GNA1 construct into 7107-18 has led to production of N-acetylglucosamine, described previously in Example 16. To develop N-acetylglucosamine production strains capable of metabolizing galactose, T7-lac-glmS*54 expression cassette was integrated at the nagD::Tet$^r$ site, followed by the insertion of the T7-lac-Sc GNA1 expression cassette at the manXYZ site.

The steps involved in the construction of strains containing nagΔ::T7-lac-glmS*54 and manXYZΔ::T7-lac-Sc GNA1 included the generation of three precursor plasmids. To generate the first precursor plasmid the T7-lac-glmS*54 fragment from pKLN23-54 (described in U.S. Pat. No. 6,372,457 B1) was PCR amplified using standard conditions with oligonucleotide primers GNglmSnagE3-5 (SEQ ID NO:129) and GNglmSnagE4-3' (SEQ ID NO:130).

GNglmSnagE3-5: 5'-GGATCTAAACCTCAGTAGC-GACCGGTCTAGAACTA-GTG-3' (SEQ ID NO:129) The primer is identical to nucleotides 1109 to 1146 of pKLN23-54 with the following exceptions: C1115A, C 1116A, GI 1120T, G1122A, G1125A, G1129A, and C1133G. The changes at nucleotides 1115 through 1125 of pKLN23-54 (corresponding to nucleotides 8, 12, 14, 17, 21 and 25 of SEQ ID NO:129) were made to increase stability of the primer in the PCR and the changes at 1129 and 1133 of pKLN23-54 add an Age I site to SEQ ID NO:129 (represented from position 21 to position 26 of SEQ ID NO:129).

GNglmSnagE4-3 5'-CCCTCGCCCCTCTAGAGCATT-TAAATTCAGTCAATT-AC-3' (SEQ ID NO:130) The primer is reverse complimentary to nucleotides 3237 to 3274 of pKLN23-54 with the following exceptions: T3251A, G3253T, G3256A, A3270C, and T3273C (represented by positions 24, 22, 19, 5, and 2, respectively, of SEQ ID NO:130). The changes at 3251 through 3256 were made to add a Swa I site (represented by positions 19 through 26 of SEQ ID NO:130) and the changes at 3270 and 3273 were made to increase stability of the primer in the PCR.

The resultant PCR product was ligated into pCR®-Blunt II-TOPO® (Invitrogen Zero Blunt® TOPO® PCR Cloning Kit, Catalog # K2800-20). The recombinant plasmid, pCALG38-2, contains the T7-lac-glmS*54 expression cassette flanked 5' by an Age I site and 3' by a Swa I site.

To generate the second precursor plasmid, the nagΔ::Tet$^r$::asn fragment was amplified from E. coli strain 7107-18 by PCR using GNnagEtetR1-5 (SEQ ID NO:131) and GNnag-EtetR2-3 (SEQ ID NO:132). The nucleotide sequence of GNnagEtetR1-5 is as follows: 5'-CACGCAGGCAGGCTT-TACCTTCTTC-3' (SEQ ID NO:131) and that of GNnag-EtetR2-3 is as follows: 5'-CGGAAGAACAAGCGACG-GAAGGAC-3' (SEQ ID NO:132).

The PCR product was ligated into pCR®-Blunt II-TOPO® to generate the recombinant plasmid pCALG35-1.

To generate the third precursor plasmid, pCALG38-2 was digested with Age I and Swa I and the T7-lac-glmS*54 fragment was purified. Additionally, pCALG35-1 was digested with Age I and Nru I and the asn-pCR®-Blunt II-TOPO®-nagD fragment was purified. The purified fragments from pCALG38-2 and pCALG35-1 were ligated to generate pCALG40. The recombinant pCALG40 plasmid contains the nagD::T7-lac-glmS*54::asn fragment in pCR®-Blunt II-TOPO®.

To generate the final plasmid needed to integrate the recombinant nagD::T7-lac-glmS*54::asn fragment into the genomes the following work was performed. pCALG40 was digested with Kpn I and Not I and the fragment containing nagD::T7-lac-glmS*54::asn was isolated. Additionally, pKLN07-21 (described previously) was digested with Kpn I and Not I to isolate the fragment containing Kan$^r$ (from pUC4K, previously described) and the temperature sensitive replication origin (from pMAK705). The nagD::T7-lac-glmS*54::asn fragment from pCALG40 and the fragment of Kan$^r$ and temperature sensitive replication origin pKLN07-21 were ligated to generate pCALG43-2.

The plasmid pCALG43-2 was transformed into 7101-17 (DE3) and clones with nagD::T7-lac-glmS*54 in the genome were generated. The correct clones were identified by PCR and confirmed by Southern blot analysis. The clones were also confirmed by the loss of resistance to tetracycline.

For PCR screening for the strains containing nagD::T7-lac-glmS*54::asn a pair of oligonucleotide primers were synthesized. The forward primer GNnagET7glmS 1-5 has the sequence of 5'-CAC GAT AAA CGG TGA AGC CAT GTC G-3' (SEQ ID NO:133.) The reverse primer GNnagET7glmS2-3 has the sequence of 5'-CGT CCA TTT TCT TGA ACG CTT CAT CCC-3' (SEQ ID NO:134.) The forward primer and the reverse primers are located 5' and 3', respectively, of the nagD::Tet$^r$::asn PCR fragment generated from the oligonucleotides GNnagEtetR1-5 (SEQ ID NO:133) and GNnagEtetR2-3 (SEQ ID NO:134). Four strains were identified by PCR and named 7107-321#1, #2, #3, and #4.

To confirm the nagΔ::T7-lac-glmS*54 integration in the 7107-321 strains, genomic DNA was isolated and analyzed by Southern blot using a nagE specific probe under standard conditions. The 7107-321 strains were found to be correct by Southern analysis. Additionally, the absence of nagΔ::Tet$^r$::asn was confirmed due to the inability of the 7107-321 strains to grow on media that contained tetracycline.

To add the manXYZΔ::T7-lac-Sc GNA1 construct, the recombinant pSW07-68 plasmid (described previously) was transformed into each of the 7107-321 strains. Clones with the manXYZΔ::T7-lac-Sc GNA1 integrated into the genome were generated using the temperature selection procedure. Clones were identified by PCR and confirmed by Southern blot analysis. Twelve strains generated the PCR products of the expected size. These strains were named 7107-325#1, #2 and #3, (derived from 7107-321#1); 7107-326#1, #2 and #3, (derived from 7107-321#2); 7107-327#1, #2, and #3 (derived from 7107-321#3); and 7107-328#1, #2, and#3 (derived from 7107-321#4). All these strains were confirmed to be correct by Southern blot analysis using a GNA1 specific probe.

Evaluation of N-Acetylglucosamine Production Strains Capable of Metabolizing Galactose in Shake Flask Experiments N-acetylglucosamine production strains capable of metabolizing galactose (7107-325#1, 7107-326#1, 7107-327#1, and 7107-328#1) were tested in shake flask experiments (Table 34). Strains were tested in flasks containing M9B medium with supplementation of 0.6 g l$^{-1}$ MgSO$_4$-7H$_2$O, and 0.05 g l$^{-1}$ CaCl$_2$-2H$_2$O. Trace metal supplementation of screens 54 and 55 included 0.2 mg l$^{-1}$ FeSO$_4$-7H$_2$O, 0.015 mg l$^{-1}$ ZnSO$_4$-7H$_2$O, 0.015 mg l$^{-1}$ MnSO$_4$—H$_2$O, 0.001 mg l$^{-1}$ CuSO$_4$-5H$_2$O, 0.001 mg l$^{-1}$ NaMoO$_4$-2H$_2$O, 0.001 mg l$^{-1}$ H$_3$BO$_3$, and 0.001 mg l$^{-1}$ CoCl$_2$-6H$_2$O while trace metal supplementation of screens 59 and 66 included 0.5 mg l$^{-1}$ FeSO$_4$-7H$_2$O, 0.38 mg l$^{-1}$ ZnSO$_4$-7H$_2$O, 0.033 mg l$^{-1}$ MnSO$_5$H$_2$O, and 0.01 mg l$^{-1}$ CoCl$_2$-6H$_2$O. As shown in Table 34, various amounts of glucose (Glu), lactose (Lac), yeast extract (YE), and Whey Permeate (WP, Formost Whey, Wisconsin) were used in the flasks. For screens 54 and 55, the cultures were grown at 30° C., with shaking at 225 rpm, for 24 hours and were then placed at 25° C., with shaking at 225 rpm, for the remainder of the experiment. For screens 59 and 66, the cultures were grown at 37° C., with shaking at 225 rpm, for 8 to 10 hours and were then placed at 30° C., with shaking at 225 rpm, for the remainder of the experiment; In screens 59 and 66, at 10 hours pH was adjusted to 7.2 and if the cultures were glucose depleted 20-25 g l$^{-1}$ glucose was added. For all four screens, at 24 and 48 hours, each culture was adjusted to pH 7.2, glucose was added to the flasks to approximately 30 g l$^{-1}$, and 5 g l$^{-1}$ (NH$_4$)$_2$SO$_4$ was added to the cultures in which the level of ammonia had fallen below 1 g l$^{-1}$. In screen 66, at 30 and 54 hours glucose was added if necessary, the pH was adjusted to 7.2, and if the ammonia levels fell below 1 g l$^{-1}$, 2.5 g l$^{-1}$ (NH$_4$)$_2$SO$_4$ was added. For all four screens, samples were collected at 24 and 48 hours and the N-acetylglucosamine and galactose concentrations in the culture supernatant were measured using an HPLC carbohydrate column.

N-acetylglucosamine concentrations in different samples are shown in Table 34. It can be concluded from these experiments that under some conditions integration of T7lac-glmS*54 at the nagΔ site instead of the galK site improves N-acetylglucosamine production. Table 34 also shows galactose concentrations in different cultures. As expected, integration of T7-lac glmS*54 at the nagΔ site instead of the galK site abolished galactose accumulation.

TABLE 34

Levels of N-acetylglucosamine and galactose under different growth conditions

| Shake Flask Screen # | Strain* Number (7107-) | Addition to the medium (g l$^{-1}$) | | | | GlcNAc (g l$^{-1}$) | | | Galactose (g l$^{-1}$) | | |
|---|---|---|---|---|---|---|---|---|---|---|---|
| | | Glu | Lac | YE | WP | 24 hrs | 48 hrs | 72 hrs | 24 hrs | 48 hrs | 72 hrs |
| 54 | Control | 10 | 40 | 5 | 0 | 2.0 | 7.0 | 13.0 | 2.6 | 3.4 | 4.0 |
| | 325#1 | | | | | 3.6 | 9.9 | 14.6 | 0 | 0 | 0 |
| 55 | Control | 10 | 40 | 5 | 0 | 2.4 | 9.6 | 16.0 | 2.9 | 3.3 | 3.5 |
| | 325#1 | | | | | 4.1 | 12.3 | 17.0 | 0 | 0 | 0 |
| | 326#1 | | | | | 4.1 | 11.9 | 16.6 | 0 | 0 | 0 |
| | 327#1 | | | | | 4.1 | 11.4 | 15.2 | 0 | 0 | 0 |
| | 328#1 | | | | | 4.1 | 14.6 | 21.5 | 0 | 0 | 0 |
| 59 | Control | 8 | 20 | 0 | 0 | 11.3 | 20.5 | 26.3 | 1.6 | 2.7 | 3.6 |
| | | | 10 | | 0 | 10.9 | 21.3 | 24.3 | 1.6 | 2.3 | 2.9 |
| | | | 5 | | 0 | 11.8 | 21.3 | 26.2 | 1.6 | 2.2 | 2.0 |
| | | | 2.5 | | 0 | 9.6 | 18.4 | 21.0 | 1.0 | 1.1 | 0.8 |
| | | | 1.25 | | 0 | 10.6 | 18.7 | 22.5 | 0.8 | 0 | 0 |
| | | | 0 | | 10 | 12.3 | 21.7 | 26.3 | 1.8 | 3.1 | 3.5 |
| | | | 0 | | 5 | 10.7 | 21.4 | 27.4 | 1.6 | 2.4 | 2.4 |
| | | | 0 | | 2.5 | 12.6 | 21.7 | 28.3 | 1.5 | 1.4 | 1.2 |
| | 325#1 | | 20 | | 0 | 10.8 | 18.6 | 21.2 | 0 | 0 | 0 |
| | | | 10 | | 0 | 11.6 | 20.6 | 23.6 | 0 | 0 | 0 |
| | | | 5 | | 0 | 11.7 | 20.7 | 24.2 | 0 | 0 | 0 |
| | | | 2.5 | | 0 | 7.4 | 14.0 | 16.1 | 0 | 0 | 0 |
| | | | 1.25 | | 0 | 9.7 | 16.1 | 18.8 | 0 | 0 | 0 |
| | | | 0 | | 10 | 11.2 | 19.2 | 22.2 | 0 | 0 | 0 |
| | | | 0 | | 5 | 11.2 | 19.6 | 22.5 | 0 | 0 | 0 |
| | | | 0 | | 2.5 | 11.8 | 18.9 | 21.3 | 0 | 0 | 0 |

TABLE 34-continued

Levels of N-acetylglucosamine and galactose under different growth conditions

| Shake Flask Screen # | Strain* Number (7107-) | Addition to the medium (g l$^{-1}$) | | | | GlcNAc (g l$^{-1}$) | | | Galactose (g l$^{-1}$) | | |
|---|---|---|---|---|---|---|---|---|---|---|---|
| | | Glu | Lac | YE | WP | 24 hrs | 48 hrs | 72 hrs | 24 hrs | 48 hrs | 72 hrs |
| 66 | Control | 8 | 10 | 0 | 0 | 10.1 | 23.9 | 26.2 | 1.2 | 1.6 | 1.9 |
| | 328#1 | | | | | 12.1 | 26.7 | 28.8 | 0 | 0 | 0 |

*Control: non-galactose user strain 7107-92
All other strains are galactose user siblings
Glu = Glucose, Lac = Lactose, YE = yeast extract, WP = Whey Permeate Evaluation of N-Acetylglucosamine Production Strains Capable of Metabolizing Galactose in 1-Liter Fermentors Strains capable of using galactose (7107-325#1 and 7107-328#1) were compared to galactose-non user (7107-92#1) in 1-liter fermentors. The fermentors were set up with an initial volume of 475 ml with fermentation medium: 4.79 g l$^{-1}$ H$_3$PO$_4$, 3.15 g l$^{-1}$ KOH, 3.56 g l$^{-1}$ citric acid-H$_2$O, 5 l$^{-1}$ (NH$_2$)$_2$SO$_4$, 2.5 g l$^{-1}$ MgSO$_4$-7H$_2$O, 0.05 g l$^{-1}$ CaCl$_2$-2H$_2$O, trace metals (5 mg l$^{-1}$ FeSO$_4$-7H$_2$O, 3.75 mg l$^{-1}$ ZnSO$_4$-7H$_2$O, 0.6 mg l$^{l-1}$ CuSO$_4$-5H$_2$O, and 0.1002 mg l$^{-1}$ CoCl$_2$-6H$_2$O), and 0.25 g l$^{-1}$ Mazu 204 Antifoam. The pH was adjusted to 7.0 using 45% KOH. The pH (6.9) of the medium was maintained using 75% NH$_4$OH, the temperature was maintained at 37° C., and aeration and agitation rates were used to maintain dissolved oxygen at a concentration of 20% saturation. A 65% glucose solution was fed to the cultures with the feed rate controlled by computer program to achieve a growth rate of 0.4 hr$^{-1}$ at inoculation and a maximum rate of 5 ml h$^{-1}$ by 6 hours. Cultures were induced with food grade lactose added at a concentration of 5 g l$^{-1}$ at around 10 hours, with continued glucose feed.

Seven samples were collected at approximately 10, 21, 28, 35, 45, 52, and 60 hours during the fermentation run. For each sample, the N-acetylglucosamine and galactose concentrations, in addition to the concentrations of several other components for the monitoring of the health of the culture, were determined using an HPLC carbohydrate column. As expected, while galactose was detected in the medium from control strain 7107-92#1 (0.6 g l$^{-1}$ in Sample 7), galactose did not accumulate in the media harboring strains 7107-325#1 and 7107-328#1. Expressing GlmS*54 under these conditions, in a strain that is able to consume galactose, does not improve N-acetylglucosamine production. However, the medium used for this fermentation was optimized for 7107-92#1. The galactose-user strains may require somewhat different fermentation conditions for optimal performance. It is likely that a medium could be generated that would allow the 7107-325#1 and 7107-328#1 strains to produce a higher amount of N-acetylglucosamine than 7107-92#1. Therefore, it can be envisioned that integration of the T7-lac-glmS*54 expression cassette at the nagD site instead of at galK site could prove beneficial for N-acetylglucosamine and/or glucosamine production.

Fermentation Process Development for N-Acetylglucosamine Production

Example 30

This Example describes shake flask experiments for optimizing NAG production with strains containing ScGNA1 plasmids.

Having determined that overexpression of the ScGNA1 resulted in high levels of NAG in E. coli glucosamine production strains, the next step was to optimize conditions for the production of NAG. The approach taken was to increase cell density and therefore NAG titers without producing excess acetate in shake flask. Strain 7107-87#25, expressing the ScGNA1 from the T7 promoter of plasmid pET24d(+), was used for initial optimization experiments.

Yeast Extract Addition and Later Induction

Shake flask screening tested the effect of yeast extract addition on growth, acetate accumulation, and NAG production in strain 7107-87#25. It also tested the effect of earlier versus later induction with 0.2 mM IPTG. Strains were grown in M9B medium (previously described), but with the (NH$_4$)$_2$SO$_4$ decreased to 7.5 g l$^1$. The M9B medium was supplemented with 30 g l$^{-1}$ glucose, 0.6 g l$^{-1}$ MgSO$_4$-7H$_2$O, 0.05 g l$^{-1}$ CaCl$_2$-2 H$_2$O, and 25 mg/ml kanamycin. 0.2 mM IPTG was added to all flasks except those for late induction, to which it was added 24 hours after inoculation. To the control flask no yeast extract was added. For the test flasks, yeast extract (ranging from 0.5 to 4.0 g l$^{-1}$) was added at the start or at 24 hours after inoculation. Cultures were grown at 30° C. until 24 hours and then placed at 25° C. At 24 and 48 hours, 5 g l$^{-1}$ (NH$_4$)$_2$SO$_4$ and 20 g l$^{-1}$ glucose were added to each flask and pH was adjusted to 7.2.

As seen in Table 35, addition of yeast extract resulted in increased growth and NAG production. In fact, the flask with 4 g l$^{-1}$ yeast extract added at the start performed the best, achieving 8.9 g l$^{-1}$ NAG, compared with 2.9 g l$^{-1}$ NAG produced in the control flask. However, 3.0 g l$^{-1}$ acetate also accumulated in these flasks. Flasks with yeast extract added after 24 hours grew nearly as well as those with yeast extract added at the start and accumulated less acetate. However, under these conditions NAG production reached only at 4.9 g l$^{-1}$ at 48 hours in the flask with 4 g l$^{-1}$ yeast extract. Moreover, the flasks with later induction grew better than those initially induced with 0.2 mM IPTG, although NAG production was delayed. This suggests that induction of N-acetylglucosamine synthesis has some negative effects on cell growth.

TABLE 35

Effect of yeast extract addition and later induction on growth, acetate accumulation, and NAG production in strain 7107-87#25.

| Conditions | | | | |
|---|---|---|---|---|
| Yeast Extract (g l$^{-1}$) | Time of yeast extract addition | OD$_{600}$ | Acetate (g l$^{-1}$) | GlcNAc (g l$^{-1}$) |
| IPTG added at the start: | | | | |
| None (control) | | 2.7 | 0 | 2.9 |
| 0.5 | Start (0 hr) | 3.2 | 0 | 2.1 |
| 1.0 | Start (0 hr) | 4.0 | 0 | 2.9 |
| 2.0 | Start (0 hr) | 5.7 | 1.9 | 5.0 |
| 4.0 | Start (0 hr) | 8.4 | 3.0 | 8.9 |

TABLE 35-continued

Effect of yeast extract addition and later induction on growth, acetate accumulation, and NAG production in strain 7107-87#25.

| Conditions | | | | |
|---|---|---|---|---|
| Yeast Extract (g l$^{-1}$) | Time of yeast extract addition | OD$_{600}$ | Acetate (g l$^{-1}$) | GlcNAc (g l$^{-1}$) |
| 0.5 | 24 hr | 2.3 | 0 | 2.4 |
| 1.0 | 24 hr | 2.7 | 0 | 2.8 |
| 2.0 | 24 hr | 4.2 | 0 | 3.5 |
| 4.0 | 24 hr | 6.3 | 0 | 4.9 |
| IPTG added at 24 hours: | | | | |
| None | | 6.6 | 2.8 | 0 |
| 2.0 | Start (0 hr) | 6.9 | 4.0 | 3.1 |

1) Results taken from 48-hour timepoint.

Addition of Various Sugars and Yeast Extract

Shake flask screening was conducted to evaluate the effect of various sugars with yeast extract on growth, acetate accumulation, and NAG production in strain 7107-87#25. Strains were grown in M9B medium (previously described), but with the (NH$_4$)$_2$SO$_4$ decreased to 7.5 g l$^{-1}$. The M9B medium was supplemented with 0.6 g l$^{-1}$ MgSO$_4$-7H$_2$O, 0.05 g l$^{-1}$ CaCl$_2$-2H$_2$O, and 25 mg/ml kanamycin. Due to the positive effects of yeast extract seen in previous experiment, 5 g l$^{-1}$ yeast extract was included in all flasks. 0.2 mM IPTG and varying mixes and concentrations of the sugars lactose, glucose, fructose, and ribose were added to the flasks as indicated in Table 36. It is important to note that strain 7107-87#25 grown in the presence of lactose does not require IPTG for induction, as it is lactose-inducible. Cultures were grown at 30° C. for 24 hours and then shifted to 25° C.

At about 24 hours, the pH of each culture was adjusted to 7.2. 5 g l$^{-1}$ (NH$_4$)$_2$SO$_4$ was added to each flask and glucose was added to about 30 g l$^{-1}$ per day total based on HPLC results. At 32.5 hours, 15 g l$^{-1}$ glucose, 2.5 g l$^{-1}$ ribose, and 2.5 g l$^{-1}$ (NH$_4$)$_2$SO$_4$ were added to flask 7. At 48 hours, 10 g l$^{-1}$ glucose was added to each flask. An additional 2.5 g l$^{-1}$ ribose and 5.0 g l$^{-1}$ (NH$_4$)$_2$SO$_4$ was added to flask 7 at 49.5 hours. Samples were from the flasks at about 24, 48, and 72 hours to monitor OD$_{600}$, N-acetyl glucosamine levels, and acetate levels.

TABLE 36

Effect of various sugar mixes on growth, acetate accumulation, and NAG production in strain 7107-87#25.

| | Conditions | | | | | |
|---|---|---|---|---|---|---|
| Flask | Glucose (g l$^{-1}$) | Other sugars (g l$^{-1}$) | IPTG (mM) | OD$_{600}$ | Acetate (g l$^{-1}$) | GlcNAc (g l$^{-1}$) |
| 1 | 0 | lactose (40) | 0 | 10.0 | 2.5 | 9.0 |
| 2 | 10 | lactose (30) | 0 | 13.5 | 0 | 13.7 |
| 3 | 0 | None | 0.2 | 11.0 | 4.7 | 12.3 |
| 4 | 0 | fructose (30) | 0.2 | 5.0 | 0 | 9.1 |
| 5 | 0 | ribose (20) | 0.2 | 11.0 | 4.8 | 10.6 |
| 6 | 15 | fructose (15) | 0.2 | 11.0 | 4.4 | 14.8 |
| 7 | 20 | ribose (10) | 0.2 | 13.5 | 3.1 | 27.0 |

1) Results taken from 72-hour timepoint.
2) Yeast extract (5.0 g l$^{-1}$) was included in all flasks.

Results shown in Table 36 indicate that three sugars (lactose, glucose and ribose) supported growth well and resulted in significant accumulation of NAG. Flasks containing fructose did not achieve a high OD$^{600}$, although NAG titer reached 9.1 g l$^{-1}$. Initial inclusion of glucose in flasks containing fructose or lactose improved growth as well as NAG titer. However, the best result was achieved in the flask initially containing both glucose and ribose.

Literature describes E. coli isolates incapable of growing on NAG or GlcN (J. Bac., 1970, 101:384-391). The authors speculated that the accumulation of amino sugar phosphates may inhibit the reactions catalyzed by phosphohexose isomerase and glucose-6-phosphate dehydrogenase, resulting in pentose starvation. Addition of pentoses or gluconate reversed the growth inhibition of the mutants. NAG-producing strain 7107-87#25 may also accumulate amino sugar phosphates (GlcN-6-P and/or GlcNAc-6-P), thereby resulting in pentose starvation. If this is the case, addition of ribose or gluconate should result in improved growth and NAG production. Indeed, growth and N-acetylglucosamine were improved by addition of ribose. In this experiment, the flask containing 20 g l$^{-1}$ glucose plus 10 g l$^{-1}$ ribose produced the highest level of NAG, achieving 27 g l$^{-1}$. This is twice the amount produced in the flask containing 30 g l$^{-1}$ glucose. Growth was also improved in the flask containing both ribose and glucose Glucose and Ribose Levels Previous experiments indicated that the addition of ribose to flasks containing glucose has a significant positive effect on NAG production in strain 7107-87#25. Shake Flask Screen #35 was conducted to test the effect of different glucose/ribose mixes on growth and NAG production. Strain 7107-87#25 was grown in M9B medium (previously described), supplemented with 0.6 g l$^{-1}$ MgSO$_4$-7H$_2$O, 0.05 g l$^{-1}$ CaCl$_2$-2H$_2$kanamycin, 0.2 mM IPTG, and 5.0 g l$^{-1}$ yeast extract. Varying mixes of glucose and ribose were added to each flask as listed in Table 37. Cultures were grown at 30° C. for 24 hours and then shifted to 25° C. At about 24 and 48 hours, the pH of the flasks was adjusted to 7.2. An addition of 5 g l$^{-1}$ (NH$_4$)$_2$SO$_4$ was made to all flasks at 24 hours. An additional 2.5 g l$^{-1}$ (NH$_4$)$_2$SO$_4$ was added to flasks 4 through 9 and an additional 5.0 g l$^{-1}$ (NH$_4$)$_2$SO$_4$ was added to flasks 10 through 15 at 29 hours. At about 48 hours, 5 g l$^{-1}$ (NH$_4$)$_2$SO$_4$ was added to flasks 7 through 9, and 2.5 g l$^{-1}$ (NH$_4$)$_2$SO$_4$ was added to flasks 10 through 15. Glucose was added to adjust the glucose level to about 30 g l$^{-1}$ at 24 and 48 hr. Samples were removed from the flasks at about 24, 29, 48, and 72 hours to monitor OD$_{600}$, N-acetyl glucosamine levels, and acetate levels. Selected flasks were harvested at 72 hours for enzyme analysis.

As seen on Table 37, glucose concentration did not significantly affect NAG production, as long as there was residual glucose. On the other hand, as little as 5 g l$^{-1}$ ribose resulted in a large increase in NAG levels, reaching about 30 g l$^{-1}$ by 72 hours in flasks 4, 5, and 6 compared to about 14 g l$^{-1}$ in flasks without ribose. The best results were seen with 10 g l$^{-1}$ ribose. In these flasks NAG levels reached about 36 g l$^{-1}$ at 72 hours. Growth was also positively affected in cultures containing ribose. Enzyme analysis from selected flasks revealed that ribose addition did not directly affect GlmS or GNA1 activity, as activity levels for both enzymes were the same with or without ribose in the medium. This suggests that the effect of ribose addition was most likely a result of the relief from the shortage in pentose phosphate pathway intermediates.

TABLE 37

Effect of glucose and ribose on growth, acetate accumulation, and NAG production in strain 7107-87#25.

| | Conditions | | | | | Enzyme Activity ($\mu$mol min$^{-1}$ mg$^{-1}$ protein) | |
|---|---|---|---|---|---|---|---|
| Flask | glucose (g l$^{-1}$) | ribose (g l$^{-1}$) | OD$_{600}$ | Acetate (g l$^{-1}$) | GlcNAc (g l$^{-1}$) | GlmS | GNA1 |
| 1 | 20 | None | 12.5 | 5.4 | 14.0 | | |
| 2 | 30 | None | 13.0 | 5.4 | 14.7 | | |
| 3 | 40 | None | 12.8 | 5.5 | 14.5 | 0.114 | 7.8 |
| 4 | 20 | 5 | 15.6 | 0 | 28.1 | | |
| 5 | 30 | 5 | 14.5 | 2.9 | 30.6 | | |
| 6 | 40 | 5 | 14.5 | 3.1 | 29.0 | 0.140 | 7.9 |
| 7 | 20 | 10 | 16.0 | 2.8 | 35.2 | | |
| 8 | 30 | 10 | 14.5 | 0 | 37.1 | | |
| 9 | 40 | 10 | 15.0 | 0 | 36.4 | 0.105 | 8.0 |
| 10 | 20 | 15 | 15.5 | 4.3 | 31.3 | | |
| 11 | 30 | 15 | 16.5 | 0 | 33.4 | | |
| 12 | 40 | 15 | 16.0 | 0 | 34.0 | 0.101 | 8.2 |
| 13 | 20 | 20 | 15.0 | 4.4 | 30.0 | | |
| 14 | 30 | 20 | 15.0 | 4.7 | 26.3 | | |
| 15 | 40 | 20 | 16.0 | 4.5 | 28.4 | 0.121 | 7.7 |

1) Results obtained from 72-hour timepoint.
2) Yeast extract (5.0 g l$^{-1}$) was included in all flasks.

Ribose and Other Intermediates of the Pentose Phosphate Pathway

In light of the positive results seen with cultures grown in glucose and ribose, Shake Flask Screen #36 was conducted to determine the effect of several other 5-carbon sugars and gluconate on growth and NAG production. Strain 7107-87#25 was grown in M9B medium (previously described) supplemented with 0.6 g l$^{-1}$ MgSO$_4$-7H$_2$O, 0.05 g l$^{-1}$ CaCl$_2$-2H$_2$O, 5.0 g l$^{-1}$ yeast extract, 25 mg/ml kanamycin, and 0.2 mM IPTG. Glucose, ribose, xylose, arabinose, and gluconic acid (potassium salt) were added to flasks as indicated in Table 38. Cultures were grown at 30° C. for 24 hours and then shifted to 25° C. At 24 and 48 hours, pH was adjusted to 7.2. At about 24 hours, glucose was added to about 30 g l$^{-1}$ per day total based on HPLC results from the 24 hours sample. 5 g l$^{-1}$ (NH$_4$)$_2$SO$_4$ was also added to all flasks. 10 g l$^{-1}$ additional ribose was added to flasks 11 and 12 at both 24 and 48 hours, and 5 g l$^{-1}$ ribose was added to flasks 3 and 4 at 48 hours. An additional 10 g l$^{-1}$ gluconic acid was added to flask 10 at 28.5 hours. At about 48 hours, glucose was added to adjust glucose levels to about 30 g l$^{-1}$. Additionally, 5 g l$^{-1}$ (NH$_4$)$_2$SO$_4$ was added to flasks 11 and 12. Samples were removed from the each flask at about 24, 30, 48, 54 and 72 hours to monitor OD$_{600}$, N-acetyl glucosamine levels, and acetate levels. Selected flasks were harvested at 72 hours for enzyme analysis.

TABLE 38

Effects of 5-carbon compounds and glucuronic acid on growth and N-acetylglucosamine production.

| | Conditions | | | | | Enzyme Activity ($\mu$mol min$^{-1}$ mg$^{-1}$ protein) | |
|---|---|---|---|---|---|---|---|
| Flask | glucose (g l$^{-1}$) | Other sugars (10 g l$^{-1}$) | OD$_{600}$ | Acetate (g l$^{-1}$) | GlcNAc (g l$^{-1}$) | GlmS | GNA1 |
| 1 | 30 | None | 11.0 | 4.5 | 14.6 | .230 | 11.4 |
| 2 | 40 | None | 12.5 | 4.8 | 15.0 | | |
| 3 | 30 | Ribose | 14.0 | 1.6 | 29.1 | .215 | 12.5 |
| 4 | 40 | Ribose | 14.0 | 1.2 | 30.8 | | |
| 5 | 30 | Xylose | 12.0 | 4.1 | 17.1 | .211 | 12.5 |
| 6 | 40 | Xylose | 11.5 | 4.1 | 17.0 | | |
| 7 | 30 | Arabinose | 12.5 | 3.2 | 20.3 | .180 | 11.4 |
| 8 | 30 | Arabinose | 12.5 | 3.3 | 20.4 | | |
| 9 | 30 | Gluconic acid | 12.0 | 4.0 | 24.3 | .190 | 9.0 |
| 10 | 40 | Gluconic acid | 13.0 | 3.8 | 22.1 | | |
| 11 | 30 | Ribose + ribose | 13.0 | 2.8 | 25.0 | | |
| 12 | 40 | Ribose + ribose | 13.0 | 3.0 | 24.9 | | |

1) Results are from 72-hour timepoint.
2) Additional ribose (10 g l$^{-1}$) was added to flasks 11 and 12 at 24 and 48 hours.
3) Yeast extract (5.0 g l$^{-1}$) was included in all flasks.

Addition of pentoses and gluconic acid resulted in increased NAG titer and improved growth when compared with the control (FIG. 18). These cultures also contained lower acetate levels than the control. However, the addition of ribose resulted in the highest NAG production. Gluconic acid is less expensive than the other sugars, and is therefore attractive for use at industrial scale. Because gluconic acid addition resulted in increased NAG production compared to the control strain, this experiment confirms its potential value in relieving pentose starvation in industrial fermentations. Enzyme activity levels from selected flasks indicate that the dramatic effect of ribose and gluconate on N-acetylglucosamine production can not be attributed to an influence on the activity of GlmS or GNA1. As seen in shake flask screening comparing the effects of different levels of glucose/ribose on growth and production, activity levels are similar with or without ribose in the culture medium.

Example 31

This example describes experiments conducted in 1-liter fermentors to optimize NAG production using the strain 7107-87 #25 which contained ScGNA1 plasmids.

Timing of IPTG Induction:

A fermentation experiment was conducted to evaluate induction with IPTG from the beginning and after 24 hours of growth (cell mass at about 13 g l$^{-1}$). Growth was greatly inhibited by early induction, which also led to very low NAG titers (<5 g/l) compared to late induction (50 g l$^{-1}$ by 70 hours) as shown in FIG. 19. It is believed that the growth was inhibited because amino sugar phosphates accumulated in the cell inhibited specific enzymes of the pentose phosphate pathway. This hypothesis is supported by findings of positive effects of pentose phosphate intermediates on cell growth and NAG production.

Effect of Pentose Phosphate Pathway (PPP) Intermediates:

Fermentors were inoculated with cells at three different densities: low (OD=20), intermediate (OD=30) and high (OD=40). The later induction scheme was used (induction at about 24 hrs after inoculation. Higher cell density inoculation led to higher NAG production. Regardless the inoculation cell density, addition of ribose showed improved NAG production, even with a late induction scheme.

Example 32

This example describes different fermentation experiments to optimize NAG production using strains containing integrated ScGNA1 constructs. In previous experiments with strains containing ScGNA1 plasmids, IPTG had to be used to induce NAG production since lactose was very inefficient. With integrated ScGNA1 constructs NAG production could be induced effectively by lactose addition.

Lactose Induction:

The development of the strain, 7107-92 #1 which contained one copy of the ScGNA1 construct integrated in the chromosome allowed for development of the lactose induction process for NAG production. In light of shake flask results showing growth inhibition by early IPTG induction, a later induction scheme was tested in fermentors. Cells were first inoculated and grown to approximately 15 and ~20 g $l^{-1}$ cells. Lactose was then fed to 10, 20, or 30 g $l^{-1}$ for 7 hrs during the period glucose feeding was stoped. Later, glucose feed was re-instated for continued growth and NAG production. It was found that lactose levels as low as 10 g $l^{-1}$ were effective, reaching to 50 g $l^{-1}$ NAG by 78 hours.

Because the separate lactose feeding method introduces complexity to the process, an experiment was carried out to evaluate different options: lactose feed of 10 g $l^{-1}$ with discontinued glucose feed, IPTG induction with continued glucose feed, and a single point addition of 10 g $l^{-1}$ lactose with and without discontinuation of the glucose feed. Another variable tested was an extended lactose feed to 40 g $l^{-1}$, followed by a glucose feed. The single point lactose addition was as effective as other induction strategy. All achieved a NAG production level between 45-55 g $l^{-1}$. Even though the glucose feed was continuous, its concentration was still limiting to the cells (consumed as quickly as it was added). Because the lac operon is normally repressed by the presence of glucose, the limiting feed rate of glucose apparently allowed for non-repressive conditions for lactose induction. The use of a single point lactose addition greatly simplified the process.

An experiment evaluated the level of single point lactose induction (1.25 to 10 g $l^{-1}$) after an initial growth period. A two-point induction (5 g $l^{-1}$ each time) was also tried. Lactose as low as 1.25 g $l^{-1}$ was very effective, reaching titers near 100 g $l^{-1}$ NAG. However, the lactose induction at 5 g $l^{-1}$ reached NAG levels over 100 g $l^{-1}$. Therefore, lactose induction at 5 g $l^{-1}$ was applied in further tests as a safe level. The two-point induction was also effective, even resulting in faster initial NAG production rates, but the final titer did not exceed that of single point induction with 5 or 10 g $l^{-1}$ lactose.

Effect of Higher Operating pH and Temperature:

The use of lower temperature and pH were key factors in stabilizing the GLcN fermentation, primarily due to the labile nature of GLcN at higher pH and temperature. However, it was shown that NAG was stable at neutral pH. Fermentation for NAG production was operated in the pH range of 6.7 to 7.0 throughout the program. Experimental data showed that NAG was stable for at least 50 hours after the cessation of glucose feed at 37° C. and pH 7.0.

The relatively low temperatures (30° C. and 25° C.) used in the GLcN process are expensive and difficult to maintain at industrial scale. Moreover, cell growth rate is much lower at 30° C. than at 37° C. The use of 30° C. temperature requires a relatively long period to achieve the biomass required for high NAG production. Therefore, a trial was conducted at 37° C. to evaluate four different growth rates before induction. In this way, the required biomass could be achieved earlier, resulting in an overall more productive process. All fermentors were induced at 10 hours, opposed to the 22 to 24 hours required at 30° C., and all performed well, achieving over 100 g $l^{-1}$ NAG within 50 hours, and some achieving nearly 120 g $l^{-1}$ by 70 hours. From this point forward, 37° C. was used as the growth and production temperature.

Effect of Glucose Feeding Rate:

A nominal rate of 6 g $l^{-1}$ $hr^{-1}$ (based on volume after inoculation) was used in most trials. To see if the rate of NAG production was limited by glucose restriction, higher glucose feed rates were tested. Increasing the feed rate to 7.5 g $l^{-1}$ $hr^{-1}$ led to faster initial rates of NAG production, but the final titers were not higher or reached faster. Further increasing the feed rate to 9.5 g $l^{-1}$ $hr^{-1}$ showed even faster initial rates of NAG production. However, these cultures appeared to stop production much earlier and actually had decreased final titer (85 to 65 g $l^{-1}$ NAG). In the same experiment, slow feed rate (6 g $l^{-1}$ $hr^{-1}$) allowed for NAG levels of 100 g $l^{-1}$. From this time point forward, glucose feed rate was kept at 6.5 g $l^{-1}$ $hr^{-1}$ in NAG fermentation.

Effect of Phosphate Level:

The fermentation medium contains as much as 30 g $l^{-1}$ total potassium phosphate salts. High phosphate salt level presented a significant problem for recovery as most of the salt is unused by the cells, and has to be removed during product purification. In the NAG process, the high phosphate level was shown not to be critical. The total phosphates were reduced by four times to 7.5 g $l^{-1}$ with little effect on NAG production. This phosphate level was used in subsequent experiments.

Importance of Magnesium and Iron:

Magnesium and iron are two required nutrients to achieve higher biomass and stabilize the culture. In the GLcN process, the iron level was seen as a critical factor. A certain level was needed to achieve higher biomass and lactose induction, but too much iron resulted in higher acetate and lower GLcN levels. The iron level determined for the GLcN process was 3 mg $l^{-1}$ $FeSO_4$-$7H_2O$ in the medium with additional iron fed by including $FeSO_4$-$7H_2O$ in glucose feed (5 µg $g^{-1}$ glucose). The same iron level was selected for initial NAG production experiments. Iron addition to the glucose feed complicates the process. Therefore, effort was made to evaluate the effects initial iron concentrations and iron feeding. Effects of magnesium feed were also studied.

Results of the first experiment showed that levels of 5 to 10 mg $l^{-1}$ $FeSO_4$-$7H_2O$ led to comparable NAG production levels, and that the iron level may not be as critical as in the GLcN process. A follow up study with iron, magnesium showed that iron wasn't absolutely necessary in the feed. Magnesium in the feed may have stabilizing effects. This test was conducted at the high feed rate of 7.5 g $l^{-1}$ $hr^{-1}$, and another follow up test at 6.5 g $l^{-1}$ $hr^{-1}$ showed that both could be removed from the feed without significant reduction of productivity.

While the importance of both iron and magnesium was recognized, removal of them from the feed was desirable from point of simplifying production process. Therefore iron and magnesium were deleted from the glucose feed and iron held at an initial concentration of 5 mg l$^{-1}$ FeSO$_4$-7H$_2$O. Magnesium had been added at an initial rate of 0.6 g l$^{-1}$ MgSO$_4$-7H$_2$O, and if used in the glucose feed at a rate of 5 to 10 mg g$^{-1}$ glucose.

Magnesium was also recognized as important to the culture and should not be limiting. Magnesium can be sequestered by phosphate under certain sterilization conditions (excessive heat, exposure time, and pH), becoming unavailable to the organism as insoluble magnesium phosphate salt precipitates. A flask study using excess magnesium or limiting magnesium showed that the level was indeed critical to NAG production, and that addition of the magnesium after sterilization was desirable to reduce precipitation effects, if the magnesium level was higher. A fermentation experiment was conducted to compare magnesium addition before and after sterilization. Results showed that cultures with magnesium added before sterilization performed poorly.

The initial magnesium level was then nearly doubled to 1 g l$^{-1}$ MgSO$_4$-7H$_2$O, and studies showed that this level could be used if added after sterilization or if increased levels of citric acid was added and the medium acidified before sterilization. This had very positive implications for simplification of the protocol. The acidification also allowed for all trace elements to be added before sterilization. Thus, a medium preparation protocol was developed, in which all components except glucose can be added before sterilization. The acidification of the medium initially was achieved by using phosphoric acid instead of potassium phosphate salts to supply phosphorus. pH was adjusted to required operating pH (7.0) after sterilization with potassium hydroxide, which also supply potassium to the medium. However, this method introduced unnecessarily high amount of potassium. The protocol was further modified by using monobasic potassium phosphate to acidify the medium and adjusting pH with ammonium hydroxide after sterilization. This even further simplified the protocol by allowing for removal of ammonium sulfate from the medium.

Trace Element Removal and Importance of Zinc:

The trace element package originally consisted of salts of the following elements, added in μg to mg/l quantities: iron, zinc, manganese, copper, cobalt, molybdenum, and boron. Molybdenum and boron presented toxicity issues if found in the final product, and the effects of some other elements were not known. Therefore single deletion experiments were conducted to determine which if any could be removed. The first trial showed that both molybdenum and boron deletion had no significant negative effect on NAG production, so these were removed from further experiments. Cobalt deletion may have also had a positive effect, but was not deleted because this recognized as a necessary for full function of vitamin B$_{12}$, and a follow up study showed no effect on deletion.

Results showed a positive effect of removing zinc on NAG production. Further studies confirmed that complete zinc restriction resulted in lower biomass levels, and significantly higher NAG levels, up to 118 g l$^{-1}$ NAG by 60 hours (FIG. 20). This was especially interesting because higher initial iron levels, up to 10 mg l$^{-1}$ FeSO$_4$-7H$_2$O could even be used.

Example 33

This Example describes preferred fermentation protocols for NAG production. The fermentation protocol is shown below.

| | |
|---|---|
| Strain: | Recombinant *E. coli* |
| Induction: | 5 to 10 g l$^{-1}$ lactose added in a single point addition after a cell density of 15 to 20 g l$^{-1}$ is reached. Glucose feed is not suspended during this procedure, but remains steady at 6.5 g l$^{-1}$ hr$^{-1}$ (based on initial volume). |
| Feed: | 65% glucose without any amendments, glucose fed at limiting concentrations |
| Fermentation Time: | 60 to 72 hours |
| Fermentation Mode: | Fed Batch, with 65% glucose added as required, maintain limiting concentrations of glucose |
| Inoculum: | 2.5% to 5% by volume |
| pH: | 6.9 throughout, controlled with 12 N NH$_4$OH |
| Temperature: | 37 C. throughout |
| Oxygen: | Dissolved O$_2$ at 20% or greater, controlled by agitation |
| Aeration: | 0.5 to 1 vvm |
| Medium: | |

| Component | Concentration (amount per liter) |
|---|---|
| KH$_2$PO$_4$ | 6.67 g |
| Citric acid | 3.25 g |
| CaCl$_2$—H$_2$O | 0.05 g |
| MgSO$_4$—7H$_2$O | 2.5 g |
| FeSO$_4$—7H$_2$O | 5 mg |
| ZnSO$_4$—7H$_2$O | 3.8 mg |
| MnSO$_4$—H$_2$O | 0.33 mg |
| CuSO$_4$—5H$_2$O | 0.1 mg |
| CoCl$_2$—6H$_2$O | 0.1 mg |
| Glucose | >200 g, as needed |
| Mazu 204 defoamer | 0.25 g |

All components are added before sterilization except glucose (added incrementally). Initial pH is near 3.0 after sterilization and adjusted to 6.9 with NH$_4$OH before inoculation.

Example 34

This Example describes purification of N-acetylglucosamine by double crystallization.

Fermentation broth was subject to cell removal by filtration and micro-filtration. Depending on the fermentation conditions, the percentage of N-acetylglucosamine in the dissolved solid ranged from 70 to 87% (w, on a dry solids basis). Therefore, the crude N-acetylglucosamine product must be purified. This can be done by a combination of cation and anion deionization steps to increase N-acetylglucosamine purity in the crude broth. Different crystallization protocols can also be used. The following Examples describe different experiments to establish protocols and conditions for the purification of N-acetylglucosamine. As demonstrated, N-acetylglucosamine of ≧98% pure was obtained using methods described in Examples 34, 35, 36, 40 and 41. The purity was further increased by the method described in Example 37.

N-acetylglucosamine was determined by liquid chromatography using a Supelcosil LC-18-DB (250×4.6 mm, 5 μm) column (obtained from Supelco, Bellefonte, Pa.) and a mobile phase of 10% (v) acetonitrile at 1 ml min$^{-1}$. N-acetylglucosamine was measured at 210 nm using a commercial N-acetylglucosamine (Sigma, ≧99%) as external standard. The detector showed a linear response up to 5 g l$^{-1}$ N-acetylglucosamine when the injection volume was 4

μL. Samples and standard were routinely prepared at approximately 3 g l$^{-1}$ and were injected at least twice. The deviation in peak area was less than 2% from the average values.

Activated carbon (100 mesh G-60, available from Norit Americas, Atlanta, Ga.) was added to a fermentation sample (30 g/L) containing 70% (w) N-acetylglucosamine in the dissolved solid and the mixture was stirred at room temperature for an hour followed by filtration using medium filter paper. The filtrate showed reduced color and was pale yellowish brown. The amount of solid was measured and the percentage of N-acetylglucosamine in the solid was 75% (w).

The carbon treated sample obtained above containing 77.5 g dissolved solid (58.1 g of which as N-acetylglucosamine) was concentrated at 45° C.-50° C. under vacuum to 51% (w) solid (calculated from sample weight assuming there was no loss of solid during concentrating). It was left at room temperature with occasional mixing for 2 hours. The precipitate was collected by filtration on medium filter paper and redissolved in 100-ml water. The solids content was then determined to be 19.7% (w) solid (total solid 26.2 g).

The redissolved sample was concentrated again to 44% (w) dissolved solid. Approximately 2 mg pure N-acetylglucosamine powder was added and the sample was mixed on a shaker at room temperature for 2 hours. The precipitate was collected by filtration and washed with ethanol (twice without suspending the solid and twice by suspending it). The white solid was dried at room temperature under vacuum until the weight stayed constant to afford 5.32 g product (98% N-acetylglucosamine, 9% overall recovery).

Example 35

This Example describes purification of N-acetylglucosamine by single crystallization from 50° C.

Another batch of fermentation sample containing 87% (w) N-acetylglucosamine in the dissolved solid was treated with activated carbon as described in Example 34. The amount of dissolved solid was measured and the percentage of N-acetylglucosamine in the solid was 88% (w). The carbon treated sample containing 80.5 g solid (71 g of which as N-acetylglucosamine) was concentrated at 45° C.-50° C. under vacuum to 45% (w) solid (calculated from the weight assuming there was no loss of solid during concentrating) and shaken at room temperature for 16 hours. The precipitate was collected by filtration on medium filter paper and washed with ethanol (twice without suspending the solid and twice by suspending it). After drying under vacuum, 33.2 grams of white solid was obtained (100% pure N-acetylglucosamine, 47% recovery).

Example 36

This Example describes purification of N-acetylglucosamine by single crystallization from 70° C.

Partially purified N-acetylglucosamine could be obtained by one crystallization of a carbon treated fermentation sample (see Example 34). The purity of N-acetylglucosamine ranged from 86% to 90% depending on the degree of concentrating before crystallization and the initial percentage of N-acetylglucosamine in the dissolved solid.

A solid sample containing 86% or 90% N-acetylglucosamine was mixed with water to 44% (w) solid. The mixture was heated at 70° C. with occasional mixing to dissolve. It was then left at room temperature for approximately 16 hours. The crystals were collected by filtration and washed with ethanol (twice without suspending the solid and twice by suspending it). After drying at room temperature under vacuum, the product contained 99% N-acetylglucosamine (24-30% recovery).

Example 37

This Example describes N-acetylglucosamine purification by cation exchange treatment.

Decolorized fermentation broth was used as the input feed to a cation exchange column. The column was 1.6×15 cm, and contained 20 g DOWEX™ Monosphere 88 resin (available from Dow Corp., Midland, Mich.) in the hydrogen form. The experiments were done using a Pharmacia FPLC™ setup (available from Amersham Biosciences, Piscataway, N.J.) at 4° C. Input feed was about 76% N-acetylglucosamine on a solids basis, conductivity of 10.5 mS/cm, and pH was about 6.5. The material was pumped at a rate of 1 ml/minute. Initial output pH was about 2.3. As the column capacity was reached pH rose and eventually was the same as that of the input feed. Conductivity decreased from around 10.5 mS/cm to around 2.5 mS/cm at about 125 ml. Conductivity then increased with the rise in pH. N-acetylglucosamine purity, measured on a solids basis, also increased rapidly while the pH remained around 2.5. Purity increased to about 85% N-acetylglucosamine. Purity decreased as column capacity became exhausted, and was essentially the same as the input stream by 200 ml. N-acetylglucosamine purity is increased by cation treatment.

Example 38

This Example describes N-acetylglucosamine purification by anion exchange treatment. N-acetylglucosamine broth, which has been decolorized and treated with the cation exchange resin, was used as input material for the anion exchange resin-Dow Monosphere 77. Experimental conditions were as described above for the cation exchange resin experiments. Input feed was about 81% N-acetylglucosamine on a solids basis, conductivity of 3.8 mS/cm, and pH was about 3.0. Output pH rose quickly to around 8.0, and later fell to about 3.8 at 250 ml. Conductivity quickly decreased to less than 1 mS/cm, and stayed at that level throughout the run. N-acetylglucosamine purity increased and remained significantly higher as well. N-acetylglucosamine purity increased to about 87% N-acetylglucosamine from an input stream purity of about 81%.

The combined cation and anion treatments provide a simple method to significantly increase N-acetylglucosamine purity in the crude broth based on a total dry solids basis.

Example 39

This Example describes treatment of fermentation broth with activated carbon and mixed-bed ion exchange.

Fermentation samples were first treated with activated carbon as described in Example 34 and then by mix-bed ion exchange resin AG501-X8(D) (from Bio-Rad, Hercules, Calif.) in a column based on the manufacturer's recommendation. Samples were slowly loaded and flow was driven by gravity. The amount of sample load was to exhaust two thirds of the bed as indicated by the blue indicator changing to gold. Samples containing initially 70% (w) and 87% (w) N-acetylglucosamine in the dissolved solid showed a final N-acetylglucosamine purity of 89% (w) and 93% (w), respectively, in the dissolved solid.

Example 40

This Example describes stabilization of purified N-acetyl-glucosamine.

A sample N-acetylglucosamine (98% pure) generated by crystallization described above turned light brown in 2 hours at 105° C. and lost 4.7% weight. This color change and weight loss upon heating can be eliminated using one of the following treatments (described below) involving isopropyl alcohol (IPA). It has been demonstrated that IPA (isopropyl alcohol) is a useful reagent in the precipitation of N-acetyl-glucosamine and in the removal of sample darkening at 105° C. However, it is very likely that a skilled person can choose other organic solvents that are miscible with water such as acetonitrile or ethanol to replace IPA and achieve the same effect.

Preheat Followed by Water/IPA Precipitation

A sample (0.30 g) was heated at 105° C. for 2.5 hours. After cooling to room temperature, 0.7 ml water was added to form a yellow suspension. IPA (2.8 ml) was added and the mixture was stirred for 2 hours. The precipitation was collected by filtration and washed twice with IPA by suspending the solid. The mother liquor was pale yellow. The solid was dried under vacuum till the weight was constant (0.18 g, 60% recovery).

Soak Treatment in 80:20 or 85:15 IPA/Water (v/v)

A sample was stirred in 80:20 or 85:15 (v/v) IPA/water at 5 or 12 ml solvent mixture/gram solid for 3 hours or overnight. Recovery (same procedure as above) ranged from 56 to 67%.

Dissolution and Precipitation with IPA

A sample (0.50 g) was dissolved in 2.27 ml water. PA (12.86 ml, IPA/water=85:15 v/v) was added and the mixture was stirred at room temperature over night. Recovery procedure (56%) was the same as above.

Dissolution in Water, Followed with Concentration and Precipitation with IPA

A sample (89.6 g) was dissolved in water to 20% solid (w/w). It was concentrated at 45-50° C. under vacuum. A precipitation started to form when the concentration of solid reached approximately 42% (w/w). It was further concentrated to 55% solid (calculated based on the total sample weight assuming there is no loss of solid during concentrating). IPA was added (IPA/water=85:15 v/v) and it was stirred overnight. The solid was collected by filtration and washed twice with IPA by suspending the solid. The mother liquor was concentrated to dryness to afford 13 g wet solid that was subsequently suspended in 20 ml 85:15 IPA/water (v/v). It was filtered and washed twice with IPA. The wet solid was combined with the solid obtained after the first filtration and dried under vacuum until a constant weight was obtained (82.1 g, 98% N-acetylglucosamine, 92% recovery).

Example 41

This Example describes purifying N-acetyl glucosamine with IPA.

IPA is used to purify N-acetylglucosamine in order to obtain higher recovery. A mixture of PA and water (probably from 70:30 to 85:15 v/v ratio) is used to precipitate N-acetyl-glucosamine while keeping all the impurities in solution. The purified N-acetylglucosamine thus obtained shows no darkening at 105° C. The required amount of this solvent mixture depends on the amount of impurity in the initial sample and its solubility.

Example 42

This Example describes purifying N-acetyl glucosamine with ethanol. A 95% pure NAG sample (40 g) was dissolved in 160-ml water. Ethanol (640 ml) was slowly added while the mixture was stirred. The suspension was stirred at room temperature overnight. The solid was collected by filtration and washed twice by suspending it in ethanol. Drying under vacuum afforded 16.12 g white solid (98% NAG with 42% recovery of NAG). This material showed no darkening at 105° C. in two hours. Any skilled in the art can use other water miscible solvents such as IPA, acetonitrile, or methanol to replace ethanol to achieve the same result.

Example 43

This Example demonstrates processes for the chemical hydrolysis of N-acetylglucosamine to glucosamine.

It is anticipated that N-acetylglucosamine produced by fermentation can be recovered and purified in the form of N-acetylglucosamine as the final product. N-acetylglucosamine produced by fermentation can also be chemically converted to glucosamine before or after being isolated and purified. Simple pilot experiments were conducted to demonstrate chemical conversion of N-acetylglucosamine to glucosamine. In the first experiment N-acetylglucosamine (10 g/l in M9A medium without glucose) was hydrolyzed at 100° C. with various levels of hydrochloric acid. In a parallel experiment, glucosamine was subjected to the same treatments to determine its stability under hydrolysis conditions. Results are shown in FIGS. 21 and 22.

Conversion of N-acetylglucosamine to glucosamine was determined by monitoring the amount of glucosamine generated by the hydrolysis reaction. Glucosamine was determined by an HPLC method based on that described by Way et al. (Journal of Liquid Chromatography and Related Technologies, 23:2861, 2000). Some specific details of the HPLC method are given below: column: Phenomenex prodigy ODS(3) C 18-5 µm (available from Phenomenex, Torrance, Calif.), 150×4.6 mm; mobile phase: methanol: aqueous buffer (4:1, v:v) containing 10 mM sodium acetate, 10 mM sodium octanesulfonate, pH 5.1; flow rate: 0.7 ml per min; detector: refractive index detector at 30° C.

FIG. 21 demonstrates quantitative conversion of N-acetylglucosamine to glucosamine when heated at sufficiently low pH (<1). At higher pH, either no hydrolysis occurred, or the glucosamine formed was degraded. FIG. 22 shows that glucosamine was stable with heating at a pH of 1.0 or lower. At higher pH a significant amount of glucosamine was lost.

Acid hydrolysis of N-acetylglucosamine using 1.0 N hydrochloric acid (pH<1) was examined at different temperatures. Both the amount of remaining N-acetylglucosamine and the amount of formed glucosamine were monitored. N-acetylglucosamine was measured by HPLC using a standard carbohydrate system. Some specific details are given below: column: Bio-Rad HPX-87H, 7.8 mm×300 mm; mobile phase: 0.1% $HNO_3$ in $H_2O$: flow rate: 0.8 ml per min; detector: refractive index detector at 30° C. Glucosamine was measured using the ion pair HPLC column as described above. N-acetylglucosamine (20 g/l) in M9A medium (described previously herein) acidified with 1 N hydrochloric acid to pH<1.0 was incubated at 35° C., 60° C., or 100° C. Results are shown in FIG. 23. At 100° C. conversion was complete by 2.5 hours. No significant degradation of the glucosamine formed was observed. At lower temperatures, some hydrolysis was observed, but this was much slower.

In a parallel experiment, glucosamine (20 g/l) was incubated with 1 N hydrochloric acid at different temperatures as above. No degradation was observed after 24 hours of incubation as measured by HPLC (data not shown).

In summary, it is clear that N-acetylglucosamine can easily be chemically converted to glucosamine and that glucosamine, the hydrolysis product, is very stable under the hydrolysis conditions used in these experiments.

Acid hydrolysis of N-acetyl glucosamine to glucosamine is a key step in the whole glucosamine production process. Therefore, hydrolysis experiments were conducted using crystallized N-acetyl glucosamine material from fermentation or purified N-acetyl glucosamine.

Example 44

This Example describes deacetylation of N-acetylglucosamine at high hydrochloric acid concentrations and short times.

Acid hydrolysis of N-acetylglucosamine at 90° C. was performed. N-acetylglucosamine (10% and 20% w/v) in hydrochloric acid (12% and 16%— diluted by volume from 37%) solutions were used. A series of 12-ml glass screw capped tubes with Teflon lined caps were employed. Each tube represented a separate time point (0, 15, 30, 45, 60, 90 minutes) and contained 2 ml of the N-acetylglucosamine/hydrochloric acid solution. Tubes were heated in a heating block equilibrated at 90° C. Tubes were removed at appropriate times and quick cooled in ice water. Appropriate dilutions were made in and samples analyzed by HPLC for glucosamine and N-acetylglucosamine. FIG. 24 shows the disappearance of N-acetylglucosamine and the formation of glucosamine. Kinetics of N-acetylglucosamine disappearance were essentially the same for all four solutions. Hydrolysis is very rapid at 90° C. By 30 minutes about 95% of the N-acetylglucosamine had been hydrolyzed in all four cases. After 45 minutes less than 1% of the initial concentration of N-acetylglucosamine remained. No N-acetylglucosamine was detected at 60 or 90 minutes. After 1 hour at 90° C., N-acetylglucosamine was no longer detected even with 20% N-acetylglucosamine. FIG. 24 also shows formation of glucosamine in the tubes containing 10% glucosamine. No large loss of glucosamine was observed after 90 minutes.

Example 45

This Example describes deacetylation of N-acetylglucosamine at high hydrochloric acid concentrations for a long period (24 hrs).

Glucosamine degradation was examined at 90° C. and 100° C. using 5% and 10% glucosamine hydrochloride (w/w) with 12% and 20% hydrochloric acid by weight. Samples were incubated from 1-24 hours and assayed enzymatically for ammonia using glutamate dehydrogenase. Glucosamine refers to glucosamine hydrochloride. All percentages are w/w. Glucosamine degradation is based on ammonia formation. Percent degradation was essentially the same for 5% and 10% solutions. Degradation was significantly higher with higher acid concentration. Similar trends were seen for the 100° C. experiment. The 10 degree temperature increase clearly greatly increases glucosamine degradation.

Example 46

This Example describes chemical deacetylation of N-acetylglucosamine at high hydrochloric acid concentrations (30%).

N-acetylglucosamine was hydrolyzed to glucosamine at 90° C. using the hybridization oven. The reaction was carried out inside a screw capped glass tube. The 30% hydrochloric acid (30 g) was preincubated at 90° C. for 1 hour. After this 10 g solid N-acetylglucosamine was added, quickly dissolved, and a $T_o$ sample taken. Samples were taken at 30-minute intervals over the next three hours. The solution rapidly turned dark orange/brown within 30 minutes. This darkening was noticeably faster than that previously observed with lower acid concentrations. By 45-60 minutes significant solid glucosamine was observed, converting the mixture into a slurry of glucosamine hydrochloride in hydrochloric acid. Samples were analyzed for ammonia enzymatically. Results are shown in FIG. 25. FIG. 25 also shows data from the glucosamine degradation experiments done at 90° C. using lower concentrations of hydrochloric acid. Degradation of N-acetylglucosamine is significant, and based on ammonia levels is around 3.5% at 3 hours. This is clearly much higher than that observed using glucosamine in 12% or 20% hydrochloric acid.

Example 47

This Example describes enzymatic deacetylation of N-acetylglucosamine.

Enzyme processes to hydrolyze N-acetylglucosamine in the fermentation broth or after its recovery are described below. Three types of enzymes are candidates: N-acetylglucosamine-6-P deacetylase (EC 3.5.1.25, NagA), N-acetylglucosamine deacetylase (EC 3.5.1.33), chitin deacetylase and acyl transferases.

N-Acetylglucosamine-6-P Deacetylase and N-Acetylglucosamine Deacetylase

There are enzymes that have been shown to deacetylate N-acetylglucosamine. Roseman reported enzyme activity that catalyzed deacetylation of N-acetylglucosamine (EC 3.5.1.33) in *E. coli*, *Bacillus cadaveris* and *Streptococcus* (Roseman S. 1957. J. Biol. Chem., 226:115-124). A Japanese group (Yamano, Fujishima et al, Osaka National Research Institute, Agency of Industrial Science and Technology) studied the N-acetylglucosamine deacetylases from a chitinase-producing bacterium *Vibrio cholerae* non-O1 and a marine bacterium *Alteromonas*. Preparation, properties and use of both N-acetylglucosamine-6-P deacetylase and N-acetylglucosamine deacetylases from specified native organisms were disclosed in the following patents and publications: Fujishima S. et al., 1996, entitled N-acetylglucosamine 6-phosphate deacetylase, JP9234064A2; Fujishima S. et al., 1997, entitled Process for producing N-acetylglucosamine-6-phosphate deacetylase, U.S. Pat. No. 5,744,325; and Fujishima et al., 1996, entitled Process for producing N-acetyl-D-glucosamine deacetylase, EP 0 732 400 B1, which are incorporated herein by reference in their entirety.

The deacetylases described by Fujishima et al. were identified as N-acetylglucosamine-6-P deacetylases (EC 3.5.1.25, NagA). Their affinity and efficacy with N-acetylglucosamine 6-P were much higher than with N-acetylglucosamine. However, N-acetylglucosamine-6-P deacetylase purified from *E. coli* does not act on N-acetylglucosamine.

The enzyme N-acetylglucosamine-6-P deacetylase (EC 3.5.1.25, NagA) is well known for its role of converting N-acetylglucosamine-6-P to glucosamine-6-P, a necessary step in the cellular metabolism of N-acetylglucosamine, N-acetylmannosamine and neuraminic acid. Normally, this enzyme such the recombinant E. coli NagA protein is not active on non-phosphorylated N-acetylglucosamine. DNA sequences coding for the N-acetylglucosamine 6-P deacetylase (nagA gene) were determined in many different organisms. It is not know if there exists a deacetylase that is only active on N-acetylglucosamine (thus distinctive from NagA).

Chitin Deacetylase

Chitin deacetylase (EC 3.5.1.41) catalyzes deacetylation of the N-acetylglucosamine units in chitin, resulting in chitosan. Chitin deacetylase activity is usually determined by using as substrate glycol chitin (partially O-hydroxyethylated chitin) radiolabeled in N-acetyl groups. The enzyme also acts on mycrocrystalline chitin and carboxymethylchitin (soluble derivative). However, it was reported that chitin deacetylase from Mucor rouxii does not deacetylate N-acetylglucosamine monomer or 2-3 oligomers (Araki and Ito, 1975. Eur. J. Biochem. 55:71-78, which is incorporated herein by reference in its entirety). Although there were no indications that normal chitin deacetylase deacetylate glucosamine monomer, chitin deacetylase variants with such activity could be isolated from nature or created in vitro.

Deacetylation of N-acetylglucosamine could be carried out by a deacetylase contained in or isolated from organisms with a native deacetylase or organisms with a recombinant deacetylase. Recombinant deacetylases could be improved by random or directed mutagenesis.

The following describe experiments of N-acetylglucosamine hydrolysis using N-acetylglucosamine deacetylase and/or N-acetylglucosamine-6-P deacetylase.

Acyl Transferases

A number of acyl transferases can remove the acetyl group from a substrate and transfer it to another substrate (Konecny, et al.). Although there were no indications that such enzymes can deacetylate N-acetylglucosamine, acyl trnasferase variants with such activity could be isolated from nature or generated in vitro.

Deacetylation of N-acetylglucosamine could be carried out by an acyl transferase contained in or isolated from organisms with a native acyl transferase or organisms with a recombinant acyl transferase. Recombinant acyl transferase could be improved by random or directed mutagenesis and/or by protein engineering.

Defining Enzymatic Hydrolysis Conditions

Native or recombinant cells expressing a deacetylase are grown under standard conditions or optimized conditions. N-acetylglucosamine hydrolysis is carried out using whole cells, crude enzyme extracts or purified enzymes as catalysts. First, 0.3 ml of 10% solution of N-acetylglucosamine is added as substrate to 0.1 ml of 200 mM phosphate buffer solution (pH 4.5, 5.0, 5.5, 6.0, 6.5, 7.0, 7.5 and 8.0). Secondly, 0.1 ml of an enzyme solution is added. The reaction mixture is incubated at 25, 30, 35, 40, 45 and 50° C. for 30, 60 and 120 min. The formation of the hydrolysis product, glucosamine, is determined by a HPLC method. The remaining substrate, N-acetylglucosamine, is monitored by a different HPLC method. Both HPLC methods were described in previous Examples.

Hydrolysis of N-Acetylglucosamine Produced in Fermentation

N-acetylglucosamine in the fermentation broth or after its recovery is hydrolyzed using crude enzyme extracts or purified deacetylase as catalysts under conditions defined above. Glucosamine is recovered by crystallization in a hydrochloric acid solution and washed by ethanol, methanol or isopropyl alcohol.

Example 48

This Example describes hydrolysis of high purity N-acetylglucosamine.

The apparatus for this test consisted of a 1 liter round bottom vessel heated with a heating mantel. The ingredients, 150 grams of water, 21 g of 98% N-acetylglucosamine and 238 grams of 36.7% hydrochloric acid, were mixed together and added to the reaction vessel. The stirred reaction mix was heated up to 70° C. and mixed for 3 hours at which time the mixture was transferred to a beaker and cooled to 20° C. Few crystals were present. The mixture was transferred back into the reaction vessel and 10 grams of N-acetylglucosamine added. The reactor was reheated to 70° C. and reacted for 3 hours, cooled to 4° C. overnight. The crystals present were filtered and washed with ethanol, vacuum dried and assayed (20 g of glucosamine hydrochloride at 99.9%). The filtrate was transferred back into the reaction vessel and 10 g of N-acetylglucosamine were added. The reactor was again heated to 70° C., reacted for 3 hours, cooled overnight to 4° C., filtered, ethanol washed, vacuum dried and assayed (16.1 g of glucosamine hydrochloride at 99.6%). The filtrate was again returned to the reactor, 41.5 grams added and the reaction cycle repeated. Thirty-three grams of glucosamine hydrochloride resulted from the $4^{th}$ cycle with an assay of 99.5%. The total yield was 86% with all the glucosamine hydrochloride produced 99+in assay and white in color. This material did not need recrystallization.

Example 49

This Example describes hydrolysis of low purity N-acetylglucosamine.

This test repeated the conditions of Example 47 using N-acetylglucosamine concentrated and dried from fermentation broth. The solids contained 52% N-acetylglucosamine. Three cycles were performed. The glucosamine hydrochloride produced was darker with each cycle. The first two samples had assays of 99.7% and 99.4% and would not require recrystallization. The third sample had an assay of 97.7% and was darker in color and would require recrystallization. The overall yield was 71%. The final filtrate was brownish-black as opposed to the translucent light brown color of the Example 48 final filtrate.

Example 50

This Example describes hydrolysis of fermentation broth concentrated to 21.8% N-acetylglucosamine.

The apparatus for this test consisted of a 4-liter jacketed glass vessel. Water was used to heat the reaction vessel to the required temperature. Two thousand ml of concentrated fermentation broth, containing 218 g/l N-acetylglucosamine, was added to the reaction vessel. Fifteen hundred ml of 36.7% hydrochloric acid was added. The reaction vessel was stirred under vacuum and heated to 70° C. The reaction proceeded for 90 minutes with 310 ml of condensate being collected. The reaction mixture was cooled to 4° C. and filtered. The solids were washed with 265 ml of ethanol and dried. The conversion based on N-acetylglucosamine analysis in the broth and filtrate was 89.5%. The washed glucosamine hydrochloride was dissolved in water, to give a 1550-ml of solution. Fifteen grams of Darco G-60 activated carbon was added to the solution. After mixing for 30 minutes, the solution was filtered; colorless filtrate resulted. The filtrate was vacuum evaporated at 50° C. with a vacuum of 55-cm Hg. The solids were ethanol washed and dried. The overall yield was 82%.

Example 51

This Example describes hydrolysis of low purity N-acetylglucosamine with extra rinsing steps.

The purpose of this test was to determine if extra washing steps after hydrolysis would produce a high purity product that would not require recrystallization. The apparatus used in Example 49 without the condensate recovery was used. Dried fermentation broth containing 54% N-acetylglucosamine was added to 20% hydrochloric acid. The acid to N-acetylglucosamine ratio was 2.5:1. The reaction conditions for this series were 80° C. for 103 minutes. The wet cake after filtration was washed with 500 g of water, 529 g of 37% acid and 407 g of ethanol. The goal was to determine if extra washing could produce a product that required no re-crystallization. The glucosamine hydrochloride crystals were still slightly tan and still required re-crystallization. The overall yield was 70%, with 7% yield loss due to the first water wash. The acid wash resulted in a 1% yield loss while the ethanol wash attributed 1.6% loss.

Example 52

This Example describes carbon treatment during hydrolysis of N-acetylglucosamine.

Activated carbon is used after hydrolysis and before recrystallization to remove impurities. This test involved adding activated carbon to the hydrolysis solution prior to the reaction. A total of 34 g of Darco G-60 activated carbon was added to the N-acetylglucosamine and hydrochloric acid reaction mixture and mixed for 30 minutes then filtered and added to the reactor. A 1000-g water rinse of the activated carbon was added to the reactor. The resulting glucosamine hydrochloride was lighter, but still required recrystallization. The reaction conditions were 80° C. for 60 minutes. The overall yield of 29% was low due to dilution of the reaction media by the additional water, which reduced the initial hydrochloric acid concentration to 14%.

Example 53

This Example describes hydrolysis of low purity N-acetylglucosamine.

The reaction condition used for this Example was a temperature of 90° C. for 30 minutes. A 3:1 ratio of 30% hydrochloric acid to N-acetylglucosamine was used. The apparatus used in Example 49 was used here. The hydrolysis yield was 86%. The raw glucosamine hydrochloride was re-dissolved in water; treated with activated carbon, filtered and vacuum crystallized at 50° C. and 60 cm HG. The final assay was 99.7% with an overall yield of 58%.

Example 54

This Example describes carbon treatment during hydrolysis of N-acetylglucosamine.

A second test using activated carbon treatment of the hydrolysis solution was attempted. The reaction conditions were those used in Example 52 except that 50 g of activated carbon was added to the hydrolysis mix, filtered and the activated carbon rinsed with 1,000 g of water. The reaction was conducted at 90° C. for 30 minutes with a 3:1 ratio of 20% hydrochloric acid to N-acetylglucosamine. No improvement in color over the results described in Example 52 was apparent. As with the previous test with activated carbon before hydrolysis, acid was added during filtration and cooling to decrease the solubility and improve yield. The final yield was 36% with an assay of 98.4%.

Example 55

This Example describes hydrolysis of high-purity N-acetylglucosamine.

The purpose of this Example was to determine if high quality glucosamine could be produced without requiring recrystallization from high quality N-acetylglucosamine at 90° C. Using the apparatus of Example 49, 320 grams of N-acetylglucosamine were mixed with 941 grams of 30% w/w hydrochloric acid. The mixture was added to the jacketed vessel and was then heated to 90° C. The reaction was allowed to occur during the heating time and for and additional 47 minutes while holding at 90° C. After cooling to 20° C., the wet cake was filtered, washed with ethanol and vacuum dried at 50° C. The overall yield was 71%, which is consistent with a single use of hydrolysis liquor. The glucosamine hydrochloride produced was white with a black tint and required recrystallization.

Example 56

This Example describes hydrolysis of impure N-acetylglucosamine.

The same procedures described in Example 54 were carried out, using solid N-acetylglucosamine isolated from fermentation broth. The purity of the N-acetylglucosamine solids was 48%. A mixture containing 1,411 grams of N-acetylglucosamine were reacted with 4,236 grams of 30% w/w hydrochloric acid at 70° C. for 3 hours and then cooled to 20° C. The wet cake after filtration was washed with ethanol and vacuum dried at 50° C. The overall yield was 90%.

Example 57

This Example describes hydrolysis of high purity N-acetylglucosamine.

Hydrolysis was performed using a 2:1 ratio of 36.7% hydrochloric acid to pure N-acetylglucosamine. Using the apparatus of Example 49, 2,004 grams of N-acetylglucosamine were reacted with 4,009 grams of 36.7% w/w hydrochloric acid at 80° C. for 58 minutes and then cooled to 20° C. The wet cake after filtration was not washed, but left to dry overnight at room temperature. The final cake contained 6% hydrochloric acid and 75.2% glucosamine hydrochloride. The reaction mixture was fairly viscous with black solids on the sides of the reactor. The overall yield was 70%.

Example 58

This Example describes hydrolysis of high purity N-acetylglucosamine using recycled hydrochloric acid.

One of the ways to increase the overall recovered glucosamine hydrochloride yield is to recycle the hydrolysis mother liquor. After the hydrolysis reaction, the mixture is cooled and filtered. The filtrate is weighed and recycled back into the reactor. Fresh 36.7% hydrochloric acid is added to make up the difference in weight between the initial acid weight and the returned filtrate. This series involved reacting a 2.5:1 ratio of 36.7% hydrochloric acid to N-acetylglucosamine at 80° C. for 60 minutes. The hydrochloric acid was added to a 74° C. reactor containing pure, solid N-acetylglucosamine. The reaction mixture was heated to temperature and reacted for 60 minutes, then cooled to 20° C. and filtered. Glucosamine hydrochloride solids were recovered by filtration after this first use of the hydrochloric acid, and the yield was measured at 88%. The filtrate was weighed and returned to the reactor. A second and equal quantity of solid N-acetylglucosamine was added along with enough 36.7% hydrochloric acid to return the acid weight to the level of the first reaction cycle. The reaction was repeated for the same time and temperature for this second use of the acid, and after cooling and filtration, the recovered yield was 105%, indicating some of the glucosamine hydrochloride left in solution from the first acid cycle was recovered during the second cycle filtration. A third cycle was performed in the same manner as the second, with a recovered yield of 60%. The overall recovered yield for the three cycles was 87%. The filtrate from the third cycle was saved for future cycles.

Example 59

This Example describes chromatographic purification of N-acetylglucosamine.

To purify N-acetyl glucosamine, chromatography using the DOWEX™ Monosphere 99/K resin was performed. The resin was used to pack a 2.6×23 cm column. Column bed volume was about 120 ml, with a void volume estimated at 35 ml (measured by draining liquid from the column using a syringe). For these experiments, broth deionized by treatment with cation and anion resins was used. This input material had a N-acetylglucosamine concentration of about 75.7 g/l, total solids of about 83.4 g/l, giving a purity of around 91%. Conductivity was around 0.1 mS/cm.

In the first experiment, 30 ml of sample was pumped through the column at 2 ml/min. It was clear that N-acetylglucosamine interacted in some manner with the resin. N-acetylglucosamine was not detected until about 60 ml, and eluted in a very broad peak centered on 90 ml, far past the void volume. N-acetylglucosamine purity also varied greatly, with the highest value of about 94.5% N-acetylglucosamine at 90 ml. Purity measured in this narrow region was higher than that of the input material. Variability for the purity values obtained were about 2-3%. In fractions containing lower concentrations of N-acetylglucosamine, purity fell off rapidly above 125 ml and below 75 ml.

A second experiment using the same column was performed. Here a smaller 5-ml sample was applied at a slower flow rate of 1 ml/min. Results are similar to those seen with the larger sample and faster flow rate. The only difference is the peak of N-acetylglucosamine centers around 80 ml rather than 90 ml.

N-acetylglucosamine purity measured as percent of total solids varied significantly during the run. This suggested some chromatographic separation or differences in interaction from N-acetylglucosamine between the resin and the other, presumably nonionic compounds present. If the other compounds were interacting with the resin in a manner identical to N-acetylglucosamine, N-acetylglucosamine should have been present at the same level of purity in all fractions containing N-acetylglucosamine, which was not the case.

The resin used in this Example is then converted to the calcium form using methods known in the art and the same procedure, as outlined above, is used.

Example 60

This Example describes simultaneous hydrolysis of high-purity N-acetylglucosamine and acetic acid removal.

The major coproduct from aqueous hydrochloric acid hydrolysis of N-acetylglucosamine was acetic acid, which has a relatively high boiling point and was not easily removed during the hydrolysis step. Providing an alcohol, such as ethanol or methanol, during the hydrolysis step results in esterification of acetic acid, forming ethyl- or methyl acetate respectively as a coproduct that was removed more readily due to a reduced boiling point. Removing the coproduct, the major impurity present in spent hydrolysate, permitted extending the number of reuses of the hydrochloric acid in the hydrolysis solution.

A mixture of 173 grams of methanol, 189.4 grams of 36.7 w % aqueous hydrochloric acid, and 201 grams of N-acetylglucosamine was added to a stirred, heated glass vessel and mixed under reflux at 65° C. A sample was taken at 1 hour. The analysis showed 8.3% glucosamine hydrochloride, 11.6% hydrochloric acid and no significant amount of acetic acid by titration. The reaction was stopped after 2 hours and cooled to 20° C. The solids were rinsed with methanol and dried. The initial yield of glucosamine hydrochloride was 25.6%. The hydrolysate was then cooled overnight at 4° C., and filtered. Another 10% glucosamine hydrochloride yield was obtained. The purity of the initial solids was 85%. No acetic acid was present in the filtrate.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to produce N-acetylglucosamine-6-phosphate or N-acetylglucosamine by fermentation, comprising:
   a) culturing in a fermentation medium a microorganism that is transformed with at least one recombinant nucleic acid molecule comprising a nucleic acid sequence encoding a glucosamine-6-phosphate acetyltransferase that has an amino acid sequence that is at least 95% identical to SEQ ID NO:30; and
   b) collecting a product produced from the step of culturing which is selected from the group consisting of N-acetylglucosamine-6-phosphate and N-acetylglucosamine.

2. The method of claim 1, wherein the recombinant nucleic acid molecule further comprises a non-native promoter.

3. The method of claim 1, wherein the glucosamine-6-phosphate acetyltransferase has the amino acid sequence of SEQ ID NO:30.

4. The method of claim 1, wherein expression of the recombinant nucleic acid molecule is inducible.

5. The method of claim 4, wherein expression of the recombinant nucleic acid molecule is inducible by lactose.

6. The method of claim 5, wherein the microorganism further comprises a partial or complete deletion or inactivation of a gene encoding a LacI repressor protein.

7. The method of claim 1, wherein the microorganism further comprises a partial or complete deletion of an endogenous gene encoding a glucosamine-6-phosphate deaminase.

8. The method of claim 1, wherein the step of culturing includes the step of maintaining the carbon source at a concentration of from about 0.5% to about 5% in the fermentation medium.

9. The method of claim 1, wherein the step of culturing is performed in a fermentation medium comprising yeast extract.

10. The method of claim 1, wherein the step of culturing is performed in a fermentation medium comprising a carbon source selected from the group consisting of glucose, fructose, a pentose sugar, lactose and gluconic acid.

11. The method of claim 10, wherein the pentose sugar is selected from the group consisting of ribose, xylose, and arabinose.

12. The method of claim 1, wherein the step of culturing is performed in a fermentation medium comprising glucose and ribose.

13. The method of claim 1, wherein the step of culturing is performed in a fermentation medium comprising glucose and gluconic acid.

14. The method of claim 1, wherein the step of culturing is performed at a temperature of from about 25° C. to about 45° C.

15. The method of claim 1, wherein the step of culturing is performed at about 37° C.

16. The method of claim 1, wherein the step of culturing is performed at a pH of from about pH 4 to about pH 7.5.

17. The method of claim 1, wherein the step of culturing is performed at a pH of from about pH 6.7 to about pH 7.5.

18. The method of claim 1, wherein the step of culturing is performed at a pH of from about pH 4.5 to about pH 5.

19. The method of claim 1, wherein the microorganism is a bacterium or yeast.

20. The method of claim 1, wherein the microorganism is a bacterium.

21. The method of claim 20, wherein the bacterium is a bacterium from a genus selected from the group consisting of: *Escherichia, Bacillus, Lactobacillus, Pseudomonas* and *Streptomyces*.

22. The method of claim 20, wherein the bacterium is a bacterium from a species selected from the group consisting of: *Escherichia coil, Bacillus subtilis, Bacillus licheniformis, Lactobacillus brevis, Pseudomonas aeruginosa* and *Streptomyces lividans*.

23. The method of claim 1, wherein the microorganism is a yeast.

24. The method of claim 1, further comprising the step of contacting the fermentation medium with at least one ion exchange resin.

25. The method of claim 23, wherein the yeast is a yeast from a genus selected from the group consisting of: *Saccharomyces, Candida, Hansenula, Pichia, Kluveromyces*, and *Phaffia*.

26. The method of claim 23, wherein the yeast is a yeast from a species selected from the group consisting of: *Saccharomyces cerevisiae, Schizosaccharomyces pombe, Candida albicans, Hansenula polymorpha, Pichia pastoris, P. canadensis, Kluyveromyces marxianus* and *Phaffia phodozyma*.

27. The method of claim 1, wherein the microorganism is transformed with a recombinant nucleic acid molecule comprising a nucleic acid sequence encoding a bacterial or yeast phosphoglucoisomerase.

28. The method of claim 27, wherein the phosphoglucoisomerase comprises the amino acid sequence of SEQ ID NO:105.

29. The method of claim 1, wherein the microorganism further comprises a partial or complete deletion of an endogenous gene encoding a phosphofructokinase.

30. The method of claim 1, wherein the microorganism has been transformed with a recombinant nucleic acid molecule comprising a nucleic acid sequence encoding a bacterial or yeast glutamine synthetase.

31. The method of claim 30, wherein the glutamine synthetase comprises the amino acid sequence of SEQ ID NO:89.

32. The method of claim 1, wherein the microorganism has been transformed with a recombinant nucleic acid molecule comprising a nucleic acid sequence encoding a bacterial or yeast glucose-6-phosphate dehydrogenase.

33. The method of claim 32, wherein the glucose-6-phosphate dehydrogenase comprises the amino acid sequence of SEQ ID NO:95.

34. The method of claim 1, wherein the microorganism further comprises a partial or complete deletion of at least one endogenous gene encoding an enzyme involved in glycogen synthesis selected from the group consisting of: ADP-glucose pyrophosphorylase, glycogen synthase and a branching enzyme.

35. The method of claim 1, further comprising recovering an intracellular product from the microorganism selected from the group consisting of: intracellular glucosamine-6-phosphate, glucosamine-1-phosphate, N-acetylglucosamine-1-phosphate, and glucosamine.

36. A method to produce N-acetylglucosamine-6-phosphate, N-acetylglucosamine, glucosamine or glucosamine HCl by fermentation, comprising:
    culturing in a fermentation medium a microorganism that is transformed with at least one recombinant nucleic acid molecule comprising a nucleic acid sequence encoding a glucosamine-6-phosphate acetyltransferase that has an amino acid sequence that is at least 95% identical to SEQ ID NO: 30; and
    collecting a product produced from the step of culturing which is selected from the group consisting of N-acetylglucosamine-6-phosphate and N-acetylglucosamine;
    and wherein the method further comprises a step selected from the group consisting of:
    (a) purifying N-acetylglucosamine from the fermentation medium;
    (b) dephosphorylating N-acetylglucosamine-6-phosphate to produce N-acetylglucosamine; and
    (c) treating N-acetylglucosamine to produce a glucosamine product selected from the group consisting of: glucosamine and glucosamine HCl.

37. The method of cliam 36, wherein step (c) comprises hydrolyzing N-acetylglucosamine under acid and heat conditions or by enzymatic deacetylation.

38. The method of claim 1, wherein N-acetylglucosamine produced by the fermentation method is recovered by precipitating N-acetylglucosamine-containing solids from the fermentation broth.

39. The method of claim 1, wherein N-acetylglucosamine produced by the fermentation method is recovered by crystallizing N-acetylglucosamine-containing solids from the fermentation broth.

40. A method to produce N-acetylalucosamine-6-phosphate or N-acetylglucosamine by fermentation, comprising:
    a) culturing in a fermentation medium a microorganism that expresses:
        i) a recombinant nucleic acid molecule encoding a glucosamine-6-phosphate acetyltransferase that has an amino acid sequence that is at least 95% identical to SEQ ID NO:30; and
        ii) a recombinant nucleic acid molecule encoding a glucosamine-6-phosphate synthase that has an amino acid sequence that is at least 95% identical to the amino acid sequence selected from the group consisting of: SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20; and
    b) collecting a product produced from the step of culturing which is selected from the group consisting of N-acetylglucosamine-6-phosphate and N-acetylglucosamine.

41. The method of claim 40, wherein the glucosamine-6-phosphate acetyltransferase has the amino acid sequence of SEQ ID NO:30.

42. The method of claim 40, wherein the glucosamine-6-phosphate synthase has the amino acid sequence of SEQ ID NO:6.

43. A method to produce N-acetylalucosamine-6-phosphate or N-acetylglucosamine by fermentation, comprising:
    a) culturing in a fermentation medium an *E. coli* that expresses:
        i) a recombinant nucleic acid molecule encoding a glucosamine-6-phosphate acetyltransferase that is at least 95% identical to the amino acid sequence of SEQ ID NO:30; and
        ii) a recombinant nucleic acid molecule encoding a glucosamine-6-phosphate synthase that is at least 95% identical to the amino acid sequence of SEQ ID NO:6; and b) collecting a product produced from the step of culturing which is selected from the group consisting of N-acetylglucosamine-6-phosphate and N-acetylglucosamine.

44. The method of claim 43, wherein the *E. coli* further comprises a partial or complete deletion of the pfkA gene.

45. The method of claim 44, wherein the *E. coli* further comprises a partial or complete deletion of the nagA, nagB, and nagE genes.

46. The method of claim 44, wherein the *E. coli* further comprises a partial or complete deletion of the manXYZ gene.

47. The method of claim 44, wherein the recombinant nucleic acid molecules of (a)(i) and (a)(ii) are inducible by lactose or galactose.

48. The method of claim 44, wherein the step of culturing is performed in a fermentation medium comprising glucose and fructose.

49. The method of claim 40, wherein the microorganism further comprises a partial or complete deletion of an endogenous gene encoding a phosphofructokinase.

50. The method of claim 49, wherein the microorganism further comprises a partial or complete deletion of endogenous genes encoding N-acetylglucosamine-6-phosphate deacetylase, glucosamine-6-phosphate deaminase, and N-acetyl-glucosamine-specific enzyme $II^{Nag}$.

51. The method of claim 49, wherein the microorganism further comprises a partial or complete deletion of an endogenous gene encoding mannose transporter EIIM,P/$III^{Man}$.

52. The method of claim 49, wherein the recombinant nucleic acid molecules of (a)(i) and (a)(ii) are inducible by lactose or galactose.

53. The method of claim 49, wherein the step of culturing is performed in a fermentation medium comprising glucose and fructose.

54. The method of claim 40, wherein the glucosamine-6-phosphate synthase has an amino acid sequence that is at least 95% identical to SEQ ID NO:4.

55. The method of claim 40, wherein the glucosamine-6-phosphate synthase has an amino acid sequence that is at least 95% identical to SEQ ID NO:6.

56. The method of claim 40, wherein the glucosamine-6-phosphate synthase has an amino acid sequence that is at least 95% identical to SEQ ID NO:8.

57. The method of claim 40, wherein the glucosamine-6-phosphate synthase has an amino acid sequence that is at least 95% identical to SEQ ID NO:10.

58. The method of claim 40, wherein the glucosamine-6-phosphate synthase has an amino acid sequence that is at least 95% identical to SEQ ID NO:12.

59. The method of claim 40, wherein the glucosamine-6-phosphate synthase has an amino acid sequence that is at least 95% identical to SEQ ID NO:14.

60. The method of claim 40, wherein the glucosamine-6-phosphate synthase has an amino acid sequence that is at least 95% identical to SEQ ID NO:16.

61. The method of claim 40, wherein the glucosamine-6-phosphate synthase has an amino acid sequence that is at least 95% identical to SEQ ID NO:18.

62. The method of claim 40, wherein the glucosamine-6-phosphate synthase has an amino acid sequence that is at least 95% identical to SEQ ID NO:20.

63. The method of claim 40, wherein the microorganism is a bacterium or yeast.

64. The method of claim 40, wherein the microorganism is a bacterium.

65. The method of claim 40, wherein the microorganism is a yeast.

66. The method of claim 43, wherein the glucosamine-6-phosphate acetyltransferase has the amino acid sequence of SEQ ID NO:30.

67. The method of claim 43, wherein the glucosamine-6-phosphate synthase has the amino acid sequence of SEQ ID NO:6.

* * * * *

(12) EX PARTE REEXAMINATION CERTIFICATE (9972nd)
United States Patent
Deng et al.

(10) Number: US 7,332,304 C1
(45) Certificate Issued: Dec. 6, 2013

(54) PROCESS AND MATERIALS FOR PRODUCTION OF GLUCOSAMINE AND N-ACETYLGLUCOSAMINE

(75) Inventors: Ming-De Deng, Manitowoc, WI (US); J. David Angerer, Hockessin, DE (US); Don Cyron, Lincoln University, PA (US); Alan D. Grund, Manitowoc, WI (US); Thomas A. Jerrell, Jr., Manitowoc, WI (US); Candice Leanna, Green Bay, WI (US); Owen Mathre, Wilmington, DE (US); Reinhardt Rosson, Manitowoc, WI (US); Jeff Running, Manitowoc, WI (US); Dave Severson, Two Rivers, WI (US); Linsheng Song, Manitowoc, WI (US); Sarah Wassink, Sheboygan, WI (US)

(73) Assignee: Arkion Life Sciences LLC, Wilmington, DE (US)

Reexamination Request:
No. 90/012,527, Sep. 13, 2012

Reexamination Certificate for:
Patent No.: 7,332,304
Issued: Feb. 19, 2008
Appl. No.: 10/612,779
Filed: Jul. 1, 2003

Related U.S. Application Data

(60) Provisional application No. 60/393,348, filed on Jul. 1, 2002.

(51) Int. Cl.
*C12P 19/26* (2006.01)
*C12Q 1/48* (2006.01)
*C07K 14/00* (2006.01)
*C12N 1/20* (2006.01)
*C12N 15/52* (2006.01)

(52) U.S. Cl.
CPC .................. *C12N 15/52* (2013.01); *C12P 19/26* (2013.01)
USPC ............... 435/84; 435/15; 435/183; 435/193; 435/252.3; 435/252.33; 435/320.1; 435/325; 435/69.1; 530/23.2

(58) Field of Classification Search
None
See application file for complete search history.

(56) References Cited

To view the complete listing of prior art documents cited during the proceeding for Reexamination Control Number 90/012,527, please refer to the USPTO's public Patent Application Information Retrieval (PAIR) system under the Display References tab.

*Primary Examiner* — Shri Ponnaluri

(57) ABSTRACT

A biosynthetic method for producing glucosamine and N-acetylglucosamine is disclosed. Such a method includes the fermentation of a genetically modified microorganism to produce glucosamine and/or N-acetylglucosamine. Also disclosed are genetically modified microorganisms that are useful for producing glucosamine and N-acetylglucosamine. In addition, methods of recovering N-acetylglucosamine that has been produced by a fermentation process, including methods that result in N-acetylglucosamine of high purity, are described. Also disclosed is a method to produce glucosamine from N-acetylglucosamine.

US 7,332,304 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 36, 40 and 43 are determined to be patentable as amended.

Claims 2-5, 8-26, 35, 37-39, 41-42, 55 and 63-67, dependent on an amended claim, are determined to be patentable.

Claims 6-7, 27-34, 44-54 and 56-62 were not reexamined.

1. A method to produce N-acetylglucosamine-6-phosphate or N-acetylglucosamine by fermentation, comprising:
   a) culturing in a fermentation medium a microorganism that is transformed with at least one recombinant nucleic acid molecule comprising a nucleic acid sequence encoding a glucosamine-6-phosphate acetyltransferase that has an amino acid sequence that is at least 95% identical to SEQ ID NO:30
   *wherein the culturing produces N-acetylglucosamine in an amount greater than 24 grams/liter in the fermentation medium within 48 hours of commencing the culturing step*; and
   b) collecting a product produced from the step of culturing which is selected from the group consisting of N-acetylglucosamine-6-phosphate and N-acetylglucosamine.

36. A method to produce N-acetylglucosamine-6-phosphate, N-acetylglucosamine, glucosamine or glucosamine HCl by fermentation, comprising:
   culturing in a fermentation medium a microorganism that is transformed with at least one recombinant nucleic acid molecule comprising a nucleic acid sequence encoding a glucosamine-6-phosphate acetyltransferase that has an amino acid sequence that is at least 95% identical to SEQ ID NO:30
   *wherein the culturing produces N-acetylglucosamine in an amount greater than 24 grams/liter in the fermentation medium within 48 hours of commencing the culturing step*; and
   collecting a product produced from the step of culturing which is selected from the group consisting of N-acetylglucosamine-6-phosphate and N-acetylglucosamine;
   and wherein the method further comprises a step selected from the group consisting of:
   a) purifying N-acetylglucosamine from the fermentation medium;
   b) dephosphorylating N-acetylglucosamine-6-phosphate to produce N-acetylglucosamine; and
   c) treating N-acetylglucosamine to produce a glucosamine product selected from the group consisting of: glucosamine and glucosamine HCl.

40. A method to produce [N-acetylalucosamine-6-phosphate] *N-acetylglucosamine-6-phosphate* or N-acetylglucosamine by fermentation, comprising:
   a) culturing in a fermentation medium a microorganism that expresses:
      i) a recombinant nucleic acid molecule encoding a glucosamine-6-phosphate acetyltransferase that has an amino acid sequence that is at least 95% identical to SEQ ID NO:30; and
      ii) a recombinant nucleic acid molecule encoding a glucosamine-6-phosphate synthase that has an amino acid sequence that is at least 95% identical to the amino acid sequence selected from the group consisting of: SEQ ID NO:4, SEQ ID NO:6, SEQ ID NO:8, SEQ ID NO:10, SEQ ID NO:12, SEQ ID NO:14, SEQ ID NO:16, SEQ ID NO:18, and SEQ ID NO:20
   *wherein the culturing produces N-acetylglucosamine in an amount greater than 24 grams/liter in the fermentation medium within 48 hours of commencing the culturing step*; and
   b) collecting a product produced from the step of culturing which is selected from the group consisting of N-acetylglucosamine-6-phosphate and N-acetylglucosamine.

43. A method to produce [N-acetylalucosamine-6-phosphate] *N-acetylglucosamine-6-phosphate* or N-acetylglucosamine by fermentation, comprising:
   a) culturing in a fermentation medium an E. coli that expresses:
      i) a recombinant nucleic acid molecule encoding a glucosamine-6-phosphate acetyltransferase that is at least 95% identical to the amino acid sequence of SEQ ID NO:30; and
      ii) a recombinant nucleic acid molecule encoding a glucosamine-6-phosphate synthase that is at least 95% identical to the amino acid sequence of SEQ ID NO:6
   *wherein the culturing produces N-acetylglucosamine in an amount greater than 24 grams/liter in the fermentation medium within 48 hours of commencing the culturing step*; and
   b) collecting a product produced from the step of culturing which is selected from the group consisting of N-acetylglucosamine-6-phosphate and N-acetylglucosamine.

* * * * *

SEQUENCE LISTING

<160> NUMBER OF SEQ ID NOS: 137

<210> SEQ ID NO 1
<211> LENGTH: 1830
<212> TYPE: DNA
<213> ORGANISM: Escherichia coli
<220> FEATURE:
<221> NAME/KEY: CDS
<222> LOCATION: (1)..(1830)
<223> OTHER INFORMATION:

<400> SEQUENCE: 1

```
atg tgt gga att gtt ggc gcg atc gcg caa cgt gat gta gca gaa atc      48
Met Cys Gly Ile Val Gly Ala Ile Ala Gln Arg Asp Val Ala Glu Ile
1               5                   10                  15 ctt ctt gaa ggt tta cgt cgt ctg gaa tac cgc gga tat gac tct gcc      96
Leu Leu Glu Gly Leu Arg Arg Leu Glu Tyr Arg Gly Tyr Asp Ser Ala
                20                  25                  30 ggt ctg gcc gtt gtt gat gca gaa ggt cat atg acc cgc ctg cgt cgc     144
Gly Leu Ala Val Val Asp Ala Glu Gly His Met Thr Arg Leu Arg Arg
            35                  40                  45 ctc ggt aaa gtc cag atg ctg gca cag gca gcg gaa gaa cat cct ctg     192
Leu Gly Lys Val Gln Met Leu Ala Gln Ala Ala Glu Glu His Pro Leu
        50                  55                  60 cat ggc ggc act ggt att gct cac act cgc tgg gcg acc cac ggt gaa     240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg     288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta     336
Val His Asn Gly Ile Ile Glu Asn His Glu Pro Leu Arg Glu Glu Leu
                100                 105                 110 aaa gcg cgt ggc tat acc ttc gtt tct gaa acc gac acc gaa gtg att     384
Lys Ala Arg Gly Tyr Thr Phe Val Ser Glu Thr Asp Thr Glu Val Ile
            115                 120                 125 gcc cat ctg gtg aac tgg gag ctg aaa caa ggc ggg act ctg cgt gag     432
Ala His Leu Val Asn Trp Glu Leu Lys Gln Gly Gly Thr Leu Arg Glu
        130                 135                 140 gcc gtt ctg cgt gct atc ccg cag ctg cgt ggt gcg tac ggt aca gtg     480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt     528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct     576
Ser Pro Leu Val Ile Gly Leu Gly Met Gly Glu Asn Phe Ile Ala Ser
                180                 185                 190 gac cag ctg gcg ctg ttg ccg gtg acc cgt cgc ttt atc ttc ctt gaa     624
Asp Gln Leu Ala Leu Leu Pro Val Thr Arg Arg Phe Ile Phe Leu Glu
            195                 200                 205 gag ggc gat att gcg gaa atc act cgc cgt tcg gta aac atc ttc gat     672
Glu Gly Asp Ile Ala Glu Ile Thr Arg Arg Ser Val Asn Ile Phe Asp
        210                 215                 220 aaa act ggc gcg gaa gta aaa cgt cag gat atc gaa tcc aat ctg caa     720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag     768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc atc     816
Ile Tyr Glu Gln Pro Asn Ala Ile Lys Asn Thr Leu Thr Gly Arg Ile
                260                 265                 270 agc cac ggt cag gtt gat tta agc gag ctg gga ccg aac gcc gac gaa     864
Ser His Gly Gln Val Asp Leu Ser Glu Leu Gly Pro Asn Ala Asp Glu
            275                 280                 285 ctg ctg tcg aag gtt gag cat att cag atc ctc gcc tgt ggt act tct     912
Leu Leu Ser Lys Val Glu His Ile Gln Ile Leu Ala Cys Gly Thr Ser
        290                 295                 300
```

```
tat aac tcc ggt atg gtt tcc cgc tac tgg ttt gaa tcg cta gca ggt       960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct      1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa      1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac      1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc      1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg      1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg      1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat      1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg      1344
Asp Ile Val His Gly Leu Gln Ala Leu Pro Ser Arg Ile Glu Gln Met
        435                 440                 445 ctg tct cag gac aaa cgc att gaa gcg ctg gca gaa gat ttc tct gac      1392
Leu Ser Gln Asp Lys Arg Ile Glu Ala Leu Ala Glu Asp Phe Ser Asp
    450                 455                 460 aaa cat cac gcg ctg ttc ctg ggc cgt ggc gat cag tac cca atc gcg      1440
Lys His His Ala Leu Phe Leu Gly Arg Gly Asp Gln Tyr Pro Ile Ala
465                 470                 475                 480 ctg gaa ggc gca ttg aag ttg aaa gag atc tct tac att cac gct gaa      1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat      1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa      1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg      1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg      1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc      1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa      1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt      1824
Gly Thr Asp Val Asp Gln Pro Arg Asn Leu Ala Lys Ser Val Thr Val
        595                 600                 605 gag taa                                                               1830
Glu
```

```
<210> SEQ ID NO 2
<211> LENGTH: 609
<212> TYPE: PRT
<213> ORGANISM: Escherichia coli

<400> SEQUENCE: 2

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365

Leu Gly Ser Leu Ala Ile Cys Asn Val Pro Gly Ser Ser Leu Val Arg
370                 375                 380
```

```
Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
            405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
            435                 440                 445

Leu Ser Gln Asp Lys Arg Ile Glu Ala Leu Ala Glu Asp Phe Ser Asp
    450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
            515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
            595                 600                 605

Glu

<210> SEQ ID NO 3
<211> LENGTH: 1830
<212> TYPE: DNA
<213> ORGANISM: Escherichia coli
<220> FEATURE:
<221> NAME/KEY: CDS
<222> LOCATION: (1)..(1830)
<223> OTHER INFORMATION:

<400> SEQUENCE: 3 atg tgt gga act gtt ggc gcg atc gcg caa cgt gat gta gca gaa atc      48
Met Cys Gly Thr Val Gly Ala Ile Ala Gln Arg Asp Val Ala Glu Ile
1               5                   10                  15 ctt ctt gaa ggt tta cgt cgt ctg gaa tac cgc gga tat gac tct gcc      96
Leu Leu Glu Gly Leu Arg Arg Leu Glu Tyr Arg Gly Tyr Asp Ser Ala
            20                  25                  30 ggt ctg gcc gtt gtt gat gca gaa ggt cat atg acc cgc ctg cgt cgc     144
Gly Leu Ala Val Val Asp Ala Glu Gly His Met Thr Arg Leu Arg Arg
        35                  40                  45 ctc ggt aaa gtc cag atg ctg gca cag gca gcg gaa gaa cat cct ctg     192
Leu Gly Lys Val Gln Met Leu Ala Gln Ala Ala Glu Glu His Pro Leu
    50                  55                  60 cat ggc ggc act ggt att gct cac act cgc tgg gcg acc cac ggt gaa     240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg     288
Pro Ser Glu Val Asn Ala His Pro His Val Ser Glu His Ile Val Val
```

-continued

|  |  |  | 85 |  |  |  | 90 |  |  |  | 95 |  |  |  |
|---|---|---|---|---|---|---|---|---|---|---|---|---|---|---|
| gtg | cat | aac | ggc | atc | atc | gaa | aac | cat | gaa | ccg | ctg | cgt | gaa | gag | cta | 336 |
| Val | His | Asn | Gly | Ile | Ile | Glu | Asn | His | Glu | Pro | Leu | Arg | Glu | Glu | Leu |
|  |  |  | 100 |  |  |  | 105 |  |  |  | 110 |  |  |  |

```
gtg cat aac ggc atc atc gaa aac cat gaa ccg ctg cgt gaa gag cta       336
Val His Asn Gly Ile Ile Glu Asn His Glu Pro Leu Arg Glu Glu Leu
                100                 105                 110 aaa gcg cgt ggc tat acc ttc gtt tct gaa acc gac acc gaa gtg att       384
Lys Ala Arg Gly Tyr Thr Phe Val Ser Glu Thr Asp Thr Glu Val Ile
                115                 120                 125 gcc cat ctg gtg aac tgg gag ctg aaa caa ggc ggg act ctg cgt gag       432
Ala His Leu Val Asn Trp Glu Leu Lys Gln Gly Gly Thr Leu Arg Glu
            130                 135                 140 gcc gtt ctg cgt gct atc ccg cag ctg cgt ggt gcg tac ggt aca gtg       480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt       528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct       576
Ser Pro Leu Val Ile Gly Leu Gly Met Gly Glu Asn Phe Ile Ala Ser
            180                 185                 190 gac cag ctg gcg ctg ttg ccg gtg acc cgt cgc ttt atc ttc ctt gaa       624
Asp Gln Leu Ala Leu Leu Pro Val Thr Arg Arg Phe Ile Phe Leu Glu
                195                 200                 205 gag ggc gat att gcg gaa atc act cgc cgt tcg gta aac atc ttc gat       672
Glu Gly Asp Ile Ala Glu Ile Thr Arg Arg Ser Val Asn Ile Phe Asp
            210                 215                 220 aaa act ggc gcg gaa gta aaa cgt cag gat atc gaa tcc aat ctg caa       720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag       768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc acc       816
Ile Tyr Glu Gln Pro Asn Ala Ile Lys Asn Thr Leu Thr Gly Arg Thr
            260                 265                 270 agc cac ggt cag gtt gat tta agc gag ctg gga ccg aac gcc gac gaa       864
Ser His Gly Gln Val Asp Leu Ser Glu Leu Gly Pro Asn Ala Asp Glu
                275                 280                 285 ctg ctg tcg aag gtt gag cat att cag atc ctc gcc tgt ggt act tct       912
Leu Leu Ser Lys Val Glu His Ile Gln Ile Leu Ala Cys Gly Thr Ser
            290                 295                 300 tat aac tcc ggt atg gtt tcc cgc tac tgg ttt gaa tcg cta gca ggt       960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct      1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa      1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac      1104
Thr Ala Asp Thr Leu Ala Gly Leu Arg Leu Ser Lys Glu Leu Gly Tyr
                355                 360                 365 ctt ggt tca ctg gca atc tgt aac gtt ccg ggt tct tct ctg gtg cgc      1152
Leu Gly Ser Leu Ala Ile Cys Asn Val Pro Gly Ser Ser Leu Val Arg
            370                 375                 380 gaa tcc gat ctg gcg cta atg acc aac gcg ggt aca gaa atc ggc gtg      1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg      1248
```

```
Ala Ser Thr Lys Ala Phe Thr Thr Gln Leu Thr Val Leu Leu Met Leu
            405                 410                 415 gtg gcg aag ctg tct cgc ctg aaa ggt ctg gat gcc tcc att gaa cat    1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg    1344
Asp Ile Val His Gly Leu Gln Ala Leu Pro Ser Arg Ile Glu Gln Met
            435                 440                 445 ctg cct cag gac aaa cgc att gaa gcg ctg gca gaa gat ttc tct gac    1392
Leu Pro Gln Asp Lys Arg Ile Glu Ala Leu Ala Glu Asp Phe Ser Asp
        450                 455                 460 aaa cat cac gcg ctg ttc ctg ggc cgt ggc gat cag tac cca atc gcg    1440
Lys His His Ala Leu Phe Leu Gly Arg Gly Asp Gln Tyr Pro Ile Ala
465                 470                 475                 480 ctg gaa ggc gca ttg aag ttg aaa gag atc tct tac att cac gct gaa    1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat    1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc    1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
        595                 600                 605 gag taa                                                             1830
Glu

<210> SEQ ID NO 4
<211> LENGTH: 609
<212> TYPE: PRT
<213> ORGANISM: Escherichia coli

<400> SEQUENCE: 4

Met Cys Gly Thr Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95
```

```
Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
            115                 120                 125

Ala His Leu Val Asn Trp Glu Leu Lys Gln Gly Gly Thr Leu Arg Glu
            130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
            195                 200                 205

Glu Gly Asp Ile Ala Glu Ile Thr Arg Arg Ser Val Asn Ile Phe Asp
            210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Thr
            260                 265                 270

Ser His Gly Gln Val Asp Leu Ser Glu Leu Gly Pro Asn Ala Asp Glu
            275                 280                 285

Leu Leu Ser Lys Val Glu His Ile Gln Ile Leu Ala Cys Gly Thr Ser
290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
            370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
            435                 440                 445

Leu Pro Gln Asp Lys Arg Ile Glu Ala Leu Ala Glu Asp Phe Ser Asp
450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510
```

```
Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
        530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
                580                 585                 590

Gly Thr Asp Val Asp Gln Pro Arg Asn Leu Ala Lys Ser Val Thr Val
        595                 600                 605

Glu

<210> SEQ ID NO 5
<211> LENGTH: 1830
<212> TYPE: DNA
<213> ORGANISM: Escherichia coli
<220> FEATURE:
<221> NAME/KEY: CDS
<222> LOCATION: (1)..(1830)
<223> OTHER INFORMATION:

<400> SEQUENCE: 5 atg tgt gga att gtt ggc gcg atc gcg caa cgt gat gta gca gaa atc       48
Met Cys Gly Ile Val Gly Ala Ile Ala Gln Arg Asp Val Ala Glu Ile
1               5                   10                  15 ctt ctt gaa ggt tta cgt cgt ctg gaa tac cgc gga tat gac tct gcc       96
Leu Leu Glu Gly Leu Arg Arg Leu Glu Tyr Arg Gly Tyr Asp Ser Ala
                20                  25                  30 ggt ctg gcc gtt gtt gat aca gaa ggt cat atg acc cgc ctg cgt cgc      144
Gly Leu Ala Val Val Asp Thr Glu Gly His Met Thr Arg Leu Arg Arg
            35                  40                  45 ctc ggt aaa gtc cag atg ctg gca cag gca gcg gaa gaa cat cct ctg      192
Leu Gly Lys Val Gln Met Leu Ala Gln Ala Ala Glu Glu His Pro Leu
        50                  55                  60 cat ggc ggc act ggt att gct cac act cgc tgg gcg acc cac ggt gaa      240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg      288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta      336
Val His Asn Gly Ile Ile Glu Asn His Glu Pro Leu Arg Glu Glu Leu
                100                 105                 110 aaa gcg cgt ggc tat acc ttc gtt tct gaa acc gac acc gaa gtg att      384
Lys Ala Arg Gly Tyr Thr Phe Val Ser Glu Thr Asp Thr Glu Val Ile
            115                 120                 125 gcc cat ctg gtg aac tgg gag ctg aaa caa ggc ggg act ctg cgt gag      432
Ala His Leu Val Asn Trp Glu Leu Lys Gln Gly Gly Thr Leu Arg Glu
        130                 135                 140 gcc gtt ctg cgt gct atc ccg cag ctg cgt ggt gcg tac ggt aca gtg      480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt      528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct      576
Ser Pro Leu Val Ile Gly Leu Gly Met Gly Glu Asn Phe Ile Ala Ser
                180                 185                 190
```

-continued

```
gac cag ctg gcg ctg ttg ccg gtg acc cgt cgc ttt atc ttc ctt gaa      624
Asp Gln Leu Ala Leu Leu Pro Val Thr Arg Arg Phe Ile Phe Leu Glu
            195                 200                 205 gag ggc gat att gcg gaa atc act cgc gtt tcg gta aac atc ttc gat      672
Glu Gly Asp Ile Ala Glu Ile Thr Arg Arg Ser Val Asn Ile Phe Asp
210                 215                 220 aaa act ggc gcg gaa gta aaa cgt cag gat atc gaa tcc aat ctg caa      720
Lys Thr Gly Ala Glu Val Lys Arg Gln Asp Ile Glu Ser Asn Leu Gln
225                 230                 235                 240 tat gac gcg ggc gat aaa ggc att tac tgt cac tac atg cag aaa gag      768
Tyr Asp Ala Gly Asp Lys Gly Ile Tyr Cys His Tyr Met Gln Lys Glu
                245                 250                 255 atc tac gaa cag ccg aac gcg atc aaa aac acc ctt acc gga cgc atc      816
Ile Tyr Glu Gln Pro Asn Ala Ile Lys Asn Thr Leu Thr Gly Arg Ile
                    260                 265                 270 agc cac ggt cag gtt gat tta agc gag ctg gga ccg aac gcc gac gaa      864
Ser His Gly Gln Val Asp Leu Ser Glu Leu Gly Pro Asn Ala Asp Glu
                275                 280                 285 ctg ctg tcg aag gtt gag cat att cag atc ctc gcc tgt ggt act tct      912
Leu Leu Ser Lys Val Glu His Ile Gln Ile Leu Ala Cys Gly Thr Ser
290                 295                 300 tat aac tcc ggt atg gtt tcc cgc tac tgg ttt gaa tcg cta gca ggt      960
Tyr Asn Ser Gly Met Val Ser Arg Tyr Trp Phe Glu Ser Leu Ala Gly
305                 310                 315                 320 att ccg tgc gac gtc gaa atc gcc tcc gaa ttc cgc tat cgc aaa tct     1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa     1056
Ala Val Arg Arg Asn Ser Leu Met Ile Thr Leu Ser Gln Ser Gly Glu
                340                 345                 350 acc gcg gat acc ctg gct ggc ctg cgt ctg tcg aaa gag ctg ggt tac     1104
Thr Ala Asp Thr Leu Ala Gly Leu Arg Leu Ser Lys Glu Leu Gly Tyr
                355                 360                 365 ctt ggt tca ctg gca atc tgt aac gtt ccg ggt tct tct ctg gtg cgc     1152
Leu Gly Ser Leu Ala Ile Cys Asn Val Pro Gly Ser Ser Leu Val Arg
370                 375                 380 gaa tcc gat ctg gcg cta atg acc aac gcg ggt aca gaa atc ggc gtg     1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg     1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat     1296
Val Ala Lys Leu Ser Arg Leu Lys Gly Leu Asp Ala Ser Ile Glu His
                420                 425                 430 gac atc gtg cat ggt ctg cag gcg ctg ccg agc cgt att gag cag atg     1344
Asp Ile Val His Gly Leu Gln Ala Leu Pro Ser Arg Ile Glu Gln Met
                435                 440                 445 ctg tct cag gac aaa cgc att gaa gcg ctg gca gaa gat ttc tct gac     1392
Leu Ser Gln Asp Lys Arg Ile Glu Ala Leu Ala Glu Asp Phe Ser Asp
450                 455                 460 aaa cat cac gcg ctg ttc ctg agc cgt ggc gat cag tac cca atc gcg     1440
Lys His His Ala Leu Phe Leu Ser Arg Gly Asp Gln Tyr Pro Ile Ala
465                 470                 475                 480 ctg gaa ggc gca ttg aag ttg aaa gag atc tct tac att cac gct gaa     1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat     1536
Ala Tyr Ala Ala Gly Glu Leu Lys His Gly Pro Leu Ala Leu Ile Asp
```

```
                500               505               510
gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
        515               520               525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
    530               535               540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545               550               555               560 cac atc atc gag atg ccg cat gtg gaa gag gtg att gca ccg atc ttc    1728
His Ile Ile Glu Met Pro His Val Glu Glu Val Ile Ala Pro Ile Phe
                565               570               575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
            580               585               590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
        595               600               605 gag taa                                                             1830
Glu

<210> SEQ ID NO 6
<211> LENGTH: 609
<212> TYPE: PRT
<213> ORGANISM: Escherichia coli

<400> SEQUENCE: 6

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Thr Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220
```

```
Lys Thr Gly Ala Glu Val Lys Arg Gln Asp Ile Glu Ser Asn Leu Gln
225                 230                 235                 240

Tyr Asp Ala Gly Asp Lys Gly Ile Tyr Cys His Tyr Met Gln Lys Glu
                245                 250                 255

Ile Tyr Glu Gln Pro Asn Ala Ile Lys Asn Thr Leu Thr Gly Arg Ile
                260                 265                 270

Ser His Gly Gln Val Asp Leu Ser Glu Leu Gly Pro Asn Ala Asp Glu
            275                 280                 285

Leu Leu Ser Lys Val Glu His Ile Gln Ile Leu Ala Cys Gly Thr Ser
        290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
                340                 345                 350

Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
        370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
                420                 425                 430

Asp Ile Val His Gly Leu Gln Ala Leu Pro Ser Arg Ile Glu Gln Met
            435                 440                 445

Leu Ser Gln Asp Lys Arg Ile Glu Ala Leu Ala Glu Asp Phe Ser Asp
        450                 455                 460

Lys His His Ala Leu Phe Leu Ser Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
        530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
            595                 600                 605

Glu

<210> SEQ ID NO 7
<211> LENGTH: 1830
<212> TYPE: DNA
<213> ORGANISM: Escherichia coli
```

```
<220> FEATURE:
<221> NAME/KEY: CDS
<222> LOCATION: (1)..(1830)
<223> OTHER INFORMATION:

<400> SEQUENCE: 7 atg tgt gga att gtt ggc gcg atc gcg caa cgt gat gta gca gaa atc      48
Met Cys Gly Ile Val Gly Ala Ile Ala Gln Arg Asp Val Ala Glu Ile
1               5                   10                  15 ctt ctt gaa ggt tta cgt cgt ctg gaa tac cgc gga tat gac tct gcc      96
Leu Leu Glu Gly Leu Arg Arg Leu Glu Tyr Arg Gly Tyr Asp Ser Ala
            20                  25                  30 ggt ctg gcc gtt gtt gat gca gaa ggt cat atg acc cgc ctg cgt cgc     144
Gly Leu Ala Val Val Asp Ala Glu Gly His Met Thr Arg Leu Arg Arg
        35                  40                  45 ctc ggt aaa gtc cag atg ctg gca cag gca gcg gaa gaa cat cct ctg     192
Leu Gly Lys Val Gln Met Leu Ala Gln Ala Ala Glu Glu His Pro Leu
    50                  55                  60 cat ggc ggc act ggt att gct cac act cgc tgg gcg acc cac ggt gaa     240
His Gly Gly Thr Gly Ile Ala His Thr Arg Trp Ala Thr His Gly Glu
65                  70                  75                  80 cct tca gaa gtg aat gcg cat ccg cat gtt tcc gaa cac att gtg gtg     288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta     336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att     384
Lys Ala Arg Gly Tyr Thr Phe Val Ser Glu Thr Asp Thr Glu Val Ile
        115                 120                 125 gcc cat ctg gtg aac tgg gag ctg aaa caa ggc ggg act ctg cgt gag     432
Ala His Leu Val Asn Trp Glu Leu Lys Gln Gly Gly Thr Leu Arg Glu
    130                 135                 140 gcc gtt ctg cgt gct atc ccg cag ctg cgt ggt gcg tac ggt aca gtg     480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt     528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct     576
Ser Pro Leu Val Ile Gly Leu Gly Met Gly Glu Asn Phe Ile Ala Ser
            180                 185                 190 gac cag ctg gcg ctg ttg ccg gtg acc cgt cgc ttt atc ttc ctt gaa     624
Asp Gln Leu Ala Leu Leu Pro Val Thr Arg Arg Phe Ile Phe Leu Glu
        195                 200                 205 gag ggc gat att gcg gaa atc act cgc cgt tcg gta aac atc ttc gat     672
Glu Gly Asp Ile Ala Glu Ile Thr Arg Arg Ser Val Asn Ile Phe Asp
    210                 215                 220 aaa act ggc gcg gaa gta aaa cgt cag gat atc gaa tcc aat ctg caa     720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag     768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc atc     816
Ile Tyr Glu Gln Pro Asn Ala Ile Lys Asn Thr Leu Thr Gly Arg Ile
            260                 265                 270 agc cac ggt cag gtt gat tta agc gag ctg gga ccg aac gcc gac gaa     864
Ser His Gly Gln Val Asp Leu Ser Glu Leu Gly Pro Asn Ala Asp Glu
        275                 280                 285
```

```
ctg ctg tcg aag gtt gag cat att cag atc ctc gcc tgt ggt act tct    912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt    960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct   1008
Ile Pro Cys Asp Val Glu Ile Ala Ser Glu Phe Arg Tyr Arg Lys Ser
                325                 330                 335 gcc gtg cgt cgt aac agc ctg atg atc acc ttg tca cag tct ggc gaa   1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac   1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc   1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg   1200
Glu Ser Asp Leu Ala Leu Met Thr Asn Ala Gly Thr Glu Ile Gly Val
385                 390                 395                 400 gca tcc act aaa gca ttc acc act cag tta act gtg ctg ttg atg ctg   1248
Ala Ser Thr Lys Ala Phe Thr Thr Gln Leu Thr Val Leu Leu Met Leu
                405                 410                 415 gtg gcg aag ctg tct cgc ctg aaa ggt ctg gat gcc tcc att gaa cat   1296
Val Ala Lys Leu Ser Arg Leu Lys Gly Leu Asp Ala Ser Ile Glu His
            420                 425                 430 gac atc gtg cat ggt ctg cag gcg ctg ccg agc cgt att gag cag atg   1344
Asp Ile Val His Gly Leu Gln Ala Leu Pro Ser Arg Ile Glu Gln Met
        435                 440                 445 ctg tct cag gac aaa cgc att gaa gcg ctg gca gaa gat ttc tct gac   1392
Leu Ser Gln Asp Lys Arg Ile Glu Ala Leu Ala Glu Asp Phe Ser Asp
    450                 455                 460 aaa cat cac gcg ccg ttc ctg ggc cgt ggc gat cag tac cca atc gcg   1440
Lys His His Ala Pro Phe Leu Gly Arg Gly Asp Gln Tyr Pro Ile Ala
465                 470                 475                 480 ctg gaa ggc gca ttg aag ttg aaa gag atc tct tac att cac gct gaa   1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat   1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa   1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg   1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg   1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc   1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa   1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt   1824
Gly Thr Asp Val Asp Gln Pro Arg Asn Leu Ala Lys Ser Val Thr Val
        595                 600                 605
``` gag taa                                                                1830
Glu

<210> SEQ ID NO 8
<211> LENGTH: 609
<212> TYPE: PRT
<213> ORGANISM: Escherichia coli

<400> SEQUENCE: 8

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr

-continued

```
            355                 360                 365
Leu Gly Ser Leu Ala Ile Cys Asn Val Pro Gly Ser Ser Leu Val Arg
        370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
    450                 455                 460

Lys His His Ala Pro Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu
```

<210> SEQ ID NO 9
<211> LENGTH: 1830
<212> TYPE: DNA
<213> ORGANISM: Escherichia coli
<220> FEATURE:
<221> NAME/KEY: CDS
<222> LOCATION: (1)..(1830)
<223> OTHER INFORMATION:

<400> SEQUENCE: 9

```
atg tgt gga att gtt ggc gcg atc gcg caa cgt gat gta gca gaa atc    48
Met Cys Gly Ile Val Gly Ala Ile Ala Gln Arg Asp Val Ala Glu Ile
1               5                   10                  15 ctt ctt gaa ggt tta cgt cgt ctg gaa tac cgc gga tat gac tct gcc    96
Leu Leu Glu Gly Leu Arg Arg Leu Glu Tyr Arg Gly Tyr Asp Ser Ala
                20                  25                  30 ggt ctg gcc gtt gtt gat gca gaa ggt cat atg acc cgc ctg cgt cgc   144
Gly Leu Ala Val Val Asp Ala Glu Gly His Met Thr Arg Leu Arg Arg
            35                  40                  45 ctc ggt aaa gtc cag atg ctg gca cag gca gcg gaa gaa cat cct ctg   192
Leu Gly Lys Val Gln Met Leu Ala Gln Ala Ala Glu Glu His Pro Leu
        50                  55                  60 cat ggc ggc act ggt att gct cac act cgc tgg gcg acc cac ggt gaa   240
His Gly Gly Thr Gly Ile Ala His Thr Arg Trp Ala Thr His Gly Glu
```

```
                65                  70                  75                  80
cct tca gaa gtg aat gcg cat ccg cat gtt tct gaa cac att gtg gtg       288
Pro Ser Glu Val Asn Ala His Pro His Val Ser Glu His Ile Val Val
                    85                  90                  95 gtg cat aac ggc atc atc gaa aac cat gaa ccg ctg cgt gaa gag cta       336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att       384
Lys Ala Arg Gly Tyr Thr Phe Val Ser Glu Thr Asp Thr Glu Val Ile
        115                 120                 125 gcc cat ctg gtg aac tgg gag ctg aaa caa ggc ggg act ctg cgt gag       432
Ala His Leu Val Asn Trp Glu Leu Lys Gln Gly Gly Thr Leu Arg Glu
    130                 135                 140 gcc gtt ctg cgt gct atc ccg cag ctg cgt ggt gcg tac ggt aca gtg       480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt       528
Ile Met Asp Ser Arg His Pro Asp Thr Leu Leu Ala Ala Arg Ser Gly
                    165                 170                 175 agt ccg ctg gtg att ggc ctg ggg atg ggc gaa aac ttt atc gct tct       576
Ser Pro Leu Val Ile Gly Leu Gly Met Gly Glu Asn Phe Ile Ala Ser
            180                 185                 190 gac cag ctg gcg ctg ttg ccg gtg acc cgt cgc ttt atc ttc ctt gaa       624
Asp Gln Leu Ala Leu Leu Pro Val Thr Arg Arg Phe Ile Phe Leu Glu
        195                 200                 205 gag ggc gat att gcg gaa atc act cgc cgt tcg gta aac atc ttc gat       672
Glu Gly Asp Ile Ala Glu Ile Thr Arg Arg Ser Val Asn Ile Phe Asp
    210                 215                 220 aaa act ggc gcg gaa gta aaa cgt cag gat atc gaa tcc aat ctg caa       720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag       768
Tyr Asp Ala Gly Asp Lys Gly Ile Tyr Arg His Tyr Met Gln Lys Glu
                    245                 250                 255 atc tac gaa cag ccg aac gcg atc aaa aac acc ctt acc gga cgc atc       816
Ile Tyr Glu Gln Pro Asn Ala Ile Lys Asn Thr Leu Thr Gly Arg Ile
            260                 265                 270 agc cac ggt cag gtt gat tta agc gag ctg gga ccg aac gcc gac gaa       864
Ser His Gly Gln Val Asp Leu Ser Glu Leu Gly Pro Asn Ala Asp Glu
        275                 280                 285 ctg ctg tcg aag gtt gag cat att cag atc ctc gcc tgt ggt act tct       912
Leu Leu Ser Lys Val Glu His Ile Gln Ile Leu Ala Cys Gly Thr Ser
    290                 295                 300 tat aac tcc ggt atg gtt tcc cgc tac tgg ttt gaa tcg cta gca ggt       960
Tyr Asn Ser Gly Met Val Ser Arg Tyr Trp Phe Glu Ser Leu Ala Gly
305                 310                 315                 320 att ccg tgc gac gtc gaa atc gcc tct gaa ttc cgc tat cgc aaa tct      1008
Ile Pro Cys Asp Val Glu Ile Ala Ser Glu Phe Arg Tyr Arg Lys Ser
                    325                 330                 335 gcc gtg cgt cgt aac agc ctg atg atc acc ttg tca cag tct ggc gaa      1056
Ala Val Arg Arg Asn Ser Leu Met Ile Thr Leu Ser Gln Ser Gly Glu
            340                 345                 350 acc gcg gat acc ctg gct ggc ctg cgt ctg tcg aaa gag ctg ggt tac      1104
Thr Ala Asp Thr Leu Ala Gly Leu Arg Leu Ser Lys Glu Leu Gly Tyr
        355                 360                 365 ctt ggt tca ctg gca atc tgt aac gtt ccg ggt tct tct ctg gtg cgc      1152
Leu Gly Ser Leu Ala Ile Cys Asn Val Pro Gly Ser Ser Leu Val Arg
    370                 375                 380 gaa tcc gat ctg gcg cta atg acc aac gcg ggt aca gaa atc ggc gtg      1200
Glu Ser Asp Leu Ala Leu Met Thr Asn Ala Gly Thr Glu Ile Gly Val
```

-continued

| | | | | | | | | | | | | | | | |
|---|---|---|---|---|---|---|---|---|---|---|---|---|---|---|---|
|Glu|Ser|Asp|Leu|Ala|Leu|Met|Thr|Asn|Ala|Gly|Thr|Glu|Ile|Gly|Val|
|385| | | |390| | | |395| | | |400| | | |

```
gca tcc act aaa gca ttc acc act cag tta act gtg ctg ttg atg ctg    1248
Ala Ser Thr Lys Ala Phe Thr Thr Gln Leu Thr Val Leu Leu Met Leu
            405                 410                 415 gtg gcg aag ctg tct cgc ctg aaa ggt ctg gat gcc tcc att gaa cat    1296
Val Ala Lys Leu Ser Arg Leu Lys Gly Leu Asp Ala Ser Ile Glu His
        420                 425                 430 gac atc gtg cat ggt ctg cag gcg ctg ccg agc cgt att gag cag atg    1344
Asp Ile Val His Gly Leu Gln Ala Leu Pro Ser Arg Ile Glu Gln Met
    435                 440                 445 ctg tct cag gac aaa cgc att gaa gcg ctg gca gaa gat ttc tct gac    1392
Leu Ser Gln Asp Lys Arg Ile Glu Ala Leu Ala Glu Asp Phe Ser Asp
450                 455                 460 aaa cat cac gcg ctg ttc ctg agc cgt ggc gat cag tac cca atc gcg    1440
Lys His His Ala Leu Phe Leu Ser Arg Gly Asp Gln Tyr Pro Ile Ala
465                 470                 475                 480 ctg gaa ggc gca ttg aag ttg aaa gag atc tct tac att cac gct gaa    1488
Leu Glu Gly Ala Leu Lys Leu Lys Glu Ile Ser Tyr Ile His Ala Glu
                485                 490                 495 gcc tac gct gct ggc gaa ctg aaa cac ggt ccg ctg gcg cta att gat    1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc    1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
        595                 600                 605 gag taa                                                            1830
Glu

<210> SEQ ID NO 10
<211> LENGTH: 609
<212> TYPE: PRT
<213> ORGANISM: Escherichia coli

<400> SEQUENCE: 10

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
```

-continued

```
                65                  70                  75                  80
        Pro Ser Glu Val Asn Ala His Pro His Val Ser Glu His Ile Val Val
                        85                  90                  95
        Val His Asn Gly Ile Ile Glu Asn His Glu Pro Leu Arg Glu Leu
                        100                 105                 110
        Lys Ala Arg Gly Tyr Thr Phe Val Ser Glu Thr Asp Thr Glu Val Ile
                        115                 120                 125
        Ala His Leu Val Asn Trp Glu Leu Lys Gln Gly Gly Thr Leu Arg Glu
                        130                 135                 140
        Ala Val Leu Arg Ala Ile Pro Gln Leu Arg Gly Ala Tyr Gly Thr Val
        145                 150                 155                 160
        Ile Met Asp Ser Arg His Pro Asp Thr Leu Leu Ala Ala Arg Ser Gly
                                165                 170                 175
        Ser Pro Leu Val Ile Gly Leu Gly Met Gly Glu Asn Phe Ile Ala Ser
                        180                 185                 190
        Asp Gln Leu Ala Leu Leu Pro Val Thr Arg Arg Phe Ile Phe Leu Glu
                        195                 200                 205
        Glu Gly Asp Ile Ala Glu Ile Thr Arg Arg Ser Val Asn Ile Phe Asp
                        210                 215                 220
        Lys Thr Gly Ala Glu Val Lys Arg Gln Asp Ile Glu Ser Asn Leu Gln
        225                 230                 235                 240
        Tyr Asp Ala Gly Asp Lys Gly Ile Tyr Arg His Tyr Met Gln Lys Glu
                                245                 250                 255
        Ile Tyr Glu Gln Pro Asn Ala Ile Lys Asn Thr Leu Thr Gly Arg Ile
                        260                 265                 270
        Ser His Gly Gln Val Asp Leu Ser Glu Leu Gly Pro Asn Ala Asp Glu
                        275                 280                 285
        Leu Leu Ser Lys Val Glu His Ile Gln Ile Leu Ala Cys Gly Thr Ser
                        290                 295                 300
        Tyr Asn Ser Gly Met Val Ser Arg Tyr Trp Phe Glu Ser Leu Ala Gly
        305                 310                 315                 320
        Ile Pro Cys Asp Val Glu Ile Ala Ser Glu Phe Arg Tyr Arg Lys Ser
                                325                 330                 335
        Ala Val Arg Arg Asn Ser Leu Met Ile Thr Leu Ser Gln Ser Gly Glu
                        340                 345                 350
        Thr Ala Asp Thr Leu Ala Gly Leu Arg Leu Ser Lys Glu Leu Gly Tyr
                        355                 360                 365
        Leu Gly Ser Leu Ala Ile Cys Asn Val Pro Gly Ser Ser Leu Val Arg
                        370                 375                 380
        Glu Ser Asp Leu Ala Leu Met Thr Asn Ala Gly Thr Glu Ile Gly Val
        385                 390                 395                 400
        Ala Ser Thr Lys Ala Phe Thr Thr Gln Leu Thr Val Leu Leu Met Leu
                                405                 410                 415
        Val Ala Lys Leu Ser Arg Leu Lys Gly Leu Asp Ala Ser Ile Glu His
                        420                 425                 430
        Asp Ile Val His Gly Leu Gln Ala Leu Pro Ser Arg Ile Glu Gln Met
                        435                 440                 445
        Leu Ser Gln Asp Lys Arg Ile Glu Ala Leu Ala Glu Asp Phe Ser Asp
                        450                 455                 460
        Lys His His Ala Leu Phe Leu Ser Arg Gly Asp Gln Tyr Pro Ile Ala
        465                 470                 475                 480
        Leu Glu Gly Ala Leu Lys Leu Lys Glu Ile Ser Tyr Ile His Ala Glu
                                485                 490                 495
```

-continued

```
Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
        530                 535                 540

Tyr Val Phe Ala Asp Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 11
<211> LENGTH: 1830
<212> TYPE: DNA
<213> ORGANISM: Escherichia coli
<220> FEATURE:
<221> NAME/KEY: CDS
<222> LOCATION: (1)..(1830)
<223> OTHER INFORMATION:

<400> SEQUENCE: 11 atg tgt gga att gtt ggc gcg atc gcg caa cgt gat gta gca gaa atc      48
Met Cys Gly Ile Val Gly Ala Ile Ala Gln Arg Asp Val Ala Glu Ile
1               5                   10                  15 ctt ctt gaa ggt tta cgt cgt ctg gaa tac cgc gga tat gac tct gcc      96
Leu Leu Glu Gly Leu Arg Arg Leu Glu Tyr Arg Gly Tyr Asp Ser Ala
            20                  25                  30 ggt ctg gcc gtt gtt gat gca gaa ggt cat atg acc cgc ctg cgt cgc     144
Gly Leu Ala Val Val Asp Ala Glu Gly His Met Thr Arg Leu Arg Arg
        35                  40                  45 ctc ggt aaa gtc cag atg ctg gca cag gca gcg gaa gaa cat cct ctg     192
Leu Gly Lys Val Gln Met Leu Ala Gln Ala Ala Glu Glu His Pro Leu
    50                  55                  60 cat ggc ggc act ggt att gct cac act cgc tgg gcg acc cac ggt gaa     240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg     288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta     336
Val His Asn Gly Ile Ile Glu Asn His Glu Pro Leu Arg Glu Glu Leu
            100                 105                 110 aaa gcg cgt ggc tat acc ttc gtt tct gaa acc gac acc gaa gtg att     384
Lys Ala Arg Gly Tyr Thr Phe Val Ser Glu Thr Asp Thr Glu Val Ile
        115                 120                 125 gcc cat ctg gtg aac tgg gag ctg aaa caa ggc ggg act ctg cgt gag     432
Ala His Leu Val Asn Trp Glu Leu Lys Gln Gly Gly Thr Leu Arg Glu
    130                 135                 140 gcc gtt ctg cgt gct atc ccg cag ctg cgt ggt gcg tac ggt aca gtg     480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt     528
Ile Met Asp Ser Arg His Pro Asp Thr Leu Leu Ala Ala Arg Ser Gly
                165                 170                 175
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agt | ccg | ctg | gtg | att | ggc | ctg | ggg | atg | ggc | gaa | aac | ttt | atc | gct | tct | 576  |
| Ser | Pro | Leu | Val | Ile | Gly | Leu | Gly | Met | Gly | Glu | Asn | Phe | Ile | Ala | Ser |      |
|     |     | 180 |     |     |     |     | 185 |     |     |     |     | 190 |     |     |     |      |
| gac | cag | ctg | gcg | ctg | ttg | ccg | gtg | acc | cgt | cgc | ttt | atc | ttc | ctt | gaa | 624  |
| Asp | Gln | Leu | Ala | Leu | Leu | Pro | Val | Thr | Arg | Arg | Phe | Ile | Phe | Leu | Glu |      |
| 195 |     |     |     |     | 200 |     |     |     |     | 205 |     |     |     |     |     |      |
| gag | ggc | gat | att | gcg | gaa | atc | act | cgc | cgt | tcg | gta | aac | atc | ttc | gat | 672  |
| Glu | Gly | Asp | Ile | Ala | Glu | Ile | Thr | Arg | Arg | Ser | Val | Asn | Ile | Phe | Asp |      |
| 210 |     |     |     |     | 215 |     |     |     |     | 220 |     |     |     |     |     |      |
| aaa | act | ggc | gcg | gaa | gta | aaa | cgt | cag | gat | atc | gaa | tcc | aat | ctg | caa | 720  |
| Lys | Thr | Gly | Ala | Glu | Val | Lys | Arg | Gln | Asp | Ile | Glu | Ser | Asn | Leu | Gln |      |
| 225 |     |     |     |     | 230 |     |     |     |     | 235 |     |     |     |     | 240 |      |
| tat | gac | gcg | ggc | gat | aaa | ggc | att | tac | cgt | cac | tac | atg | cag | aaa | gag | 768  |
| Tyr | Asp | Ala | Gly | Asp | Lys | Gly | Ile | Tyr | Arg | His | Tyr | Met | Gln | Lys | Glu |      |
|     |     |     |     | 245 |     |     |     |     | 250 |     |     |     |     | 255 |     |      |
| atc | tac | gaa | cag | ccg | aac | gcg | atc | aaa | aac | acc | ctt | acc | gga | cgc | atc | 816  |
| Ile | Tyr | Glu | Gln | Pro | Asn | Ala | Ile | Lys | Asn | Thr | Leu | Thr | Gly | Arg | Ile |      |
|     |     |     |     | 260 |     |     |     |     | 265 |     |     |     |     | 270 |     |      |
| agc | cac | ggt | cag | gtt | gat | tta | agc | gag | ctg | gga | ccg | aac | gcc | gac | gaa | 864  |
| Ser | His | Gly | Gln | Val | Asp | Leu | Ser | Glu | Leu | Gly | Pro | Asn | Ala | Asp | Glu |      |
|     |     | 275 |     |     |     |     | 280 |     |     |     |     | 285 |     |     |     |      |
| ctg | ctg | tcg | aag | gtt | gag | cat | att | cag | atc | ctc | gcc | tgt | ggt | act | tct | 912  |
| Leu | Leu | Ser | Lys | Val | Glu | His | Ile | Gln | Ile | Leu | Ala | Cys | Gly | Thr | Ser |      |
|     | 290 |     |     |     |     | 295 |     |     |     |     | 300 |     |     |     |     |      |
| tat | aac | tcc | ggt | atg | gtt | tcc | cgc | tac | tgg | ttt | gaa | tcg | cta | gca | ggt | 960  |
| Tyr | Asn | Ser | Gly | Met | Val | Ser | Arg | Tyr | Trp | Phe | Glu | Ser | Leu | Ala | Gly |      |
| 305 |     |     |     |     | 310 |     |     |     |     | 315 |     |     |     |     | 320 |      |
| att | ccg | tgc | gac | gtc | gaa | atc | gcc | tct | gaa | ttc | cgc | tat | cgc | aaa | tct | 1008 |
| Ile | Pro | Cys | Asp | Val | Glu | Ile | Ala | Ser | Glu | Phe | Arg | Tyr | Arg | Lys | Ser |      |
|     |     |     |     | 325 |     |     |     |     | 330 |     |     |     |     | 335 |     |      |
| gcc | gtg | cgt | cgt | aac | agc | ctg | atg | atc | acc | ttg | tca | cag | tct | ggc | gaa | 1056 |
| Ala | Val | Arg | Arg | Asn | Ser | Leu | Met | Ile | Thr | Leu | Ser | Gln | Ser | Gly | Glu |      |
|     |     |     | 340 |     |     |     |     | 345 |     |     |     |     | 350 |     |     |      |
| acc | gcg | gat | acc | ctg | gct | ggc | ctg | cgt | ctg | tcg | aaa | gag | ctg | ggt | tac | 1104 |
| Thr | Ala | Asp | Thr | Leu | Ala | Gly | Leu | Arg | Leu | Ser | Lys | Glu | Leu | Gly | Tyr |      |
|     |     | 355 |     |     |     |     | 360 |     |     |     |     | 365 |     |     |     |      |
| ctt | ggt | tca | ctg | gca | atc | tgt | aac | gtt | ccg | ggt | tct | tct | ctg | gtg | cgc | 1152 |
| Leu | Gly | Ser | Leu | Ala | Ile | Cys | Asn | Val | Pro | Gly | Ser | Ser | Leu | Val | Arg |      |
|     | 370 |     |     |     |     | 375 |     |     |     |     | 380 |     |     |     |     |      |
| gaa | tcc | gat | ctg | gcg | cta | atg | acc | aac | gcg | ggt | aca | gaa | atc | ggc | gtg | 1200 |
| Glu | Ser | Asp | Leu | Ala | Leu | Met | Thr | Asn | Ala | Gly | Thr | Glu | Ile | Gly | Val |      |
| 385 |     |     |     |     | 390 |     |     |     |     | 395 |     |     |     |     | 400 |      |
| gca | tcc | act | aaa | gca | ttc | acc | act | cag | tta | act | gtg | ctg | ttg | atg | ctg | 1248 |
| Ala | Ser | Thr | Lys | Ala | Phe | Thr | Thr | Gln | Leu | Thr | Val | Leu | Leu | Met | Leu |      |
|     |     |     |     | 405 |     |     |     |     | 410 |     |     |     |     | 415 |     |      |
| gtg | gcg | aag | ctg | tct | cgc | ctg | aaa | ggt | ctg | gat | gcc | tcc | att | gaa | cat | 1296 |
| Val | Ala | Lys | Leu | Ser | Arg | Leu | Lys | Gly | Leu | Asp | Ala | Ser | Ile | Glu | His |      |
|     |     |     | 420 |     |     |     |     | 425 |     |     |     |     | 430 |     |     |      |
| gac | atc | gtg | cat | ggt | ctg | cag | gcg | ctg | ccg | agc | cgt | att | gag | cag | atg | 1344 |
| Asp | Ile | Val | His | Gly | Leu | Gln | Ala | Leu | Pro | Ser | Arg | Ile | Glu | Gln | Met |      |
|     |     | 435 |     |     |     |     | 440 |     |     |     |     | 445 |     |     |     |      |
| ctg | tct | cag | gac | aaa | cgc | att | gaa | gcg | ctg | gca | gaa | gat | ttc | tct | gac | 1392 |
| Leu | Ser | Gln | Asp | Lys | Arg | Ile | Glu | Ala | Leu | Ala | Glu | Asp | Phe | Ser | Asp |      |
|     | 450 |     |     |     |     | 455 |     |     |     |     | 460 |     |     |     |     |      |
| aaa | cat | cac | gcg | ctg | ttc | ctg | agc | cgt | ggc | gat | cag | tac | cca | atc | gcg | 1440 |
| Lys | His | His | Ala | Leu | Phe | Leu | Ser | Arg | Gly | Asp | Gln | Tyr | Pro | Ile | Ala |      |
| 465 |     |     |     |     | 470 |     |     |     |     | 475 |     |     |     |     | 480 |      |
| ctg | gaa | ggc | gca | ttg | aag | ttg | aaa | gag | atc | tct | tac | att | cac | gct | gaa | 1488 |
| Leu | Glu | Gly | Ala | Leu | Lys | Leu | Lys | Glu | Ile | Ser | Tyr | Ile | His | Ala | Glu |      |

```
                    485                 490                 495
gcc tac gct gct ggc gaa ctg aaa cac ggt ccg ctg gcg cta att gat    1536
Ala Tyr Ala Ala Gly Glu Leu Lys His Gly Pro Leu Ala Leu Ile Asp
            500                 505                 510 gcc gat atg ccg gtt att gtt gtt gca ccg aac aac gaa ttg ctg gaa    1584
Ala Asp Met Pro Val Ile Val Val Ala Pro Asn Asn Glu Leu Leu Glu
        515                 520                 525 aaa ctg aaa tcc aac att gaa gaa gtt cgc gcg cgt ggc ggt cag ttg    1632
Lys Leu Lys Ser Asn Ile Glu Glu Val Arg Ala Arg Gly Gly Gln Leu
    530                 535                 540 tat gtc ttc gcc gat cag gat gcg ggt ttt gta agt agc gat aac atg    1680
Tyr Val Phe Ala Asp Gln Asp Ala Gly Phe Val Ser Ser Asp Asn Met
545                 550                 555                 560 cac atc atc gag atg ccg cat gtg gaa gag gtg att gca ccg atc ttc    1728
His Ile Ile Glu Met Pro His Val Glu Glu Val Ile Ala Pro Ile Phe
                565                 570                 575 tac acc gtt ccg ctg cag ctg ctg gct tac cat gtc gcg ctg atc aaa    1776
Tyr Thr Val Pro Leu Gln Leu Leu Ala Tyr His Val Ala Leu Ile Lys
            580                 585                 590 ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
        595                 600                 605 gag taa                                                            1830
Glu

<210> SEQ ID NO 12
<211> LENGTH: 609
<212> TYPE: PRT
<213> ORGANISM: Escherichia coli

<400> SEQUENCE: 12

Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205
```

-continued

```
Glu Gly Asp Ile Ala Glu Ile Thr Arg Arg Ser Val Asn Ile Phe Asp
    210                 215                 220
Lys Thr Gly Ala Glu Val Lys Arg Gln Asp Ile Glu Ser Asn Leu Gln
225                 230                 235                 240
Tyr Asp Ala Gly Asp Lys Gly Ile Tyr Arg His Tyr Met Gln Lys Glu
                245                 250                 255
Ile Tyr Glu Gln Pro Asn Ala Ile Lys Asn Thr Leu Thr Gly Arg Ile
                260                 265                 270
Ser His Gly Gln Val Asp Leu Ser Glu Leu Gly Pro Asn Ala Asp Glu
            275                 280                 285
Leu Leu Ser Lys Val Glu His Ile Gln Ile Leu Ala Cys Gly Thr Ser
    290                 295                 300
Tyr Asn Ser Gly Met Val Ser Arg Tyr Trp Phe Glu Ser Leu Ala Gly
305                 310                 315                 320
Ile Pro Cys Asp Val Glu Ile Ala Ser Glu Phe Arg Tyr Arg Lys Ser
                325                 330                 335
Ala Val Arg Arg Asn Ser Leu Met Ile Thr Leu Ser Gln Ser Gly Glu
                340                 345                 350
Thr Ala Asp Thr Leu Ala Gly Leu Arg Leu Ser Lys Glu Leu Gly Tyr
            355                 360                 365
Leu Gly Ser Leu Ala Ile Cys Asn Val Pro Gly Ser Ser Leu Val Arg
    370                 375                 380
Glu Ser Asp Leu Ala Leu Met Thr Asn Ala Gly Thr Glu Ile Gly Val
385                 390                 395                 400
Ala Ser Thr Lys Ala Phe Thr Thr Gln Leu Thr Val Leu Leu Met Leu
                405                 410                 415
Val Ala Lys Leu Ser Arg Leu Lys Gly Leu Asp Ala Ser Ile Glu His
                420                 425                 430
Asp Ile Val His Gly Leu Gln Ala Leu Pro Ser Arg Ile Glu Gln Met
            435                 440                 445
Leu Ser Gln Asp Lys Arg Ile Glu Ala Leu Ala Glu Asp Phe Ser Asp
    450                 455                 460
Lys His His Ala Leu Phe Leu Ser Arg Gly Asp Gln Tyr Pro Ile Ala
465                 470                 475                 480
Leu Glu Gly Ala Leu Lys Leu Lys Glu Ile Ser Tyr Ile His Ala Glu
                485                 490                 495
Ala Tyr Ala Ala Gly Glu Leu Lys His Gly Pro Leu Ala Leu Ile Asp
            500                 505                 510
Ala Asp Met Pro Val Ile Val Val Ala Pro Asn Asn Glu Leu Leu Glu
    515                 520                 525
Lys Leu Lys Ser Asn Ile Glu Glu Val Arg Ala Arg Gly Gly Gln Leu
    530                 535                 540
Tyr Val Phe Ala Asp Gln Asp Ala Gly Phe Val Ser Ser Asp Asn Met
545                 550                 555                 560
His Ile Ile Glu Met Pro His Val Glu Val Ile Ala Pro Ile Phe
                565                 570                 575
Tyr Thr Val Pro Leu Gln Leu Leu Ala Tyr His Val Ala Leu Ile Lys
                580                 585                 590
Gly Thr Asp Val Asp Gln Pro Arg Asn Leu Ala Lys Ser Val Thr Val
            595                 600                 605
Glu
```

```
<210> SEQ ID NO 13
<211> LENGTH: 1830
<212> TYPE: DNA
<213> ORGANISM: Escherichia coli
<220> FEATURE:
<221> NAME/KEY: CDS
<222> LOCATION: (1)..(1830)
<223> OTHER INFORMATION:

<400> SEQUENCE: 13 atg tgt gga att gtt ggc gcg atc gcg caa cgt gat gta gca aaa atc      48
Met Cys Gly Ile Val Gly Ala Ile Ala Gln Arg Asp Val Ala Lys Ile
1               5                   10                  15 ctt ctt gaa ggt tta cgt cgt ctg gaa tac cgc gga tat gac tct gcc      96
Leu Leu Glu Gly Leu Arg Arg Leu Glu Tyr Arg Gly Tyr Asp Ser Ala
                20                  25                  30 ggt ctg gcc gtt gtt gat gca gaa ggt cat atg acc cgc ctg cgt cgc     144
Gly Leu Ala Val Val Asp Ala Glu Gly His Met Thr Arg Leu Arg Arg
            35                  40                  45 ctc ggt aaa gtc cag atg ctg gca cag gca gcg gaa gaa cat cct ctg     192
Leu Gly Lys Val Gln Met Leu Ala Gln Ala Ala Glu Glu His Pro Leu
        50                  55                  60 cat ggc ggc act ggt att gct cac act cgc tgg gcg acc cac ggt gaa     240
His Gly Gly Thr Gly Ile Ala His Thr Arg Trp Ala Thr His Gly Glu
65                  70                  75                  80 cct tca gaa gtg aat gcg cat ccg cat gtt tct gaa cac att gtg gtg     288
Pro Ser Glu Val Asn Ala His Pro His Val Ser Glu His Ile Val Val
                85                  90                  95 gtg cat aac ggc atc atc gaa aac cat gaa ccg ctg cgt gaa gag cta     336
Val His Asn Gly Ile Ile Glu Asn His Glu Pro Leu Arg Glu Glu Leu
                100                 105                 110 aaa gcg cgt ggc tat acc ttc gtt tct gaa acc gac acc gaa gtg att     384
Lys Ala Arg Gly Tyr Thr Phe Val Ser Glu Thr Asp Thr Glu Val Ile
            115                 120                 125 gcc cat ctg gtg aac tgg gag ctg aaa caa ggc ggg act ctg cgt gag     432
Ala His Leu Val Asn Trp Glu Leu Lys Gln Gly Gly Thr Leu Arg Glu
        130                 135                 140 gcc gtt ctg cgt gct atc ccg cag ctg cgt ggt gcg tac ggt aca gtg     480
Ala Val Leu Arg Ala Ile Pro Gln Leu Arg Gly Ala Tyr Gly Thr Val
145                 150                 155                 160 atc atg gac tcc cgt cac ccg gat acc ctg ctg gcg gca cgt tct ggt     528
Ile Met Asp Ser Arg His Pro Asp Thr Leu Leu Ala Ala Arg Ser Gly
                165                 170                 175 agt ccg ctg gtg att ggc ctg ggg atg ggc gaa aac ttt atc gct tct     576
Ser Pro Leu Val Ile Gly Leu Gly Met Gly Glu Asn Phe Ile Ala Ser
                180                 185                 190 gac cag ctg gcg ctg ttg ccg gtg acc cgt cgc ttt atc ttc ctt gaa     624
Asp Gln Leu Ala Leu Leu Pro Val Thr Arg Arg Phe Ile Phe Leu Glu
            195                 200                 205 gag ggc gat att gcg gaa atc act cgc cgt tcg gta aac atc ttc gat     672
Glu Gly Asp Ile Ala Glu Ile Thr Arg Arg Ser Val Asn Ile Phe Asp
        210                 215                 220 aaa act ggc gcg gaa gta aaa cgt cag gat atc gaa tcc aat ctg caa     720
Lys Thr Gly Ala Glu Val Lys Arg Gln Asp Ile Glu Ser Asn Leu Gln
225                 230                 235                 240 tat gac gcg ggc gat aaa ggc att tac cgt cac tac atg cag aaa gag     768
Tyr Asp Ala Gly Asp Lys Gly Ile Tyr Arg His Tyr Met Gln Lys Glu
                245                 250                 255 atc tac gaa cag ccg aac gcg atc aaa aac acc ctt acc gga cgc atc     816
Ile Tyr Glu Gln Pro Asn Ala Ile Lys Asn Thr Leu Thr Gly Arg Ile
                260                 265                 270
```

-continued

| | |
|---|---|
| agc cac ggt cag gtt gat tta agc gag ctg gga ccg aac gcc gac gaa<br>Ser His Gly Gln Val Asp Leu Ser Glu Leu Gly Pro Asn Ala Asp Glu<br>                275                      280                      285 | 864 |
| ctg ctg tcg aag gtt gag cat att cag atc ctc gcc tgt ggt act tct<br>Leu Leu Ser Lys Val Glu His Ile Gln Ile Leu Ala Cys Gly Thr Ser<br>        290                      295                      300 | 912 |
| tat aac tcc ggt atg gtt tcc cgc tac tgg ttt gaa tcg cta gca ggt<br>Tyr Asn Ser Gly Met Val Ser Arg Tyr Trp Phe Glu Ser Leu Ala Gly<br>305                      310                      315                  320 | 960 |
| att ccg tgc gac gtc gaa atc gcc tct gaa ttc cgc tat cgc aaa tct<br>Ile Pro Cys Asp Val Glu Ile Ala Ser Glu Phe Arg Tyr Arg Lys Ser<br>                  325                      330                      335 | 1008 |
| gcc gtg cgt cgt aac agc ctg atg atc acc ttg tca cag tct ggc gaa<br>Ala Val Arg Arg Asn Ser Leu Met Ile Thr Leu Ser Gln Ser Gly Glu<br>        340                      345                      350 | 1056 |
| acc gcg gat acc ctg gct ggc ctg cgt ctg tcg aaa gag ctg ggt tac<br>Thr Ala Asp Thr Leu Ala Gly Leu Arg Leu Ser Lys Glu Leu Gly Tyr<br>                355                      360                      365 | 1104 |
| ctt ggt tca ctg gca atc tgt aac gtt ccg ggt tct tct ctg gtg cgc<br>Leu Gly Ser Leu Ala Ile Cys Asn Val Pro Gly Ser Ser Leu Val Arg<br>370                      375                      380 | 1152 |
| gaa tcc gtt ctg gcg cta atg acc aac gcg ggt aca gaa atc ggc gtg<br>Glu Ser Val Leu Ala Leu Met Thr Asn Ala Gly Thr Glu Ile Gly Val<br>385                      390                      395                  400 | 1200 |
| gca tcc act aaa gca ttc acc act cag tta act gtg ctg ttg atg ctg<br>Ala Ser Thr Lys Ala Phe Thr Thr Gln Leu Thr Val Leu Leu Met Leu<br>                405                      410                      415 | 1248 |
| gtg gcg aag ctg tct cgc ctg aaa ggt ctg gat gcc tcc att gaa cat<br>Val Ala Lys Leu Ser Arg Leu Lys Gly Leu Asp Ala Ser Ile Glu His<br>        420                      425                      430 | 1296 |
| gac atc gtg cat ggt ctg cag gcg ctg ccg agc cgt att gag cag atg<br>Asp Ile Val His Gly Leu Gln Ala Leu Pro Ser Arg Ile Glu Gln Met<br>                435                      440                      445 | 1344 |
| ctg cct cag gac aaa cgc att gaa gcg ctg gca gaa gat ttc tct gac<br>Leu Pro Gln Asp Lys Arg Ile Glu Ala Leu Ala Glu Asp Phe Ser Asp<br>        450                      455                      460 | 1392 |
| aaa cat cac gcg ctg ttc ctg ggc cgt ggc gat cag tac cca atc gcg<br>Lys His His Ala Leu Phe Leu Gly Arg Gly Asp Gln Tyr Pro Ile Ala<br>465                      470                      475                  480 | 1440 |
| ctg gaa ggc gca ttg aag ttg aaa gag atc tct tac att cac gct gaa<br>Leu Glu Gly Ala Leu Lys Leu Lys Glu Ile Ser Tyr Ile His Ala Glu<br>                485                      490                      495 | 1488 |
| gcc tac gct gct ggc gaa ctg aaa cac ggt ccg ctg gcg cta att gat<br>Ala Tyr Ala Ala Gly Glu Leu Lys His Gly Pro Leu Ala Leu Ile Asp<br>        500                      505                      510 | 1536 |
| gcc gat atg ccg gtt att gtt gtt gca ccg aac aac gga ttg ctg gaa<br>Ala Asp Met Pro Val Ile Val Val Ala Pro Asn Asn Gly Leu Leu Glu<br>                515                      520                      525 | 1584 |
| aaa ctg aaa tcc aac att gaa gaa gtt cgc gcg cgt ggc ggt cag ttg<br>Lys Leu Lys Ser Asn Ile Glu Glu Val Arg Ala Arg Gly Gly Gln Leu<br>530                      535                      540 | 1632 |
| tat gtc ttc gcc gat cag gat gcg ggt ttt gta agt agc gat aac atg<br>Tyr Val Phe Ala Asp Gln Asp Ala Gly Phe Val Ser Ser Asp Asn Met<br>545                      550                      555                  560 | 1680 |
| cac atc atc gag atg ccg cat gtg gaa gag gtg att gca ccg atc ttc<br>His Ile Ile Glu Met Pro His Val Glu Glu Val Ile Ala Pro Ile Phe<br>                  565                      570                      575 | 1728 |
| tac acc gtt ccg ctg cag ctg ctg gct tac cat gtc gcg ctg atc aaa<br>Tyr Thr Val Pro Leu Gln Leu Leu Ala Tyr His Val Ala Leu Ile Lys<br>        580                      585                      590 | 1776 |

```
ggc acc gac gtt gac cag ccg cgt aac ctg gca aaa tcg gtt acg gtt    1824
Gly Thr Asp Val Asp Gln Pro Arg Asn Leu Ala Lys Ser Val Thr Val
        595                 600                 605 gag taa                                                             1830
Glu

<210> SEQ ID NO 14
<211> LENGTH: 609
<212> TYPE: PRT
<213> ORGANISM: Escherichia coli

<400> SEQUENCE: 14

Met Cys Gly Ile Val Gly Ala Ile Ala Gln Arg Asp Val Ala Lys Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335
```

```
Ala Val Arg Arg Asn Ser Leu Met Ile Thr Leu Ser Gln Ser Gly Glu
                340                 345                 350

Thr Ala Asp Thr Leu Ala Gly Leu Arg Leu Ser Lys Glu Leu Gly Tyr
            355                 360                 365

Leu Gly Ser Leu Ala Ile Cys Asn Val Pro Gly Ser Ser Leu Val Arg
        370                 375                 380

Glu Ser Val Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Pro Gln Asp Lys Arg Ile Glu Ala Leu Ala Glu Asp Phe Ser Asp
    450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Val Ala Pro Asn Asn Gly Leu Leu Glu
        515                 520                 525

Lys Leu Lys Ser Asn Ile Glu Glu Val Arg Ala Arg Gly Gly Gln Leu
    530                 535                 540

Tyr Val Phe Ala Asp Gln Asp Ala Gly Phe Val Ser Ser Asp Asn Met
545                 550                 555                 560

His Ile Ile Glu Met Pro His Val Glu Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 15
<211> LENGTH: 1803
<212> TYPE: DNA
<213> ORGANISM: Bacillus subtilis
<220> FEATURE:
<221> NAME/KEY: CDS
<222> LOCATION: (1)..(1803)
<223> OTHER INFORMATION:

<400> SEQUENCE: 15 atg tgt gga atc gta ggt tat atc ggt cag ctt gat gcg aag gaa att      48
Met Cys Gly Ile Val Gly Tyr Ile Gly Gln Leu Asp Ala Lys Glu Ile
1               5                  10                  15 tta tta aaa ggg tta gag aag ctt gag tat cgc ggt tat gac tct gct     96
Leu Leu Lys Gly Leu Glu Lys Leu Glu Tyr Arg Gly Tyr Asp Ser Ala
            20                  25                  30 ggt att gct gtt gcc aac gaa cag gga atc cat gtg ttc aaa gaa aaa    144
Gly Ile Ala Val Ala Asn Glu Gln Gly Ile His Val Phe Lys Glu Lys
        35                  40                  45 gga cgc att gca gat ctt cgt gaa gtt gtg gat gcc aat gta gaa gcg    192
Gly Arg Ile Ala Asp Leu Arg Glu Val Val Asp Ala Asn Val Glu Ala
```

|  |  |
|---|---|
| aaa gcc gga att ggg cat act cgc tgg gcg aca cac ggc gaa cca agc<br>Lys Ala Gly Ile Gly His Thr Arg Trp Ala Thr His Gly Glu Pro Ser<br>65                       70                      75                  80 | 240 |
| tat ctg aac gct cac ccg cat caa agc gca ctg ggc cgc ttt aca ctt<br>Tyr Leu Asn Ala His Pro His Gln Ser Ala Leu Gly Arg Phe Thr Leu<br>                 85                      90                      95 | 288 |
| gtt cac aac ggc gtg atc gag aac tat gtt cag ctg aag caa gag tat<br>Val His Asn Gly Val Ile Glu Asn Tyr Val Gln Leu Lys Gln Glu Tyr<br>                100                    105                   110 | 336 |
| ttg caa gat gta gag ctc aaa agt gac acc gat aca gaa gta gtc gtt<br>Leu Gln Asp Val Glu Leu Lys Ser Asp Thr Asp Thr Glu Val Val Val<br>          115                    120                   125 | 384 |
| caa gta atc gag caa ttc gtc aat gga gga ctt gag aca gaa gaa gcg<br>Gln Val Ile Glu Gln Phe Val Asn Gly Gly Leu Glu Thr Glu Glu Ala<br>          130                    135                   140 | 432 |
| ttc cgc aaa aca ctt aca ctg tta aaa ggc tct tat gca att gct tta<br>Phe Arg Lys Thr Leu Thr Leu Leu Lys Gly Ser Tyr Ala Ile Ala Leu<br>145                      150                    155                160 | 480 |
| ttc gat aac gac aac aga gaa acg att ttt gta gcg aaa aac aaa agc<br>Phe Asp Asn Asp Asn Arg Glu Thr Ile Phe Val Ala Lys Asn Lys Ser<br>                 165                    170                   175 | 528 |
| cct cta tta gta ggt ctt gga gat aca ttc aac gtc gta gca tct gat<br>Pro Leu Leu Val Gly Leu Gly Asp Thr Phe Asn Val Val Ala Ser Asp<br>                180                    185                   190 | 576 |
| gcg atg gcg atg ctt caa gta acc aac gaa tac gta gag ctg atg gat<br>Ala Met Ala Met Leu Gln Val Thr Asn Glu Tyr Val Glu Leu Met Asp<br>          195                    200                   205 | 624 |
| aaa gaa atg gtt atc gtc act gat gac caa gtt gtc atc aaa aac ctt<br>Lys Glu Met Val Ile Val Thr Asp Asp Gln Val Val Ile Lys Asn Leu<br>210                      215                    220 | 672 |
| gat ggt gac gtg att aca cgt gcg tct tat att gct gag ctt gat gcc<br>Asp Gly Asp Val Ile Thr Arg Ala Ser Tyr Ile Ala Glu Leu Asp Ala<br>225                      230                    235                240 | 720 |
| agt gat atc gaa aaa ggc acg tac cct cac tac atg ttg aaa gaa acg<br>Ser Asp Ile Glu Lys Gly Thr Tyr Pro His Tyr Met Leu Lys Glu Thr<br>                245                    250                   255 | 768 |
| gat gag cag cct gtt gtt atg cgc aaa atc atc caa acg tat caa gat<br>Asp Glu Gln Pro Val Val Met Arg Lys Ile Ile Gln Thr Tyr Gln Asp<br>          260                    265                   270 | 816 |
| gaa aac ggc aag ctg tct gtg cct ggc gat atc gct gcc gct gta gcg<br>Glu Asn Gly Lys Leu Ser Val Pro Gly Asp Ile Ala Ala Ala Val Ala<br>                275                    280                   285 | 864 |
| gaa gcg gac cgc atc tat atc att ggc tgc gga aca agc tac cat gca<br>Glu Ala Asp Arg Ile Tyr Ile Ile Gly Cys Gly Thr Ser Tyr His Ala<br>          290                    295                   300 | 912 |
| gga ctt gtc ggt aaa caa tat att gaa atg tgg gca aac gtg ccg gtt<br>Gly Leu Val Gly Lys Gln Tyr Ile Glu Met Trp Ala Asn Val Pro Val<br>305                      310                    315                320 | 960 |
| gaa gtg cat gta gcg agt gaa ttc tcc tac aac atg ccg ctt ctg tct<br>Glu Val His Val Ala Ser Glu Phe Ser Tyr Asn Met Pro Leu Leu Ser<br>                325                    330                   335 | 1008 |
| aag aaa ccg ctc ttc att ttc ctt tct caa agc gga gaa aca gca gac<br>Lys Lys Pro Leu Phe Ile Phe Leu Ser Gln Ser Gly Glu Thr Ala Asp<br>          340                    345                   350 | 1056 |
| agc cgc gcg gta ctc gtt caa gtc aaa gcg ctc gga cac aaa gcc ctg<br>Ser Arg Ala Val Leu Val Gln Val Lys Ala Leu Gly His Lys Ala Leu<br>                355                    360                   365 | 1104 |
| aca atc aca aac gta cct gga tca acg ctt tct cgt gaa gct gac tat | 1152 |

```
                Thr Ile Thr Asn Val Pro Gly Ser Thr Leu Ser Arg Glu Ala Asp Tyr
                    370                 375                 380 aca ttg ctg ctt cat gca ggc cct gag atc gct gtt gcg tca acg aaa     1200
Thr Leu Leu Leu His Ala Gly Pro Glu Ile Ala Val Ala Ser Thr Lys
385                 390                 395                 400 gca tac act gca caa atc gca gtt ctg gcg gtt ctt gct tct gtg gct     1248
Ala Tyr Thr Ala Gln Ile Ala Val Leu Ala Val Leu Ala Ser Val Ala
                405                 410                 415 gct gac aaa aat ggc atc aat atc gga ttt gac ctc gtc aaa gaa ctc     1296
Ala Asp Lys Asn Gly Ile Asn Ile Gly Phe Asp Leu Val Lys Glu Leu
            420                 425                 430 ggt atc gct gca aac gca atg gaa gct cta tgc gac cag aaa gac gaa     1344
Gly Ile Ala Ala Asn Ala Met Glu Ala Leu Cys Asp Gln Lys Asp Glu
        435                 440                 445 atg gaa atg atc gct cgt gaa tac ctg act gta tcc aga aat gct ttc     1392
Met Glu Met Ile Ala Arg Glu Tyr Leu Thr Val Ser Arg Asn Ala Phe
    450                 455                 460 ttc atc gga cgc ggc ctt gac tac ttc gta tgt gtc gaa ggc gca ctg     1440
Phe Ile Gly Arg Gly Leu Asp Tyr Phe Val Cys Val Glu Gly Ala Leu
465                 470                 475                 480 aag ctg aaa gag att tct tac atc cag gca gaa ggt ttt gcc ggc ggt     1488
Lys Leu Lys Glu Ile Ser Tyr Ile Gln Ala Glu Gly Phe Ala Gly Gly
                485                 490                 495 gag cta aag cac gga acg att gcc ttg atc gaa caa gga aca cca gta     1536
Glu Leu Lys His Gly Thr Ile Ala Leu Ile Glu Gln Gly Thr Pro Val
            500                 505                 510 ttc gca ctg gca act caa gag cat gta aac cta agc atc cgc gga aac     1584
Phe Ala Leu Ala Thr Gln Glu His Val Asn Leu Ser Ile Arg Gly Asn
        515                 520                 525 gtc aaa gaa gtt gct gct cgc gga gca aac aca tgc atc atc tca ctg     1632
Val Lys Glu Val Ala Ala Arg Gly Ala Asn Thr Cys Ile Ile Ser Leu
    530                 535                 540 aaa ggc cta gac gat gcg gat gac aga ttc gta ttg ccg gaa gta aac     1680
Lys Gly Leu Asp Asp Ala Asp Asp Arg Phe Val Leu Pro Glu Val Asn
545                 550                 555                 560 cca gcg ctt gct ccg ttg gta tct gtt gtt cca ttg cag ctg atc gct     1728
Pro Ala Leu Ala Pro Leu Val Ser Val Val Pro Leu Gln Leu Ile Ala
                565                 570                 575 tac tat gct gca ctg cat cgc ggc tgt gat gtg gat aaa cct cgt aac     1776
Tyr Tyr Ala Ala Leu His Arg Gly Cys Asp Val Asp Lys Pro Arg Asn
            580                 585                 590 ctt gcg aag agt gtt act gtg gag taa                                  1803
Leu Ala Lys Ser Val Thr Val Glu
        595                 600

<210> SEQ ID NO 16
<211> LENGTH: 600
<212> TYPE: PRT
<213> ORGANISM: Bacillus subtilis

<400> SEQUENCE: 16

Met Cys Gly Ile Val Gly Tyr Ile Gly Gln Leu Asp Ala Lys Glu Ile
1               5                   10                  15

Leu Leu Lys Gly Leu Glu Lys Leu Glu Tyr Arg Gly Tyr Asp Ser Ala
                20                  25                  30

Gly Ile Ala Val Ala Asn Glu Gln Gly Ile His Val Phe Lys Glu Lys
            35                  40                  45

Gly Arg Ile Ala Asp Leu Arg Glu Val Val Asp Ala Asn Val Glu Ala
        50                  55                  60
```

-continued

```
Lys Ala Gly Ile Gly His Thr Arg Trp Ala Thr His Gly Glu Pro Ser
 65                  70                  75                  80

Tyr Leu Asn Ala His Pro His Gln Ser Ala Leu Gly Arg Phe Thr Leu
                 85                  90                  95

Val His Asn Gly Ile Glu Asn Tyr Val Gln Leu Lys Gln Glu Tyr
            100                 105                 110

Leu Gln Asp Val Glu Leu Lys Ser Asp Thr Asp Thr Glu Val Val Val
            115                 120                 125

Gln Val Ile Glu Gln Phe Val Asn Gly Gly Leu Glu Thr Glu Glu Ala
            130                 135                 140

Phe Arg Lys Thr Leu Thr Leu Leu Lys Gly Ser Tyr Ala Ile Ala Leu
145                 150                 155                 160

Phe Asp Asn Asp Asn Arg Glu Thr Ile Phe Val Ala Lys Asn Lys Ser
                165                 170                 175

Pro Leu Leu Val Gly Leu Gly Asp Thr Phe Asn Val Val Ala Ser Asp
            180                 185                 190

Ala Met Ala Met Leu Gln Val Thr Asn Glu Tyr Val Glu Leu Met Asp
            195                 200                 205

Lys Glu Met Val Ile Val Thr Asp Asp Gln Val Val Ile Lys Asn Leu
210                 215                 220

Asp Gly Asp Val Ile Thr Arg Ala Ser Tyr Ile Ala Glu Leu Asp Ala
225                 230                 235                 240

Ser Asp Ile Glu Lys Gly Thr Tyr Pro His Tyr Met Leu Lys Glu Thr
            245                 250                 255

Asp Glu Gln Pro Val Val Met Arg Lys Ile Ile Gln Thr Tyr Gln Asp
            260                 265                 270

Glu Asn Gly Lys Leu Ser Val Pro Gly Asp Ile Ala Ala Ala Val Ala
            275                 280                 285

Glu Ala Asp Arg Ile Tyr Ile Ile Gly Cys Gly Thr Ser Tyr His Ala
            290                 295                 300

Gly Leu Val Gly Lys Gln Tyr Ile Glu Met Trp Ala Asn Val Pro Val
305                 310                 315                 320

Glu Val His Val Ala Ser Glu Phe Ser Tyr Asn Met Pro Leu Leu Ser
                325                 330                 335

Lys Lys Pro Leu Phe Ile Phe Leu Ser Gln Ser Gly Glu Thr Ala Asp
            340                 345                 350

Ser Arg Ala Val Leu Val Gln Val Lys Ala Leu Gly His Lys Ala Leu
            355                 360                 365

Thr Ile Thr Asn Val Pro Gly Ser Thr Leu Ser Arg Glu Ala Asp Tyr
            370                 375                 380

Thr Leu Leu His Ala Gly Pro Glu Ile Ala Val Ala Ser Thr Lys
385                 390                 395                 400

Ala Tyr Thr Ala Gln Ile Ala Val Leu Ala Val Leu Ala Ser Val Ala
            405                 410                 415

Ala Asp Lys Asn Gly Ile Asn Ile Gly Phe Asp Leu Val Lys Glu Leu
            420                 425                 430

Gly Ile Ala Ala Asn Ala Met Glu Ala Leu Cys Asp Gln Lys Asp Glu
            435                 440                 445

Met Glu Met Ile Ala Arg Glu Tyr Leu Thr Val Ser Arg Asn Ala Phe
450                 455                 460

Phe Ile Gly Arg Gly Leu Asp Tyr Phe Val Cys Val Glu Gly Ala Leu
465                 470                 475                 480

Lys Leu Lys Glu Ile Ser Tyr Ile Gln Ala Glu Gly Phe Ala Gly Gly
```

```
                    485             490             495
Glu Leu Lys His Gly Thr Ile Ala Leu Ile Glu Gln Gly Thr Pro Val
            500             505             510

Phe Ala Leu Ala Thr Gln Glu His Val Asn Leu Ser Ile Arg Gly Asn
            515             520             525

Val Lys Glu Val Ala Ala Arg Gly Ala Asn Thr Cys Ile Ile Ser Leu
            530             535             540

Lys Gly Leu Asp Asp Ala Asp Asp Arg Phe Val Leu Pro Glu Val Asn
545             550             555             560

Pro Ala Leu Ala Pro Leu Val Ser Val Pro Leu Gln Leu Ile Ala
            565             570             575

Tyr Tyr Ala Ala Leu His Arg Gly Cys Asp Val Asp Lys Pro Arg Asn
            580             585             590

Leu Ala Lys Ser Val Thr Val Glu
            595             600

<210> SEQ ID NO 17
<211> LENGTH: 2154
<212> TYPE: DNA
<213> ORGANISM: Saccharomyces cerevisiae
<220> FEATURE:
<221> NAME/KEY: CDS
<222> LOCATION: (1)..(2154)
<223> OTHER INFORMATION:

<400> SEQUENCE: 17 atg tgt ggt atc ttt ggt tac tgc aat tat cta gtg gaa aga tcc aga     48
Met Cys Gly Ile Phe Gly Tyr Cys Asn Tyr Leu Val Glu Arg Ser Arg
1               5                   10                  15 gga gaa att atc gac acc tta gtg gat ggt tta caa aga tta gaa tat     96
Gly Glu Ile Ile Asp Thr Leu Val Asp Gly Leu Gln Arg Leu Glu Tyr
            20                  25                  30 aga ggc tat gat tcc acc ggt att gct atc gat ggt gac gaa gct gat    144
Arg Gly Tyr Asp Ser Thr Gly Ile Ala Ile Asp Gly Asp Glu Ala Asp
        35                  40                  45 tct act ttc atc tat aag caa atc ggt aaa gtg agt gct ttg aaa gag    192
Ser Thr Phe Ile Tyr Lys Gln Ile Gly Lys Val Ser Ala Leu Lys Glu
    50                  55                  60 gag att act aag caa aat ccg aac aga gac gtt act ttt gtc tct cat    240
Glu Ile Thr Lys Gln Asn Pro Asn Arg Asp Val Thr Phe Val Ser His
65                  70                  75                  80 tgt ggt att gcg cat act aga tgg gct act cac ggt cga cca gaa caa    288
Cys Gly Ile Ala His Thr Arg Trp Ala Thr His Gly Arg Pro Glu Gln
                85                  90                  95 gtt aac tgt cac cct caa aga tct gac cca gaa gac caa ttt gtg gtc    336
Val Asn Cys His Pro Gln Arg Ser Asp Pro Glu Asp Gln Phe Val Val
            100                 105                 110 gtt cat aat ggt atc atc aca aat ttt aga gaa ctg aag act ctt tta    384
Val His Asn Gly Ile Ile Thr Asn Phe Arg Glu Leu Lys Thr Leu Leu
        115                 120                 125 att aac aaa ggt tat aaa ttc gaa agt gat acc gat acc gag tgt att    432
Ile Asn Lys Gly Tyr Lys Phe Glu Ser Asp Thr Asp Thr Glu Cys Ile
    130                 135                 140 gct aaa cta tat ttg cat tta tac aat aca aat tta caa aat ggg cat    480
Ala Lys Leu Tyr Leu His Leu Tyr Asn Thr Asn Leu Gln Asn Gly His
145                 150                 155                 160 gac tta gat ttc cac gaa tta acc aag cta gtt ctt tta gaa cta gaa    528
Asp Leu Asp Phe His Glu Leu Thr Lys Leu Val Leu Leu Glu Leu Glu
                165                 170                 175
```

```
ggt tca tac ggg tta tta tgt aaa tct tgt cac tat cct aat gag gtt        576
Gly Ser Tyr Gly Leu Leu Cys Lys Ser Cys His Tyr Pro Asn Glu Val
        180                 185                 190 atc gcc act aga aaa ggg tcc cct tta ctg att ggt gtc aaa tct gaa        624
Ile Ala Thr Arg Lys Gly Ser Pro Leu Leu Ile Gly Val Lys Ser Glu
        195                 200                 205 aaa aaa cta aaa gtc gac ttc gtg gat gtg gaa ttt ccc gaa gaa aac        672
Lys Lys Leu Lys Val Asp Phe Val Asp Val Glu Phe Pro Glu Glu Asn
        210                 215                 220 gct ggt caa ccg gaa att cca ttg aaa tct aac aac aaa tca ttt ggc        720
Ala Gly Gln Pro Glu Ile Pro Leu Lys Ser Asn Asn Lys Ser Phe Gly
225                 230                 235                 240 ttg ggc cca aag aaa gct cgt gaa ttt gaa gct ggt tcc caa aat gcc        768
Leu Gly Pro Lys Lys Ala Arg Glu Phe Glu Ala Gly Ser Gln Asn Ala
                245                 250                 255 aat tta cta cca att gcc gcc aat gaa ttt aac ttg aga cat tct caa        816
Asn Leu Leu Pro Ile Ala Ala Asn Glu Phe Asn Leu Arg His Ser Gln
                260                 265                 270 tcc agg gct ttc cta tca gaa gat gga tct cca aca ccg gtg gaa ttt        864
Ser Arg Ala Phe Leu Ser Glu Asp Gly Ser Pro Thr Pro Val Glu Phe
            275                 280                 285 ttt gtt tct tcg gat gcg gca tct gtt gtt aaa cat acc aag aag gtg        912
Phe Val Ser Ser Asp Ala Ala Ser Val Val Lys His Thr Lys Lys Val
        290                 295                 300 cta ttt tta gaa gat gac gat ttg gct cat att tac gat ggt gag tta        960
Leu Phe Leu Glu Asp Asp Asp Leu Ala His Ile Tyr Asp Gly Glu Leu
305                 310                 315                 320 cat att cat aga tct aga aga gaa gta ggc gca tca atg aca agg tcc       1008
His Ile His Arg Ser Arg Arg Glu Val Gly Ala Ser Met Thr Arg Ser
                325                 330                 335 att caa act tta gag atg gag tta gct cag atc atg aag ggc cct tac       1056
Ile Gln Thr Leu Glu Met Glu Leu Ala Gln Ile Met Lys Gly Pro Tyr
                340                 345                 350 gac cat ttt atg caa aag gaa atc tat gag caa cca gaa tct act ttc       1104
Asp His Phe Met Gln Lys Glu Ile Tyr Glu Gln Pro Glu Ser Thr Phe
            355                 360                 365 aat act atg aga ggt aga atc gac tat gaa aat aat aaa gtg ata ttg       1152
Asn Thr Met Arg Gly Arg Ile Asp Tyr Glu Asn Asn Lys Val Ile Leu
        370                 375                 380 ggt ggt tta aag gca tgg tta cca gtt gtc aga aga gca cgg aga ctg       1200
Gly Gly Leu Lys Ala Trp Leu Pro Val Val Arg Arg Ala Arg Arg Leu
385                 390                 395                 400 atc atg atc gca tgc ggt act tct tat cat tca tgt ttg gct act cgt       1248
Ile Met Ile Ala Cys Gly Thr Ser Tyr His Ser Cys Leu Ala Thr Arg
                405                 410                 415 gct atc ttc gaa gaa tta tca gat atc cca gtt agt gtg gaa tta gcg       1296
Ala Ile Phe Glu Glu Leu Ser Asp Ile Pro Val Ser Val Glu Leu Ala
                420                 425                 430 tct gac ttt ctg gac aga aaa tgc cct gtc ttc aga gac gat gta tgc       1344
Ser Asp Phe Leu Asp Arg Lys Cys Pro Val Phe Arg Asp Asp Val Cys
            435                 440                 445 gtg ttt gtt tca caa agt ggt gaa act gcg gat acc atg ctg gct cta       1392
Val Phe Val Ser Gln Ser Gly Glu Thr Ala Asp Thr Met Leu Ala Leu
        450                 455                 460 aat tat tgt tta gaa aga gga gcc tta act gtc gga att gtt aac agt       1440
Asn Tyr Cys Leu Glu Arg Gly Ala Leu Thr Val Gly Ile Val Asn Ser
465                 470                 475                 480 gtt ggt tct tct atc tct cgt gtc acc cac tgt ggt gtt cat att aac       1488
Val Gly Ser Ser Ile Ser Arg Val Thr His Cys Gly Val His Ile Asn
                485                 490                 495
```

```
gct ggt cct gaa att ggt gtt gcc tct aca aaa gct tat act tcc cag    1536
Ala Gly Pro Glu Ile Gly Val Ala Ser Thr Lys Ala Tyr Thr Ser Gln
            500                 505                 510 tat att gcc tta gtg atg ttt gct cta tcg ctg tca gat gac cgt gta    1584
Tyr Ile Ala Leu Val Met Phe Ala Leu Ser Leu Ser Asp Asp Arg Val
        515                 520                 525 tcg aaa ata gac aga aga att gaa atc att caa ggc ttg aag tta atc    1632
Ser Lys Ile Asp Arg Arg Ile Glu Ile Ile Gln Gly Leu Lys Leu Ile
530                 535                 540 ccg ggc caa att aag cag gta tta aag ctg gaa cca aga ata aaa aag    1680
Pro Gly Gln Ile Lys Gln Val Leu Lys Leu Glu Pro Arg Ile Lys Lys
545                 550                 555                 560 ctc tgt gcg act gaa tta aag gat caa aaa tct cta ttg tta ttg ggt    1728
Leu Cys Ala Thr Glu Leu Lys Asp Gln Lys Ser Leu Leu Leu Leu Gly
                565                 570                 575 aga ggt tac caa ttt gct gct gct ctg gaa ggt gct ttg aag atc aaa    1776
Arg Gly Tyr Gln Phe Ala Ala Ala Leu Glu Gly Ala Leu Lys Ile Lys
            580                 585                 590 gaa att tct tat atg cat tct gaa ggt gtt ttg gca ggt gag ttg aag    1824
Glu Ile Ser Tyr Met His Ser Glu Gly Val Leu Ala Gly Glu Leu Lys
        595                 600                 605 cac ggt gtc ttg gcc ttg gtg gac gaa aac ttg cca atc att gct ttt    1872
His Gly Val Leu Ala Leu Val Asp Glu Asn Leu Pro Ile Ile Ala Phe
610                 615                 620 ggt acc aga gac tct cta ttc cct aaa gta gtt tcc tct att gag caa    1920
Gly Thr Arg Asp Ser Leu Phe Pro Lys Val Val Ser Ser Ile Glu Gln
625                 630                 635                 640 gtt act gca aga aag ggc cat cca att att att tgt aac gaa aat gat    1968
Val Thr Ala Arg Lys Gly His Pro Ile Ile Ile Cys Asn Glu Asn Asp
                645                 650                 655 gaa gtg tgg gcg caa aaa tct aaa tca atc gac ctg caa acc tta gaa    2016
Glu Val Trp Ala Gln Lys Ser Lys Ser Ile Asp Leu Gln Thr Leu Glu
            660                 665                 670 gtt cca caa act gtt gat tgt tta caa ggt cta att aat att att cca    2064
Val Pro Gln Thr Val Asp Cys Leu Gln Gly Leu Ile Asn Ile Ile Pro
        675                 680                 685 tta caa cta atg tca tat tgg ttg gct gtt aat aaa ggg att gat gtt    2112
Leu Gln Leu Met Ser Tyr Trp Leu Ala Val Asn Lys Gly Ile Asp Val
690                 695                 700 gat ttt cca aga aac ttg gct aaa tct gtt acc gtc gaa taa            2154
Asp Phe Pro Arg Asn Leu Ala Lys Ser Val Thr Val Glu
705                 710                 715

<210> SEQ ID NO 18
<211> LENGTH: 717
<212> TYPE: PRT
<213> ORGANISM: Saccharomyces cerevisiae

<400> SEQUENCE: 18

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Lys Glu
    50                  55                  60

Glu Ile Thr Lys Gln Asn Pro Asn Arg Asp Val Thr Phe Val Ser His
65                  70                  75                  80
```

-continued

```
Cys Gly Ile Ala His Thr Arg Trp Ala Thr His Gly Arg Pro Glu Gln
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
    130                 135                 140

Ala Lys Leu Tyr Leu His Leu Tyr Asn Thr Asn Leu Gln Asn Gly His
145                 150                 155                 160

Asp Leu Asp Phe His Glu Leu Thr Lys Leu Val Leu Leu Glu Leu Glu
                165                 170                 175

Gly Ser Tyr Gly Leu Leu Cys Lys Ser Cys His Tyr Pro Asn Glu Val
            180                 185                 190

Ile Ala Thr Arg Lys Gly Ser Pro Leu Leu Ile Gly Val Lys Ser Glu
        195                 200                 205

Lys Lys Leu Lys Val Asp Phe Val Asp Val Glu Phe Pro Glu Glu Asn
    210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
            260                 265                 270

Ser Arg Ala Phe Leu Ser Glu Asp Gly Ser Pro Thr Pro Val Glu Phe
        275                 280                 285

Phe Val Ser Ser Asp Ala Ala Ser Val Val Lys His Thr Lys Lys Val
    290                 295                 300

Leu Phe Leu Glu Asp Asp Leu Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile Gln Thr Leu Glu Met Glu Leu Ala Gln Ile Met Lys Gly Pro Tyr
            340                 345                 350

Asp His Phe Met Gln Lys Glu Ile Tyr Glu Gln Pro Glu Ser Thr Phe
        355                 360                 365

Asn Thr Met Arg Gly Arg Ile Asp Tyr Glu Asn Asn Lys Val Ile Leu
    370                 375                 380

Gly Gly Leu Lys Ala Trp Leu Pro Val Val Arg Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
            420                 425                 430

Ser Asp Phe Leu Asp Arg Lys Cys Pro Val Phe Arg Asp Asp Val Cys
        435                 440                 445

Val Phe Val Ser Gln Ser Gly Glu Thr Ala Asp Thr Met Leu Ala Leu
    450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Gly Val His Ile Asn
                485                 490                 495
```

```
Ala Gly Pro Glu Ile Gly Val Ala Ser Thr Lys Ala Tyr Thr Ser Gln
            500                 505                 510

Tyr Ile Ala Leu Val Met Phe Ala Leu Ser Leu Ser Asp Asp Arg Val
            515                 520                 525

Ser Lys Ile Asp Arg Arg Ile Glu Ile Ile Gln Gly Leu Lys Leu Ile
            530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
                565                 570                 575

Arg Gly Tyr Gln Phe Ala Ala Leu Glu Gly Ala Leu Lys Ile Lys
            580                 585                 590

Glu Ile Ser Tyr Met His Ser Glu Gly Val Leu Ala Gly Glu Leu Lys
            595                 600                 605

His Gly Val Leu Ala Leu Val Asp Glu Asn Leu Pro Ile Ile Ala Phe
            610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Ile Cys Asn Glu Asn Asp
                645                 650                 655

Glu Val Trp Ala Gln Lys Ser Lys Ser Ile Asp Leu Gln Thr Leu Glu
            660                 665                 670

Val Pro Gln Thr Val Asp Cys Leu Gln Gly Leu Ile Asn Ile Pro
            675                 680                 685

Leu Gln Leu Met Ser Tyr Trp Leu Ala Val Asn Lys Gly Ile Asp Val
            690                 695                 700

Asp Phe Pro Arg Asn Leu Ala Lys Ser Val Thr Val Glu
705                 710                 715

<210> SEQ ID NO 19
<211> LENGTH: 2142
<212> TYPE: DNA
<213> ORGANISM: Candida albicans
<220> FEATURE:
<221> NAME/KEY: CDS
<222> LOCATION: (1)..(2142)
<223> OTHER INFORMATION:

<400> SEQUENCE: 19 atg tgt ggt att ttt ggt tac gtc aat ttc ttg gtc gac aag agt aga      48
Met Cys Gly Ile Phe Gly Tyr Val Asn Phe Leu Val Asp Lys Ser Arg
1               5                  10                  15 ggt gaa atc att gat aat tta att gaa ggt ttg caa cga tta gaa tat      96
Gly Glu Ile Ile Asp Asn Leu Ile Glu Gly Leu Gln Arg Leu Glu Tyr
                20                  25                  30 aga ggt tat gat tca gca ggc att gct gtt gat ggg aaa tta act aaa     144
Arg Gly Tyr Asp Ser Ala Gly Ile Ala Val Asp Gly Lys Leu Thr Lys
            35                  40                  45 gat cct tct aat ggt gat gaa gaa tat atg gat tct att att gtt aaa     192
Asp Pro Ser Asn Gly Asp Glu Glu Tyr Met Asp Ser Ile Ile Val Lys
        50                  55                  60 act act ggt aaa gtt aaa gtt ttg aaa caa aaa atc att gat gat caa     240
Thr Thr Gly Lys Val Lys Val Leu Lys Gln Lys Ile Ile Asp Asp Gln
65                  70                  75                  80 atc gat aga tcg gcc att ttt gat aat cat gtt ggt att gct cat act     288
Ile Asp Arg Ser Ala Ile Phe Asp Asn His Val Gly Ile Ala His Thr
                85                  90                  95 aga tgg gct aca cat ggt caa cca aaa act gaa aat tgt cat cct cat     336
```

-continued

```
        Arg Trp Ala Thr His Gly Gln Pro Lys Thr Glu Asn Cys His Pro His
                    100                 105                 110 aaa tca gat cca aag ggg gaa ttc att gtt gtt cat aat ggt att att       384
Lys Ser Asp Pro Lys Gly Glu Phe Ile Val Val His Asn Gly Ile Ile
        115                 120                 125 act aat tat gct gct tta aga aaa tat ctt tta tca aaa gga cat gtt       432
Thr Asn Tyr Ala Ala Leu Arg Lys Tyr Leu Leu Ser Lys Gly His Val
        130                 135                 140 ttt gaa agt gaa act gat act gaa tgt att gct aaa tta ttt aaa cat       480
Phe Glu Ser Glu Thr Asp Thr Glu Cys Ile Ala Lys Leu Phe Lys His
145                 150                 155                 160 ttt tat gat ttg aat gtt aaa gct ggt gtt ttc cct gat ctt aat gaa       528
Phe Tyr Asp Leu Asn Val Lys Ala Gly Val Phe Pro Asp Leu Asn Glu
                165                 170                 175 ttg act aaa caa gtt ttg cat gaa tta gaa ggt tct tat ggg tta tta       576
Leu Thr Lys Gln Val Leu His Glu Leu Glu Gly Ser Tyr Gly Leu Leu
            180                 185                 190 gtt aaa tct tat cat tat cct gga gaa gtt tgt ggt act aga aaa ggt       624
Val Lys Ser Tyr His Tyr Pro Gly Glu Val Cys Gly Thr Arg Lys Gly
        195                 200                 205 tct cca tta ttg gtt ggt gtt aaa act gat aag aaa tta aaa gtt gat       672
Ser Pro Leu Leu Val Gly Val Lys Thr Asp Lys Lys Leu Lys Val Asp
    210                 215                 220 ttt gtt gac gtt gaa ttt gaa gct caa cag caa cat cga cca caa caa       720
Phe Val Asp Val Glu Phe Glu Ala Gln Gln Gln His Arg Pro Gln Gln
225                 230                 235                 240 cca caa atc aat cat aat ggt gcc act tca gct gct gaa ttg ggc ttt       768
Pro Gln Ile Asn His Asn Gly Ala Thr Ser Ala Ala Glu Leu Gly Phe
                245                 250                 255 atc cca gtg gct cca ggt gaa caa aat tta aga act tct caa tca aga       816
Ile Pro Val Ala Pro Gly Glu Gln Asn Leu Arg Thr Ser Gln Ser Arg
            260                 265                 270 gct ttc ctt tct gaa gat gat tta cct atg cca gtt gaa ttc ttt tta       864
Ala Phe Leu Ser Glu Asp Asp Leu Pro Met Pro Val Glu Phe Phe Leu
        275                 280                 285 tct tct gat cct gca tca gtg gtt caa cac acc aaa aaa gtt tta ttt       912
Ser Ser Asp Pro Ala Ser Val Val Gln His Thr Lys Lys Val Leu Phe
    290                 295                 300 tta gaa gat gat gat att gct cat atc tat gat ggg gaa tta cgt att       960
Leu Glu Asp Asp Asp Ile Ala His Ile Tyr Asp Gly Glu Leu Arg Ile
305                 310                 315                 320 cat aga gct tcg act aaa tct gct ggg gaa tct act gtt aga cca att      1008
His Arg Ala Ser Thr Lys Ser Ala Gly Glu Ser Thr Val Arg Pro Ile
                325                 330                 335 caa act tta gaa atg gaa ttg aat gaa att atg aaa ggc ccc tat aaa      1056
Gln Thr Leu Glu Met Glu Leu Asn Glu Ile Met Lys Gly Pro Tyr Lys
            340                 345                 350 cat ttt atg caa aaa gaa att ttc gaa caa cca gat tct gct ttt aat      1104
His Phe Met Gln Lys Glu Ile Phe Glu Gln Pro Asp Ser Ala Phe Asn
        355                 360                 365 act atg aga ggt aga att gat ttt gaa aat tgt gtt gtt acc ctt ggt      1152
Thr Met Arg Gly Arg Ile Asp Phe Glu Asn Cys Val Val Thr Leu Gly
    370                 375                 380 gga tta aaa tca tgg tta tct aca att aga aga tgt aga aga atc att      1200
Gly Leu Lys Ser Trp Leu Ser Thr Ile Arg Arg Cys Arg Arg Ile Ile
385                 390                 395                 400 atg att gct tgt ggt act tca tat cat tca tgt tta gcc acg aga tca      1248
Met Ile Ala Cys Gly Thr Ser Tyr His Ser Cys Leu Ala Thr Arg Ser
                405                 410                 415
```

```
-continued att ttt gaa gaa ttg aca gaa atc ccc gtt tcg gtt gaa tta gct tct      1296
Ile Phe Glu Glu Leu Thr Glu Ile Pro Val Ser Val Glu Leu Ala Ser
        420                 425                 430 gat ttc ttg gat aga aga tct cca gtt ttc aga gat gat act tgt gta      1344
Asp Phe Leu Asp Arg Arg Ser Pro Val Phe Arg Asp Asp Thr Cys Val
    435                 440                 445 ttt gtt tct caa tcg ggt gaa act gcc gac tcc att ttg gct tta caa      1392
Phe Val Ser Gln Ser Gly Glu Thr Ala Asp Ser Ile Leu Ala Leu Gln
450                 455                 460 tat tgt ttg gaa aga gga gct tta act gtt ggt atc gtt aac tct gtt      1440
Tyr Cys Leu Glu Arg Gly Ala Leu Thr Val Gly Ile Val Asn Ser Val
465                 470                 475                 480 ggt tct tca atg tct aga caa acc cat tgt ggg gtt cat att aat gct      1488
Gly Ser Ser Met Ser Arg Gln Thr His Cys Gly Val His Ile Asn Ala
            485                 490                 495 ggg cca gaa att ggt gtt gcc tca act aaa gct tac aca tct caa tat      1536
Gly Pro Glu Ile Gly Val Ala Ser Thr Lys Ala Tyr Thr Ser Gln Tyr
        500                 505                 510 att gcc ttg gtg atg ttt gcc ctt tct tta tct aat gat tct att tcc      1584
Ile Ala Leu Val Met Phe Ala Leu Ser Leu Ser Asn Asp Ser Ile Ser
    515                 520                 525 aga aag gga aga cat gaa gaa att att aaa ggt tta caa aaa atc cct      1632
Arg Lys Gly Arg His Glu Glu Ile Ile Lys Gly Leu Gln Lys Ile Pro
530                 535                 540 gaa caa att aaa caa gtt ttg aaa tta gaa aac aag atc aaa gat tta      1680
Glu Gln Ile Lys Gln Val Leu Lys Leu Glu Asn Lys Ile Lys Asp Leu
545                 550                 555                 560 tgt aat agt tca ttg aat gat caa aaa tct tta tta tta tta ggt aga      1728
Cys Asn Ser Ser Leu Asn Asp Gln Lys Ser Leu Leu Leu Leu Gly Arg
            565                 570                 575 ggt tat caa ttt gct act gct tta gaa ggg gct tta aaa att aaa gaa      1776
Gly Tyr Gln Phe Ala Thr Ala Leu Glu Gly Ala Leu Lys Ile Lys Glu
        580                 585                 590 att tct tat atg cat tct gaa ggg gta tta gct ggt gaa tta aaa cat      1824
Ile Ser Tyr Met His Ser Glu Gly Val Leu Ala Gly Glu Leu Lys His
    595                 600                 605 ggt ata tta gca tta gtc gat gaa gat tta cca att att gcc ttt gcc      1872
Gly Ile Leu Ala Leu Val Asp Glu Asp Leu Pro Ile Ile Ala Phe Ala
610                 615                 620 act aga gat tca tta ttt cct aaa gtt atg tcc gct att gaa caa gtc      1920
Thr Arg Asp Ser Leu Phe Pro Lys Val Met Ser Ala Ile Glu Gln Val
625                 630                 635                 640 act gct aga gat ggt aga cca att gtt att tgt aat gaa ggt gat gct      1968
Thr Ala Arg Asp Gly Arg Pro Ile Val Ile Cys Asn Glu Gly Asp Ala
            645                 650                 655 att att tct aat gat aaa gtt cat act act tta gaa gtt cca gaa acc      2016
Ile Ile Ser Asn Asp Lys Val His Thr Thr Leu Glu Val Pro Glu Thr
        660                 665                 670 gtt gat tgt tta caa ggg tta tta aat gtt att cca tta caa ttg att      2064
Val Asp Cys Leu Gln Gly Leu Leu Asn Val Ile Pro Leu Gln Leu Ile
    675                 680                 685 agt tat tgg ttg gct gtg aat aga ggt att gat gtt gat ttc cct cgt      2112
Ser Tyr Trp Leu Ala Val Asn Arg Gly Ile Asp Val Asp Phe Pro Arg
690                 695                 700 aac ttg gct aaa tca gtt act gtt gag taa                              2142
Asn Leu Ala Lys Ser Val Thr Val Glu
705                 710

<210> SEQ ID NO 20
<211> LENGTH: 713
```

```
<212> TYPE: PRT
<213> ORGANISM: Candida albicans

<400> SEQUENCE: 20

Met Cys Gly Ile Phe Gly Tyr Val Asn Phe Leu Val Asp Lys Ser Arg
1               5                   10                  15

Gly Glu Ile Ile Asp Asn Leu Ile Glu Gly Leu Gln Arg Leu Glu Tyr
            20                  25                  30

Arg Gly Tyr Asp Ser Ala Gly Ile Ala Val Asp Gly Lys Leu Thr Lys
        35                  40                  45

Asp Pro Ser Asn Gly Asp Glu Glu Tyr Met Asp Ser Ile Ile Val Lys
    50                  55                  60

Thr Thr Gly Lys Val Lys Val Leu Lys Gln Lys Ile Ile Asp Asp Gln
65                  70                  75                  80

Ile Asp Arg Ser Ala Ile Phe Asp Asn His Val Gly Ile Ala His Thr
                85                  90                  95

Arg Trp Ala Thr His Gly Gln Pro Lys Thr Glu Asn Cys His Pro His
            100                 105                 110

Lys Ser Asp Pro Lys Gly Glu Phe Ile Val Val His Asn Gly Ile Ile
        115                 120                 125

Thr Asn Tyr Ala Ala Leu Arg Lys Tyr Leu Leu Ser Lys Gly His Val
    130                 135                 140

Phe Glu Ser Glu Thr Asp Thr Glu Cys Ile Ala Lys Leu Phe Lys His
145                 150                 155                 160

Phe Tyr Asp Leu Asn Val Lys Ala Gly Val Phe Pro Asp Leu Asn Glu
                165                 170                 175

Leu Thr Lys Gln Val Leu His Glu Leu Glu Gly Ser Tyr Gly Leu Leu
            180                 185                 190

Val Lys Ser Tyr His Tyr Pro Gly Glu Val Cys Gly Thr Arg Lys Gly
        195                 200                 205

Ser Pro Leu Leu Val Gly Val Lys Thr Asp Lys Lys Leu Lys Val Asp
    210                 215                 220

Phe Val Asp Val Glu Phe Glu Ala Gln Gln His Arg Pro Gln Gln
225                 230                 235                 240

Pro Gln Ile Asn His Asn Gly Ala Thr Ser Ala Ala Glu Leu Gly Phe
                245                 250                 255

Ile Pro Val Ala Pro Gly Glu Gln Asn Leu Arg Thr Ser Gln Ser Arg
            260                 265                 270

Ala Phe Leu Ser Glu Asp Asp Leu Pro Met Pro Val Glu Phe Phe Leu
        275                 280                 285

Ser Ser Asp Pro Ala Ser Val Val Gln His Thr Lys Lys Val Leu Phe
    290                 295                 300

Leu Glu Asp Asp Asp Ile Ala His Ile Tyr Asp Gly Glu Leu Arg Ile
305                 310                 315                 320

His Arg Ala Ser Thr Lys Ser Ala Gly Glu Ser Thr Val Arg Pro Ile
                325                 330                 335

Gln Thr Leu Glu Met Glu Leu Asn Glu Ile Met Lys Gly Pro Tyr Lys
            340                 345                 350

His Phe Met Gln Lys Glu Ile Phe Glu Gln Pro Asp Ser Ala Phe Asn
        355                 360                 365

Thr Met Arg Gly Arg Ile Asp Phe Glu Asn Cys Val Val Thr Leu Gly
    370                 375                 380

Gly Leu Lys Ser Trp Leu Ser Thr Ile Arg Arg Cys Arg Arg Ile Ile
385                 390                 395                 400
```

-continued

```
Met Ile Ala Cys Gly Thr Ser Tyr His Ser Cys Leu Ala Thr Arg Ser
                405                 410                 415

Ile Phe Glu Glu Leu Thr Glu Ile Pro Val Ser Val Glu Leu Ala Ser
            420                 425                 430

Asp Phe Leu Asp Arg Arg Ser Pro Val Phe Arg Asp Thr Cys Val
        435                 440                 445

Phe Val Ser Gln Ser Gly Glu Thr Ala Asp Ser Ile Leu Ala Leu Gln
    450                 455                 460

Tyr Cys Leu Glu Arg Gly Ala Leu Thr Val Gly Ile Val Asn Ser Val
465                 470                 475                 480

Gly Ser Ser Met Ser Arg Gln Thr His Cys Gly Val His Ile Asn Ala
                485                 490                 495

Gly Pro Glu Ile Gly Val Ala Ser Thr Lys Ala Tyr Thr Ser Gln Tyr
            500                 505                 510

Ile Ala Leu Val Met Phe Ala Leu Ser Leu Ser Asn Asp Ser Ile Ser
        515                 520                 525

Arg Lys Gly Arg His Glu Glu Ile Ile Lys Gly Leu Gln Lys Ile Pro
    530                 535                 540

Glu Gln Ile Lys Gln Val Leu Lys Leu Glu Asn Lys Ile Lys Asp Leu
545                 550                 555                 560

Cys Asn Ser Ser Leu Asn Asp Gln Lys Ser Leu Leu Leu Leu Gly Arg
                565                 570                 575

Gly Tyr Gln Phe Ala Thr Ala Leu Glu Gly Ala Leu Lys Ile Lys Glu
            580                 585                 590

Ile Ser Tyr Met His Ser Glu Gly Val Leu Ala Gly Glu Leu Lys His
        595                 600                 605

Gly Ile Leu Ala Leu Val Asp Glu Asp Leu Pro Ile Ile Ala Phe Ala
    610                 615                 620

Thr Arg Asp Ser Leu Phe Pro Lys Val Met Ser Ala Ile Glu Gln Val
625                 630                 635                 640

Thr Ala Arg Asp Gly Arg Pro Ile Val Ile Cys Asn Glu Gly Asp Ala
                645                 650                 655

Ile Ile Ser Asn Asp Lys Val His Thr Thr Leu Glu Val Pro Glu Thr
            660                 665                 670

Val Asp Cys Leu Gln Gly Leu Leu Asn Val Ile Pro Leu Gln Leu Ile
        675                 680                 685

Ser Tyr Trp Leu Ala Val Asn Arg Gly Ile Asp Val Asp Phe Pro Arg
    690                 695                 700

Asn Leu Ala Lys Ser Val Thr Val Glu
705                 710
```

<210> SEQ ID NO 21
<211> LENGTH: 40
<212> TYPE: DNA
<213> ORGANISM: Artificial sequence
<220> FEATURE:
<223> OTHER INFORMATION: primer

<400> SEQUENCE: 21
gatcggtctc gcatgtgtgg aatcgtaggt tatatcggtc        40

<210> SEQ ID NO 22
<211> LENGTH: 43
<212> TYPE: DNA
<213> ORGANISM: Artificial sequence
<220> FEATURE:

```
<223> OTHER INFORMATION: primer

<400> SEQUENCE: 22
gatcctcgag ttactccaca gtaacactct tcgcaaggtt acg                    43

<210> SEQ ID NO 23
<211> LENGTH: 33
<212> TYPE: DNA
<213> ORGANISM: Artificial sequence
<220> FEATURE:
<223> OTHER INFORMATION: primer

<400> SEQUENCE: 23
gatcggtctc gcatgtgtgg tatctttggt tac                               33

<210> SEQ ID NO 24
<211> LENGTH: 33
<212> TYPE: DNA
<213> ORGANISM: Artificial sequence
<220> FEATURE:
<223> OTHER INFORMATION: primer

<400> SEQUENCE: 24
gatcgaattc ttattcgacg gtaacagatt tag                               33

<210> SEQ ID NO 25
<211> LENGTH: 36
<212> TYPE: DNA
<213> ORGANISM: Artificial sequence
<220> FEATURE:
<223> OTHER INFORMATION: primer

<400> SEQUENCE: 25
gatcggtctc gcatgtgtgg tatttttggt tacgtc                            36

<210> SEQ ID NO 26
<211> LENGTH: 35
<212> TYPE: DNA
<213> ORGANISM: Artificial sequence
<220> FEATURE:
<223> OTHER INFORMATION: primer

<400> SEQUENCE: 26
gatcctcgag ttactcaaca gtaactgatt tagcc                             35

<210> SEQ ID NO 27
<211> LENGTH: 35
<212> TYPE: DNA
<213> ORGANISM: Artificial sequence
<220> FEATURE:
<223> OTHER INFORMATION: primer

<400> SEQUENCE: 27
gcgggtaccc atatgtgtgg tatttttggt tacgt                             35

<210> SEQ ID NO 28
<211> LENGTH: 35
<212> TYPE: DNA
<213> ORGANISM: Artificial sequence
<220> FEATURE:
<223> OTHER INFORMATION: primer

<400> SEQUENCE: 28
gcgggatcct tactcaacag taactgattt agcca                             35
```

<210> SEQ ID NO 29
<211> LENGTH: 480
<212> TYPE: DNA
<213> ORGANISM: Saccharomyces cerevisiae
<220> FEATURE:
<221> NAME/KEY: CDS
<222> LOCATION: (1)..(480)
<223> OTHER INFORMATION:

<400> SEQUENCE: 29

```
atg agc tta ccc gat gga ttt tat ata agg cga atg gaa gag ggg gat      48
Met Ser Leu Pro Asp Gly Phe Tyr Ile Arg Arg Met Glu Glu Gly Asp
1               5                   10                  15 ttg gaa cag gtc act gag acg cta aag gtt ttg acc acc gtg ggc act      96
Leu Glu Gln Val Thr Glu Thr Leu Lys Val Leu Thr Thr Val Gly Thr
                20                  25                  30 att acc ccc gaa tcc ttc agc aaa ctc ata aaa tac tgg aat gaa gcc     144
Ile Thr Pro Glu Ser Phe Ser Lys Leu Ile Lys Tyr Trp Asn Glu Ala
            35                  40                  45 aca gta tgg aat gat aac gaa gat aaa aaa ata atg caa tat aac ccc     192
Thr Val Trp Asn Asp Asn Glu Asp Lys Lys Ile Met Gln Tyr Asn Pro
        50                  55                  60 atg gtg att gtg gac aag cgc acc gag acg gtt gcc gct acg ggg aat     240
Met Val Ile Val Asp Lys Arg Thr Glu Thr Val Ala Ala Thr Gly Asn
65                  70                  75                  80 atc atc atc gaa aga aag atc att cat gaa ctg ggg cta tgt ggc cac     288
Ile Ile Ile Glu Arg Lys Ile Ile His Glu Leu Gly Leu Cys Gly His
                85                  90                  95 atc gag gac att gca gta aac tcc aag tat cag ggc caa ggt ttg ggc     336
Ile Glu Asp Ile Ala Val Asn Ser Lys Tyr Gln Gly Gln Gly Leu Gly
            100                 105                 110 aag ctc ttg att gat caa ttg gta act atc ggc ttt gac tac ggt tgt     384
Lys Leu Leu Ile Asp Gln Leu Val Thr Ile Gly Phe Asp Tyr Gly Cys
        115                 120                 125 tat aag att att tta gat tgc gat gag aaa aat gtc aaa ttc tat gaa     432
Tyr Lys Ile Ile Leu Asp Cys Asp Glu Lys Asn Val Lys Phe Tyr Glu
    130                 135                 140 aaa tgt ggg ttt agc aac gca ggc gtg gaa atg caa att aga aaa tag     480
Lys Cys Gly Phe Ser Asn Ala Gly Val Glu Met Gln Ile Arg Lys
145                 150                 155
```

<210> SEQ ID NO 30
<211> LENGTH: 159
<212> TYPE: PRT
<213> ORGANISM: Saccharomyces cerevisiae

<400> SEQUENCE: 30

```
Met Ser Leu Pro Asp Gly Phe Tyr Ile Arg Arg Met Glu Glu Gly Asp
1               5                   10                  15

Leu Glu Gln Val Thr Glu Thr Leu Lys Val Leu Thr Thr Val Gly Thr
                20                  25                  30

Ile Thr Pro Glu Ser Phe Ser Lys Leu Ile Lys Tyr Trp Asn Glu Ala
            35                  40                  45

Thr Val Trp Asn Asp Asn Glu Asp Lys Lys Ile Met Gln Tyr Asn Pro
        50                  55                  60

Met Val Ile Val Asp Lys Arg Thr Glu Thr Val Ala Ala Thr Gly Asn
65                  70                  75                  80

Ile Ile Ile Glu Arg Lys Ile Ile His Glu Leu Gly Leu Cys Gly His
                85                  90                  95

Ile Glu Asp Ile Ala Val Asn Ser Lys Tyr Gln Gly Gln Gly Leu Gly
            100                 105                 110
```

```
Lys Leu Leu Ile Asp Gln Leu Val Thr Ile Gly Phe Asp Tyr Gly Cys
        115                 120                 125

Tyr Lys Ile Ile Leu Asp Cys Asp Glu Lys Asn Val Lys Phe Tyr Glu
    130                 135                 140

Lys Cys Gly Phe Ser Asn Ala Gly Val Glu Met Gln Ile Arg Lys
145                 150                 155

<210> SEQ ID NO 31
<211> LENGTH: 450
<212> TYPE: DNA
<213> ORGANISM: Candida albicans
<220> FEATURE:
<221> NAME/KEY: CDS
<222> LOCATION: (1)..(450)
<223> OTHER INFORMATION:

<400> SEQUENCE: 31 atg atg tta cca caa ggt tat aca ttc aga aaa cta aaa ctt act gat      48
Met Met Leu Pro Gln Gly Tyr Thr Phe Arg Lys Leu Lys Leu Thr Asp
1               5                   10                  15 tat gat aat caa tat tta gaa act tta aaa gtt ttg acg aca gtt ggt      96
Tyr Asp Asn Gln Tyr Leu Glu Thr Leu Lys Val Leu Thr Thr Val Gly
            20                  25                  30 gaa att tcc aaa gaa gat ttc act gaa ttg tat aat cat tgg tct tca     144
Glu Ile Ser Lys Glu Asp Phe Thr Glu Leu Tyr Asn His Trp Ser Ser
        35                  40                  45 ttg cca tct att tat cat cca tat gta atc acc aat gca tca ggt ata     192
Leu Pro Ser Ile Tyr His Pro Tyr Val Ile Thr Asn Ala Ser Gly Ile
    50                  55                  60 gtg gta gcc acg ggg atg tta ttt gtg gag aaa aaa ttg att cat gaa     240
Val Val Ala Thr Gly Met Leu Phe Val Glu Lys Lys Leu Ile His Glu
65                  70                  75                  80 tgt ggt aaa gtt ggt cat att gaa gat att tca gtt gct aaa tct gaa     288
Cys Gly Lys Val Gly His Ile Glu Asp Ile Ser Val Ala Lys Ser Glu
                85                  90                  95 caa ggt aaa aaa ttg gga tat tat tta gtc act tca tta acc aaa gtt     336
Gln Gly Lys Lys Leu Gly Tyr Tyr Leu Val Thr Ser Leu Thr Lys Val
            100                 105                 110 gct caa gag aat gat tgt tac aaa gtc att tta gat tgt tct cct gaa     384
Ala Gln Glu Asn Asp Cys Tyr Lys Val Ile Leu Asp Cys Ser Pro Glu
        115                 120                 125 aat gtt ggc ttt tat gaa aaa tgt ggt tat aaa gat ggt ggt gtt gaa     432
Asn Val Gly Phe Tyr Glu Lys Cys Gly Tyr Lys Asp Gly Gly Val Glu
    130                 135                 140 atg gta tgt aga ttc tag                                             450
Met Val Cys Arg Phe
145

<210> SEQ ID NO 32
<211> LENGTH: 149
<212> TYPE: PRT
<213> ORGANISM: Candida albicans

<400> SEQUENCE: 32

Met Met Leu Pro Gln Gly Tyr Thr Phe Arg Lys Leu Lys Leu Thr Asp
1               5                   10                  15

Tyr Asp Asn Gln Tyr Leu Glu Thr Leu Lys Val Leu Thr Thr Val Gly
            20                  25                  30

Glu Ile Ser Lys Glu Asp Phe Thr Glu Leu Tyr Asn His Trp Ser Ser
        35                  40                  45
```

```
Leu Pro Ser Ile Tyr His Pro Tyr Val Ile Thr Asn Ala Ser Gly Ile
     50                  55                  60

Val Val Ala Thr Gly Met Leu Phe Val Glu Lys Lys Leu Ile His Glu
 65                  70                  75                  80

Cys Gly Lys Val Gly His Ile Glu Asp Ile Ser Val Ala Lys Ser Glu
                 85                  90                  95

Gln Gly Lys Lys Leu Gly Tyr Tyr Leu Val Thr Ser Leu Thr Lys Val
            100                 105                 110

Ala Gln Glu Asn Asp Cys Tyr Lys Val Ile Leu Asp Cys Ser Pro Glu
        115                 120                 125

Asn Val Gly Phe Tyr Glu Lys Cys Gly Tyr Lys Asp Gly Gly Val Glu
130                 135                 140

Met Val Cys Arg Phe
145

<210> SEQ ID NO 33
<211> LENGTH: 450
<212> TYPE: DNA
<213> ORGANISM: Arabidopsis thaliana
<220> FEATURE:
<221> NAME/KEY: CDS
<222> LOCATION: (1)..(450)
<223> OTHER INFORMATION:

<400> SEQUENCE: 33 atg gct gag aca ttc aag atc cga aaa ctg gag atc tcc gat aag aga      48
Met Ala Glu Thr Phe Lys Ile Arg Lys Leu Glu Ile Ser Asp Lys Arg
 1               5                  10                  15 aaa gga ttc atc gag ctt cta ggt caa cta acc gtc acc gga tca gta      96
Lys Gly Phe Ile Glu Leu Leu Gly Gln Leu Thr Val Thr Gly Ser Val
             20                  25                  30 aca gac gaa gaa ttc gat cgg cga ttc gaa gaa atc aga tcg tat ggt     144
Thr Asp Glu Glu Phe Asp Arg Arg Phe Glu Glu Ile Arg Ser Tyr Gly
         35                  40                  45 gac gac cac gtg atc tgc gtg atc gaa gaa gaa act tcg gga aaa atc     192
Asp Asp His Val Ile Cys Val Ile Glu Glu Glu Thr Ser Gly Lys Ile
     50                  55                  60 gct gct acg ggt agt gtg atg ata gag aag aag ttt ctg agg aat tgc     240
Ala Ala Thr Gly Ser Val Met Ile Glu Lys Lys Phe Leu Arg Asn Cys
 65                  70                  75                  80 ggt aaa gct ggg cac att gaa gac gtt gtt gtg gat tca agg ttt cgc     288
Gly Lys Ala Gly His Ile Glu Asp Val Val Val Asp Ser Arg Phe Arg
                 85                  90                  95 ggg aaa cag ctg ggg aag aaa gtt gtt gag ttt ctt atg gat cat tgc     336
Gly Lys Gln Leu Gly Lys Lys Val Val Glu Phe Leu Met Asp His Cys
            100                 105                 110 aaa tca atg ggt tgc tat aag gtg att cta gat tgt agt gtg gag aac     384
Lys Ser Met Gly Cys Tyr Lys Val Ile Leu Asp Cys Ser Val Glu Asn
        115                 120                 125 aaa gtg ttc tat gag aaa tgt ggg atg agt aat aaa tcg att caa atg     432
Lys Val Phe Tyr Glu Lys Cys Gly Met Ser Asn Lys Ser Ile Gln Met
130                 135                 140 tct aag tac ttc gat taa                                             450
Ser Lys Tyr Phe Asp
145

<210> SEQ ID NO 34
<211> LENGTH: 149
<212> TYPE: PRT
<213> ORGANISM: Arabidopsis thaliana
```

<400> SEQUENCE: 34

Met Ala Glu Thr Phe Lys Ile Arg Lys Leu Glu Ile Ser Asp Lys Arg
1               5                   10                  15

Lys Gly Phe Ile Glu Leu Leu Gly Gln Leu Thr Val Thr Gly Ser Val
            20                  25                  30

Thr Asp Glu Glu Phe Asp Arg Arg Phe Glu Glu Ile Arg Ser Tyr Gly
        35                  40                  45

Asp Asp His Val Ile Cys Val Ile Glu Glu Glu Thr Ser Gly Lys Ile
    50                  55                  60

Ala Ala Thr Gly Ser Val Met Ile Glu Lys Lys Phe Leu Arg Asn Cys
65              70                  75                  80

Gly Lys Ala Gly His Ile Glu Asp Val Val Asp Ser Arg Phe Arg
            85                  90                  95

Gly Lys Gln Leu Gly Lys Lys Val Val Glu Phe Leu Met Asp His Cys
        100                 105                 110

Lys Ser Met Gly Cys Tyr Lys Val Ile Leu Asp Cys Ser Val Glu Asn
        115                 120                 125

Lys Val Phe Tyr Glu Lys Cys Gly Met Ser Asn Lys Ser Ile Gln Met
    130                 135                 140

Ser Lys Tyr Phe Asp
145

<210> SEQ ID NO 35
<211> LENGTH: 43
<212> TYPE: DNA
<213> ORGANISM: Artificial sequence
<220> FEATURE:
<223> OTHER INFORMATION: primer

<400> SEQUENCE: 35
gatcggtctc gcatgagctt acccgatgga ttttatataa ggc          43

<210> SEQ ID NO 36
<211> LENGTH: 40
<212> TYPE: DNA
<213> ORGANISM: Artificial sequence
<220> FEATURE:
<223> OTHER INFORMATION: primer

<400> SEQUENCE: 36
gatcctcgag ctatttctaa atttgcattt ccacgcctgc             40

<210> SEQ ID NO 37
<211> LENGTH: 35
<212> TYPE: DNA
<213> ORGANISM: Artificial sequence
<220> FEATURE:
<223> OTHER INFORMATION: primer

<400> SEQUENCE: 37
gatcggtctc gcatgatgtt accacaaggt tatac                  35

<210> SEQ ID NO 38
<211> LENGTH: 34
<212> TYPE: DNA
<213> ORGANISM: Artificial sequence
<220> FEATURE:
<223> OTHER INFORMATION: primer

<400> SEQUENCE: 38
gatcctcgag ctagaatcta cataccattt caac                   34

<210> SEQ ID NO 39
<211> LENGTH: 32
<212> TYPE: DNA
<213> ORGANISM: Artificial sequence
<220> FEATURE:
<223> OTHER INFORMATION: primer

<400> SEQUENCE: 39
gatggtctcg catggctgag acattcaaga tc　　　　　　　　　　　　　　　　32

<210> SEQ ID NO 40
<211> LENGTH: 38
<212> TYPE: DNA
<213> ORGANISM: Artificial sequence
<220> FEATURE:
<223> OTHER INFORMATION: primer

<400> SEQUENCE: 40
gatcctcgag ttaatcgaag tacttagaca tttgaatc　　　　　　　　　　　　38

<210> SEQ ID NO 41
<211> LENGTH: 801
<212> TYPE: DNA
<213> ORGANISM: Escherichia coli
<220> FEATURE:
<221> NAME/KEY: CDS
<222> LOCATION: (1)..(801)
<223> OTHER INFORMATION:

<400> SEQUENCE: 41

| | | |
|---|---|---|
| atg aga ctg atc ccc ctg act acc gct gaa cag gtc ggc aaa tgg gct<br>Met Arg Leu Ile Pro Leu Thr Thr Ala Glu Gln Val Gly Lys Trp Ala<br>1               5                   10                  15 | | 48 |
| gct cgc cat atc gtc aat cgt atc aat gcg ttc aaa ccg act gcc gat<br>Ala Arg His Ile Val Asn Arg Ile Asn Ala Phe Lys Pro Thr Ala Asp<br>            20                  25                  30 | | 96 |
| cgt ccg ttt gta ctg ggc ctg ccg act ggc ggc acg ccg atg acc acc<br>Arg Pro Phe Val Leu Gly Leu Pro Thr Gly Gly Thr Pro Met Thr Thr<br>        35                  40                  45 | | 144 |
| tat aaa gcg tta gtc gaa atg cat aaa gca ggc cag gtc agc ttt aag<br>Tyr Lys Ala Leu Val Glu Met His Lys Ala Gly Gln Val Ser Phe Lys<br>    50                  55                  60 | | 192 |
| cac gtt gtc acc ttc aac atg gac gaa tat gtc ggt ctg ccg aaa gag<br>His Val Val Thr Phe Asn Met Asp Glu Tyr Val Gly Leu Pro Lys Glu<br>65                  70                  75                  80 | | 240 |
| cat ccg gaa agc tac tac agc ttt atg cac cgt aat ttc ttc gat cac<br>His Pro Glu Ser Tyr Tyr Ser Phe Met His Arg Asn Phe Phe Asp His<br>                85                  90                  95 | | 288 |
| gtt gat att cca gca gaa aac atc aac ctt ctc aac ggc aac gcc ccg<br>Val Asp Ile Pro Ala Glu Asn Ile Asn Leu Leu Asn Gly Asn Ala Pro<br>            100                 105                 110 | | 336 |
| gat atc gac gcc gag tgc cgc cag tat gaa gaa aaa atc cgt tct tac<br>Asp Ile Asp Ala Glu Cys Arg Gln Tyr Glu Glu Lys Ile Arg Ser Tyr<br>        115                 120                 125 | | 384 |
| gga aaa att cat ctg ttt atg ggc ggt gta ggt aac gac ggt cat att<br>Gly Lys Ile His Leu Phe Met Gly Gly Val Gly Asn Asp Gly His Ile<br>    130                 135                 140 | | 432 |
| gca ttt aac gaa ccg gcg tct tct ctg gct tct cgt act cgt atc aaa<br>Ala Phe Asn Glu Pro Ala Ser Ser Leu Ala Ser Arg Thr Arg Ile Lys<br>145                 150                 155                 160 | | 480 |
| acc ctg act cat gac act cgc gtc gca aac tct cgt ttc ttt gat aac<br>Thr Leu Thr His Asp Thr Arg Val Ala Asn Ser Arg Phe Phe Asp Asn | | 528 |

```
                165                 170                 175
gat gtt aat cag gtg cca aaa tat gcc ctg act gtc ggt gtt ggt aca          576
Asp Val Asn Gln Val Pro Lys Tyr Ala Leu Thr Val Gly Val Gly Thr
        180                 185                 190 ctg ctg gat gcc gaa gaa gtg atg att ctg gtg ctg ggt agc cag aaa          624
Leu Leu Asp Ala Glu Glu Val Met Ile Leu Val Leu Gly Ser Gln Lys
        195                 200                 205 gca ctg gcg ctg cag gcc gcc gtt gaa ggt tgc gtg aac cat atg tgg          672
Ala Leu Ala Leu Gln Ala Ala Val Glu Gly Cys Val Asn His Met Trp
    210                 215                 220 acc atc agc tgt ctg caa ctg cat ccg aaa gcg atc atg gtg tgc gat          720
Thr Ile Ser Cys Leu Gln Leu His Pro Lys Ala Ile Met Val Cys Asp
225                 230                 235                 240 gaa cct tcc acc atg gag ctg aaa gtt aag act tta aga tat ttc aat          768
Glu Pro Ser Thr Met Glu Leu Lys Val Lys Thr Leu Arg Tyr Phe Asn
                245                 250                 255 gaa tta gaa gca gaa aat atc aaa ggt ctg taa                              801
Glu Leu Glu Ala Glu Asn Ile Lys Gly Leu
                260                 265

<210> SEQ ID NO 42
<211> LENGTH: 266
<212> TYPE: PRT
<213> ORGANISM: Escherichia coli

<400> SEQUENCE: 42

Met Arg Leu Ile Pro Leu Thr Thr Ala Glu Gln Val Gly Lys Trp Ala
1               5                   10                  15

Ala Arg His Ile Val Asn Arg Ile Asn Ala Phe Lys Pro Thr Ala Asp
                20                  25                  30

Arg Pro Phe Val Leu Gly Leu Pro Thr Gly Gly Thr Pro Met Thr Thr
            35                  40                  45

Tyr Lys Ala Leu Val Glu Met His Lys Ala Gly Gln Val Ser Phe Lys
        50                  55                  60

His Val Thr Phe Asn Met Asp Glu Tyr Val Gly Leu Pro Lys Glu
65                  70                  75                  80

His Pro Glu Ser Tyr Tyr Ser Phe Met His Arg Asn Phe Phe Asp His
                85                  90                  95

Val Asp Ile Pro Ala Glu Asn Ile Asn Leu Leu Asn Gly Asn Ala Pro
            100                 105                 110

Asp Ile Asp Ala Glu Cys Arg Gln Tyr Glu Glu Lys Ile Arg Ser Tyr
        115                 120                 125

Gly Lys Ile His Leu Phe Met Gly Gly Val Gly Asn Asp Gly His Ile
    130                 135                 140

Ala Phe Asn Glu Pro Ala Ser Ser Leu Ala Ser Arg Thr Arg Ile Lys
145                 150                 155                 160

Thr Leu Thr His Asp Thr Arg Val Ala Asn Ser Arg Phe Phe Asp Asn
                165                 170                 175

Asp Val Asn Gln Val Pro Lys Tyr Ala Leu Thr Val Gly Val Gly Thr
            180                 185                 190

Leu Leu Asp Ala Glu Glu Val Met Ile Leu Val Leu Gly Ser Gln Lys
        195                 200                 205

Ala Leu Ala Leu Gln Ala Ala Val Glu Gly Cys Val Asn His Met Trp
    210                 215                 220

Thr Ile Ser Cys Leu Gln Leu His Pro Lys Ala Ile Met Val Cys Asp
225                 230                 235                 240
```

```
Glu Pro Ser Thr Met Glu Leu Lys Val Lys Thr Leu Arg Tyr Phe Asn
                245                 250                 255
Glu Leu Glu Ala Glu Asn Ile Lys Gly Leu
            260                 265
```

<210> SEQ ID NO 43
<211> LENGTH: 31
<212> TYPE: DNA
<213> ORGANISM: Artificial sequence
<220> FEATURE:
<223> OTHER INFORMATION: primer

<400> SEQUENCE: 43
gatggtctcg catgagactg atcccctga c     31

<210> SEQ ID NO 44
<211> LENGTH: 43
<212> TYPE: DNA
<213> ORGANISM: Artificial sequence
<220> FEATURE:
<223> OTHER INFORMATION: primer

<400> SEQUENCE: 44
gatcctcgag ttacagacct ttgatatttt ctgcttctaa ttc     43

<210> SEQ ID NO 45
<211> LENGTH: 43
<212> TYPE: DNA
<213> ORGANISM: Artificial sequence
<220> FEATURE:
<223> OTHER INFORMATION: primer

<400> SEQUENCE: 45
gatcctcgag ttacagacct ttgatatttt ctgcttctaa ttc     43

<210> SEQ ID NO 46
<211> LENGTH: 32
<212> TYPE: DNA
<213> ORGANISM: Artificial sequence
<220> FEATURE:
<223> OTHER INFORMATION: primer

<400> SEQUENCE: 46
gatcctgcag tcatgctgct aataatctat cc     32

<210> SEQ ID NO 47
<211> LENGTH: 28
<212> TYPE: DNA
<213> ORGANISM: Artificial sequence
<220> FEATURE:
<223> OTHER INFORMATION: primer

<400> SEQUENCE: 47
gatctacgta agcaaccgca cctgtggc     28

<210> SEQ ID NO 48
<211> LENGTH: 36
<212> TYPE: DNA
<213> ORGANISM: Artificial sequence
<220> FEATURE:
<223> OTHER INFORMATION: primer

<400> SEQUENCE: 48
gatccaattg atccggatat agttcctcct ttcagc     36

<210> SEQ ID NO 49
<211> LENGTH: 41
<212> TYPE: DNA
<213> ORGANISM: Artificial sequence
<220> FEATURE:
<223> OTHER INFORMATION: primer

<400> SEQUENCE: 49
gatgcggccg catgttgaat aatgctatga gcgtagtgat c     41

<210> SEQ ID NO 50
<211> LENGTH: 37
<212> TYPE: DNA
<213> ORGANISM: Artificial sequence
<220> FEATURE:
<223> OTHER INFORMATION: primer

<400> SEQUENCE: 50
gatcgtcgac ttagtacagc ggcttaccgc tactgtc     37

<210> SEQ ID NO 51
<211> LENGTH: 35
<212> TYPE: DNA
<213> ORGANISM: Artificial sequence
<220> FEATURE:
<223> OTHER INFORMATION: primer

<400> SEQUENCE: 51
gatgcggccg catggcaatg acttaccacc tggac     35

<210> SEQ ID NO 52
<211> LENGTH: 29
<212> TYPE: DNA
<213> ORGANISM: Artificial sequence
<220> FEATURE:
<223> OTHER INFORMATION: primer

<400> SEQUENCE: 52
cgtacccagc tgctctgcct gaagcaccc     29

<210> SEQ ID NO 53
<211> LENGTH: 1338
<212> TYPE: DNA
<213> ORGANISM: Escherichia coli
<220> FEATURE:
<221> NAME/KEY: CDS
<222> LOCATION: (1)..(1338)
<223> OTHER INFORMATION:

<400> SEQUENCE: 53

| atg | agt | aat | cgt | aaa | tat | ttc | ggt | acc | gat | ggg | att | cgt | ggt | cgt | gta | 48 |
|---|---|---|---|---|---|---|---|---|---|---|---|---|---|---|---|---|
| Met | Ser | Asn | Arg | Lys | Tyr | Phe | Gly | Thr | Asp | Gly | Ile | Arg | Gly | Arg | Val | |
| 1 | | | | 5 | | | | | 10 | | | | | 15 | | |

| ggg | gat | gcg | ccg | atc | aca | cct | gat | ttt | gtg | ctt | aag | ctg | ggt | tgg | gcc | 96 |
|---|---|---|---|---|---|---|---|---|---|---|---|---|---|---|---|---|
| Gly | Asp | Ala | Pro | Ile | Thr | Pro | Asp | Phe | Val | Leu | Lys | Leu | Gly | Trp | Ala | |
| | | | 20 | | | | | 25 | | | | | 30 | | | |

| gcg | ggt | aaa | gtg | ctg | gcg | cgc | cac | ggc | tcc | cgt | aag | att | att | att | ggt | 144 |
|---|---|---|---|---|---|---|---|---|---|---|---|---|---|---|---|---|
| Ala | Gly | Lys | Val | Leu | Ala | Arg | His | Gly | Ser | Arg | Lys | Ile | Ile | Ile | Gly | |
| | 35 | | | | | 40 | | | | | 45 | | | | | |

| aaa | gac | acg | cgt | att | tct | ggc | tat | atg | ctg | gag | tca | gca | ctg | gaa | gcg | 192 |
|---|---|---|---|---|---|---|---|---|---|---|---|---|---|---|---|---|
| Lys | Asp | Thr | Arg | Ile | Ser | Gly | Tyr | Met | Leu | Glu | Ser | Ala | Leu | Glu | Ala | |
| 50 | | | | | 55 | | | | | 60 | | | | | | |

| ggt | ctg | gcg | gca | gcg | ggc | ctt | tcc | gca | ctc | ttc | act | ggc | ccg | atg | cca | 240 |
|---|---|---|---|---|---|---|---|---|---|---|---|---|---|---|---|---|
| Gly | Leu | Ala | Ala | Ala | Gly | Leu | Ser | Ala | Leu | Phe | Thr | Gly | Pro | Met | Pro | |
| 65 | | | | | 70 | | | | | 75 | | | | | 80 | |

-continued

| | |
|---|---|
| aca ccg gcc gtg gct tat ctg acg cgt acc ttc cgc gca gag gcc gga<br>Thr Pro Ala Val Ala Tyr Leu Thr Arg Thr Phe Arg Ala Glu Ala Gly<br>                85                       90                    95 | 288 |
| att gtg ata tct gca tcg cat aac ccg ttc tac gat aat ggc att aaa<br>Ile Val Ile Ser Ala Ser His Asn Pro Phe Tyr Asp Asn Gly Ile Lys<br>              100                   105                 110 | 336 |
| ttc ttc tct atc gac ggc acc aaa ctg ccg gat gcg gta gaa gag gcc<br>Phe Phe Ser Ile Asp Gly Thr Lys Leu Pro Asp Ala Val Glu Glu Ala<br>              115                   120                 125 | 384 |
| atc gaa gcg gaa atg gaa aag gag atc agc tgc gtt gat tcg gca gaa<br>Ile Glu Ala Glu Met Glu Lys Glu Ile Ser Cys Val Asp Ser Ala Glu<br>130                    135                 140 | 432 |
| ctg ggt aaa gcc agc cgt atc gtt gat gcc gcg ggt cgc tat atc gag<br>Leu Gly Lys Ala Ser Arg Ile Val Asp Ala Ala Gly Arg Tyr Ile Glu<br>145                  150                 155               160 | 480 |
| ttt tgc aaa gcc acg ttc ccg aac gaa ctt agc ctc agt gaa ctg aag<br>Phe Cys Lys Ala Thr Phe Pro Asn Glu Leu Ser Leu Ser Glu Leu Lys<br>              165                   170                 175 | 528 |
| att gtg gtg gat tgt gca aac ggt gcg act tat cac atc gcg ccg aac<br>Ile Val Val Asp Cys Ala Asn Gly Ala Thr Tyr His Ile Ala Pro Asn<br>                  180                   185               190 | 576 |
| gtg ctg cgc gaa ctg ggg gcg aac gtt atc gct atc ggt tgt gag cca<br>Val Leu Arg Glu Leu Gly Ala Asn Val Ile Ala Ile Gly Cys Glu Pro<br>                 195                 200               205 | 624 |
| aac ggt gta aac atc aat gcc gaa gtg ggg gct acc gac gtt cgc gcg<br>Asn Gly Val Asn Ile Asn Ala Glu Val Gly Ala Thr Asp Val Arg Ala<br>              210                   215               220 | 672 |
| ctc cag gct cgt gtg ctg gct gaa aaa gcg gat ctc ggt att gcc ttc<br>Leu Gln Ala Arg Val Leu Ala Glu Lys Ala Asp Leu Gly Ile Ala Phe<br>225                  230                 235               240 | 720 |
| gac ggc gat ggc gat cgc gtg att atg gtt gac cat gaa ggc aat aaa<br>Asp Gly Asp Gly Asp Arg Val Ile Met Val Asp His Glu Gly Asn Lys<br>                  245                 250               255 | 768 |
| gtc gat ggc gat cag atc atg tat atc atc gcg cgt gaa ggt ctt cgt<br>Val Asp Gly Asp Gln Ile Met Tyr Ile Ile Ala Arg Glu Gly Leu Arg<br>                  260                 265               270 | 816 |
| cag ggc cag ctg cgt ggt ggc gct gtg ggt aca ttg atg agc aac atg<br>Gln Gly Gln Leu Arg Gly Gly Ala Val Gly Thr Leu Met Ser Asn Met<br>              275                   280               285 | 864 |
| ggg ctt gaa ctg gcg ctg aaa cag tta gga att cca ttt gcg cgc gcg<br>Gly Leu Glu Leu Ala Leu Lys Gln Leu Gly Ile Pro Phe Ala Arg Ala<br>              290                   295               300 | 912 |
| aaa gtg ggt gac cgc tac gta ctg gaa aaa atg cag gag aaa ggc tgg<br>Lys Val Gly Asp Arg Tyr Val Leu Glu Lys Met Gln Glu Lys Gly Trp<br>305                  310                 315               320 | 960 |
| cgt atc ggt gca gag aat tcc ggt cat gtg atc ctg ctg gat aaa act<br>Arg Ile Gly Ala Glu Asn Ser Gly His Val Ile Leu Leu Asp Lys Thr<br>                  325                 330               335 | 1008 |
| act acc ggt gac ggc atc gtt gct ggc ttg cag gtg ctg gcg gcg atg<br>Thr Thr Gly Asp Gly Ile Val Ala Gly Leu Gln Val Leu Ala Ala Met<br>              340                   345               350 | 1056 |
| gca cgt aac cat atg agc ctg cac gac ctt tgc agc ggc atg aaa atg<br>Ala Arg Asn His Met Ser Leu His Asp Leu Cys Ser Gly Met Lys Met<br>              355                   360               365 | 1104 |
| ttc ccg cag att ctg gtt aac gta cgt tac acc gca ggt agc ggc gat<br>Phe Pro Gln Ile Leu Val Asn Val Arg Tyr Thr Ala Gly Ser Gly Asp<br>              370                   375               380 | 1152 |
| cca ctt gag cat gag tca gtt aaa gcc gtg acc gca gag gtt gaa gct<br>Pro Leu Glu His Glu Ser Val Lys Ala Val Thr Ala Glu Val Glu Ala<br>385                  390                 395               400 | 1200 |

```
gcg ctg ggc aac cgt gga cgc gtg ttg ctg cgt aaa tcc ggc acc gaa      1248
Ala Leu Gly Asn Arg Gly Arg Val Leu Leu Arg Lys Ser Gly Thr Glu
            405                 410                 415 ccg tta att cgc gtg atg gtg gaa ggc gaa gac gaa gcg cag gtg act      1296
Pro Leu Ile Arg Val Met Val Glu Gly Glu Asp Glu Ala Gln Val Thr
        420                 425                 430 gaa ttt gca cac cgc atc gcc gat gca gta aaa gcc gtt taa              1338
Glu Phe Ala His Arg Ile Ala Asp Ala Val Lys Ala Val
            435                 440                 445

<210> SEQ ID NO 54
<211> LENGTH: 445
<212> TYPE: PRT
<213> ORGANISM: Escherichia coli

<400> SEQUENCE: 54
```

Met Ser Asn Arg Lys Tyr Phe Gly Thr Asp Gly Ile Arg Gly Arg Val
1               5                   10                  15

Gly Asp Ala Pro Ile Thr Pro Asp Phe Val Leu Lys Leu Gly Trp Ala
            20                  25                  30

Ala Gly Lys Val Leu Ala Arg His Gly Ser Arg Lys Ile Ile Ile Gly
        35                  40                  45

Lys Asp Thr Arg Ile Ser Gly Tyr Met Leu Glu Ser Ala Leu Glu Ala
    50                  55                  60

Gly Leu Ala Ala Ala Gly Leu Ser Ala Leu Phe Thr Gly Pro Met Pro
65                  70                  75                  80

Thr Pro Ala Val Ala Tyr Leu Thr Arg Thr Phe Arg Ala Glu Ala Gly
                85                  90                  95

Ile Val Ile Ser Ala Ser His Asn Pro Phe Tyr Asp Asn Gly Ile Lys
            100                 105                 110

Phe Phe Ser Ile Asp Gly Thr Lys Leu Pro Asp Ala Val Glu Glu Ala
        115                 120                 125

Ile Glu Ala Glu Met Glu Lys Glu Ile Ser Cys Val Asp Ser Ala Glu
    130                 135                 140

Leu Gly Lys Ala Ser Arg Ile Val Asp Ala Ala Gly Arg Tyr Ile Glu
145                 150                 155                 160

Phe Cys Lys Ala Thr Phe Pro Asn Glu Leu Ser Leu Ser Glu Leu Lys
                165                 170                 175

Ile Val Val Asp Cys Ala Asn Gly Ala Thr Tyr His Ile Ala Pro Asn
            180                 185                 190

Val Leu Arg Glu Leu Gly Ala Asn Val Ile Ala Ile Gly Cys Glu Pro
        195                 200                 205

Asn Gly Val Asn Ile Asn Ala Glu Val Gly Ala Thr Asp Val Arg Ala
    210                 215                 220

Leu Gln Ala Arg Val Leu Ala Glu Lys Ala Asp Leu Gly Ile Ala Phe
225                 230                 235                 240

Asp Gly Asp Gly Asp Arg Val Ile Met Val Asp His Glu Gly Asn Lys
                245                 250                 255

Val Asp Gly Asp Gln Ile Met Tyr Ile Ala Arg Glu Gly Leu Arg
            260                 265                 270

Gln Gly Gln Leu Arg Gly Gly Ala Val Gly Thr Leu Met Ser Asn Met
        275                 280                 285

Gly Leu Glu Leu Ala Leu Lys Gln Leu Gly Ile Pro Phe Ala Arg Ala
    290                 295                 300

Lys Val Gly Asp Arg Tyr Val Leu Glu Lys Met Gln Glu Lys Gly Trp

```
                305                 310                 315                 320
Arg Ile Gly Ala Glu Asn Ser Gly His Val Ile Leu Leu Asp Lys Thr
                    325                 330                 335
Thr Thr Gly Asp Gly Ile Val Ala Gly Leu Gln Val Leu Ala Ala Met
                340                 345                 350
Ala Arg Asn His Met Ser Leu His Asp Leu Cys Ser Gly Met Lys Met
                    355                 360                 365
Phe Pro Gln Ile Leu Val Asn Val Arg Tyr Thr Ala Gly Ser Gly Asp
                370                 375                 380
Pro Leu Glu His Glu Ser Val Lys Ala Val Thr Ala Glu Val Glu Ala
385                 390                 395                 400
Ala Leu Gly Asn Arg Gly Arg Val Leu Leu Arg Lys Ser Gly Thr Glu
                    405                 410                 415
Pro Leu Ile Arg Val Met Val Glu Gly Glu Asp Glu Ala Gln Val Thr
                420                 425                 430
Glu Phe Ala His Arg Ile Ala Asp Ala Val Lys Ala Val
                    435                 440                 445

<210> SEQ ID NO 55
<211> LENGTH: 1371
<212> TYPE: DNA
<213> ORGANISM: Escherichia coli
<220> FEATURE:
<221> NAME/KEY: CDS
<222> LOCATION: (1)..(1371)
<223> OTHER INFORMATION:

<400> SEQUENCE: 55 atg ttg aat aat gct atg agc gta gtg atc ctt gcc gca ggc aaa ggc      48
Met Leu Asn Asn Ala Met Ser Val Val Ile Leu Ala Ala Gly Lys Gly
1               5                   10                  15 acg cgc atg tat tcc gat ctt ccg aaa gtg ctg cat acc ctt gcc ggg      96
Thr Arg Met Tyr Ser Asp Leu Pro Lys Val Leu His Thr Leu Ala Gly
                20                  25                  30 aaa gcg atg gtt cag cat gtc att gat gct gcg aat gaa tta ggc gca     144
Lys Ala Met Val Gln His Val Ile Asp Ala Ala Asn Glu Leu Gly Ala
            35                  40                  45 gcg cac gtt cac ctg gtg tac ggt cac ggc ggc gat ctg cta aaa cag     192
Ala His Val His Leu Val Tyr Gly His Gly Gly Asp Leu Leu Lys Gln
        50                  55                  60 gcg ctg aaa gac gac aac ctt aac tgg gtg ctt cag gca gag cag ctg     240
Ala Leu Lys Asp Asp Asn Leu Asn Trp Val Leu Gln Ala Glu Gln Leu
65                  70                  75                  80 ggt acg ggt cat gca atg cag cag gcc gca cct ttc ttt gcc gat gat     288
Gly Thr Gly His Ala Met Gln Gln Ala Ala Pro Phe Phe Ala Asp Asp
                85                  90                  95 gaa gac att tta atg ctc tac ggc gac gtg ccg ctg atc tct gtc gaa     336
Glu Asp Ile Leu Met Leu Tyr Gly Asp Val Pro Leu Ile Ser Val Glu
                100                 105                 110 aca ctc cag cgt ctg cgt gat gct aaa ccg cag ggt ggc att ggt ctg     384
Thr Leu Gln Arg Leu Arg Asp Ala Lys Pro Gln Gly Gly Ile Gly Leu
            115                 120                 125 ctg acg gtg aaa ctg gat gat ccg acc ggt tat gga cgt atc acc cgt     432
Leu Thr Val Lys Leu Asp Asp Pro Thr Gly Tyr Gly Arg Ile Thr Arg
        130                 135                 140 gaa aac ggc aaa gtt acc ggc att gtt gag cac aaa gat gcc acc gac     480
Glu Asn Gly Lys Val Thr Gly Ile Val Glu His Lys Asp Ala Thr Asp
145                 150                 155                 160 gag cag cgt cag att cag gag atc aac acc ggc att ctg att gcc aac     528
```

-continued

```
                Glu Gln Arg Gln Ile Gln Glu Ile Asn Thr Gly Ile Leu Ile Ala Asn
                                165                 170                 175 ggc gca gat atg aaa cgc tgg ctg gcg aag ctg acc aac aat aat gct        576
Gly Ala Asp Met Lys Arg Trp Leu Ala Lys Leu Thr Asn Asn Asn Ala
            180                 185                 190 cag ggc gaa tac tac atc acc gac att att gcg ctg gcg tat cag gaa        624
Gln Gly Glu Tyr Tyr Ile Thr Asp Ile Ile Ala Leu Ala Tyr Gln Glu
        195                 200                 205 ggg cgt gaa atc gtc gcc gtt cat ccg caa cgt tta agc gaa gta gaa        672
Gly Arg Glu Ile Val Ala Val His Pro Gln Arg Leu Ser Glu Val Glu
    210                 215                 220 ggc gtg aat aac cgc ctg caa ctc tcc cgt ctg gag cgt gtt tat cag        720
Gly Val Asn Asn Arg Leu Gln Leu Ser Arg Leu Glu Arg Val Tyr Gln
225                 230                 235                 240 tcc gaa cag gct gaa aaa ctg ctg tta gca ggc gtt atg ctg cgc gat        768
Ser Glu Gln Ala Glu Lys Leu Leu Leu Ala Gly Val Met Leu Arg Asp
                245                 250                 255 cca gcg cgt ttt gat ctg cgt ggt acg cta act cac ggg cgc gat gtt        816
Pro Ala Arg Phe Asp Leu Arg Gly Thr Leu Thr His Gly Arg Asp Val
            260                 265                 270 gaa att gat act aac gtt atc atc gag ggc aac gtg act ctc ggt cat        864
Glu Ile Asp Thr Asn Val Ile Ile Glu Gly Asn Val Thr Leu Gly His
        275                 280                 285 cgc gtg aaa att ggc acc ggt tgc gtg att aaa aac agc gtg att ggc        912
Arg Val Lys Ile Gly Thr Gly Cys Val Ile Lys Asn Ser Val Ile Gly
    290                 295                 300 gat gat tgc gaa atc agt ccg tat acc gtt gtg gaa gat gcg aat ctg        960
Asp Asp Cys Glu Ile Ser Pro Tyr Thr Val Val Glu Asp Ala Asn Leu
305                 310                 315                 320 gca gcg gcc tgt acc att ggc ccg ttt gcc cgt ttg cgt cct ggt gct       1008
Ala Ala Ala Cys Thr Ile Gly Pro Phe Ala Arg Leu Arg Pro Gly Ala
                325                 330                 335 gag ttg ctg gaa ggt gct cac gtc ggt aac ttc gtt gag atg aaa aaa       1056
Glu Leu Leu Glu Gly Ala His Val Gly Asn Phe Val Glu Met Lys Lys
            340                 345                 350 gcg cgt ctg ggt aaa ggc tcg aaa gct ggt cat ctg act tac ctg ggc       1104
Ala Arg Leu Gly Lys Gly Ser Lys Ala Gly His Leu Thr Tyr Leu Gly
        355                 360                 365 gat gcg gaa att ggc gat aac gtt aac atc ggc gcg gga acc att acc       1152
Asp Ala Glu Ile Gly Asp Asn Val Asn Ile Gly Ala Gly Thr Ile Thr
    370                 375                 380 tgc aac tac gat ggt gcg aat aaa ttt aag acc att atc ggc gac gat       1200
Cys Asn Tyr Asp Gly Ala Asn Lys Phe Lys Thr Ile Ile Gly Asp Asp
385                 390                 395                 400 gtg ttt gtt ggt tcc gac act cag ctg gtg gcc ccg gta aca gta ggc       1248
Val Phe Val Gly Ser Asp Thr Gln Leu Val Ala Pro Val Thr Val Gly
                405                 410                 415 aaa ggc gcg acc att gct gcg ggt aca act gtg acg cgt aat gtc ggc       1296
Lys Gly Ala Thr Ile Ala Ala Gly Thr Thr Val Thr Arg Asn Val Gly
            420                 425                 430 gaa aat gca tta gct atc agc cgt gtg ccg cag act cag aaa gaa ggc       1344
Glu Asn Ala Leu Ala Ile Ser Arg Val Pro Gln Thr Gln Lys Glu Gly
        435                 440                 445 tgg cgt cgt ccg gta aag aaa aag tga                                   1371
Trp Arg Arg Pro Val Lys Lys Lys
    450                 455

<210> SEQ ID NO 56
<211> LENGTH: 456
<212> TYPE: PRT
```

<213> ORGANISM: Escherichia coli

<400> SEQUENCE: 56

```
Met Leu Asn Asn Ala Met Ser Val Val Ile Leu Ala Ala Gly Lys Gly
1               5                   10                  15
Thr Arg Met Tyr Ser Asp Leu Pro Lys Val Leu His Thr Leu Ala Gly
            20                  25                  30
Lys Ala Met Val Gln His Val Ile Asp Ala Ala Asn Glu Leu Gly Ala
        35                  40                  45
Ala His Val His Leu Val Tyr Gly His Gly Asp Leu Leu Lys Gln
    50                  55                  60
Ala Leu Lys Asp Asp Asn Leu Asn Trp Val Leu Gln Ala Glu Gln Leu
65                  70                  75                  80
Gly Thr Gly His Ala Met Gln Gln Ala Ala Pro Phe Phe Ala Asp Asp
                85                  90                  95
Glu Asp Ile Leu Met Leu Tyr Gly Asp Val Pro Leu Ile Ser Val Glu
            100                 105                 110
Thr Leu Gln Arg Leu Arg Asp Ala Lys Pro Gln Gly Gly Ile Gly Leu
        115                 120                 125
Leu Thr Val Lys Leu Asp Asp Pro Thr Gly Tyr Gly Arg Ile Thr Arg
130                 135                 140
Glu Asn Gly Lys Val Thr Gly Ile Val Glu His Lys Asp Ala Thr Asp
145                 150                 155                 160
Glu Gln Arg Gln Ile Gln Glu Ile Asn Thr Gly Ile Leu Ile Ala Asn
                165                 170                 175
Gly Ala Asp Met Lys Arg Trp Leu Ala Lys Leu Thr Asn Asn Asn Ala
            180                 185                 190
Gln Gly Glu Tyr Tyr Ile Thr Asp Ile Ile Ala Leu Ala Tyr Gln Glu
        195                 200                 205
Gly Arg Glu Ile Val Ala Val His Pro Gln Arg Leu Ser Glu Val Glu
    210                 215                 220
Gly Val Asn Asn Arg Leu Gln Leu Ser Arg Leu Glu Arg Val Tyr Gln
225                 230                 235                 240
Ser Glu Gln Ala Glu Lys Leu Leu Leu Ala Gly Val Met Leu Arg Asp
                245                 250                 255
Pro Ala Arg Phe Asp Leu Arg Gly Thr Leu Thr His Gly Arg Asp Val
            260                 265                 270
Glu Ile Asp Thr Asn Val Ile Ile Glu Gly Asn Val Thr Leu Gly His
        275                 280                 285
Arg Val Lys Ile Gly Thr Gly Cys Val Ile Lys Asn Ser Val Ile Gly
    290                 295                 300
Asp Asp Cys Glu Ile Ser Pro Tyr Thr Val Val Glu Asp Ala Asn Leu
305                 310                 315                 320
Ala Ala Ala Cys Thr Ile Gly Pro Phe Ala Arg Leu Arg Pro Gly Ala
                325                 330                 335
Glu Leu Leu Glu Gly Ala His Val Gly Asn Phe Val Glu Met Lys Lys
            340                 345                 350
Ala Arg Leu Gly Lys Gly Ser Lys Ala Gly His Leu Thr Tyr Leu Gly
        355                 360                 365
Asp Ala Glu Ile Gly Asp Asn Val Asn Ile Gly Ala Gly Thr Ile Thr
    370                 375                 380
Cys Asn Tyr Asp Gly Ala Asn Lys Phe Lys Thr Ile Ile Gly Asp Asp
385                 390                 395                 400
```

```
Val Phe Val Gly Ser Asp Thr Gln Leu Val Ala Pro Val Thr Val Gly
            405                 410                 415

Lys Gly Ala Thr Ile Ala Ala Gly Thr Thr Val Thr Arg Asn Val Gly
            420                 425                 430

Glu Asn Ala Leu Ala Ile Ser Arg Val Pro Gln Thr Gln Lys Glu Gly
            435                 440                 445

Trp Arg Arg Pro Val Lys Lys Lys
    450                 455

<210> SEQ ID NO 57
<211> LENGTH: 1143
<212> TYPE: DNA
<213> ORGANISM: Escherichia coli
<220> FEATURE:
<221> NAME/KEY: CDS
<222> LOCATION: (1)..(1143)
<223> OTHER INFORMATION:

<400> SEQUENCE: 57 atg gag cag ctg ggt acg ggt cat gca atg cag cag gcc gca cct ttc      48
Met Glu Gln Leu Gly Thr Gly His Ala Met Gln Gln Ala Ala Pro Phe
1               5                  10                  15 ttt gcc gat gat gaa gac att tta atg ctc tac ggc gac gtg ccg ctg      96
Phe Ala Asp Asp Glu Asp Ile Leu Met Leu Tyr Gly Asp Val Pro Leu
            20                  25                  30 atc tct gtc gaa aca ctc cag cgt ctg cgt gat gct aaa ccg cag ggt     144
Ile Ser Val Glu Thr Leu Gln Arg Leu Arg Asp Ala Lys Pro Gln Gly
        35                  40                  45 ggc att ggt ctg ctg acg gtg aaa ctg gat gat ccg acc ggt tat gga     192
Gly Ile Gly Leu Leu Thr Val Lys Leu Asp Asp Pro Thr Gly Tyr Gly
    50                  55                  60 cgt atc acc cgt gaa aac ggc aaa gtt acc ggc att gtt gag cac aaa     240
Arg Ile Thr Arg Glu Asn Gly Lys Val Thr Gly Ile Val Glu His Lys
65                  70                  75                  80 gat gcc acc gac gag cag cgt cag att cag gag atc aac acc ggc att     288
Asp Ala Thr Asp Glu Gln Arg Gln Ile Gln Glu Ile Asn Thr Gly Ile
                85                  90                  95 ctg att gcc aac ggc gca gat atg aaa cgc tgg ctg gcg aag ctg acc     336
Leu Ile Ala Asn Gly Ala Asp Met Lys Arg Trp Leu Ala Lys Leu Thr
            100                 105                 110 aac aat aat gct cag ggc gaa tac tac atc acc gac att att gcg ctg     384
Asn Asn Asn Ala Gln Gly Glu Tyr Tyr Ile Thr Asp Ile Ile Ala Leu
        115                 120                 125 gcg tat cag gaa ggg cgt gaa atc gtc gcc gtt cat ccg caa cgt tta     432
Ala Tyr Gln Glu Gly Arg Glu Ile Val Ala Val His Pro Gln Arg Leu
    130                 135                 140 agc gaa gta gaa ggc gtg aat aac cgc ctg caa ctc tcc cgt ctg gag     480
Ser Glu Val Glu Gly Val Asn Asn Arg Leu Gln Leu Ser Arg Leu Glu
145                 150                 155                 160 cgt gtt tat cag tcc gaa cag gct gaa aaa ctg ctg tta gca ggc gtt     528
Arg Val Tyr Gln Ser Glu Gln Ala Glu Lys Leu Leu Leu Ala Gly Val
                165                 170                 175 atg ctg cgc gat cca gcg cgt ttt gat ctg cgt ggt acg cta act cac     576
Met Leu Arg Asp Pro Ala Arg Phe Asp Leu Arg Gly Thr Leu Thr His
            180                 185                 190 ggg cgc gat gtt gaa att gat act aac gtt atc atc gag ggc aac gtg     624
Gly Arg Asp Val Glu Ile Asp Thr Asn Val Ile Ile Glu Gly Asn Val
        195                 200                 205 act ctc ggt cat cgc gtg aaa att ggc acc ggt tgc gtg att aaa aac     672
Thr Leu Gly His Arg Val Lys Ile Gly Thr Gly Cys Val Ile Lys Asn
    210                 215                 220
```

```
agc gtg att ggc gat gat tgc gaa atc agt ccg tat acc gtt gtg gaa        720
Ser Val Ile Gly Asp Asp Cys Glu Ile Ser Pro Tyr Thr Val Val Glu
225                 230                 235                 240 gat gcg aat ctg gca gcg gcc tgt acc att ggc ccg ttt gcc cgt ttg        768
Asp Ala Asn Leu Ala Ala Ala Cys Thr Ile Gly Pro Phe Ala Arg Leu
                245                 250                 255 cgt cct ggt gct gag ttg ctg gaa ggt gct cac gtc ggt aac ttc gtt        816
Arg Pro Gly Ala Glu Leu Leu Glu Gly Ala His Val Gly Asn Phe Val
            260                 265                 270 gag atg aaa aaa gcg cgt ctg ggt aaa ggc tcg aaa gct ggt cat ctg        864
Glu Met Lys Lys Ala Arg Leu Gly Lys Gly Ser Lys Ala Gly His Leu
        275                 280                 285 act tac ctg ggc gat gcg gaa att ggc gat aac gtt aac atc ggc gcg        912
Thr Tyr Leu Gly Asp Ala Glu Ile Gly Asp Asn Val Asn Ile Gly Ala
    290                 295                 300 gga acc att acc tgc aac tac gat ggt gcg aat aaa ttt aag acc att        960
Gly Thr Ile Thr Cys Asn Tyr Asp Gly Ala Asn Lys Phe Lys Thr Ile
305                 310                 315                 320 atc ggc gac gat gtg ttt gtt ggt tcc gac act cag ctg gtg gcc ccg       1008
Ile Gly Asp Asp Val Phe Val Gly Ser Asp Thr Gln Leu Val Ala Pro
                325                 330                 335 gta aca gta ggc aaa ggc gcg acc att gct gcg ggt aca act gtg acg       1056
Val Thr Val Gly Lys Gly Ala Thr Ile Ala Ala Gly Thr Thr Val Thr
            340                 345                 350 cgt aat gtc ggc gaa aat gca tta gct atc agc cgt gtg ccg cag act       1104
Arg Asn Val Gly Glu Asn Ala Leu Ala Ile Ser Arg Val Pro Gln Thr
        355                 360                 365 cag aaa gaa ggc tgg cgt cgt ccg gta aag aaa aag tga                    1143
Gln Lys Glu Gly Trp Arg Arg Pro Val Lys Lys Lys
    370                 375                 380

<210> SEQ ID NO 58
<211> LENGTH: 380
<212> TYPE: PRT
<213> ORGANISM: Escherichia coli

<400> SEQUENCE: 58

Met Glu Gln Leu Gly Thr Gly His Ala Met Gln Gln Ala Ala Pro Phe
1               5                   10                  15

Phe Ala Asp Asp Glu Asp Ile Leu Met Leu Tyr Gly Asp Val Pro Leu
            20                  25                  30

Ile Ser Val Glu Thr Leu Gln Arg Leu Arg Asp Ala Lys Pro Gln Gly
        35                  40                  45

Gly Ile Gly Leu Leu Thr Val Lys Leu Asp Asp Pro Thr Gly Tyr Gly
    50                  55                  60

Arg Ile Thr Arg Glu Asn Gly Lys Val Thr Gly Ile Val Glu His Lys
65                  70                  75                  80

Asp Ala Thr Asp Glu Gln Arg Gln Ile Gln Glu Ile Asn Thr Gly Ile
                85                  90                  95

Leu Ile Ala Asn Gly Ala Asp Met Lys Arg Trp Leu Ala Lys Leu Thr
            100                 105                 110

Asn Asn Asn Ala Gln Gly Glu Tyr Tyr Ile Thr Asp Ile Ile Ala Leu
        115                 120                 125

Ala Tyr Gln Glu Gly Arg Glu Ile Val Ala Val His Pro Gln Arg Leu
    130                 135                 140

Ser Glu Val Glu Gly Val Asn Asn Arg Leu Gln Leu Ser Arg Leu Glu
145                 150                 155                 160
```

-continued

```
Arg Val Tyr Gln Ser Glu Gln Ala Glu Lys Leu Leu Ala Gly Val
                165                 170                 175
Met Leu Arg Asp Pro Ala Arg Phe Asp Leu Arg Gly Thr Leu Thr His
            180                 185                 190
Gly Arg Asp Val Glu Ile Asp Thr Asn Val Ile Ile Glu Gly Asn Val
        195                 200                 205
Thr Leu Gly His Arg Val Lys Ile Gly Thr Gly Cys Val Ile Lys Asn
    210                 215                 220
Ser Val Ile Gly Asp Asp Cys Glu Ile Ser Pro Tyr Thr Val Val Glu
225                 230                 235                 240
Asp Ala Asn Leu Ala Ala Cys Thr Ile Gly Pro Phe Ala Arg Leu
                245                 250                 255
Arg Pro Gly Ala Glu Leu Leu Gly Ala His Val Gly Asn Phe Val
            260                 265                 270
Glu Met Lys Lys Ala Arg Leu Gly Lys Gly Ser Lys Ala Gly His Leu
        275                 280                 285
Thr Tyr Leu Gly Asp Ala Glu Ile Gly Asp Asn Val Asn Ile Gly Ala
    290                 295                 300
Gly Thr Ile Thr Cys Asn Tyr Asp Gly Ala Asn Lys Phe Lys Thr Ile
305                 310                 315                 320
Ile Gly Asp Asp Val Phe Val Gly Ser Asp Thr Gln Leu Val Ala Pro
                325                 330                 335
Val Thr Val Gly Lys Gly Ala Thr Ile Ala Ala Gly Thr Thr Val Thr
            340                 345                 350
Arg Asn Val Gly Glu Asn Ala Leu Ala Ile Ser Arg Val Pro Gln Thr
        355                 360                 365
Gln Lys Glu Gly Trp Arg Arg Pro Val Lys Lys
    370                 375                 380
```

<210> SEQ ID NO 59
<211> LENGTH: 33
<212> TYPE: DNA
<213> ORGANISM: Artificial sequence
<220> FEATURE:
<223> OTHER INFORMATION: primer

<400> SEQUENCE: 59
gatcggtctc gcatgagtaa tcgtaaatat ttc                33

<210> SEQ ID NO 60
<211> LENGTH: 31
<212> TYPE: DNA
<213> ORGANISM: Artificial sequence
<220> FEATURE:
<223> OTHER INFORMATION: primer

<400> SEQUENCE: 60
gatcctcgag ttaaacggct tttactgcat c                  31

<210> SEQ ID NO 61
<211> LENGTH: 33
<212> TYPE: DNA
<213> ORGANISM: Artificial sequence
<220> FEATURE:
<223> OTHER INFORMATION: primer

<400> SEQUENCE: 61
gatcggtctc gcatgttgaa taatgctatg agc                33

<210> SEQ ID NO 62
<211> LENGTH: 33
<212> TYPE: DNA
<213> ORGANISM: Artificial sequence
<220> FEATURE:
<223> OTHER INFORMATION: primer

<400> SEQUENCE: 62
gatcctcgag tcacttttc tttaccggac gac                            33

<210> SEQ ID NO 63
<211> LENGTH: 33
<212> TYPE: DNA
<213> ORGANISM: Artificial sequence
<220> FEATURE:
<223> OTHER INFORMATION: primer

<400> SEQUENCE: 63
gatggtctcg catggagcag ctgggtacgg gtc                           33

<210> SEQ ID NO 64
<211> LENGTH: 32
<212> TYPE: DNA
<213> ORGANISM: Artificial sequence
<220> FEATURE:
<223> OTHER INFORMATION: primer

<400> SEQUENCE: 64
gcgacgctct cccgggtgcg actcctgcat ta                            32

<210> SEQ ID NO 65
<211> LENGTH: 46
<212> TYPE: DNA
<213> ORGANISM: Artificial sequence
<220> FEATURE:
<223> OTHER INFORMATION: primer

<400> SEQUENCE: 65
gatctgtaca atccggatat agttcctcct ttcagcaaaa aacccc             46

<210> SEQ ID NO 66
<211> LENGTH: 32
<212> TYPE: DNA
<213> ORGANISM: Artificial sequence
<220> FEATURE:
<223> OTHER INFORMATION: primer

<400> SEQUENCE: 66
gcgacgctct cccgggtgcg actcctgcat ta                            32

<210> SEQ ID NO 67
<211> LENGTH: 36
<212> TYPE: DNA
<213> ORGANISM: Artificial sequence
<220> FEATURE:
<223> OTHER INFORMATION: primer

<400> SEQUENCE: 67
gcgctaatca agttttcccg ggtcgaggtg ccgtaa                        36

<210> SEQ ID NO 68
<211> LENGTH: 35
<212> TYPE: DNA
<213> ORGANISM: Artificial sequence
<220> FEATURE:
<223> OTHER INFORMATION: primer

```
<400> SEQUENCE: 68
gatgcggccg cactgcagta attaccgcat ccaac                           35

<210> SEQ ID NO 69
<211> LENGTH: 34
<212> TYPE: DNA
<213> ORGANISM: Artificial sequence
<220> FEATURE:
<223> OTHER INFORMATION: primer

<400> SEQUENCE: 69
gatgtcgaca ccgattgatg cagcaaatgc atcc                            34

<210> SEQ ID NO 70
<211> LENGTH: 32
<212> TYPE: DNA
<213> ORGANISM: Artificial sequence
<220> FEATURE:
<223> OTHER INFORMATION: primer

<400> SEQUENCE: 70
gatgcggccg cgcaaggcaa cagcaaactg gc                              32

<210> SEQ ID NO 71
<211> LENGTH: 42
<212> TYPE: DNA
<213> ORGANISM: Artificial sequence
<220> FEATURE:
<223> OTHER INFORMATION: primer

<400> SEQUENCE: 71
gatcggatcc tcaggctgtt accaaagaag ttgcaacctg gc                   42

<210> SEQ ID NO 72
<211> LENGTH: 28
<212> TYPE: DNA
<213> ORGANISM: Artificial sequence
<220> FEATURE:
<223> OTHER INFORMATION: primer

<400> SEQUENCE: 72
gatctgtaca agcaaccgca cctgtggc                                   28

<210> SEQ ID NO 73
<211> LENGTH: 46
<212> TYPE: DNA
<213> ORGANISM: Artificial sequence
<220> FEATURE:
<223> OTHER INFORMATION: primer

<400> SEQUENCE: 73
gatcagcgct atccggatat agttcctcct ttcagcaaaa aacccc               46

<210> SEQ ID NO 74
<211> LENGTH: 31
<212> TYPE: DNA
<213> ORGANISM: Artificial sequence
<220> FEATURE:
<223> OTHER INFORMATION: primer

<400> SEQUENCE: 74
gagcggccgc atgcaaaatc ggctgaccat c                               31

<210> SEQ ID NO 75
<211> LENGTH: 37
```

```
<212> TYPE: DNA
<213> ORGANISM: Artificial sequence
<220> FEATURE:
<223> OTHER INFORMATION: primer

<400> SEQUENCE: 75
gatcgggccc ttacttctgt aaccaccaga cagcctc                              37

<210> SEQ ID NO 76
<211> LENGTH: 34
<212> TYPE: DNA
<213> ORGANISM: Artificial sequence
<220> FEATURE:
<223> OTHER INFORMATION: primer

<400> SEQUENCE: 76
gatgcggccg cttagccggg aaacgtctgg cggc                                 34

<210> SEQ ID NO 77
<211> LENGTH: 37
<212> TYPE: DNA
<213> ORGANISM: Artificial sequence
<220> FEATURE:
<223> OTHER INFORMATION: primer

<400> SEQUENCE: 77
gatcgtcgac tcaggctttc acatcactca ctgcacc                              37

<210> SEQ ID NO 78
<211> LENGTH: 27
<212> TYPE: DNA
<213> ORGANISM: Artificial sequence
<220> FEATURE:
<223> OTHER INFORMATION: primer

<400> SEQUENCE: 78
gatggatcca gcaaccgcac ctgtggc                                         27

<210> SEQ ID NO 79
<211> LENGTH: 39
<212> TYPE: DNA
<213> ORGANISM: Artificial sequence
<220> FEATURE:
<223> OTHER INFORMATION: primer

<400> SEQUENCE: 79
gatgcgatcg ctatagttcc tcctttcagc aaaaaaccc                            39

<210> SEQ ID NO 80
<211> LENGTH: 32
<212> TYPE: DNA
<213> ORGANISM: Artificial sequence
<220> FEATURE:
<223> OTHER INFORMATION: primer

<400> SEQUENCE: 80
agctgagctc atgtgtggaa ttgttggcgc ga                                   32

<210> SEQ ID NO 81
<211> LENGTH: 32
<212> TYPE: DNA
<213> ORGANISM: Artificial sequence
<220> FEATURE:
<223> OTHER INFORMATION: primer

<400> SEQUENCE: 81
```

```
tacgaagctt actcaaccgt aaccgattt gc                                         32
```

<210> SEQ ID NO 82
<211> LENGTH: 34
<212> TYPE: DNA
<213> ORGANISM: Artificial sequence
<220> FEATURE:
<223> OTHER INFORMATION: primer

<400> SEQUENCE: 82

```
agctggtacc atgtgtggaa tcgtaggtta tatc                                      34
```

<210> SEQ ID NO 83
<211> LENGTH: 34
<212> TYPE: DNA
<213> ORGANISM: Artificial sequence
<220> FEATURE:
<223> OTHER INFORMATION: primer

<400> SEQUENCE: 83

```
tacgcatgct tactccacag taacactctt cgca                                      34
```

<210> SEQ ID NO 84
<211> LENGTH: 382
<212> TYPE: PRT
<213> ORGANISM: Escherichia coli

<400> SEQUENCE: 84

```
Met Tyr Ala Leu Thr Gln Gly Arg Ile Phe Thr Gly His Glu Phe Leu
  1               5                  10                  15

Asp Asp His Ala Val Val Ile Ala Asp Gly Leu Ile Lys Ser Val Cys
             20                  25                  30

Pro Val Ala Glu Leu Pro Pro Glu Ile Glu Gln Arg Ser Leu Asn Gly
         35                  40                  45

Ala Ile Leu Ser Pro Gly Phe Ile Asp Val Gln Leu Asn Gly Cys Gly
     50                  55                  60

Gly Val Gln Phe Asn Asp Thr Ala Glu Ala Val Ser Val Glu Thr Leu
 65                  70                  75                  80

Glu Ile Met Gln Lys Ala Asn Glu Lys Ser Gly Cys Thr Asn Tyr Leu
                 85                  90                  95

Pro Thr Leu Ile Thr Thr Ser Asp Glu Leu Met Lys Gln Gly Val Arg
            100                 105                 110

Val Met Arg Glu Tyr Leu Ala Lys His Pro Asn Gln Ala Leu Gly Leu
        115                 120                 125

His Leu Glu Gly Pro Trp Leu Asn Leu Val Lys Lys Gly Thr His Asn
    130                 135                 140

Pro Asn Phe Val Arg Lys Pro Asp Ala Ala Leu Val Asp Phe Leu Cys
145                 150                 155                 160

Glu Asn Ala Asp Val Ile Thr Lys Val Thr Leu Ala Pro Glu Met Val
                165                 170                 175

Pro Ala Glu Val Ile Ser Lys Leu Ala Asn Ala Gly Ile Val Val Ser
            180                 185                 190

Ala Gly His Ser Asn Ala Thr Leu Lys Glu Ala Lys Ala Gly Phe Arg
        195                 200                 205

Ala Gly Ile Thr Phe Ala Thr His Leu Tyr Asn Ala Met Pro Tyr Ile
    210                 215                 220

Thr Gly Arg Glu Pro Gly Leu Ala Gly Ala Ile Leu Asp Glu Ala Asp
225                 230                 235                 240
```

```
Ile Tyr Cys Gly Ile Ile Ala Asp Gly Leu His Val Asp Tyr Ala Asn
                245                 250                 255

Ile Arg Asn Ala Lys Arg Leu Lys Gly Asp Lys Leu Cys Leu Val Thr
            260                 265                 270

Asp Ala Thr Ala Pro Ala Gly Ala Asn Ile Glu Gln Phe Ile Phe Ala
        275                 280                 285

Gly Lys Thr Ile Tyr Tyr Arg Asn Gly Leu Cys Val Asp Glu Asn Gly
    290                 295                 300

Thr Leu Ser Gly Ser Ser Leu Thr Met Ile Glu Gly Val Arg Asn Leu
305                 310                 315                 320

Val Glu His Cys Gly Ile Ala Leu Asp Glu Val Leu Arg Met Ala Thr
                325                 330                 335

Leu Tyr Pro Ala Arg Ala Ile Gly Val Glu Lys Arg Leu Gly Thr Leu
            340                 345                 350

Ala Ala Gly Lys Val Ala Asn Leu Thr Ala Phe Thr Pro Asp Phe Lys
        355                 360                 365

Ile Thr Lys Thr Ile Val Asn Gly Asn Glu Val Val Thr Gln
    370                 375                 380

<210> SEQ ID NO 85
<211> LENGTH: 1149
<212> TYPE: DNA
<213> ORGANISM: Escherichia coli

<400> SEQUENCE: 85
atgtatgcat taacccaggg ccggatcttt accggccacg aatttcttga tgaccacgcg      60
gttgttatcg ctgatggcct gattaaaagc gtctgtccgg tagcggaact gccgccagag     120
atcgaacaac gttcactgaa cggggccatt ctctcccccg ttttatcga tgtgcagtta     180 aacggctgcg gcggcgtaca gtttaacgac accgctgaag cggtcagcgt ggaaacgctg     240
gaaatcatgc agaaagccaa tgagaaatca ggctgtacta actatctgcc gacgcttatc     300
accaccagcg atgagctgat gaaacagggc gtgcgcgtta tgcgcgagta cctggcaaaa     360
catccgaatc aggcgttagg tctgcatctg aaggtccgt ggctgaatct ggtaaaaaaa     420
ggcacccata tccgaattt tgtgcgtaag cctgatgccg cgctggtcga tttcctgtgt     480
gaaaacgccg acgtcattac caaagtgacc ctggcaccgg aaatggttcc tgcgaagtc     540 atcagcaaac tggcaaatgc cgggattgtg gtttctgccg gtcactccaa cgcgacgttg     600
aaagaagcaa aagccggttt ccgcgcgggg attaccttttg ccacccatct gtacaacgcg     660
atgccgtata ttaccggtcg tgaacctggc ctggcgggcg cgatcctcga cgaagctgac     720
atttattgcg gtattattgc tgatggcctg catgttgatt acgccaacat tcgcaacgct     780
aaacgtctga aggcgacaa actgtgtctg gttactgacg ccaccgcgcc agcaggtgcc     840
aacattgaac agttcatttt tgcgggtaaa acaatatact accgtaacgg actttgtgtg     900
gatgagaacg gtacgttaag cggttcatcc ttaaccatga ttgaaggcgt gcgtaatctg     960
gtcgaacatt gcggtatcgc actggatgaa gtgctacgta tggcgacgct ctatccggcg    1020
cgtgcgattg gcgttgagaa acgtctcggc acactcgccg caggtaaagt agccaacctg    1080
actgcattca cacctgattt taaaatcacc aagaccatcg ttaacggtaa cgaggtcgta    1140
actcaataa                                                           1149

<210> SEQ ID NO 86
<211> LENGTH: 32
<212> TYPE: DNA
```

```
<213> ORGANISM: Artificial sequence
<220> FEATURE:
<223> OTHER INFORMATION: primer

<400> SEQUENCE: 86
gagcggccgc atgaatcaat cttatggacg gc                                     32

<210> SEQ ID NO 87
<211> LENGTH: 37
<212> TYPE: DNA
<213> ORGANISM: Artificial sequence
<220> FEATURE:
<223> OTHER INFORMATION: primer

<400> SEQUENCE: 87
gagtcgactc agcgtttgct gatctgatcg aacgtac                                37

<210> SEQ ID NO 88
<211> LENGTH: 1410
<212> TYPE: DNA
<213> ORGANISM: Escherichia coli
<220> FEATURE:
<221> NAME/KEY: CDS
<222> LOCATION: (1)..(1410)
<223> OTHER INFORMATION:

<400> SEQUENCE: 88
```

| | | | | | | | | | | | | | | | | |
|---|---|---|---|---|---|---|---|---|---|---|---|---|---|---|---|---|
| atg | tcc | gct | gaa | cac | gta | ctg | acg | atg | ctg | aac | gag | cac | gaa | gtg | aag | 48 |
| Met | Ser | Ala | Glu | His | Val | Leu | Thr | Met | Leu | Asn | Glu | His | Glu | Val | Lys | |
| 1 | | | | 5 | | | | | 10 | | | | | 15 | | |
| ttt | gtt | gat | ttg | cgc | ttc | acc | gat | act | aaa | ggt | aaa | gaa | cag | cac | gtc | 96 |
| Phe | Val | Asp | Leu | Arg | Phe | Thr | Asp | Thr | Lys | Gly | Lys | Glu | Gln | His | Val | |
| | | | 20 | | | | | 25 | | | | | 30 | | | |
| act | atc | cct | gct | cat | cag | gtg | aat | gct | gaa | ttc | ttc | gaa | gaa | ggc | aaa | 144 |
| Thr | Ile | Pro | Ala | His | Gln | Val | Asn | Ala | Glu | Phe | Phe | Glu | Glu | Gly | Lys | |
| | | 35 | | | | | 40 | | | | | 45 | | | | |
| atg | ttt | gac | ggc | tcc | tcg | att | ggc | ggc | tgg | aaa | ggc | att | aac | gag | tcc | 192 |
| Met | Phe | Asp | Gly | Ser | Ser | Ile | Gly | Gly | Trp | Lys | Gly | Ile | Asn | Glu | Ser | |
| | 50 | | | | | 55 | | | | | 60 | | | | | |
| gac | atg | gtg | ctg | atg | cca | gac | gca | tcc | acc | gca | gtg | att | gac | ccg | ttc | 240 |
| Asp | Met | Val | Leu | Met | Pro | Asp | Ala | Ser | Thr | Ala | Val | Ile | Asp | Pro | Phe | |
| 65 | | | | | 70 | | | | | 75 | | | | | 80 | |
| ttc | gcc | gac | tcc | acc | ctg | att | atc | cgt | tgc | gac | atc | ctt | gaa | cct | ggc | 288 |
| Phe | Ala | Asp | Ser | Thr | Leu | Ile | Ile | Arg | Cys | Asp | Ile | Leu | Glu | Pro | Gly | |
| | | | | 85 | | | | | 90 | | | | | 95 | | |
| acc | ctg | caa | ggc | tat | gac | cgt | gac | ccg | cgc | tcc | att | gcg | aag | cgc | gcc | 336 |
| Thr | Leu | Gln | Gly | Tyr | Asp | Arg | Asp | Pro | Arg | Ser | Ile | Ala | Lys | Arg | Ala | |
| | | | 100 | | | | | 105 | | | | | 110 | | | |
| gaa | gat | tac | ctg | cgt | tcc | act | ggc | att | gcc | gac | acc | gta | ctg | ttc | ggg | 384 |
| Glu | Asp | Tyr | Leu | Arg | Ser | Thr | Gly | Ile | Ala | Asp | Thr | Val | Leu | Phe | Gly | |
| | | | 115 | | | | | 120 | | | | | 125 | | | |
| cca | gaa | cct | gaa | ttc | ttc | ctg | ttc | gat | gac | atc | cgt | ttc | gga | tca | tct | 432 |
| Pro | Glu | Pro | Glu | Phe | Phe | Leu | Phe | Asp | Asp | Ile | Arg | Phe | Gly | Ser | Ser | |
| | | 130 | | | | | 135 | | | | | 140 | | | | |
| atc | tcc | ggt | tcc | cac | gtt | gct | atc | gac | gat | atc | gaa | ggc | gca | tgg | aac | 480 |
| Ile | Ser | Gly | Ser | His | Val | Ala | Ile | Asp | Asp | Ile | Glu | Gly | Ala | Trp | Asn | |
| 145 | | | | | 150 | | | | | 155 | | | | | 160 | |
| tcc | tcc | acc | caa | tac | gaa | ggt | ggt | aac | aaa | ggt | cac | cgt | ccg | gca | gtg | 528 |
| Ser | Ser | Thr | Gln | Tyr | Glu | Gly | Gly | Asn | Lys | Gly | His | Arg | Pro | Ala | Val | |
| | | | | 165 | | | | | 170 | | | | | 175 | | |
| aaa | ggc | ggt | tac | ttc | ccg | gtt | cca | ccg | gta | gac | tcg | gct | cag | gat | att | 576 |
| Lys | Gly | Gly | Tyr | Phe | Pro | Val | Pro | Pro | Val | Asp | Ser | Ala | Gln | Asp | Ile | |
| | | | 180 | | | | | 185 | | | | | 190 | | | |

```
                                                  -continued cgt tct gaa atg tgt ctg gtg atg gaa cag atg ggt ctg gtg gtt gaa      624
Arg Ser Glu Met Cys Leu Val Met Glu Gln Met Gly Leu Val Val Glu
        195                 200                 205 gcc cat cac cac gaa gta gcg act gct ggt cag aac gaa gtg gct acc      672
Ala His His His Glu Val Ala Thr Ala Gly Gln Asn Glu Val Ala Thr
210                 215                 220 cgc ttc aat acc atg acc aaa aaa gct gac gaa att cag atc tac aaa      720
Arg Phe Asn Thr Met Thr Lys Lys Ala Asp Glu Ile Gln Ile Tyr Lys
225                 230                 235                 240 tat gtt gtg cac aac gta gcg cac cgc ttc ggt aaa acc gcg acc ttt      768
Tyr Val Val His Asn Val Ala His Arg Phe Gly Lys Thr Ala Thr Phe
                245                 250                 255 atg cca aaa ccg atg ttc ggt gat aac ggc tcc ggt atg cac tgc cac      816
Met Pro Lys Pro Met Phe Gly Asp Asn Gly Ser Gly Met His Cys His
            260                 265                 270 atg tct ctg tct aaa aac ggc gtt aac ctg ttc gca ggc gac aaa tac      864
Met Ser Leu Ser Lys Asn Gly Val Asn Leu Phe Ala Gly Asp Lys Tyr
        275                 280                 285 gca ggt ctg tct gag cag gcg ctg tac tac att ggc ggc gta atc aaa      912
Ala Gly Leu Ser Glu Gln Ala Leu Tyr Tyr Ile Gly Gly Val Ile Lys
290                 295                 300 cac gct aaa gcg att aac gcc ctg gca aac ccg acc acc aac tct tat      960
His Ala Lys Ala Ile Asn Ala Leu Ala Asn Pro Thr Thr Asn Ser Tyr
305                 310                 315                 320 aag cgt ctg gtc ccg ggc tat gaa gca ccg gta atg ctg gct tac tct     1008
Lys Arg Leu Val Pro Gly Tyr Glu Ala Pro Val Met Leu Ala Tyr Ser
                325                 330                 335 gcg cgt aac cgt tct gcg tct atc cgt att ccg gtg gtt tct tct ccg     1056
Ala Arg Asn Arg Ser Ala Ser Ile Arg Ile Pro Val Val Ser Ser Pro
            340                 345                 350 aaa gca cgt cgt atc gaa gta cgt ttc ccg gat ccg gca gct aac ccg     1104
Lys Ala Arg Arg Ile Glu Val Arg Phe Pro Asp Pro Ala Ala Asn Pro
        355                 360                 365 tac ctg tgc ttt gct gcc ctg ctg atg gcc ggt ctt gat ggt atc aag     1152
Tyr Leu Cys Phe Ala Ala Leu Leu Met Ala Gly Leu Asp Gly Ile Lys
370                 375                 380 aac aag atc cat ccg ggc gaa gcc atg gac aaa aac ctg tat gac ctg     1200
Asn Lys Ile His Pro Gly Glu Ala Met Asp Lys Asn Leu Tyr Asp Leu
385                 390                 395                 400 ccg cca gaa gaa gcg aaa gag atc cca cag gtt gca ggc tct ctg gaa     1248
Pro Pro Glu Glu Ala Lys Glu Ile Pro Gln Val Ala Gly Ser Leu Glu
                405                 410                 415 gaa gca ctg aac gaa ctg gat ctg gac cgc gag ttc ctg aaa gcc ggt     1296
Glu Ala Leu Asn Glu Leu Asp Leu Asp Arg Glu Phe Leu Lys Ala Gly
            420                 425                 430 ggc gtg ttc act gac gaa gca att gat gcg tac atc gct ctg cgt cgc     1344
Gly Val Phe Thr Asp Glu Ala Ile Asp Ala Tyr Ile Ala Leu Arg Arg
        435                 440                 445 gaa gaa gat gac cgc gtg cgt atg act ccg cat ccg gta gag ttt gag     1392
Glu Glu Asp Asp Arg Val Arg Met Thr Pro His Pro Val Glu Phe Glu
450                 455                 460 ctg tac tac agc gtc taa                                             1410
Leu Tyr Tyr Ser Val
465

<210> SEQ ID NO 89
<211> LENGTH: 469
<212> TYPE: PRT
<213> ORGANISM: Escherichia coli
```

<400> SEQUENCE: 89

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Glu Phe Phe Glu Glu Gly Lys
        35                  40                  45

Met Phe Asp Gly Ser Ser Ile Gly Gly Trp Lys Gly Ile Asn Glu Ser
50                  55                  60

Asp Met Val Leu Met Pro Asp Ala Ser Thr Ala Val Ile Asp Pro Phe
65                  70                  75                  80

Phe Ala Asp Ser Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
            100                 105                 110

Glu Asp Tyr Leu Arg Ser Thr Gly Ile Ala Asp Thr Val Leu Phe Gly
        115                 120                 125

Pro Glu Pro Glu Phe Phe Leu Phe Asp Asp Ile Arg Phe Gly Ser Ser
130                 135                 140

Ile Ser Gly Ser His Val Ala Ile Asp Asp Ile Glu Gly Ala Trp Asn
145                 150                 155                 160

Ser Ser Thr Gln Tyr Glu Gly Gly Asn Lys Gly His Arg Pro Ala Val
                165                 170                 175

Lys Gly Gly Tyr Phe Pro Val Pro Pro Val Asp Ser Ala Gln Asp Ile
            180                 185                 190

Arg Ser Glu Met Cys Leu Val Met Glu Gln Met Gly Leu Val Val Glu
        195                 200                 205

Ala His His His Glu Val Ala Thr Ala Gly Gln Asn Glu Val Ala Thr
210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Val Asn Leu Phe Ala Gly Asp Lys Tyr
        275                 280                 285

Ala Gly Leu Ser Glu Gln Ala Leu Tyr Tyr Ile Gly Gly Val Ile Lys
290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ser Ser Pro
            340                 345                 350

Lys Ala Arg Arg Ile Glu Val Arg Phe Pro Asp Pro Ala Ala Asn Pro
        355                 360                 365

Tyr Leu Cys Phe Ala Ala Leu Leu Met Ala Gly Leu Asp Gly Ile Lys
370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                405                 410                 415
```

```
Glu Ala Leu Asn Glu Leu Asp Leu Asp Arg Glu Phe Leu Lys Ala Gly
        420                 425                 430

Gly Val Phe Thr Asp Glu Ala Ile Asp Ala Tyr Ile Ala Leu Arg Arg
        435                 440                 445

Glu Glu Asp Asp Arg Val Arg Met Thr Pro His Pro Val Glu Phe Glu
    450                 455                 460

Leu Tyr Tyr Ser Val
465
```

<210> SEQ ID NO 90
<211> LENGTH: 35
<212> TYPE: DNA
<213> ORGANISM: Artificial sequence
<220> FEATURE:
<223> OTHER INFORMATION: primer

<400> SEQUENCE: 90
gatcggtctc gcatgtccgc tgaacacgta ctgac                              35

<210> SEQ ID NO 91
<211> LENGTH: 31
<212> TYPE: DNA
<213> ORGANISM: Artificial sequence
<220> FEATURE:
<223> OTHER INFORMATION: primer

<400> SEQUENCE: 91
gatcctcgag ttagacgctg tagtacagct c                                  31

<210> SEQ ID NO 92
<211> LENGTH: 29
<212> TYPE: DNA
<213> ORGANISM: Artificial sequence
<220> FEATURE:
<223> OTHER INFORMATION: primer

<400> SEQUENCE: 92
gatcgccggc ttacatgctg tagcccagc                                     29

<210> SEQ ID NO 93
<211> LENGTH: 32
<212> TYPE: DNA
<213> ORGANISM: Artificial sequence
<220> FEATURE:
<223> OTHER INFORMATION: primer

<400> SEQUENCE: 93
gatcctgcag tcatgctgct aataatctat cc                                 32

<210> SEQ ID NO 94
<211> LENGTH: 1476
<212> TYPE: DNA
<213> ORGANISM: Escherichia coli
<220> FEATURE:
<221> NAME/KEY: CDS
<222> LOCATION: (1)..(1476)
<223> OTHER INFORMATION:

<400> SEQUENCE: 94

```
atg gcg gta acg caa aca gcc cag gtc tgt gac ttg gtc att ttc ggc      48
Met Ala Val Thr Gln Thr Ala Gln Val Cys Asp Leu Val Ile Phe Gly
1               5                  10                  15 gcg aaa ggc gac ctt gcg cgt cgt aaa ttg ctg cct tcc ctg tat caa      96
Ala Lys Gly Asp Leu Ala Arg Arg Lys Leu Leu Pro Ser Leu Tyr Gln
```

-continued

```
              20                  25                  30
ctg gaa aaa gcc ggt cag ctc aac ccg gac acc cgg att atc ggc gta      144
Leu Glu Lys Ala Gly Gln Leu Asn Pro Asp Thr Arg Ile Ile Gly Val
         35                  40                  45 ggg cgt gct gac tgg gat aaa gcg gca tat acc aaa gtt gtc cgc gag      192
Gly Arg Ala Asp Trp Asp Lys Ala Ala Tyr Thr Lys Val Val Arg Glu
 50                  55                  60 gcg ctc gaa act ttc atg aaa gaa acc att gat gaa ggt tta tgg gac      240
Ala Leu Glu Thr Phe Met Lys Glu Thr Ile Asp Glu Gly Leu Trp Asp
 65                  70                  75                  80 acc ctg agc gca cgt ctg gat ttt tgt aat ctc gat gtc aat gac act      288
Thr Leu Ser Ala Arg Leu Asp Phe Cys Asn Leu Asp Val Asn Asp Thr
                 85                  90                  95 gct gca ttc agc cgt ctc ggc gcg atg ctg gat caa aaa aat cgt atc      336
Ala Ala Phe Ser Arg Leu Gly Ala Met Leu Asp Gln Lys Asn Arg Ile
                100                 105                 110 acc att aac tac ttt gcc atg ccg ccc agc act ttt ggc gca att tgc      384
Thr Ile Asn Tyr Phe Ala Met Pro Pro Ser Thr Phe Gly Ala Ile Cys
                115                 120                 125 aaa ggg ctt ggc gag gca aaa ctg aat gct aaa ccg gca cgc gta gtc      432
Lys Gly Leu Gly Glu Ala Lys Leu Asn Ala Lys Pro Ala Arg Val Val
130                 135                 140 atg gag aaa ccg ctg ggg acg tcg ctg gcg acc tcg cag gaa atc aat      480
Met Glu Lys Pro Leu Gly Thr Ser Leu Ala Thr Ser Gln Glu Ile Asn
145                 150                 155                 160 gat cag gtt ggc gaa tac ttc gag gag tgc cag gtt tac cgt atc gac      528
Asp Gln Val Gly Glu Tyr Phe Glu Glu Cys Gln Val Tyr Arg Ile Asp
                165                 170                 175 cac tat ctt ggt aaa gaa acg gtg ctg aac ctg ttg gcg ctg cgt ttt      576
His Tyr Leu Gly Lys Glu Thr Val Leu Asn Leu Leu Ala Leu Arg Phe
                180                 185                 190 gct aac tcc ctg ttt gtg aat aac tgg gac aat cgc acc att gat cat      624
Ala Asn Ser Leu Phe Val Asn Asn Trp Asp Asn Arg Thr Ile Asp His
                195                 200                 205 gtt gag att acc gtg gca gaa gaa gtg ggg atc gaa ggg cgc tgg ggc      672
Val Glu Ile Thr Val Ala Glu Glu Val Gly Ile Glu Gly Arg Trp Gly
210                 215                 220 tat ttt gat aaa gcc ggt cag atg cgc gac atg atc cag aac cac ctg      720
Tyr Phe Asp Lys Ala Gly Gln Met Arg Asp Met Ile Gln Asn His Leu
225                 230                 235                 240 ctg caa att ctt tgc atg att gcg atg tct ccg ccg tct gac ctg agc      768
Leu Gln Ile Leu Cys Met Ile Ala Met Ser Pro Pro Ser Asp Leu Ser
                245                 250                 255 gca gac agc atc cgc gat gaa aaa gtg aaa gta ctg aag tct ctg cgc      816
Ala Asp Ser Ile Arg Asp Glu Lys Val Lys Val Leu Lys Ser Leu Arg
                260                 265                 270 cgc atc gac cgc tcc aac gta cgc gaa aaa acc gta cgc ggg caa tat      864
Arg Ile Asp Arg Ser Asn Val Arg Glu Lys Thr Val Arg Gly Gln Tyr
                275                 280                 285 act gcg ggc ttc gcc cag ggc aaa aaa gtg ccg gga tat ctg gaa gaa      912
Thr Ala Gly Phe Ala Gln Gly Lys Lys Val Pro Gly Tyr Leu Glu Glu
                290                 295                 300 gag ggc gcg aac aag agc agc aat aca gaa acc ttc gtg gcg atc cgc      960
Glu Gly Ala Asn Lys Ser Ser Asn Thr Glu Thr Phe Val Ala Ile Arg
305                 310                 315                 320 gtc gac att gat aac tgg cgc tgg gcc ggt gtg cca ttc tac ctg cgt     1008
Val Asp Ile Asp Asn Trp Arg Trp Ala Gly Val Pro Phe Tyr Leu Arg
                325                 330                 335 act ggt aaa cgt ctg ccg acc aaa tgt tct gaa gtc gtg gtc tat ttc     1056
```

-continued

```
                    Thr Gly Lys Arg Leu Pro Thr Lys Cys Ser Glu Val Val Tyr Phe
                                340                 345                 350 aaa aca cct gaa ctg aat ctg ttt aaa gag tcg tgg cag gat ctg ccg        1104
Lys Thr Pro Glu Leu Asn Leu Phe Lys Glu Ser Trp Gln Asp Leu Pro
        355                 360                 365 cag aat aaa ctg act atc cgt ctg caa cct gat gaa ggc gtg gat atc        1152
Gln Asn Lys Leu Thr Ile Arg Leu Gln Pro Asp Glu Gly Val Asp Ile
    370                 375                 380 cag gta ctg aat aaa gtt cct ggc ctt gac cac aaa cat aac ctg caa        1200
Gln Val Leu Asn Lys Val Pro Gly Leu Asp His Lys His Asn Leu Gln
385                 390                 395                 400 atc acc aag ctg gat ctg agc tat tca gaa acc ttt aat cag acg cat        1248
Ile Thr Lys Leu Asp Leu Ser Tyr Ser Glu Thr Phe Asn Gln Thr His
                405                 410                 415 ctg gcg gat gcc tat gaa cgt ttg ctg ctg gaa acc atg cgt ggt att        1296
Leu Ala Asp Ala Tyr Glu Arg Leu Leu Leu Glu Thr Met Arg Gly Ile
            420                 425                 430 cag gca ctg ttt gta cgt cgc gat gaa gtg gaa gaa gcc tgg aaa tgg        1344
Gln Ala Leu Phe Val Arg Arg Asp Glu Val Glu Glu Ala Trp Lys Trp
        435                 440                 445 gta gac tcc att act gag gcg tgg gcg atg gac aat gat gcg ccg aaa        1392
Val Asp Ser Ile Thr Glu Ala Trp Ala Met Asp Asn Asp Ala Pro Lys
    450                 455                 460 ccg tat cag gcc gga acc tgg gga ccc gtt gcc tcg gtg gcg atg att        1440
Pro Tyr Gln Ala Gly Thr Trp Gly Pro Val Ala Ser Val Ala Met Ile
465                 470                 475                 480 acc cgt gat ggt cgt tcc tgg aat gag ttt gag taa                        1476
Thr Arg Asp Gly Arg Ser Trp Asn Glu Phe Glu
                485                 490

<210> SEQ ID NO 95
<211> LENGTH: 491
<212> TYPE: PRT
<213> ORGANISM: Escherichia coli

<400> SEQUENCE: 95

Met Ala Val Thr Gln Thr Ala Gln Val Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175
```

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205

Val Glu Ile Thr Val Ala Glu Glu Val Gly Ile Glu Gly Arg Trp Gly
    210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
            260                 265                 270

Arg Ile Asp Arg Ser Asn Val Arg Glu Lys Thr Val Arg Gly Gln Tyr
        275                 280                 285

Thr Ala Gly Phe Ala Gln Gly Lys Lys Val Pro Gly Tyr Leu Glu Glu
    290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Tyr Phe
            340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
    370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Glu Ala Trp Lys Trp
        435                 440                 445

Val Asp Ser Ile Thr Glu Ala Trp Ala Met Asp Asn Asp Ala Pro Lys
    450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 96
<211> LENGTH: 32
<212> TYPE: DNA
<213> ORGANISM: Artificial sequence
<220> FEATURE:
<223> OTHER INFORMATION: primer

<400> SEQUENCE: 96
gatcggtctc gcatggcggt aacgcaaaca gc                        32

<210> SEQ ID NO 97
<211> LENGTH: 37
<212> TYPE: DNA
<213> ORGANISM: Artificial sequence
<220> FEATURE:

<223> OTHER INFORMATION: primer

<400> SEQUENCE: 97
gatcctcgag ttactcaaac tcattccagg aacgacc         37

<210> SEQ ID NO 98
<211> LENGTH: 27
<212> TYPE: DNA
<213> ORGANISM: Artificial sequence
<220> FEATURE:
<223> OTHER INFORMATION: primer

<400> SEQUENCE: 98
cgaatatcac gcggtgacca gttaaac         27

<210> SEQ ID NO 99
<211> LENGTH: 24
<212> TYPE: DNA
<213> ORGANISM: Artificial sequence
<220> FEATURE:
<223> OTHER INFORMATION: primer

<400> SEQUENCE: 99
cacagtgtgc cgatgatttt gacc         24

<210> SEQ ID NO 100
<211> LENGTH: 35
<212> TYPE: DNA
<213> ORGANISM: Artificial sequence
<220> FEATURE:
<223> OTHER INFORMATION: primer

<400> SEQUENCE: 100
gaccaatggc ctaatggagc aaccgcacct gtggc         35

<210> SEQ ID NO 101
<211> LENGTH: 46
<212> TYPE: DNA
<213> ORGANISM: Artificial sequence
<220> FEATURE:
<223> OTHER INFORMATION: primer

<400> SEQUENCE: 101
gatcagcgct atccggatat agttcctcct ttcagcaaaa aacccc         46

<210> SEQ ID NO 102
<211> LENGTH: 28
<212> TYPE: DNA
<213> ORGANISM: Artificial sequence
<220> FEATURE:
<223> OTHER INFORMATION: primer

<400> SEQUENCE: 102
gatgctagct aaccggagct catagggc         28

<210> SEQ ID NO 103
<211> LENGTH: 32
<212> TYPE: DNA
<213> ORGANISM: Artificial sequence
<220> FEATURE:
<223> OTHER INFORMATION: primer

<400> SEQUENCE: 103
gatttcgaat gatcagtgtc agatttttac cc         32

<210> SEQ ID NO 104
<211> LENGTH: 1650
<212> TYPE: DNA
<213> ORGANISM: Escherichia coli
<220> FEATURE:
<221> NAME/KEY: CDS
<222> LOCATION: (1)..(1650)
<223> OTHER INFORMATION:

<400> SEQUENCE: 104

| | | | | | | | | | | | | | | | | |
|---|---|---|---|---|---|---|---|---|---|---|---|---|---|---|---|---|
| atg | aaa | aac | atc | aat | cca | acg | cag | acc | gct | gcc | tgg | cag | gca | cta | cag | 48 |
| Met | Lys | Asn | Ile | Asn | Pro | Thr | Gln | Thr | Ala | Ala | Trp | Gln | Ala | Leu | Gln | |
| 1 | | | | 5 | | | | | 10 | | | | | 15 | | |
| aaa | cac | ttc | gat | gaa | atg | aaa | gac | gtt | acg | atc | gcc | gat | ctt | ttt | gct | 96 |
| Lys | His | Phe | Asp | Glu | Met | Lys | Asp | Val | Thr | Ile | Ala | Asp | Leu | Phe | Ala | |
| | | | 20 | | | | | 25 | | | | | 30 | | | |
| aaa | gac | ggc | gat | cgt | ttt | tct | aag | ttc | tcc | gca | acc | ttc | gac | gat | cag | 144 |
| Lys | Asp | Gly | Asp | Arg | Phe | Ser | Lys | Phe | Ser | Ala | Thr | Phe | Asp | Asp | Gln | |
| | 35 | | | | | 40 | | | | | 45 | | | | | |
| atg | ctg | gtg | gat | tac | tcc | aaa | aac | cgc | atc | act | gaa | gag | acg | ctg | gcg | 192 |
| Met | Leu | Val | Asp | Tyr | Ser | Lys | Asn | Arg | Ile | Thr | Glu | Glu | Thr | Leu | Ala | |
| 50 | | | | | 55 | | | | | 60 | | | | | | |
| aaa | tta | cag | gat | ctg | gcg | aaa | gag | tgc | gat | ctg | gcg | ggc | gcg | att | aag | 240 |
| Lys | Leu | Gln | Asp | Leu | Ala | Lys | Glu | Cys | Asp | Leu | Ala | Gly | Ala | Ile | Lys | |
| 65 | | | | 70 | | | | | 75 | | | | | 80 | | |
| tcg | atg | ttc | tct | ggc | gag | aag | atc | aac | cgc | act | gaa | aac | cgc | gcc | gtg | 288 |
| Ser | Met | Phe | Ser | Gly | Glu | Lys | Ile | Asn | Arg | Thr | Glu | Asn | Arg | Ala | Val | |
| | | | 85 | | | | | 90 | | | | | 95 | | | |
| ctg | cac | gta | gcg | ctg | cgt | aac | cgt | agc | aat | acc | ccg | att | ttg | gtt | gat | 336 |
| Leu | His | Val | Ala | Leu | Arg | Asn | Arg | Ser | Asn | Thr | Pro | Ile | Leu | Val | Asp | |
| | | | 100 | | | | | 105 | | | | | 110 | | | |
| ggc | aaa | gac | gta | atg | ccg | gaa | gtc | aac | gcg | gtg | ctg | gag | aag | atg | aaa | 384 |
| Gly | Lys | Asp | Val | Met | Pro | Glu | Val | Asn | Ala | Val | Leu | Glu | Lys | Met | Lys | |
| | | 115 | | | | | 120 | | | | | 125 | | | | |
| acc | ttc | tca | gaa | gcg | att | att | tcc | ggt | gag | tgg | aaa | ggt | tat | acc | ggc | 432 |
| Thr | Phe | Ser | Glu | Ala | Ile | Ile | Ser | Gly | Glu | Trp | Lys | Gly | Tyr | Thr | Gly | |
| | 130 | | | | | 135 | | | | | 140 | | | | | |
| aaa | gca | atc | act | gac | gta | gtg | aac | atc | ggg | atc | ggc | ggt | tct | gac | ctc | 480 |
| Lys | Ala | Ile | Thr | Asp | Val | Val | Asn | Ile | Gly | Ile | Gly | Gly | Ser | Asp | Leu | |
| 145 | | | | | 150 | | | | | 155 | | | | | 160 | |
| ggc | cca | tac | atg | gtg | acc | gaa | gct | ctg | cgt | ccg | tac | aaa | aac | cac | ctg | 528 |
| Gly | Pro | Tyr | Met | Val | Thr | Glu | Ala | Leu | Arg | Pro | Tyr | Lys | Asn | His | Leu | |
| | | | | 165 | | | | | 170 | | | | | 175 | | |
| aac | atg | cac | ttt | gtt | tct | aac | gtc | gat | ggg | act | cac | atc | gcg | gaa | gtg | 576 |
| Asn | Met | His | Phe | Val | Ser | Asn | Val | Asp | Gly | Thr | His | Ile | Ala | Glu | Val | |
| | | | 180 | | | | | 185 | | | | | 190 | | | |
| ctg | aaa | aaa | gta | aac | ccg | gaa | acc | acg | ctg | ttc | ttg | gta | gca | tct | aaa | 624 |
| Leu | Lys | Lys | Val | Asn | Pro | Glu | Thr | Thr | Leu | Phe | Leu | Val | Ala | Ser | Lys | |
| | | 195 | | | | | 200 | | | | | 205 | | | | |
| acc | ttc | acc | act | cag | gaa | act | atg | acc | aac | gcc | cat | agc | gcg | cgt | gac | 672 |
| Thr | Phe | Thr | Thr | Gln | Glu | Thr | Met | Thr | Asn | Ala | His | Ser | Ala | Arg | Asp | |
| | 210 | | | | | 215 | | | | | 220 | | | | | |
| tgg | ttc | ctg | aaa | gcg | gca | ggt | gat | gaa | aaa | cac | gtt | gca | aaa | cac | ttt | 720 |
| Trp | Phe | Leu | Lys | Ala | Ala | Gly | Asp | Glu | Lys | His | Val | Ala | Lys | His | Phe | |
| 225 | | | | | 230 | | | | | 235 | | | | | 240 | |
| gcg | gcg | ctt | tcc | acc | aat | gcc | aaa | gcc | gtt | ggc | gag | ttt | ggt | att | gat | 768 |
| Ala | Ala | Leu | Ser | Thr | Asn | Ala | Lys | Ala | Val | Gly | Glu | Phe | Gly | Ile | Asp | |
| | | | | 245 | | | | | 250 | | | | | 255 | | |
| act | gcc | aac | atg | ttc | gag | ttc | tgg | gac | tgg | gtt | ggc | ggc | cgt | tac | tct | 816 |
| Thr | Ala | Asn | Met | Phe | Glu | Phe | Trp | Asp | Trp | Val | Gly | Gly | Arg | Tyr | Ser | |
| | | | 260 | | | | | 265 | | | | | 270 | | | |

-continued

```
ttg tgg tca gcg att ggc ctg tcg att gtt ctc tcc atc ggc ttt gat      864
Leu Trp Ser Ala Ile Gly Leu Ser Ile Val Leu Ser Ile Gly Phe Asp
        275                 280                 285 aac ttc gtt gaa ctg ctt tcc ggc gca cac gcg atg gac aag cat ttc      912
Asn Phe Val Glu Leu Leu Ser Gly Ala His Ala Met Asp Lys His Phe
    290                 295                 300 tcc acc acg cct gcc gag aaa aac ctg cct gta ctg ctg gcg ctg att      960
Ser Thr Thr Pro Ala Glu Lys Asn Leu Pro Val Leu Leu Ala Leu Ile
305                 310                 315                 320 ggc atc tgg tac aac aat ttc ttt ggt gcg gaa act gaa gcg att ctg     1008
Gly Ile Trp Tyr Asn Asn Phe Phe Gly Ala Glu Thr Glu Ala Ile Leu
                325                 330                 335 ccg tat gac cag tat atg cac cgt ttc gcg gcg tac ttc cag cag ggc     1056
Pro Tyr Asp Gln Tyr Met His Arg Phe Ala Ala Tyr Phe Gln Gln Gly
            340                 345                 350 aat atg gag tcc aac ggt aag tat gtt gac cgt aac ggt aac gtt gtg     1104
Asn Met Glu Ser Asn Gly Lys Tyr Val Asp Arg Asn Gly Asn Val Val
        355                 360                 365 gat tac cag act ggc ccg att atc tgg ggt gaa cca ggc act aac ggt     1152
Asp Tyr Gln Thr Gly Pro Ile Ile Trp Gly Glu Pro Gly Thr Asn Gly
    370                 375                 380 cag cac gcg ttc tac cag ctg atc cac cag gga acc aaa atg gta ccg     1200
Gln His Ala Phe Tyr Gln Leu Ile His Gln Gly Thr Lys Met Val Pro
385                 390                 395                 400 tgc gat ttc atc gct ccg gct atc acc cat aac ccg ctc tct gat cat     1248
Cys Asp Phe Ile Ala Pro Ala Ile Thr His Asn Pro Leu Ser Asp His
                405                 410                 415 cac cag aaa ctg ctg tct aac ttc ttc gcc cag acc gaa gcg ctg gcg     1296
His Gln Lys Leu Leu Ser Asn Phe Phe Ala Gln Thr Glu Ala Leu Ala
            420                 425                 430 ttt ggt aaa tcc cgc gaa gtg gtt gag cag gaa tat cgt gat cag ggt     1344
Phe Gly Lys Ser Arg Glu Val Val Glu Gln Glu Tyr Arg Asp Gln Gly
        435                 440                 445 aaa gat ccg gca acg ctt gac tac gtg gtg ccg ttc aaa gta ttc gaa     1392
Lys Asp Pro Ala Thr Leu Asp Tyr Val Val Pro Phe Lys Val Phe Glu
    450                 455                 460 ggt aac cgc ccg acc aac tcc atc ctg ctg cgt gaa atc act ccg ttc     1440
Gly Asn Arg Pro Thr Asn Ser Ile Leu Leu Arg Glu Ile Thr Pro Phe
465                 470                 475                 480 agc ctg ggt gcg ttg att gcg ctg tat gag cac aaa atc ttt act cag     1488
Ser Leu Gly Ala Leu Ile Ala Leu Tyr Glu His Lys Ile Phe Thr Gln
                485                 490                 495 ggc gtg atc ctg aac atc ttc acc ttc gac cag tgg ggc gtg gaa ctg     1536
Gly Val Ile Leu Asn Ile Phe Thr Phe Asp Gln Trp Gly Val Glu Leu
            500                 505                 510 ggt aaa cag ctg gcg aac cgt att ctg cca gag ctg aaa gat gat aaa     1584
Gly Lys Gln Leu Ala Asn Arg Ile Leu Pro Glu Leu Lys Asp Asp Lys
        515                 520                 525 gaa atc agc agc cac gat agc tcg acc aat ggt ctg att aac cgc tat     1632
Glu Ile Ser Ser His Asp Ser Ser Thr Asn Gly Leu Ile Asn Arg Tyr
    530                 535                 540 aaa gcg tgg cgc ggt taa                                              1650
Lys Ala Trp Arg Gly
545
```

<210> SEQ ID NO 105
<211> LENGTH: 549
<212> TYPE: PRT
<213> ORGANISM: Escherichia coli

<400> SEQUENCE: 105

-continued

```
Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
                20                  25                  30

Lys Asp Gly Asp Arg Phe Ser Lys Phe Ser Ala Thr Phe Asp Asp Gln
            35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
                100                 105                 110

Gly Lys Asp Val Met Pro Glu Val Asn Ala Val Leu Glu Lys Met Lys
            115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
                180                 185                 190

Leu Lys Lys Val Asn Pro Glu Thr Thr Leu Phe Leu Val Ala Ser Lys
            195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
                260                 265                 270

Leu Trp Ser Ala Ile Gly Leu Ser Ile Val Leu Ser Ile Gly Phe Asp
    275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
    355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415
```

```
His Gln Lys Leu Leu Ser Asn Phe Phe Ala Gln Thr Glu Ala Leu Ala
            420                 425                 430

Phe Gly Lys Ser Arg Glu Val Val Gln Glu Tyr Arg Asp Gln Gly
        435                 440                 445

Lys Asp Pro Ala Thr Leu Asp Tyr Val Val Pro Phe Lys Val Phe Glu
450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
            485                 490                 495

Gly Val Ile Leu Asn Ile Phe Thr Phe Asp Gln Trp Gly Val Glu Leu
                500                 505                 510

Gly Lys Gln Leu Ala Asn Arg Ile Leu Pro Glu Leu Lys Asp Lys
        515                 520                 525

Glu Ile Ser Ser His Asp Ser Ser Thr Asn Gly Leu Ile Asn Arg Tyr
            530                 535                 540

Lys Ala Trp Arg Gly
545
```

<210> SEQ ID NO 106
<211> LENGTH: 38
<212> TYPE: DNA
<213> ORGANISM: Artificial sequence
<220> FEATURE:
<223> OTHER INFORMATION: primer

<400> SEQUENCE: 106
gatcggtctc gcatgaaaaa catcaatcca acgcagac                                38

<210> SEQ ID NO 107
<211> LENGTH: 33
<212> TYPE: DNA
<213> ORGANISM: Artificial sequence
<220> FEATURE:
<223> OTHER INFORMATION: primer

<400> SEQUENCE: 107
gatcctcgag ttaaccgcgc cacgctttat agc                                     33

<210> SEQ ID NO 108
<211> LENGTH: 31
<212> TYPE: DNA
<213> ORGANISM: Artificial sequence
<220> FEATURE:
<223> OTHER INFORMATION: primer

<400> SEQUENCE: 108
ggatcctacc tgacgctttt tatcgcaact c                                       31

<210> SEQ ID NO 109
<211> LENGTH: 24
<212> TYPE: DNA
<213> ORGANISM: Artificial sequence
<220> FEATURE:
<223> OTHER INFORMATION: primer

<400> SEQUENCE: 109
cggacgcaca tcggcctcgt agac                                               24

<210> SEQ ID NO 110
<211> LENGTH: 27
<212> TYPE: DNA

<213> ORGANISM: Artificial sequence
<220> FEATURE:
<223> OTHER INFORMATION: primer

<400> SEQUENCE: 110
gattccggaa gcaaccgcac ctgtggc                                                    27

<210> SEQ ID NO 111
<211> LENGTH: 39
<212> TYPE: DNA
<213> ORGANISM: Artificial sequence
<220> FEATURE:
<223> OTHER INFORMATION: primer

<400> SEQUENCE: 111
gatcacctgg ttatagttcc tcctttcagc aaaaaaccc                                       39

<210> SEQ ID NO 112
<211> LENGTH: 24
<212> TYPE: DNA
<213> ORGANISM: Artificial sequence
<220> FEATURE:
<223> OTHER INFORMATION: primer

<400> SEQUENCE: 112
gagtcatccg gatacagtac gcga                                                       24

<210> SEQ ID NO 113
<211> LENGTH: 21
<212> TYPE: DNA
<213> ORGANISM: Artificial sequence
<220> FEATURE:
<223> OTHER INFORMATION: primer

<400> SEQUENCE: 113
ataaaccagc cgggcaaatg g                                                          21

<210> SEQ ID NO 114
<211> LENGTH: 17
<212> TYPE: DNA
<213> ORGANISM: Artificial sequence
<220> FEATURE:
<223> OTHER INFORMATION: primer

<400> SEQUENCE: 114
cgccaagctt ggtaccg                                                               17

<210> SEQ ID NO 115
<211> LENGTH: 21
<212> TYPE: DNA
<213> ORGANISM: Artificial sequence
<220> FEATURE:
<223> OTHER INFORMATION: primer

<400> SEQUENCE: 115
ccctctagat gcatgctcga g                                                          21

<210> SEQ ID NO 116
<211> LENGTH: 23
<212> TYPE: DNA
<213> ORGANISM: Artificial sequence
<220> FEATURE:
<223> OTHER INFORMATION: primer

<400> SEQUENCE: 116
attgtgcgct cagtatagga agg                                                        23

<210> SEQ ID NO 117
<211> LENGTH: 19
<212> TYPE: DNA
<213> ORGANISM: Artificial sequence
<220> FEATURE:
<223> OTHER INFORMATION: primer

<400> SEQUENCE: 117
cgatactgac gggctccag                                                     19

<210> SEQ ID NO 118
<211> LENGTH: 35
<212> TYPE: DNA
<213> ORGANISM: Artificial sequence
<220> FEATURE:
<223> OTHER INFORMATION: primer

<400> SEQUENCE: 118
gcaaaacctt tcgcggtcac ccatgatagc gcccg                                   35

<210> SEQ ID NO 119
<211> LENGTH: 35
<212> TYPE: DNA
<213> ORGANISM: Artificial sequence
<220> FEATURE:
<223> OTHER INFORMATION: primer

<400> SEQUENCE: 119
cgggcgctat catgggtgac cgcgaaaggt tttgc                                   35

<210> SEQ ID NO 120
<211> LENGTH: 30
<212> TYPE: DNA
<213> ORGANISM: Artificial sequence
<220> FEATURE:
<223> OTHER INFORMATION: primer

<400> SEQUENCE: 120
cacaggaaac acatatgacc atgattacgg                                         30

<210> SEQ ID NO 121
<211> LENGTH: 23
<212> TYPE: DNA
<213> ORGANISM: Artificial sequence
<220> FEATURE:
<223> OTHER INFORMATION: primer

<400> SEQUENCE: 121
ccaccatgat attcggcaag cag                                                23

<210> SEQ ID NO 122
<211> LENGTH: 21
<212> TYPE: DNA
<213> ORGANISM: Artificial sequence
<220> FEATURE:
<223> OTHER INFORMATION: primer

<400> SEQUENCE: 122
cctttcgcgg tcaccagcaa a                                                  21

<210> SEQ ID NO 123
<211> LENGTH: 30
<212> TYPE: DNA
<213> ORGANISM: Artificial sequence
<220> FEATURE:

<223> OTHER INFORMATION: primer

<400> SEQUENCE: 123
ccgtaatcat ggtcatatgt gtttcctgtg                                30

<210> SEQ ID NO 124
<211> LENGTH: 21
<212> TYPE: DNA
<213> ORGANISM: Artificial sequence
<220> FEATURE:
<223> OTHER INFORMATION: primer

<400> SEQUENCE: 124
gacgaagcgg ccgcgtaaac g                                         21

<210> SEQ ID NO 125
<211> LENGTH: 41
<212> TYPE: DNA
<213> ORGANISM: Artificial sequence
<220> FEATURE:
<223> OTHER INFORMATION: primer

<400> SEQUENCE: 125
cacacaggaa acagctatga ccatgattac ggattcactg g                   41

<210> SEQ ID NO 126
<211> LENGTH: 41
<212> TYPE: DNA
<213> ORGANISM: Artificial sequence
<220> FEATURE:
<223> OTHER INFORMATION: primer

<400> SEQUENCE: 126
ccagtgaatc cgtaatcatg gtcatagctg tttcctgtgt g                   41

<210> SEQ ID NO 127
<211> LENGTH: 30
<212> TYPE: DNA
<213> ORGANISM: Artificial sequence
<220> FEATURE:
<223> OTHER INFORMATION: primer

<400> SEQUENCE: 127
gatcccggga acggacgatt agagatcacc                                30

<210> SEQ ID NO 128
<211> LENGTH: 25
<212> TYPE: DNA
<213> ORGANISM: Artificial sequence
<220> FEATURE:
<223> OTHER INFORMATION: primer

<400> SEQUENCE: 128
gtcagagaag tcgttcttag cgatg                                     25

<210> SEQ ID NO 129
<211> LENGTH: 38
<212> TYPE: DNA
<213> ORGANISM: Artificial sequence
<220> FEATURE:
<223> OTHER INFORMATION: primer

<400> SEQUENCE: 129
ggatctaaac ctcagtagcg accggtctag aactagtg                       38

```
<210> SEQ ID NO 130
<211> LENGTH: 38
<212> TYPE: DNA
<213> ORGANISM: Artificial sequence
<220> FEATURE:
<223> OTHER INFORMATION: primer

<400> SEQUENCE: 130
ccctcgcccc tctagagcat ttaaattcag tcaattac                             38

<210> SEQ ID NO 131
<211> LENGTH: 25
<212> TYPE: DNA
<213> ORGANISM: Artificial sequence
<220> FEATURE:
<223> OTHER INFORMATION: primer

<400> SEQUENCE: 131
cacgcaggca ggctttacct tcttc                                           25

<210> SEQ ID NO 132
<211> LENGTH: 24
<212> TYPE: DNA
<213> ORGANISM: Artificial sequence
<220> FEATURE:
<223> OTHER INFORMATION: primer

<400> SEQUENCE: 132
cggaagaaca agcgacggaa ggac                                            24

<210> SEQ ID NO 133
<211> LENGTH: 24
<212> TYPE: DNA
<213> ORGANISM: Artificial sequence
<220> FEATURE:
<223> OTHER INFORMATION: primer

<400> SEQUENCE: 133
cacgataaac ggtgaagcca tgtc                                            24

<210> SEQ ID NO 134
<211> LENGTH: 27
<212> TYPE: DNA
<213> ORGANISM: Artificial sequence
<220> FEATURE:
<223> OTHER INFORMATION: primer

<400> SEQUENCE: 134
cgtccatttt cttgaacgct tcatccc                                         27

<210> SEQ ID NO 135
<211> LENGTH: 698
<212> TYPE: DNA
<213> ORGANISM: Escherichia coli

<400> SEQUENCE: 135
cctttcgcgg tcaccagcaa atcgcgctgt tagcgggccc attaagttct gtctcggcgc     60
gtctgcgtct ggctggctgg cataaatatc tcactcgcaa tcaaattcag ccgatagcgg    120
aacgggaagg cgactggagt gccatgtccg gttttcaaca aaccatgcaa atgctgaatg    180
agggcatcgt tcccactgcg atgctggttg ccaacgatca gatggcgctg ggcgcaatgc    240
gcgccattac cgagtccggg ctgcgcgttg gtgcggatat ctcggtagtg ggatacgacg    300
ataccgaaga cagctcatgt tatatcccgc cgttaaccac catcaaacag gattttcgcc    360
```

```
tgctggggca aaccagcgtg gaccgcttgc tgcaactctc tcagggccag gcggtgaagg    420
gcaatcagct gttgcccgtc tcactggtga aaagaaaaac caccctggcg cccaatacgc    480
aaaccgcctc tccccgcgcg ttggccgatt cattaatgca gctggcacga caggtttccc    540
gactggaaag cgggcagtga gcgcaacgca attaatgtga gttagctcac tcattaggca    600
ccccaggctt tacactttat gcttccggct cgtatgttgt gtggaattgt gagcggataa    660
caatttcaca caggaaacac atatgaccat gattacgg                            698
```

```
<210> SEQ ID NO 136
<211> LENGTH: 23
<212> TYPE: DNA
<213> ORGANISM: Artificial sequence
<220> FEATURE:
<223> OTHER INFORMATION: primer

<400> SEQUENCE: 136
ggcggcttaa aatgtcctga atg                                             23

<210> SEQ ID NO 137
<211> LENGTH: 28
<212> TYPE: DNA
<213> ORGANISM: Artificial sequence
<220> FEATURE:
<223> OTHER INFORMATION: primer

<400> SEQUENCE: 137
cgaaatcatc gttgccagta actttacg                                        28
```